United States Patent
Smith et al.

(10) Patent No.: US 9,868,704 B2
(45) Date of Patent: *Jan. 16, 2018

(54) ESTROGEN RECEPTOR MODULATORS AND USES THEREOF

(71) Applicant: GENENTECH, INC., South San Francisco, CA (US)

(72) Inventors: Nicholas D. Smith, San Diego, CA (US); Mehmet Kahraman, La Jolla, CA (US); Steven P. Govek, San Diego, CA (US); Johnny Y. Nagasawa, San Diego, CA (US); Andiliy G. Lai, San Diego, CA (US); Jackaline D. Julien, Del Mar, CA (US); Mark R. Herbert, San Diego, CA (US); Karensa L. Douglas, San Diego, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/186,246

(22) Filed: Jun. 17, 2016

(65) Prior Publication Data

US 2016/0297767 A1    Oct. 13, 2016

Related U.S. Application Data

(63) Continuation of application No. 13/821,190, filed as application No. PCT/US2011/051845 on Sep. 15, 2011, now Pat. No. 9,399,646.

(60) Provisional application No. 61/383,659, filed on Sep. 16, 2010, provisional application No. 61/410,727, filed on Nov. 5, 2010, provisional application No. 61/446,967, filed on Feb. 25, 2011.

(30) Foreign Application Priority Data

Mar. 15, 2011    (GB) .................................. 1104288.4

(51) Int. Cl.

| | |
|---|---|
| *C07D 231/56* | (2006.01) |
| *A61K 31/416* | (2006.01) |
| *C07D 209/08* | (2006.01) |
| *C07D 249/18* | (2006.01) |
| *A61K 31/7056* | (2006.01) |
| *A61K 31/7068* | (2006.01) |
| *A61K 31/7072* | (2006.01) |
| *A61K 31/7076* | (2006.01) |
| *A61K 31/708* | (2006.01) |
| *A61K 31/7105* | (2006.01) |
| *C07D 215/227* | (2006.01) |
| *C07D 217/24* | (2006.01) |
| *C07D 265/18* | (2006.01) |
| *C07D 277/68* | (2006.01) |
| *C07D 279/16* | (2006.01) |
| *C07D 401/10* | (2006.01) |
| *C07D 409/10* | (2006.01) |
| *C07D 471/04* | (2006.01) |
| *C07D 495/04* | (2006.01) |
| *C07D 401/12* | (2006.01) |
| *C07D 403/10* | (2006.01) |
| *C07D 413/10* | (2006.01) |
| *C07D 417/10* | (2006.01) |
| *C07C 215/10* | (2006.01) |

(52) U.S. Cl.
CPC .......... *C07D 231/56* (2013.01); *A61K 31/416* (2013.01); *A61K 31/708* (2013.01); *A61K 31/7056* (2013.01); *A61K 31/7068* (2013.01); *A61K 31/7072* (2013.01); *A61K 31/7076* (2013.01); *A61K 31/7105* (2013.01); *C07C 215/10* (2013.01); *C07D 209/08* (2013.01); *C07D 215/227* (2013.01); *C07D 217/24* (2013.01); *C07D 249/18* (2013.01); *C07D 265/18* (2013.01); *C07D 277/68* (2013.01); *C07D 279/16* (2013.01); *C07D 401/10* (2013.01); *C07D 401/12* (2013.01); *C07D 403/10* (2013.01); *C07D 409/10* (2013.01); *C07D 413/10* (2013.01); *C07D 417/10* (2013.01); *C07D 471/04* (2013.01); *C07D 495/04* (2013.01)

(58) Field of Classification Search
CPC ............................ C07D 231/56; A61K 31/416
See application file for complete search history.

(56) References Cited

PUBLICATIONS

'Cancer Prevention Overview', http://www.cancer.gov/cancertopics/pdq/prevention/overview/patient, accessed Apr. 9, 2010.*

* cited by examiner

Primary Examiner — Rebecca L Anderson
Assistant Examiner — Karen Cheng
(74) Attorney, Agent, or Firm — Kevin M. Clark

(57) ABSTRACT

Described herein are compounds that are estrogen receptor modulators. Also described are pharmaceutical compositions and medicaments that include the compounds described herein, as well as methods of using such estrogen receptor modulators, alone and in combination with other compounds, for treating diseases or conditions that are mediated or dependent upon estrogen receptors.

18 Claims, No Drawings

ESTROGEN RECEPTOR MODULATORS AND USES THEREOF

RELATED APPLICATIONS

This continuing application claims the benefit of U.S. patent application Ser. No. 13/821,190 filed on May 21, 2013, a National Stage application of PCT/US2011/51845 filed on Sep. 15, 2011, which claims the benefit of U.S. provisional patent application No. 61/383,659 filed on Sep. 16, 2010; U.S. provisional patent application No. 61/410,727 filed on Nov. 5, 2010; U.S. provisional patent application No. 61/446,967 filed on Feb. 25, 2011; United Kingdom Patent Application No 11 04288.4 filed on Mar. 15, 2011; each of which is incorporated by reference in its entirety.

FIELD OF THE INVENTION

Described herein are compounds, including pharmaceutically acceptable salts, solvates, metabolites, prodrugs thereof, methods of making such compounds, pharmaceutical compositions comprising such compounds, and methods of using such compounds to treat, prevent or diagnose diseases or conditions that are estrogen sensitive, estrogen receptor dependent or estrogen receptor mediated.

BACKGROUND OF THE INVENTION

The estrogen receptor ("ER") is a ligand-activated transcriptional regulatory protein that mediates induction of a variety of biological effects through its interaction with endogenous estrogens. Endogenous estrogens include 17β-estradiol and estrones. ER has been found to have two isoforms, ER-α and ER-β.

Estrogens and estrogen receptors are implicated in a number of diseases or conditions, such as breast cancer, ovarian cancer, colon cancer, prostate cancer, endometrial cancer, uterine cancer, as well as others diseases or conditions.

SUMMARY OF THE INVENTION

In one aspect, presented herein are compounds of Formula (I) that diminish the effects of estrogens with estrogen receptors and/or lower the concentrations of estrogen receptors, and therefore, are useful as agents for the treatment or prevention of diseases or conditions in which the actions of estrogens and/or estrogen receptors are involved in the etiology or pathology of the disease or condition or contribute to at least one symptom of the disease or condition and wherein such actions of estrogens and/or estrogen receptors are undesirable. In some embodiments, compounds disclosed herein are estrogen receptor degrader compounds.

In one aspect, the compound of Formula (I), or a pharmaceutically acceptable salt, or N-oxide thereof, is useful for the treatment of ER-related diseases or conditions including, but not limited to, ER-α dysfunction associated with cancer (e.g. bone cancer, breast cancer, colorectal cancer, endometrial cancer, prostate cancer, ovarian and uterine cancer), leiomyoma (e.g. uterine leiomyoma), central nervous system (CNS) defects (e.g. alcoholism, migraine), cardiovascular system defects (e.g. aortic aneurysm, susceptibility to myocardial infarction, aortic valve sclerosis, cardiovascular disease, coronary artery disease, hypertension), hematological system defects (e.g. deep vein thrombosis), immune and inflammation diseases (e.g. Graves' Disease, arthritis, multiple sclerosis, cirrhosis), susceptibility to infection (e.g. hepatitis B, chronic liver disease), metabolic defects (e.g. bone density, cholestosis, hypospadias, obesity, osteoarthritis, osteopenia, osteoporosis), neurological defects (e.g. Alzheimer's disease, Parkinson's disease, migraine, vertigo), psychiatric defects (e.g. anorexia nervosa, attention deficity hyperactivity disorder (ADHD), dementia, major depressive disorder, psychosis) and reproductive defects (e.g. age of menarche, endometriosis, infertility).

In one aspect, described herein are compounds of Formula (I), pharmaceutically acceptable salts, solvates, metabolites and prodrugs thereof. Compounds of Formula (I) are estrogen receptor modulators. In some embodiments, the compound of Formula (I) is an estrogen receptor antagonist. In some embodiments, the compound of Formula (I) is an estrogen receptor degrader. In some embodiments, the compound of Formula (I) is an estrogen receptor antagonist as well as an estrogen receptor degrader. In some embodiments, the compound of Formula (I) displays minimal or no estrogen receptor agonist activity. In some embodiments, in the context of treating cancers, the compound of Formula (I) offer improved therapeutic activity characterized by complete or longer-lasting tumor regression, a lower incidence or rate of development of resistance to treatment, and/or a reduction in tumor invasiveness.

In one aspect, provided herein is a compound of Formula (I), or a pharmaceutically acceptable salt, solvate, metabolite or prodrug thereof:

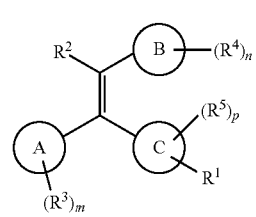

Formula (I)

wherein, ring A is indanyl, indenyl, naphthyl, 5- or 6-membered monocyclic heteroaryl, or 8-, 9- or 10-membered bicyclic heterocycle;

ring B is phenyl, indanyl, indenyl, naphthyl, 5- or 6-membered monocyclic heteroaryl or 8-, 9- or 10-membered bicyclic heterocycle;

ring C is phenyl, indanyl, indenyl, naphthyl, 5- or 6-membered monocyclic heteroaryl or 8-, 9- or 10-membered bicyclic heterocycle;

$R^1$ is Y, —X—$C_1$-$C_6$alkylene-Y, —$C_1$-$C_6$alkylene-Y, —$C_2$-$C_6$alkynylene-Y, —C($R^6$)=C($R^7$)—Y, —X—$C_1$-$C_6$alkynylene-Y, —X—$C_3$-$C_6$cycloalkylene-Y or —$C_3$-$C_6$cycloalkylene-Y;

X is $NR^8$, O, S, S(=O) or S(=O)$_2$;

Y is —C(=O)—Z, tetrazolyl, carboxylic acid bioisostere, optionally substituted piperidinyl, optionally substituted pyrrolidinyl, —$NR^8R^{8'}$, -AR—OH, —$SO_3H$, —$SO_2NHR^9$, and —P(=O)(OH)$_2$ wherein AR is phenyl or monocyclic heteroaryl;

Z is —OH, —$OR^{10}$, —$NR^8R^{8'}$, —$NR^8S$(=O)$_2R^{10}$, —NHOH or —$NR^8OR^{10}$;

$R^2$ is halogen, CN, $NO_2$, —$SR^9$, —S(=O)$R^{10}$, —S(=O)$_2$ $R^{10}$, —NHS(=O)$_2R^{10}$, $C_1$-$C_6$alkyl, $C_1$-$C_6$fluoroalkyl, $C_1$-$C_6$deuteroalkyl, $C_1$-$C_4$alkoxy, $C_1$-$C_4$fluoroalkoxy, $C_3$-$C_6$cycloalkyl, —$C_1$-$C_4$alkylene-W, —$C_1$-$C_4$fluoroalkylene-W, —$C_3$-$C_6$cycloalkylene-W;

W is hydroxy, halogen, CN, NO$_2$, C$_1$-C$_6$alkyl, C$_1$-C$_6$haloalkyl, C$_1$-C$_6$alkoxy, C$_1$-C$_6$haloalkoxy, and C$_3$-C$_6$cycloalkyl;

each R$^3$, R$^4$, R$^5$ is independently selected from H, halogen, —NO$_2$, —NR$^8$R$^{8'}$, —CN, —OH, —OR$^9$, —SR$^9$, —S(=O)R$^{10}$, —S(=O)$_2$R$^{10}$, —NHS(=O)$_2$R$^{10}$, —S(=O)$_2$N(R$^9$)$_2$, —C(=O)R$^{10}$, —OC(=O)R$^{10}$, —CO$_2$R$^9$, —OCO$_2$R$^{10}$, —C(=O)N(R$^9$)$_2$, —OC(=O)N(R$^9$)$_2$, —NR$^9$C(=O)N(R$^9$)$_2$, —NR$^9$C(=O)R$^{10}$, —NR$^9$C(=O)OR$^{10}$, substituted or unsubstituted C$_1$-C$_6$alkyl, substituted or unsubstituted C$_2$-C$_6$alkenyl, substituted or unsubstituted C$_2$-C$_6$alkynyl, substituted or unsubstituted C$_1$-C$_6$fluoroalkyl, substituted or unsubstituted C$_1$-C$_6$heteroalkyl, substituted or unsubstituted C$_1$-C$_6$fluoroalkoxy, substituted or unsubstituted C$_1$-C$_6$alkoxy, substituted or unsubstituted phenyl and substituted or unsubstituted monocyclic heteroaryl;

R$^6$ and R$^7$ is independently H, OR$^9$, NR$^8$R$^{8'}$, C$_1$-C$_6$alkyl, C$_2$-C$_6$alkenyl, C$_2$-C$_6$alkynyl, —X—C$_1$-C$_6$alkyl, —X—C$_2$-C$_6$alkenyl, —X—C$_2$-C$_6$alkynyl, or halogen;

R$^8$ and R$^{8'}$ is independently H, substituted or unsubstituted C$_1$-C$_6$alkyl, substituted or unsubstituted C$_2$-C$_6$alkenyl, substituted or unsubstituted C$_2$-C$_6$alkynyl, substituted or unsubstituted C$_1$-C$_6$fluoroalkyl, substituted or unsubstituted C$_1$-C$_6$heteroalkyl, substituted or unsubstituted C$_3$-C$_{10}$cycloalkyl, substituted or unsubstituted C$_2$-C$_{10}$heterocycloalkyl, substituted or unsubstituted phenyl, substituted or unsubstituted monocyclic heteroaryl, or substituted or unsubstituted benzyl;

each R$^9$ is independently selected from H, substituted or unsubstituted C$_1$-C$_6$alkyl, substituted or unsubstituted C$_1$-C$_6$heteroalkyl, substituted or unsubstituted C$_1$-C$_6$fluoroalkyl, substituted or unsubstituted C$_3$-C$_{10}$cycloalkyl, substituted or unsubstituted C$_2$-C$_{10}$heterocycloalkyl, substituted or unsubstituted aryl, substituted or unsubstituted heteroaryl and substituted or unsubstituted benzyl;

each R$^{10}$ is independently selected from substituted or unsubstituted C$_1$-C$_6$alkyl, substituted or unsubstituted C$_1$-C$_6$heteroalkyl, substituted or unsubstituted C$_1$-C$_6$fluoroalkyl, substituted or unsubstituted C$_3$-C$_{10}$cycloalkyl, substituted or unsubstituted C$_2$-C$_{10}$heterocycloalkyl, substituted or unsubstituted aryl, substituted or unsubstituted heteroaryl and substituted or unsubstituted benzyl;

m is 0, 1, 2, 3, or 4;

n is 0, 1, 2, 3, or 4; and p is 0, 1, 2, 3, or 4.

For any and all of the embodiments, substituents are selected from among from a subset of the listed alternatives. For example, in some embodiments, R$^1$ is Y, —X—C$_1$-C$_6$alkylene-Y, —C$_1$-C$_6$alkylene-Y, —C$_2$-C$_6$alkynylene-Y, —C(R$^6$)=C(R$^7$)—Y, —X—C$_1$-C$_6$alkynylene-Y, —X—C$_3$-C$_6$cycloalkylene-Y or —C$_3$-C$_6$cycloalkylene-Y. In some embodiments, R$^1$ is —C(R$^6$)=C(R$^7$)—Y.

In some embodiments, Y is —C(=O)—Z or carboxylic bioisostere. In some embodiments, Y is —C(=O)—Z or tetrazolyl. In some embodiments, Y is —C(=O)—Z. In some embodiments, Y is carboxylic bioisostere.

In some embodiments, Z is —OH, —OR$^{10}$, —NR$^8$R$^{8'}$, —NR$^8$S(=O)$_2$R$^{10}$, —NHOH or —NR$^8$OR$^{10}$. In some embodiments, Z is —OH, —OR$^{10}$, —NR$^8$R$^{8'}$, —NR$^8$S(=O)$_2$R$^{10}$, or —NHOH. In some embodiments, Z is —OH or —OR$^{10}$. In some embodiments, Z is —OH or —O(C$_1$-C$_4$alkyl). In some embodiments, Z is —OH. In some embodiments, Y is —C(=O)—OH.

In some embodiments, ring A is 5- or 6-membered monocyclic heteroaryl or 8-, 9- or 10-membered bicyclic heterocycle; ring B is phenyl, naphthyl, 5- or 6-membered monocyclic heteroaryl or 8-, 9- or 10-membered bicyclic heterocycle; ring C is phenyl or 5- or 6-membered monocyclic heteroaryl.

In some embodiments, ring A is a 5- or 6-membered monocyclic heteroaryl.

In some embodiments, ring A is furanyl, thienyl, oxazolyl, thiazolyl, pyrrolyl, imidazolyl, pyrazolyl, triazolyl, tetrazolyl, pyridinyl, pyridazinyl, pyrimidinyl, pyrazinyl, or triazinyl.

In some embodiments, ring A is a 8-, 9- or 10-membered bicyclic heterocycle with at least one nitrogen atom in the ring.

In some embodiments, ring A is a 8-, 9- or 10-membered bicyclic heteroaryl with at least one nitrogen atom in the ring.

In some embodiments, ring A is quinolinyl, isoquinolinyl, cinnolinyl, phthalazinyl, quinazolinyl, quinoxalinyl, naphthyridinyl, pteridinyl, indolizinyl, azaindolizinyl, indolyl, azaindolyl, indazolyl, azaindazolyl, benzimidazolyl, azabenzimidazolyl, benzotriazolyl, azabenzotriazolyl, benzoxazolyl, azabenzoxazolyl, benzisoxazolyl, azabenzisoxazolyl, benzofuranyl, azabenzofuranyl, benzothienyl, azabenzothienyl, benzothiazolyl, azabenzothiazolyl, or purinyl.

In some embodiments, ring A is indazolyl.

In some embodiments, ring A is benzothiazolyl.

In some embodiments, ring A is 5- or 6-membered monocyclic heteroaryl or 8-, 9- or 10-membered bicyclic heterocycle; ring B is phenyl, naphthyl, 5- or 6-membered monocyclic heteroaryl or 8-, 9- or 10-membered bicyclic heterocycle; ring C is phenyl, or 5- or 6-membered monocyclic heteroaryl; each R$^3$ is independently selected from H, halogen, —NR$^8$R$^{8'}$, —CN, —OH, —OR$^9$, —SR$^9$, —S(=O)R$^{10}$, —S(=O)$_2$R$^{10}$, —NHS(=O)$_2$R$^{10}$, —S(=O)$_2$N(R$^9$)$_2$, —C(=O)R$^{10}$, —OC(=O)R$^{10}$, —CO$_2$R$^9$, —C(=O)N(R$^9$)$_2$, C$_1$-C$_4$alkyl, C$_2$-C$_4$alkenyl, C$_2$-C$_4$alkynyl, C$_1$-C$_4$fluoroalkyl, C$_1$-C$_4$heteroalkyl, C$_1$-C$_4$fluoroalkoxy, and C$_1$-C$_4$alkoxy; each R$^4$ is independently selected from H, halogen, —NO$_2$, —NR$^8$R$^{8'}$, —CN, —OH, —OR$^9$, —SR$^9$, —S(=O)R$^{10}$, —S(=O)$_2$R$^{10}$, —NHS(=O)$_2$R$^{10}$, —S(=O)$_2$N(R$^9$)$_2$, —C(=O)R$^{10}$, —OC(=O)R$^{10}$, —CO$_2$R$^9$, —OCO$_2$R$^{10}$, —C(=O)N(R$^9$)$_2$, —OC(=O)N(R$^9$)$_2$, —NR$^9$C(=O)N(R$^9$)$_2$, —NR$^9$C(=O)R$^{10}$, —NR$^9$C(=O)OR$^{10}$, substituted or unsubstituted C$_1$-C$_6$alkyl, substituted or unsubstituted C$_2$-C$_6$alkenyl, substituted or unsubstituted C$_2$-C$_6$alkynyl, substituted or unsubstituted C$_1$-C$_6$fluoroalkyl, substituted or unsubstituted C$_1$-C$_6$heteroalkyl, substituted or unsubstituted C$_1$-C$_6$fluoroalkoxy, substituted or unsubstituted C$_1$-C$_6$alkoxy, substituted or unsubstituted phenyl and substituted or unsubstituted monocyclic heteroaryl; each R$^5$ is independently selected from H, halogen, —NR$^8$R$^{8'}$, —CN, —OH, —OR$^9$, —SR$^9$, —S(=O)R$^{10}$, —S(=O)$_2$R$^{10}$, —NHS(=O)$_2$R$^{10}$, —S(=O)$_2$N(R$^9$)$_2$, —C(=O)R$^{10}$, —OC(=O)R$^{10}$, —CO$_2$R$^9$, —C(=O)N(R$^9$)$_2$, C$_1$-C$_4$alkyl, C$_2$-C$_4$alkenyl, C$_2$-C$_4$alkynyl, C$_1$-C$_4$fluoroalkyl, C$_1$-C$_4$heteroalkyl, C$_1$-C$_4$fluoroalkoxy, and C$_1$-C$_4$alkoxy.

It is understood that R$^3$ may be present on any open position of ring A.

It is understood that R$^4$ may be present on any open position of ring B.

It is understood that R$^5$ may be present on any open position of ring C.

In some embodiments, ring A is a 5- or 6-membered monocyclic heteroaryl.

In some embodiments, ring A is furanyl, thienyl, oxazolyl, thiazolyl, pyrrolyl, imidazolyl, pyrazolyl, triazolyl, tetrazolyl, pyridinyl, pyridazinyl, pyrimidinyl, pyrazinyl, or triazinyl.

In some embodiments, ring A is a 8-, 9- or 10-membered bicyclic heterocycle with at least one nitrogen atom in the ring; ring B is phenyl, naphthyl, indanyl, indenyl, furanyl, thienyl, oxazolyl, thiazolyl, pyrrolyl, imidazolyl, pyrazolyl, triazolyl, tetrazolyl, pyridinyl, pyridazinyl, pyrimidinyl, pyrazinyl, triazinyl, quinolinyl, isoquinolinyl, cinnolinyl, phthalazinyl, quinazolinyl, quinoxalinyl, naphthyridinyl, pteridinyl, inolizinyl, azainolizinyl, indolyl, azaindolyl, indazolyl, azaindazolyl, benzimidazolyl, azabenzimidazolyl, benzotriazolyl, azabenzotriazolyl, benzoxazolyl, azabenzoxazolyl, benzisoxazolyl, azabenzisoxazolyl, benzofuranyl, azabenzofuranyl, benzothienyl, azabenzothienyl, benzothiazolyl, azabenzothiazolyl, or purinyl.

In some embodiments, ring A is a 8-, 9- or 10-membered bicyclic heteroaryl with at least one nitrogen atom in the ring; ring B is phenyl, a 5-membered heteroaryl or a 6-membered heteroaryl; ring C is phenyl, a 5-membered heteroaryl or a 6-membered heteroaryl.

In some embodiments, ring A is quinolinyl, isoquinolinyl, cinnolinyl, phthalazinyl, quinazolinyl, quinoxalinyl, naphthyridinyl, pteridinyl, indolizinyl, azaindolizinyl, indolyl, azaindolyl, indazolyl, azaindazolyl, benzimidazolyl, azabenzimidazolyl, benzotriazolyl, azabenzotriazolyl, benzoxazolyl, azabenzoxazolyl, benzisoxazolyl, azabenzisoxazolyl, benzofuranyl, azabenzofuranyl, benzothienyl, azabenzothienyl, benzothiazolyl, azabenzothiazolyl, or purinyl; ring B is phenyl, furanyl, thienyl, pyrrolyl, imidazolyl, pyrazolyl, triazolyl, pyridinyl, pyrimidinyl, pyrazinyl, pyridazinyl, or triazinyl; ring C is phenyl, furanyl, thienyl, oxazolyl, thiazolyl, pyrrolyl, imidazolyl, pyrazolyl, triazolyl, pyridinyl, pyridazinyl, pyrimidinyl, pyrazinyl, or triazinyl.

In some embodiments, ring A is

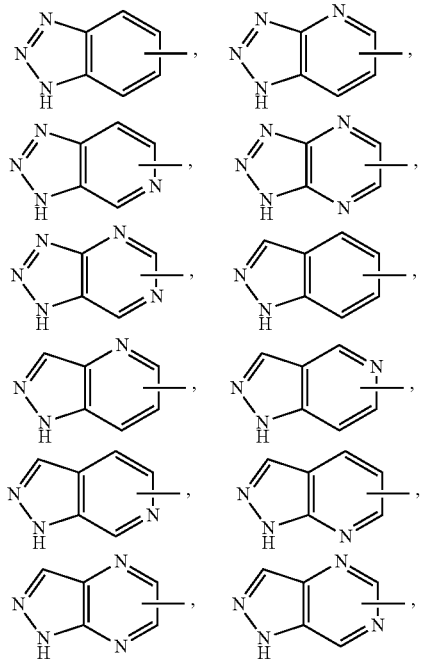

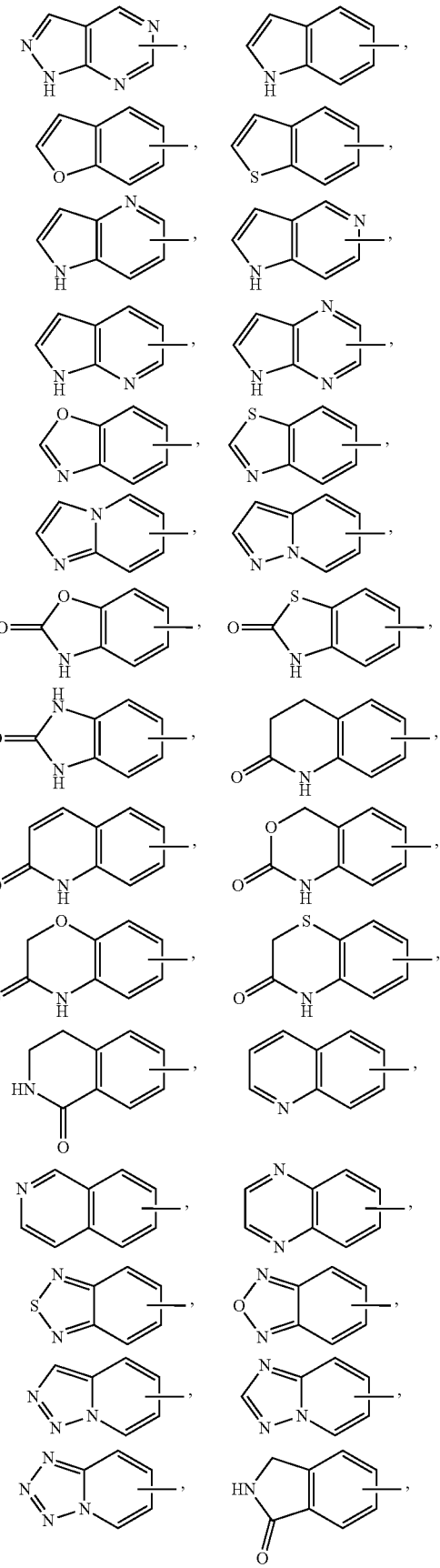

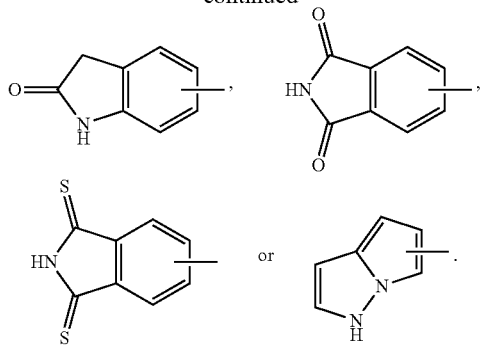

In some embodiments, ring A is

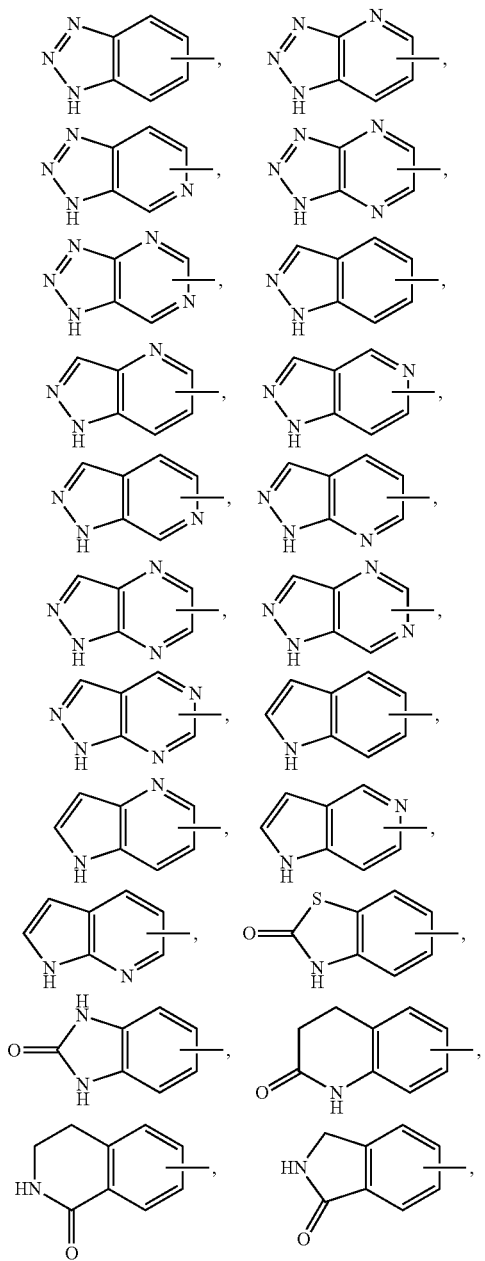

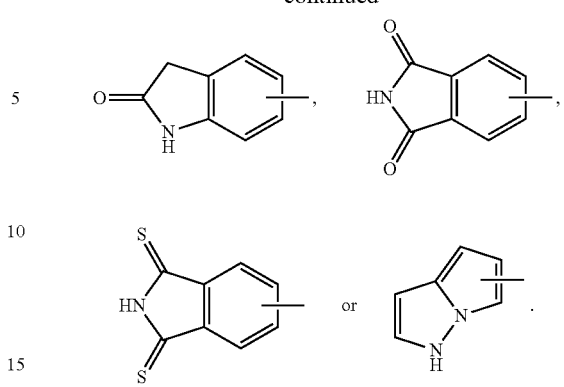

In some embodiments, ring A is indolyl, azaindolyl, indazolyl, azaindazolyl, benzimidazolyl, azabenzimidazolyl, benzotriazolyl or azabenzotriazolyl.

In some embodiments, the compound of Formula (I) has the structure of Formula (II):

Formula (II)

In some embodiments, the compound of Formula (II) has the structure of Formula (III) or (IV):

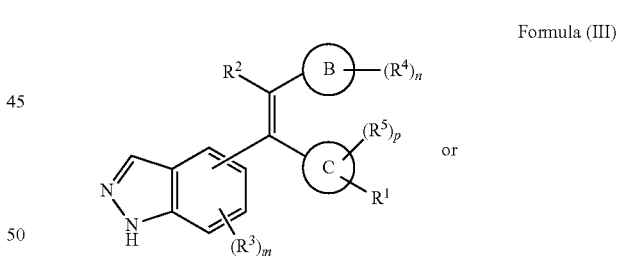

Formula (III)

or

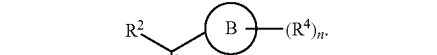

Formula (IV)

In some embodiments, the compound of Formula (I) has the structure of Formula (V):

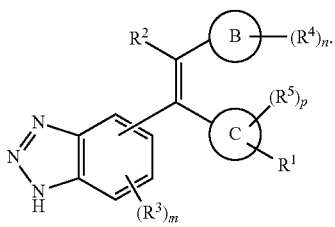

Formula (V)

In some embodiments, the compound of Formula (I) has the structure of Formula (XI):

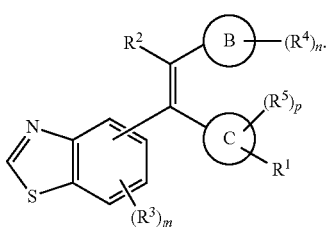

Formula (XI)

In some embodiments, ring C is phenyl, a 5-membered heteroaryl or a 6-membered heteroaryl.

In some embodiments, ring C is phenyl, furanyl, thienyl, oxazolyl, thiazolyl, pyrrolyl, imidazolyl, pyrazolyl, triazolyl, pyridinyl, pyridazinyl, pyrimidinyl, pyrazinyl, or triazinyl.

In some embodiments, ring C is phenyl or a 6-membered heteroaryl.

In some embodiments, ring C is phenyl, pyridinyl, pyridazinyl, pyrimidinyl, pyrazinyl, or triazinyl.

In some embodiments, ring C is phenyl.

In some embodiments, ring B is phenyl, naphthyl, indanyl, indenyl, furanyl, thienyl, oxazolyl, thiazolyl, pyrrolyl, imidazolyl, pyrazolyl, triazolyl, tetrazolyl, pyridinyl, pyridazinyl, pyrimidinyl, pyrazinyl, triazinyl, quinolinyl, isoquinolinyl, cinnolinyl, phthalazinyl, quinazolinyl, quinoxalinyl, naphthyridinyl, pteridinyl, inolizinyl, azainolizinyl, indolyl, azaindolyl, indazolyl, azaindazolyl, benzimidazolyl, azabenzimidazolyl, benzotriazolyl, azabenzotriazolyl, benzoxazolyl, azabenzoxazolyl, benzisoxazolyl, azabenzisoxazolyl, benzofuranyl, azabenzofuranyl, benzothienyl, azabenzothienyl, benzothiazolyl, azabenzothiazolyl, or purinyl.

In some embodiments, ring B is phenyl, a 5-membered heteroaryl or a 6-membered heteroaryl.

In some embodiments, ring B is phenyl, furanyl, thienyl, pyrrolyl, imidazolyl, pyrazolyl, triazolyl, pyridinyl, pyrimidinyl, pyrazinyl, pyridazinyl, or triazinyl.

In some embodiments, ring B is phenyl, thienyl, or pyridinyl. In some embodiments, ring B is thienyl. In some embodiments, ring B is pyridinyl.

In some embodiments, ring B is phenyl.

In some embodiments, ring B is phenyl; and ring C is phenyl.

In some embodiments, Y is —C(=O)—Z, tetrazolyl, optionally substituted piperidinyl, optionally substituted pyrrolidinyl, —NR$^8$R$^{8'}$, -AR—OH, —SO$_3$H, and —P(=O)(OH)$_2$ wherein AR is phenyl or monocyclic heteroaryl; Z is —OH, —OR$^{10}$, —NR$^8$R$^{8'}$, —NR$^8$S(=O)$_2$R$^{10}$, or —NHOH; R$^8$ and R$^{8'}$ is independently H, C$_1$-C$_6$alkyl, C$_2$-C$_6$alkenyl, or C$_2$-C$_6$alkynyl.

In some embodiments, R$^2$ is halogen, —CN, —NO$_2$, —S(=O)R$^{10}$, —S(=O)$_2$R$^{10}$, C$_1$-C$_6$alkyl, C$_1$-C$_6$fluoroalkyl, C$_1$-C$_6$deuteroalkyl, C$_3$-C$_6$cycloalkyl, —C$_1$-C$_4$alkylene-W, or —C$_1$-C$_4$fluoroalkylene-W; W is hydroxy, halogen, CN, NO$_2$, C$_1$-C$_6$alkyl, C$_1$-C$_6$haloalkyl, C$_1$-C$_6$alkoxy, C$_1$-C$_6$haloalkoxy, or C$_3$-C$_6$cycloalkyl.

In some embodiments, ring C is phenyl; R$^2$ is halogen, —CN, —NO$_2$, —S(=O)R$^{10}$, —S(=O)$_2$R$^{10}$, C$_1$-C$_6$alkyl, C$_1$-C$_6$fluoroalkyl, C$_1$-C$_6$deuteroalkyl, C$_3$-C$_6$cycloalkyl, —C$_1$-C$_4$alkylene-W, or —C$_1$-C$_4$fluoroalkylene-W; W is hydroxy, halogen, CN, NO$_2$, C$_1$-C$_6$alkyl, C$_1$-C$_6$haloalkyl, C$_1$-C$_6$alkoxy, C$_1$-C$_6$haloalkoxy, or C$_3$-C$_6$cycloalkyl.

In some embodiments, R$^2$ is —S(=O)R$^{10}$, —S(=O)$_2$R$^{10}$, —CH$_3$, —CH$_2$CH$_3$, —CH$_2$CH$_2$CH$_3$, —CH(CH$_3$)$_2$, —CH$_2$F, —CHF$_2$, —CF$_3$, —CH$_2$CF$_3$, cyclopropyl, cyclobutyl, —CH$_2$—W, —CH$_2$CH$_2$—W, or —CF$_2$—W; W is hydroxy, F, Cl, —CN, —NO$_2$, —CH$_3$, —CH$_2$CH$_3$, —CH$_2$CH$_2$CH$_3$, —CH(CH$_3$)$_2$, —CH$_2$F, —CHF$_2$, —CF$_3$, —OCH$_3$, —OCH$_2$CH$_3$, —OCH$_2$CH$_2$CH$_3$, —OCH(CH$_3$)$_2$, —OCH$_2$F, —OCHF$_2$, —OCF$_3$, cyclopropyl, or cyclobutyl.

In some embodiments, R$^1$ is —C(R$^6$)=C(R$^7$)—Y; Y is C(=O)—Z or tetrazolyl; Z is —OH, —OR$^{10}$, —NR$^8$R$^{8'}$, —NR$^8$S(=O)$_2$R$^{10}$, or —NHOH; R$^2$ is —S(=O)R$^{10}$, —S(=O)$_2$R$^{10}$, —CH$_3$, —CH$_2$CH$_3$, —CH$_2$CH$_2$CH$_3$, —CH(CH$_3$)$_2$, —CH$_2$F, —CHF$_2$, —CF$_3$, —CH$_2$CF$_3$, cyclopropyl, cyclobutyl, —CH$_2$—W, —CH$_2$CH$_2$—W, or —CF$_2$—W; W is hydroxy, F, Cl, —CN, —NO$_2$, —CH$_3$, —CH$_2$CH$_3$, —CH$_2$CH$_2$CH$_3$, —CH(CH$_3$)$_2$, —CH$_2$F, —CHF$_2$, —CF$_3$, —OCH$_3$, —OCH$_2$CH$_3$, —OCH$_2$CH$_2$CH$_3$, —OCH(CH$_3$)$_2$, —OCH$_2$F, —OCHF$_2$, —OCF$_3$, cyclopropyl, or cyclobutyl; R$^6$ is H, F, Cl, —OCH$_3$, —OCH$_2$CH$_3$, —NH$_2$, —NH(CH$_3$), —N(CH$_3$)$_2$, —CH$_3$, or —CH$_2$CH$_3$; R$^7$ is H, F, Cl, —OCH$_3$, —OCH$_2$CH$_3$, —NH$_2$, —NH(CH$_3$), —N(CH$_3$)$_2$, —CH$_3$, or —CH$_2$CH$_3$.

In some embodiments, Z is —OH, —OCH$_3$, —OCH$_2$CH$_3$, —NH$_2$, —NHCH$_3$, —NHCH$_2$CH$_3$, —NHSO$_2$CH$_3$ or —NHOH; R$^6$ is H; R$^7$ is H.

In some embodiments, ring A is benzothiazolyl; ring C is phenyl; R$^1$ is —C(R$^6$)=C(R$^7$)—Y; R$^2$ is C$_1$-C$_4$alkyl, C$_1$-C$_4$fluoroalkyl, C$_1$-C$_4$deuteroalkyl, C$_3$-C$_6$cycloalkyl, or —C$_1$-C$_4$alkylene-W; W is hydroxy, halogen, CN, C$_1$-C$_4$alkyl, C$_1$-C$_4$haloalkyl, C$_1$-C$_4$alkoxy, C$_1$-C$_4$haloalkoxy, and C$_3$-C$_6$cycloalkyl; R$^6$ is H, C$_1$-C$_4$alkyl, or halogen; R$^7$ is H, C$_1$-C$_4$alkyl, or halogen.

In some embodiments, each R$^3$ is independently halogen, C$_1$-C$_4$alkyl, or C$_1$-C$_4$fluoroalkyl; each R$^4$ is independently halogen, —CN, —OR$^9$, —S(=O)$_2$R$^{10}$, C$_1$-C$_4$alkyl, C$_1$-C$_4$fluoroalkyl, or C$_1$-C$_4$heteroalkyl; each R$^5$ is independently halogen, —CN, —OR$^9$, —S(=O)$_2$R$^{10}$, C$_1$-C$_4$alkyl, C$_1$-C$_4$fluoroalkyl, or C$_1$-C$_4$heteroalkyl; R$^9$ is H, C$_1$-C$_6$alkyl, C$_1$-C$_6$fluoroalkyl, or C$_3$-C$_6$cycloalkyl; R$^{10}$ is C$_1$-C$_6$alkyl; m is 0, 1, or 2; n is 0, 1, 2, 3, or 4; and p is 0, 1, or 2.

In some embodiments, R$^1$ is Y.

In some embodiments, Y is C(=O)—OR$^{10}$.

In some embodiments, R$^1$ is

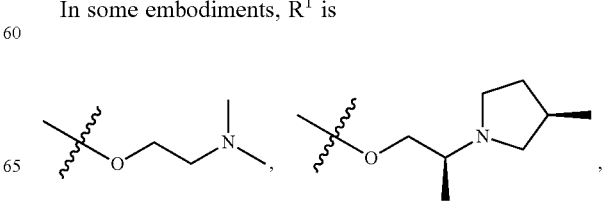

,

-continued

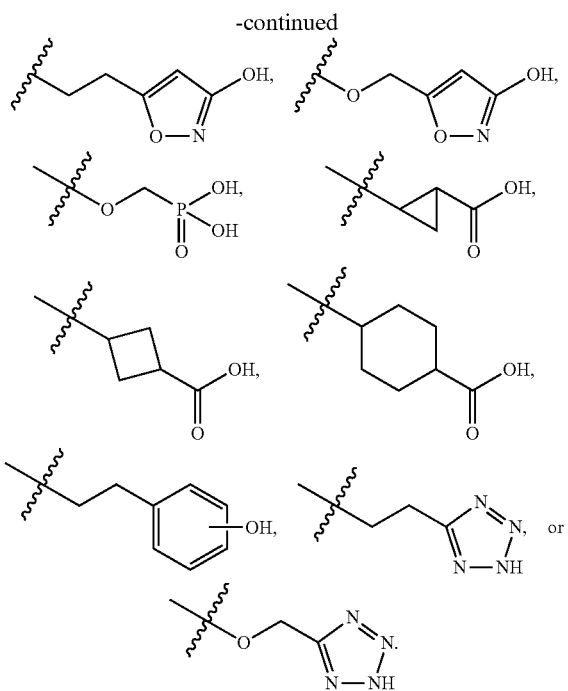

In some embodiments, $R^1$ is —C($R^6$)=C($R^7$)—Y; Y is C(=O)—Z or tetrazolyl; Z is —OH, —O$R^{10}$, —N$R^8R^{8'}$, —N$R^8$S(=O)$_2R^{10}$, or —NHOH.

In some embodiments, $R^6$ is H, F, Cl, —OCH$_3$, —OCH$_2$CH$_3$, —NH$_2$, —NH(CH$_3$), —N(CH$_3$)$_2$, —CH$_3$, or —CH$_2$CH$_3$; $R^7$ is H, F, Cl, —OCH$_3$, —OCH$_2$CH$_3$, —NH$_2$, —NH(CH$_3$), —N(CH$_3$)$_2$, —CH$_3$, or —CH$_2$CH$_3$.

In some embodiments, $R^6$ is H. In some embodiments, $R^7$ is H.

In some embodiments, Z is —OH, —OCH$_3$, —OCH$_2$CH$_3$, —NH$_2$, —NHCH$_3$, —NHCH$_2$CH$_3$, —NHSO$_2$CH$_3$ or —NHOH.

In some embodiments, the compound of Formula (I) has the structure of Formula (VI):

Formula (VI)

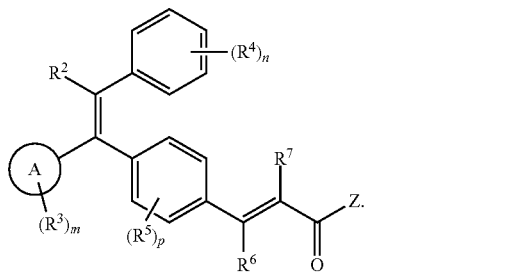

In some embodiments, ring A is a 8-, 9- or 10-membered bicyclic heteroaryl containing 1-5 N atoms in the bicyclic ring; Z is —OH, —O$R^{10}$, —N$R^8R^{8'}$, —N$R^8$S(=O)$_2R^{10}$, or —NHOH.

In some embodiments, ring A is indolyl, azaindolyl, indazolyl, azaindazolyl, benzimidazolyl, azabenzimidazolyl, benzotriazolyl or azabenzotriazolyl.

In some embodiments, ring A is indazolyl or benzotriazolyl.

In some embodiments, the compound of Formula (VI) has the structure of Formula (VII):

Formula (VII)

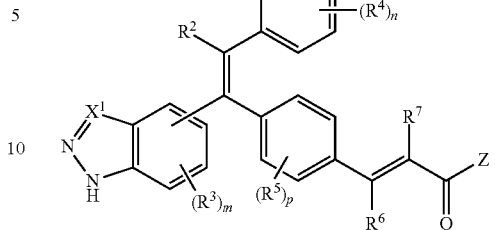

wherein,
$X^1$ is CH, C$R^3$ or N.

In some embodiments, the compound of Formula (VII) has the structure of Formula (VIII):

Formula (VIII)

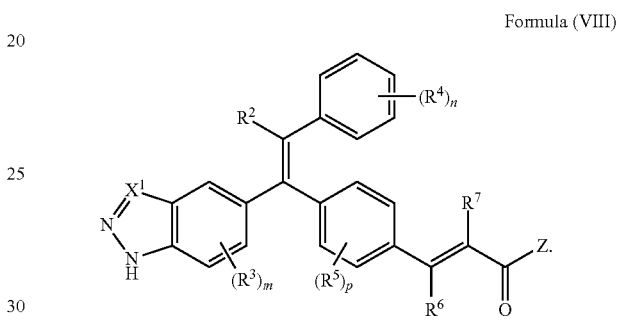

In some embodiments, the compound of Formula (VII) has the structure of Formula (IX):

Formula (IX)

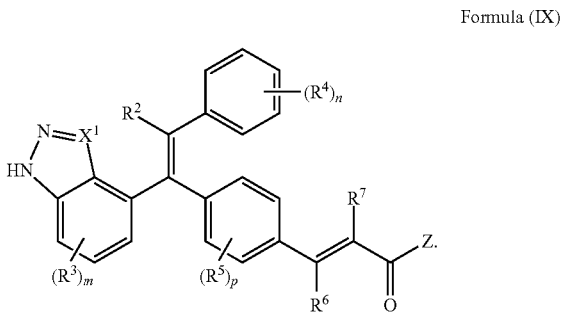

In some embodiments, the compound of Formula (VI) has the structure of Formula (X):

Formula (X)

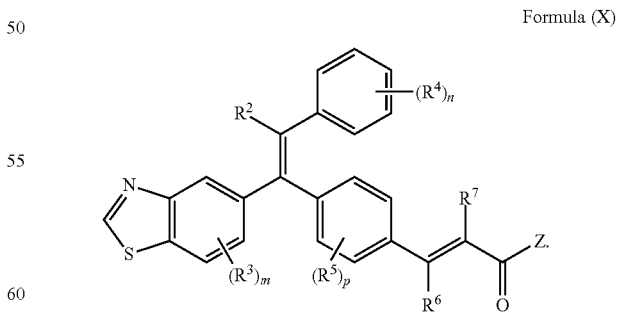

In some embodiments, $R^2$ is —S(=O)$R^{10}$, —S(=O)$_2R^{10}$, $C_1$-$C_4$alkyl, $C_1$-$C_4$fluoroalkyl, $C_1$-$C_4$deuteroalkyl, $C_3$-$C_6$cycloalkyl, —$C_1$-$C_4$alkylene-W, —$C_1$-$C_4$fluoroalkylene-W, —$C_3$-$C_6$cycloalkylene-W; W is hydroxy, halogen, CN, NO$_2$, $C_1$-$C_4$alkyl, $C_1$-$C_4$haloalkyl, $C_1$-$C_4$alkoxy, $C_1$-$C_4$haloalkoxy, and $C_3$-$C_6$cycloalkyl; each $R^3$, $R^4$, $R^5$ is independently selected from H, halogen, —NO$_2$, —NR$^8$R$^{8'}$, —CN, —OH, —OR$^9$, —SR$^9$, —S(=O)R$^{10}$, —S(=O)$_2$R$^{10}$, —NHS(=O)$_2$R$^{10}$, —S(=O)$_2$N(R$^9$)$_2$, —C(=O)R$^{10}$, —OC(=O)R$^{10}$, —CO$_2$R$^9$, —C(=O)N(R$^9$)$_2$, C$_1$-C$_4$alkyl, C$_2$-C$_4$alkenyl, C$_2$-C$_4$alkynyl, C$_1$-C$_4$fluoroalkyl, C$_1$-C$_4$heteroalkyl, C$_1$-C$_4$fluoroalkoxy, and C$_1$-C$_4$alkoxy; R$^6$ is H, F, Cl, —OCH$_3$, —OCH$_2$CH$_3$, —NH$_2$, —NH(CH$_3$), —N(CH$_3$)$_2$, —CH$_3$, or —CH$_2$CH$_3$; R$^7$ is H, F, Cl, —OCH$_3$, —OCH$_2$CH$_3$, —NH$_2$, —NH(CH$_3$), —N(CH$_3$)$_2$, —CH$_3$, or —CH$_2$CH$_3$; m is 0, 1, or 2; n is 0, 1, or 2; and p is 0, 1, or 2.

In some embodiments, Z is —OH, —O(C$_1$-C$_4$alkyl), —NH$_2$, —NH(C$_1$-C$_4$alkyl), or —NHSO$_2$(C$_1$-C$_4$alkyl); R$^2$ is —S(=O)R$^{10}$, —S(=O)$_2$R$^{10}$, —CH$_3$, —CH$_2$CH$_3$, —CH$_2$CH$_2$CH$_3$, —CH(CH$_3$)$_2$, —CH$_2$F, —CHF$_2$, —CF$_3$, —CH$_2$CF$_3$, cyclopropyl, cyclobutyl, —CH$_2$—W, —CH$_2$CH$_2$—W, or —CF$_2$—W; W is hydroxy, F, Cl, —CN, —NO$_2$, —CH$_3$, —CH$_2$CH$_3$, —CH$_2$CH$_2$CH$_3$, —CH(CH$_3$)$_2$, —CH$_2$F, —CHF$_2$, —CF$_3$, —OCH$_3$, —OCH$_2$CH$_3$, —OCH$_2$CH$_2$CH$_3$, —OCH(CH$_3$)$_2$, —OCH$_2$F, —OCHF$_2$, —OCF$_3$, cyclopropyl, or cyclobutyl; each R$^3$, R$^4$, R$^5$ is independently selected from H, halogen, —CN, —OH, —OR$^9$, —SR$^9$, —S(=O)R$^{10}$, —S(=O)$_2$R$^{10}$, —C(=O)R$^{10}$, —OC(=O)R$^{10}$, —CO$_2$R$^9$, —C(=O)N(R$^9$)$_2$, C$_1$-C$_4$alkyl, C$_2$-C$_4$alkenyl, C$_2$-C$_4$alkynyl, C$_1$-C$_4$fluoroalkyl, C$_1$-C$_4$heteroalkyl, C$_1$-C$_4$fluoroalkoxy, and C$_1$-C$_4$alkoxy; each R$^9$ is independently selected from H, C$_1$-C$_6$alkyl, C$_1$-C$_6$fluoroalkyl, C$_3$-C$_6$cycloalkyl, substituted or unsubstituted phenyl, and substituted or unsubstituted benzyl; each R$^{10}$ is independently selected from C$_1$-C$_6$alkyl, C$_1$-C$_6$fluoroalkyl, C$_3$-C$_6$cycloalkyl, substituted or unsubstituted phenyl, and substituted or unsubstituted benzyl.

In some embodiments, Z is —OH, —OCH$_3$, or —OCH$_2$CH$_3$; R$^2$ is —CH$_2$CH$_3$, —CH$_2$CF$_3$, —CH$_2$—W, or —CF$_2$—W; each R$^3$, R$^4$, R is independently selected from H, halogen, —CN, —OH, C$_1$-C$_4$alkyl, C$_2$-C$_4$alkenyl, C$_2$-C$_4$alkynyl, C$_1$-C$_4$fluoroalkyl, C$_1$-C$_4$heteroalkyl, C$_1$-C$_4$fluoroalkoxy, and C$_1$-C$_4$alkoxy.

In some embodiments, the compound of Formula (I) has the structure of Formula (XII):

Formula (XII)

wherein,
$X^1$ is CH, CR$^3$ or N;
$X^2$ is N, CH, or CR$^3$;
Z is —OH or —OR$^{10}$;
R$^2$ is C$_1$-C$_4$alkyl, C$_1$-C$_4$fluoroalkyl, C$_1$-C$_4$deuteroalkyl, C$_3$-C$_6$cycloalkyl, or —C$_1$-C$_4$alkylene-W;
    W is hydroxy, halogen, CN, C$_1$-C$_4$alkyl, C$_1$-C$_4$haloalkyl, C$_1$-C$_4$alkoxy, C$_1$-C$_4$haloalkoxy, and C$_3$-C$_6$cycloalkyl;
each R$^3$ is independently halogen, C$_1$-C$_4$alkyl, or C$_1$-C$_4$fluoroalkyl;

each R$^4$ is independently halogen, —CN, —OR$^9$, —S(=O)$_2$R$^{10}$, C$_1$-C$_4$alkyl, C$_1$-C$_4$fluoroalkyl, or C$_1$-C$_4$heteroalkyl;
each R is independently halogen, —CN, —OR$^9$, —S(=O)$_2$R$^{10}$, C$_1$-C$_4$alkyl, C$_1$-C$_4$fluoroalkyl, or C$_1$-C$_4$heteroalkyl;
R$^6$ is H, C$_1$-C$_4$alkyl, or halogen;
R$^7$ is H, C$_1$-C$_4$alkyl, or halogen;
R$^9$ is H, C$_1$-C$_6$alkyl, C$_1$-C$_6$fluoroalkyl, or C$_3$-C$_6$cycloalkyl;
R$^{10}$ is C$_1$-C$_6$alkyl;
m is 0, 1, or 2;
n is 0, 1, 2, 3, or 4; and
p is 0, 1, or 2.

In some embodiments, $X^1$ is CH or CR$^3$; and $X^2$ is N. In some embodiments, $X^1$ is CH; and $X^2$ is N. In some embodiments, $X^1$ is CH or CR$^3$; and $X^2$ is CH or CR$^3$. In some embodiments, $X^1$ is CH; and $X^2$ is CH. In some embodiments, $X^1$ is N; and $X^2$ is N.

In some embodiments, Z is —OH. In some embodiments, Z is —OR$^{10}$. In some embodiments, Z is —OH, —OCH$_3$, or —OCH$_2$CH$_3$.

In some embodiments, R$^6$ is H, —CH$_3$, F, or Cl. In some embodiments, R$^6$ is H.

In some embodiments, R$^7$ is H, —CH$_3$, F, or Cl. In some embodiments, R$^7$ is H.

In some embodiments, R$^3$ is independently halogen, C$_1$-C$_4$alkyl, or C$_1$-C$_4$fluoroalkyl. In some embodiments, each R$^3$ is independently F, Cl, or —CH$_3$.

In some embodiments, each R$^4$ is independently halogen, —CN, —OH, —OR$^9$, —S(=O)$_2$R$^{10}$, C$_1$-C$_4$alkyl, C$_1$-C$_4$fluoroalkyl, or C$_1$-C$_4$heteroalkyl. In some embodiments, each R$^4$ is independently halogen, —CN, —OH, —S(=O)$_2$CH$_3$, —S(=O)$_2$CH$_2$CH$_3$, —CH$_3$, —CH$_2$CH$_3$, —CF$_3$, —CH$_2$OH, —OCF$_3$, —OCH$_3$, or —OCH$_2$CH$_3$. In some embodiments, each R$^4$ is independently F, Cl, —CN, —OH, —CH$_3$, —CH$_2$CH$_3$, —CF$_3$, —CH$_2$OH, —OCF$_3$, —OCH$_3$, or —OCH$_2$CH$_3$. In some embodiments, each R$^4$ is independently F or Cl.

In some embodiments, each R$^5$ is independently halogen, C$_1$-C$_4$alkyl, or C$_1$-C$_4$fluoroalkyl. In some embodiments, each R$^5$ is independently F, Cl, or —CH$_3$.

In some embodiments, m is 0 or 1. In some embodiments, m is 0. In some embodiments, m is 1.

In some embodiments, n is 0, 1, or 2. In some embodiments, n is 0. In some embodiments, n is 1. In some embodiments, n is 2.

In some embodiments, p is 0 or 1. In some embodiments, p is 0. In some embodiments, p is 1.

In some embodiments, Z is —OH; R$^6$ is H, —CH$_3$, F, or Cl; R$^7$ is H, —CH$_3$, F, or Cl; each R$^3$ is independently halogen, C$_1$-C$_4$alkyl, or C$_1$-C$_4$fluoroalkyl; each R$^4$ is independently halogen, —CN, —OR$^9$, —S(=O)$_2$R$^{10}$, C$_1$-C$_4$alkyl, C$_1$-C$_4$fluoroalkyl, or C$_1$-C$_4$heteroalkyl; each R$^5$ is independently halogen, C$_1$-C$_4$alkyl, or C$_1$-C$_4$fluoroalkyl; m is 0 or 1; n is 0, 1, or 2; and p is 0 or 1.

In some embodiments, R$^2$ is C$_1$-C$_4$alkyl, C$_1$-C$_4$fluoroalkyl, C$_1$-C$_4$deuteroalkyl, C$_3$-C$_6$cycloalkyl, or —C$_1$-C$_4$alkylene-W; W is hydroxy, halogen, CN, C$_1$-C$_4$alkoxy, or C$_3$-C$_6$cycloalkyl. In some embodiments, R$^2$ is C$_1$-C$_4$alkyl, C$_1$-C$_4$fluoroalkyl, or C$_1$-C$_4$deuteroalkyl. In some embodiments, R$^2$ is C$_1$-C$_4$alkyl. In some embodiments, R$^2$ is —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH$_2$F, —CHF$_2$, —CF$_3$, —CH$_2$CF$_3$, —CD$_3$, —CH$_2$CD$_3$, —CD$_2$CD$_3$, cyclopropyl, cyclobutyl, cyclopentyl, cyclohexyl, —CH$_2$—W, or —CH$_2$CH$_2$—W; W is hydroxy, F, Cl, —CN, —OCH₃, —OCH₂CH₃, —OCH₂CH₂CH₃, —OCH(CH₃)₂, cyclopropyl, cyclobutyl, cyclopentyl, or cyclohexyl. In some embodiments, W is hydroxy, F, Cl, —CN, cyclopropyl, cyclobutyl, cyclopentyl, or cyclohexyl. In some embodiments, R² is —CH₃, —CH₂CH₃, —CH₂CH₂CH₃, —CH(CH₃)₂, —CH₂CH₂CH₂CH₃, —CH₂CH(CH₃)₂, —CH₂F, —CHF₂, —CF₃, —CH₂CF₃, —CD₃, —CH₂CD₃, —CD₂CD₃, —CH₂—W, or —CH₂CH₂—W. In some embodiments, R² is —CH₃, —CH₂CH₃, —CH₂F, —CHF₂, —CF₃, —CH₂CF₃, —CD₃, —CD₂CD₃, —CH₂CD₃, or cyclopropyl.

In some embodiments, Z is —OH; R⁶ is H; R⁷ is H; m is 0; n is 0, 1, or 2; and p is 0.

In some embodiments, the compound of Formula (X) has the structure of Formula (XIII), or a pharmaceutically acceptable salt, or N-oxide thereof:

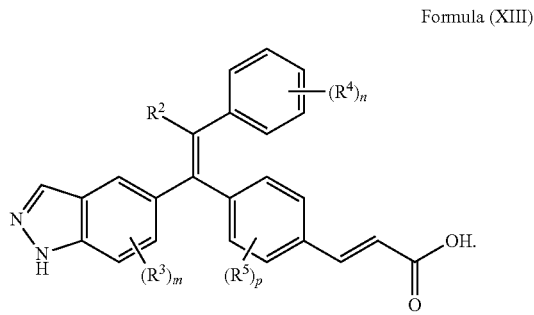

Formula (XIII)

In some embodiments, the compound of Formula (X) has the structure of Formula (XIV), or a pharmaceutically acceptable salt, or N-oxide thereof:

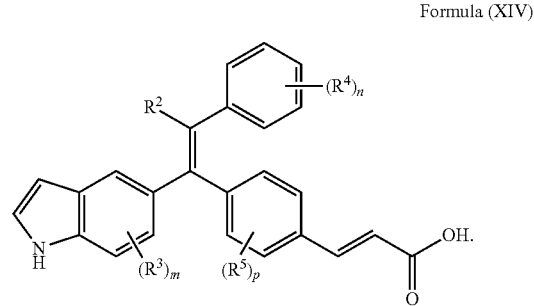

Formula (XIV)

In some embodiments, the compound of Formula (X) has the structure of Formula (XV), or a pharmaceutically acceptable salt, or N-oxide thereof:

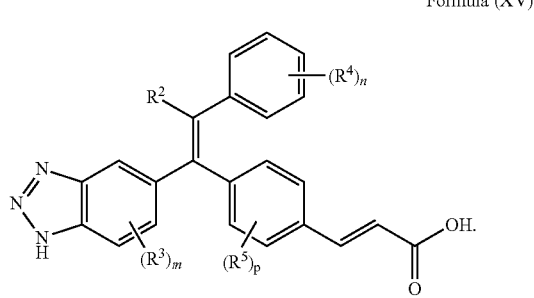

Formula (XV)

In some embodiments the compound of Formula (X) has the structure of Formula (XVI):

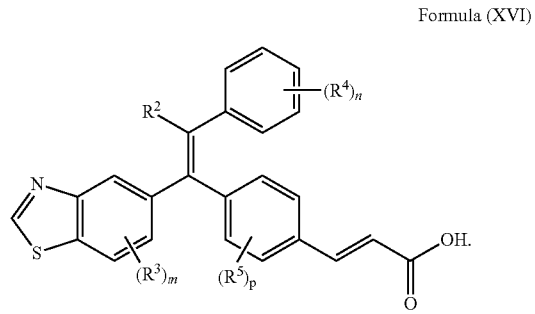

Formula (XVI)

In some embodiments, each R³ is independently F, Cl, or —CH₃; each R⁴ is independently halogen, —CN, —OH, —S(=O)₂CH₃, —S(=O)₂CH₂CH₃, —CH₃, —CH₂CH₃, —CF₃, —CH₂OH, —OCF₃, —OCH₃, or —OCH₂CH₃; each R⁵ is independently F, Cl, or —CH₃; m is 0 or 1; n is 0, 1, or 2; and p is 0 or 1.

In some embodiments, R² is —CH₃, —CH₂CH₃, —CH₂CH₂CH₃, —CH(CH₃)₂, —CH₂CH₂CH₂CH₃, —CH₂CH(CH₃)₂, —CH₂F, —CHF₂, —CF₃, —CH₂CF₃, —CD₃, —CD₂CD₃, cyclopropyl, cyclobutyl, cyclopentyl, cyclohexyl, —CH₂—W, or —CH₂CH₂—W; W is hydroxy, F, Cl, —CN, —OCH₃, —OCH₂CH₃, —OCH₂CH₂CH₃, —OCH(CH₃)₂, cyclopropyl, cyclobutyl, cyclopentyl, or cyclohexyl.

In some embodiments, W is hydroxy, F, Cl, —CN, cyclopropyl, cyclobutyl, cyclopentyl, or cyclohexyl; each R⁴ is independently F, Cl, —CN, —OH, —CH₃, —CF₃, —OCF₃, or —OCH₃; m is 0; n is 0, 1, or 2; and p is 0.

In some embodiments, R² is —CH₂CH₃ or cyclobutyl; each R⁴ is independently F, Cl, —CN, —OH, —CH₃, —CH₂CH₃, —CF₃, —CH₂OH, —OCF₃, —OCH₃, or —OCH₂CH₃; m is 0 or 1; n is 0, 1, or 2; and p is 0.

In some embodiments, the compound of Formula (I) has the structure of Formula (XVII):

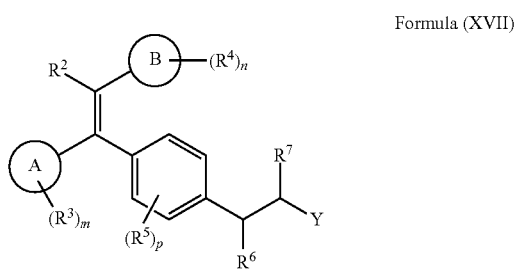

Formula (XVII)

wherein,
ring A is 8-, 9- or 10-membered bicyclic heteroaryl;
ring B is phenyl, 5- or 6-membered monocyclic heteroaryl;
Y is —C(=O)—Z, tetrazolyl, or carboxylic acid bioisostere;
  Z is —OH, —OR¹⁰, —NR⁸R⁸', —NR⁸S(=O)₂R¹⁰, —NHOH or —NR⁸OR¹⁰;
  R² is halogen, CN, NO₂, —SR⁹, —S(=O)R¹⁰, —S(=O)₂R¹⁰, —NHS(=O)₂R¹⁰, C₁-C₆alkyl, C₁-C₆fluoroalkyl, C₁-C₆deuteroalkyl, C₁-C₄alkoxy, C₁-C₄fluoroalkoxy, C$_3$-C$_6$cycloalkyl, —C$_1$-C$_4$alkylene-W, —C$_1$-C$_4$fluoroalkylene-W, —C$_3$-C$_6$cycloalkylene-W;

W is hydroxy, halogen, CN, NO$_2$, C$_1$-C$_6$alkyl, C$_1$-C$_6$haloalkyl, C$_1$-C$_6$alkoxy, C$_1$-C$_6$haloalkoxy, and C$_3$-C$_6$cycloalkyl;

each R$^3$, R$^4$, R$^5$ is independently selected from H, halogen, —NO$_2$, —NR$^8$R$^{8'}$, —CN, —OH, —OR$^9$, —SR$^9$, —S(=O)R$^{10}$, —S(=O)$_2$R$^{10}$, —NHS(=O)$_2$R$^{10}$, —S(=O)$_2$N(R$^9$)$_2$, —C(=O)R$^{10}$, —OC(=O)R$^{10}$, —CO$_2$R$^9$, —OCO$_2$R$^{10}$, —C(=O)N(R$^9$)$_2$, —OC(=O)N(R$^9$)$_2$, —NR$^9$C(=O)N(R$^9$)$_2$, —NR$^9$C(=O)R$^{10}$, —NR$^9$C(=O)OR$^{10}$, substituted or unsubstituted C$_1$-C$_6$alkyl, substituted or unsubstituted C$_2$-C$_6$alkenyl, substituted or unsubstituted C$_2$-C$_6$alkynyl, substituted or unsubstituted C$_1$-C$_6$fluoroalkyl, substituted or unsubstituted C$_1$-C$_6$heteroalkyl, substituted or unsubstituted C$_1$-C$_6$fluoroalkoxy, substituted or unsubstituted C$_1$-C$_6$alkoxy, substituted or unsubstituted phenyl and substituted or unsubstituted monocyclic heteroaryl;

R$^6$ is H, C$_1$-C$_4$alkyl, or halogen;

R$^7$ is H, C$_1$-C$_4$alkyl, or halogen;

R$^8$ and R$^{8'}$ is independently H, substituted or unsubstituted C$_1$-C$_6$alkyl, substituted or unsubstituted C$_2$-C$_6$alkenyl, substituted or unsubstituted C$_2$-C$_6$alkynyl, substituted or unsubstituted C$_1$-C$_6$fluoroalkyl, substituted or unsubstituted C$_1$-C$_6$heteroalkyl, substituted or unsubstituted C$_3$-C$_{10}$cycloalkyl, substituted or unsubstituted C$_2$-C$_{10}$heterocycloalkyl, substituted or unsubstituted phenyl, substituted or unsubstituted monocyclic heteroaryl, or substituted or unsubstituted benzyl;

each R$^9$ is independently selected from H, substituted or unsubstituted C$_1$-C$_6$alkyl, substituted or unsubstituted C$_1$-C$_6$heteroalkyl, substituted or unsubstituted C$_1$-C$_6$fluoroalkyl, substituted or unsubstituted C$_3$-C$_{10}$cycloalkyl, substituted or unsubstituted C$_2$-C$_{10}$heterocycloalkyl, substituted or unsubstituted aryl, substituted or unsubstituted heteroaryl and substituted or unsubstituted benzyl;

each R$^{10}$ is independently selected from substituted or unsubstituted C$_1$-C$_6$alkyl, substituted or unsubstituted C$_1$-C$_6$heteroalkyl, substituted or unsubstituted C$_1$-C$_6$fluoroalkyl, substituted or unsubstituted C$_3$-C$_{10}$cycloalkyl, substituted or unsubstituted C$_2$-C$_{10}$heterocycloalkyl, substituted or unsubstituted aryl, substituted or unsubstituted heteroaryl and substituted or unsubstituted benzyl;

m is 0, 1, or 2;

n is 0, 1, 2, 3 or 4; and p is 0, 1, or 2.

In some embodiments, ring A is indolizinyl, azaindolizinyl, indolyl, azaindolyl, indazolyl, azaindazolyl, benzimidazolyl, azabenzimidazolyl, benzotriazolyl, azabenzotriazolyl, benzoxazolyl, azabenzoxazolyl, benzisoxazolyl, azabenzisoxazolyl, benzofuranyl, azabenzofuranyl, benzothienyl, azabenzothienyl, benzothiazolyl, or azabenzothiazolyl; ring B is phenyl, furanyl, thienyl, pyrrolyl, imidazolyl, pyrazolyl, triazolyl, pyridinyl, pyrimidinyl, pyrazinyl, pyridazinyl, or triazinyl; Y is —C(=O)—Z,

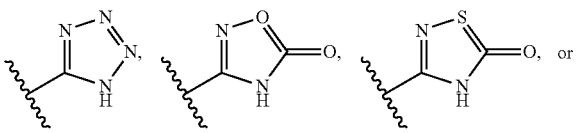

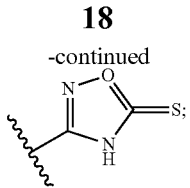

Z is —OH, —OR$^{10}$, —NR$^8$R$^{8'}$, or —NR$^8$S(=O)$_2$R$^{10}$; R$^2$ is C$_1$-C$_6$alkyl, C$_1$-C$_6$fluoroalkyl, C$_1$-C$_6$deuteroalkyl, or C$_3$-C$_6$cycloalkyl; each R$^3$ is independently halogen, —CN, C$_1$-C$_4$alkyl, or C$_1$-C$_4$fluoroalkyl; each R$^4$ is independently selected from H, halogen, —CN, —OH, —OR$^9$, —SR$^9$, —S(=O)R$^{10}$, —S(=O)$_2$R$^{10}$, —C(=O)R$^{10}$, —OC(=O)R$^{10}$, —CO$_2$R$^9$, —C(=O)N(R$^9$)$_2$, C$_1$-C$_4$alkyl, C$_2$-C$_4$alkenyl, C$_2$-C$_4$alkynyl, C$_1$-C$_4$fluoroalkyl, C$_1$-C$_4$heteroalkyl, C$_1$-C$_4$fluoroalkoxy, and C$_1$-C$_4$alkoxy; each R$^5$ is independently halogen, C$_1$-C$_4$alkyl, or C$_1$-C$_4$fluoroalkyl; R$^6$ is H, C$_1$-C$_4$alkyl, or halogen; R$^7$ is H, C$_1$-C$_4$alkyl, or halogen; R$^8$ and R$^{8'}$ is independently H or C$_1$-C$_6$alkyl; each R$^9$ is independently selected from H and C$_1$-C$_6$alkyl; R$^{10}$ is C$_1$-C$_6$alkyl; p is 0 or 1.

In some embodiments, ring A is

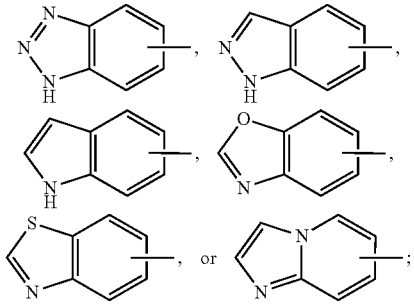

ring B is phenyl, thienyl, or pyridinyl; Y is —C(=O)—Z,

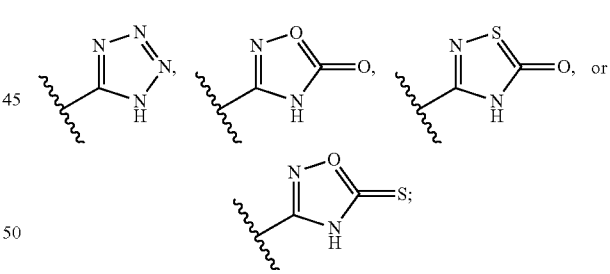

Z is —OH, —OR$^{10}$, —NR$^8$R$^{8'}$, or —NR$^8$S(=O)$_2$R$^{10}$; R$^2$ is C$_1$-C$_6$alkyl, C$_1$-C$_6$fluoroalkyl, C$_1$-C$_6$deuteroalkyl, or C$_3$-C$_6$cycloalkyl; each R$^3$ is independently halogen, —CN, C$_1$-C$_4$alkyl, or C$_1$-C$_4$fluoroalkyl; each R$^4$ is independently selected from H, halogen, —CN, —OH, —OR$^9$, —SR$^9$, —S(=O)R$^{10}$, —S(=O)$_2$R$^{10}$, —C(=O)R$^{10}$, —OC(=O)R$^{10}$, —CO$_2$R$^9$, —C(=O)N(R$^9$)$_2$, C$_1$-C$_4$alkyl, C$_2$-C$_4$alkenyl, C$_2$-C$_4$alkynyl, C$_1$-C$_4$fluoroalkyl, C$_1$-C$_4$heteroalkyl, C$_1$-C$_4$fluoroalkoxy, and C$_1$-C$_4$alkoxy; each R is independently halogen, C$_1$-C$_4$alkyl, or C$_1$-C$_4$fluoroalkyl; R$^6$ is H, C$_1$-C$_4$alkyl, or halogen; R$^7$ is H, C$_1$-C$_4$alkyl, or halogen; R$^8$ and R$^{8'}$ is independently H or C$_1$-C$_6$alkyl; each R$^9$ is independently selected from H and C$_1$-C$_6$alkyl; R$^{10}$ is C$_1$-C$_6$alkyl; p is 0 or 1.

In some embodiments, the compound of Formula (I), or a pharmaceutically acceptable salt thereof, is a compound described in Table 1, or a pharmaceutically acceptable salt thereof.

Throughout the specification, groups and substituents thereof can be chosen by one skilled in the field to provide stable moieties and compounds.

Compounds disclosed herein are estrogen receptor modulators. In some embodiments, compounds disclosed herein have high specificity for the estrogen receptor and have desirable, tissue-selective pharmacological activities. Desirable, tissue-selective pharmacological activities include, but are not limited to, ER antagonist activity in breast cells and minimal or no ER agonist activity in uterine cells. In some embodiments, compounds disclosed herein are estrogen receptor degraders that display full estrogen receptor antagonist activity with negligible or minimal estrogen receptor agonist activity.

In some embodiments, compounds disclosed herein are estrogen receptor degraders. In some embodiments, compounds disclosed herein are estrogen receptor antagonists. In some embodiments, compounds disclosed herein have minimal or negligible estrogen receptor agonist activity.

In some embodiments, presented herein are compounds selected from active metabolites, tautomers, pharmaceutically acceptable solvates, pharmaceutically acceptable salts or prodrugs of a compound of Formula (I).

Also described are pharmaceutical compositions comprising a therapeutically effective amount of a compound of Formula (I), or a pharmaceutically acceptable salt thereof. In some embodiments, the pharmaceutical composition also contains at least one pharmaceutically acceptable inactive ingredient. In some embodiments, the pharmaceutical composition is formulated for intravenous injection, subcutaneous injection, oral administration, or topical administration. In some embodiments, the pharmaceutical composition is a tablet, a pill, a capsule, a liquid, a suspension, a gel, a dispersion, a suspension, a solution, an emulsion, an ointment, or a lotion.

In some embodiments, the pharmaceutical composition further comprises one or more additional therapeutically active agents selected from: corticosteroids, anti-emetic agents, analgesics, anti-cancer agents, anti-inflammatories, kinase inhibitors, antibodies, HSP90 inhibitors, histone deacetylase (HDAC) inhibitors, poly ADP-ribose polymerase (PARP) inhibitors, and aromatase inhibitors.

In some embodiments, provided herein is a method comprising administering a compound of Formula (I), or a pharmaceutically acceptable salt thereof, to a human with a diseases or condition that is estrogen sensitive, estrogen receptor meditated or estrogen receptor dependent. In some embodiments, the human is already being administered one or more additional therapeutically active agents other than a compound of Formula (I), or a pharmaceutically acceptable salt thereof. In some embodiments, the method further comprises administering one or more additional therapeutically active agents other than a compound of Formula (I), or a pharmaceutically acceptable salt thereof.

In some embodiments, the one or more additional therapeutically active agents other than a compound of Formula (I), or a pharmaceutically acceptable salt thereof, are selected from: corticosteroids, anti-emetic agents, analgesics, anti-cancer agents, anti-inflammatories, kinase inhibitors, antibodies, HSP90 inhibitors, histone deacetylase (HDAC) inhibitors, and aromatase inhibitors.

In some embodiments, a compound of Formula (I), or a pharmaceutically acceptable salt thereof, is used to treat hormone receptor positive metastatic breast cancer in a postmenopausal woman with disease progression following anti-estrogen therapy. In some embodiments, compounds are used to treat a hormonal dependent benign or malignant disease of the breast or reproductive tract in a mammal.

Pharmaceutical formulations described herein are administered to a mammal in a variety of ways, including but not limited to, oral, parenteral (e.g., intravenous, subcutaneous, intramuscular), buccal, topical or transdermal administration routes. The pharmaceutical formulations described herein include, but are not limited to, aqueous liquid dispersions, self-emulsifying dispersions, solid solutions, liposomal dispersions, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

In some embodiments, the compound of Formula (I), or a pharmaceutically acceptable salt thereof, is administered orally to a mammal.

In some embodiments, the compound of Formula (I), or a pharmaceutically acceptable salt thereof, is administered systemically to a mammal.

In some embodiments, the compound of Formula (I), or a pharmaceutically acceptable salt thereof, is administered intravenously to a mammal.

In some embodiments, the compound of Formula (I), or a pharmaceutically acceptable salt thereof, is administered subcutaneously to a mammal.

In some embodiments, the compound of Formula (I), or a pharmaceutically acceptable salt thereof, is administered topically to a mammal. In such embodiments, the compound of Formula (I), or a pharmaceutically acceptable salt thereof, is formulated into a variety of topically administrable compositions, such as solutions, suspensions, lotions, gels, pastes, shampoos, scrubs, rubs, smears, medicated sticks, medicated bandages, balms, creams or ointments. In some embodiments, the compound of Formula (I), or a pharmaceutically acceptable salt thereof, is administered topically to the skin of mammal.

In another aspect is the use of a compound of Formula (I), or a pharmaceutically acceptable salt thereof, in the manufacture of a medicament for treating a disease, disorder or conditions in which the activity of estrogen receptors contributes to the pathology and/or symptoms of the disease or condition. In one aspect, the disease or condition is any of the diseases or conditions specified herein.

In any of the aforementioned aspects are further embodiments in which the effective amount of the compound of Formula (I), or a pharmaceutically acceptable salt thereof, is: (a) systemically administered to the mammal; and/or (b) administered orally to the mammal; and/or (c) intravenously administered to the mammal; and/or (d) administered by injection to the mammal; and/or (e) administered topically to the mammal; and/or (f) administered non-systemically or locally to the mammal.

In any of the aforementioned aspects are further embodiments comprising single administrations of the effective amount of the compound, including further embodiments in which (i) the compound is administered once; (ii) the compound is administered to the mammal multiple times over the span of one day; (iii) continually; or (iv) continuously.

In any of the aforementioned aspects are further embodiments comprising multiple administrations of the effective amount of the compound, including further embodiments in which (i) the compound is administered continuously or intermittently: as in a single dose; (ii) the time between multiple administrations is every 6 hours; (iii) the compound is administered to the mammal every 8 hours; (iv) the compound is administered to the mammal every 12 hours; (v) the compound is administered to the mammal every 24 hours. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 2 days to 1 year.

Also provided is a method of reducing ER activation in a mammal comprising administering to the mammal at least one compound having the structure of Formula (I), or a pharmaceutically acceptable salt thereof. In some embodiments, the method comprises reducing ER activation in breast cells, ovarian cells, colon cells, prostate cells, endometrial cells, or uterine cells in the mammal. In some embodiments, the method of reducing ER activation in the mammal comprises reducing the binding of estrogens to estrogen receptors in the mammal. In some embodiments, the method of reducing ER activation in the mammal comprises reducing ER concentrations in the mammal.

In one aspect is the use of a compound of Formula (I), or a pharmaceutically acceptable salt thereof, in the manufacture of a medicament for the treatment of diseases or conditions that are estrogen sensitive, estrogen receptor dependent or estrogen receptor mediated. In some embodiments, the disease or condition is breast cancer, ovarian cancer, colon cancer, prostate cancer, endometrial cancer, or uterine cancer. In some embodiments, the disease or condition is described herein.

In some cases disclosed herein is the use of a compound of Formula (I), or a pharmaceutically acceptable salt thereof, in the treatment or prevention of diseases or conditions that are estrogen sensitive, estrogen receptor dependent or estrogen receptor mediated. In some embodiments, the disease or condition is described herein.

In any of the embodiments disclosed herein, the mammal is a human.

In some embodiments, compounds provided herein are used to diminish, reduce, or eliminate the activity of estrogen receptors.

Articles of manufacture, which include: packaging material; a compound of Formula (I), or pharmaceutically acceptable salt, active metabolite, prodrug, or pharmaceutically acceptable solvate thereof, or composition thereof, within the packaging material; and a label that indicates that the compound or pharmaceutically acceptable salt, active metabolite, prodrug, or pharmaceutically acceptable solvate thereof, or composition thereof, or composition thereof, is used for reducing, diminishing or eliminating the effects of estrogen receptors, or for the treatment, prevention or amelioration of one or more symptoms of a disease or condition that would benefit from a reduction or elimination of estrogen receptor activity, are provided.

Other objects, features and advantages of the compounds, methods and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description

DETAILED DESCRIPTION OF THE INVENTION

Estrogen receptor alpha (ER-α; NR3A1) and estrogen receptor beta (ER-β; NR3A2) are steroid hormone receptors, which are members of the large nuclear receptor superfamily. Nuclear receptors share a common modular structure, which minimally includes a DNA binding domain (DBD) and a ligand binding domain (LBD). Steroid hormone receptors are soluble, intracellular proteins that act as ligand-regulated transcription factors. Vertebrates contain five closely related steroid hormone receptors (estrogen receptor, androgen receptor, progesterone receptor, glucocorticoid receptor, mineralcorticoid receptor), which regulate a wide spectrum of reproductive, metabolic and developmental activities. The activities of ER are controlled by the binding of endogenous estrogens, including 17β-estradiol and estrones.

The ER-α gene is located on 6q25.1 and encodes a 595 AA protein. The ER-β gene resides on chromosome 14q23.3 and produces a 530 AA protein. However, due to alternative splicing and translation start sites, each of these genes can give rise to multiple isoforms. In addition to the DNA binding domain (called C domain) and ligand binding domain (E domain) these receptors contain an N-terminal (A/B) domain, a hinge (D) domain that links the C and E domains, and a C-terminal extension (F domain) (Gronemeyer and Laudet; Protein Profile 2: 1173-1308, 1995). While the C and E domains of ER-α and ER-β are quite conserved (95% and 55% amino acid identity, respectively), conservation of the A/B, D and F domains is poor (below 30% amino acid identity). Both receptors are involved in the regulation and development of the female reproductive tract but also play various roles in the central nervous system, cardiovascular systems and bone metabolism.

The ligand binding pocket of steroid hormone receptors is deeply buried within the ligand binding domain. Upon binding, the ligand becomes part of the hydrophobic core of this domain. Consequently most steroid hormone receptors are instable in the absence of hormone and require assistance from chaperones, such as Hsp90, in order to maintain hormone-binding competency. The interaction with Hsp90 also controls nuclear translocation of these receptors. Ligand-binding stabilizes the receptor and initiates sequential conformational changes that release the chaperones, alter the interactions between the various receptor domains and remodel protein interaction surfaces that allow these receptors to translocate into the nucleus, bind DNA and engage in interactions with chromatin remodeling complexes and the transcriptional machinery. Although ER can interact with Hsp90, this interaction is not required for hormone binding and, dependent on the cellular context, apo-ER can be both cytoplasmic and nuclear. Biophysical studies indicated that DNA binding rather than ligand binding contributes to the stability of the receptor (Greenfield et al., Biochemistry 40: 6646-6652, 2001).

ER can interact with DNA either directly by binding to a specific DNA sequence motif called estrogen response element (ERE) (classical pathway), or indirectly via protein-protein interactions (nonclassical pathway) (Welboren et al., Endocrine-Related Cancer 16: 1073-1089, 2009). In the nonclassical pathway, ER has been shown to tether to other transcription factors including SP-1, AP-1 and NF-κB. These interactions appear to play critical roles in the ability of ER to regulate cell proliferation and differentiation.

Both types of ER DNA interactions can result in gene activation or repression dependent on the transcriptional coregulators that are recruited by the respective ER-ERE complex (Klinge, Steroid 65: 227-251, 2000). The recruitment of coregulators is primarily mediated by two protein interaction surfaces, the AF2 and AF1. AF2 is located in the ER E-domain and its conformation is directly regulated by the ligand (Brzozowski et al., Nature 389: 753-758, 1997). Full agonists appear to promote the recruitment of co-activators, whereas weak agonists and antagonists facilitate the binding of co-repressors. The regulation of protein with the AF1 is less well understood but can be controlled by serine phosphorylation (Ward and Weigel, Biofactors 35: 528-536, 2009). One of the involved phosphorylation sites (S 118) appears to control the transcriptional activity of ER in the presence of antagonists such as tamoxifen, which plays an important role in the treatment of breast cancer. While full agonists appear to arrest ER in certain conformation, weak agonists tend to maintain ER in equilibrium between different conformations, allowing cell-dependent differences in co-regulator repertoires to modulate the activity of ER in a cell-dependent manner (Tamrazi et al., Mol. Endocrinol. 17: 2593-2602, 2003). Interactions of ER with DNA are dynamic and include, but are not limited to, the degradation of ER by the proteasome (Reid et al., Mol Cell 11: 695-707, 2003). The degradation of ER with ligands provides an attractive treatment strategy for disease or conditions that estrogen-sensitive and/or resistant to available anti-hormonal treatments.

ER signaling is crucial for the development and maintenance of female reproductive organs including breasts, ovulation and thickening of the endometrium. ER signaling also has a role in bone mass, lipid metabolism, cancers, etc. About 70% of breast cancers express ER-α (ER-α positive) and are dependent on estrogens for growth and survival. Other cancers also are thought to be dependent on ER-α signaling for growth and survival, such as for example ovarian and endometrial cancers. The ER-α antagonist tamoxifen has been used to treat early and advanced ER-α positive breast cancer in both pre- and post-menopausal women. Fulvestrant (Faslodex™) a steroid-based ER antagonist is used to treat breast cancer in women which has have progressed despite therapy with tamoxifen. Steroidal and non-steroidal aromatase inhibitors are also used to treat cancers in humans. In some embodiments, the steroidal and non-steroidal aromatase inhibitors block the production of estrogen from androstenedione and testosterone in post-menopausal women, thereby blocking ER dependent growth in the cancers. In addition to these anti-hormonal agents, progressive ER positive breast cancer is treated in some cases with a variety of other chemotherapeutics, such as for example, the anthracylines, platins, taxanes. In some cases, ER positive breast cancers that harbor genetic amplication of the ERB-B/HER2 tyrosine kinase receptor are treated with the monoclonal antibody trastuzumab (Herceptin™) or the small molecule pan-ERB-B inhibitor lapatinib. Despite this battery of anti-hormonal, chemotherapeutic and small-molecule and antibody-based targeted therapies, many women with ER-α positive breast develop progressive metastatic disease and are in need of new therapies. Importantly, the majority of ER positive tumors that progress on existing anti-hormonal, as well as and other therapies, are thought to remain dependent on ER-α for growth and survival. Thus, there is a need for new ER-α targeting agents that have activity in the setting of metastatic disease and acquired resistance.

In one aspect, described herein are compounds that are selective estrogen receptor modulators (SERMs). In specific embodiments, the SERMs described herein are selective estrogen receptor degraders (SERDs). In some embodiments, in cell-based assays the compounds described herein result in a reduction in steady state ER-α levels (i.e. ER degradation) and are useful in the treatment of estrogen sensitive diseases or conditions and/or diseases or conditions that have developed resistant to anti-hormonal therapies. In some embodiments, compounds disclosed herein minimize levels of the estrogen receptor in the nucleus.

Given the central role of ER-α in breast cancer development and progression, compounds disclosed herein are useful in the treatment of breast cancer, either alone or in combination with other agent agents that modulate other critical pathways in breast cancer, including but not limited to those that target IGF1R, EGFR, erB-B2 and 3 the PI3K/AKT/mTOR axis, HSP90, PARP or histone deacetylases.

Given the central role of ER-α in breast cancer development and progression, compounds disclosed herein are useful in the treatment of breast cancer, either alone or in combination with other agent used to treat breast cancer, including but not limited to aromatase inhibitors, anthracylines, platins, nitrogen mustard alkylating agents, taxanes. Illustrative agent used to treat breast cancer, include, but are not limited to, paclitaxel, anastrozole, exemestane, cyclophosphamide, epirubicin, fulvestrant, letrozole, gemcitabine, trastuzumab, pegfilgrastim, filgrastim, tamoxifen, docetaxel, toremifene, vinorelbine, capecitabine, ixabepilone, as well as others described herein.

ER-related diseases or conditions (for which the agents disclosed herein are therapeutically relevant) include ER-α dysfunction is also associated with cancer (bone cancer, breast cancer, colorectal cancer, endometrial cancer, prostate cancer, ovarian and uterine cancer), leiomyoma (uterine leiomyoma), central nervous system (CNS) defects (alcoholism, migraine), cardiovascular system defects (aortic aneurysm, susceptibility to myocardial infarction, aortic valve sclerosis, cardiovascular disease, coronary artery disease, hypertension), hematological system defects (deep vein thrombosis), immune and inflammation diseases (Graves' Disease, arthritis, multiple sclerosis, cirrhosis), susceptibility to infection (hepatitis B, chronic liver disease), metabolic defects (bone density, cholestasis, hypospadias, obesity, osteoarthritis, osteopenia, osteoporosis), neurological defects (Alzheimer's disease, Parkinson's disease, migraine, vertigo), psychiatric defects (anorexia nervosa, attention deficit hyperactivity disorder (ADHD), dementia, major depressive disorder, psychosis) and reproductive defects (age of menarche, endometriosis, infertility.

In some embodiments, compounds disclosed herein are used to treat cancer in a mammal. In some embodiments, the cancer is breast cancer, ovarian cancer, endometrial cancer, prostate cancer, uterine cancer, cervical cancer or lung cancer. In some embodiments, the cancer is breast cancer. In some embodiments, the cancer is a hormone dependent cancer. In some embodiments, the cancer is an estrogen receptor dependent cancer. In some embodiments, the cancer is an estrogen-sensitive cancer. In some embodiments, the cancer is resistant to anti-hormonal treatment. In some embodiments, the cancer is an estrogen-sensitive cancer or an estrogen receptor dependent cancer that is resistant to anti-hormonal treatment. In some embodiments, anti-hormonal treatment includes treatment with at least one agent selected from tamoxifen, fulvestrant, steroidal aromatase inhibitors, and non-steroidal aromatase inhibitors-resistant.

In some embodiments, compounds disclosed herein are used to treat hormone receptor positive metastatic breast cancer in a postmenopausal woman with disease progression following anti-estrogen therapy.

In some embodiments, compounds disclosed herein are used to treat a hormonal dependent benign or malignant disease of the breast or reproductive tract in a mammal. In some embodiments, the benign or malignant disease is breast cancer.

In some embodiments, compounds disclosed herein are used to treat cancer in a mammal, wherein the mammal is chemotherapy-naïve.

In some embodiments, compounds disclosed herein are used to treat cancer in a mammal, wherein the mammal is being treated for cancer with at least one anti-cancer agent. In one embodiment, the cancer is a hormone refractory cancer.

In some embodiments, compounds disclosed herein are used in the treatment of endometriosis in a mammal.

In some embodiments, compounds disclosed herein are used in the treatment of leiomyoma in a mammal. In some embodiments, the leiomyoma is an uterine leiomyoma, esophageal leiomyoma, cutaneous leiomyoma or small bowel leiomyoma. In some embodiments, compounds disclosed herein are used in the treatment of fibroids in a mammal (e.g. uterine fibroids).

Compounds

Compounds of Formula (I), including pharmaceutically acceptable salts, prodrugs, active metabolites and pharmaceutically acceptable solvates thereof, are estrogen receptor modulators. In specific embodiments, the compounds described herein are estrogen receptor degraders. In specific embodiments, the compounds described herein are estrogen receptor antagonists. In specific embodiments, the compounds described herein are estrogen receptor degraders and estrogen receptor antagonists with minimal or no estrogen receptor agonist activity.

In some embodiments, compounds disclosed herein are estrogen receptor degraders and estrogen receptor antagonists that exhibit: minimal or no estrogen receptor agonism; and/or anti-proliferative activity against breast cancer, ovarian cancer, endometrial cancer, cervical cancer cell lines; and/or maximal anti-proliferative efficacy against breast cancer, ovarian cancer, endometrial cancer, cervical cell lines in-vitro; and/or minimal agonism in the human endometrial (Ishikawa) cell line; and/or no agonism in the human endometrial (Ishikawa) cell line; and/or minimal or no agonism in the immature rat uterine assay in-vivo; and/or inverse agonism in the immature rat uterine assay in-vivo; and/or anti-tumor activity in breast cancer, ovarian cancer, endometrial cancer, cervical cancer cell lines in xenograft assays in-vivo or other rodent models of these cancers.

In one aspect, provided herein is a compound of Formula (I), or a pharmaceutically acceptable salt, solvate, metabolite or prodrug thereof:

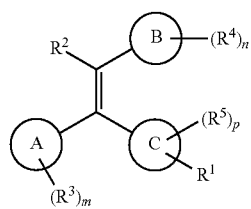

Formula (I)

wherein, ring A is indanyl, indenyl, naphthyl, 5- or 6-membered monocyclic heteroaryl, or 8-, 9- or 10-membered bicyclic heterocycle;

ring B is phenyl, indanyl, indenyl, naphthyl, 5- or 6-membered monocyclic heteroaryl or 8-, 9- or 10-membered bicyclic heterocycle;

ring C is phenyl, indanyl, indenyl, naphthyl, 5- or 6-membered monocyclic heteroaryl or 8-, 9- or 10-membered bicyclic heterocycle;

$R^1$ is Y, —X—$C_1$-$C_6$alkylene-Y, —$C_1$-$C_6$alkylene-Y, —$C_2$-$C_6$alkynylene-Y, —C($R^6$)=C($R^7$)—Y, —X—$C_1$-$C_6$alkynylene-Y, —X—$C_3$-$C_6$cycloalkylene-Y or —$C_3$-$C_6$cycloalkylene-Y;

X is $NR^8$, O, S, S(=O) or S(=O)$_2$;

Y is —C(=O)—Z, tetrazolyl, carboxylic acid bioisostere, optionally substituted piperidinyl, optionally substituted pyrrolidinyl, —$NR^8R^{8'}$, -AR—OH, —$SO_3H$, —$SO_2NHR^9$, and —P(=O)(OH)$_2$ wherein AR is phenyl or monocyclic heteroaryl;

Z is —OH, —$OR^{10}$, —$NR^8R^{8'}$, —$NR^8S(=O)_2R^{10}$, —NHOH or —$NR^8OR^{10}$;

$R^2$ is halogen, CN, $NO_2$, —$SR^9$, —S(=O)$R^{10}$, —S(=O)$_2$ $R^{10}$, —NHS(=O)$_2R^{10}$, $C_1$-$C_6$alkyl, $C_1$-$C_6$fluoroalkyl, $C_1$-$C_6$deuteroalkyl, $C_1$-$C_4$alkoxy, $C_1$-$C_4$fluoroalkoxy, $C_3$-$C_6$cycloalkyl, —$C_1$-$C_4$alkylene-W, —$C_1$-$C_4$fluoroalkylene-W, —$C_3$-$C_6$cycloalkylene-W;

W is hydroxy, halogen, CN, $NO_2$, $C_1$-$C_6$alkyl, $C_1$-$C_6$haloalkyl, $C_1$-$C_6$alkoxy, $C_1$-$C_6$haloalkoxy, and $C_3$-$C_6$cycloalkyl;

each $R^3$, $R^4$, $R^5$ is independently selected from H, halogen, —$NO_2$, —$NR^8R^{8'}$, —CN, —OH, —$OR^9$, —$SR^9$, —S(=O)$R^{10}$, —S(=O)$_2R^{10}$, —NHS(=O)$_2R^{10}$, —S(=O)$_2N(R^9)_2$, —C(=O)$R^{10}$, —OC(=O)$R^{10}$, —CO$_2R^9$, —OCO$_2R^{10}$, —C(=O)N($R^9$)$_2$, —OC(=O)N($R^9$)$_2$, —$NR^9C$(=O)N($R^9$)$_2$, —$NR^9C$(=O)$R^{10}$, —$NR^9C$(=O)$OR^{10}$, substituted or unsubstituted $C_1$-$C_6$alkyl, substituted or unsubstituted $C_2$-$C_6$alkenyl, substituted or unsubstituted $C_2$-$C_6$alkynyl, substituted or unsubstituted $C_1$-$C_6$fluoroalkyl, substituted or unsubstituted $C_1$-$C_6$heteroalkyl, substituted or unsubstituted $C_1$-$C_6$fluoroalkoxy, substituted or unsubstituted $C_1$-$C_6$alkoxy, substituted or unsubstituted phenyl and substituted or unsubstituted monocyclic heteroaryl;

$R^6$ and $R^7$ is independently H, $OR^9$, $NR^8R^{8'}$, $C_1$-$C_6$alkyl, $C_2$-$C_6$alkenyl, $C_2$-$C_6$alkynyl, —X—$C_1$-$C_6$alkyl, —X—$C_2$-$C_6$alkenyl, —X—$C_2$-$C_6$alkynyl, or halogen;

$R^8$ and $R^{8'}$ is independently H, substituted or unsubstituted $C_1$-$C_6$alkyl, substituted or unsubstituted $C_2$-$C_6$alkenyl, substituted or unsubstituted $C_2$-$C_6$alkynyl, substituted or unsubstituted $C_1$-$C_6$fluoroalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted phenyl, substituted or unsubstituted monocyclic heteroaryl, or substituted or unsubstituted benzyl;

each $R^9$ is independently selected from H, substituted or unsubstituted $C_1$-$C_6$alkyl, substituted or unsubstituted $C_1$-$C_6$heteroalkyl, substituted or unsubstituted $C_1$-$C_6$fluoroalkyl, substituted or unsubstituted $C_3$-$C_{10}$cycloalkyl, substituted or unsubstituted $C_2$-$C_{10}$heterocycloalkyl, substituted or unsubstituted aryl, substituted or unsubstituted heteroaryl and substituted or unsubstituted benzyl;

each $R^{10}$ is independently selected from substituted or unsubstituted $C_1$-$C_6$alkyl, substituted or unsubstituted $C_1$-$C_6$heteroalkyl, substituted or unsubstituted $C_1$-$C_6$fluoroalkyl, substituted or unsubstituted $C_3$-$C_{10}$cycloalkyl, substituted or unsubstituted $C_2$-$C_{10}$heterocycloalkyl, substituted or unsubstituted aryl, substituted or unsubstituted heteroaryl and substituted or unsubstituted benzyl;

m is 0, 1, 2, 3, or 4;

n is 0, 1, 2, 3, or 4; and p is 0, 1, 2, 3, or 4.

For any and all of the embodiments, substituents are selected from among from a subset of the listed alternatives. For example, in some embodiments, $R^1$ is Y, —X—$C_1$-$C_6$alkylene-Y, —$C_1$-$C_6$alkylene-Y, —$C_2$-$C_6$alkynylene-Y, —C($R^6$)=C($R^7$)—Y, —X—$C_1$-$C_6$alkynylene-Y, —X—$C_3$-$C_6$cycloalkylene-Y or —$C_3$-$C_6$cycloalkylene-Y. In some embodiments, $R^1$ is —C($R^6$)=C($R^7$)—Y.

In some embodiments, Y is —C(=O)—Z, tetrazolyl, optionally substituted piperidinyl, optionally substituted pyrrolidinyl, —$NR^8R^{8'}$, -AR—OH, —$SO_3H$, and —P(=O)(OH)$_2$ wherein AR is phenyl or monocyclic heteroaryl. In some embodiments, Y is —C(=O)—Z, tetrazolyl, carboxylic acid bioisostere, optionally substituted piperidinyl, optionally substituted pyrrolidinyl, —$NR^8R^{8'}$, -AR—OH, —$SO_3H$, —$SO_2NHR^9$, and —P(=O)(OH)$_2$ wherein AR is phenyl or monocyclic heteroaryl. In some embodiments, Y is —C(=O)—Z or carboxylic acid bioisostere. In some embodiments, Y is —C(=O)—Z or tetrazolyl. In some embodiments, Y is —C(=O)—Z. In some embodiments, Y is —C(=O)—OH. In some embodiments, Y is —C(=O)—$OR^{10}$.

In some embodiments, Z is —OH, —$OR^{10}$, —$NR^8R^{8'}$, —$NR^8S$(=O)$_2R^{10}$, —NHOH or —$NR^8OR^{10}$. In some embodiments, Z is —OH, —$OR^{10}$, —$NR^8R^{8'}$, —$NR^8S$(=O)$_2R^{10}$, or —NHOH. In some embodiments, Z is —OH or —$OR^{10}$. In some embodiments, Z is —OH or —O($C_1$-$C_4$alkyl). In some embodiments, Z is —OH.

In some embodiments, ring A is 5- or 6-membered monocyclic heteroaryl or 8-, 9- or 10-membered bicyclic heterocycle; ring B is phenyl, naphthyl, 5- or 6-membered monocyclic heteroaryl or 8-, 9- or 10-membered bicyclic heterocycle; ring C is phenyl or 5- or 6-membered monocyclic heteroaryl.

In some embodiments, ring A is a 5- or 6-membered monocyclic heteroaryl. In some embodiments, ring A is a 6-membered monocyclic heteroaryl. In some embodiments, ring A is a 6-membered monocyclic heteroaryl containing 1-3 N atoms in the ring. In some embodiments, ring A is a 6-membered monocyclic heteroaryl containing 1 or 2 N atoms in the ring.

In some embodiments, ring A is furanyl, thienyl, oxazolyl, thiazolyl, pyrrolyl, imidazolyl, pyrazolyl, triazolyl, tetrazolyl, pyridinyl, pyridazinyl, pyrimidinyl, pyrazinyl, or triazinyl.

In some embodiments, ring A is a 8-, 9- or 10-membered bicyclic heterocycle with at least one nitrogen atom in the ring.

In some embodiments, ring A is a 8-, 9- or 10-membered bicyclic heteroaryl with at least one nitrogen atom in the ring. In some embodiments, ring A is a 9-membered bicyclic heteroaryl with at least one nitrogen atom in the ring.

In some embodiments, ring A is quinolinyl, isoquinolinyl, cinnolinyl, phthalazinyl, quinazolinyl, quinoxalinyl, naphthyridinyl, pteridinyl, indolizinyl, azaindolizinyl, indolyl, azaindolyl, indazolyl, azaindazolyl, benzimidazolyl, azabenzimidazolyl, benzotriazolyl, azabenzotriazolyl, benzoxazolyl, azabenzoxazolyl, benzisoxazolyl, azabenzisoxazolyl, benzofuranyl, azabenzofuranyl, benzothienyl, azabenzothienyl, benzothiazolyl, azabenzothiazolyl, or purinyl. In some embodiments, ring A is indazolyl, azaindazolyl, benzimidazolyl, azabenzimidazolyl, benzotriazolyl, or azabenzotriazolyl.

In some embodiments, ring A is 5- or 6-membered monocyclic heteroaryl or 8-, 9- or 10-membered bicyclic heterocycle; ring B is phenyl, naphthyl, 5- or 6-membered monocyclic heteroaryl or 8-, 9- or 10-membered bicyclic heterocycle; ring C is phenyl, or 5- or 6-membered monocyclic heteroaryl; each $R^3$ is independently selected from H, halogen, —$NR^8R^{8'}$, —CN, —OH, —$OR^9$, —$SR^9$, —S(=O)$R^{10}$, —S(=O)$_2R^{10}$, —NHS(=O)$_2R^{10}$, —S(=O)$_2$N($R^9$)$_2$, —C(=O)$R^{10}$, —OC(=O)$R^{10}$, —$CO_2R^9$, —C(=O)N($R^9$)$_2$, $C_1$-$C_4$alkyl, $C_2$-$C_4$alkenyl, $C_2$-$C_4$alkynyl, $C_1$-$C_4$fluoroalkyl, $C_1$-$C_4$heteroalkyl, $C_1$-$C_4$fluoroalkoxy, and $C_1$-$C_4$alkoxy; each $R^4$ is independently selected from H, halogen, —$NO_2$, —$NR^8R^{8'}$, —CN, —OH, —$OR^9$, —$SR^9$, —S(=O)$R^{10}$, —S(=O)$_2R^{10}$, —NHS(=O)$_2R^{10}$, —S(=O)$_2$N($R^9$)$_2$, —C(=O)$R^{10}$, —OC(=O)$R^{10}$, —$CO_2R^9$, —$OCO_2R^{10}$, —C(=O)N($R^9$)$_2$, —OC(=O)N($R^9$)$_2$, —$NR^9$C(=O)N($R^9$)$_2$, —$NR^9$C(=O)$R^{10}$, —$NR^9$C(=O)$OR^{10}$, substituted or unsubstituted $C_1$-$C_6$alkyl, substituted or unsubstituted $C_2$-$C_6$alkenyl, substituted or unsubstituted $C_2$-$C_6$alkynyl, substituted or unsubstituted $C_1$-$C_6$fluoroalkyl, substituted or unsubstituted $C_1$-$C_6$heteroalkyl, substituted or unsubstituted $C_1$-$C_6$fluoroalkoxy, substituted or unsubstituted $C_1$-$C_6$alkoxy, substituted or unsubstituted phenyl and substituted or unsubstituted monocyclic heteroaryl; each $R^5$ is independently selected from H, halogen, —$NR^8R^{8'}$, —CN, —OH, —$OR^9$, —$SR^9$, —S(=O)$R^{10}$, —S(=O)$_2R^{10}$, —NHS(=O)$_2R^{10}$, —S(=O)$_2$N($R^9$)$_2$, —C(=O)$R^{10}$, —OC(=O)$R^{10}$, —$CO_2R^9$, —C(=O)N($R^9$)$_2$, $C_1$-$C_4$alkyl, $C_2$-$C_4$alkenyl, $C_2$-$C_4$alkynyl, $C_1$-$C_4$fluoroalkyl, $C_1$-$C_4$heteroalkyl, $C_1$-$C_4$fluoroalkoxy, and $C_1$-$C_4$alkoxy.

It is understood that $R^3$ may be present on any open position of ring A.

It is understood that $R^4$ may be present on any open position of ring B.

It is understood that $R^5$ may be present on any open position of ring C.

In some embodiments, ring A is a 5- or 6-membered monocyclic heteroaryl.

In some embodiments, ring A is furanyl, thienyl, oxazolyl, thiazolyl, pyrrolyl, imidazolyl, pyrazolyl, triazolyl, tetrazolyl, pyridinyl, pyridazinyl, pyrimidinyl, pyrazinyl, or triazinyl.

In some embodiments, ring A is a 8-, 9- or 10-membered bicyclic heterocycle with at least one nitrogen atom in the ring; ring B is phenyl, naphthyl, indanyl, indenyl, furanyl, thienyl, oxazolyl, thiazolyl, pyrrolyl, imidazolyl, pyrazolyl, triazolyl, tetrazolyl, pyridinyl, pyridazinyl, pyrimidinyl, pyrazinyl, triazinyl, quinolinyl, isoquinolinyl, cinnolinyl, phthalazinyl, quinazolinyl, quinoxalinyl, naphthyridinyl, pteridinyl, inolizinyl, azainolizinyl, indolyl, azaindolyl, indazolyl, azaindazolyl, benzimidazolyl, azabenzimidazolyl, benzotriazolyl, azabenzotriazolyl, benzoxazolyl, azabenzoxazolyl, benzisoxazolyl, azabenzisoxazolyl, benzofuranyl, azabenzofuranyl, benzothienyl, azabenzothienyl, benzothiazolyl, azabenzothiazolyl, or purinyl.

In some embodiments, ring A is a 8-, 9- or 10-membered bicyclic heteroaryl with at least one nitrogen atom in the ring; ring B is phenyl, a 5-membered heteroaryl or a 6-membered heteroaryl; ring C is phenyl, a 5-membered heteroaryl or a 6-membered heteroaryl.

In some embodiments, ring A is quinolinyl, isoquinolinyl, cinnolinyl, phthalazinyl, quinazolinyl, quinoxalinyl, naphthyridinyl, pteridinyl, indolizinyl, azaindolizinyl, indolyl, azaindolyl, indazolyl, azaindazolyl, benzimidazolyl, azabenzimidazolyl, benzotriazolyl, azabenzotriazolyl, benzoxazolyl, azabenzoxazolyl, benzisoxazolyl, azabenzisoxazolyl, benzofuranyl, azabenzofuranyl, benzothienyl, azabenzothienyl, benzothiazolyl, azabenzothiazolyl, or purinyl; ring B is phenyl, furanyl, thienyl, pyrrolyl, imidazolyl, pyrazolyl, triazolyl, pyridinyl, pyrimidinyl, pyrazinyl, pyridazinyl, or triazinyl; ring C is phenyl, furanyl, thienyl, oxazolyl, thiazolyl, pyrrolyl, imidazolyl, pyrazolyl, triazolyl, pyridinyl, pyridazinyl, pyrimidinyl, pyrazinyl, or triazinyl.

In some embodiments, ring A is

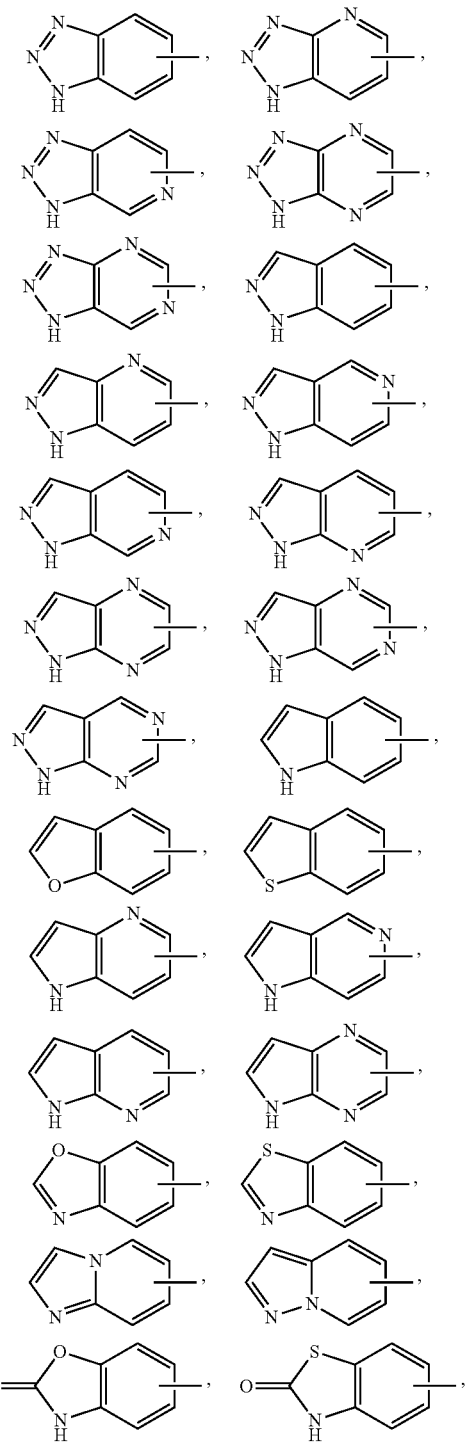

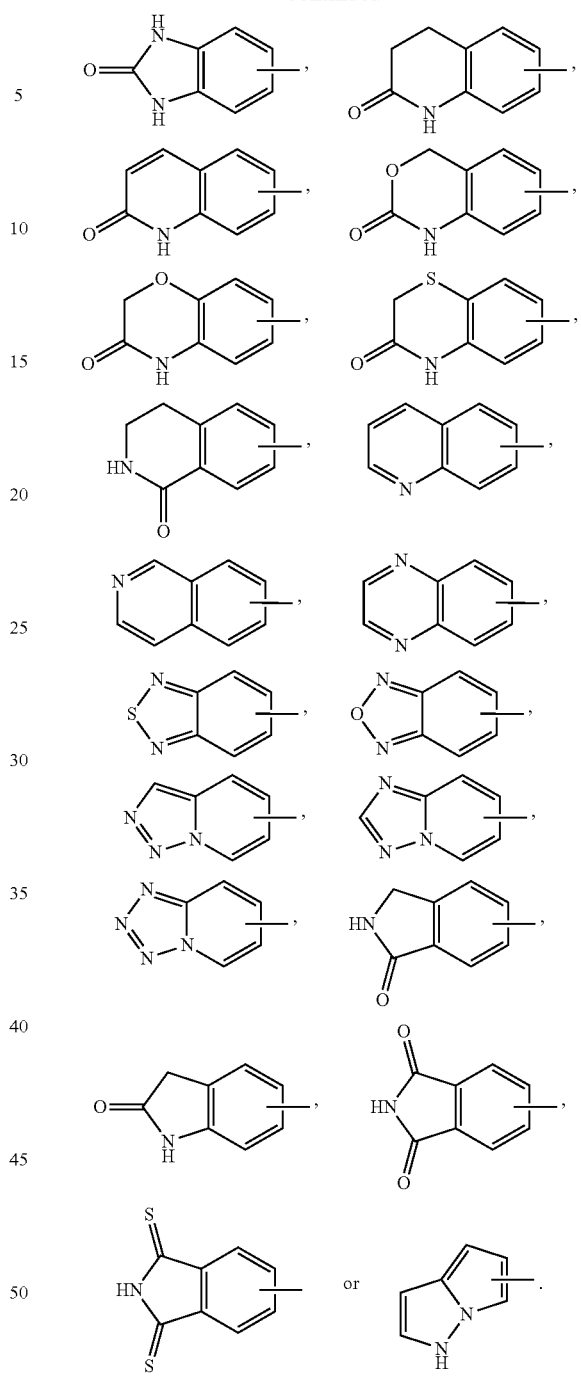

In some embodiments, ring A is

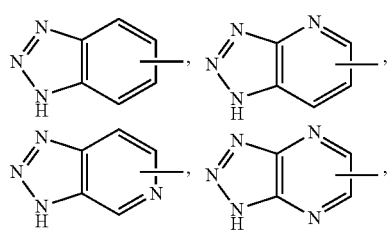

-continued

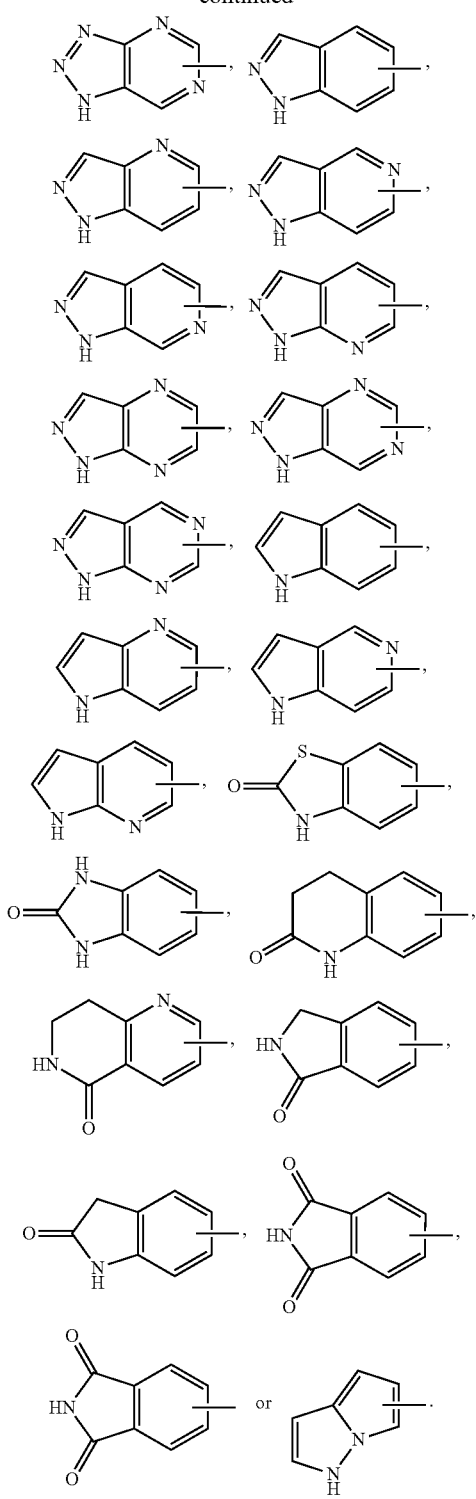

In some embodiments, ring A is

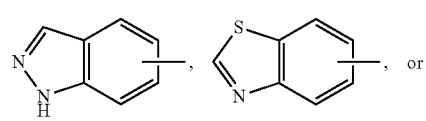

-continued

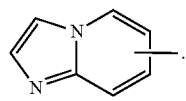

In some embodiments, ring A is

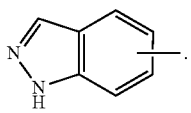

In some embodiments, ring A is

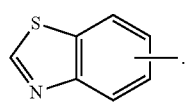

In some embodiments, ring A is

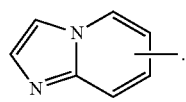

In some embodiments, ring A is indolyl, azaindolyl, indazolyl, azaindazolyl, benzimidazolyl, azabenzimidazolyl, benzotriazolyl or azabenzotriazolyl.

In some embodiments, the compound of Formula (I) has the structure of Formula (II):

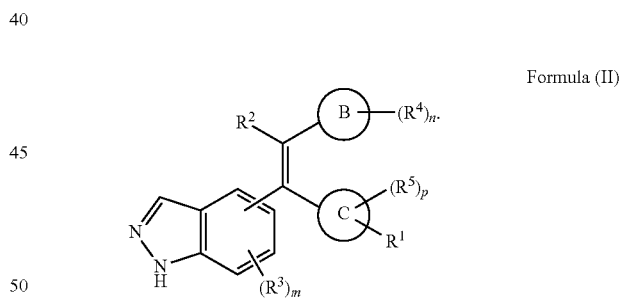

Formula (II)

In some embodiments, the compound of Formula (II) has the structure of Formula (III) or (IV):

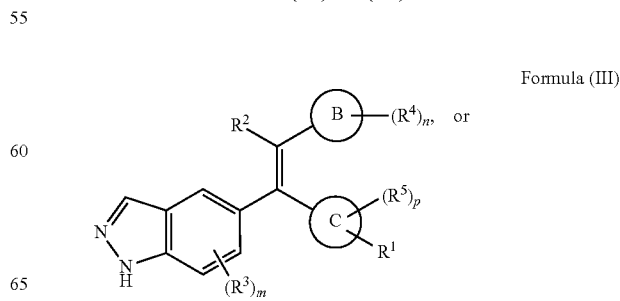

Formula (III)

-continued

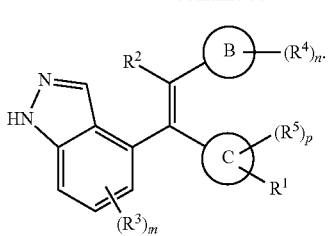

Formula (IV)

In some embodiments, the compound of Formula (I) has the structure of Formula (V):

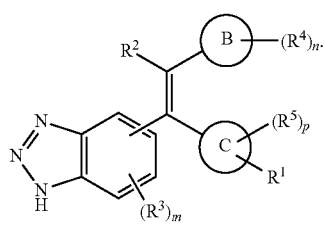

Formula (V)

In some embodiments, the compound of Formula (I) has the structure of Formula (XI):

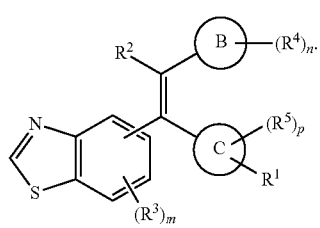

Formula (XI)

In some embodiments, Y is —C(=O)—Z, tetrazolyl, optionally substituted piperidinyl, optionally substituted pyrrolidinyl, —NR$^8$R$^{8'}$, -AR—OH, —SO$_3$H, and —P(=O)(OH)$_2$ wherein AR is phenyl or monocyclic heteroaryl; Z is —OH, —OR$^{10}$, —NR$^8$R$^{8'}$, —NR$^8$S(=O)$_2$R, or —NHOH; R$^8$ and R$^{8'}$ is independently H, C$_1$-C$_6$alkyl, C$_2$-C$_6$alkenyl, or C$_2$-C$_6$alkynyl.

In some embodiments, R$^8$ and R$^{8'}$ is independently H, substituted or unsubstituted C$_1$-C$_6$alkyl, substituted or unsubstituted C$_2$-C$_6$alkenyl, substituted or unsubstituted C$_2$-C$_6$alkynyl, substituted or unsubstituted C$_1$-C$_6$fluoroalkyl, substituted or unsubstituted C$_1$-C$_6$heteroalkyl, substituted or unsubstituted C$_3$-C$_6$cycloalkyl, substituted or unsubstituted phenyl, substituted or unsubstituted monocyclic heteroaryl, or substituted or unsubstituted benzyl. In some embodiments, R$^8$ and R$^{8'}$ is independently H, C$_1$-C$_6$alkyl, C$_2$-C$_6$alkenyl, C$_2$-C$_6$alkynyl, C$_1$-C$_6$fluoroalkyl, C$_1$-C$_6$heteroalkyl, C$_3$-C$_6$cycloalkyl, substituted or unsubstituted phenyl, substituted or unsubstituted monocyclic heteroaryl, or substituted or unsubstituted benzyl. In some embodiments, R$^8$ is H, C$_1$-C$_6$alkyl, C$_1$-C$_6$fluoroalkyl, C$_1$-C$_6$heteroalkyl, C$_3$-C$_6$cycloalkyl, substituted or unsubstituted phenyl, substituted or unsubstituted monocyclic heteroaryl, or substituted or unsubstituted benzyl. In some embodiments, R$^8$ is H, C$_1$-C$_6$alkyl, or C$_3$-C$_6$cycloalkyl. In some embodiments, R$^8$ is H, or C$_1$-C$_6$alkyl. In some embodiments, R$^8$ and R$^{8'}$ is independently H, C$_1$-C$_6$alkyl, C$_2$-C$_6$alkenyl, or C$_2$-C$_6$alkynyl. In some embodiments, R$^{8'}$ is H or C$_1$-C$_6$alkyl.

In some embodiments, ring C is phenyl, a 5-membered heteroaryl or a 6-membered heteroaryl.

In some embodiments, ring C is phenyl, furanyl, thienyl, oxazolyl, thiazolyl, pyrrolyl, imidazolyl, pyrazolyl, triazolyl, pyridinyl, pyridazinyl, pyrimidinyl, pyrazinyl, or triazinyl.

In some embodiments, ring C is phenyl or a 6-membered heteroaryl.

In some embodiments, ring C is phenyl, pyridinyl, pyridazinyl, pyrimidinyl, pyrazinyl, or triazinyl.

In some embodiments, ring C is phenyl.

In some embodiments, ring B is phenyl, naphthyl, indanyl, indenyl, furanyl, thienyl, oxazolyl, thiazolyl, pyrrolyl, imidazolyl, pyrazolyl, triazolyl, tetrazolyl, pyridinyl, pyridazinyl, pyrimidinyl, pyrazinyl, triazinyl, quinolinyl, isoquinolinyl, cinnolinyl, phthalazinyl, quinazolinyl, quinoxalinyl, naphthyridinyl, pteridinyl, inolizinyl, azainolizinyl, indolyl, azaindolyl, indazolyl, azaindazolyl, benzimidazolyl, azabenzimidazolyl, benzotriazolyl, azabenzotriazolyl, benzoxazolyl, azabenzoxazolyl, benzisoxazolyl, azabenzisoxazolyl, benzofuranyl, azabenzofuranyl, benzothienyl, azabenzothienyl, benzothiazolyl, azabenzothiazolyl, or purinyl.

In some embodiments, ring B is phenyl, a 5-membered heteroaryl or a 6-membered heteroaryl.

In some embodiments, ring B is phenyl, furanyl, thienyl, pyrrolyl, imidazolyl, pyrazolyl, triazolyl, pyridinyl, pyrimidinyl, pyrazinyl, pyridazinyl, or triazinyl. In some embodiments, ring B is phenyl, thienyl, or pyridinyl. In some embodiments, ring B is thienyl. In some embodiments, ring B is pyridinyl.

In some embodiments, ring B is phenyl.

In some embodiments,

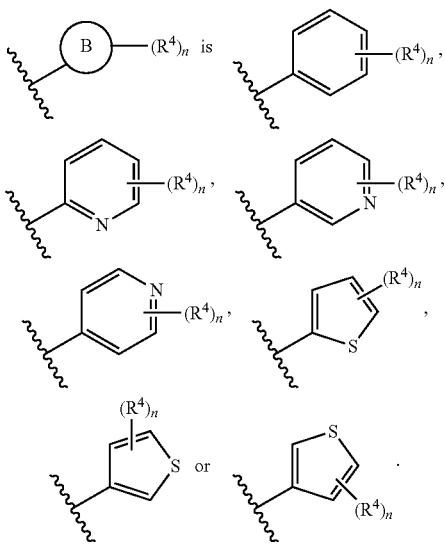

In some embodiments,

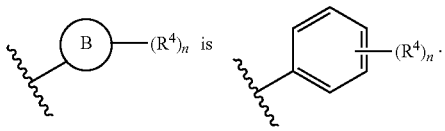

In some embodiments,

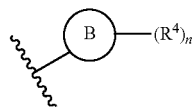

is phenyl, 2-fluorophenyl, 3-fluorophenyl, 4-fluorophenyl, 2,3-difluorophenyl, 2,4-difluorophenyl, 2,5-difluorophenyl, 2,6-difluorophenyl, 2-chlorophenyl, 3-chlorophenyl, 4-chlorophenyl, 2,3-dichlorophenyl, 2,4-dichlorophenyl, 2,5-dichlorophenyl, 2,6-dichlorophenyl, 2-bromophenyl, 3-bromophenyl, 4-bromophenyl, 2-methylphenyl, 3-methylphenyl, 4-methylphenyl, 2-ethylphenyl, 3-ethylphenyl, 4-ethylphenyl, 2-methoxyphenyl, 3-methoxyphenyl, 4-methoxyphenyl, 2-trifluoromethylphenyl, 3-trifluoromethylphenyl, 4-trifluoromethylphenyl, 2-fluoro-4-methoxyphenyl, 2-cyanophenyl, 3-cyanophenyl, 4-cyanophenyl, 2-fluoro-3-chlorophenyl, 2-fluoro-4-chlorophenyl, 2-fluoro-5-chlorophenyl, 2-fluoro-6-chlorophenyl, 2-chloro-3-fluorophenyl, 2-chloro-4-fluorophenyl, 2-chloro-5-fluorophenyl, 2-chloro-6-fluorophenyl, 2-methyl-3-chlorophenyl, 2-methyl-4-chlorophenyl, 2-methyl-5-chlorophenyl, 2-methyl-6-chlorophenyl, 2-methyl-3-fluorophenyl, 2-methyl-4-fluorophenyl, 2-methyl-5-fluorophenyl, 2-methyl-6-fluorophenyl, 3-methyl-4-fluorophenyl, 2-trifluoromethyl-3-chlorophenyl, 2-trifluoromethyl-4-chlorophenyl, 2-trifluoromethyl-5-chlorophenyl, 2-trifluoromethyl-6-chlorophenyl, 2-methyl-4-methoxyphenyl, 2-cyano-4-methoxyphenyl, 2-chloro-4-cyanophenyl, 2-hydroxyphenyl, 3-hydroxyphenyl, 4-hydroxyphenyl, 2-hydroxymethylphenyl, 3-hydroxymethylphenyl, 4-hydroxymethylphenyl, 2-methylsulfonylphenyl, 3-methylsulfonylphenyl, 4-methylsulfonylphenyl, 2-phenylphenyl, 3-phenylphenyl, 4-phenylphenyl, 2-methylthiophen-3-yl, 4-methylthiophen-3-yl, 3-methylthiophen-2-yl, 2-triflouromethylthiophen-3-yl, 4-triflouromethylthiophen-3-yl, 3-triflouromethylthiophen-2-yl, 2-ethylthiophen-3-yl, 4-ethylthiophen-3-yl, 3-ethylthiophen-2-yl, 2-chlorothiophen-3-yl, 4-chlorothiophen-3-yl, 3-chlorothiophen-2-yl, 2-flourothiophen-3-yl, 4-flourothiophen-3-yl, 3-flourothiophen-2-yl, 2-cyanothiophen-3-yl, 4-cyanothiophen-3-yl, 3-cyanothiophen-2-yl, pyridin-2-yl, pyridin-3-yl, 2-fluoropyridin-3-yl, 2-chloropyridin-3-yl, 2-methylpyridin-3-yl, 2-ethylpyridin-3-yl, 2-methoxypyridin-3-yl, 2-trifluoromethylpyridin-3-yl, 2-cyanopyridin-3-yl, 2-hydroxypyridin-3-yl, 4-fluoropyridin-3-yl, 4-chloropyridin-3-yl, 4-methylpyridin-3-yl, 4-ethylpyridin-3-yl, 4-methoxypyridin-3-yl, 4-trifluoromethylpyridin-3-yl, 4-cyanopyridin-3-yl, 4-hydroxypyridin-3-yl, pyridin-4-yl, 3-fluoropyridin-4-yl, 3-chloropyridin-4-yl, 3-methylpyridin-4-yl, 3-ethylpyridin-4-yl, 3-methoxypyridin-4-yl, 3-trifluoromethylpyridin-4-yl, 3-cyanopyridin-4-yl, or 3-hydroxypyridin-4-yl.

In some embodiments,

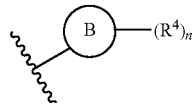

is phenyl, 2-fluorophenyl, 3-fluorophenyl, 4-fluorophenyl, 2,3-difluorophenyl, 2,4-difluorophenyl, 2,5-difluorophenyl, 2,6-difluorophenyl, 2-chlorophenyl, 3-chlorophenyl, 4-chlorophenyl, 2,3-dichlorophenyl, 2,4-dichlorophenyl, 2,5-dichlorophenyl, 2,6-dichlorophenyl, 2-bromophenyl, 3-bromophenyl, 4-bromophenyl, 2-methylphenyl, 3-methylphenyl, 4-methylphenyl, 2-ethylphenyl, 3-ethylphenyl, 4-ethylphenyl, 2-methoxyphenyl, 3-methoxyphenyl, 4-methoxyphenyl, 2-trifluoromethylphenyl, 3-trifluoromethylphenyl, 4-trifluoromethylphenyl, 2-fluoro-4-methoxyphenyl, 2-cyanophenyl, 3-cyanophenyl, 4-cyanophenyl, 2-fluoro-3-chlorophenyl, 2-fluoro-4-chlorophenyl, 2-fluoro-5-chlorophenyl, 2-fluoro-6-chlorophenyl, 2-chloro-3-fluorophenyl, 2-chloro-4-fluorophenyl, 2-chloro-5-fluorophenyl, 2-chloro-6-fluorophenyl, 2-methyl-3-chlorophenyl, 2-methyl-4-chlorophenyl, 2-methyl-5-chlorophenyl, 2-methyl-6-chlorophenyl, 2-methyl-3-fluorophenyl, 2-methyl-4-fluorophenyl, 2-methyl-5-fluorophenyl, 2-methyl-6-fluorophenyl, 3-methyl-4-fluorophenyl, 2-trifluoromethyl-3-chlorophenyl, 2-trifluoromethyl-4-chlorophenyl, 2-trifluoromethyl-5-chlorophenyl, 2-trifluoromethyl-6-chlorophenyl, 2-hydroxyphenyl, 3-hydroxyphenyl, 4-hydroxyphenyl, 2-hydroxymethylphenyl, 3-hydroxymethylphenyl, 4-hydroxymethylphenyl, 2-methylsulfonylphenyl, 3-methylsulfonylphenyl, 4-methylsulfonylphenyl, 2-phenylphenyl, 3-phenylphenyl, or 4-phenylphenyl.

In some embodiments, ring B is phenyl; and ring C is phenyl.

In some embodiments, $R^2$ is halogen, —CN, —NO$_2$, —S(=O)R$^{10}$, —S(=O)$_2$R$^{10}$, $C_1$-$C_6$alkyl, $C_1$-$C_6$fluoroalkyl, $C_1$-$C_6$deuteroalkyl, $C_3$-$C_6$cycloalkyl, —$C_1$-$C_4$alkylene-W, or —$C_1$-$C_4$fluoroalkylene-W. In some embodiments, $R^2$ is —CN, —S(=O)R$^{10}$, —S(=O)$_2$R$^{10}$, $C_1$-$C_6$alkyl, $C_1$-$C_6$fluoroalkyl, $C_3$-$C_6$cycloalkyl, —$C_1$-$C_4$alkylene-W, or —$C_1$-$C_4$fluoroalkylene-W. In some embodiments, $R^2$ is $C_1$-$C_6$alkyl, $C_1$-$C_6$fluoroalkyl, $C_3$-$C_6$cycloalkyl, —$C_1$-$C_4$alkylene-W, or —$C_1$-$C_4$fluoroalkylene-W. In some embodiments, $R^2$ is $C_1$-$C_4$alkyl, $C_1$-$C_4$fluoroalkyl, $C_1$-$C_4$deuteroalkyl, $C_3$-$C_6$cycloalkyl, —$C_1$-$C_2$alkylene-W, or —$C_1$-$C_2$fluoroalkylene-W. In some embodiments, W is hydroxy, halogen, CN, NO$_2$, $C_1$-$C_6$alkyl, $C_1$-$C_6$haloalkyl, $C_1$-$C_6$alkoxy, $C_1$-$C_6$haloalkoxy, or $C_3$-$C_6$cycloalkyl. In some embodiments, $R^2$ is $C_1$-$C_4$alkyl or —$C_1$-$C_2$alkylene-W. In some embodiments, $R^2$ is $C_1$-$C_6$alkyl, $C_1$-$C_6$fluoroalkyl, $C_1$-$C_6$deuteroalkyl, or $C_3$-$C_6$cycloalkyl. In some embodiments, $R^2$ is $C_1$-$C_6$alkyl or $C_3$-$C_6$cycloalkyl. In some embodiments, $R^2$ is $C_1$-$C_4$alkyl.

In some embodiments, $R^2$ is —S(=O)R$^{10}$, —S(=O)$_2$R$^{10}$, —CH$_3$, —CH$_2$CH$_3$, —CH$_2$CH$_2$CH$_3$, —CH(CH$_3$)$_2$, —CH$_2$F, —CHF$_2$, —CF$_3$, —CH$_2$CF$_3$, cyclopropyl, cyclobutyl, —CH$_2$—W, —CH$_2$CH$_2$—W, or —CF$_2$—W. In some embodiments, $R^2$ is —CH$_3$, —CH$_2$CH$_3$, —CH$_2$CH$_2$CH$_3$, —CH(CH$_3$)$_2$, —CH$_2$F, —CHF$_2$, —CF$_3$, —CH$_2$CF$_3$, —CH$_2$—W, —CH$_2$CH$_2$—W, or —CF$_2$—W. In some embodiments, $R^2$ is —CH$_3$, —CH$_2$CH$_3$, —CH$_2$CH$_2$CH$_3$, —CH(CH$_3$)$_2$, —CH$_2$F, —CHF$_2$, —CF$_3$, —CH$_2$CF$_3$, —CH$_2$CH$_2$F, cyclopropyl, or cyclobutyl. In some embodiments, $R^2$ is —CH$_2$CH$_3$, —CH(CH$_3$)$_2$, —CH$_2$CF$_3$, —CH$_2$CH$_2$F, cyclopropyl, or cyclobutyl. In some embodiments, $R^2$ is —CH$_2$CH$_3$, or cyclobutyl. In some embodiments, $R^2$ is —CH$_2$CH$_3$.

In some embodiments, W is hydroxy, halogen, CN, NO$_2$, $C_1$-$C_6$alkyl, $C_1$-$C_6$haloalkyl, $C_1$-$C_6$alkoxy, $C_1$-$C_6$haloalkoxy, or $C_3$-$C_6$cycloalkyl.

In some embodiments, W is hydroxy, halogen, CN, NO$_2$, $C_1$-$C_6$alkyl, $C_1$-$C_6$haloalkyl, $C_1$-$C_6$alkoxy, $C_1$-$C_6$haloalkoxy, or $C_3$-$C_6$cycloalkyl. In some embodiments, W is hydroxy, F, Cl, —CN, —NO$_2$, —CH$_3$, —CH$_2$CH$_3$, —CH$_2$CH$_2$CH$_3$, —CH(CH$_3$)$_2$, —CH$_2$F, —CHF₂, —CF₃, —OCH₃, —OCH₂CH₃, —OCH₂CH₂CH₃, —OCH(CH₃)₂, —OCH₂F, —OCHF₂, —OCF₃, cyclopropyl, or cyclobutyl.

In some embodiments, ring C is phenyl; $R^2$ is halogen, —CN, —NO₂, —S(=O)$R^{10}$, —S(=O)₂$R^{10}$, $C_1$-$C_6$alkyl, $C_1$-$C_6$fluoroalkyl, $C_1$-$C_6$deuteroalkyl, $C_3$-$C_6$cycloalkyl, —$C_1$-$C_4$alkylene-W, or —$C_1$-$C_4$fluoroalkylene-W; W is hydroxy, halogen, CN, NO₂, $C_1$-$C_6$alkyl, $C_1$-$C_6$haloalkyl, $C_1$-$C_6$alkoxy, $C_1$-$C_6$haloalkoxy, or $C_3$-$C_6$cycloalkyl.

In some embodiments, $R^2$ is halogen, —CN, —NO₂, —S(=O)$R^{10}$, —S(=O)₂$R^{10}$, $C_1$-$C_6$alkyl, $C_1$-$C_6$fluoroalkyl, $C_1$-$C_6$deuteroalkyl, $C_3$-$C_6$cycloalkyl, —$C_1$-$C_4$alkylene-W, or —$C_1$-$C_4$fluoroalkylene-W; W is hydroxy, halogen, CN, NO₂, $C_1$-$C_6$alkyl, $C_1$-$C_6$haloalkyl, $C_1$-$C_6$alkoxy, $C_1$-$C_6$haloalkoxy, or $C_3$-$C_6$cycloalkyl.

In some embodiments, $R^2$ is —S(=O)$R^{10}$, —S(=O)₂$R^{10}$, —CH₃, —CH₂CH₃, —CH₂CH₂CH₃, —CH(CH₃)₂, —CH₂F, —CHF₂, —CF₃, —CH₂CF₃, cyclopropyl, cyclobutyl, —CH₂—W, —CH₂CH₂—W, or —CF₂—W; W is hydroxy, F, Cl, —CN, —NO₂, —CH₃, —CH₂CH₃, —CH₂CH₂CH₃, —CH(CH₃)₂, —CH₂F, —CHF₂, —CF₃, —OCH₃, —OCH₂CH₃, —OCH₂CH₂CH₃, —OCH(CH₃)₂, —OCH₂F, —OCHF₂, —OCF₃, cyclopropyl, or cyclobutyl.

In some embodiments, $R^1$ is —C($R^6$)=C($R^7$)—Y; Y is C(=O)—Z or tetrazolyl; Z is —OH, —OR, —NR⁸R⁸', —NR⁸S(=O)₂$R^{10}$, or —NHOH; $R^2$ is —S(=O)$R^{10}$, —S(=O)₂$R^{10}$, —CH₃, —CH₂CH₃, —CH₂CH₂CH₃, —CH(CH₃)₂, —CH₂F, —CHF₂, —CF₃, —CH₂CF₃, cyclopropyl, cyclobutyl, —CH₂—W, —CH₂CH₂—W, or —CF₂—W; W is hydroxy, F, Cl, —CN, —NO₂, —CH₃, —CH₂CH₃, —CH₂CH₂CH₃, —CH(CH₃)₂, —CH₂F, —CHF₂, —CF₃, —OCH₃, —OCH₂CH₃, —OCH₂CH₂CH₃, —OCH(CH₃)₂, —OCH₂F, —OCHF₂, —OCF₃, cyclopropyl, or cyclobutyl; $R^6$ is H, F, Cl, —OCH₃, —OCH₂CH₃, —NH₂, —NH(CH₃), —N(CH₃)₂, —CH₃, or —CH₂CH₃; $R^7$ is H, F, Cl, —OCH₃, —OCH₂CH₃, —NH₂, —NH(CH₃), —N(CH₃)₂, —CH₃, or —CH₂CH₃.

In some embodiments, Z is —OH, —OCH₃, —OCH₂CH₃, —NH₂, —NHCH₃, —NHCH₂CH₃, —NHSO₂CH₃ or —NHOH; $R^6$ is H; $R^7$ is H.

In some embodiments, ring A is benzothiazolyl; ring C is phenyl; $R^1$ is —C($R^6$)=C($R^7$)—Y; $R^2$ is $C_1$-$C_4$alkyl, $C_1$-$C_4$fluoroalkyl, $C_1$-$C_4$deuteroalkyl, $C_3$-$C_6$cycloalkyl, or —$C_1$-$C_4$alkylene-W; W is hydroxy, halogen, CN, $C_1$-$C_4$alkyl, $C_1$-$C_4$haloalkyl, $C_1$-$C_4$alkoxy, $C_1$-$C_4$haloalkoxy, and $C_3$-$C_6$cycloalkyl; $R^6$ is H, $C_1$-$C_4$alkyl, or halogen; $R^7$ is H, $C_1$-$C_4$alkyl, or halogen.

In some embodiments, each $R^3$ is independently halogen, $C_1$-$C_4$alkyl, or $C_1$-$C_4$fluoroalkyl; each $R^4$ is independently halogen, —CN, —OR⁹, —S(=O)₂$R^{10}$, $C_1$-$C_4$alkyl, $C_1$-$C_4$fluoroalkyl, or $C_1$-$C_4$heteroalkyl; each R is independently halogen, —CN, —OR⁹, —S(=O)₂$R^{10}$, $C_1$-$C_4$alkyl, $C_1$-$C_4$fluoroalkyl, or $C_1$-$C_4$heteroalkyl; $R^9$ is H, $C_1$-$C_6$alkyl, $C_1$-$C_6$fluoroalkyl, or $C_3$-$C_6$cycloalkyl; $R^{10}$ is $C_1$-$C_6$alkyl; m is 0, 1, or 2; n is 0, 1, 2, 3, or 4; and p is 0, 1, or 2.

In some embodiments, $R^1$ is Y. In some embodiments, Y is C(=O)—$OR^{10}$.

In some embodiments, $R^1$ is

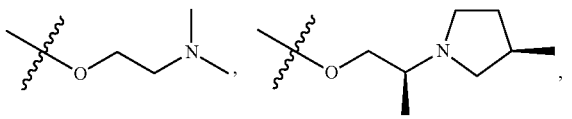

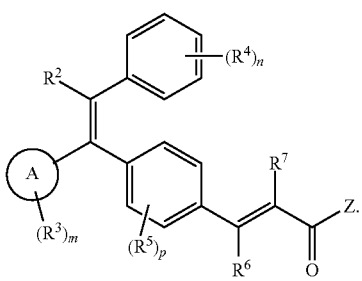

In some embodiments, $R^1$ is —C($R^6$)=C($R^7$)—Y. In some embodiments, $R^1$ is —CH=CH—Y. In some embodiments, $R^1$ is —C($R^6$)=C($R^7$)—C(=O)—Z. In some embodiments, $R^1$ is —CH=CH—C(=O)—Z.

In some embodiments, $R^1$ is —C($R^6$)=C($R^7$)—Y; Y is C(=O)—Z or tetrazolyl; Z is —OH, —$OR^{10}$, —NR⁸R⁸', —NR⁸S(=O)₂$R^{10}$, or —NHOH.

In some embodiments, $R^6$ is H, F, Cl, —OCH₃, —OCH₂CH₃, —NH₂, —NH(CH₃), —N(CH₃)₂, —CH₃, or —CH₂CH₃; $R^7$ is H, F, Cl, —OCH₃, —OCH₂CH₃, —NH₂, —NH(CH₃), —N(CH₃)₂, —CH₃, or —CH₂CH₃.

In some embodiments, $R^6$ is H. In some embodiments, $R^7$ is H. In some embodiments, $R^6$ is H; and $R^7$ is H.

In some embodiments, Z is —OH, —OCH₃, —OCH₂CH₃, —NH₂, —NHCH₃, —NHCH₂CH₃, —NHSO₂CH₃ or —NHOH. In some embodiments, Z is —OH, —OCH₃, —OCH₂CH₃, —NHSO₂CH₃ or —NHOH. In some embodiments, Z is —OH, —OCH₃, or —OCH₂CH₃.

In some embodiments, the compound of Formula (I) has the structure of Formula (VI):

Formula (VI)

In some embodiments, ring A is a 8-, 9- or 10-membered bicyclic heteroaryl containing 1-5 N atoms in the bicyclic ring; Z is —OH, —$OR^{10}$, —NR⁸R⁸', —NR⁸S(=O)₂$R^{10}$, or —NHOH.

In some embodiments, ring A is indolyl, azaindolyl, indazolyl, azaindazolyl, benzimidazolyl, azabenzimidazolyl, benzotriazolyl or azabenzotriazolyl.

In some embodiments, ring A is indazolyl or benzotriazolyl.

In some embodiments, the compound of Formula (VI) has the structure of Formula (VII):

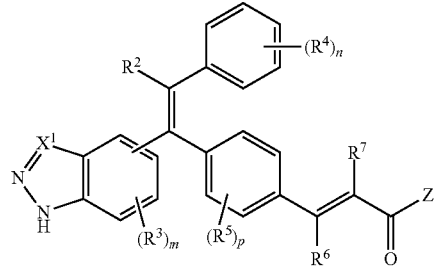

Formula (VII)

wherein,

X¹ is CH, CR³ or N.

In some embodiments, the compound of Formula (VII) has the structure of Formula (VIII):

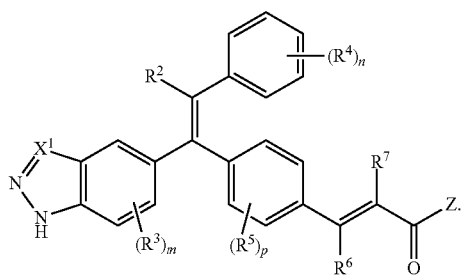

Formula (VIII)

In some embodiments, the compound of Formula (VII) has the structure of Formula (IX):

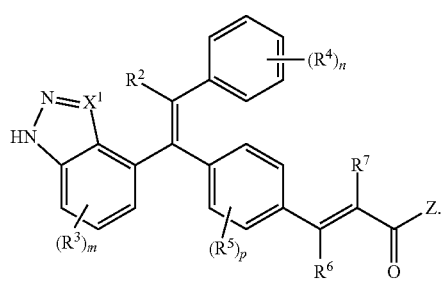

Formula (IX)

In some embodiments, the compound of Formula (VI) has the structure of Formula (X):

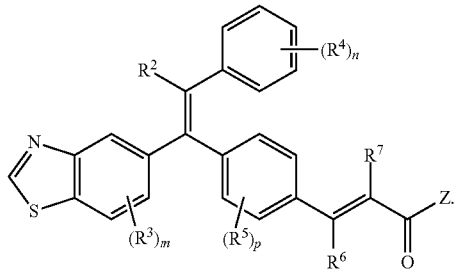

Formula (X)

In some embodiments, R² is —S(=O)R¹⁰, —S(=O)₂R¹⁰, C₁-C₄alkyl, C₁-C₄fluoroalkyl, C₁-C₄deuteroalkyl, C₃-C₆cycloalkyl, —C₁-C₄alkylene-W, —C₁-C₄fluoroalkylene-W, —C₃-C₆cycloalkylene-W; W is hydroxy, halogen, CN, NO₂, C₁-C₄alkyl, C₁-C₄haloalkyl, C₁-C₄alkoxy, C₁-C₄haloalkoxy, and C₃-C₆cycloalkyl; each R³, R⁴, R⁵ is independently selected from H, halogen, —NO₂, —NR⁸R⁸', —CN, —OH, —OR⁹, —SR⁹, —S(=O)R¹⁰, —S(=O)₂R¹⁰, —NHS(=O)₂R¹⁰, —S(=O)₂N(R⁹)₂, —C(=O)R¹⁰, —OC(=O)R¹⁰, —CO₂R⁹, —C(=O)N(R⁹)₂, C₁-C₄alkyl, C₂-C₄alkenyl, C₂-C₄alkynyl, C₁-C₄fluoroalkyl, C₁-C₄heteroalkyl, C₁-C₄fluoroalkoxy, and C₁-C₄alkoxy; R⁶ is H, F, Cl, —OCH₃, —OCH₂CH₃, —NH₂, —NH(CH₃), —N(CH₃)₂, —CH₃, or —CH₂CH₃; R⁷ is H, F, Cl, —OCH₃, —OCH₂CH₃, —NH₂, —NH(CH₃), —N(CH₃)₂, —CH₃, or —CH₂CH₃; m is 0, 1, or 2; n is 0, 1, or 2; and p is 0, 1, or 2.

In some embodiments, Z is —OH, —O(C₁-C₄alkyl), —NH₂, —NH(C₁-C₄alkyl), or —NHSO₂(C₁-C₄alkyl); R² is —S(=O)R¹⁰, —S(=O)₂R¹⁰, —CH₃, —CH₂CH₃, —CH₂CH₂CH₃, —CH(CH₃)₂, —CH₂F, —CHF₂, —CF₃, —CH₂CF₃, cyclopropyl, cyclobutyl, —CH₂—W, —CH₂CH₂—W, or —CF₂—W; W is hydroxy, F, Cl, —CN, —NO₂, —CH₃, —CH₂CH₃, —CH₂CH₂CH₃, —CH(CH₃)₂, —CH₂F, —CHF₂, —CF₃, —OCH₃, —OCH₂CH₃, —OCH₂CH₂CH₃, —OCH(CH₃)₂, —OCH₂F, —OCHF₂, —OCF₃, cyclopropyl, or cyclobutyl; each R³, R⁴, R⁵ is independently selected from H, halogen, —CN, —OH, —OR⁹, —SR⁹, —S(=O)R¹⁰, —S(=O)₂R¹⁰, —C(=O)R¹⁰, —OC(=O)R¹⁰, —CO₂R⁹, —C(=O)N(R⁹)₂, C₁-C₄alkyl, C₂-C₄alkenyl, C₂-C₄alkynyl, C₁-C₄fluoroalkyl, C₁-C₄heteroalkyl, C₁-C₄fluoroalkoxy, and C₁-C₄alkoxy; each R⁹ is independently selected from H, C₁-C₆alkyl, C₁-C₆fluoroalkyl, C₃-C₆cycloalkyl, substituted or unsubstituted phenyl, and substituted or unsubstituted benzyl; each R¹⁰ is independently selected from C₁-C₆alkyl, C₁-C₆fluoroalkyl, C₃-C₆cycloalkyl, substituted or unsubstituted phenyl, and substituted or unsubstituted benzyl.

In some embodiments, Z is —OH, —OCH₃, or —OCH₂CH₃; R² is —CH₂CH₃, —CH₂CF₃, —CH₂—W, or —CF₂—W; each R³, R⁴, R⁵ is independently selected from H, halogen, —CN, —OH, C₁-C₄alkyl, C₂-C₄alkenyl, C₂-C₄alkynyl, C₁-C₄fluoroalkyl, C₁-C₄heteroalkyl, C₁-C₄fluoroalkoxy, and C₁-C₄alkoxy.

In some embodiments, each R³, R⁴, R⁵ is independently selected from H, halogen, —NO₂, —NR⁸R⁸', —CN, —OH, —OR⁹, —SR⁹, —S(=O)R¹⁰, —S(=O)₂R¹⁰, —NHS(=O)₂R¹⁰, —S(=O)₂N(R⁹)₂, —C(=O)R¹⁰, —OC(=O)R¹⁰, —CO₂R⁹, —OCO₂R¹⁰, —C(=O)N(R⁹)₂, —OC(=O)N(R⁹)₂, —NR⁹C(=O)N(R⁹)₂, —NR⁹C(=O)R¹⁰, —NR⁹C(=O)OR¹⁰, substituted or unsubstituted C₁-C₆alkyl, substituted or unsubstituted C₂-C₆alkenyl, substituted or unsubstituted $C_2$-$C_6$alkynyl, substituted or unsubstituted $C_1$-$C_6$fluoroalkyl, substituted or unsubstituted $C_1$-$C_6$heteroalkyl, substituted or unsubstituted $C_1$-$C_6$fluoroalkoxy, and substituted or unsubstituted $C_1$-$C_6$alkoxy. In some embodiments, each $R^3$, $R^4$, $R^5$ is independently selected from H, halogen, —$NO_2$, —$NR^8R^{8'}$, —CN, —OH, —$OR^9$, —$SR^9$, —$S(=O)R^{10}$, —$S(=O)_2R^{10}$, —$NHS(=O)_2R^{10}$, —$S(=O)_2N(R^9)_2$, —$C(=O)R^{10}$, —$OC(=O)R^{10}$, —$CO_2R^9$, —$OCO_2R^{10}$, —$C(=O)N(R^9)_2$, —$OC(=O)N(R^9)_2$, —$NR^9C(=O)N(R^9)_2$, —$NR^9C(=O)R^{10}$, —$NR^9C(=O)OR^{10}$, $C_1$-$C_6$alkyl, $C_2$-$C_6$alkenyl, $C_2$-$C_6$alkynyl, $C_1$-$C_6$fluoroalkyl, $C_1$-$C_6$heteroalkyl, $C_1$-$C_6$fluoroalkoxy, and $C_1$-$C_6$alkoxy. In some embodiments, each $R^3$, $R^4$, $R^5$ is independently selected from H, halogen, —CN, —OH, —$OR^9$, —$S(=O)_2R^{10}$, $C_1$-$C_6$alkyl, $C_1$-$C_6$fluoroalkyl, $C_1$-$C_6$heteroalkyl, $C_1$-$C_6$fluoroalkoxy, and $C_1$-$C_6$alkoxy.

In some embodiments, m is 0, 1, 2, or 3. In some embodiments, m is 0, 1 or 2. In some embodiments, m is 0 or 1.

In some embodiments, n is 0, 1, 2, or 3. In some embodiments, n is 0, 1 or 2. In some embodiments, n is 0 or 1.

In some embodiments, p is 0, 1, 2, or 3. In some embodiments, p is 0, 1 or 2. In some embodiments, p is 0 or 1.

In some embodiments, $X^1$ is CH or $CR^3$. In some embodiments, $X^1$ is CH.

In some embodiments, the compound of Formula (I) has the structure of Formula (XII):

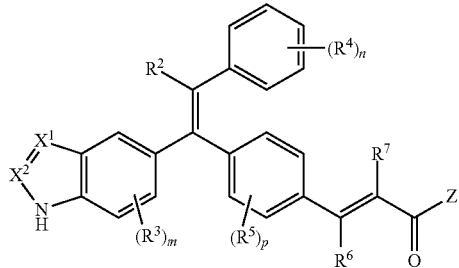

Formula (XII)

wherein,
$X^1$ is CH, $CR^3$ or N;
$X^2$ is N, CH, or $CR^3$;
Z is —OH or —$OR^{10}$;
$R^2$ is $C_1$-$C_4$alkyl, $C_1$-$C_4$fluoroalkyl, $C_1$-$C_4$deuteroalkyl, $C_3$-$C_6$cycloalkyl, or —$C_1$-$C_4$alkylene-W;
  W is hydroxy, halogen, CN, $C_1$-$C_4$alkyl, $C_1$-$C_4$haloalkyl, $C_1$-$C_4$alkoxy, $C_1$-$C_4$haloalkoxy, and $C_3$-$C_6$cycloalkyl;
each $R^3$ is independently halogen, $C_1$-$C_4$alkyl, or $C_1$-$C_4$fluoroalkyl;
each $R^4$ is independently halogen, —CN, —$OR^9$, —$S(=O)_2R^{10}$, $C_1$-$C_4$alkyl, $C_1$-$C_4$fluoroalkyl, or $C_1$-$C_4$heteroalkyl;
each $R^5$ is independently halogen, —CN, —$OR^9$, —$S(=O)_2R^{10}$, $C_1$-$C_4$alkyl, $C_1$-$C_4$fluoroalkyl, or $C_1$-$C_4$heteroalkyl;
$R^6$ is H, $C_1$-$C_4$alkyl, or halogen;
$R^7$ is H, $C_1$-$C_4$alkyl, or halogen;
$R^9$ is H, $C_1$-$C_6$alkyl, $C_1$-$C_6$fluoroalkyl, $C_3$-$C_6$cycloalkyl;

$R^{10}$ is $C_1$-$C_6$alkyl;
m is 0, 1, or 2;
n is 0, 1, 2, 3, or 4; and
p is 0, 1, or 2.

In some embodiments, $X^1$ is CH or $CR^3$; and $X^2$ is N. In some embodiments, $X^1$ is CH; and $X^2$ is N. In some embodiments, $X^1$ is CH or $CR^3$; and $X^2$ is CH or $CR^3$. In some embodiments, $X^1$ is CH; and $X^2$ is CH. In some embodiments, $X^1$ is N; and $X^2$ is N.

In some embodiments, Z is —OH. In some embodiments, Z is —$OR^{10}$. In some embodiments, Z is —OH, —$OCH_3$, or —$OCH_2CH_3$.

In some embodiments, $R^6$ is H, —$CH_3$, F, or Cl. In some embodiments, $R^6$ is H.

In some embodiments, $R^7$ is H, —$CH_3$, F, or Cl. In some embodiments, $R^7$ is H.

In some embodiments, $R^3$ is independently halogen, $C_1$-$C_4$alkyl, or $C_1$-$C_4$fluoroalkyl. In some embodiments, each $R^3$ is independently F, Cl, or —$CH_3$.

In some embodiments, each $R^4$ is independently halogen, —CN, —OH, —$OR^9$, —$S(=O)_2R^{10}$, $C_1$-$C_4$alkyl, $C_1$-$C_4$fluoroalkyl, or $C_1$-$C_4$heteroalkyl. In some embodiments, each $R^4$ is independently halogen, —CN, —OH, —$S(=O)_2CH_3$, —$S(=O)_2CH_2CH_3$, —$CH_3$, —$CH_2CH_3$, —$CF_3$, —$CH_2OH$, —$OCF_3$, —$OCH_3$, or —$OCH_2CH_3$. In some embodiments, each $R^4$ is independently F, Cl, —CN, —OH, —$CH_3$, —$CH_2CH_3$, —$CF_3$, —$CH_2OH$, —$OCF_3$, —$OCH_3$, or —$OCH_2CH_3$. In some embodiments, each $R^4$ is independently F or Cl.

In some embodiments, each $R^5$ is independently halogen, $C_1$-$C_4$alkyl, or $C_1$-$C_4$fluoroalkyl. In some embodiments, each $R^5$ is independently F, Cl, or —$CH_3$.

In some embodiments, m is 0 or 1. In some embodiments, m is 0. In some embodiments, m is 1.

In some embodiments, n is 0, 1, or 2. In some embodiments, n is 0. In some embodiments, n is 1. In some embodiments, n is 2.

In some embodiments, p is 0 or 1. In some embodiments, p is 0. In some embodiments, p is 1.

In some embodiments, Z is —OH; $R^6$ is H, —$CH_3$, F, or Cl; $R^7$ is H, —$CH_3$, F, or Cl; each $R^3$ is independently halogen, $C_1$-$C_4$alkyl, or $C_1$-$C_4$fluoroalkyl; each $R^4$ is independently halogen, —CN, —$OR^9$, —$S(=O)_2R^{10}$, $C_1$-$C_4$alkyl, $C_1$-$C_4$fluoroalkyl, or $C_1$-$C_4$heteroalkyl; each $R^5$ is independently halogen, $C_1$-$C_4$alkyl, or $C_1$-$C_4$fluoroalkyl; m is 0 or 1; n is 0, 1, or 2; and p is 0 or 1.

In some embodiments, $R^2$ is $C_1$-$C_4$alkyl, $C_1$-$C_4$fluoroalkyl, $C_1$-$C_4$deuteroalkyl, $C_3$-$C_6$cycloalkyl, or —$C_1$-$C_4$alkylene-W; W is hydroxy, halogen, CN, $C_1$-$C_4$alkoxy, or $C_3$-$C_6$cycloalkyl. In some embodiments, $R^2$ is $C_1$-$C_4$alkyl, $C_1$-$C_4$fluoroalkyl, or $C_1$-$C_4$deuteroalkyl. In some embodiments, $R^2$ is $C_1$-$C_4$alkyl. In some embodiments, $R^2$ is —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH_2F$, —$CHF_2$, —$CF_3$, —$CH_2CF_3$, —$CD_3$, —$CH_2CD_3$, —$CD_2CD_3$, cyclopropyl, cyclobutyl, cyclopentyl, cyclohexyl, —$CH_2$—W, or —$CH_2CH_2$—W; W is hydroxy, F, Cl, —CN, —$OCH_3$, —$OCH_2CH_3$, —$OCH_2CH_2CH_3$, —$OCH(CH_3)_2$, cyclopropyl, cyclobutyl, cyclopentyl, or cyclohexyl. In some embodiments, W is hydroxy, F, Cl, —CN, cyclopropyl, cyclobutyl, cyclopentyl, or cyclohexyl. In some embodiments, $R^2$ is —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH_2F$, —$CHF_2$, —$CF_3$, —$CH_2CF_3$, —$CD_3$, —$CH_2CD_3$, —$CD_2CD_3$, —$CH_2$—W, or —$CH_2CH_2$—W. In some embodiments, R² is —CH₃, —CH₂CH₃, —CH₂F, —CHF₂, —CF₃, —CH₂CF₃, —CD₃, —CD₂CD₃, —CH₂CD₃, or cyclopropyl.

In some embodiments, Z is —OH; R⁶ is H; R⁷ is H; m is 0; n is 0, 1, or 2; and p is 0.

In some embodiments, the compound of Formula (XII) has the structure of Formula (XIII), or a pharmaceutically acceptable salt, or N-oxide thereof:

Formula (XIII)

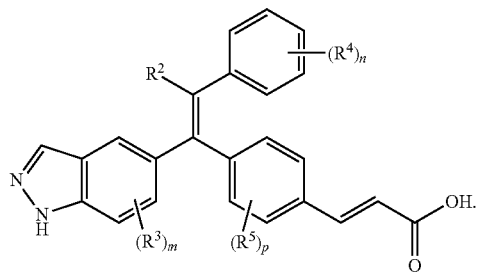

In some embodiments, the compound of Formula (XII) has the structure of Formula (XIV), or a pharmaceutically acceptable salt, or N-oxide thereof:

Formula (XVI)

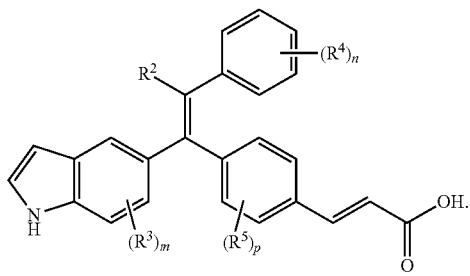

In some embodiments, the compound of Formula (X) has the structure of Formula (XV), or a pharmaceutically acceptable salt, or N-oxide thereof:

Formula (XV)

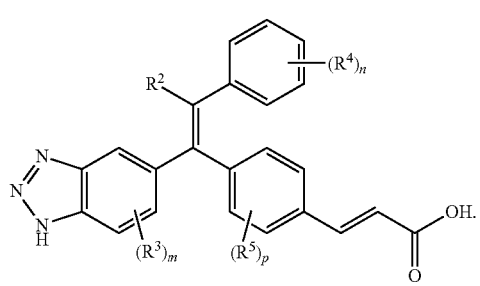

In some embodiments, the compound of Formula (X) has the structure of Formula (XVI), or a pharmaceutically acceptable salt, or N-oxide thereof:

Formula (XVI)

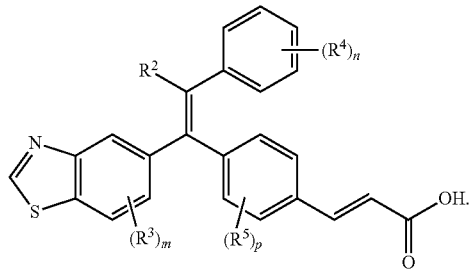

In some embodiments, each R³ is independently F, Cl, or —CH₃; each R⁴ is independently halogen, —CN, —OH, —S(=O)₂CH₃, —S(=O)₂CH₂CH₃, —CH₃, —CH₂CH₃, —CF₃, —CH₂OH, —OCF₃, —OCH₃, or —OCH₂CH₃; each R⁵ is independently F, Cl, or —CH₃; m is 0 or 1; n is 0, 1, or 2; and p is 0 or 1.

In some embodiments, R² is —CH₃, —CH₂CH₃, —CH₂CH₂CH₃, —CH(CH₃)₂, —CH₂CH₂CH₂CH₃, —CH₂CH(CH₃)₂, —CH₂F, —CHF₂, —CF₃, —CH₂CF₃, —CD₃, —CD₂CD₃, cyclopropyl, cyclobutyl, cyclopentyl, cyclohexyl, —CH₂—W, or —CH₂CH₂—W; W is hydroxy, F, Cl, —CN, —OCH₃, —OCH₂CH₃, —OCH₂CH₂CH₃, —OCH(CH₃)₂, cyclopropyl, cyclobutyl, cyclopentyl, or cyclohexyl.

In some embodiments, W is hydroxy, F, Cl, —CN, cyclopropyl, cyclobutyl, cyclopentyl, or cyclohexyl; each R⁴ is independently F, Cl, —CN, —OH, —CH₃, —CF₃, —OCF₃, or —OCH₃; m is 0; n is 0, 1, or 2; and p is 0.

In some embodiments, R² is —CH₂CH₃ or cyclobutyl; each R⁴ is independently F, Cl, —CN, —OH, —CH₃, —CH₂CH₃, —CF₃, —CH₂OH, —OCF₃, —OCH₃, or —OCH₂CH₃; m is 0; n is 0, 1, or 2; and p is 0.

In some embodiments, the compound of Formula (I) has the structure of Formula (XVII):

Formula (XVII)

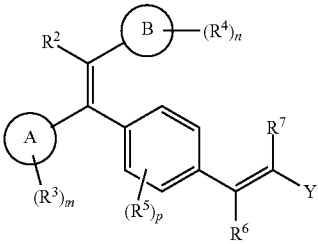

wherein,
ring A is 8-, 9- or 10-membered bicyclic heteroaryl;
ring B is phenyl, 5- or 6-membered monocyclic heteroaryl;
Y is —C(=O)—Z, tetrazolyl, or carboxylic acid bioisostere;
Z is —OH, —OR¹⁰, —NR⁸R⁸', —NR⁸S(=O)₂R¹⁰, —NHOH or —NR⁸OR¹⁰;
R² is halogen, CN, NO₂, —SR⁹, —S(=O)R¹⁰, —S(=O)₂ R¹⁰, —NHS(=O)₂R¹⁰, C₁-C₆alkyl, C₁-C₆fluoroalkyl, C₁-C₆deuteroalkyl, C₁-C₄alkoxy, C₁-C₄fluoroalkoxy, C₃-C₆cycloalkyl, —C₁-C₄alkylene-W, —C₁-C₄fluoroalkylene-W, —C₃-C₆cycloalkylene-W;
W is hydroxy, halogen, CN, NO₂, C₁-C₆alkyl, C₁-C₆haloalkyl, C₁-C₆alkoxy, C₁-C₆haloalkoxy, and C₃-C₆cycloalkyl;

each $R^3$, $R^4$, $R^5$ is independently selected from H, halogen, $-NO_2$, $-NR^8R^{8'}$, $-CN$, $-OH$, $-OR^9$, $-SR^9$, $-S(=O)R^{10}$, $-S(=O)_2R^{10}$, $-NHS(=O)_2R^{10}$, $-S(=O)_2N(R^9)_2$, $-C(=O)R^{10}$, $-OC(=O)R^{10}$, $-CO_2R^9$, $-OCO_2R^{10}$, $-C(=O)N(R^9)_2$, $-OC(=O)N(R^9)_2$, $-NR^9C(=O)N(R^9)_2$, $-NR^9C(=O)R^{10}$, $-NR^9C(=O)OR^{10}$, substituted or unsubstituted $C_1$-$C_6$alkyl, substituted or unsubstituted $C_2$-$C_6$alkenyl, substituted or unsubstituted $C_2$-$C_6$alkynyl, substituted or unsubstituted $C_1$-$C_6$fluoroalkyl, substituted or unsubstituted $C_1$-$C_6$heteroalkyl, substituted or unsubstituted $C_1$-$C_6$fluoroalkoxy, substituted or unsubstituted $C_1$-$C_6$alkoxy, substituted or unsubstituted phenyl and substituted or unsubstituted monocyclic heteroaryl;

$R^6$ is H, $C_1$-$C_4$alkyl, or halogen;

$R^7$ is H, $C_1$-$C_4$alkyl, or halogen;

$R^8$ and $R^{8'}$ is independently H, substituted or unsubstituted $C_1$-$C_6$alkyl, substituted or unsubstituted $C_2$-$C_6$alkenyl, substituted or unsubstituted $C_2$-$C_6$alkynyl, substituted or unsubstituted $C_1$-$C_6$fluoroalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted phenyl, substituted or unsubstituted monocyclic heteroaryl, or substituted or unsubstituted benzyl;

each $R^9$ is independently selected from H, substituted or unsubstituted $C_1$-$C_6$alkyl, substituted or unsubstituted $C_1$-$C_6$heteroalkyl, substituted or unsubstituted $C_1$-$C_6$fluoroalkyl, substituted or unsubstituted $C_3$-$C_{10}$cycloalkyl, substituted or unsubstituted $C_2$-$C_{10}$heterocycloalkyl, substituted or unsubstituted aryl, substituted or unsubstituted heteroaryl and substituted or unsubstituted benzyl;

each $R^{10}$ is independently selected from substituted or unsubstituted $C_1$-$C_6$alkyl, substituted or unsubstituted $C_1$-$C_6$heteroalkyl, substituted or unsubstituted $C_1$-$C_6$fluoroalkyl, substituted or unsubstituted $C_3$-$C_{10}$cycloalkyl, substituted or unsubstituted $C_2$-$C_{10}$heterocycloalkyl, substituted or unsubstituted aryl, substituted or unsubstituted heteroaryl and substituted or unsubstituted benzyl;

m is 0, 1, or 2;

n is 0, 1, 2, 3 or 4; and p is 0, 1, or 2.

In some embodiments, ring A is indolizinyl, azaindolizinyl, indolyl, azaindolyl, indazolyl, azaindazolyl, benzimidazolyl, azabenzimidazolyl, benzotriazolyl, azabenzotriazolyl, benzoxazolyl, azabenzoxazolyl, benzisoxazolyl, azabenzisoxazolyl, benzofuranyl, azabenzofuranyl, benzothienyl, azabenzothienyl, benzothiazolyl, or azabenzothiazolyl; ring B is phenyl, furanyl, thienyl, pyrrolyl, imidazolyl, pyrazolyl, triazolyl, pyridinyl, pyrimidinyl, pyrazinyl, pyridazinyl, or triazinyl; Y is $-C(=O)-Z$,

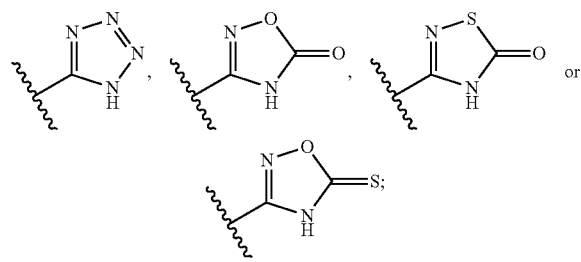

Z is $-OH$, $-OR^{10}$, $-NR^8R^{8'}$, or $-NR^8S(=O)_2R^{10}$; $R^2$ is $C_1$-$C_6$alkyl, $C_1$-$C_6$fluoroalkyl, $C_1$-$C_6$deuteroalkyl, or $C_3$-$C_6$cycloalkyl; each $R^3$ is independently halogen, $C_1$-$C_4$alkyl, or $C_1$-$C_4$fluoroalkyl; each $R^4$ is independently selected from H, halogen, $-CN$, $-OH$, $-OR^9$, $-SR^9$, $-S(=O)R^{10}$, $-S(=O)_2R^{10}$, $-C(=O)R^{10}$, $-OC(=O)R^{10}$, $-CO_2R^9$, $-C(=O)N(R^9)_2$, $C_1$-$C_4$alkyl, $C_2$-$C_4$alkenyl, $C_2$-$C_4$alkynyl, $C_1$-$C_4$fluoroalkyl, $C_1$-$C_4$heteroalkyl, $C_1$-$C_4$fluoroalkoxy, and $C_1$-$C_4$alkoxy; each $R^5$ is independently halogen, $C_1$-$C_4$alkyl, or $C_1$-$C_4$fluoroalkyl; $R^6$ is H, $C_1$-$C_4$alkyl, or halogen; $R^7$ is H, $C_1$-$C_4$alkyl, or halogen; $R^8$ and $R^{8'}$ is independently H or $C_1$-$C_6$alkyl; each $R^9$ is independently selected from H and $C_1$-$C_6$alkyl; $R^{10}$ is $C_1$-$C_6$alkyl; p is 0 or 1.

In some embodiments, ring A is indazolyl, or benzothiazolyl; ring B is phenyl, thienyl, or pyridinyl; Y is $-C(=O)-Z$,

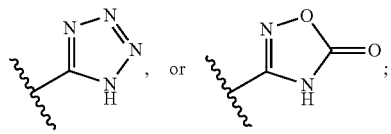 [SMILES: *c1nnn[nH]1 ; *c1noc(=O)[nH]1]

Z is $-OH$, $-OR^{10}$, $-NR^8R^{8'}$, or $-NR^8S(=O)_2R^{10}$; $R^2$ is $C_1$-$C_6$alkyl or $C_3$-$C_6$cycloalkyl; each $R^3$ is independently halogen, $C_1$-$C_4$alkyl, or $C_1$-$C_4$fluoroalkyl; each $R^4$ is independently selected from H, halogen, $-CN$, $-OH$, $-OR^9$, $-SR^9$, $-S(=O)R^{10}$, $-S(=O)_2R^{10}$, $-C(=O)R^{10}$, $-OC(=O)R^{10}$, $-CO_2R^9$, $-C(=O)N(R^9)_2$, $C_1$-$C_4$alkyl, $C_2$-$C_4$alkenyl, $C_2$-$C_4$alkynyl, $C_1$-$C_4$fluoroalkyl, $C_1$-$C_4$heteroalkyl, $C_1$-$C_4$fluoroalkoxy, and $C_1$-$C_4$alkoxy; each $R^5$ is independently halogen, $C_1$-$C_4$alkyl, or $C_1$-$C_4$fluoroalkyl; $R^6$ is H; $R^7$ is H; $R^8$ and $R^{8'}$ is independently H or $C_1$-$C_6$alkyl; each $R^9$ is independently selected from H and $C_1$-$C_6$alkyl; $R^{10}$ is $C_1$-$C_6$alkyl; p is 0.

In some embodiments, ring A is

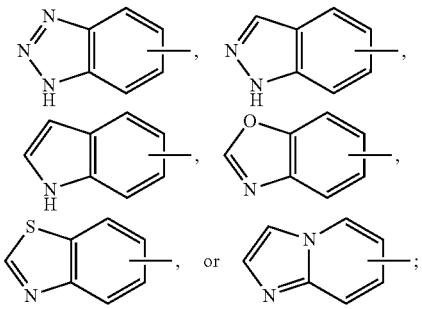

ring B is phenyl, thienyl, or pyridinyl; Y is $-C(=O)-Z$,

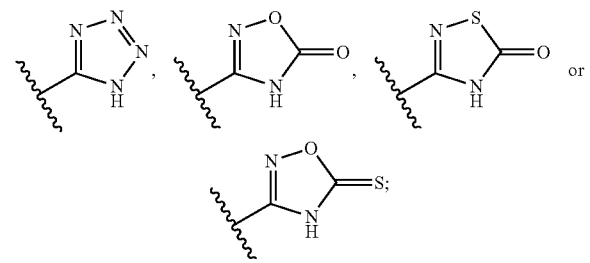

Z is $-OH$, $-OR^{10}$, $-NR^8R^{8'}$, or $-NR^8S(=O)_2R^{10}$; $R^2$ is $C_1$-$C_6$alkyl, $C_1$-$C_6$fluoroalkyl, $C_1$-$C_6$deuteroalkyl, or $C_3$-$C_6$cycloalkyl; each $R^3$ is independently halogen, $-CN$, $C_1$-$C_4$alkyl, or $C_1$-$C_4$fluoroalkyl; each $R^4$ is independently selected from H, halogen, $-CN$, $-OH$, $-OR^9$, $-SR^9$, $-S(=O)R^{10}$, $-S(=O)_2R^{10}$, $-C(=O)R^{10}$, $-OC(=O)R^{10}$, $-CO_2R^9$, $-C(=O)N(R^9)_2$, $C_1$-$C_4$alkyl, $C_2$-$C_4$alkenyl, $C_2$-$C_4$alkynyl, $C_1$-$C_4$fluoroalkyl, $C_1$-$C_4$heteroalkyl, $C_1$-$C_4$fluoroalkoxy, and $C_1$-$C_4$alkoxy; each $R^5$ is independently halogen, $C_1$-$C_4$alkyl, or $C_1$-$C_4$fluoroalkyl; $R^6$ is H, $C_1$-$C_4$alkyl, or halogen; $R^7$ is H, $C_1$-$C_4$alkyl, or halogen; $R^8$ and $R^{8'}$ is independently H or $C_1$-$C_6$alkyl; each $R^9$ is independently selected from H and $C_1$-$C_6$alkyl; $R^{10}$ is $C_1$-$C_6$alkyl; p is 0 or 1.

In some embodiments, ring A is

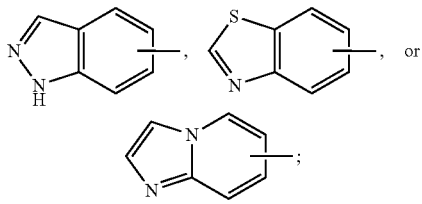

ring B is phenyl, thienyl, or pyridinyl; Y is —C(=O)—Z,

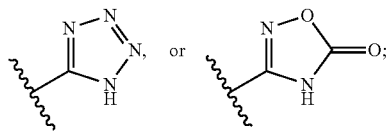 [SMILES: *c1nnn[nH]1 ; *c1noc(=O)[nH]1]

Z is —OH, —OR$^{10}$, —NR$^8$R$^{8'}$, or —NR$^8$S(=O)$_2$R$^{10}$; R$^2$ is $C_1$-$C_6$alkyl or $C_3$-$C_6$cycloalkyl; each R$^3$ is independently halogen, —CN, $C_1$-$C_4$alkyl, or $C_1$-$C_4$fluoroalkyl; each R$^4$ is independently selected from H, halogen, —CN, —OH, —OR$^9$, —SR$^9$, —S(=O)R$^{10}$, —S(=O)$_2$R$^{10}$, —C(=O)R$^{10}$, —OC(=O)R$^{10}$, —CO$_2$R$^9$, —C(=O)N(R$^9$)$_2$, $C_1$-$C_4$alkyl, $C_2$-$C_4$alkenyl, $C_2$-$C_4$alkynyl, $C_1$-$C_4$fluoroalkyl, $C_1$-$C_4$heteroalkyl, $C_1$-$C_4$fluoroalkoxy, and $C_1$-$C_4$alkoxy; each R$^5$ is independently halogen, $C_1$-$C_4$alkyl, or $C_1$-$C_4$fluoroalkyl; R$^6$ is H; R$^7$ is H; R$^8$ and R$^{8'}$ is independently H or $C_1$-$C_6$alkyl; each R$^9$ is independently selected from H and $C_1$-$C_6$alkyl; R$^{10}$ is $C_1$-$C_6$alkyl; p is 0.

Throughout the specification, groups and substituents thereof can be chosen by one skilled in the field to provide stable moieties and compounds.

In some embodiments, the compound of Formula (I) has the structure of Formula (II), Formula (III), Formula (IV), Formula (V), Formula (VI), Formula (VII), Formula (VIII), Formula (IX), Formula (X), Formula (XI), Formula (XII), Formula (XIII), Formula (XIV) Formula (XV), Formula (XVI) or Formula (XVII).

In some embodiments, the compound of Formula (I) is a compound presented in Table 1, or a pharmaceutically acceptable salt thereof:

TABLE 1

| Compound | Name | Structure | LCMS [M + H]$^+$ |
|---|---|---|---|
| 1 | (E)-Ethyl 3-(4-((E)-1-(1H-indazol-5-yl)-2-phenylbut-1-en-1-yl)phenyl)acrylate | 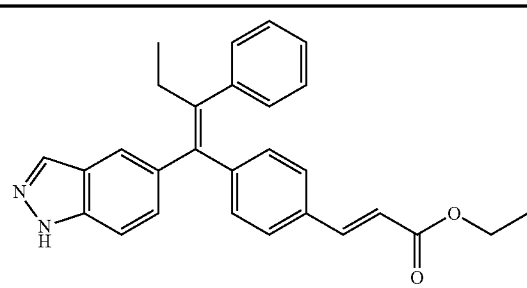 | 423 |
| 2 | (E)-3-(4-((E)-1-(1H-Indazol-5-yl)-2-phenylbut-1-en-1-yl)phenyl)acrylic acid | 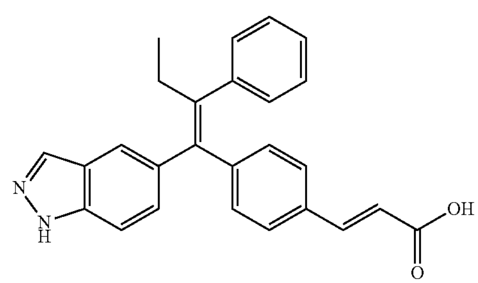 [SMILES: CC/C(=C(/c1ccc(/C=C/C(=O)O)cc1)c1ccc2[nH]ncc2c1)c1ccccc1] | 395 |
| 3 | (E)-3-(4-((E)-1-(1H-Benzo[d][1,2,3]triazol-5-yl)-2-phenylbut-1-en-1-yl)phenyl)acrylic acid | 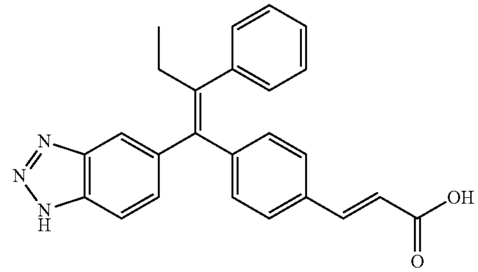 [SMILES: CC/C(=C(/c1ccc(/C=C/C(=O)O)cc1)c1ccc2[nH]nnc2c1)c1ccccc1] | 396 |

TABLE 1-continued

| Compound | Name | Structure | LCMS [M + H]+ |
|---|---|---|---|
| 4 | (E)-3-(4-((E)-2-(4-Fluorophenyl)-1-(1H-indazol-5-yl)but-1-en-1-yl)phenyl)acrylic acid | 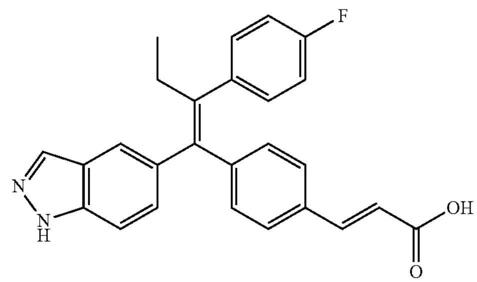 [SMILES: CC/C(=C(/c1ccc(/C=C/C(=O)O)cc1)c1ccc2[nH]ncc2c1)c1ccc(F)cc1] | 413 |
| 5 | (E)-3-(4-((E)-1-(1H-Indazol-6-yl)-2-phenylbut-1-en-1-yl)phenyl)acrylic acid | 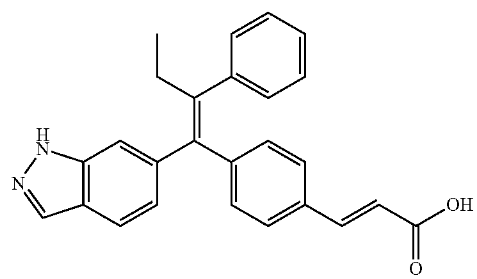 [SMILES: CC/C(=C(/c1ccc(/C=C/C(=O)O)cc1)c1ccc2cn[nH]c2c1)c1ccccc1] | 395 |
| 6 | (E)-3-(4-((E)-2-(4-Chlorophenyl)-1-(1H-indazol-5-yl)but-1-en-1-yl)phenyl)acrylic acid | 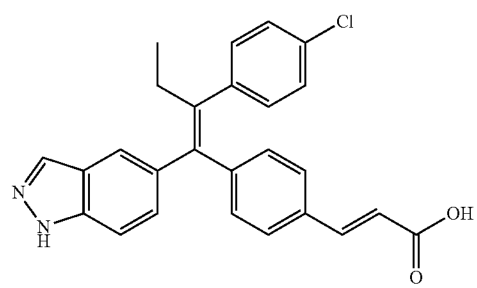 [SMILES: CC/C(=C(/c1ccc(/C=C/C(=O)O)cc1)c1ccc2[nH]ncc2c1)c1ccc(Cl)cc1] | 429 |
| 7 | (E)-3-(4-((E)-1-(1H-Indazol-5-yl)-2-(3-methoxyphenyl)but-1-en-1-yl)phenyl)acrylic acid | 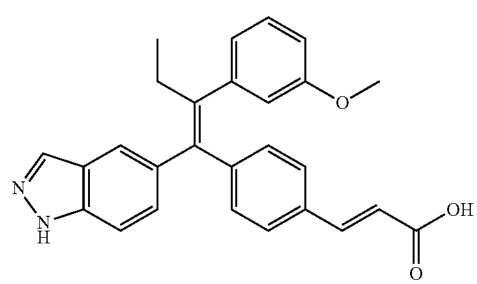 [SMILES: CC/C(=C(/c1ccc(/C=C/C(=O)O)cc1)c1ccc2[nH]ncc2c1)c1cccc(OC)c1] | 425 |
| 8 | (E)-3-(4-((E)-2-(3-(Hydroxymethyl)phenyl)-1-(1H-indazol-5-yl)but-1-en-1-yl)phenyl)acrylic acid | 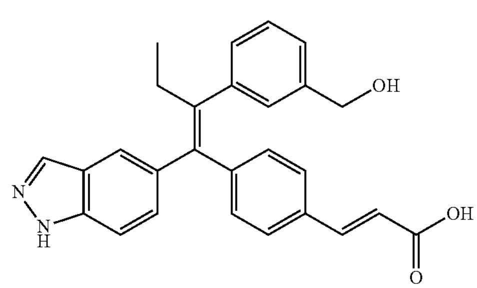 [SMILES: CC/C(=C(/c1ccc(/C=C/C(=O)O)cc1)c1ccc2[nH]ncc2c1)c1cccc(CO)c1] | 425 |

TABLE 1-continued

| Compound | Name | Structure | LCMS [M + H]+ |
|---|---|---|---|
| 9 | (E)-3-(4-((E)-2-(4-(Hydroxymethyl)phenyl)-1-(1H-indazol-5-yl)but-1-en-1-yl)phenyl)acrylic acid | 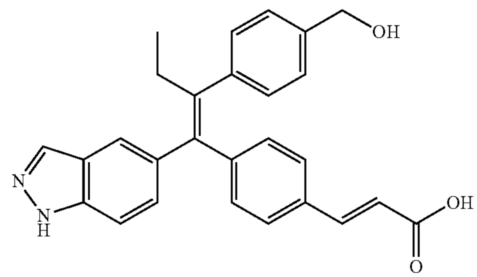 [SMILES: CC/C(=C(/c1ccc(/C=C/C(=O)O)cc1)c1ccc2[nH]ncc2c1)c1ccc(CO)cc1] | 425 |
| 10 | (E)-3-(4-((E)-2-(2-(Hydroxymethyl)phenyl)-1-(1H-indazol-5-yl)but-1-en-1-yl)phenyl)acrylic acid | 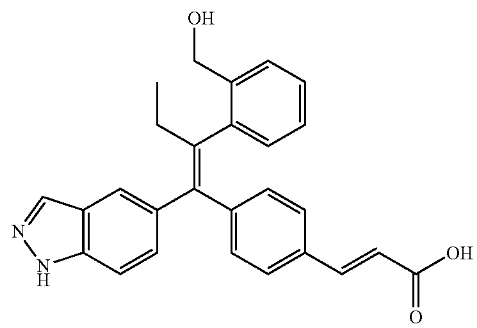 [SMILES: CC/C(=C(/c1ccc(/C=C/C(=O)O)cc1)c1ccc2[nH]ncc2c1)c1ccccc1CO] | 425 |
| 11 | (E)-3-(4-((E)-1-(1H-Indazol-5-yl)-2-(o-tolyl)but-1-en-1-yl)phenyl)acrylic acid | 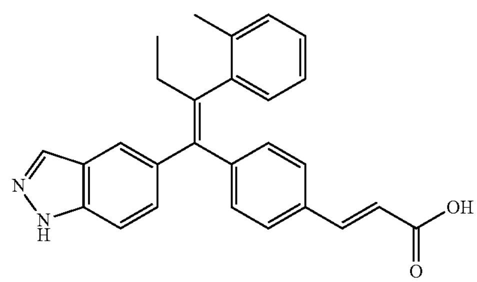 | 409 |
| 12 | (E)-3-(4-((E)-1-(1H-Indazol-5-yl)-2-(m-tolyl)but-1-en-1-yl)phenyl)acrylic acid | 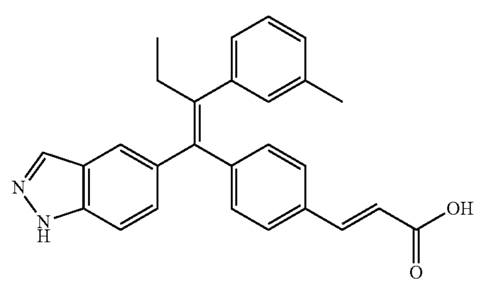 [SMILES: CC/C(=C(/c1ccc(/C=C/C(=O)O)cc1)c1ccc2[nH]ncc2c1)c1cccc(C)c1] | 409 |
| 13 | (E)-3-(4-((E)-1-(1H-Indazol-5-yl)-2-(p-tolyl)but-1-en-1-yl)phenyl)acrylic acid | 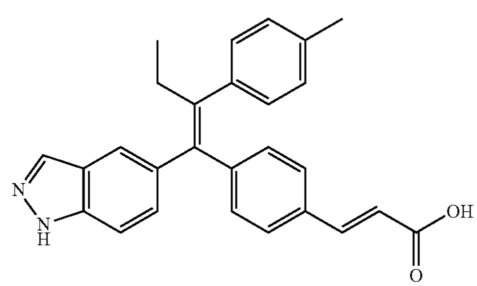 [SMILES: CC/C(=C(/c1ccc(/C=C/C(=O)O)cc1)c1ccc2[nH]ncc2c1)c1ccc(C)cc1] | 409 |

TABLE 1-continued

| Compound | Name | Structure | LCMS [M + H]+ |
|---|---|---|---|
| 14 | (E)-3-(4-((E)-1-(1H-Indazol-5-yl)-2-(2-methoxyphenyl)but-1-en-1-yl)phenyl)acrylic acid | 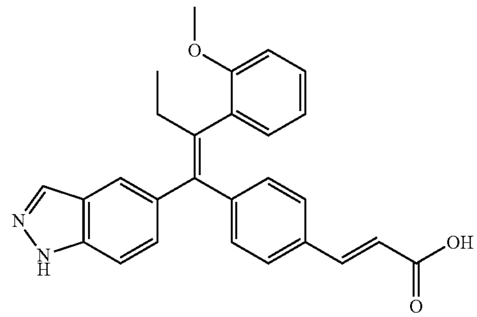 [SMILES: CC/C(=C(/c1ccc(/C=C/C(=O)O)cc1)c1ccc2[nH]ncc2c1)c1ccccc1OC] | 425 |
| 15 | (E)-3-(4-((E)-1-(1H-Indazol-5-yl)-2-(4-methoxyphenyl)but-1-en-1-yl)phenyl)acrylic acid | 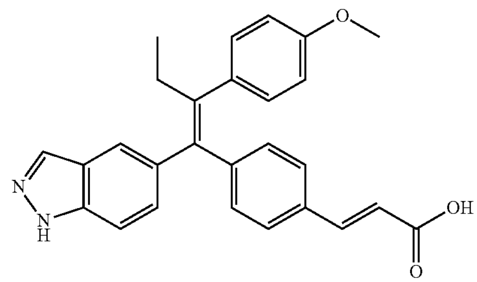 [SMILES: CC/C(=C(/c1ccc(/C=C/C(=O)O)cc1)c1ccc2[nH]ncc2c1)c1ccc(OC)cc1] | 425 |
| 16 | ((E)-3-(4-((E)-2-(2-Chlorophenyl)-1-(1H-indazol-5-yl)but-1-en-1-yl)phenyl)acrylic acid | 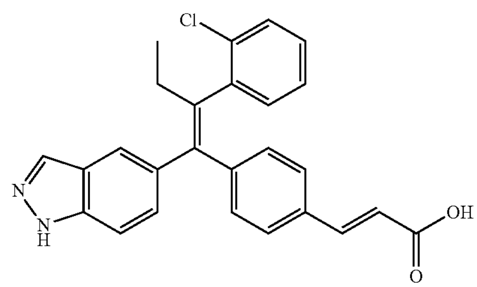 | 429 |
| 17 | (E)-3-(4-((E)-2-(3-Chlorophenyl)-1-(1H-indazol-5-yl)but-1-en-1-yl)phenyl)acrylic acid | 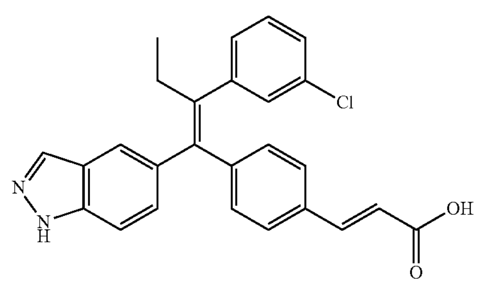 [SMILES: CC/C(=C(/c1ccc(/C=C/C(=O)O)cc1)c1ccc2[nH]ncc2c1)c1cccc(Cl)c1] | 429 |
| 18 | (E)-3-(4-((E)-1-(1H-Indazol-4-yl)-2-phenylbut-1-en-1-yl)phenyl)acrylic acid | 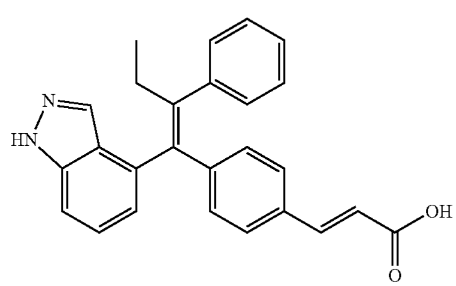 [SMILES: CC/C(=C(/c1ccc(/C=C/C(=O)O)cc1)c1cccc2[nH]ncc12)c1ccccc1] | 395 |

TABLE 1-continued

| Compound | Name | Structure | LCMS [M + H]+ |
|---|---|---|---|
| 19 | (E)-3-(4-((E)-2-(2-Fluorophenyl)-1-(1H-indazol-5-yl)but-1-en-1-yl)phenyl)acrylic acid | 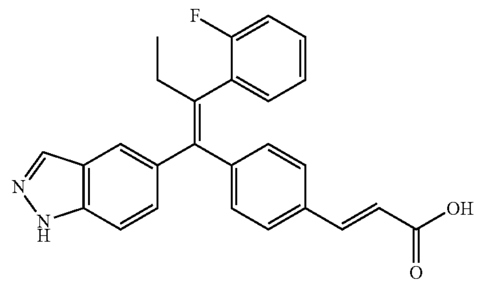 [SMILES: CC/C(=C(/c1ccc(/C=C/C(=O)O)cc1)c1ccc2[nH]ncc2c1)c1ccccc1F] | 413 |
| 20 | (E)-3-(4-((E)-2-(3-Fluorophenyl)-1-(1H-indazol-5-yl)but-1-en-1-yl)phenyl)acrylic acid | 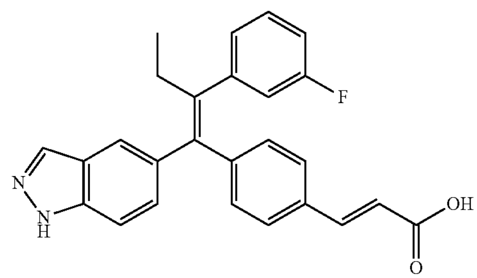 [SMILES: CC/C(=C(/c1ccc(/C=C/C(=O)O)cc1)c1ccc2[nH]ncc2c1)c1cccc(F)c1] | 413 |
| 21 | (E)-3-(4-((E)-1-(1H-Indazol-4-yl)-2-(o-tolyl)but-1-en-1-yl)phenyl)acrylic acid | 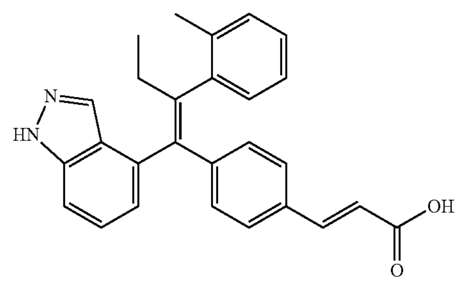 [SMILES: CC/C(=C(/c1ccc(/C=C/C(=O)O)cc1)c1cccc2[nH]ncc12)c1ccccc1C] | 409 |
| 22 | (E)-3-(4-((E)-2-(2-Chlorophenyl)-1-(1H-indazol-4-yl)but-1-en-1-yl)phenyl)acrylic acid | 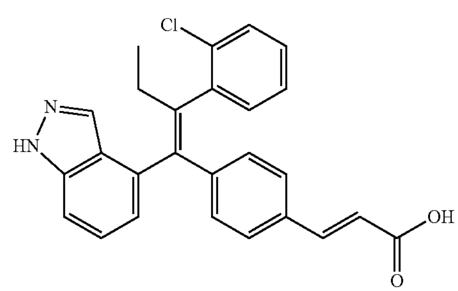 [SMILES: CC/C(=C(/c1ccc(/C=C/C(=O)O)cc1)c1cccc2[nH]ncc12)c1ccccc1Cl] | 429 |
| 23 | (E)-3-(4-((E)-1-(1H-Indazol-5-yl)-2-(thiophen-2-yl)but-1-en-1-yl)phenyl)acrylic acid | 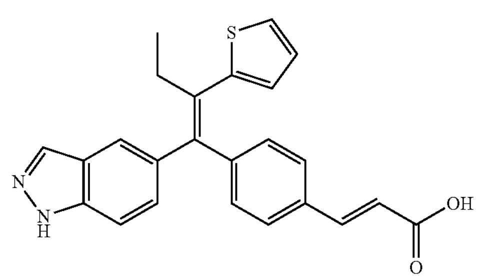 [SMILES: CC/C(=C(/c1ccc(/C=C/C(=O)O)cc1)c1ccc2[nH]ncc2c1)c1cccs1] | 401 |

TABLE 1-continued

| Compound | Name | Structure | LCMS [M + H]+ |
|---|---|---|---|
| 24 | (E)-3-(4-((E)-1-(1H-Indazol-5-yl)-2-(thiophen-3-yl)but-1-en-1-yl)phenyl)acrylic acid | 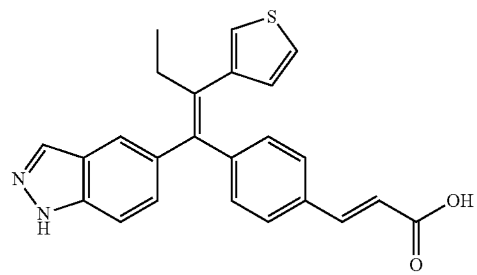 [SMILES: CC/C(=C(/c1ccc(/C=C/C(=O)O)cc1)c1ccc2[nH]ncc2c1)c1ccsc1] | 401 |
| 25 | (E)-3-(4-((E)-1-(1H-Indazol-5-yl)-2-(pyridin-2-yl)but-1-en-1-yl)phenyl)acrylic acid | 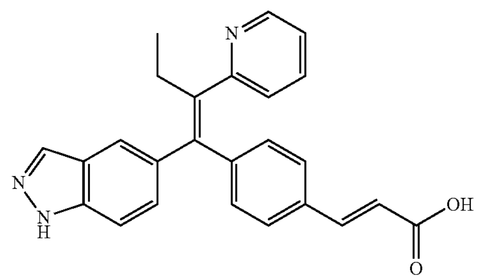 [SMILES: CC/C(=C(/c1ccc(/C=C/C(=O)O)cc1)c1ccc2[nH]ncc2c1)c1ccccn1] | 396 |
| 26 | (E)-3-(4-((E)-2-(2-Ethylphenyl)-1-(1H-indazol-5-yl)but-1-en-1-yl)phenyl)acrylic acid | 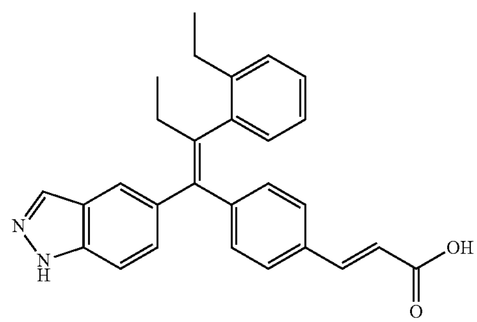 [SMILES: CC/C(=C(/c1ccc(/C=C/C(=O)O)cc1)c1ccc2[nH]ncc2c1)c1ccccc1CC] | 423 |
| 27 | (E)-3-(4-((E)-1-(1H-Indazol-5-yl)-2-(2-(trifluoromethyl)phenyl)but-1-en-1-yl)phenyl)acrylic acid | 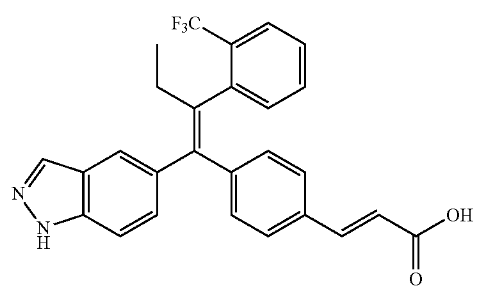 [SMILES: CC/C(=C(/c1ccc(/C=C/C(=O)O)cc1)c1ccc2[nH]ncc2c1)c1ccccc1C(F)(F)F] | 463 |
| 28 | (E)-3-(4-((E)-2-([1,1'-Biphenyl]-2-yl)-1-(1H-indazol-5-yl)but-1-en-1-yl)phenyl)acrylic acid | 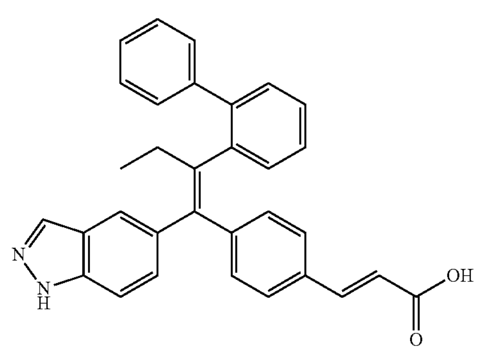 [SMILES: CC/C(=C(/c1ccc(/C=C/C(=O)O)cc1)c1ccc2[nH]ncc2c1)c1ccccc1-c1ccccc1] | 471 |

TABLE 1-continued

| Compound | Name | Structure | LCMS [M + H]+ |
|---|---|---|---|
| 29 | (E)-3-(4-((E)-4-Chloro-1-(1H-indazol-5-yl)-2-phenylbut-1-en-1-yl)phenyl)acrylic acid | 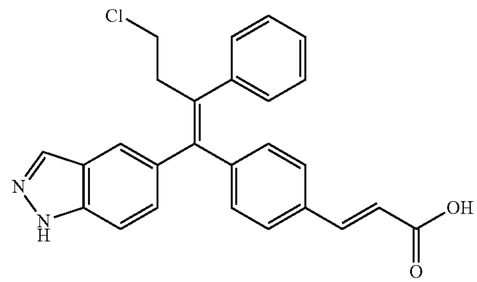 [SMILES: O=C(O)/C=C/c1ccc(/C(=C(/CCCl)c2ccccc2)c2ccc3[nH]ncc3c2)cc1] | 429 |
| 30 | (E)-3-(4-((E)-2-(2-Chloro-4-fluorophenyl)-1-(1H-indazol-4-yl)but-1-en-1-yl)phenyl)acrylic acid | 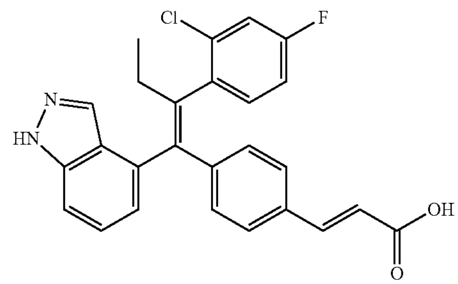 [SMILES: CC/C(=C(/c1ccc(/C=C/C(=O)O)cc1)c1cccc2[nH]ncc12)c1ccc(F)cc1Cl] | 447 |
| 31 | (E)-3-(4-((E)-2-(2-Fluorophenyl)-1-(1H-indazol-4-yl)but-1-en-1-yl)phenyl)acrylic acid | 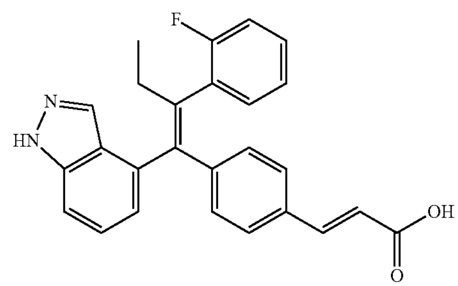 [SMILES: CC/C(=C(/c1ccc(/C=C/C(=O)O)cc1)c1cccc2[nH]ncc12)c1ccccc1F] | 413 |
| 32 | (E)-3-(4-((E)-2-(2-Cyanophenyl)-1-(1H-indazol-5-yl)but-1-en-1-yl)phenyl)acrylic acid | 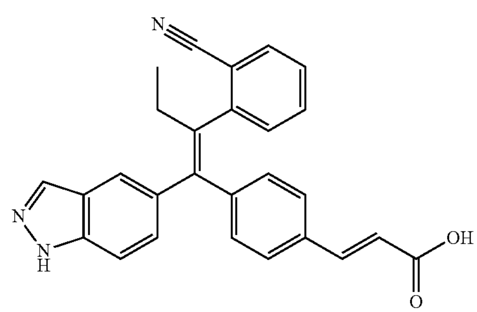 [SMILES: CC/C(=C(/c1ccc(/C=C/C(=O)O)cc1)c1ccc2[nH]ncc2c1)c1ccccc1C#N] | 420 |
| 33 | (E)-3-(4-((E)-2-(2,4-Difluorophenyl)-1-(1H-indazol-5-yl)but-1-en-1-yl)phenyl)acrylic acid | 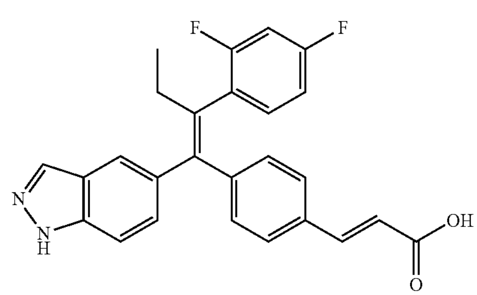 [SMILES: CC/C(=C(/c1ccc(/C=C/C(=O)O)cc1)c1ccc2[nH]ncc2c1)c1ccc(F)cc1F] | 431 |

TABLE 1-continued

| Compound | Name | Structure | LCMS [M + H]+ |
|---|---|---|---|
| 34 | (E)-3-(4-((E)-2-(2-Chloro-3-fluorophenyl)-1-(1H-indazol-5-yl)but-1-en-1-yl)phenyl)acrylic acid | 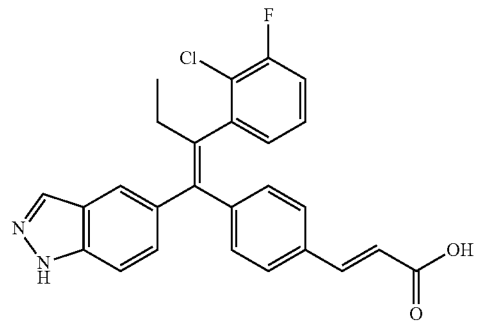 [SMILES: CC/C(=C(/c1ccc(/C=C/C(=O)O)cc1)c1ccc2[nH]ncc2c1)c1cccc(F)c1Cl] | 447 |
| 35 | (E)-3-(4-((E)-2-Cyclopropyl-1-(1H-indazol-5-yl)-2-phenylvinyl)phenyl)acrylic acid | 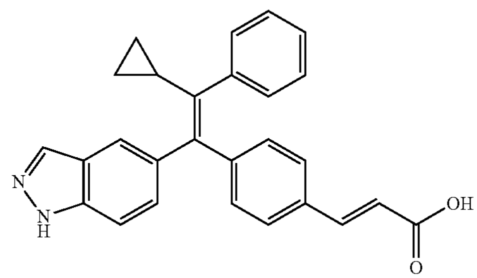 [SMILES: O=C(O)/C=C/c1ccc(/C(=C(\c2ccccc2)C2CC2)c2ccc3[nH]ncc3c2)cc1] | 407 |
| 36 | (E)-3-(4-((E)-2-(4-Fluoro-2-methylphenyl)-1-(1H-indazol-5-yl)but-1-en-1-yl)phenyl)acrylic acid | 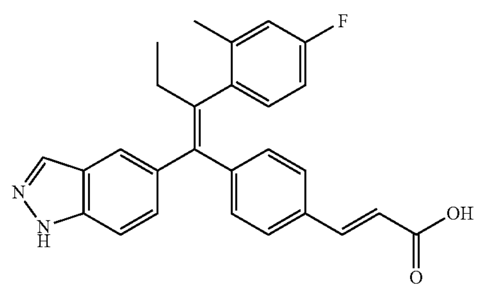 [SMILES: CC/C(=C(/c1ccc(/C=C/C(=O)O)cc1)c1ccc2[nH]ncc2c1)c1ccc(F)cc1C] | 427 |
| 37 | (E)-3-(4-((E)-2-(2,6-Difluorophenyl)-1-(1H-indazol-5-yl)but-1-en-1-yl)phenyl)acrylic acid | 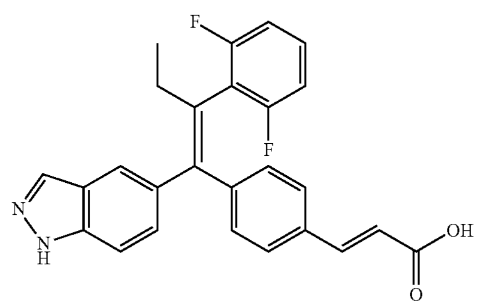 [SMILES: CC/C(=C(/c1ccc(/C=C/C(=O)O)cc1)c1ccc2[nH]ncc2c1)c1c(F)cccc1F] | 431 |
| 38 | (E)-3-(4-((E)-2-(2,6-Dichlorophenyl)-1-(1H-indazol-5-yl)but-1-en-1-yl)phenyl)acrylic acid | 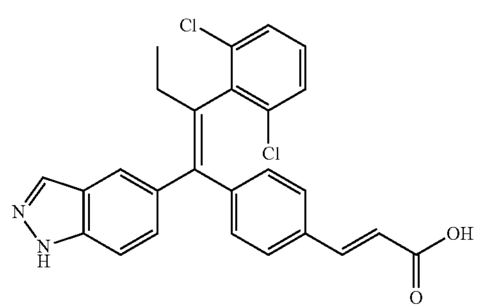 [SMILES: CC/C(=C(/c1ccc(/C=C/C(=O)O)cc1)c1ccc2[nH]ncc2c1)c1c(Cl)cccc1Cl] | 463 |

TABLE 1-continued

| Compound | Name | Structure | LCMS [M + H]+ |
|---|---|---|---|
| 39 | (E)-3-(4-((E)-4,4,4-Trideutero-1-(1H-indazol-5-yl)-2-phenylbut-1-en-1-yl)phenyl)acrylic acid | 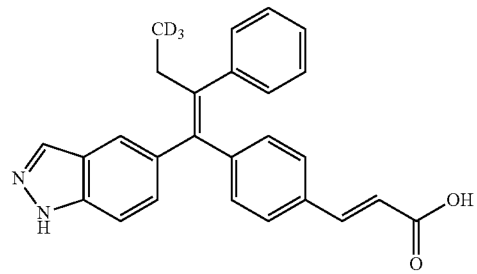 [SMILES: [2H]C([2H])([2H])C/C(=C(/c1ccc(/C=C/C(=O)O)cc1)c1ccc2[nH]ncc2c1)c1ccccc1] | 398 |
| 40 | (E)-3-(4-((E)-2-(4-Fluoro-3-methylphenyl)-1-(1H-indazol-5-yl)but-1-en-1-yl)phenyl)acrylic acid | 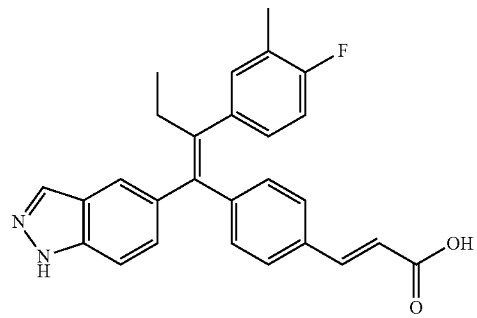 [SMILES: CC/C(=C(/c1ccc(/C=C/C(=O)O)cc1)c1ccc2[nH]ncc2c1)c1ccc(F)c(C)c1] | 427 |
| 41 | (E)-3-(4-((E)-2-(5-Fluoro-2-methylphenyl)-1-(1H-indazol-5-yl)but-1-en-1-yl)phenyl)acrylic acid | 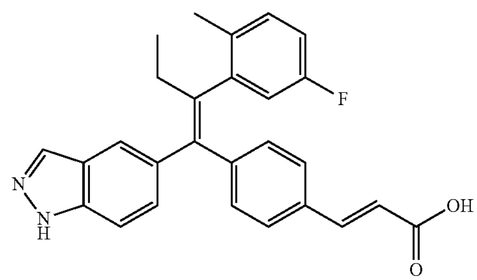 [SMILES: CC/C(=C(/c1ccc(/C=C/C(=O)O)cc1)c1ccc2[nH]ncc2c1)c1cc(F)ccc1C] | 427 |
| 42 | (E)-3-(4-((E)-2-(2,3-Difluorophenyl)-1-(1H-indazol-5-yl)but-1-en-1-yl)phenyl)acrylic acid | 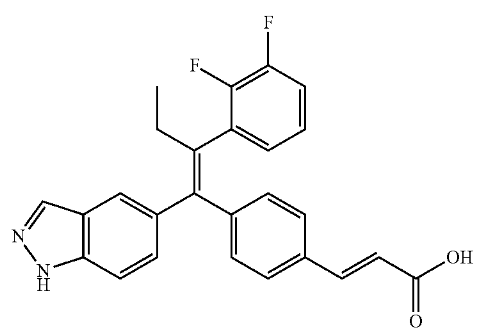 [SMILES: CC/C(=C(/c1ccc(/C=C/C(=O)O)cc1)c1ccc2[nH]ncc2c1)c1cccc(F)c1F] | 431 |
| 43 | (E)-3-(4-((E)-2-(2,5-Difluorophenyl)-1-(1H-indazol-5-yl)but-1-en-1-yl)phenyl)acrylic acid | 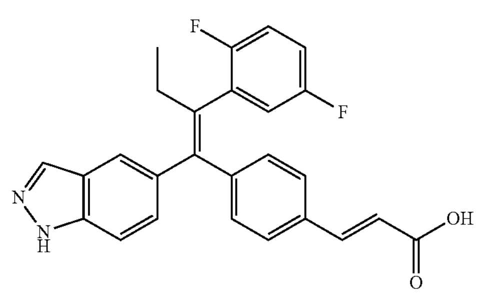 | 431 |

TABLE 1-continued

| Compound | Name | Structure | LCMS [M + H]+ |
|---|---|---|---|
| 44 | (E)-3-(4-((E)-2-(2-Chloro-5-fluorophenyl)-1-(1H-indazol-5-yl)but-1-en-1-yl)phenyl)acrylic acid | 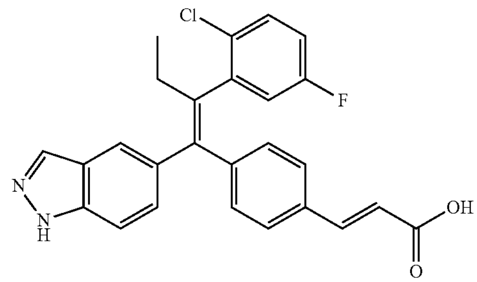 [SMILES: CC/C(=C(/c1ccc(/C=C/C(=O)O)cc1)c1ccc2[nH]ncc2c1)c1cc(F)ccc1Cl] | 447 |
| 45 | (E)-3-(4-((E)-2-(2-Chloro-6-methylphenyl)-1-(1H-indazol-5-yl)but-1-en-1-yl)phenyl)acrylic acid | 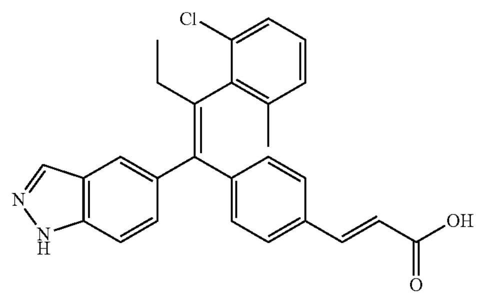 [SMILES: CC/C(=C(/c1ccc(/C=C/C(=O)O)cc1)c1ccc2[nH]ncc2c1)c1c(C)cccc1Cl] | 443 |
| 46 | (E)-3-(4-((E)-1-(7-Chloro-1H-indazol-5-yl)-2-phenylbut-1-en-1-yl)phenyl)acrylic acid | 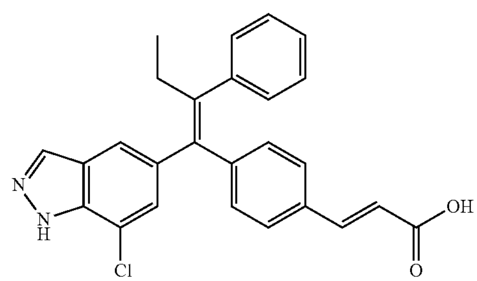 [SMILES: CC/C(=C(/c1ccc(/C=C/C(=O)O)cc1)c1cc(Cl)c2[nH]ncc2c1)c1ccccc1] | 429 |
| 47 | (E)-3-(4-((E)-1-(4-Methyl-1H-indazol-5-yl)-2-phenylbut-1-en-1-yl)phenyl)acrylic acid | 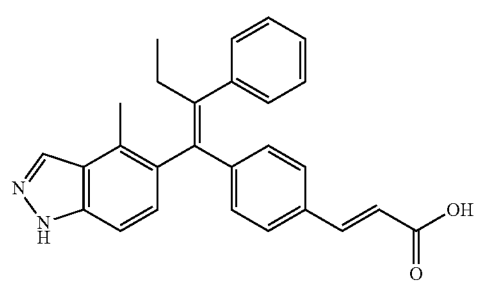 [SMILES: CC/C(=C(/c1ccc(/C=C/C(=O)O)cc1)c1ccc2[nH]ncc2c1C)c1ccccc1] | 409 |
| 48 | (E)-3-(4-((E)-1-(7-Methyl-1H-indazol-5-yl)-2-phenylbut-1-en-1-yl)phenyl)acrylic acid | 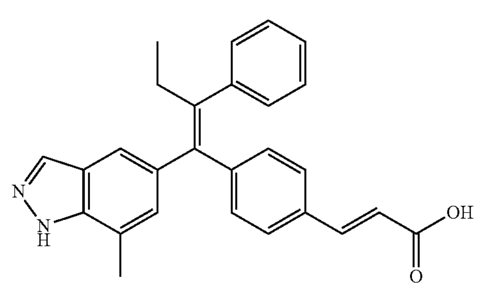 [SMILES: CC/C(=C(/c1ccc(/C=C/C(=O)O)cc1)c1cc(C)c2[nH]ncc2c1)c1ccccc1] | 409 |

TABLE 1-continued
| Compound | Name | Structure | LCMS [M + H]+ |
|---|---|---|---|
| 49 | (E)-3-(4-((E)-1-(6-Methyl-1H-indazol-5-yl)-2-phenylbut-1-en-1-yl)phenyl)acrylic acid | 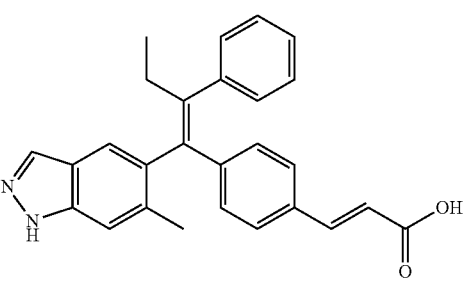 [SMILES: CC/C(=C(/c1ccc(/C=C/C(=O)O)cc1)c1cc2cn[nH]c2cc1C)c1ccccc1] | 409 |
| 50 | (E)-3-(4-((E)-1-(1H-Indazol-5-yl)-2-(naphthalen-1-yl)but-1-en-1-yl)phenyl)acrylic acid | 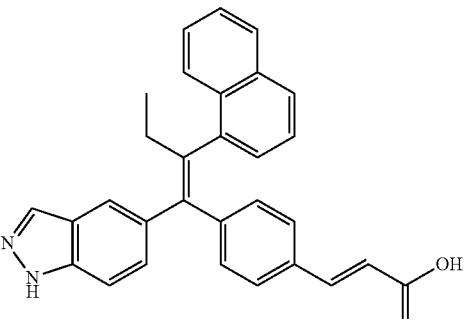 | 445 |
| 51 | (E)-3-(4-((E)-1-(3-Methyl-1H-indazol-5-yl)-2-phenylbut-1-en-1-yl)phenyl)acrylic acid | 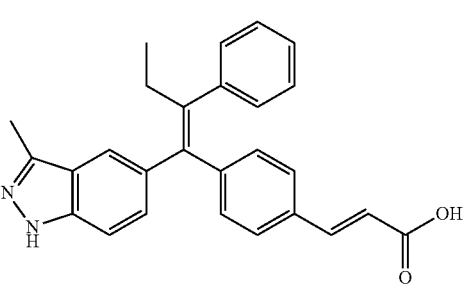 [SMILES: CC/C(=C(/c1ccc(/C=C/C(=O)O)cc1)c1ccc2[nH]nc(C)c2c1)c1ccccc1] | 409 |
| 52 | (E)-3-(4-((E)-1-(3-Chloro-1H-indazol-5-yl)-2-phenylbut-1-en-1-yl)phenyl)acrylic acid | 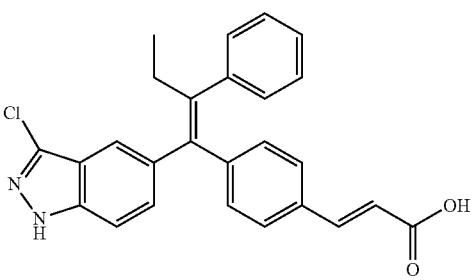 [SMILES: CC/C(=C(/c1ccc(/C=C/C(=O)O)cc1)c1ccc2[nH]nc(Cl)c2c1)c1ccccc1] | 429 |
| 53 | (E)-3-(4-((E)-2-(4-Chloro-2-methylphenyl)-1-(1H-indazol-5-yl)but-1-en-1-yl)phenyl)acrylic acid | 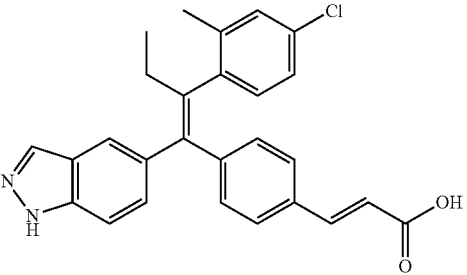 | 443 |

TABLE 1-continued

| Compound | Name | Structure | LCMS [M + H]+ |
|---|---|---|---|
| 54 | (E)-3-(4-((E)-1-(1H-Indazol-5-yl)-2-phenylprop-1-en-1-yl)phenyl)acrylic acid | 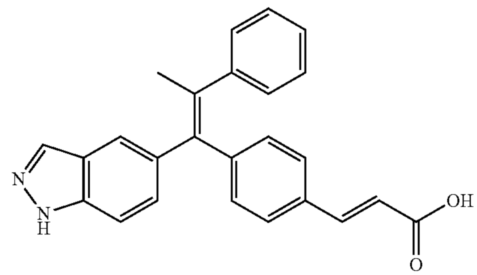 [SMILES: C/C(=C(/c1ccc(/C=C/C(=O)O)cc1)c1ccc2[nH]ncc2c1)c1ccccc1] | 381 |
| 55 | (E)-3-(4-((E)-1-(1H-Indazol-5-yl)-2-phenylpent-1-en-1-yl)phenyl)acrylic acid | 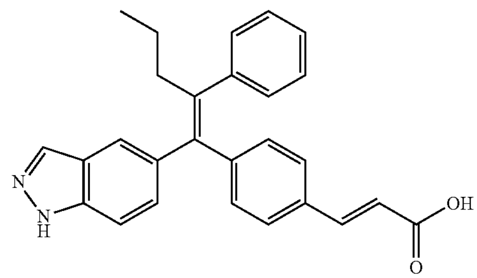 [SMILES: CCC/C(=C(/c1ccc(/C=C/C(=O)O)cc1)c1ccc2[nH]ncc2c1)c1ccccc1] | 409 |
| 56 | (E)-3-(4-((E)-2-Phenyl-1-(1H-pyrazolo[3,4-b]pyridin-4-yl)but-1-en-1-yl)phenyl)acrylic acid | 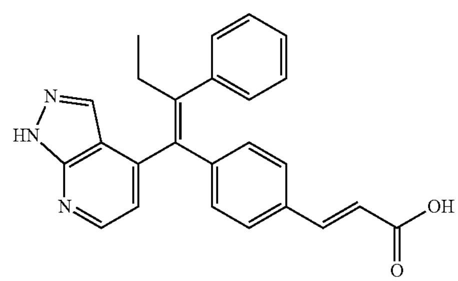 [SMILES: CC/C(=C(/c1ccc(/C=C/C(=O)O)cc1)c1ccnc2[nH]ncc12)c1ccccc1] | 396 |
| 57 | (E)-3-(4-((E)-2-(3-Cyanophenyl)-1-(1H-indazol-5-yl)but-1-en-1-yl)phenyl)acrylic acid | 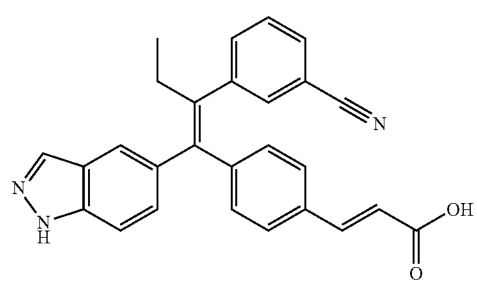 [SMILES: CC/C(=C(/c1ccc(/C=C/C(=O)O)cc1)c1ccc2[nH]ncc2c1)c1cccc(C#N)c1] | 420 |
| 58 | (E)-3-(4-((E)-2-(4-Cyanophenyl)-1-(1H-indazol-5-yl)but-1-en-1-yl)phenyl)acrylic acid | 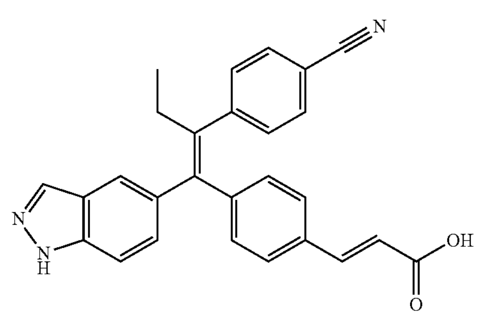 [SMILES: CC/C(=C(/c1ccc(/C=C/C(=O)O)cc1)c1ccc2[nH]ncc2c1)c1ccc(C#N)cc1] | 420 |

TABLE 1-continued

| Compound | Name | Structure | LCMS [M + H]+ |
|---|---|---|---|
| 59 | (E)-3-(4-((E)-4-Hydroxy-1-(1H-indazol-5-yl)-2-phenylbut-1-en-1-yl)phenyl)acrylic acid | 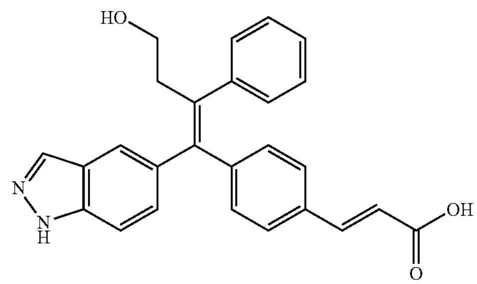 [SMILES: O=C(O)/C=C/c1ccc(/C(=C(/CCO)c2ccccc2)c2ccc3[nH]ncc3c2)cc1] | 411 |
| 60 | (E)-3-(4-((E)-1-(1H-Indazol-5-yl)-4-methoxy-2-phenylbut-1-en-1-yl)phenyl)acrylic acid | 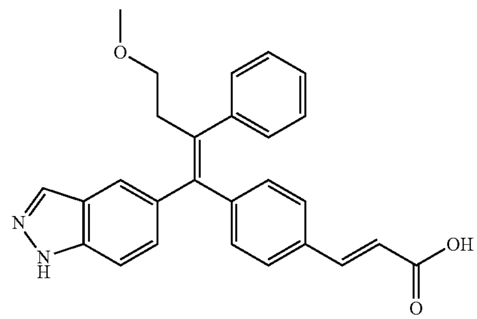 [SMILES: COCC/C(=C(/c1ccc(/C=C/C(=O)O)cc1)c1ccc2[nH]ncc2c1)c1ccccc1] | 425 |
| 61 | (E)-3-(4-((Z)-1-(1H-Indazol-5-yl)-3-methoxy-2-phenylprop-1-en-1-yl)phenyl)acrylic acid | 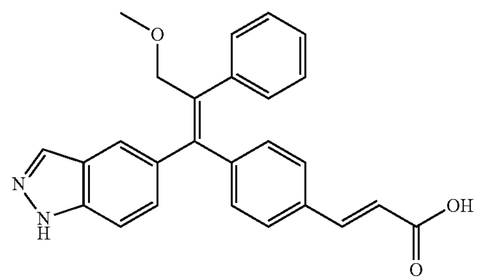 | 411 |
| 62 | (E)-3-(4-((E)-2-(4-(Dimethylamino)phenyl)-1-(1H-indazol-5-yl)but-1-en-1-yl)phenyl)acrylic acid | 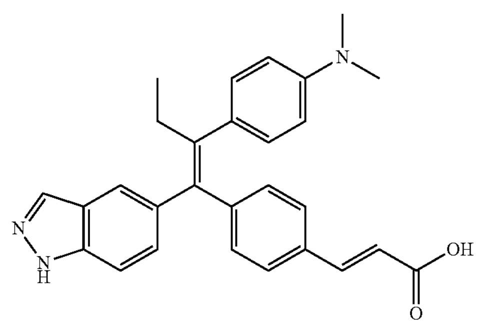 [SMILES: CC/C(=C(/c1ccc(/C=C/C(=O)O)cc1)c1ccc2[nH]ncc2c1)c1ccc(N(C)C)cc1] | 438 |
| 63 | (E)-3-(4-((E)-1-(4-Fluoro-1H-indazol-5-yl)-2-phenylbut-1-en-1-yl)phenyl)acrylic acid | 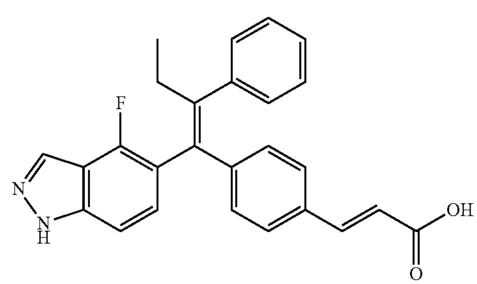 [SMILES: CC/C(=C(/c1ccc(/C=C/C(=O)O)cc1)c1ccc2[nH]ncc2c1F)c1ccccc1] | 413 |

TABLE 1-continued

| Compound | Name | Structure | LCMS [M + H]+ |
|---|---|---|---|
| 64 | (E)-3-(4-((E)-1-(1H-Indol-5-yl)-2-phenylbut-1-en-1-yl)phenyl)acrylic acid | 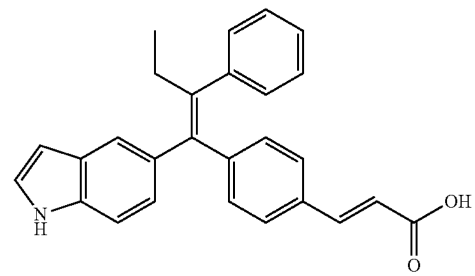 [SMILES: CC/C(=C(/c1ccc(/C=C/C(=O)O)cc1)c1ccc2[nH]ccc2c1)c1ccccc1] | 394 |
| 65 | (E)-3-(4-((E)-1-(6-Chloro-1H-indazol-5-yl)-2-phenylbut-1-en-1-yl)phenyl)acrylic acid | 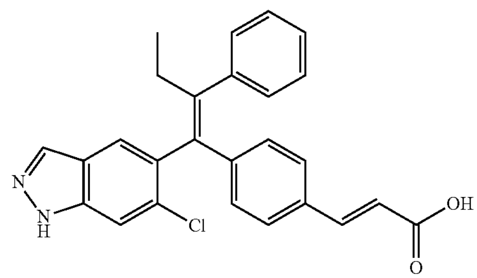 | 429 |
| 66 | (E)-3-(4-((E)-1-(2-Oxo-2,3-dihydrobenzo[d]oxazol-6-yl)-2-phenylbut-1-en-1-yl)phenyl)acrylic acid | 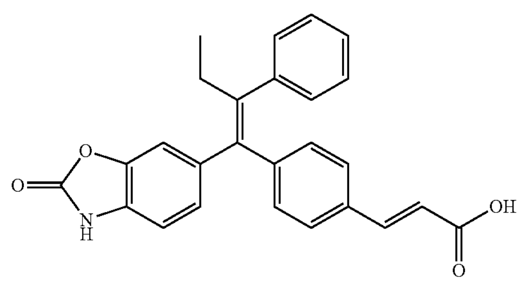 [SMILES: CC/C(=C(/c1ccc(/C=C/C(=O)O)cc1)c1ccc2[nH]c(=O)oc2c1)c1ccccc1] | 412 |
| 67 | (E)-3-(4-((E)-2-Phenyl-1-(1H-pyrazolo[3,4-b]pyridin-5-yl)but-1-en-1-yl)phenyl)acrylic acid | 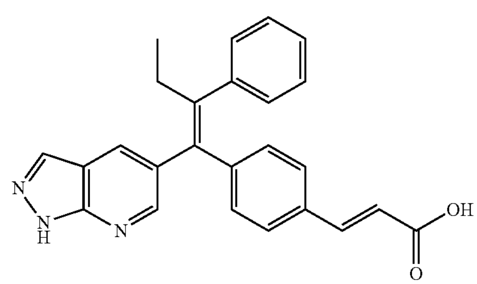 [SMILES: CC/C(=C(/c1ccc(/C=C/C(=O)O)cc1)c1cnc2[nH]ncc2c1)c1ccccc1] | 396 |
| 68 | (E)-3-(4-((E)-2-Phenyl-1-(1H-pyrrolo[2,3-b]pyridin-5-yl)but-1-en-1-yl)phenyl)acrylic acid | 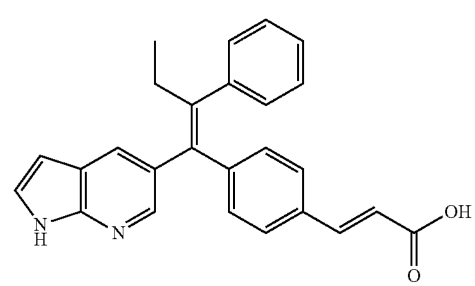 [SMILES: CC/C(=C(/c1ccc(/C=C/C(=O)O)cc1)c1cnc2[nH]ccc2c1)c1ccccc1] | 395 |

TABLE 1-continued

| Compound | Name | Structure | LCMS [M + H]+ |
|---|---|---|---|
| 69 | (E)-3-(4-((E)-1-(1H-Indazol-5-yl)-4-methyl-2-phenylpent-1-en-1-yl)phenyl)acrylic acid | 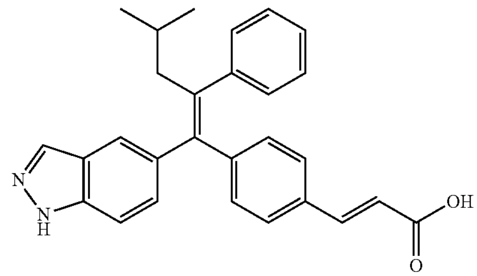 [SMILES: CC(C)C/C(=C(/c1ccc(/C=C/C(=O)O)cc1)c1ccc2[nH]ncc2c1)c1ccccc1] | 423 |
| 70 | (E)-3-(4-((E)-2-Cyclopropyl-1-(1H-indazol-4-yl)-2-phenylvinyl)phenyl)acrylic acid | 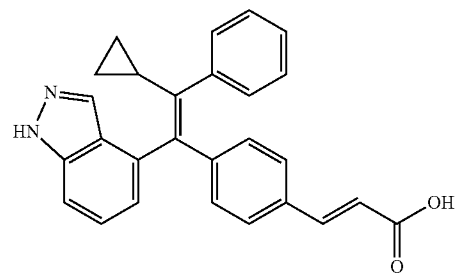 [SMILES: O=C(O)/C=C/c1ccc(/C(=C(\c2ccccc2)C2CC2)c2cccc3[nH]ncc23)cc1] | 407 |
| 71 | (E)-3-(4-((E)-2-(2-Chlorophenyl)-2-cyclopropyl-1-(1H-indazol-4-yl)vinyl)phenyl)acrylic acid | 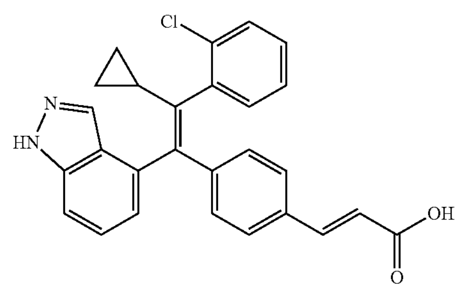 [SMILES: O=C(O)/C=C/c1ccc(/C(=C(\c2ccccc2Cl)C2CC2)c2cccc3[nH]ncc23)cc1] | 441 |
| 72 | (E)-3-(4-((E)-1-(1H-Benzo[d][1,2,3]triazol-5-yl)-2-(2-chloro-4-fluorophenyl)but-1-en-1-yl)phenyl)acrylic acid | 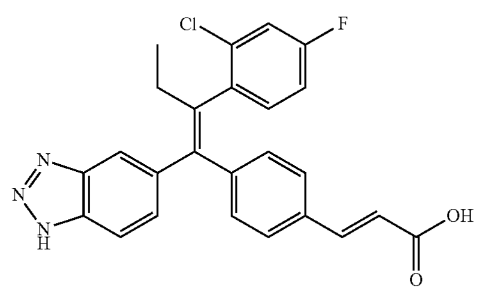 [SMILES: CC/C(=C(/c1ccc(/C=C/C(=O)O)cc1)c1ccc2[nH]nnc2c1)c1ccc(F)cc1Cl] | 448 |
| 73 | (E)-3-(4-((E)-2-(2-Chloro-4-fluorophenyl)-2-cyclopropyl-1-(1H-indazol-4-yl)vinyl)phenyl)acrylic acid | 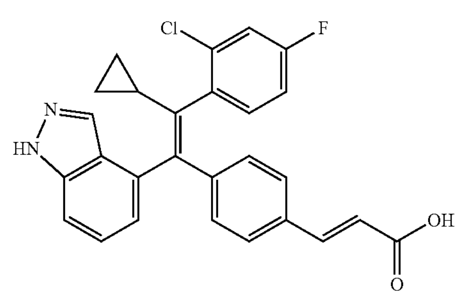 [SMILES: O=C(O)/C=C/c1ccc(/C(=C(\c2ccc(F)cc2Cl)C2CC2)c2cccc3[nH]ncc23)cc1] | 459 |

TABLE 1-continued

| Compound | Name | Structure | LCMS [M + H]+ |
|---|---|---|---|
| 74 | (E)-3-(4-((E)-1-(4-Chloro-1H-indazol-5-yl)-2-phenylbut-1-en-1-yl)phenyl)acrylic acid | 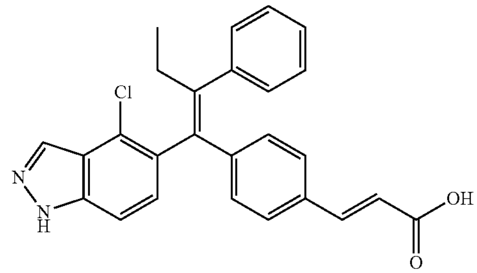 [SMILES: CC/C(=C(/c1ccc(/C=C/C(=O)O)cc1)c1ccc2[nH]ncc2c1Cl)c1ccccc1] | 429 |
| 75 | (E)-3-(4-((E)-1-(2-Oxo-2,3-dihydrobenzo[d]thiazol-6-yl)-2-phenylbut-1-en-1-yl)phenyl)acrylic acid | 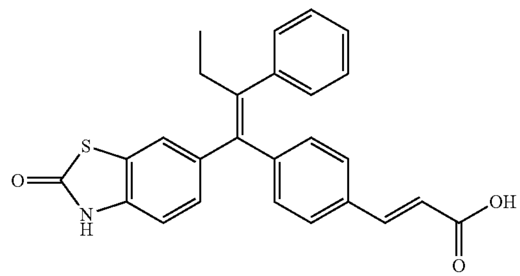 [SMILES: CC/C(=C(/c1ccc(/C=C/C(=O)O)cc1)c1ccc2[nH]c(=O)sc2c1)c1ccccc1] | 428 |
| 76 | (E)-3-(4-((E)-2-Cyclopentyl-1-(1H-indazol-5-yl)-2-phenylvinyl)phenyl)acrylic acid | 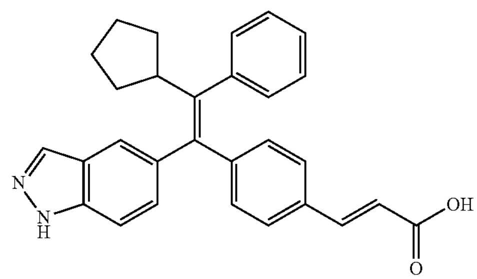 [SMILES: O=C(O)/C=C/c1ccc(/C(=C(\c2ccccc2)C2CCCC2)c2ccc3[nH]ncc3c2)cc1] | 435 |
| 77 | (E)-3-(4-((E)-2-Cyclohexyl-1-(1H-indazol-5-yl)-2-phenylvinyl)phenyl)acrylic acid | 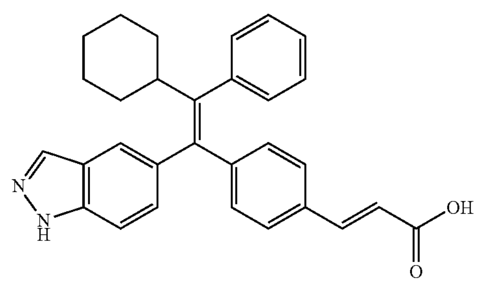 [SMILES: O=C(O)/C=C/c1ccc(/C(=C(\c2ccccc2)C2CCCCC2)c2ccc3[nH]ncc3c2)cc1] | 449 |
| 78 | (E)-3-(4-((E)-1-(1H-Indazol-5-yl)-3-methyl-2-phenylbut-1-en-1-yl)phenyl)acrylic acid | 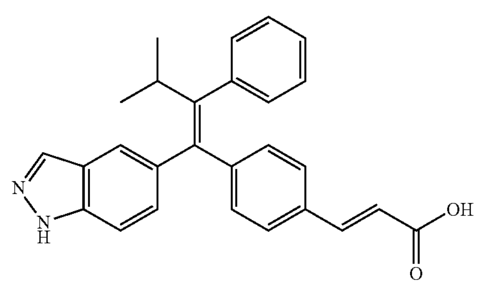 | 409 |

TABLE 1-continued

| Compound | Name | Structure | LCMS [M + H]+ |
|---|---|---|---|
| 79 | (E)-3-(4-((E)-3-Cyclopropyl-1-(1H-indazol-5-yl)-2-phenylprop-1-en-1-yl)phenyl)acrylic acid | 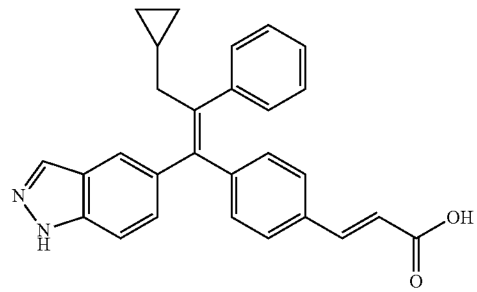 [SMILES: O=C(O)/C=C/c1ccc(/C(=C(/CC2CC2)c2ccccc2)c2ccc3[nH]ncc3c2)cc1] | 421 |
| 80 | (E)-3-(4-((E)-2-(2-Chlorophenyl)-2-cyclopropyl-1-(1H-indazol-5-yl)vinyl)phenyl)acrylic acid | 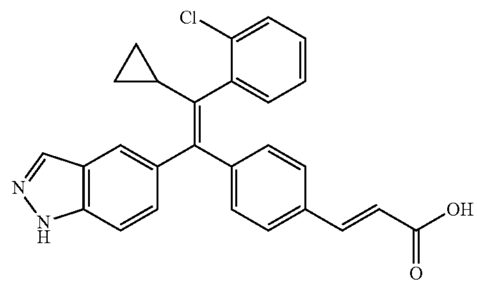 [SMILES: O=C(O)/C=C/c1ccc(/C(=C(\c2ccccc2Cl)C2CC2)c2ccc3[nH]ncc3c2)cc1] | 441 |
| 81 | (E)-3-(4-((E)-2-Phenyl-1-(1H-pyrazolo[3,4-c]pyridin-5-yl)but-1-en-1-yl)phenyl)acrylic acid | 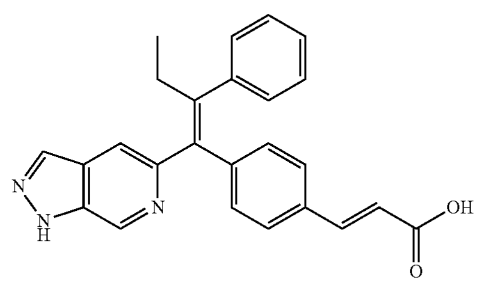 [SMILES: CC/C(=C(/c1ccc(/C=C/C(=O)O)cc1)c1cc2cn[nH]c2cn1)c1ccccc1] | 396 |
| 82 | (E)-3-(4-((E)-1-(6-Fluoro-1H-indazol-5-yl)-2-phenylbut-1-en-1-yl)phenyl)acrylic acid | 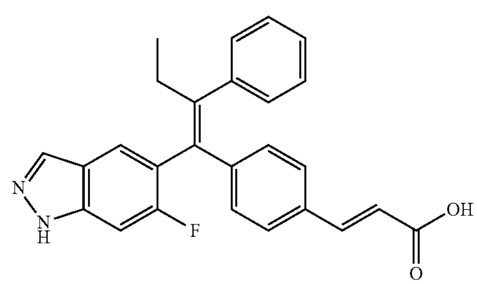 | 413 |
| 83 | (E)-3-(4-((E)-1-(1H-Benzo[d]imidazol-5-yl)-2-phenylbut-1-en-1-yl)phenyl)acrylic acid | 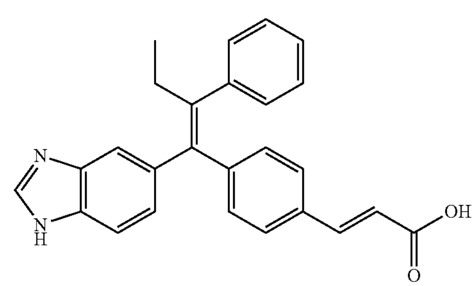 [SMILES: CC/C(=C(/c1ccc(/C=C/C(=O)O)cc1)c1ccc2[nH]cnc2c1)c1ccccc1] | 395 |

TABLE 1-continued

| Compound | Name | Structure | LCMS [M + H]+ |
|---|---|---|---|
| 84 | (E)-3-(4-((E)-1-(1H-Indazol-5-yl)-2-phenylhex-1-en-1-yl)phenyl)acrylic acid | 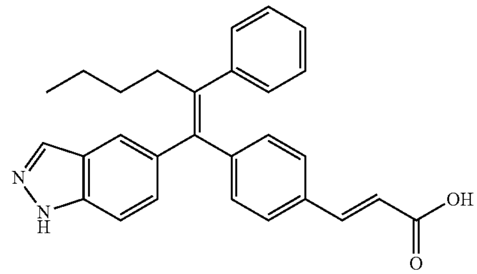 [SMILES: CCCC/C(=C(/c1ccc(/C=C/C(=O)O)cc1)c1ccc2[nH]ncc2c1)c1ccccc1] | 423 |
| 85 | (E)-3-(4-((E)-3-Cyclopentyl-1-(1H-indazol-5-yl)-2-phenylprop-1-en-1-yl)phenyl)acrylic acid | 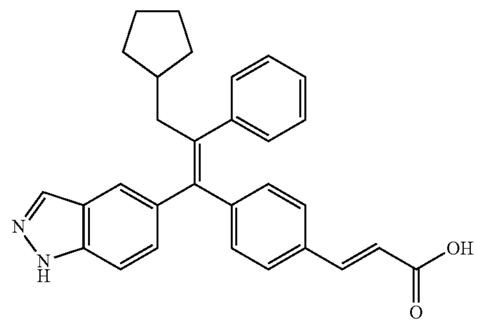 [SMILES: O=C(O)/C=C/c1ccc(/C(=C(/CC2CCCC2)c2ccccc2)c2ccc3[nH]ncc3c2)cc1] | 449 |
| 86 | (E)-3-(4-((E)-1-(6-Fluoro-1H-indazol-4-yl)-2-phenylbut-1-en-1-yl)phenyl)acrylic acid | 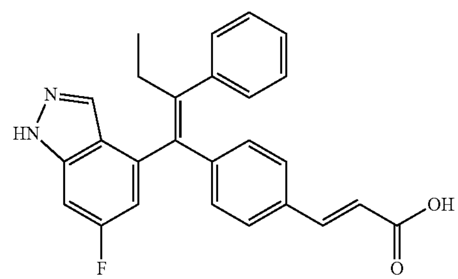 [SMILES: CC/C(=C(/c1ccc(/C=C/C(=O)O)cc1)c1cc(F)cc2[nH]ncc12)c1ccccc1] | 413 |
| 87 | (E)-3-(4-((E)-2-(2-Chloro-4-fluorophenyl)-1-(4-fluoro-1H-indazol-5-yl)but-1-en-1-yl)phenyl)acrylic acid | 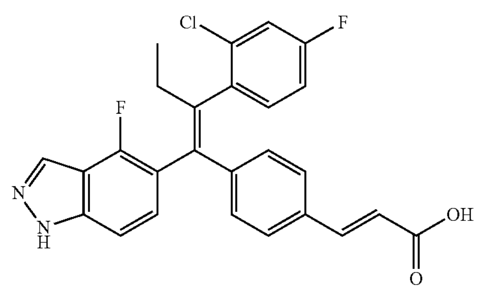 | 465 |
| 88 | (E)-3-(4-((E)-1-(1H-Benzo[d][1,2,3]triazol-4-yl)-2-phenylbut-1-en-1-yl)phenyl)acrylic acid | 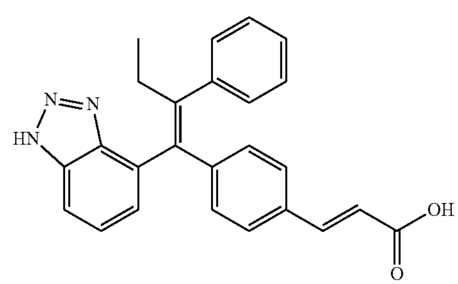 [SMILES: CC/C(=C(/c1ccc(/C=C/C(=O)O)cc1)c1cccc2[nH]nnc12)c1ccccc1] | 396 |

TABLE 1-continued

| Compound | Name | Structure | LCMS [M + H]+ |
|---|---|---|---|
| 89 | (E)-3-(4-((E)-1-(1H-Benzo[d][1,2,3]triazol-4-yl)-2-(2-chloro-4-fluorophenyl)but-1-en-1-yl)phenyl)acrylic acid | 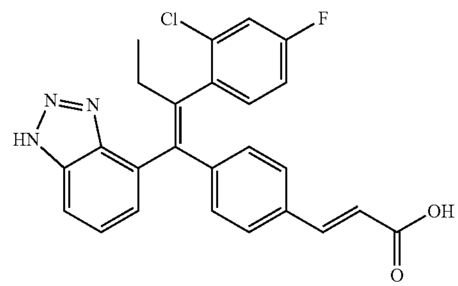 [SMILES: CC/C(=C(/c1ccc(/C=C/C(=O)O)cc1)c1cccc2[nH]nnc12)c1ccc(F)cc1Cl] | 448 |
| 90 | (E)-3-(4-((E)-1-(3-Oxo-2,3-dihydroisoquinolin-6-yl)-2-phenylbut-1-en-1-yl)phenyl)acrylic acid | 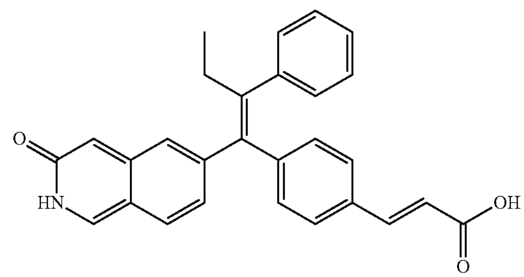 [SMILES: CC/C(=C(/c1ccc(/C=C/C(=O)O)cc1)c1ccc2c[nH]c(=O)cc2c1)c1ccccc1] | 422 |
| 91 | (E)-3-(4-((E)-1-(7-Fluoro-1H-indazol-5-yl)-2-phenylbut-1-en-1-yl)phenyl)acrylic acid | 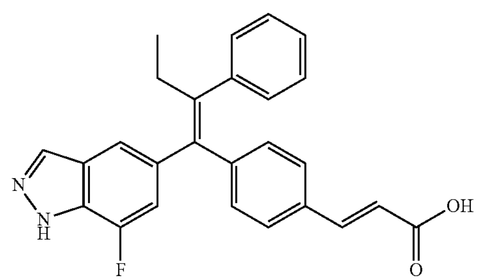 | 413 |
| 92 | (E)-3-(4-((E)-1-(7-Fluoro-1H-indol-5-yl)-2-phenylbut-1-en-1-yl)phenyl)acrylic acid | 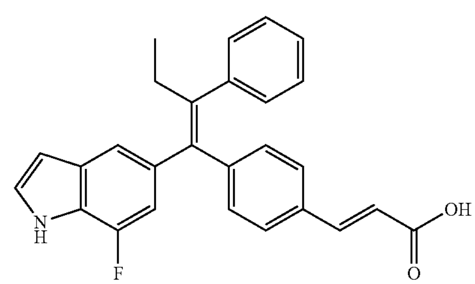 [SMILES: CC/C(=C(/c1ccc(/C=C/C(=O)O)cc1)c1cc(F)c2[nH]ccc2c1)c1ccccc1] | 412 |
| 93 | (E)-3-(4-((E)-2-(2-Chloro-4-fluorophenyl)-1-(1H-indazol-5-yl)-4-methylpent-1-en-1-yl)phenyl)acrylic acid | 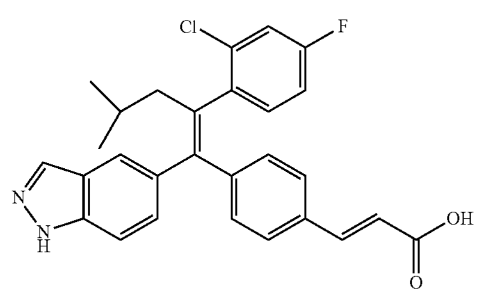 [SMILES: CC(C)C/C(=C(/c1ccc(/C=C/C(=O)O)cc1)c1ccc2[nH]ncc2c1)c1ccc(F)cc1Cl] | 475 |

TABLE 1-continued

| Compound | Name | Structure | LCMS [M + H]+ |
|---|---|---|---|
| 94 | (E)-3-(4-((Z)-3,3-Difluoro-1-(1H-indazol-5-yl)-2-phenylprop-1-en-1-yl)phenyl)acrylic acid | 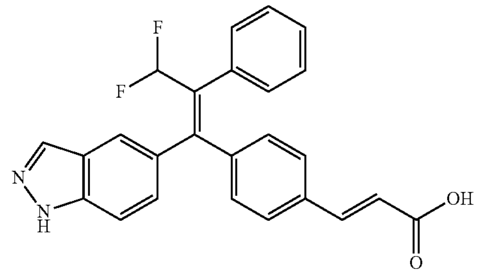 [SMILES: O=C(O)/C=C/c1ccc(/C(=C(\c2ccccc2)C(F)F)c2ccc3[nH]ncc3c2)cc1] | 417 |
| 95 | (E)-3-(4-((E)-2-(2-Chloro-4-fluorophenyl)-1-(7-fluoro-1H-indazol-5-yl)but-1-en-1-yl)phenyl)acrylic acid | 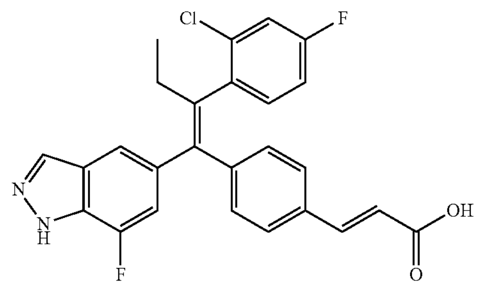 [SMILES: CC/C(=C(/c1ccc(/C=C/C(=O)O)cc1)c1cc(F)c2[nH]ncc2c1)c1ccc(F)cc1Cl] | 465 |
| 96 | (E)-3-(4-((E)-2-(Benzofuran-4-yl)-1-(1H-indazol-5-yl)but-1-en-1-yl)phenyl)acrylic acid | 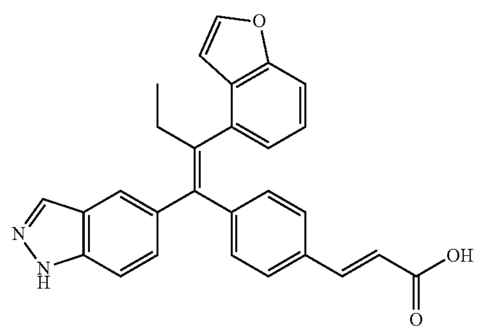 [SMILES: CC/C(=C(/c1ccc(/C=C/C(=O)O)cc1)c1ccc2[nH]ncc2c1)c1cccc2occc12] | 435 |
| 97 | (E)-3-(4-((E)-1-(1-Oxo-1,2-dihydroisoquinolin-6-yl)-2-phenylbut-1-en-1-yl)phenyl)acrylic acid | 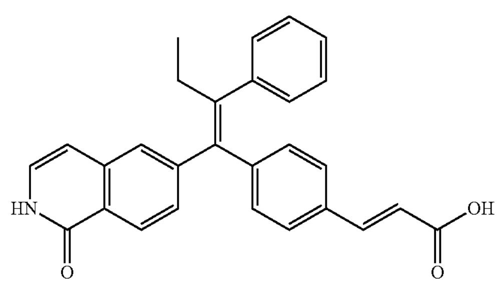 [SMILES: CC/C(=C(/c1ccc(/C=C/C(=O)O)cc1)c1ccc2c(=O)[nH]ccc2c1)c1ccccc1] | 422 |
| 98 | (E)-3-(4-((E)-4-Fluoro-1-(1H-indazol-5-yl)-2-phenylbut-1-en-1-yl)phenyl)acrylic acid | 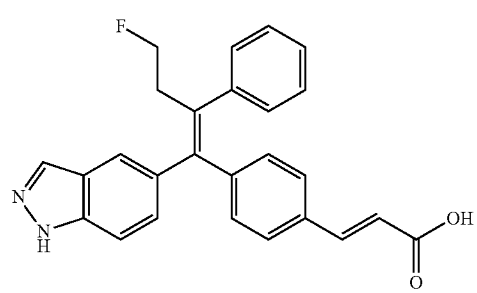 [SMILES: O=C(O)/C=C/c1ccc(/C(=C(/CCF)c2ccccc2)c2ccc3[nH]ncc3c2)cc1] | 413 |

TABLE 1-continued

| Compound | Name | Structure | LCMS [M + H]+ |
|---|---|---|---|
| 99 | (E)-3-(4-((E)-4-Chloro-2-(2-chloro-4-fluorophenyl)-1-(1H-indazol-5-yl)but-1-en-1-yl)phenyl)acrylic acid | 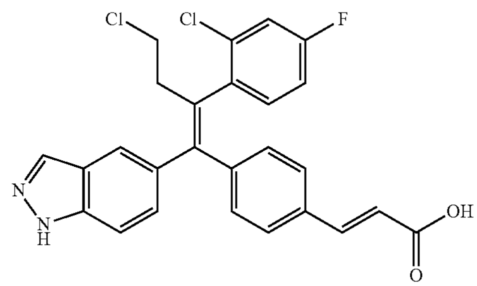 [SMILES: O=C(O)/C=C/c1ccc(/C(=C(/CCCl)c2ccc(F)cc2Cl)c2ccc3[nH]ncc3c2)cc1] | 481 |
| 100 | (E)-3-(4-((E)-1-(2-Oxo-1,2,3,4-tetrahydroquinolin-6-yl)-2-phenylbut-1-en-1-yl)phenyl)acrylic acid | 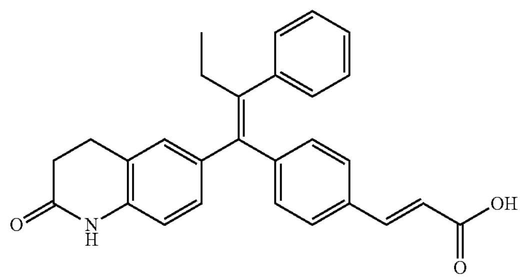 [SMILES: CC/C(=C(/c1ccc(/C=C/C(=O)O)cc1)c1ccc2c(c1)CCC(=O)N2)c1ccccc1] | 424 |
| 101 | (E)-3-(4-((E)-1-(2-Oxo-2,4-dihydro-1H-benzo[d][1,3]oxazin-6-yl)-2-phenylbut-1-en-1-yl)phenyl)acrylic acid | 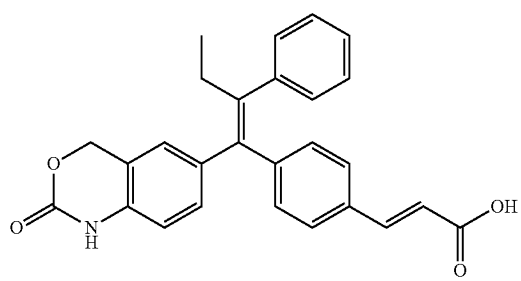 [SMILES: CC/C(=C(/c1ccc(/C=C/C(=O)O)cc1)c1ccc2c(c1)COC(=O)N2)c1ccccc1] | 426 |
| 102 | (E)-3-(4-((E)-1-(2-Oxo-1,2-dihydroquinolin-5-yl)-2-phenylbut-1-en-1-yl)phenyl)acrylic acid | 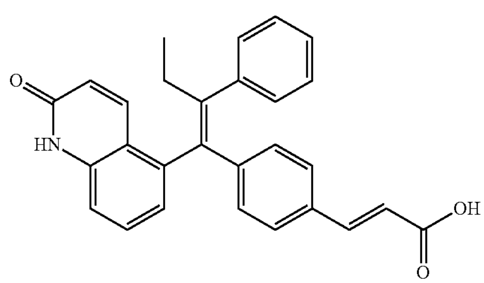 [SMILES: CC/C(=C(/c1ccc(/C=C/C(=O)O)cc1)c1cccc2[nH]c(=O)ccc12)c1ccccc1] | 422 |
| 103 | (E)-3-(4-((E)-1-(3-Oxo-3,4-dihydro-2H-benzo[b][1,4]thiazin-7-yl)-2-phenylbut-1-en-1-yl)phenyl)acrylic acid | 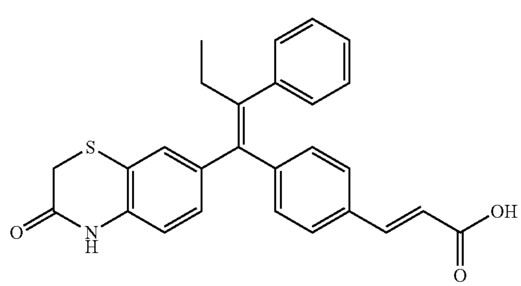 [SMILES: CC/C(=C(/c1ccc(/C=C/C(=O)O)cc1)c1ccc2c(c1)SCC(=O)N2)c1ccccc1] | 442 |

TABLE 1-continued

| Compound | Name | Structure | LCMS [M + H]+ |
|---|---|---|---|
| 104 | (E)-3-(4-((E)-1-(3-Oxoisoindolin-5-yl)-2-phenylbut-1-en-1-yl)phenyl)acrylic acid | 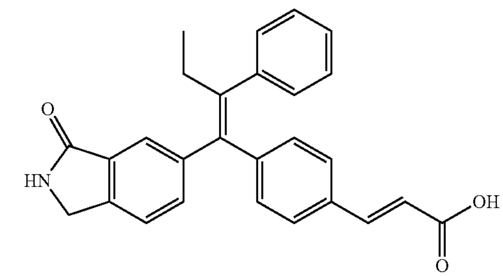 [SMILES: CC/C(=C(/c1ccc(/C=C/C(=O)O)cc1)c1ccc2c(c1)C(=O)NC2)c1ccccc1] | 410 |
| 105 | (E)-3-(4-((E)-1-(2-Oxo-1,2-dihydroquinolin-6-yl)-2-phenylbut-1-en-1-yl)phenyl)acrylic acid | 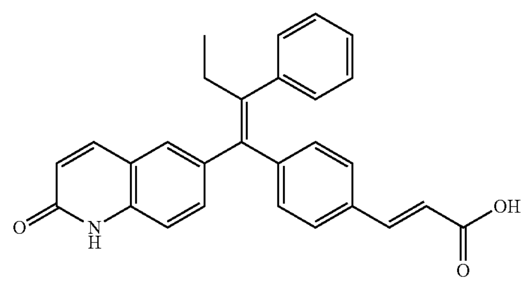 [SMILES: CC/C(=C(/c1ccc(/C=C/C(=O)O)cc1)c1ccc2[nH]c(=O)ccc2c1)c1ccccc1] | 422 |
| 106 | (E)-3-(4-((Z)-3,3,3-Trifluoro-1-(1H-indazol-5-yl)-2-phenylprop-1-en-1-yl)phenyl)acrylic acid | 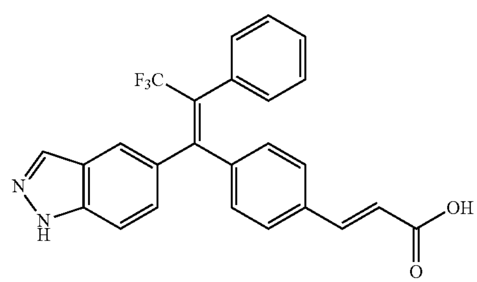 [SMILES: O=C(O)/C=C/c1ccc(/C(=C(\c2ccccc2)C(F)(F)F)c2ccc3[nH]ncc3c2)cc1] | not observed |
| 107 | (E)-3-(4-((E)-1-(3-Oxo-3,4-dihydro-2H-benzo[b][1,4]oxazin-7-yl)-2-phenylbut-1-en-1-yl)phenyl)acrylic acid | 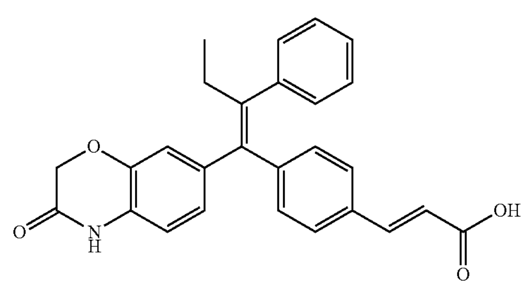 [SMILES: CC/C(=C(/c1ccc(/C=C/C(=O)O)cc1)c1ccc2c(c1)OCC(=O)N2)c1ccccc1] | not observed |
| 108 | (E)-3-(4-((E)-1-(4-Fluoro-1H-indazol-5-yl)-2-(4-fluoro-2-methylphenyl)but-1-en-1-yl)phenyl)acrylic acid | 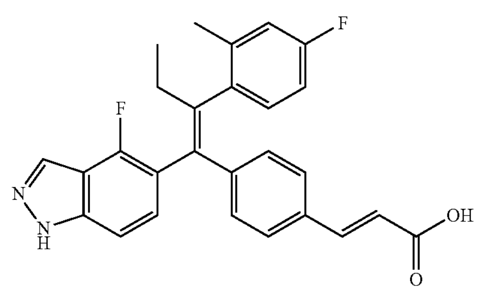 [SMILES: CC/C(=C(/c1ccc(/C=C/C(=O)O)cc1)c1ccc2[nH]ncc2c1F)c1ccc(F)cc1C] | 445 |

TABLE 1-continued

| Compound | Name | LCMS [M + H]+ |
|---|---|---|
| 109 | (E)-3-(4-((E)-2-(4-Chloro-2-methylphenyl)-1-(4-fluoro-1H-indazol-5-yl)but-1-en-1-yl)phenyl)acrylic acid | 461 |
| 110 | (E)-3-(4-((E)-1-(1-Oxoisoindolin-5-yl)-2-phenylbut-1-en-1-yl)phenyl)acrylic acid | 410 |
| 111 | (E)-3-(4-((E)-2-Cyclopropyl-1-(4-fluoro-1H-indazol-5-yl)-2-(4-fluoro-2-methylphenyl)vinyl)phenyl)acrylic acid | 457 |
| 112 | (E)-3-(4-((E)-2-(4-Chloro-2-methylphenyl)-2-cyclopropyl-1-(4-fluoro-1H-indazol-5-yl)vinyl)phenyl)acrylic acid | 473 |
| 113 | (E)-3-(4-((E)-1-(4-Chloro-1H-indazol-5-yl)-2-(2-chloro-4-fluorophenyl)but-1-en-1-yl)phenyl)acrylic acid | 481 |

TABLE 1-continued

| Compound | Name | Structure | LCMS [M + H]+ |
|---|---|---|---|
| 114 | (E)-3-(4-((Z)-2-(2-Chloro-4-fluorophenyl)-3,3-difluoro-1-(1H-indazol-5-yl)prop-1-en-1-yl)phenyl)acrylic acid | 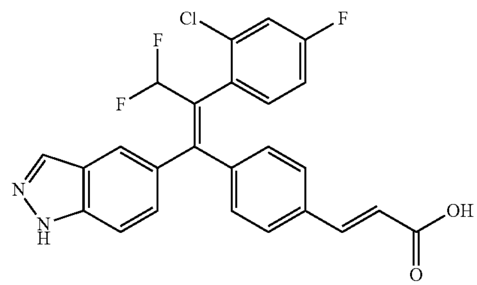 [SMILES: O=C(O)/C=C/c1ccc(/C(=C(\c2ccc(F)cc2Cl)C(F)F)c2ccc3[nH]ncc3c2)cc1] | 469 |
| 115 | (E)-3-(4-((E)-2-Cyclopropyl-1-(4-fluoro-1H-indazol-5-yl)-2-phenylvinyl)phenyl)acrylic acid | 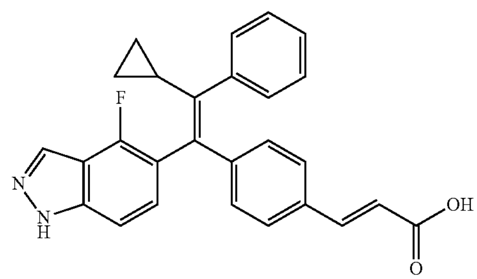 [SMILES: O=C(O)/C=C/c1ccc(/C(=C(\c2ccccc2)C2CC2)c2ccc3[nH]ncc3c2F)cc1] | 425 |
| 116 | (E)-3-(4-((E)-4-Chloro-1-(4-fluoro-1H-indazol-5-yl)-2-phenylbut-1-en-1-yl)phenyl)acrylic acid | 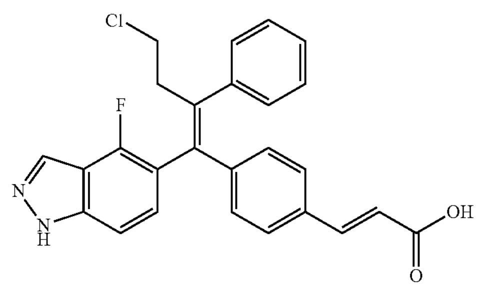 | 447 |
| 117 | (E)-3-(4-((E)-4-Chloro-2-(2-chloro-4-fluorophenyl)-1-(4-fluoro-1H-indazol-5-yl)but-1-en-1-yl)phenyl)acrylic acid | 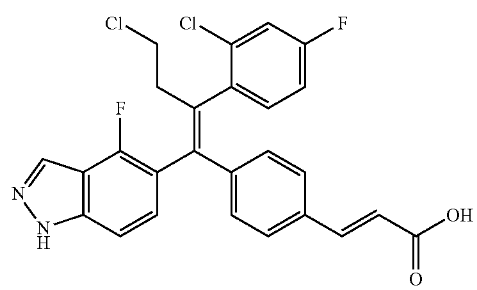 [SMILES: O=C(O)/C=C/c1ccc(/C(=C(/CCCl)c2ccc(F)cc2Cl)c2ccc3[nH]ncc3c2F)cc1] | 499 |
| 118 | (E)-3-(4-((E)-2-(4-Fluorophenyl)-1-(quinolin-6-yl)but-1-en-1-yl)phenyl)acrylic acid | 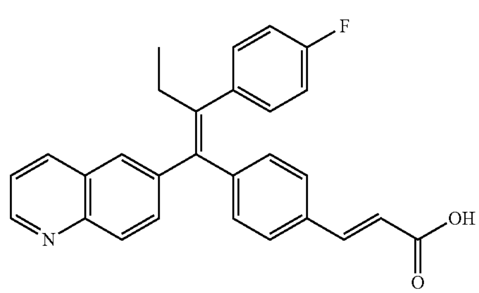 [SMILES: CC/C(=C(/c1ccc(/C=C/C(=O)O)cc1)c1ccc2ncccc2c1)c1ccc(F)cc1] | 406 |

TABLE 1-continued

| Compound | Name | Structure | LCMS [M + H]+ |
|---|---|---|---|
| 119 | (E)-3-(4-((E)-4-Fluoro-2-(4-fluorophenyl)-1-(1H-indazol-5-yl)but-1-en-1-yl)phenyl)acrylic acid | 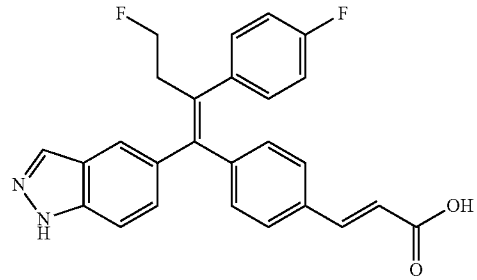 [SMILES: O=C(O)/C=C/c1ccc(/C(=C(/CCF)c2ccc(F)cc2)c2ccc3[nH]ncc3c2)cc1] | 431 |
| 120 | (E)-3-(4-((E)-2-Phenyl-1-(1H-pyrazolo[4,3-b]pyridin-5-yl)but-1-en-1-yl)phenyl)acrylic acid | 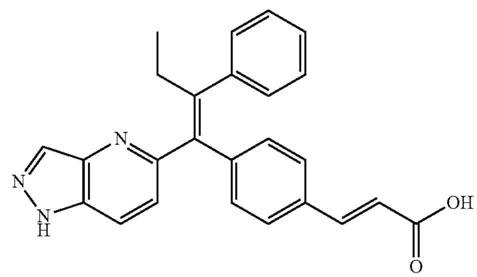 [SMILES: CC/C(=C(/c1ccc(/C=C/C(=O)O)cc1)c1ccc2[nH]ncc2n1)c1ccccc1] | 396 |
| 121 | (E)-3-(4-((E)-4-Fluoro-1-(4-fluoro-1H-indazol-5-yl)-2-phenylbut-1-en-1-yl)phenyl)acrylic acid | 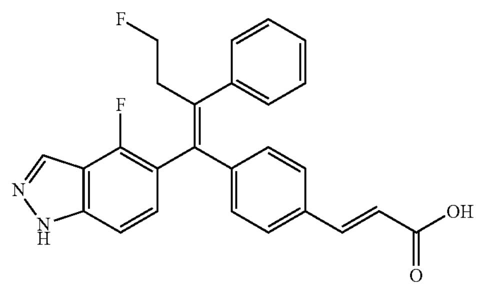 [SMILES: O=C(O)/C=C/c1ccc(/C(=C(/CCF)c2ccccc2)c2ccc3[nH]ncc3c2F)cc1] | 431 |
| 122 | (E)-3-(4-((E)-1-(2-Oxo-2,3-dihydro-1H-benzo[d]imidazol-5-yl)-2-phenylbut-1-en-1-yl)phenyl)acrylic acid | 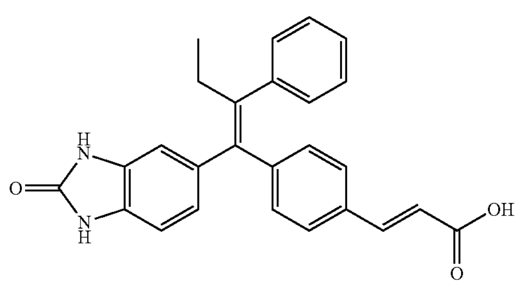 [SMILES: CC/C(=C(/c1ccc(/C=C/C(=O)O)cc1)c1ccc2[nH]c(=O)[nH]c2c1)c1ccccc1] | 411 |
| 123 | (E)-3-(4-((E)-1-(Naphthalen-2-yl)-2-phenylbut-1-en-1-yl)phenyl)acrylic acid | 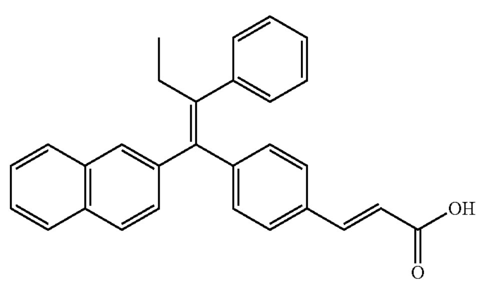 [SMILES: CC/C(=C(/c1ccc(/C=C/C(=O)O)cc1)c1ccc2ccccc2c1)c1ccccc1] | 404 |

TABLE 1-continued

| Compound | Name | Structure | LCMS [M + H]+ |
|---|---|---|---|
| 124 | (E)-3-(4-((E)-2-Phenyl-1-(quinoxalin-6-yl)but-1-en-1-yl)phenyl)acrylic acid | 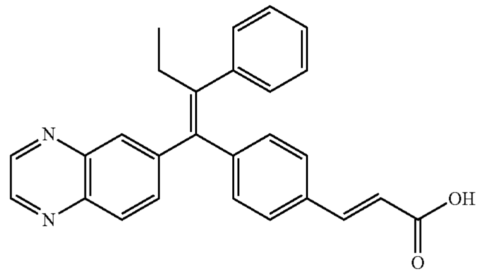 [SMILES: CC/C(=C(/c1ccc(/C=C/C(=O)O)cc1)c1ccc2nccnc2c1)c1ccccc1] | 407 |
| 125 | (E)-3-(4-((E)-2-Phenyl-1-(pyrazolo[1,5-a]pyridin-5-yl)but-1-en-1-yl)phenyl)acrylic acid | 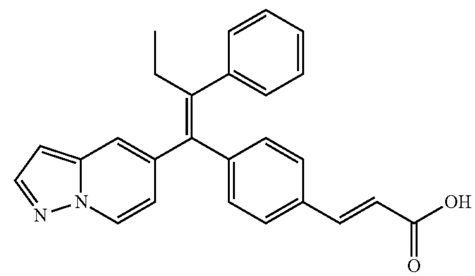 [SMILES: CC/C(=C(/c1ccc(/C=C/C(=O)O)cc1)c1ccn2nccc2c1)c1ccccc1] | 395 |
| 126 | (E)-3-(4-((E)-1-(Imidazo[1,2-a]pyridin-6-yl)-2-phenylbut-1-en-1-yl)phenyl)acrylic acid | 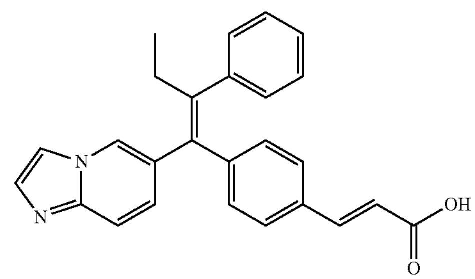 [SMILES: CC/C(=C(/c1ccc(/C=C/C(=O)O)cc1)c1ccc2nccn2c1)c1ccccc1] | 395 |
| 127 | (E)-3-(4-((E)-1-([1,2,4]Triazolo[4,3-a]pyridin-6-yl)-2-phenylbut-1-en-1-yl)phenyl)acrylic acid | 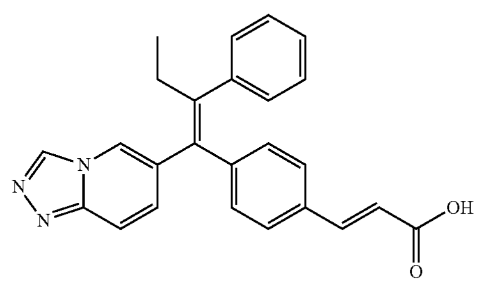 [SMILES: CC/C(=C(/c1ccc(/C=C/C(=O)O)cc1)c1ccc2nncn2c1)c1ccccc1] | 396 |
| 128 | (E)-3-(4-((E)-1-(Benzo[d][1,3]dioxol-5-yl)-2-phenylbut-1-en-1-yl)phenyl)acrylic acid | 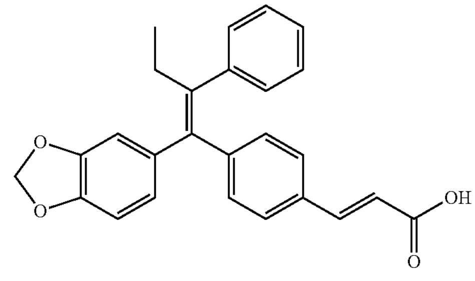 [SMILES: CC/C(=C(/c1ccc(/C=C/C(=O)O)cc1)c1ccc2c(c1)OCO2)c1ccccc1] | 397 (ES-) |

TABLE 1-continued

| Compound | Name | Structure | LCMS [M + H]+ |
|---|---|---|---|
| 129 | (E)-3-(4-((E)-1-(Imidazo[1,2-a]pyridin-6-yl)-2-(o-tolyl)but-1-en-1-yl)phenyl)acrylic acid | 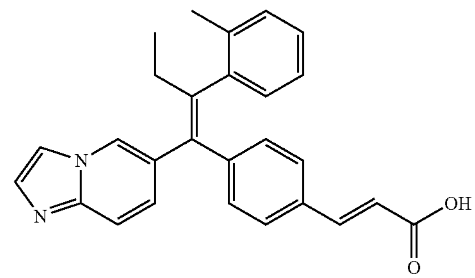 [SMILES: CC/C(=C(/c1ccc(/C=C/C(=O)O)cc1)c1ccc2nccn2c1)c1ccccc1C] | 409 |
| 130 | (E)-3-(4-((E)-1-(Benzo[d]thiazol-6-yl)-2-phenylbut-1-en-1-yl)phenyl)acrylic acid | 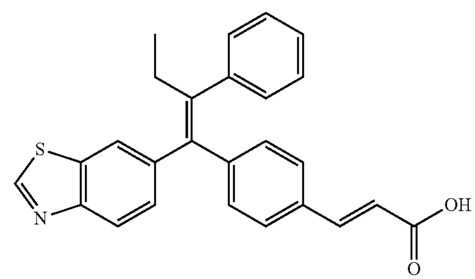 [SMILES: CC/C(=C(/c1ccc(/C=C/C(=O)O)cc1)c1ccc2ncsc2c1)c1ccccc1] | 412 |
| 131 | (E)-3-(4-((E)-1-([1,2,4]Triazolo[1,5-a]pyridin-6-yl)-2-phenylbut-1-en-1-yl)phenyl)acrylic acid | | 396 |
| 131 | (E)-3-(4-((E)-2-Phenyl-1-(tetrazolo[1,5-a]pyridin-6-yl)but-1-en-1-yl)phenyl)acrylic acid | | 397 |
| 133 | (E)-3-(4-((E)-1-(Imidazo[1,5-a]pyridin-6-yl)-2-phenylbut-1-en-1-yl)phenyl)acrylic acid | 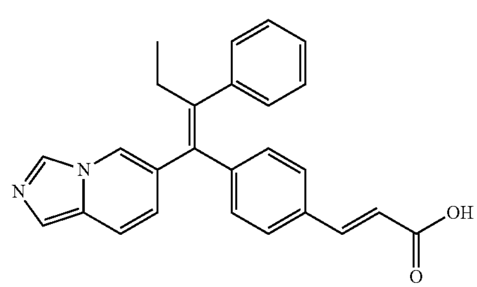 [SMILES: CC/C(=C(/c1ccc(/C=C/C(=O)O)cc1)c1ccc2cncn2c1)c1ccccc1] | 395 |

TABLE 1-continued

| Compound | Name | Structure | LCMS [M + H]+ |
|---|---|---|---|
| 134 | (E)-3-(4-((E)-1-([1,2,4]Triazolo[4,3-a]pyridin-7-yl)-2-phenylbut-1-en-1-yl)phenyl)acrylic acid | 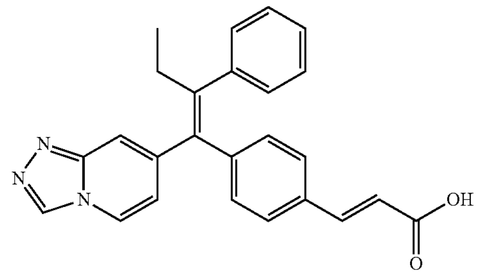 [SMILES: CC/C(=C(/c1ccc(/C=C/C(=O)O)cc1)c1ccn2cnnc2c1)c1ccccc1] | 396 |
| 135 | (E)-3-(4-((E)-1-(Imidazo[1,5-a]pyridin-7-yl)-2-phenylbut-1-en-1-yl)phenyl)acrylic acid | 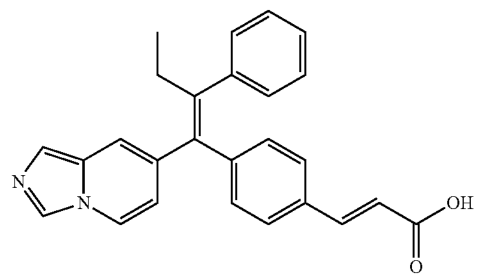 [SMILES: CC/C(=C(/c1ccc(/C=C/C(=O)O)cc1)c1ccn2cncc2c1)c1ccccc1] | 395 |
| 136 | (E)-3-(4-((E)-1-([1,2,4]Triazolo[1,5-a]pyridin-7-yl)-2-phenylbut-1-en-1-yl)phenyl)acrylic acid | 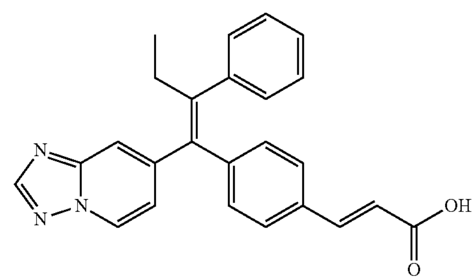 [SMILES: CC/C(=C(/c1ccc(/C=C/C(=O)O)cc1)c1ccn2ncnc2c1)c1ccccc1] | 396 |
| 137 | (E)-3-(4-((E)-1-(Benzo[c][1,2,5]oxadiazol-5-yl)-2-phenylbut-1-en-1-yl)phenyl)acrylic acid | 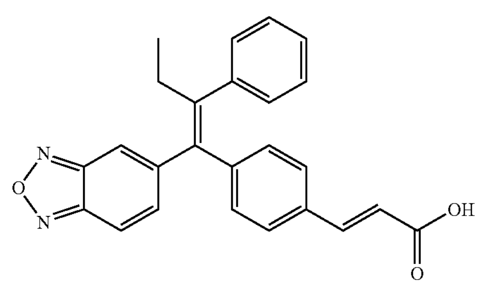 [SMILES: CC/C(=C(/c1ccc(/C=C/C(=O)O)cc1)c1ccc2nonc2c1)c1ccccc1] | 397 |
| 138 | (E)-3-(4-((E)-1-([1,2,3]Triazolo[1,5-a]pyridin-5-yl)-2-phenylbut-1-en-1-yl)phenyl)acrylic acid | 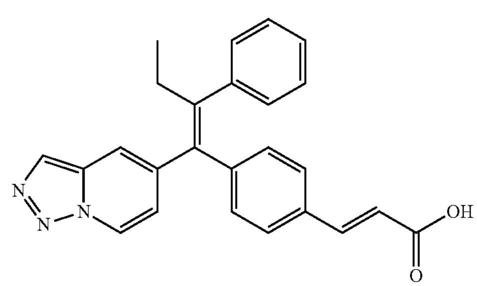 [SMILES: CC/C(=C(/c1ccc(/C=C/C(=O)O)cc1)c1ccn2nncc2c1)c1ccccc1] | 396 |

TABLE 1-continued

| Compound | Name | Structure | LCMS [M + H]+ |
|---|---|---|---|
| 139 | (E)-3-(4-((E)-1-(1H-Indazol-5-yl)-5-methoxy-2-phenylpent-1-en-1-yl)phenyl)acrylic acid | 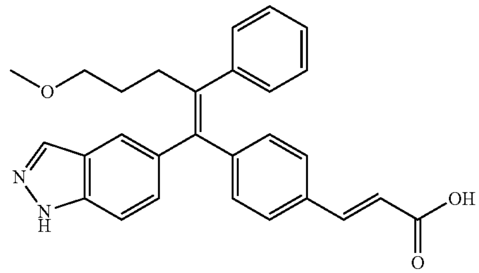 [SMILES: COCCC/C(=C(/c1ccc(/C=C/C(=O)O)cc1)c1ccc2[nH]ncc2c1)c1ccccc1] | 439 |
| 140 | (E)-3-(4-((E)-1-(1H-Indazol-5-yl)-6-methoxy-2-phenylhex-1-en-1-yl)phenyl)acrylic acid | 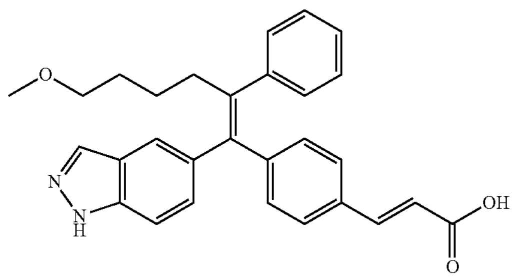 [SMILES: COCCCC/C(=C(/c1ccc(/C=C/C(=O)O)cc1)c1ccc2[nH]ncc2c1)c1ccccc1] | 453 |
| 141 | (E)-3-(4-((E)-1-(Benzo[d]thiazol-5-yl)-2-phenylbut-1-en-1-yl)phenyl)acrylic acid | 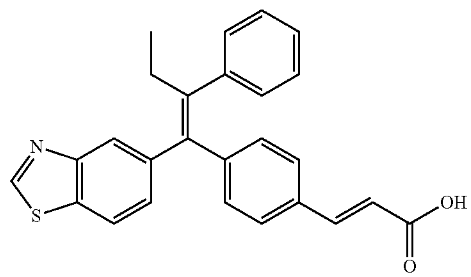 [SMILES: CC/C(=C(/c1ccc(/C=C/C(=O)O)cc1)c1ccc2scnc2c1)c1ccccc1] | 412 |
| 142 | (E)-3-(4-((E)-1-(Benzo[b]thiophen-2-yl)-2-phenylbut-1-en-1-yl)phenyl)acrylic acid | 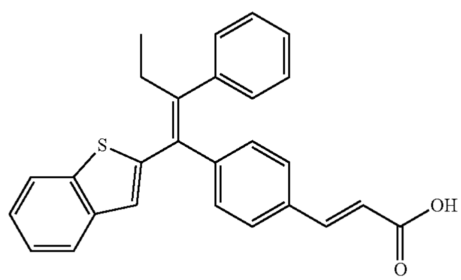 [SMILES: CC/C(=C(/c1ccc(/C=C/C(=O)O)cc1)c1cc2ccccc2s1)c1ccccc1] | 409 |
| 143 | (E)-3-(4-((E)-2-Phenyl-1-(1-phenyl-1H-indazol-5-yl)but-1-en-1-yl)phenyl)acrylic acid | 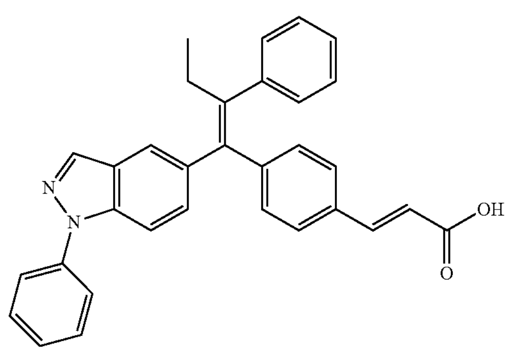 [SMILES: CC/C(=C(/c1ccc(/C=C/C(=O)O)cc1)c1ccc2c(cnn2-c2ccccc2)c1)c1ccccc1] | 471 |

TABLE 1-continued

| Compound | Name | Structure | LCMS [M + H]+ |
|---|---|---|---|
| 144 | (E)-3-(4-((E)-1-(Benzo[c][1,2,5]thiadiazol-5-yl)-2-phenylbut-1-en-1-yl)phenyl)acrylic acid | 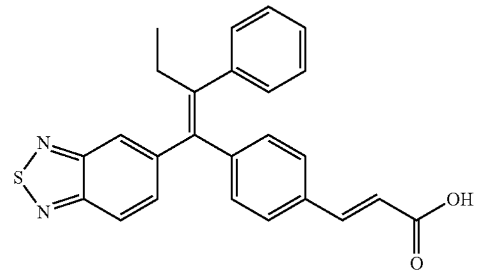 [SMILES: CC/C(=C(/c1ccc(/C=C/C(=O)O)cc1)c1ccc2nsnc2c1)c1ccccc1] | 413 |
| 145 | (E)-3-(4-((E)-2-Phenyl-1-(1-(pyridin-3-yl)-1H-indazol-5-yl)but-1-en-1-yl)phenyl)acrylic acid | 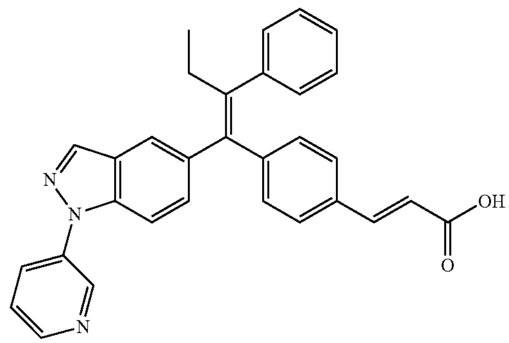 [SMILES: CC/C(=C(/c1ccc(/C=C/C(=O)O)cc1)c1ccc2c(cnn2-c2cccnc2)c1)c1ccccc1] | 472 |
| 146 | (E)-3-(4-((E)-1-(Benzo[d]oxazol-5-yl)-2-phenylbut-1-en-1-yl)phenyl)acrylic acid | 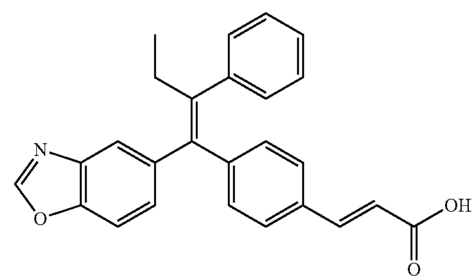 [SMILES: CC/C(=C(/c1ccc(/C=C/C(=O)O)cc1)c1ccc2ocnc2c1)c1ccccc1] | 396 |
| 147 | (E)-3-(4-((E)-1-(1H-Indazol-5-yl)-2-(2-phenoxyphenyl)but-1-en-1-yl)phenyl)acrylic acid | 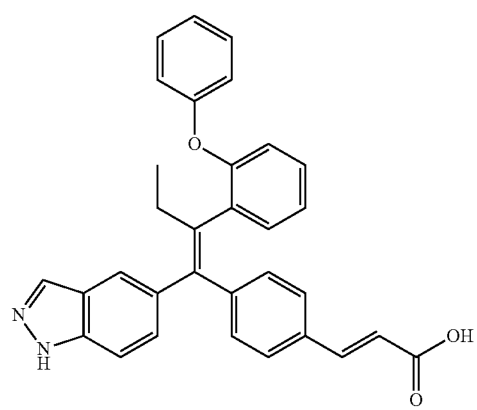 [SMILES: CC/C(=C(/c1ccc(/C=C/C(=O)O)cc1)c1ccc2[nH]ncc2c1)c1ccccc1Oc1ccccc1] | 487 |
| 148 | (E)-3-(4-((E)-2-Phenyl-1-(pyrazolo[1,5-a]pyridin-3-yl)but-1-en-1-yl)phenyl)acrylic acid | 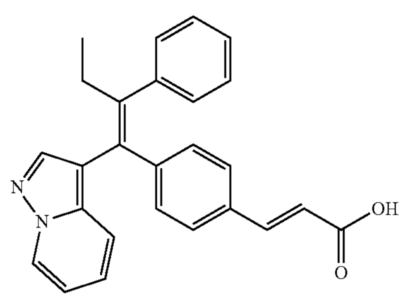 [SMILES: CC/C(=C(/c1ccc(/C=C/C(=O)O)cc1)c1cnn2ccccc12)c1ccccc1] | 395 |

TABLE 1-continued

| Compound | Name | Structure | LCMS [M + H]+ |
|---|---|---|---|
| 149 | (E)-3-(4-((E)-2-Phenyl-1-(1H-pyrazolo[4,3-d]pyrimidin-5-yl)but-1-en-1-yl)phenyl)acrylic acid | 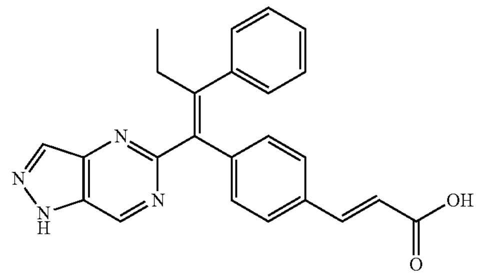 [SMILES: CC/C(=C(/c1ccc(/C=C/C(=O)O)cc1)c1ncc2[nH]ncc2n1)c1ccccc1] | 397 |
| 150 | (E)-3-(4-((E)-2-(3-(Carboxymethoxy)phenyl)-1-(1H-indazol-5-yl)but-1-en-1-yl)phenyl)acrylic acid | 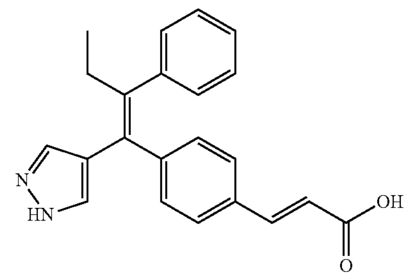 [SMILES: CC/C(=C(/c1ccc(/C=C/C(=O)O)cc1)c1cn[nH]c1)c1ccccc1] | 345 |
| 151 | (E)-3-(4-((E)-2-(2-Chloro-4-fluorophenyl)-1-(1H-indazol-5-yl)-3-methylbut-1-en-1-yl)phenyl)acrylic acid | 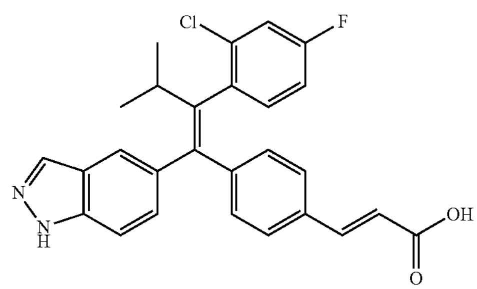 [SMILES: CC(C)/C(=C(/c1ccc(/C=C/C(=O)O)cc1)c1ccc2[nH]ncc2c1)c1ccc(F)cc1Cl] | 461 |
| 152 | (E)-3-(4-((E)-1-(6-Hydroxypyridin-3-yl)-2-phenylbut-1-en-1-yl)phenyl)acrylic acid | 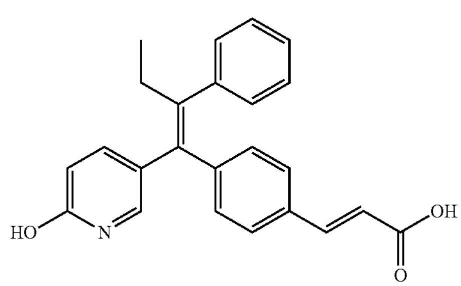 [SMILES: CC/C(=C(/c1ccc(/C=C/C(=O)O)cc1)c1ccc(O)nc1)c1ccccc1] | 372 |
| 153 | (E)-3-(4-((E)-1-(1H-Indazol-5-yl)-2-(3-(trifluoromethoxy)phenyl)but-1-en-1-yl)phenyl)acrylic acid | 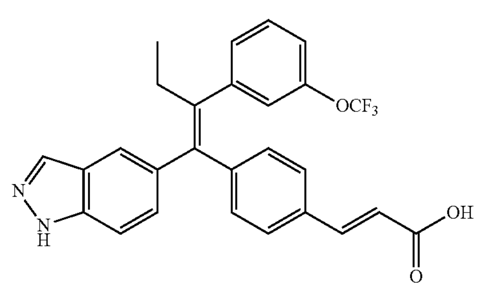 [SMILES: CC/C(=C(/c1ccc(/C=C/C(=O)O)cc1)c1ccc2[nH]ncc2c1)c1cccc(OC(F)(F)F)c1] | 479 |

TABLE 1-continued

| Compound | Name | Structure | LCMS [M + H]+ |
|---|---|---|---|
| 154 | (E)-3-(4-((E)-1-(1H-Indazol-5-yl)-3-methyl-2-(4-methylthiophen-3-yl)but-1-en-1-yl)phenyl)acrylic acid | 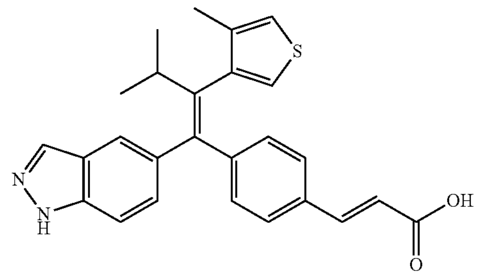 [SMILES: Cc1cscc1/C(=C(\c1ccc(/C=C/C(=O)O)cc1)c1ccc2[nH]ncc2c1)C(C)C] | 429 |
| 155 | (E)-3-(4-((E)-2-Cyclobutyl-1-(1H-indazol-5-yl)-2-phenylvinyl)phenyl)acrylic acid | 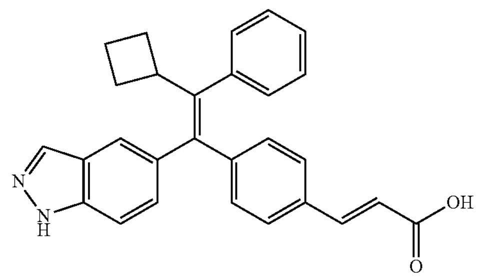 [SMILES: O=C(O)/C=C/c1ccc(/C(=C(\c2ccccc2)C2CCC2)c2ccc3[nH]ncc3c2)cc1] | 421 |
| 156 | (E)-3-(4-((E)-1-(Benzo[d]isothiazol-5-yl)-2-phenylbut-1-en-1-yl)phenyl)acrylic acid | 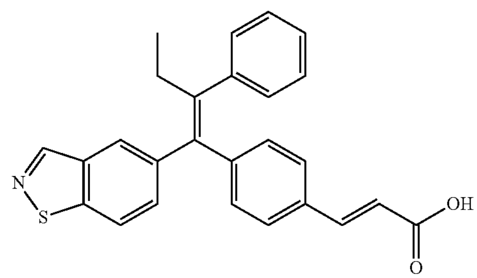 [SMILES: CC/C(=C(/c1ccc(/C=C/C(=O)O)cc1)c1ccc2sncc2c1)c1ccccc1] | 412 |
| 157 | (E)-3-(4-((E)-2-(2-Chloro-4-fluorophenyl)-2-cyclobutyl-1-(1H-indazol-5-yl)vinyl)phenyl)acrylic acid | 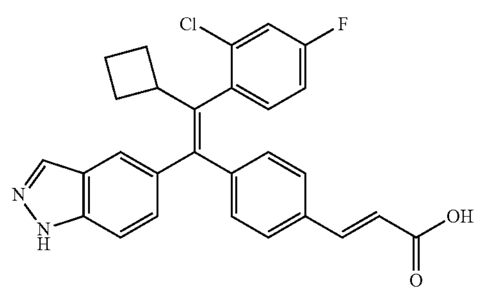 [SMILES: O=C(O)/C=C/c1ccc(/C(=C(\c2ccc(F)cc2Cl)C2CCC2)c2ccc3[nH]ncc3c2)cc1] | 473 |
| 158 | (E)-3-(4-((E)-1-(3-Fluoro-1H-indazol-5-yl)-2-phenylbut-1-en-1-yl)phenyl)acrylic acid | 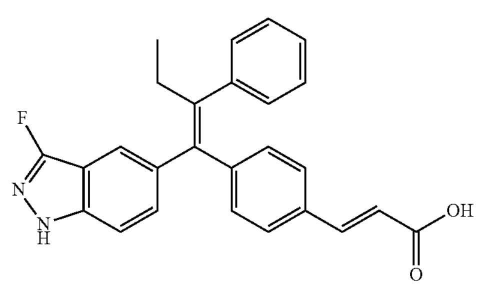 [SMILES: CC/C(=C(/c1ccc(/C=C/C(=O)O)cc1)c1ccc2[nH]nc(F)c2c1)c1ccccc1] | 413 |

TABLE 1-continued

| Compound | Name | Structure | LCMS [M + H]+ |
|---|---|---|---|
| 159 | (E)-3-(4-((E)-1-(2-Methylbenzo[d]thiazol-5-yl)-2-phenylbut-1-en-1-yl)phenyl)acrylic acid | 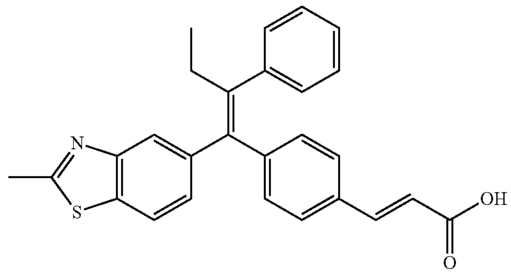 [SMILES: CC/C(=C(/c1ccc(/C=C/C(=O)O)cc1)c1ccc2sc(C)nc2c1)c1ccccc1] | 426 |
| 160 | (E)-3-(4-((E)-1-(4-Fluoro-1H-indazol-5-yl)-2-(4-(pyrimidin-2-yloxy)phenyl)but-1-en-1-yl)phenyl)acrylic acid | 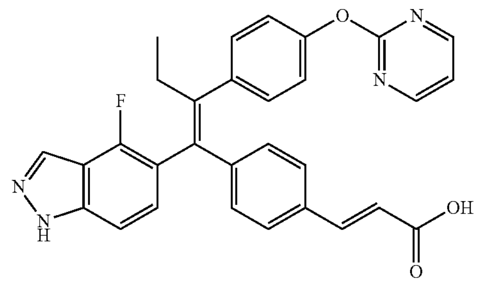 [SMILES: CC/C(=C(/c1ccc(/C=C/C(=O)O)cc1)c1ccc2[nH]ncc2c1F)c1ccc(Oc2ncccn2)cc1] | 507 |
| 161 | (E)-3-(4-((E)-1-(4-Fluoro-1H-indazol-5-yl)-2-(4-(pyrazin-2-yloxy)phenyl)but-1-en-1-yl)phenyl)acrylic acid | 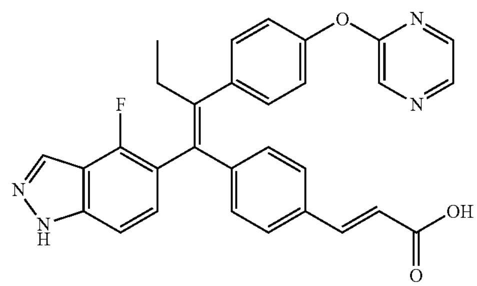 [SMILES: CC/C(=C(/c1ccc(/C=C/C(=O)O)cc1)c1ccc2[nH]ncc2c1F)c1ccc(Oc2cnccn2)cc1] | 507 |
| 162 | (E)-3-(4-((E)-2-Cyclobutyl-1-(1H-indazol-5-yl)-2-(4-((5-(methylsulfonyl)pyridin-2-yl)oxy)phenyl)vinyl)phenyl)acrylic acid | 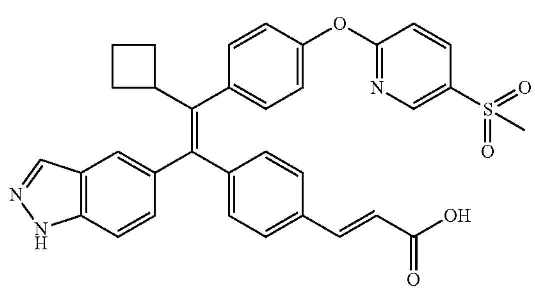 [SMILES: CS(=O)(=O)c1ccc(Oc2ccc(/C(=C(\c3ccc(/C=C/C(=O)O)cc3)c3ccc4[nH]ncc4c3)C3CCC3)cc2)nc1] | 592 |
| 163 | (E)-3-(4-((E)-1-(7-Methoxybenzofuran-3-yl)-2-phenylbut-1-en-1-yl)phenyl)acrylic acid | 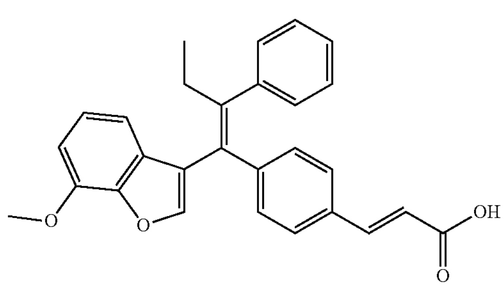 [SMILES: CC/C(=C(/c1ccc(/C=C/C(=O)O)cc1)c1coc2c(OC)cccc12)c1ccccc1] | not observed |

TABLE 1-continued

| Compound | Name | Structure | LCMS [M + H]+ |
|---|---|---|---|
| 164 | (E)-3-(4-((E)-2-(2-Chloro-4-fluorophenyl)-1-(7-methoxybenzofuran-3-yl)but-1-en-1-yl)phenyl)acrylic acid | 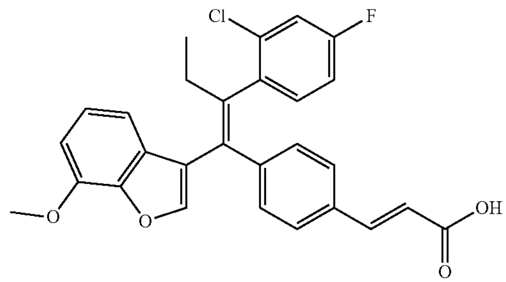 [SMILES: CC/C(=C(/c1ccc(/C=C/C(=O)O)cc1)c1coc2c(OC)cccc12)c1ccc(F)cc1Cl] | 477 |
| 165 | (E)-3-(4-((E)-2-Cyclobutyl-1-(3-fluoro-1H-indazol-5-yl)-2-phenylvinyl)phenyl)acrylic acid | 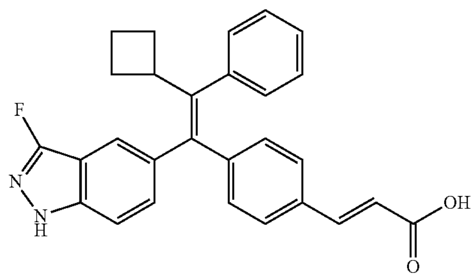 [SMILES: O=C(O)/C=C/c1ccc(/C(=C(\c2ccccc2)C2CCC2)c2ccc3[nH]nc(F)c3c2)cc1] | 439 |
| 166 | (E)-3-(4-((E)-2-(2-Chloro-4-fluorophenyl)-1-(3-fluoro-1H-indazol-5-yl)but-1-en-1-yl)phenyl)acrylic acid | 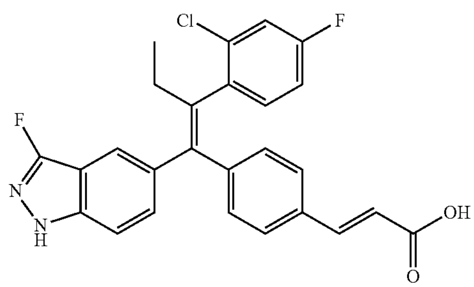 [SMILES: CC/C(=C(/c1ccc(/C=C/C(=O)O)cc1)c1ccc2[nH]nc(F)c2c1)c1ccc(F)cc1Cl] | 465 |
| 167 | (E)-3-(4-((E)-2-(2-Chloro-4-fluorophenyl)-2-cyclobutyl-1-(3-fluoro-1H-indazol-5-yl)vinyl)phenyl)acrylic acid | 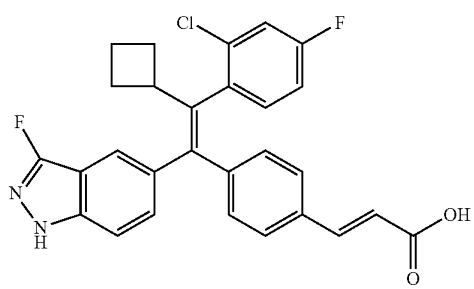 [SMILES: O=C(O)/C=C/c1ccc(/C(=C(\c2ccc(F)cc2Cl)C2CCC2)c2ccc3[nH]nc(F)c3c2)cc1] | 491 |
| 168 | (E)-3-(4-((E)-1-(Isoquinolin-7-yl)-2-phenylbut-1-en-1-yl)phenyl)acrylic acid | 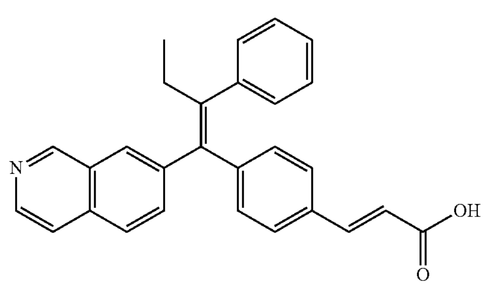 [SMILES: CC/C(=C(/c1ccc(/C=C/C(=O)O)cc1)c1ccc2ccncc2c1)c1ccccc1] | 405 |

TABLE 1-continued

| Compound | Name | Structure | LCMS [M + H]+ |
|---|---|---|---|
| 169 | (E)-3-(4-((E)-1-(Benzofuran-2-yl)-2-(2-chloro-4-fluorophenyl)but-1-en-1-yl)phenyl)acrylic acid | 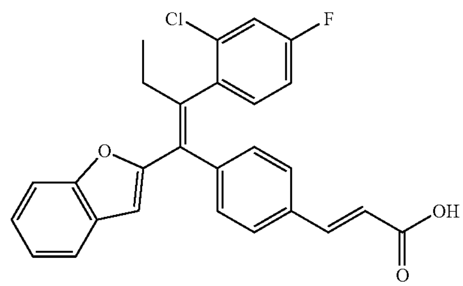 [SMILES: CC/C(=C(/c1ccc(/C=C/C(=O)O)cc1)c1cc2ccccc2o1)c1ccc(F)cc1Cl] | 447 |
| 170 | (E)-3-(4-((E)-1-(Benzofuran-3-yl)-2-(2-chloro-4-fluorophenyl)but-1-en-1-yl)phenyl)acrylic acid | 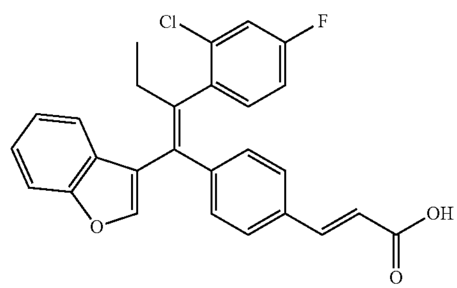 [SMILES: CC/C(=C(/c1ccc(/C=C/C(=O)O)cc1)c1coc2ccccc12)c1ccc(F)cc1Cl] | 447 |
| 171 | (E)-Ethyl 3-(4-((E)-2-(4-fluorophenyl)-1-(1H-indazol-5-yl)but-1-en-1-yl)phenyl)acrylate | 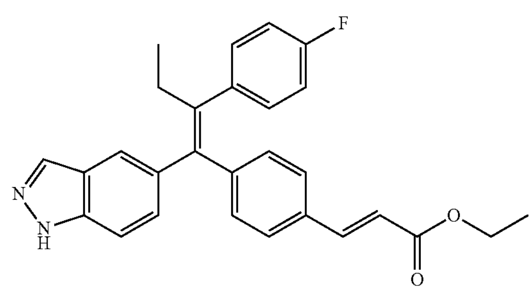 [SMILES: CCOC(=O)/C=C/c1ccc(/C(=C(/CC)c2ccc(F)cc2)c2ccc3[nH]ncc3c2)cc1] | 441 |
| 172 | (E)-Ethyl 3-(4-((E)-1-(1H-indazol-6-yl)-2-phenylbut-1-en-1-yl)phenyl)acrylate | 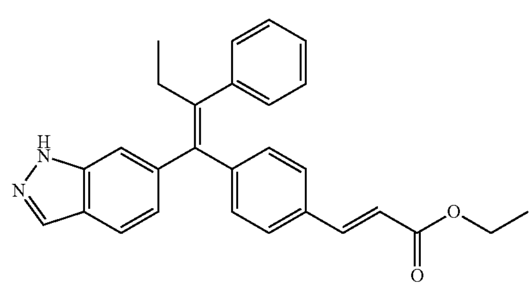 [SMILES: CCOC(=O)/C=C/c1ccc(/C(=C(/CC)c2ccccc2)c2ccc3cn[nH]c3c2)cc1] | 423 |
| 173 | (E)-Ethyl 3-(4-((E)-1-(1H-Indazol-5-yl)-2-(2-methoxyphenyl)but-1-en-1-yl)phenyl)acrylate | 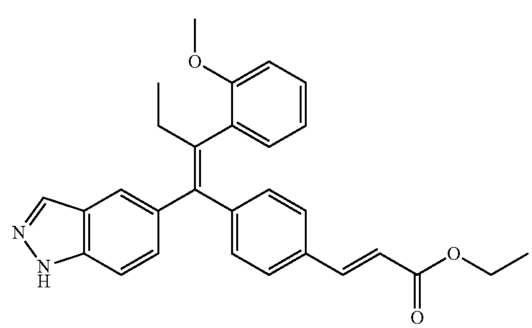 [SMILES: CCOC(=O)/C=C/c1ccc(/C(=C(/CC)c2ccccc2OC)c2ccc3[nH]ncc3c2)cc1] | 453 |

TABLE 1-continued

| Compound | Name | Structure | LCMS [M + H]+ |
|---|---|---|---|
| 174 | (E)-Ethyl 3-(4-((E)-1-(1H-Indazol-5-yl)-2-(4-methoxyphenyl)but-1-en-1-yl)phenyl)acrylate | 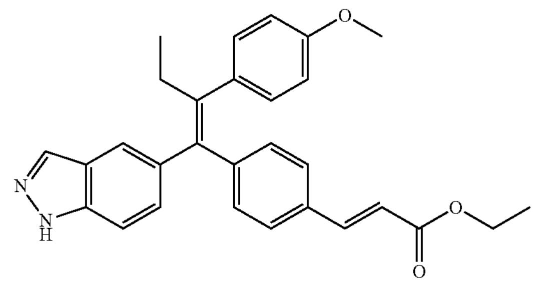 [SMILES: CCOC(=O)/C=C/c1ccc(/C(=C(/CC)c2ccc(OC)cc2)c2ccc3[nH]ncc3c2)cc1] | 453 |
| 175 | (E)-Ethyl 3-(4-((E)-1-(1H-Indazol-4-yl)-2-phenylbut-1-en-1-yl)phenyl)acrylate | 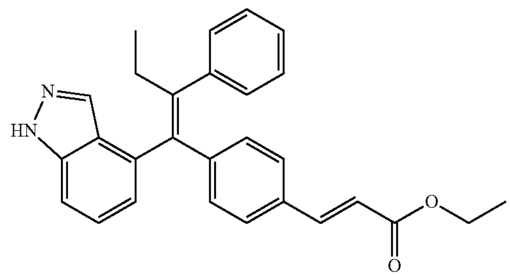 [SMILES: CCOC(=O)/C=C/c1ccc(/C(=C(/CC)c2ccccc2)c2cccc3[nH]ncc23)cc1] | 423 |
| 176 | (E)-3-(4-((E)-1-(1H-Indazol-5-yl)-2-phenylbut-1-en-1-yl)phenyl)-2-methylacrylic acid | 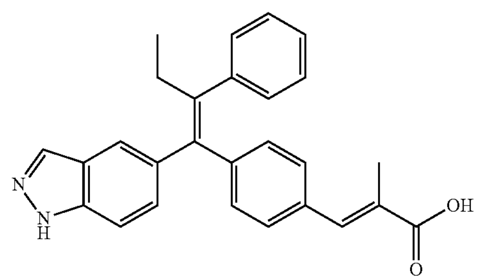 [SMILES: CC/C(=C(/c1ccc(/C=C(\C)C(=O)O)cc1)c1ccc2[nH]ncc2c1)c1ccccc1] | 409 |
| 177 | (E)-3-(4-((Z)-1-(1H-Indazol-5-yl)-2-phenylbut-1-en-1-yl)-3-methylphenyl)acrylic acid | 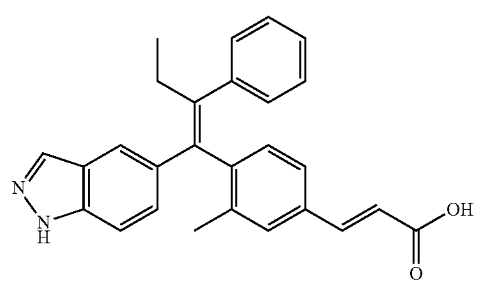 [SMILES: CC/C(=C(\c1ccc2[nH]ncc2c1)c1ccc(/C=C/C(=O)O)cc1C)c1ccccc1] | 409 |
| 178 | (E)-3-(4-((E)-1-(1H-Indazol-5-yl)-2-phenylbut-1-en-1-yl)-2-methylphenyl)acrylic acid | 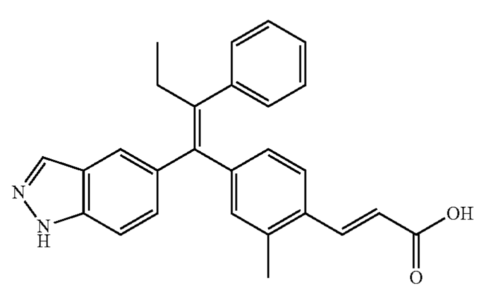 [SMILES: CC/C(=C(/c1ccc(/C=C/C(=O)O)c(C)c1)c1ccc2[nH]ncc2c1)c1ccccc1] | 409 |

TABLE 1-continued

| Compound | Name | Structure | LCMS [M + H]+ |
|---|---|---|---|
| 179 | (E)-3-(4-((Z)-1-(1H-Indazol-5-yl)-2-phenylbut-1-en-1-yl)-2-chlorophenyl)acrylic acid | 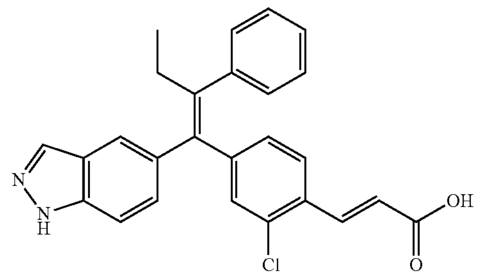 | 429 |
| 180 | (E)-3-(6-((E)-1-(1H-Indazol-5-yl)-2-phenylbut-1-en-1-yl)naphthalen-2-yl)acrylic acid | 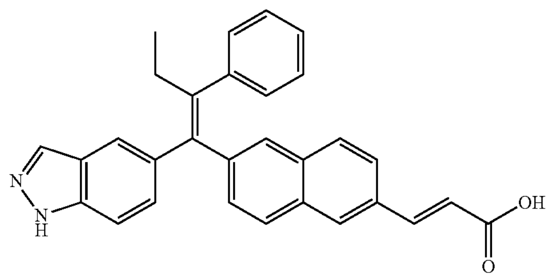 [SMILES: CC/C(=C(/c1ccc2cc(/C=C/C(=O)O)ccc2c1)c1ccc2[nH]ncc2c1)c1ccccc1] | 445 |
| 181 | (Z)-3-(4-((E)-1-(1H-Indazol-5-yl)-2-phenylbut-1-en-1-yl)phenyl)-2-fluoroacrylic acid | 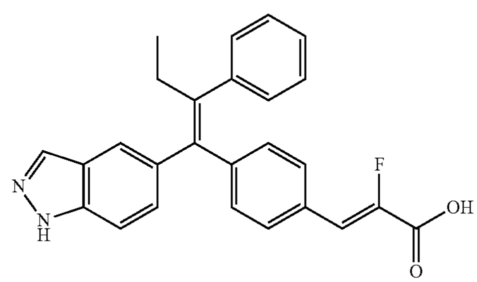 | 413 |
| 182 | (Z)-3-(4-((E)-1-(1H-Indazol-5-yl)-2-phenylbut-1-en-1-yl)phenyl)-2-chloroacrylic acid | 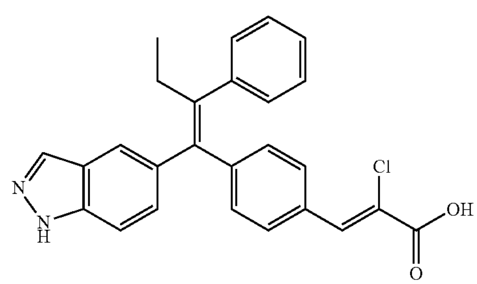 | 429 |
| 183 | (E)-3-(4-((Z)-1-(1H-Indazol-5-yl)-2-phenylbut-1-en-1-yl)-3-fluorophenyl)acrylic acid | 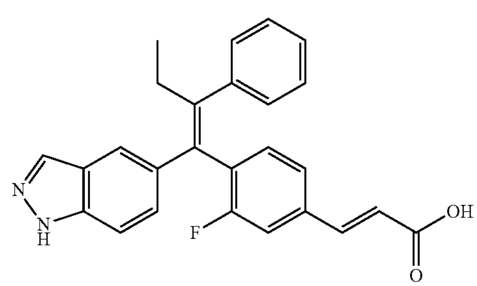 [SMILES: CC/C(=C(\c1ccc2[nH]ncc2c1)c1ccc(/C=C/C(=O)O)cc1F)c1ccccc1] | 413 |

TABLE 1-continued

| Compound | Name | Structure | LCMS [M + H]+ |
|---|---|---|---|
| 184 | (E)-3-(4-((Z)-1-(1H-Indazol-5-yl)-2-phenylbut-1-en-1-yl)-2-fluorophenyl)acrylic acid | 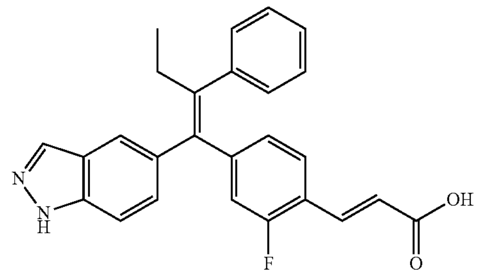 [SMILES: CC/C(=C(/c1ccc(/C=C/C(=O)O)c(F)c1)c1ccc2[nH]ncc2c1)c1ccccc1] | 413 |
| 185 | (E)-3-(4-((Z)-1-(1H-Indazol-5-yl)-2-phenylbut-1-en-1-yl)-2-(trifluoromethyl)phenyl)acrylic acid | 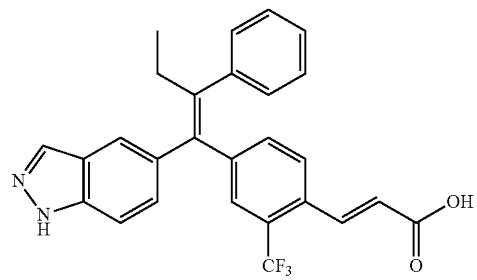 [SMILES: CC/C(=C(/c1ccc(/C=C/C(=O)O)c(C(F)(F)F)c1)c1ccc2[nH]ncc2c1)c1ccccc1] | 463 |
| 186 | (E)-3-(4-((Z)-1-(1H-Indazol-5-yl)-2-phenylbut-1-en-1-yl)thiophen-2-yl)acrylic acid | 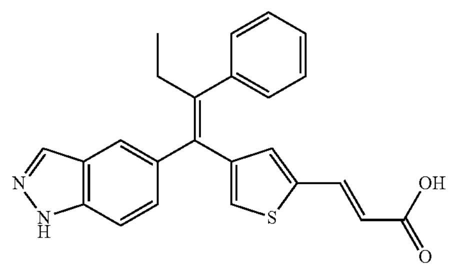 [SMILES: CC/C(=C(/c1csc(/C=C/C(=O)O)c1)c1ccc2[nH]ncc2c1)c1ccccc1] | 401 |
| 187 | (E)-3-(4-((Z)-1-(1H-Indazol-5-yl)-2-phenylbut-1-en-1-yl)-3-methoxyphenyl)acrylic acid | 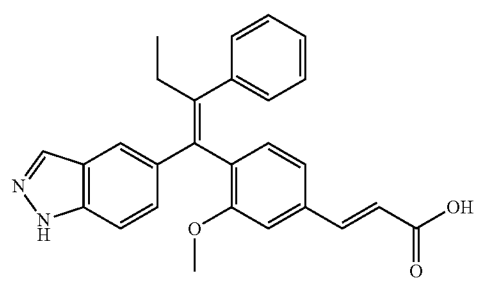 [SMILES: CC/C(=C(\c1ccc2[nH]ncc2c1)c1ccc(/C=C/C(=O)O)cc1OC)c1ccccc1] | 425 |
| 188 | (E)-3-(4-((Z)-1-(1H-Indazol-5-yl)-2-phenylbut-1-en-1-yl)-2-methoxyphenyl)acrylic acid | 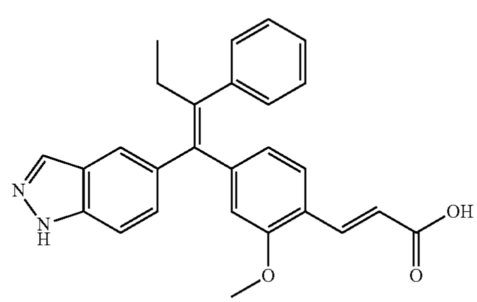 [SMILES: CC/C(=C(/c1ccc(/C=C/C(=O)O)c(OC)c1)c1ccc2[nH]ncc2c1)c1ccccc1] | 425 |

TABLE 1-continued

| Compound | Name | Structure | LCMS [M + H]+ |
|---|---|---|---|
| 189 | (E)-3-(5-((Z)-1-(1H-Indazol-5-yl)-2-phenylbut-1-en-1-yl)pyridin-2-yl)acrylic acid | 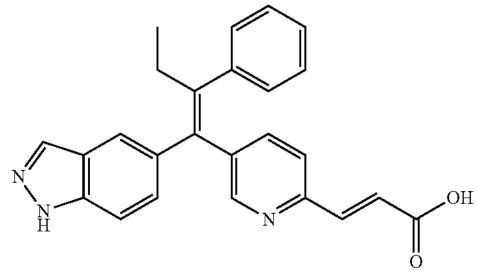 [SMILES: CC/C(=C(/c1ccc(/C=C/C(=O)O)nc1)c1ccc2[nH]ncc2c1)c1ccccc1] | 396 |
| 190 | (E)-2-(4-(1-(1H-Indazol-5-yl)-2-phenylbut-1-en-1-yl)phenoxy)acetic acid | 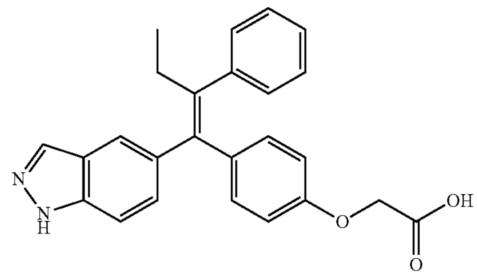 [SMILES: CC/C(=C(/c1ccc(OCC(=O)O)cc1)c1ccc2[nH]ncc2c1)c1ccccc1] | 399 |
| 191 | (E)-5-(2-Phenyl-1-(4-(2-(pyrrolidin-1-yl)ethoxy)phenyl)but-1-en-1-yl)-1H-indazole | 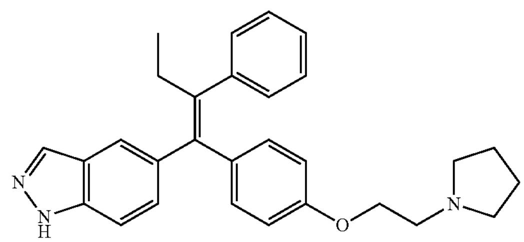 [SMILES: CC/C(=C(/c1ccc(OCCN2CCCC2)cc1)c1ccc2[nH]ncc2c1)c1ccccc1] | 438 |
| 192 | (E)-5-(1-(1H-Indazol-5-yl)-2-phenylbut-1-en-1-yl)-2,3-dihydro-1H-indene-2-carboxylic acid | 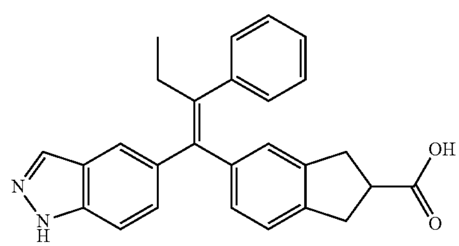 [SMILES: CC/C(=C(/c1ccc2c(c1)CC(C(=O)O)C2)c1ccc2[nH]ncc2c1)c1ccccc1] | 409 |
| 193 | (E)-Ethyl 3-(4-((E)-2-(2-chloro-4-fluorophenyl)-1-(1-(tetrahydro-2H-pyran-2-yl)-1H-indazol-5-yl)but-1-en-1-yl)phenyl)acrylate | 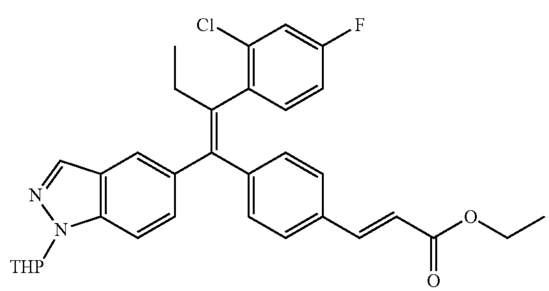 | 475 [(M − THP + H) + H]+ |

TABLE 1-continued

| Compound | Name | Structure | LCMS [M + H]+ |
|---|---|---|---|
| 194 | (E)-Ethyl 3-(4-((E)-2-(2-chloro-4-fluorophenyl)-1-(1H-indazol-5-yl)but-1-en-1-yl)phenyl)acrylate hydrochloride | 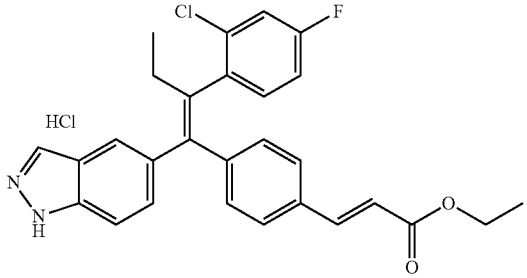 [SMILES: CCOC(=O)/C=C/c1ccc(/C(=C(/CC)c2ccc(F)cc2Cl)c2ccc3[nH]ncc3c2)cc1 ; Cl] | 475 |
| 195 | (E)-3-(4-((E)-2-(2-Chloro-4-fluorophenyl)-1-(1H-indazol-5-yl)but-1-en-1-yl)phenyl)acrylic acid | 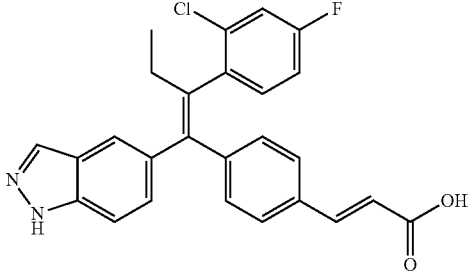 [SMILES: CC/C(=C(/c1ccc(/C=C/C(=O)O)cc1)c1ccc2[nH]ncc2c1)c1ccc(F)cc1Cl] | 447 |
| 196 | (E)-Ethyl 3-(4-((E)-2-(2,4-dichlorophenyl)-1-(1H-indazol-5-yl)but-1-en-1-yl)phenyl)acrylate | 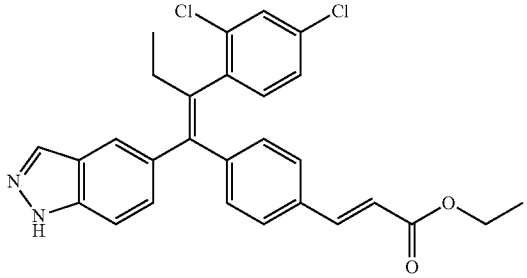 [SMILES: CCOC(=O)/C=C/c1ccc(/C(=C(/CC)c2ccc(Cl)cc2Cl)c2ccc3[nH]ncc3c2)cc1] | 491 |
| 197 | (E)-3-(4-((E)-2-(2,4-Dichlorophenyl)-1-(1H-indazol-5-yl)but-1-en-1-yl)phenyl)acrylic acid | 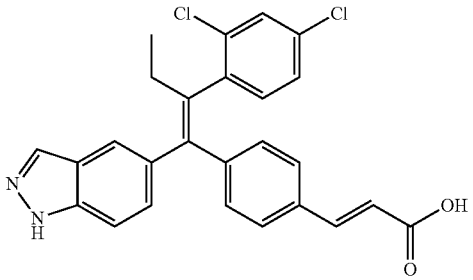 [SMILES: CC/C(=C(/c1ccc(/C=C/C(=O)O)cc1)c1ccc2[nH]ncc2c1)c1ccc(Cl)cc1Cl] | 463 |
| 198 | (E)-3-(4-((E)-2-(4-Chloro-2-(trifluoromethyl)phenyl)-1-(1H-indazol-5-yl)but-1-en-1-yl)phenyl)acrylic acid | 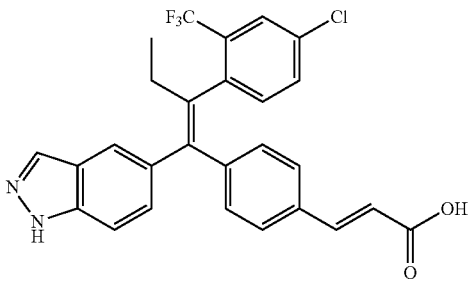 | 497 |

TABLE 1-continued

| Compound | Name | Structure | LCMS [M + H]+ |
|---|---|---|---|
| 199 | (E)-3-(4-((E)-2-(2-Chloro-4-fluorophenyl)-2-cyclopropyl-1-(1H-indazol-5-yl)vinyl)phenyl)acrylic acid | 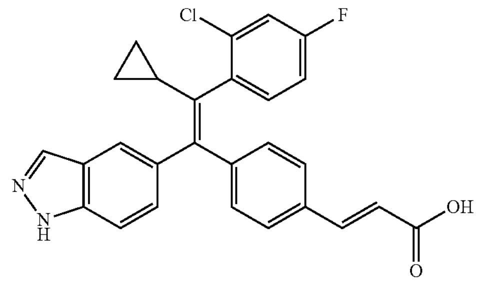 [SMILES: O=C(O)/C=C/c1ccc(/C(=C(\c2ccc(F)cc2Cl)C2CC2)c2ccc3[nH]ncc3c2)cc1] | 459 |
| 200 | (E)-3-(4-((E)-2-(4-Fluoro-2-(trifluoromethyl)phenyl)-1-(1H-indazol-5-yl)but-1-en-1-yl)phenyl)acrylic acid | 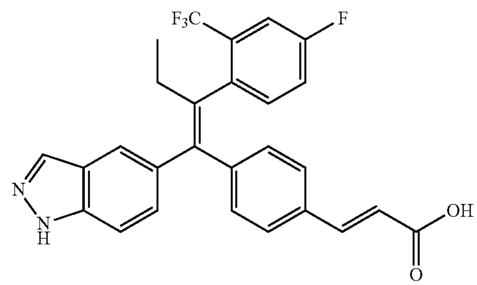 [SMILES: CC/C(=C(/c1ccc(/C=C/C(=O)O)cc1)c1ccc2[nH]ncc2c1)c1ccc(F)cc1C(F)(F)F] | 481 |
| 201 | (E)-3-(4-(1-(4-Fluoro-1H-indazol-5-yl)-2-(4-fluoro-2-(trifluoromethyl)phenyl)butyl)phenyl)acrylic acid | 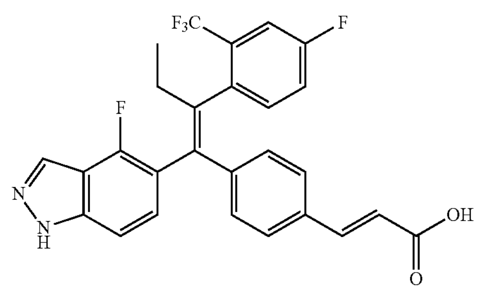 [SMILES: CC/C(=C(/c1ccc(/C=C/C(=O)O)cc1)c1ccc2[nH]ncc2c1F)c1ccc(F)cc1C(F)(F)F] | 499 |
| 202 | (E)-3-(4-((E)-2-(2,4-Dichlorophenyl)-1-(4-fluoro-1H-indazol-5-yl)but-1-en-1-yl)phenyl)acrylic acid | 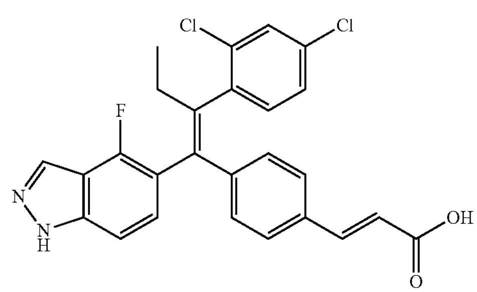 [SMILES: CC/C(=C(/c1ccc(/C=C/C(=O)O)cc1)c1ccc2[nH]ncc2c1F)c1ccc(Cl)cc1Cl] | 481 |
| 203 | (E)-3-(4-((E)-2-(4-Chloro-2-(trifluoromethyl)phenyl)-1-(4-fluoro-1H-indazol-5-yl)but-1-en-1-yl)phenyl)acrylic acid | 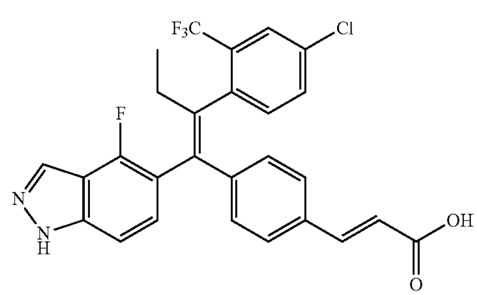 [SMILES: CC/C(=C(/c1ccc(/C=C/C(=O)O)cc1)c1ccc2[nH]ncc2c1F)c1ccc(Cl)cc1C(F)(F)F] | 515 |

TABLE 1-continued

| Compound | Name | Structure | LCMS [M + H]+ |
|---|---|---|---|
| 204 | (E)-3-(4-((E)-2-(3-Chloropyridin-4-yl)-1-(1H-indazol-5-yl)but-1-en-1-yl)phenyl)acrylic acid | 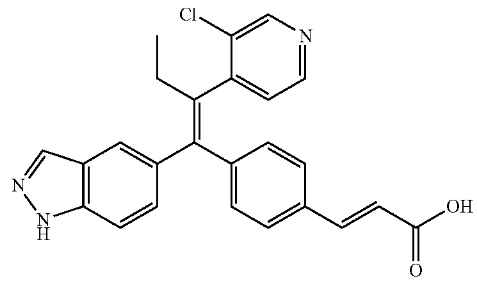 [SMILES: CC/C(=C(/c1ccc(/C=C/C(=O)O)cc1)c1ccc2[nH]ncc2c1)c1ccncc1Cl] | 430 |
| 205 | (E)-3-(4-((E)-2-(2-Chloro-4-fluorophenyl)-4-fluoro-1-(1H-indazol-5-yl)but-1-en-1-yl)phenyl)acrylic acid | 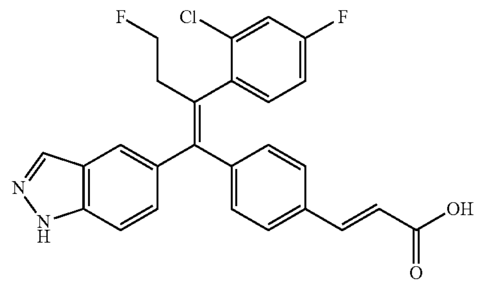 [SMILES: O=C(O)/C=C/c1ccc(/C(=C(/CCF)c2ccc(F)cc2Cl)c2ccc3[nH]ncc3c2)cc1] | 465 |
| 206 | (E)-3-(4-((E)-2-(2-Chloro-4-methoxyphenyl)-1-(1H-indazol-5-yl)but-1-en-1-yl)phenyl)acrylic acid | 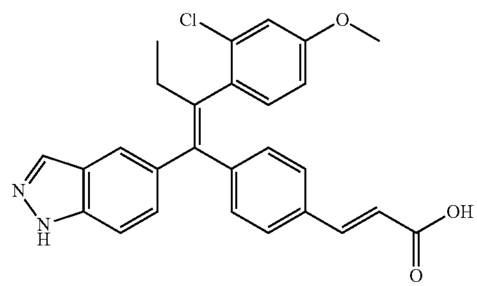 [SMILES: CC/C(=C(/c1ccc(/C=C/C(=O)O)cc1)c1ccc2[nH]ncc2c1)c1ccc(OC)cc1Cl] | 459 |
| 207 | (E)-3-(4-((E)-1-(1H-Indazol-5-yl)-2-(4-(trifluoromethyl)pyridin-3-yl)but-1-en-1-yl)phenyl)acrylic acid | 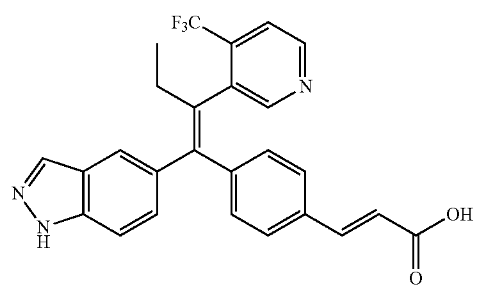 | 464 |
| 208 | (E)-3-(4-((E)-1-(1H-Indazol-5-yl)-2-(1-methyl-1H-pyrazol-5-yl)but-1-en-1-yl)phenyl)acrylic acid | 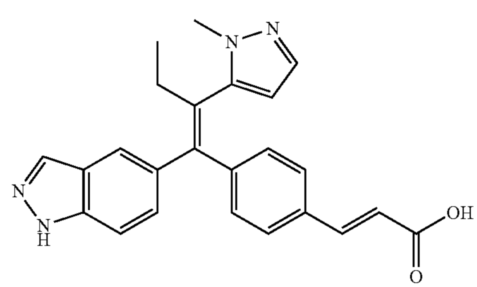 | 399 |

TABLE 1-continued

| Compound | Name | Structure | LCMS [M + H]+ |
|---|---|---|---|
| 209 | (E)-3-(4-((E)-2-(2,4-Dichlorophenyl)-4-fluoro-1-(4-fluoro-1H-indazol-5-yl)but-1-en-1-yl)phenyl)acrylic acid | 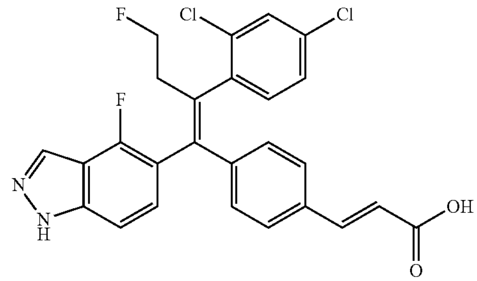 | 499 |
| 210 | (E)-3-(4-((E)-2-Cyclopropyl-2-(2,4-dichlorophenyl)-1-(4-fluoro-1H-indazol-5-yl)vinyl)phenyl)acrylic acid | 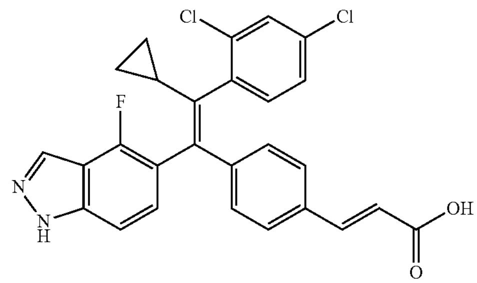 [SMILES: O=C(O)/C=C/c1ccc(/C(=C(\c2ccc(Cl)cc2Cl)C2CC2)c2ccc3[nH]ncc3c2F)cc1] | 493 |
| 211 | (E)-3-(4-((E)-2-(2-Chloro-4-fluorophenyl)-2-cyclopropyl-1-(4-fluoro-1H-indazol-5-yl)vinyl)phenyl)acrylic acid | 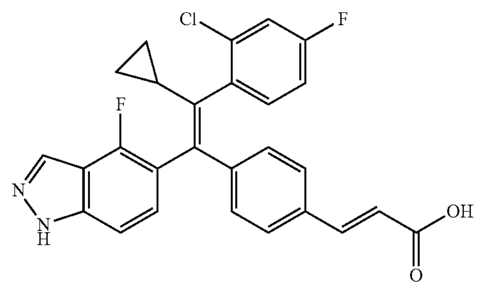 [SMILES: O=C(O)/C=C/c1ccc(/C(=C(\c2ccc(F)cc2Cl)C2CC2)c2ccc3[nH]ncc3c2F)cc1] | 477 |
| 212 | (E)-3-(4-((E)-2-(4-(Dimethylcarbamoyl)-2-fluorophenyl)-1-(1H-indazol-5-yl)but-1-en-1-yl)phenyl)acrylic acid | 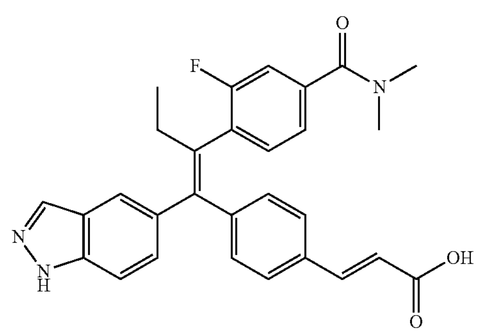 [SMILES: CC/C(=C(/c1ccc(/C=C/C(=O)O)cc1)c1ccc2[nH]ncc2c1)c1ccc(C(=O)N(C)C)cc1F] | 484 |
| 213 | (E)-3-(4-((E)-2-(2-Fluoro-4-(methylcarbamoyl)phenyl)-1-(1H-indazol-5-yl)but-1-en-1-yl)phenyl)acrylic acid | 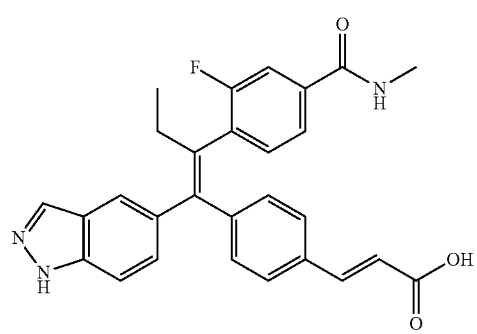 [SMILES: CC/C(=C(/c1ccc(/C=C/C(=O)O)cc1)c1ccc2[nH]ncc2c1)c1ccc(C(=O)NC)cc1F] | 470 |

TABLE 1-continued

| Compound | Name | Structure | LCMS [M + H]+ |
|---|---|---|---|
| 214 | (E)-3-(4-((E)-1-(1H-Indazol-5-yl)-2-(2-methylthiophen-3-yl)but-1-en-1-yl)phenyl)acrylic acid | 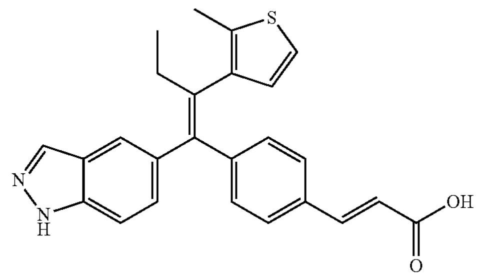 [SMILES: CC/C(=C(/c1ccc(/C=C/C(=O)O)cc1)c1ccc2[nH]ncc2c1)c1ccsc1C] | 415 |
| 215 | (E)-3-(4-((E)-2-Cyclopropyl-2-(2,4-dichlorophenyl)-1-(1H-indazol-5-yl)vinyl)phenyl)acrylic acid | 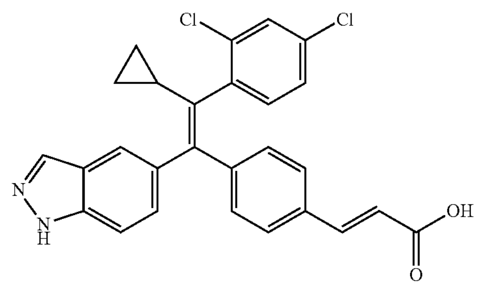 [SMILES: O=C(O)/C=C/c1ccc(/C(=C(\c2ccc(Cl)cc2Cl)C2CC2)c2ccc3[nH]ncc3c2)cc1] | 475 |
| 216 | (E)-3-(4-((E)-2-(4-Chloro-2-methylphenyl)-2-cyclopropyl-1-(1H-indazol-5-yl)vinyl)phenyl)acrylic acid | 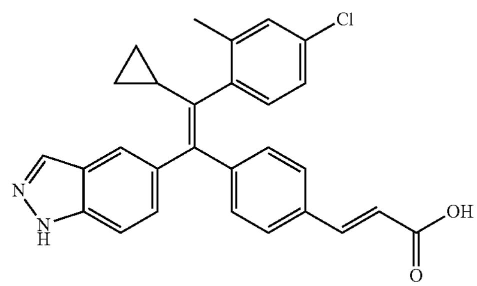 [SMILES: Cc1cc(Cl)ccc1/C(=C(\c1ccc(/C=C/C(=O)O)cc1)c1ccc2[nH]ncc2c1)C1CC1] | 455 |
| 217 | (E)-3-(4-((E)-1-(1H-Indazol-5-yl)-2-(2-methylpyridin-3-yl)but-1-en-1-yl)phenyl)acrylic acid | 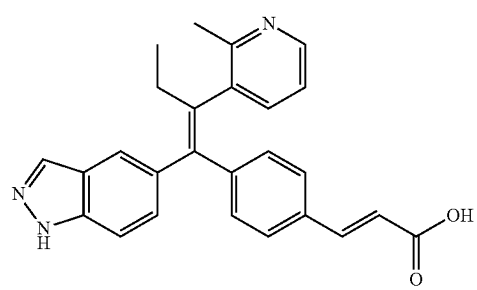 [SMILES: CC/C(=C(/c1ccc(/C=C/C(=O)O)cc1)c1ccc2[nH]ncc2c1)c1cccnc1C] | 410 |
| 218 | (E)-3-(4-((E)-1-(1H-Indazol-5-yl)-2-(4-methylpyridin-3-yl)but-1-en-1-yl)phenyl)acrylic acid | 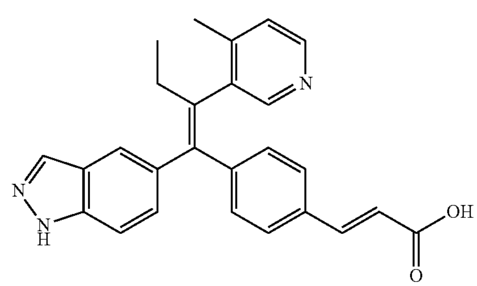 [SMILES: CC/C(=C(/c1ccc(/C=C/C(=O)O)cc1)c1ccc2[nH]ncc2c1)c1cnccc1C] | 410 |

135

136

TABLE 1-continued

| Compound | Name | Structure | LCMS [M + H]+ |
|---|---|---|---|
| 219 | (E)-3-(4-((E)-1-(1H-Indazol-5-yl)-2-(pyrazin-2-yl)but-1-en-1-yl)phenyl)acrylic acid | 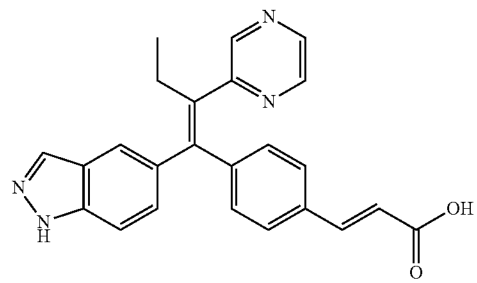 [SMILES: CC/C(=C(/c1ccc(/C=C/C(=O)O)cc1)c1ccc2[nH]ncc2c1)c1cnccn1] | 397 |
| 220 | (E)-3-(4-((E)-1-(1H-Indazol-5-yl)-2-(pyrimidin-5-yl)but-1-en-1-yl)phenyl)acrylic acid | 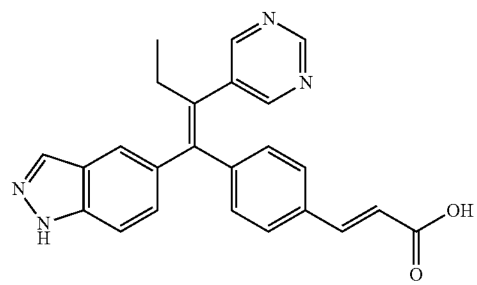 [SMILES: CC/C(=C(/c1ccc(/C=C/C(=O)O)cc1)c1ccc2[nH]ncc2c1)c1cncnc1] | 397 |
| 221 | (E)-3-(4-((E)-1-(1H-Indazol-5-yl)-2-(1-methyl-1H-1,2,3-triazol-5-yl)but-1-en-1-yl)phenyl)acrylic acid | 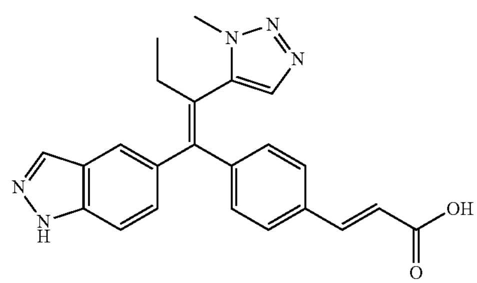 [SMILES: CC/C(=C(/c1ccc(/C=C/C(=O)O)cc1)c1ccc2[nH]ncc2c1)c1cnnn1C] | 400 |
| 222 | (E)-3-(4-((E)-1-(1H-Indazol-5-yl)-2-(2-(trifluoromethyl)pyridin-3-yl)but-1-en-1-yl)phenyl)acrylic acid | 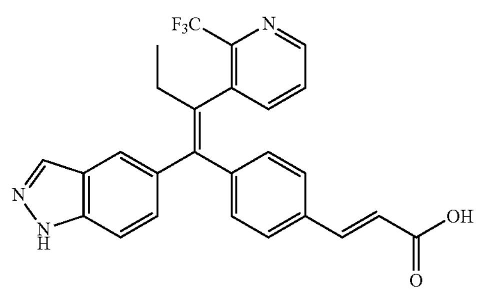 [SMILES: CC/C(=C(/c1ccc(/C=C/C(=O)O)cc1)c1ccc2[nH]ncc2c1)c1cccnc1C(F)(F)F] | 464 |
| 223 | (E)-3-(4-((E)-1-(1H-Indazol-5-yl)-2-(4-methylthiophen-3-yl)but-1-en-1-yl)phenyl)acrylic acid | 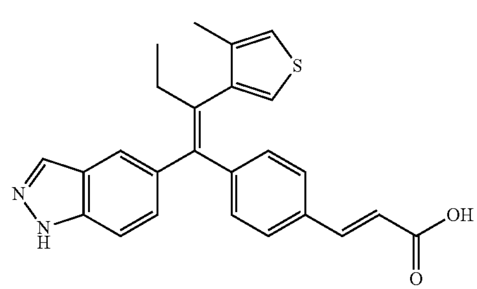 [SMILES: CC/C(=C(/c1ccc(/C=C/C(=O)O)cc1)c1ccc2[nH]ncc2c1)c1cscc1C] | 415 |

TABLE 1-continued

| Compound | Name | Structure | LCMS [M + H]+ |
|---|---|---|---|
| 224 | (E)-3-(4-((E)-2-(3-Chloropyridin-4-yl)-1-(4-fluoro-1H-indazol-5-yl)but-1-en-1-yl)phenyl)acrylic acid | 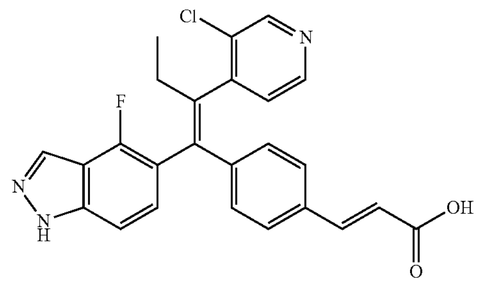 [SMILES: CC/C(=C(/c1ccc(/C=C/C(=O)O)cc1)c1ccc2[nH]ncc2c1F)c1ccncc1Cl] | 448 |
| 225 | (E)-3-(4-((E)-1-(1H-Indazol-5-yl)-2-(isothiazol-4-yl)but-1-en-1-yl)phenyl)acrylic acid | 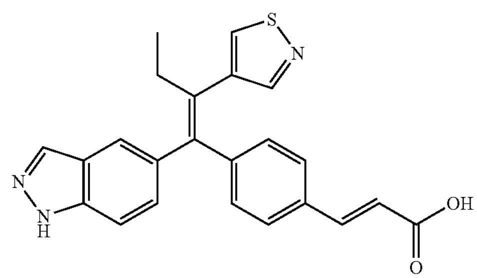 [SMILES: CC/C(=C(/c1ccc(/C=C/C(=O)O)cc1)c1ccc2[nH]ncc2c1)c1cnsc1] | 402 |
| 226 | (E)-3-(4-((E)-1-(1H-Indazol-5-yl)-2-(3-methylpyridin-4-yl)but-1-en-1-yl)phenyl)acrylic acid | 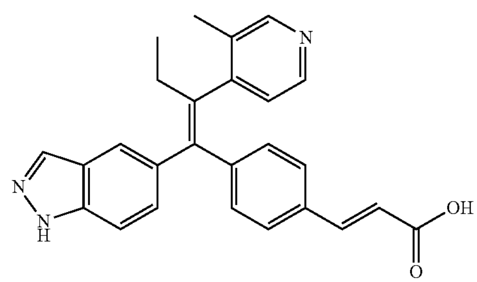 [SMILES: CC/C(=C(/c1ccc(/C=C/C(=O)O)cc1)c1ccc2[nH]ncc2c1)c1ccncc1C] | 410 |
| 227 | (E)-3-(4-((E)-1-(1H-Indazol-5-yl)-2-(5-methylthiophen-2-yl)but-1-en-1-yl)phenyl)acrylic acid | 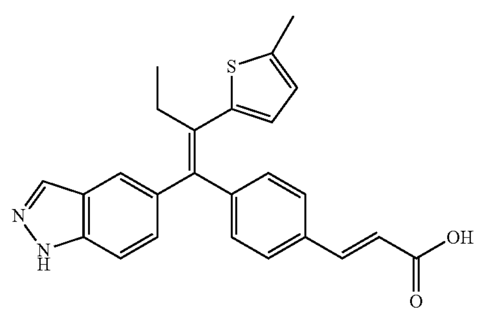 [SMILES: CC/C(=C(/c1ccc(/C=C/C(=O)O)cc1)c1ccc2[nH]ncc2c1)c1ccc(C)s1] | 415 |
| 228 | (E)-3-(4-((E)-1-(1H-Indazol-5-yl)-2-(2-methyl-5-(methylsulfonyl)phenyl)but-1-en-1-yl)phenyl)acrylic acid | 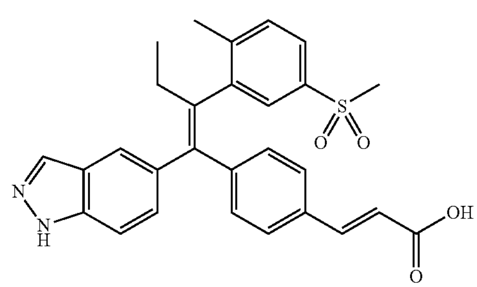 [SMILES: CC/C(=C(/c1ccc(/C=C/C(=O)O)cc1)c1ccc2[nH]ncc2c1)c1cc(S(C)(=O)=O)ccc1C] | 487 |

TABLE 1-continued

| Compound | Name | Structure | LCMS [M + H]+ |
|---|---|---|---|
| 229 | (E)-3-(4-((E)-1-(1H-Indazol-5-yl)-2-(2-methylthiazol-5-yl)but-1-en-1-yl)phenyl)acrylic acid | 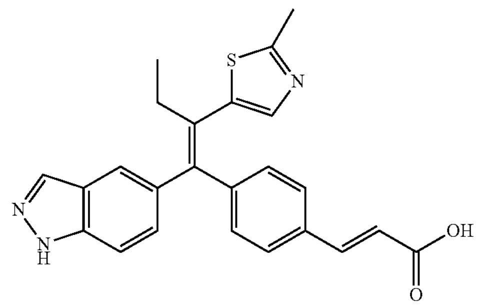 [SMILES: CC/C(=C(/c1ccc(/C=C/C(=O)O)cc1)c1ccc2[nH]ncc2c1)c1cnc(C)s1] | 416 |
| 230 | (E)-3-(4-((E)-2-(3-Chloropyridin-4-yl)-4-fluoro-1-(1H-indazol-5-yl)but-1-en-1-yl)phenyl)acrylic acid | 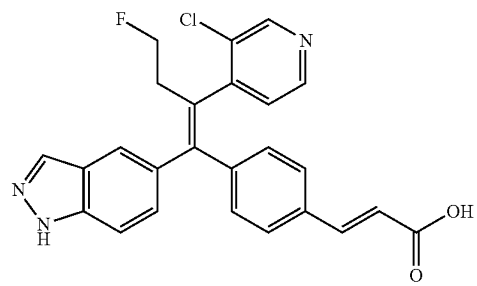 [SMILES: O=C(O)/C=C/c1ccc(/C(=C(/CCF)c2ccncc2Cl)c2ccc3[nH]ncc3c2)cc1] | 448 |
| 231 | (E)-3-(4-((E)-2-(3-Fluoropyridin-4-yl)-1-(1H-indazol-5-yl)but-1-en-1-yl)phenyl)acrylic acid | 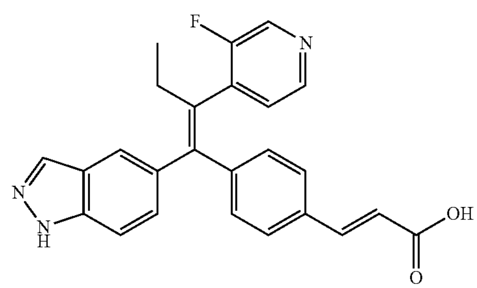 [SMILES: CC/C(=C(/c1ccc(/C=C/C(=O)O)cc1)c1ccc2[nH]ncc2c1)c1ccncc1F] | 414 |
| 232 | (E)-3-(4-((E)-2-(2,4-Dichlorophenyl)-1-(imidazo[1,2-a]pyridin-6-yl)but-1-en-1-yl)phenyl)acrylic acid | 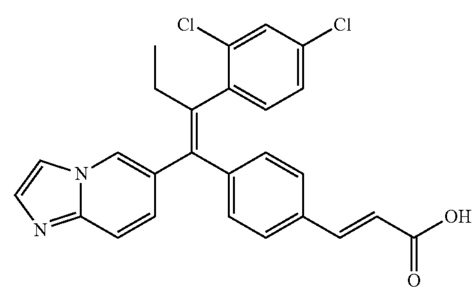 [SMILES: CC/C(=C(/c1ccc(/C=C/C(=O)O)cc1)c1ccc2nccn2c1)c1ccc(Cl)cc1Cl] | 463 |
| 233 | (E)-3-(4-((E)-2-(4-Fluoro-2-(trifluoromethyl)phenyl)-1-(imidazo[1,2-a]pyridin-6-yl)but-1-en-1-yl)phenyl)acrylic acid | 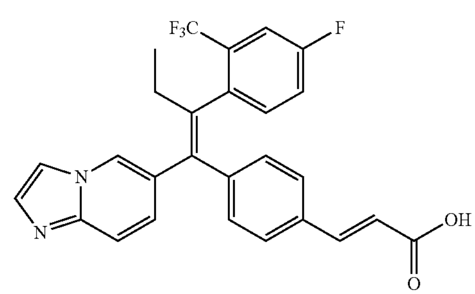 [SMILES: CC/C(=C(/c1ccc(/C=C/C(=O)O)cc1)c1ccc2nccn2c1)c1ccc(F)cc1C(F)(F)F] | 481 |

TABLE 1-continued

| Compound | Name | Structure | LCMS [M + H]+ |
|---|---|---|---|
| 234 | (E)-3-(4-((E)-1-(1H-Indazol-5-yl)-2-(4-methoxy-2-methylphenyl)but-1-en-1-yl)phenyl)acrylic acid | 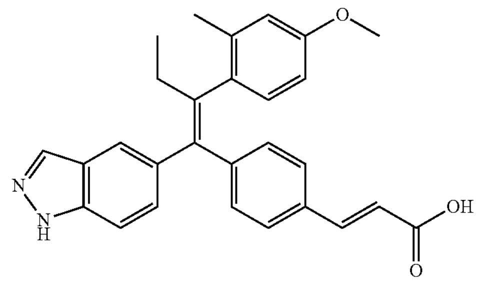 [SMILES: CC/C(=C(/c1ccc(/C=C/C(=O)O)cc1)c1ccc2[nH]ncc2c1)c1ccc(OC)cc1C] | 439 |
| 235 | (E)-3-(4-((E)-2-(2-Fluoro-4-methoxyphenyl)-1-(1H-indazol-5-yl)but-1-en-1-yl)phenyl)acrylic acid | 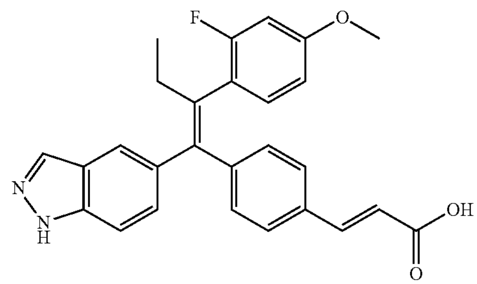 [SMILES: CC/C(=C(/c1ccc(/C=C/C(=O)O)cc1)c1ccc2[nH]ncc2c1)c1ccc(OC)cc1F] | 443 |
| 236 | (E)-3-(4-((E)-1-(1H-Indazol-5-yl)-2-(2-methoxypyridin-4-yl)but-1-en-1-yl)phenyl)acrylic acid | 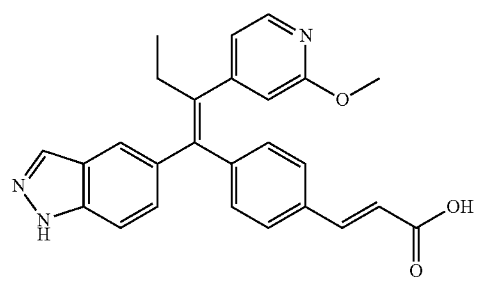 [SMILES: CC/C(=C(/c1ccc(/C=C/C(=O)O)cc1)c1ccc2[nH]ncc2c1)c1ccnc(OC)c1] | 426 |
| 237 | (E)-3-(4-((E)-2-(2-Chloro-5-methoxyphenyl)-1-(1H-indazol-5-yl)but-1-en-1-yl)phenyl)acrylic acid | 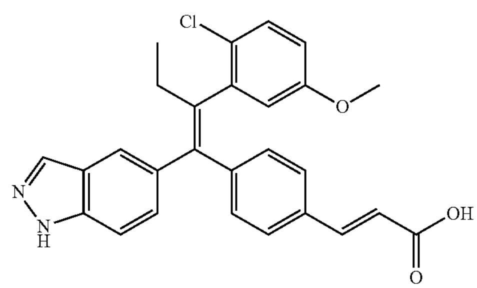 [SMILES: CC/C(=C(/c1ccc(/C=C/C(=O)O)cc1)c1ccc2[nH]ncc2c1)c1cc(OC)ccc1Cl] | 459 |
| 238 | (E)-3-(4-((E)-2-(2-Fluoro-4-(methylsulfonyl)phenyl)-1-(1H-indazol-5-yl)but-1-en-1-yl)phenyl)acrylic acid | 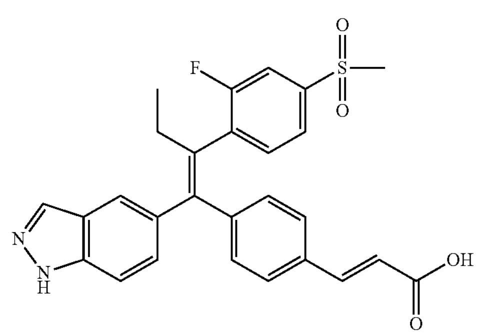 [SMILES: CC/C(=C(/c1ccc(/C=C/C(=O)O)cc1)c1ccc2[nH]ncc2c1)c1ccc(S(C)(=O)=O)cc1F] | 491 |

TABLE 1-continued

| Compound | Name | Structure | LCMS [M + H]+ |
|---|---|---|---|
| 239 | (E)-3-(4-((E)-2-(2,4-Dichlorophenyl)-3,3,4,4,4-pentadeutero-1-(1H-indazol-5-yl)but-1-en-1-yl)phenyl)acrylic acid | 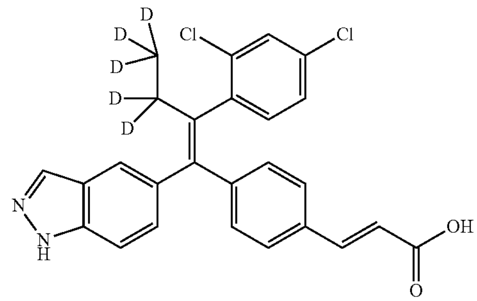 [SMILES: [2H]C([2H])([2H])C([2H])([2H])/C(=C(/c1ccc(/C=C/C(=O)O)cc1)c1ccc2[nH]ncc2c1)c1ccc(Cl)cc1Cl] | 468 |
| 240 | (E)-3-(4-((E)-2-(Benzo[d][1,3]dioxol-5-yl)-1-(1H-indazol-5-yl)but-1-en-1-yl)phenyl)acrylic acid | 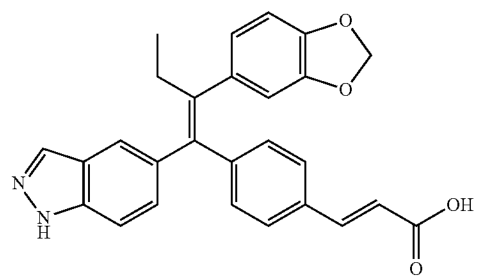 [SMILES: CC/C(=C(/c1ccc(/C=C/C(=O)O)cc1)c1ccc2[nH]ncc2c1)c1ccc2c(c1)OCO2] | 439 |
| 241 | (E)-3-(4-((E)-1-(1H-Indazol-5-yl)-2-(3-methylthiophen-2-yl)but-1-en-1-yl)phenyl)acrylic acid | 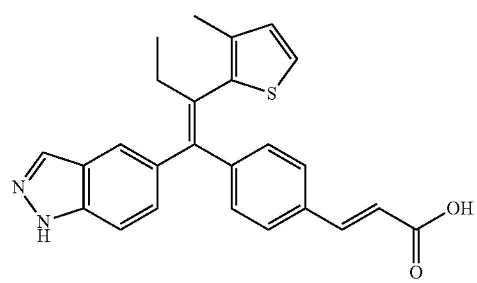 [SMILES: CC/C(=C(/c1ccc(/C=C/C(=O)O)cc1)c1ccc2[nH]ncc2c1)c1sccc1C] | 415 |
| 242 | (E)-3-(4-((E)-1-(4-Fluoro-1H-indazol-5-yl)-2-(4-methylthiophen-3-yl)but-1-en-1-yl)phenyl)acrylic acid | 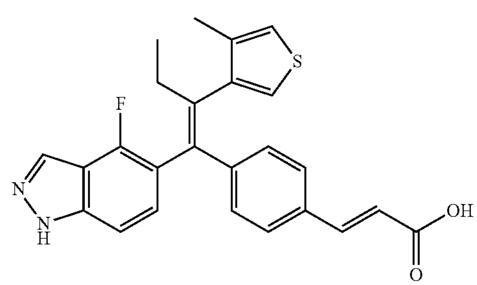 [SMILES: CC/C(=C(/c1ccc(/C=C/C(=O)O)cc1)c1ccc2[nH]ncc2c1F)c1cscc1C] | 433 |
| 243 | (E)-3-(4-((E)-1-(1H-Indazol-5-yl)-2-(3-(methylsulfonyl)phenyl)but-1-en-1-yl)phenyl)acrylic acid | 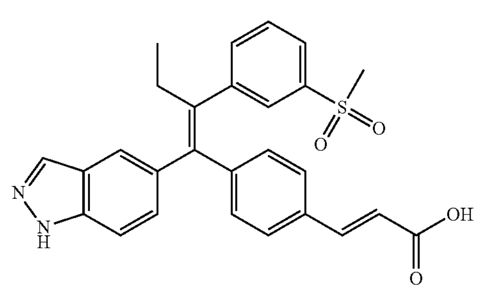 [SMILES: CC/C(=C(/c1ccc(/C=C/C(=O)O)cc1)c1ccc2[nH]ncc2c1)c1cccc(S(C)(=O)=O)c1] | 473 |

TABLE 1-continued

| Compound | Name | Structure | LCMS [M + H]+ |
|---|---|---|---|
| 244 | (E)-3-(4-((E)-2-(2,4-Dichlorophenyl)-1-(7-fluoro-1H-indazol-5-yl)but-1-en-1-yl)phenyl)acrylic acid | 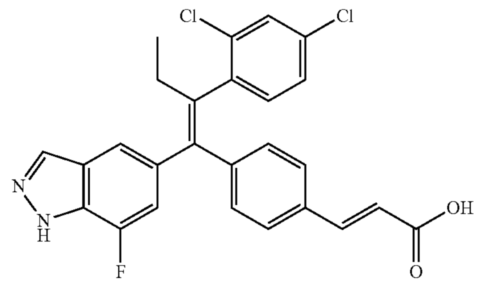 [SMILES: CC/C(=C(/c1ccc(/C=C/C(=O)O)cc1)c1cc(F)c2[nH]ncc2c1)c1ccc(Cl)cc1Cl] | 481 |
| 245 | (E)-3-(4-((E)-2-(3-Chloropyridin-4-yl)-1-(7-fluoro-1H-indazol-5-yl)but-1-en-1-yl)phenyl)acrylic acid | 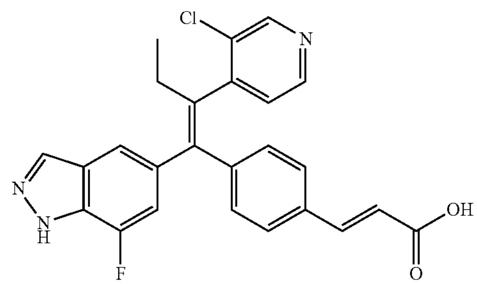 [SMILES: CC/C(=C(/c1ccc(/C=C/C(=O)O)cc1)c1cc(F)c2[nH]ncc2c1)c1ccncc1Cl] | 448 |
| 246 | (E)-3-(4-((E)-2-Phenyl-1-(5H-pyrrolo[2,3-b]pyrazin-2-yl)but-1-en-1-yl)phenyl)acrylic acid | 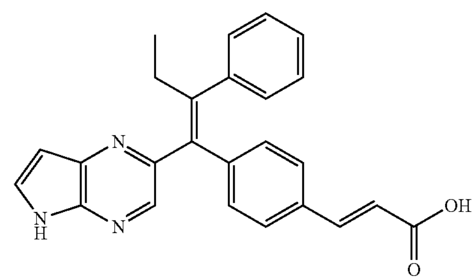 [SMILES: CC/C(=C(/c1ccc(/C=C/C(=O)O)cc1)c1cnc2[nH]ccc2n1)c1ccccc1] | 396 |
| 247 | (E)-3-(4-((E)-2-(Benzofuran-5-yl)-1-(1H-indazol-5-yl)but-1-en-1-yl)phenyl)acrylic acid | 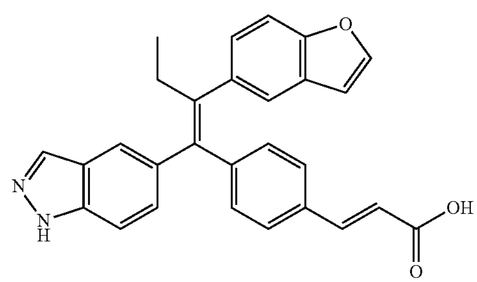 [SMILES: CC/C(=C(/c1ccc(/C=C/C(=O)O)cc1)c1ccc2[nH]ncc2c1)c1ccc2occc2c1] | 435 |
| 248 | (E)-3-(4-((E)-2-(2-Chloro-3-methoxyphenyl)-1-(1H-indazol-5-yl)but-1-en-1-yl)phenyl)acrylic acid | 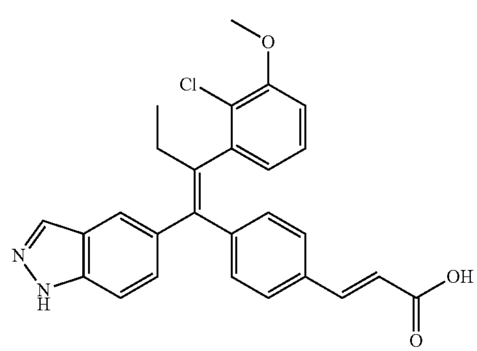 [SMILES: CC/C(=C(/c1ccc(/C=C/C(=O)O)cc1)c1ccc2[nH]ncc2c1)c1cccc(OC)c1Cl] | 459 |

TABLE 1-continued

| Compound | Name | Structure | LCMS [M + H]+ |
|---|---|---|---|
| 249 | (E)-3-(4-((E)-1-(1H-Indazol-5-yl)-2-(3-(pyrrolidin-1-yl)phenyl)but-1-en-1-yl)phenyl)acrylic acid | 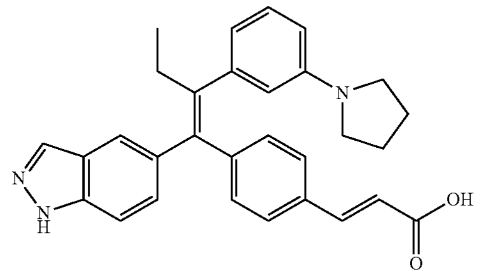 [SMILES: CC/C(=C(/c1ccc(/C=C/C(=O)O)cc1)c1ccc2[nH]ncc2c1)c1cccc(N2CCCC2)c1] | 464 |
| 250 | (E)-3-(4-((E)-2-(2,3-Dihydrobenzo[b][1,4]dioxin-6-yl)-1-(1H-indazol-5-yl)but-1-en-1-yl)phenyl)acrylic acid | 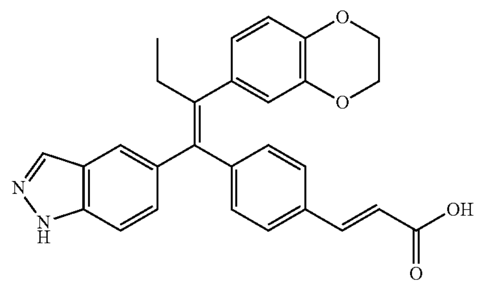 [SMILES: CC/C(=C(/c1ccc(/C=C/C(=O)O)cc1)c1ccc2[nH]ncc2c1)c1ccc2c(c1)OCCO2] | 453 |
| 251 | (E)-3-(4-((E)-1-(1H-Indazol-5-yl)-2-(1H-indazol-6-yl)but-1-en-1-yl)phenyl)acrylic acid | 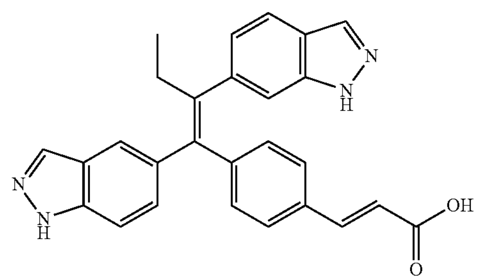 [SMILES: CC/C(=C(/c1ccc(/C=C/C(=O)O)cc1)c1ccc2[nH]ncc2c1)c1ccc2cn[nH]c2c1] | 435 |
| 252 | (E)-3-(4-((E)-2-(3-(1H-Pyrazol-1-yl)phenyl)-1-(1H-indazol-5-yl)but-1-en-1-yl)phenyl)acrylic acid | 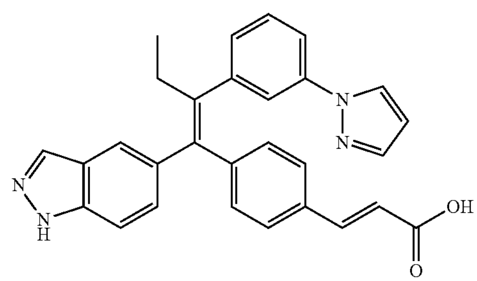 [SMILES: CC/C(=C(/c1ccc(/C=C/C(=O)O)cc1)c1ccc2[nH]ncc2c1)c1cccc(-n2cccn2)c1] | 461 |
| 253 | (E)-3-(4-((E)-2-(2,4-Dichlorophenyl)-1-(7-fluoro-1H-indol-5-yl)but-1-en-1-yl)phenyl)acrylic acid | 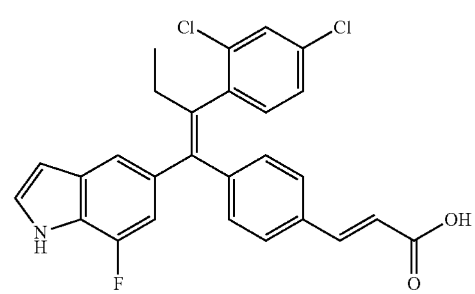 [SMILES: CC/C(=C(/c1ccc(/C=C/C(=O)O)cc1)c1cc(F)c2[nH]ccc2c1)c1ccc(Cl)cc1Cl] | 478 |

TABLE 1-continued

| Compound | Name | Structure | LCMS [M + H]+ |
|---|---|---|---|
| 254 | (E)-3-(4-((E)-2-(2-Chloro-4-fluorophenyl)-1-(7-fluoro-1H-indol-5-yl)but-1-en-1-yl)phenyl)acrylic acid | 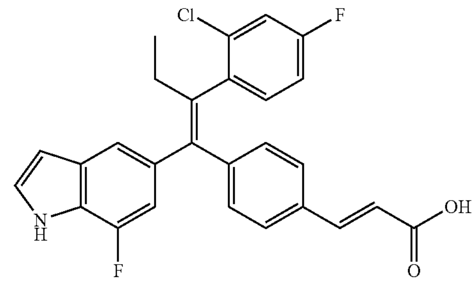 [SMILES: CC/C(=C(/c1ccc(/C=C/C(=O)O)cc1)c1cc(F)c2[nH]ccc2c1)c1ccc(F)cc1Cl] | not observed |
| 255 | (E)-3-(4-((E)-2-(Benzo[d]thiazol-5-yl)-1-(1H-indazol-5-yl)but-1-en-1-yl)phenyl)acrylic acid | 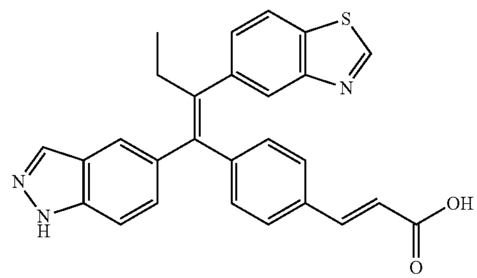 | 452 |
| 256 | (E)-3-(4-((E)-2-(2,3-Dihydrobenzofuran-5-yl)-1-(1H-indazol-5-yl)but-1-en-1-yl)phenyl)acrylic acid | 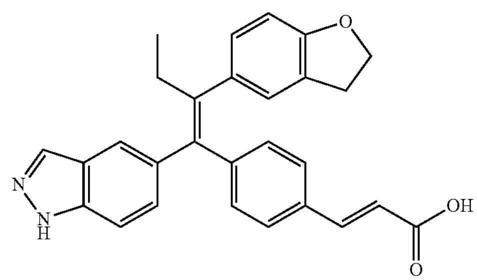 [SMILES: CC/C(=C(/c1ccc(/C=C/C(=O)O)cc1)c1ccc2[nH]ncc2c1)c1ccc2c(c1)CCO2] | 437 |
| 257 | (E)-3-(4-((E)-1-(1H-Indazol-5-yl)-4-methyl-2-(4-methylthiophen-3-yl)pent-1-en-1-yl)phenyl)acrylic acid | 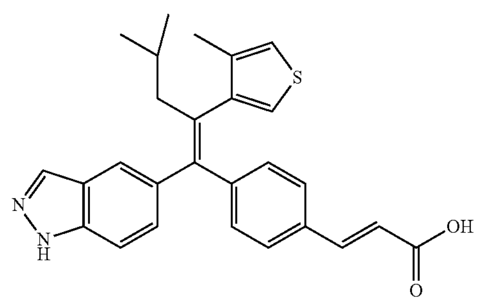 [SMILES: Cc1cscc1/C(CC(C)C)=C(\c1ccc(/C=C/C(=O)O)cc1)c1ccc2[nH]ncc2c1] | 443 |
| 258 | (E)-3-(4-((E)-1-(1H-Indazol-5-yl)-2-(1-methyl-1H-indazol-6-yl)but-1-en-1-yl)phenyl)acrylic acid | 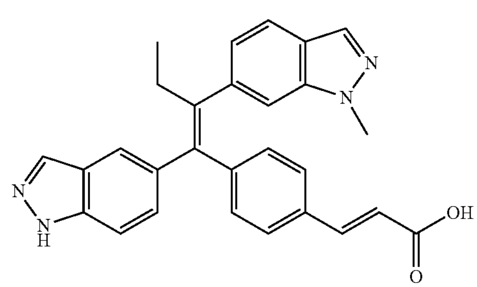 [SMILES: CC/C(=C(/c1ccc(/C=C/C(=O)O)cc1)c1ccc2[nH]ncc2c1)c1ccc2cnn(C)c2c1] | 449 |

TABLE 1-continued

| Compound | Name | Structure | LCMS [M + H]+ |
|---|---|---|---|
| 259 | (E)-3-(4-((E)-2-(Benzo[d]thiazol-6-yl)-1-(1H-indazol-5-yl)but-1-en-1-yl)phenyl)acrylic acid | 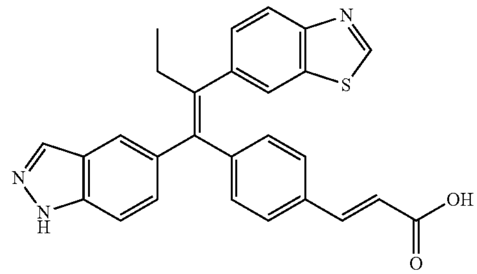 [SMILES: CC/C(=C(/c1ccc(/C=C/C(=O)O)cc1)c1ccc2[nH]ncc2c1)c1ccc2ncsc2c1] | 452 |
| 260 | (E)-3-(4-((E)-2-(Imidazo[1,2-a]pyridin-6-yl)-1-(1H-indazol-5-yl)but-1-en-1-yl)phenyl)acrylic acid | 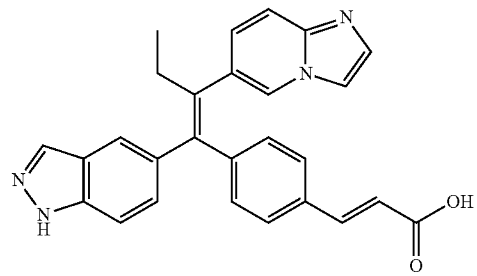 [SMILES: CC/C(=C(/c1ccc(/C=C/C(=O)O)cc1)c1ccc2[nH]ncc2c1)c1ccc2nccn2c1] | 435 |
| 261 | (E)-3-(4-((E)-1-(1H-Indazol-5-yl)-2-(3-phenoxyphenyl)but-1-en-1-yl)phenyl)acrylic acid | 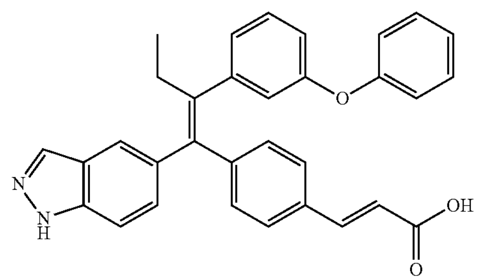 [SMILES: CC/C(=C(/c1ccc(/C=C/C(=O)O)cc1)c1ccc2[nH]ncc2c1)c1cccc(Oc2ccccc2)c1] | 487 |
| 262 | (E)-3-(4-((E)-1-(1H-Indazol-5-yl)-2-(4-methyl-3-oxo-3,4-dihydro-2H-benzo[b][1,4]oxazin-6-yl)but-1-en-1-yl)phenyl)acrylic acid | 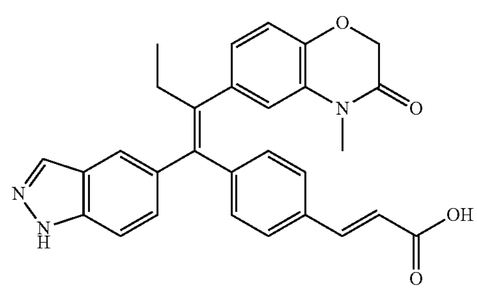 [SMILES: CC/C(=C(/c1ccc(/C=C/C(=O)O)cc1)c1ccc2[nH]ncc2c1)c1ccc2c(c1)N(C)C(=O)CO2] | 480 |
| 263 | (E)-3-(4-((E)-1-(1H-Indazol-5-yl)-2-(4-phenoxyphenyl)but-1-en-1-yl)phenyl)acrylic acid | 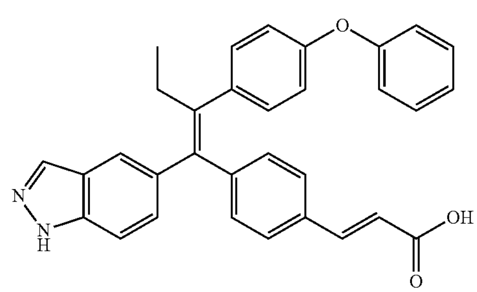 [SMILES: CC/C(=C(/c1ccc(/C=C/C(=O)O)cc1)c1ccc2[nH]ncc2c1)c1ccc(Oc2ccccc2)cc1] | 487 |

//

TABLE 1-continued

| Compound | Name | Structure | LCMS [M + H]+ |
|---|---|---|---|
| 264 | (E)-3-(4-((E)-2-(4-(1H-Pyrazol-1-yl)phenyl)-1-(1H-indazol-5-yl)but-1-en-1-yl)phenyl)acrylic acid | 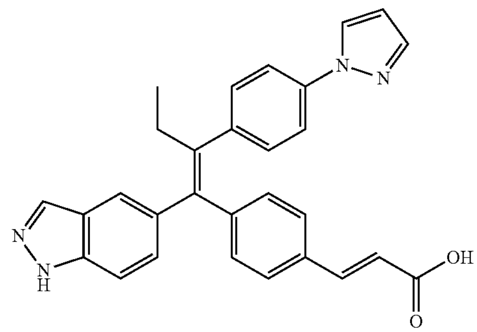 [SMILES: CC/C(=C(/c1ccc(/C=C/C(=O)O)cc1)c1ccc2[nH]ncc2c1)c1ccc(-n2cccn2)cc1] | 461 |
| 265 | (E)-3-(4-((E)-1-(1H-Indazol-5-yl)-2-(3-morpholinophenyl)but-1-en-1-yl)phenyl)acrylic acid | 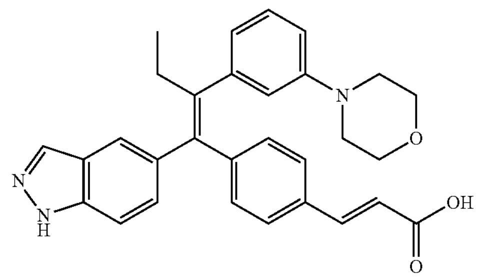 [SMILES: CC/C(=C(/c1ccc(/C=C/C(=O)O)cc1)c1ccc2[nH]ncc2c1)c1cccc(N2CCOCC2)c1] | 480 |
| 266 | (E)-3-(4-((E)-1-(1H-Indazol-5-yl)-2-(quinoxalin-6-yl)but-1-en-1-yl)phenyl)acrylic acid | 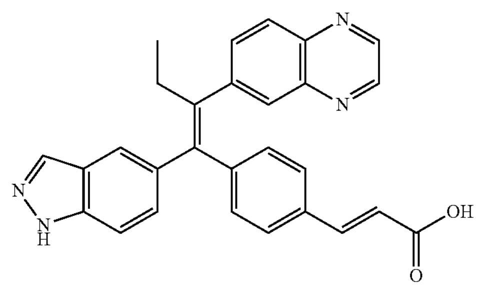 [SMILES: CC/C(=C(/c1ccc(/C=C/C(=O)O)cc1)c1ccc2[nH]ncc2c1)c1ccc2nccnc2c1] | 447 |
| 267 | (E)-3-(4-((E)-2-(2-Chlorothiophen-3-yl)-1-(1H-indazol-5-yl)but-1-en-1-yl)phenyl)acrylic acid | 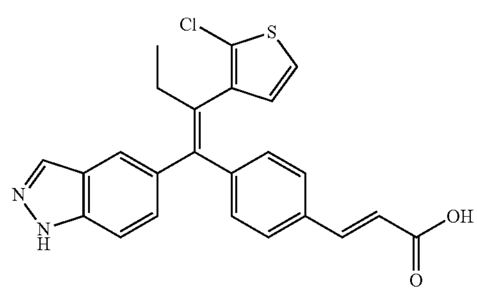 [SMILES: CC/C(=C(/c1ccc(/C=C/C(=O)O)cc1)c1ccc2[nH]ncc2c1)c1ccsc1Cl] | 435 |
| 268 | (E)-3-(4-((E)-2-(Benzo[b]thiophen-2-yl)-1-(1H-indazol-5-yl)but-1-en-1-yl)phenyl)acrylic acid | 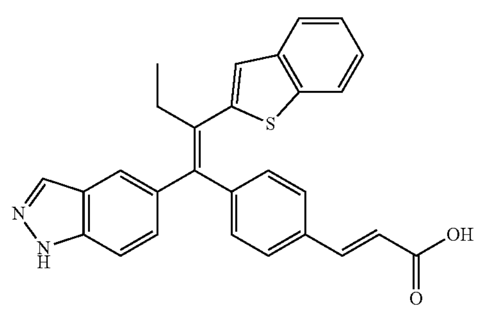 [SMILES: CC/C(=C(/c1ccc(/C=C/C(=O)O)cc1)c1ccc2[nH]ncc2c1)c1cc2ccccc2s1] | 451 |

TABLE 1-continued

| Compound | Name | Structure | LCMS [M + H]+ |
|---|---|---|---|
| 269 | (E)-3-(4-((E)-2-(3-(4-Fluorophenoxy)phenyl)-1-(1H-indazol-5-yl)but-1-en-1-yl)phenyl)acrylic acid | 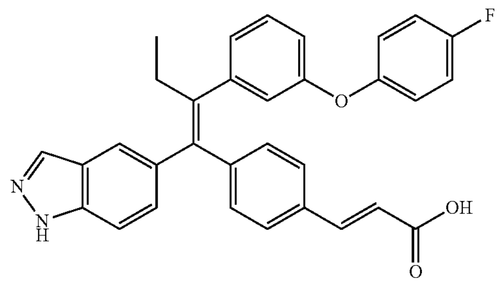 [SMILES: CC/C(=C(/c1ccc(/C=C/C(=O)O)cc1)c1ccc2[nH]ncc2c1)c1cccc(Oc2ccc(F)cc2)c1] | 505 |
| 270 | (E)-3-(4-((E)-1-(1H-Indazol-5-yl)-2-(5-methyl-4,5,6,7-tetrahydrothieno[3,2-c]pyridin-2-yl)but-1-en-1-yl)phenyl)acrylic acid | 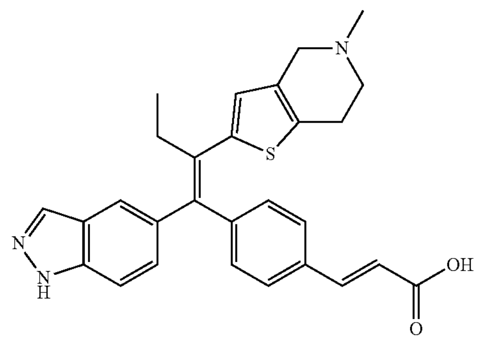 [SMILES: CC/C(=C(/c1ccc(/C=C/C(=O)O)cc1)c1ccc2[nH]ncc2c1)c1cc2c(s1)CCN(C)C2] | 470 |
| 271 | (E)-3-(4-((E)-1-(1H-Indazol-5-yl)-2-(5-phenylthiophen-3-yl)but-1-en-1-yl)phenyl)acrylic acid | 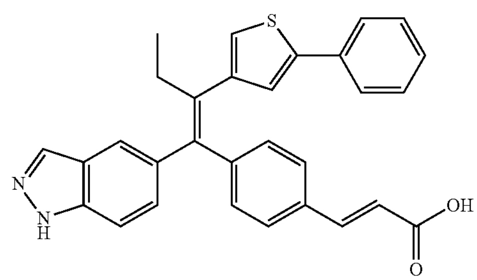 [SMILES: CC/C(=C(/c1ccc(/C=C/C(=O)O)cc1)c1ccc2[nH]ncc2c1)c1csc(-c2ccccc2)c1] | 477 |
| 272 | (E)-3-(4-((E)-2-(Benzo[b]thiophen-5-yl)-1-(1H-indazol-5-yl)but-1-en-1-yl)phenyl)acrylic acid | 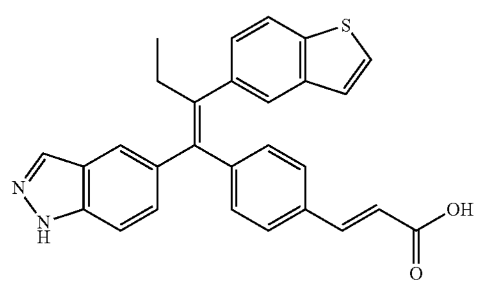 | 451 |
| 273 | (E)-3-(4-((E)-1-(1H-Indazol-5-yl)-2-(2-methylbenzo[d]thiazol-5-yl)but-1-en-1-yl)phenyl)acrylic acid | 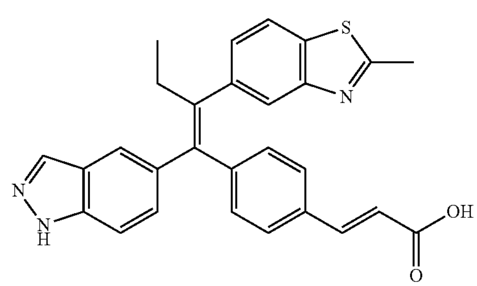 [SMILES: CC/C(=C(/c1ccc(/C=C/C(=O)O)cc1)c1ccc2[nH]ncc2c1)c1ccc2sc(C)nc2c1] | 466 |

TABLE 1-continued

| Compound | Name | Structure | LCMS [M + H]+ |
|---|---|---|---|
| 274 | (E)-3-(4-((E)-2-(2,5-Dimethylthiophen-3-yl)-1-(1H-indazol-5-yl)but-1-en-1-yl)phenyl)acrylic acid | 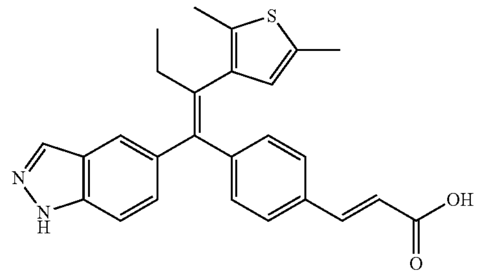 [SMILES: CC/C(=C(/c1ccc(/C=C/C(=O)O)cc1)c1ccc2[nH]ncc2c1)c1cc(C)sc1C] | 429 |
| 275 | (E)-3-(4-((E)-1-(Benzo[d]thiazol-5-yl)-2-(2-chloro-4-fluorophenyl)but-1-en-1-yl)phenyl)acrylic acid | 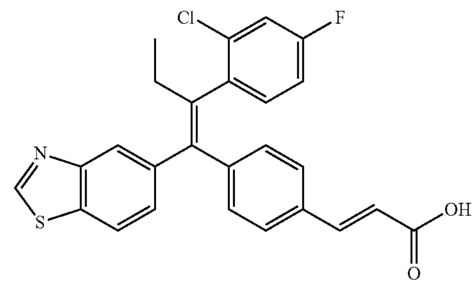 [SMILES: CC/C(=C(/c1ccc(/C=C/C(=O)O)cc1)c1ccc2scnc2c1)c1ccc(F)cc1Cl] | 464 |
| 276 | (E)-3-(4-((E)-1-(Benzo[d]thiazol-5-yl)-2-(4-methylthiophen-3-yl)but-1-en-1-yl)phenyl)acrylic acid | 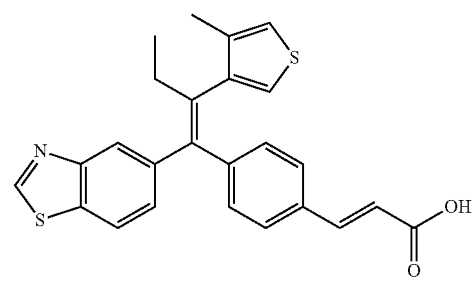 [SMILES: CC/C(=C(/c1ccc(/C=C/C(=O)O)cc1)c1ccc2scnc2c1)c1cscc1C] | 432 |
| 277 | (E)-3-(4-((E)-2-(2-Chloro-4-fluorophenyl)-3,3,4,4,4-pentadeutero-1-(1H-indazol-5-yl)but-1-en-1-yl)phenyl)acrylic acid | 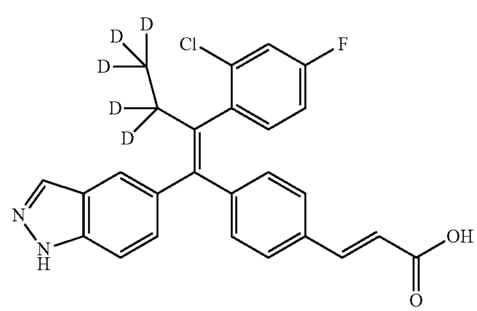 [SMILES: [2H]C([2H])([2H])C([2H])([2H])/C(=C(/c1ccc(/C=C/C(=O)O)cc1)c1ccc2[nH]ncc2c1)c1ccc(F)cc1Cl] | 452 |
| 278 | (E)-3-(4-((E)-1-(Benzo[d]thiazol-5-yl)-2-(2-chloro-4-fluorophenyl)-2-cyclobutylvinyl)phenyl)acrylic acid | 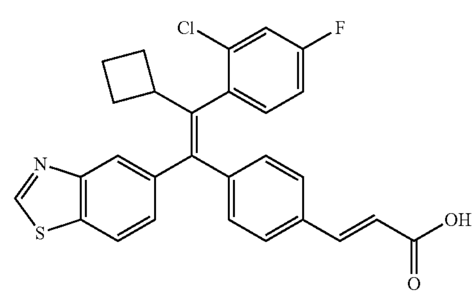 [SMILES: O=C(O)/C=C/c1ccc(/C(=C(\c2ccc(F)cc2Cl)C2CCC2)c2ccc3scnc3c2)cc1] | 490 |

TABLE 1-continued

| Compound | Name | Structure | LCMS [M + H]+ |
|---|---|---|---|
| 279 | (E)-3-(4-((E)-1-(Benzo[d]thiazol-5-yl)-2-cyclobutyl-2-(4-methylthiophen-3-yl)vinyl)phenyl)acrylic acid | 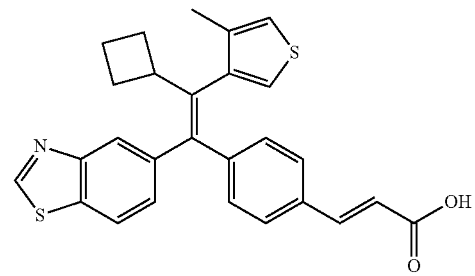 [SMILES: Cc1cscc1/C(=C(\c1ccc(/C=C/C(=O)O)cc1)c1ccc2scnc2c1)C1CCC1] | 458 |
| 280 | (E)-3-(4-((E)-1-(Benzo[d]thiazol-5-yl)-2-(2-chlorophenyl)but-1-en-1-yl)phenyl)acrylic acid | 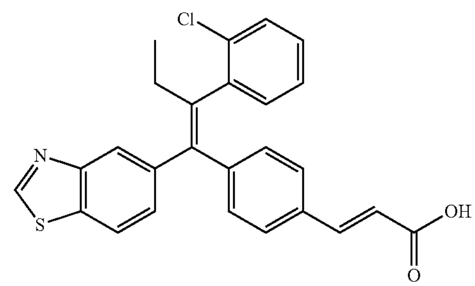 [SMILES: CC/C(=C(/c1ccc(/C=C/C(=O)O)cc1)c1ccc2scnc2c1)c1ccccc1Cl] | 446 |
| 281 | (E)-3-(4-((E)-1-(Benzo[d]thiazol-5-yl)-2-(4-fluorophenyl)but-1-en-1-yl)phenyl)acrylic acid | 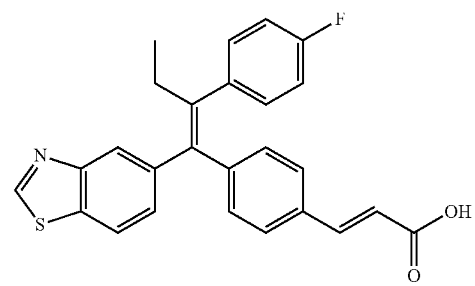 [SMILES: CC/C(=C(/c1ccc(/C=C/C(=O)O)cc1)c1ccc2scnc2c1)c1ccc(F)cc1] | 430 |
| 282 | (E)-3-(4-((E)-1-(Benzo[d]thiazol-5-yl)-2-(4-fluoro-2-methylphenyl)but-1-en-1-yl)phenyl)acrylic acid | 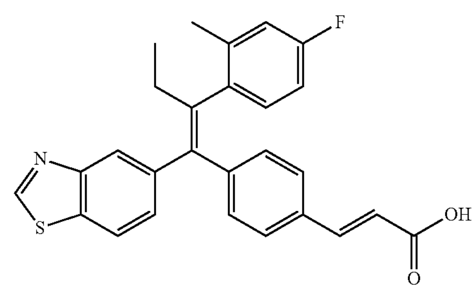 [SMILES: CC/C(=C(/c1ccc(/C=C/C(=O)O)cc1)c1ccc2scnc2c1)c1ccc(F)cc1C] | 444 |
| 283 | (E)-3-(4-((E)-1-(Benzo[d]thiazol-5-yl)-2-(o-tolyl)but-1-en-1-yl)phenyl)acrylic acid | 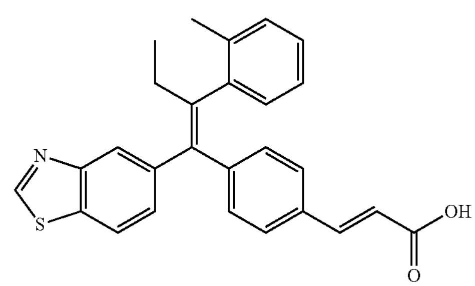 [SMILES: CC/C(=C(/c1ccc(/C=C/C(=O)O)cc1)c1ccc2scnc2c1)c1ccccc1C] | 426 |

TABLE 1-continued

| Compound | Name | Structure | LCMS [M + H]+ |
|---|---|---|---|
| 284 | (E)-3-(4-((E)-1-(Benzo[d]thiazol-5-yl)-2-(3-chloropyridin-4-yl)but-1-en-1-yl)phenyl)acrylic acid | 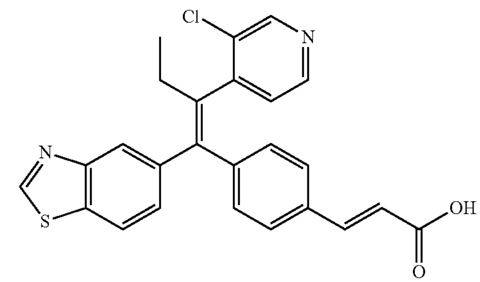 [SMILES: CC/C(=C(/c1ccc(/C=C/C(=O)O)cc1)c1ccc2scnc2c1)c1ccncc1Cl] | 447 |
| 285 | (E)-3-(4-((E)-1-(Benzo[d]thiazol-5-yl)-2-(3-chloropyridin-4-yl)but-1-en-1-yl)phenyl)acrylic acid | 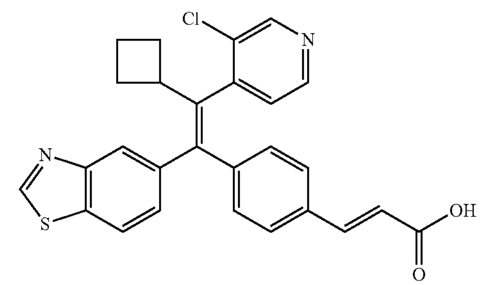 [SMILES: O=C(O)/C=C/c1ccc(/C(=C(\c2ccncc2Cl)C2CCC2)c2ccc3scnc3c2)cc1] | 473 |
| 286 | (E)-3-(4-((E)-1-(Benzo[d]thiazol-5-yl)-2-cyclobutyl-2-phenylvinyl)phenyl)acrylic acid | 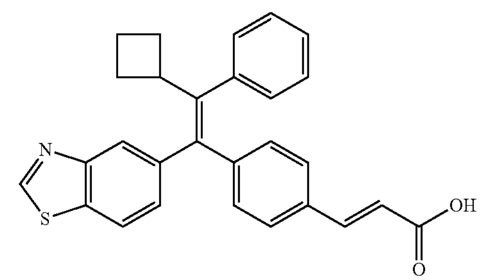 [SMILES: O=C(O)/C=C/c1ccc(/C(=C(\c2ccccc2)C2CCC2)c2ccc3scnc3c2)cc1] | 438 |
| 287 | (E)-3-(4-((E)-2-(2-Chloro-4-fluorophenyl)-1-(1-oxoisoindolin-5-yl)but-1-en-1-yl)phenyl)acrylic acid | 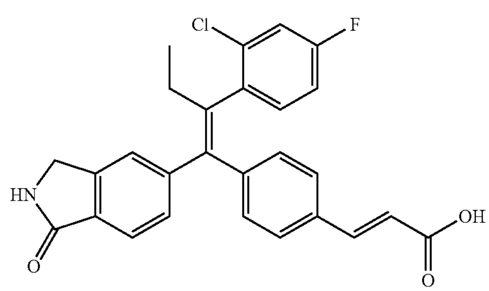 [SMILES: CC/C(=C(/c1ccc(/C=C/C(=O)O)cc1)c1ccc2c(c1)CNC2=O)c1ccc(F)cc1Cl] | 462 |
| 288 | (E)-3-(4-((E)-1-(1H-Indazol-5-yl)-2-(3-(4-((trifluoromethyl)sulfonyl)phenoxy)phenyl)but-1-en-1-yl)phenyl)acrylic acid | 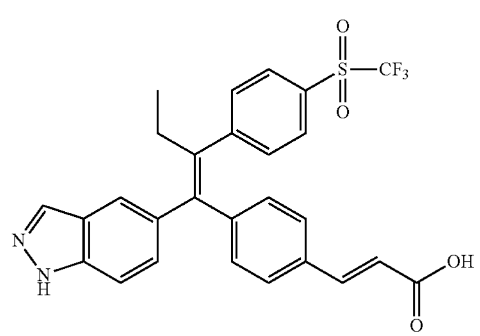 [SMILES: CC/C(=C(/c1ccc(/C=C/C(=O)O)cc1)c1ccc2[nH]ncc2c1)c1ccc(S(=O)(=O)C(F)(F)F)cc1] | 527 |

TABLE 1-continued

| Compound | Name | Structure | LCMS [M + H]+ |
|---|---|---|---|
| 289 | (E)-3-(4-((E)-2-(2-Chloro-4-fluorophenyl)-1-(quinolin-7-yl)but-1-en-1-yl)phenyl)acrylic acid | 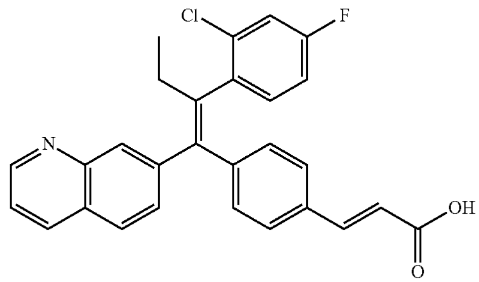 [SMILES: CC/C(=C(/c1ccc(/C=C/C(=O)O)cc1)c1ccc2cccnc2c1)c1ccc(F)cc1Cl] | 458 |
| 290 | (E)-3-(4-((E)-1-(1H-Indazol-5-yl)-2-(4-(pyrimidin-2-yloxy)phenyl)but-1-en-1-yl)phenyl)acrylic acid | 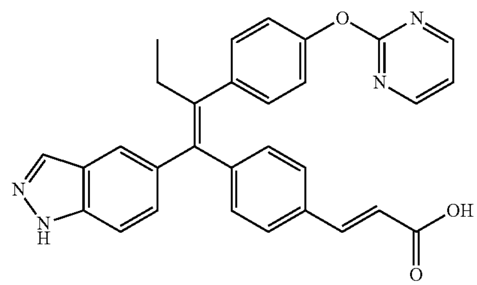 [SMILES: CC/C(=C(/c1ccc(/C=C/C(=O)O)cc1)c1ccc2[nH]ncc2c1)c1ccc(Oc2ncccn2)cc1] | 489 |
| 291 | (E)-3-(4-((E)-2-(2-Chloro-4-phenoxyphenyl)-1-(1H-indazol-5-yl)but-1-en-1-yl)phenyl)acrylic acid | 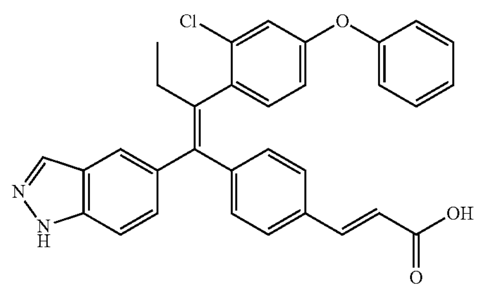 [SMILES: CC/C(=C(/c1ccc(/C=C/C(=O)O)cc1)c1ccc2[nH]ncc2c1)c1ccc(Oc2ccccc2)cc1Cl] | 521 |
| 292 | (E)-3-(4-((E)-1-(1H-Indazol-5-yl)-2-(4-(pyridin-3-yloxy)phenyl)but-1-en-1-yl)phenyl)acrylic acid | 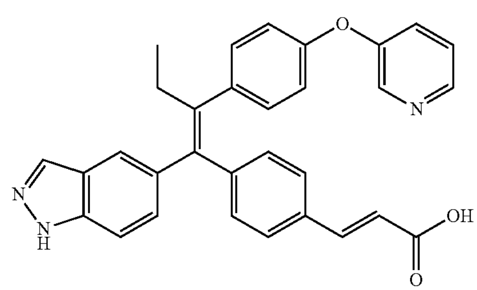 [SMILES: CC/C(=C(/c1ccc(/C=C/C(=O)O)cc1)c1ccc2[nH]ncc2c1)c1ccc(Oc2cccnc2)cc1] | 488 |
| 293 | (E)-3-(4-((E)-1-(1H-Indazol-5-yl)-2-(4-(pyrazin-2-yloxy)phenyl)but-1-en-1-yl)phenyl)acrylic acid | 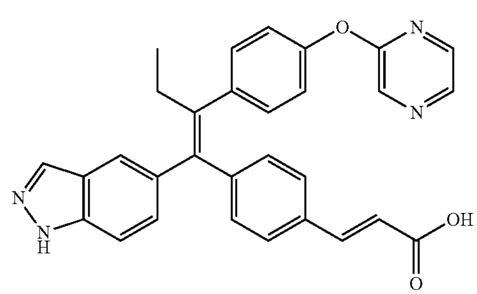 [SMILES: CC/C(=C(/c1ccc(/C=C/C(=O)O)cc1)c1ccc2[nH]ncc2c1)c1ccc(Oc2cnccn2)cc1] | 489 |

TABLE 1-continued

| Compound | Name | Structure | LCMS [M + H]+ |
|---|---|---|---|
| 294 | (E)-3-(4-((E)-2-(4-Fluoro-3-phenoxyphenyl)-1-(1H-indazol-5-yl)but-1-en-1-yl)phenyl)acrylic acid | 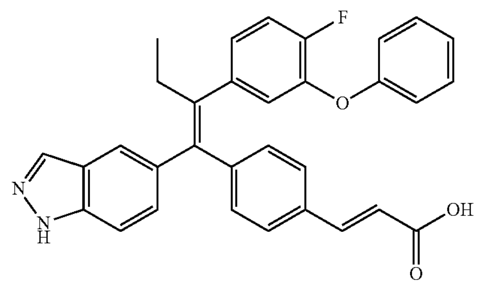 [SMILES: CC/C(=C(/c1ccc(/C=C/C(=O)O)cc1)c1ccc2[nH]ncc2c1)c1ccc(F)c(Oc2ccccc2)c1] | 505 |
| 295 | (E)-3-(4-((E)-2-(3-Fluoro-4-phenoxyphenyl)-1-(1H-indazol-5-yl)but-1-en-1-yl)phenyl)acrylic acid | 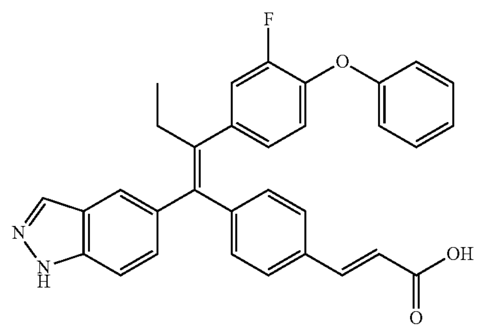 [SMILES: CC/C(=C(/c1ccc(/C=C/C(=O)O)cc1)c1ccc2[nH]ncc2c1)c1ccc(Oc2ccccc2)c(F)c1] | 505 |
| 296 | (E)-3-(4-((E)-1-(4-Fluoro-1H-indazol-5-yl)-2-(4-(pyridin-2-yloxy)phenyl)but-1-en-1-yl)phenyl)acrylic acid | 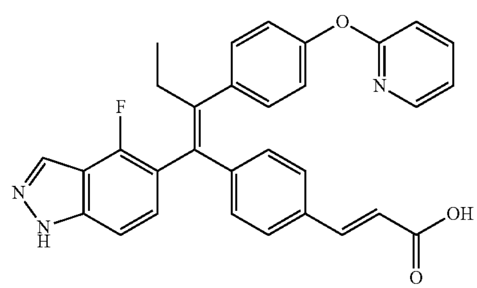 [SMILES: CC/C(=C(/c1ccc(/C=C/C(=O)O)cc1)c1ccc2[nH]ncc2c1F)c1ccc(Oc2ccccn2)cc1] | 506 |
| 297 | (E)-3-(4-((E)-1-(1H-Indazol-5-yl)-2-(2-methyl-5-phenoxyphenyl)but-1-en-1-yl)phenyl)acrylic acid | 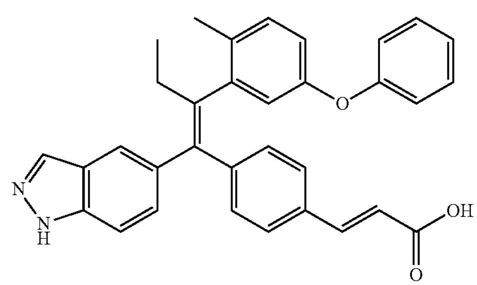 [SMILES: CC/C(=C(/c1ccc(/C=C/C(=O)O)cc1)c1ccc2[nH]ncc2c1)c1cc(Oc2ccccc2)ccc1C] | 501 |
| 298 | (E)-3-(4-((E)-2-(2-Fluoro-3-phenoxyphenyl)-1-(1H-indazol-5-yl)but-1-en-1-yl)phenyl)acrylic acid | 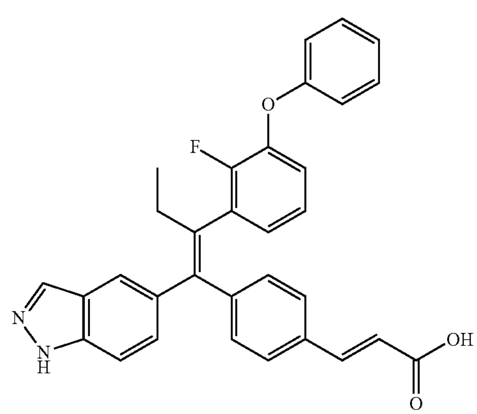 [SMILES: CC/C(=C(/c1ccc(/C=C/C(=O)O)cc1)c1ccc2[nH]ncc2c1)c1cccc(Oc2ccccc2)c1F] | 505 |

TABLE 1-continued

| Compound | Name | Structure | LCMS [M + H]+ |
|---|---|---|---|
| 299 | (E)-3-(4-((E)-1-(Benzo[d]thiazol-5-yl)-2-(3-phenoxyphenyl)but-1-en-1-yl)phenyl)acrylic acid | 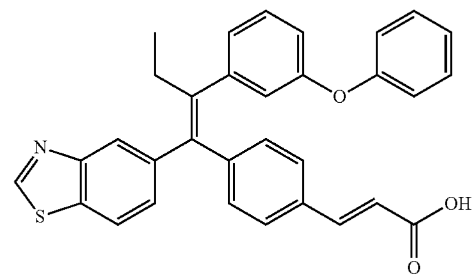 [SMILES: CC/C(=C(/c1ccc(/C=C/C(=O)O)cc1)c1ccc2scnc2c1)c1cccc(Oc2ccccc2)c1] | 504 |
| 300 | (E)-3-(4-((E)-1-(Benzo[d]thiazol-5-yl)-2-(3-(pyridin-2-yloxy)phenyl)but-1-en-1-yl)phenyl)acrylic acid | 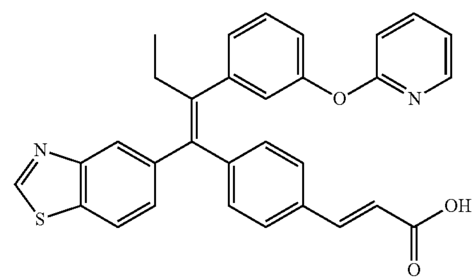 [SMILES: CC/C(=C(/c1ccc(/C=C/C(=O)O)cc1)c1ccc2scnc2c1)c1cccc(Oc2ccccn2)c1] | 505 |
| 301 | (E)-3-(4-((E)-1-(Benzo[d]thiazol-5-yl)-2-(3-(pyrazin-2-yloxy)phenyl)but-1-en-1-yl)phenyl)acrylic acid | 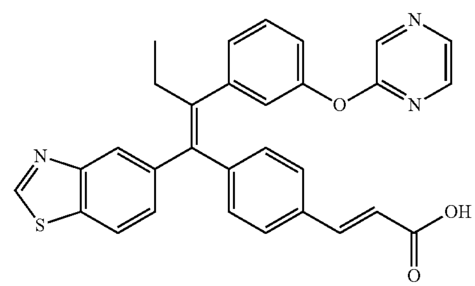 [SMILES: CC/C(=C(/c1ccc(/C=C/C(=O)O)cc1)c1ccc2scnc2c1)c1cccc(Oc2cnccn2)c1] | 506 |
| 302 | (E)-3-(4-((E)-1-(1H-Indazol-5-yl)-2-(4-((trifluoromethyl)sulfinyl)phenyl)but-1-en-1-yl)phenyl)acrylic acid | 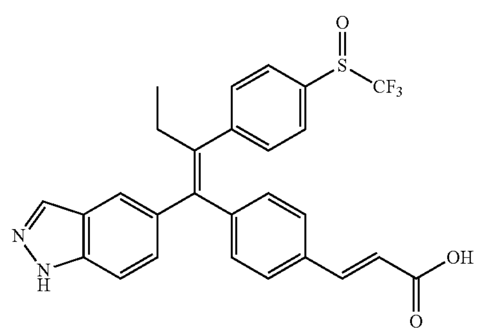 [SMILES: CC/C(=C(/c1ccc(/C=C/C(=O)O)cc1)c1ccc2[nH]ncc2c1)c1ccc(S(=O)C(F)(F)F)cc1] | 511 |
| 303 | (E)-3-(4-((E)-2-(3-Cyanopyridin-4-yl)-1-(1H-indazol-5-yl)but-1-en-1-yl)phenyl)acrylic acid | 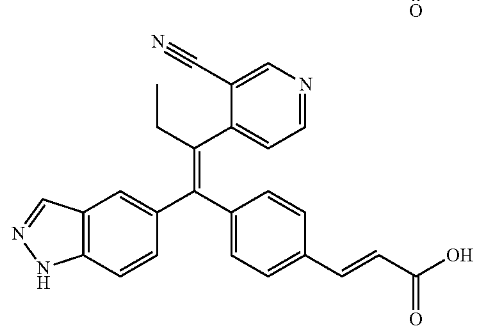 | 421 |

TABLE 1-continued

| Compound | Name | Structure | LCMS [M + H]+ |
|---|---|---|---|
| 304 | (E)-3-(4-((E)-1-(1H-Indazol-5-yl)-2-(3-(trifluoromethyl)pyridin-4-yl)but-1-en-1-yl)phenyl)acrylic acid | 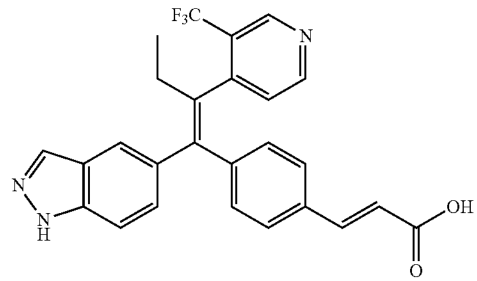 [SMILES: CC/C(=C(/c1ccc(/C=C/C(=O)O)cc1)c1ccc2[nH]ncc2c1)c1ccncc1C(F)(F)F] | 464 |
| 305 | (E)-3-(4-((E)-2-(3-Chloropyridin-4-yl)-2-cyclobutyl-1-(1H-indazol-5-yl)vinyl)phenyl)acrylic acid | 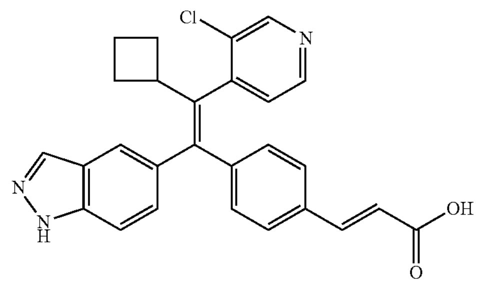 [SMILES: O=C(O)/C=C/c1ccc(/C(=C(\c2ccncc2Cl)C2CCC2)c2ccc3[nH]ncc3c2)cc1] | 456 |
| 306 | (E)-3-(4-((E)-2-(3-Chloropyridin-4-yl)-1-(3-fluoro-1H-indazol-5-yl)but-1-en-1-yl)phenyl)acrylic acid | 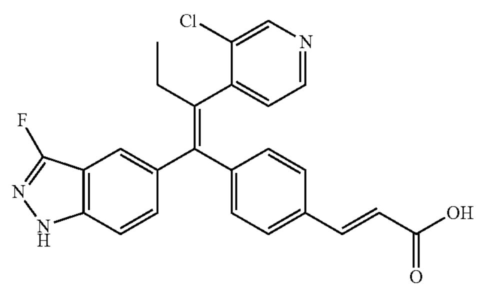 [SMILES: CC/C(=C(/c1ccc(/C=C/C(=O)O)cc1)c1ccc2[nH]nc(F)c2c1)c1ccncc1Cl] | 448 |
| 307 | (E)-3-(4-((E)-2-(3-Chloropyridin-4-yl)-2-cyclobutyl-1-(3-fluoro-1H-indazol-5-yl)vinyl)phenyl)acrylic acid | 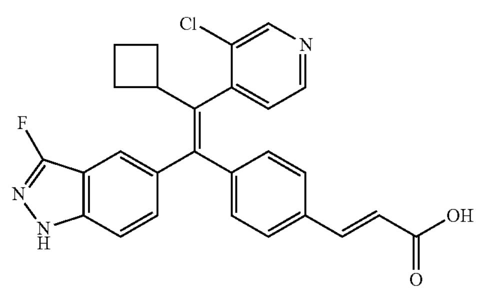 [SMILES: O=C(O)/C=C/c1ccc(/C(=C(\c2ccncc2Cl)C2CCC2)c2ccc3[nH]nc(F)c3c2)cc1] | 474 |
| 308 | (E)-3-(4-((E)-2-(4-Chloro-2-cyanophenyl)-1-(1H-indazol-5-yl)but-1-en-1-yl)phenyl)acrylic acid | 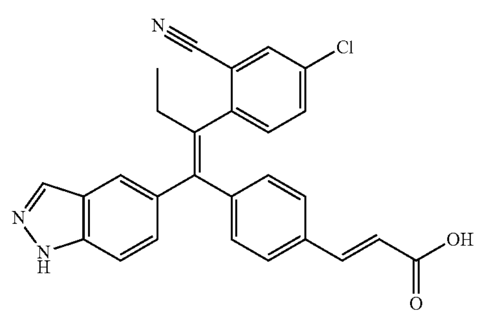 [SMILES: CC/C(=C(/c1ccc(/C=C/C(=O)O)cc1)c1ccc2[nH]ncc2c1)c1ccc(Cl)cc1C#N] | 454 |

TABLE 1-continued

| Compound | Name | Structure | LCMS [M + H]+ |
|---|---|---|---|
| 309 | (E)-3-(4-((E)-2-(2-Cyano-4-fluorophenyl)-1-(1H-indazol-5-yl)but-1-en-1-yl)phenyl)acrylic acid | 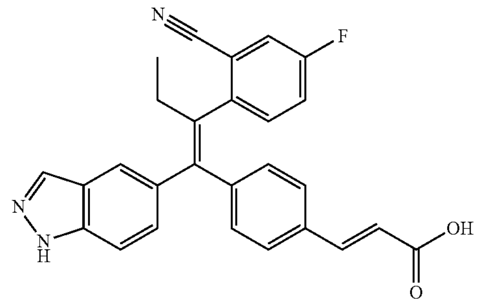 [SMILES: CC/C(=C(/c1ccc(/C=C/C(=O)O)cc1)c1ccc2[nH]ncc2c1)c1ccc(F)cc1C#N] | 438 |
| 310 | (E)-3-(4-((E)-2-(2-Cyano-4-(trifluoromethyl)phenyl)-1-(1H-indazol-5-yl)but-1-en-1-yl)phenyl)acrylic acid | 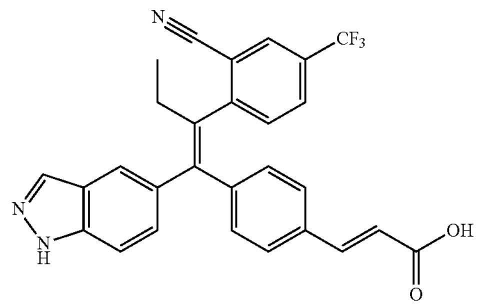 [SMILES: CC/C(=C(/c1ccc(/C=C/C(=O)O)cc1)c1ccc2[nH]ncc2c1)c1ccc(C(F)(F)F)cc1C#N] | 488 |
| 311 | (E)-3-(4-((E)-2-(2-Chloro-4-fluorophenyl)-2-cyclobutyl-1-(imidazo[1,2-a]pyridin-6-yl)vinyl)phenyl)acrylic acid | 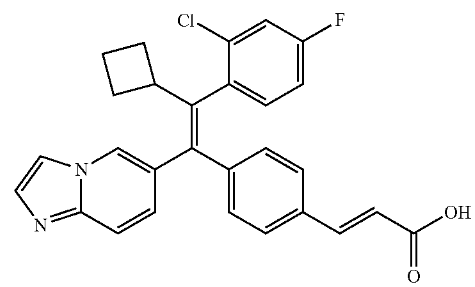 [SMILES: O=C(O)/C=C/c1ccc(/C(=C(\c2ccc(F)cc2Cl)C2CCC2)c2ccc3nccn3c2)cc1] | 473 |
| 312 | (E)-3-(4-((E)-1-(3-Fluoro-1H-indazol-5-yl)-2-(4-methylthiophen-3-yl)but-1-en-1-yl)phenyl)acrylic acid | 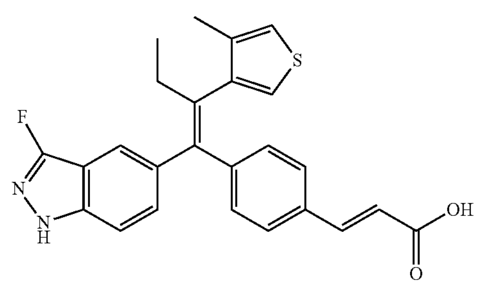 [SMILES: CC/C(=C(/c1ccc(/C=C/C(=O)O)cc1)c1ccc2[nH]nc(F)c2c1)c1cscc1C] | 433 |
| 313 | (E)-3-(4-((E)-2-Cyclobutyl-1-(3-fluoro-1H-indazol-5-yl)-2-(4-methylthiophen-3-yl)vinyl)phenyl)acrylic acid | 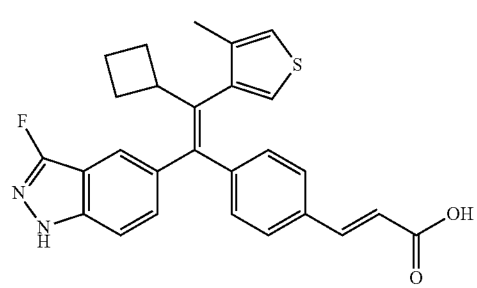 [SMILES: Cc1cscc1/C(=C(\c1ccc(/C=C/C(=O)O)cc1)c1ccc2[nH]nc(F)c2c1)C1CCC1] | 459 |

TABLE 1-continued

| Compound | Name | Structure | LCMS [M + H]+ |
|---|---|---|---|
| 314 | (E)-3-(4-((E)-2-(Benzo[d]isothiazol-5-yl)-1-(1H-indazol-5-yl)but-1-en-1-yl)phenyl)acrylic acid | 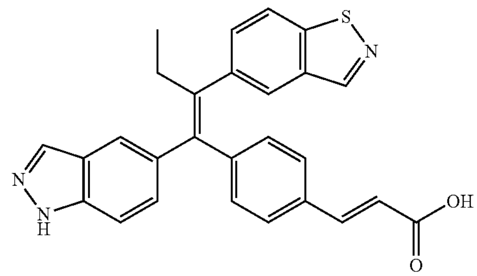 | 452 |
| 315 | (E)-3-(4-((E)-1-(1H-Indazol-5-yl)-2-(4-(pyridin-4-yloxy)phenyl)but-1-en-1-yl)phenyl)acrylic acid | 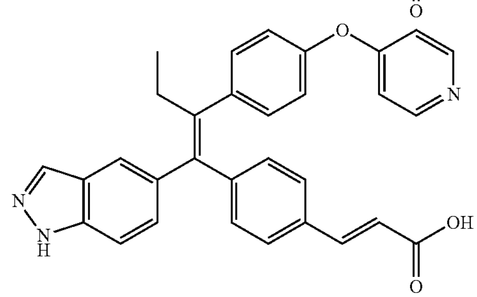 | 488 |
| 316 | (E)-3-(4-((E)-1-(1H-Indazol-5-yl)-2-(4-(pyridin-2-yloxy)phenyl)but-1-en-1-yl)phenyl)acrylic acid | 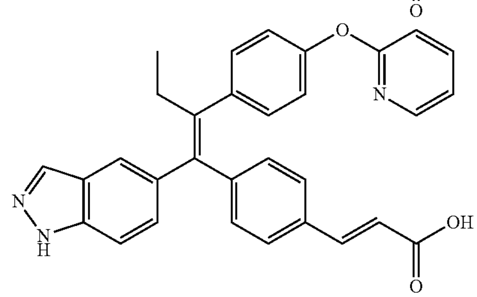 | 488 |
| 317 | (E)-3-(4-((E)-2-(4-Benzylphenyl)-1-(1H-indazol-5-yl)but-1-en-1-yl)phenyl)acrylic acid | 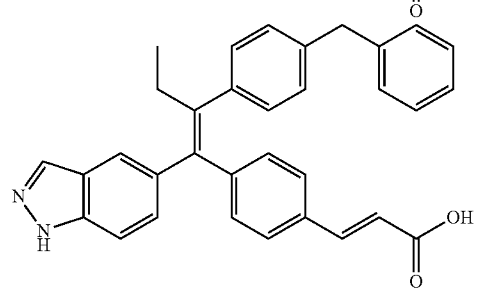 | 485 |
| 318 | (E)-3-(4-((E)-1-(1H-Indazol-5-yl)-2-(4-methyl-3-phenoxyphenyl)but-1-en-1-yl)phenyl)acrylic acid | 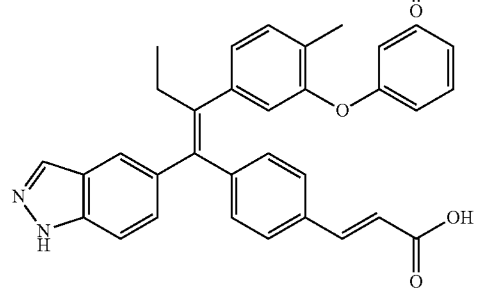 | 501 |
| 319 | (E)-3-(4-((E)-1-(1H-Indazol-5-yl)-2-(2-methyl-4-phenoxyphenyl)but-1-en-1-yl)phenyl)acrylic acid | 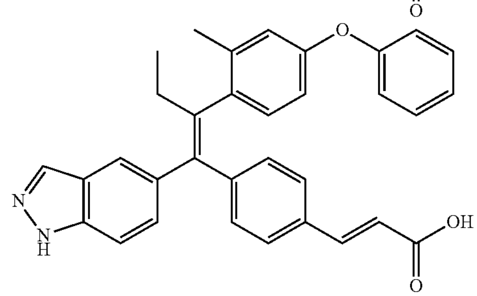 | 501 |

TABLE 1-continued

| Compound | Name | Structure | LCMS [M + H]+ |
|---|---|---|---|
| 320 | (E)-3-(4-((E)-1-(1H-Indazol-5-yl)-2-(3-methyl-4-phenoxyphenyl)but-1-en-1-yl)phenyl)acrylic acid | 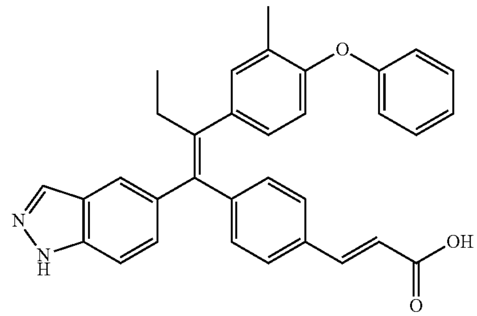 [SMILES: CC/C(=C(/c1ccc(/C=C/C(=O)O)cc1)c1ccc2[nH]ncc2c1)c1ccc(Oc2ccccc2)c(C)c1] | 501 |
| 321 | (E)-3-(4-((E)-1-(1H-Indazol-5-yl)-2-(3-(3-(methylsulfonyl)phenoxy)phenyl)but-1-en-1-yl)phenyl)acrylic acid | 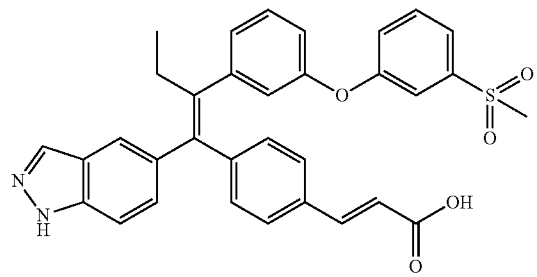 [SMILES: CC/C(=C(/c1ccc(/C=C/C(=O)O)cc1)c1ccc2[nH]ncc2c1)c1cccc(Oc2cccc(S(C)(=O)=O)c2)c1] | 565 |
| 322 | (E)-3-(4-((E)-2-(2-Chloro-4-cyanophenyl)-1-(1H-indazol-5-yl)but-1-en-1-yl)phenyl)acrylic acid | 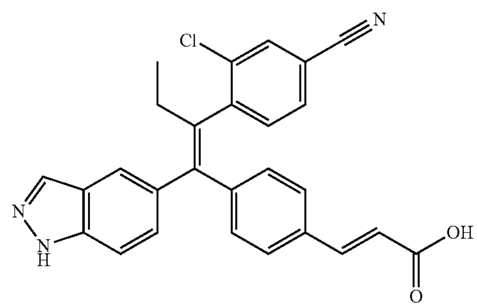 [SMILES: CC/C(=C(/c1ccc(/C=C/C(=O)O)cc1)c1ccc2[nH]ncc2c1)c1ccc(C#N)cc1Cl] | 454 |
| 323 | (E)-3-(4-((E)-2-(3-Cyano-2-methylphenyl)-1-(1H-indazol-5-yl)but-1-en-1-yl)phenyl)acrylic acid | 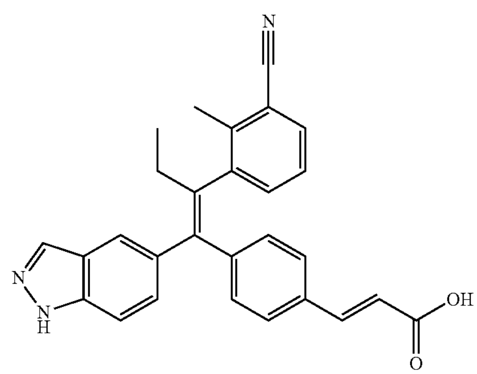 [SMILES: CC/C(=C(/c1ccc(/C=C/C(=O)O)cc1)c1ccc2[nH]ncc2c1)c1cccc(C#N)c1C] | 434 |
| 324 | (E)-3-(4-((E)-2-(4-Cyano-2-methylphenyl)-1-(1H-indazol-5-yl)but-1-en-1-yl)phenyl)acrylic acid | 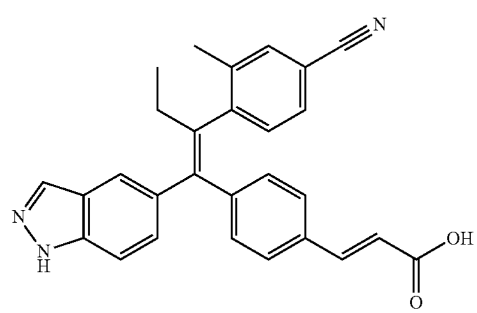 [SMILES: CC/C(=C(/c1ccc(/C=C/C(=O)O)cc1)c1ccc2[nH]ncc2c1)c1ccc(C#N)cc1C] | 434 |

TABLE 1-continued

| Compound | Name | Structure | LCMS [M + H]+ |
|---|---|---|---|
| 325 | (E)-3-(4-((E)-2-(5-Cyano-2-methylphenyl)-1-(1H-indazol-5-yl)but-1-en-1-yl)phenyl)acrylic acid | 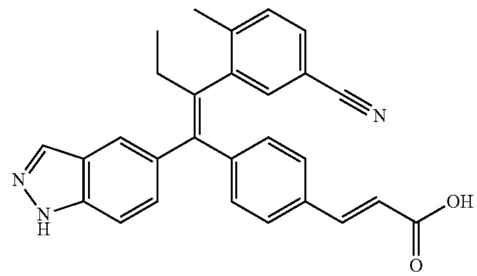 [SMILES: CC/C(=C(/c1ccc(/C=C/C(=O)O)cc1)c1ccc2[nH]ncc2c1)c1cc(C#N)ccc1C] | 434 |
| 326 | (E)-3-(4-((E)-2-(2-Cyano-4-methoxyphenyl)-1-(1H-indazol-5-yl)but-1-en-1-yl)phenyl)acrylic acid | 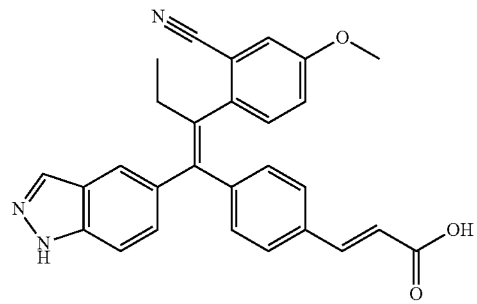 [SMILES: CC/C(=C(/c1ccc(/C=C/C(=O)O)cc1)c1ccc2[nH]ncc2c1)c1ccc(OC)cc1C#N] | 450 |
| 327 | (E)-3-(4-((E)-2-(3-(Carboxymethyl)phenyl)-1-(1H-indazol-5-yl)but-1-en-1-yl)phenyl)acrylic acid | 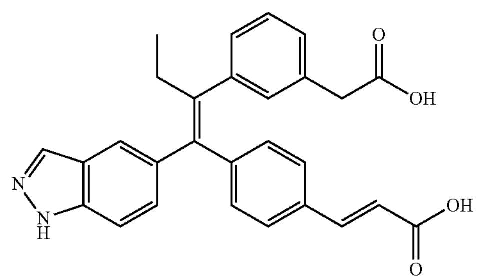 [SMILES: CC/C(=C(/c1ccc(/C=C/C(=O)O)cc1)c1ccc2[nH]ncc2c1)c1cccc(CC(=O)O)c1] | 453 |
| 328 | (E)-3-(4-((E)-2-(4-(Carboxymethyl)phenyl)-1-(1H-indazol-5-yl)but-1-en-1-yl)phenyl)acrylic acid | 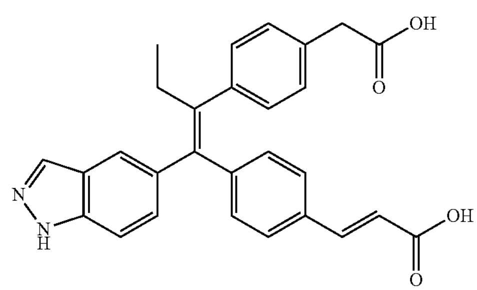 [SMILES: CC/C(=C(/c1ccc(/C=C/C(=O)O)cc1)c1ccc2[nH]ncc2c1)c1ccc(CC(=O)O)cc1] | 453 |
| 329 | 5-((E)-1-(4-((S)-2-((R)-3-Methylpyrrolidin-1-yl)propoxy)phenyl)-2-phenylbut-1-en-1-yl)-1H-indazole | 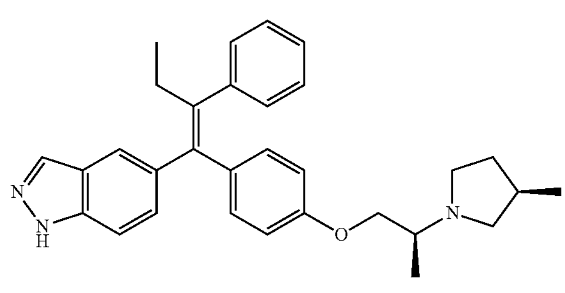 [SMILES: CC/C(=C(/c1ccc(OC[C@H](C)N2CC[C@@H](C)C2)cc1)c1ccc2[nH]ncc2c1)c1ccccc1] | 466 |

TABLE 1-continued

| Compound | Name | Structure | LCMS [M + H]+ |
|---|---|---|---|
| 330 | 5-((E)-2-(2-Chlorophenyl)-1-(4-((S)-2-((R)-3-methylpyrrolidin-1-yl)propoxy)phenyl)but-1-en-1-yl)-1H-indazole | 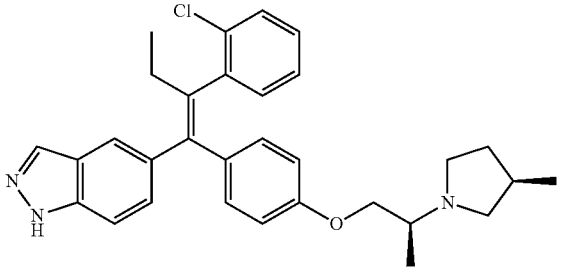 [SMILES: CC/C(=C(/c1ccc(OC[C@H](C)N2CC[C@@H](C)C2)cc1)c1ccc2[nH]ncc2c1)c1ccccc1Cl] | 500 |
| 331 | 5-((E)-2-(3-Chloropyridin-4-yl)-1-(4-((S)-2-((R)-3-methylpyrrolidin-1-yl)propoxy)phenyl)but-1-en-1-yl)-1H-indazole | 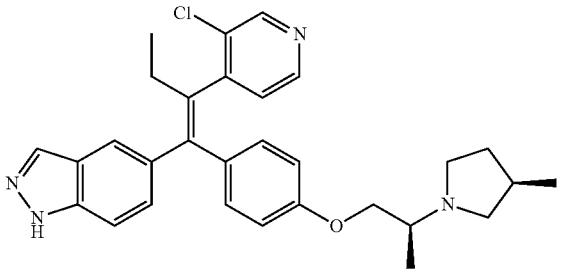 [SMILES: CC/C(=C(/c1ccc(OC[C@H](C)N2CC[C@@H](C)C2)cc1)c1ccc2[nH]ncc2c1)c1ccncc1Cl] | 501 |
| 332 | (E)-1-(4-(2-(2-Chloro-4-fluorophenyl)-1-(1H-indazol-5-yl)but-1-en-1-yl)phenoxy)cyclopropanecarboxylic acid | 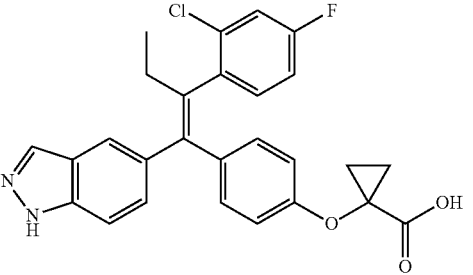 [SMILES: CC/C(=C(/c1ccc(OC2(C(=O)O)CC2)cc1)c1ccc2[nH]ncc2c1)c1ccc(F)cc1Cl] | 477 |
| 333 | (E)-5-(4-(2-(2-Chloro-4-fluorophenyl)-1-(1H-indazol-5-yl)but-1-en-1-yl)phenyl)isoxazol-3-ol | 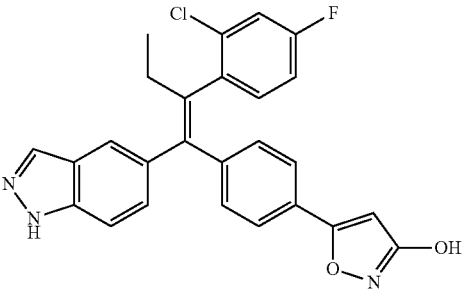 [SMILES: CC/C(=C(/c1ccc(-c2cc(O)no2)cc1)c1ccc2[nH]ncc2c1)c1ccc(F)cc1Cl] | 460 |
| 334 | (E)-3-(4-(2-(2-Chloro-4-fluorophenyl)-1-(1H-indazol-5-yl)but-1-en-1-yl)phenyl)isoxazol-5-ol | 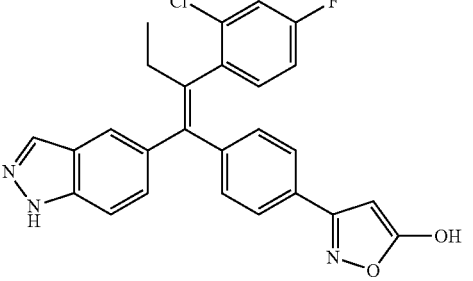 | 460 |

TABLE 1-continued

| Compound | Name | Structure | LCMS [M + H]+ |
|---|---|---|---|
| 335 | (E)-3-(4-((E)-2-(3-Hydroxyphenyl)-1-(1H-indazol-5-yl)but-1-en-1-yl)phenyl)acrylic acid | 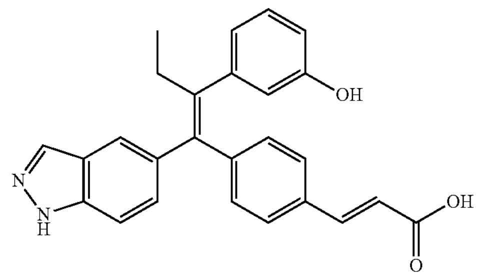 | 411 |
| 336 | (E)-3-(4-((E)-2-(2-Hydroxyphenyl)-1-(1H-indazol-5-yl)but-1-en-1-yl)phenyl)acrylic acid | 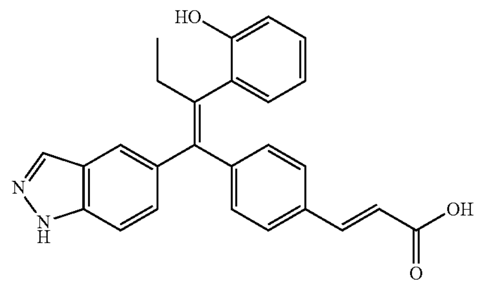 [SMILES: CC/C(=C(/c1ccc(/C=C/C(=O)O)cc1)c1ccc2[nH]ncc2c1)c1ccccc1O] | 411 |
| 337 | (E)-3-(4-((E)-2-(4-Hydroxyphenyl)-1-(1H-indazol-5-yl)but-1-en-1-yl)phenyl)acrylic acid | 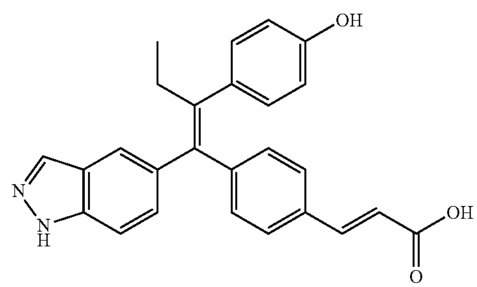 | 411 |
| 338 | (E)-3-(4-(1-(1H-Indazol-5-yl)-2-phenylbut-1-en-1-yl)phenyl)propanoic acid | 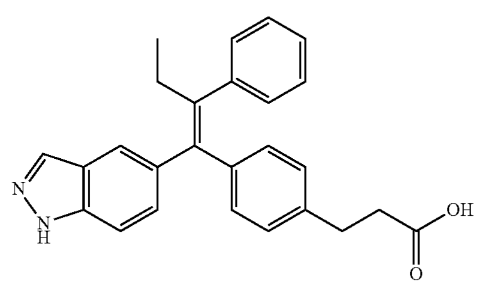 [SMILES: CC/C(=C(/c1ccc(CCC(=O)O)cc1)c1ccc2[nH]ncc2c1)c1ccccc1] | 397 |
| 339 | (E)-3-(4-((E)-1-(1H-Indazol-5-yl)-2-(4-(2-methoxyethoxy)phenyl)but-1-en-1-yl)phenyl)acrylic acid | 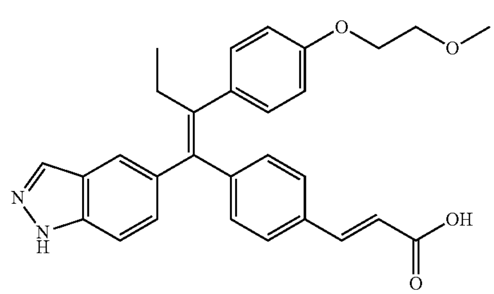 [SMILES: CC/C(=C(/c1ccc(/C=C/C(=O)O)cc1)c1ccc2[nH]ncc2c1)c1ccc(OCCOC)cc1] | 469 |

TABLE 1-continued

| Compound | Name | Structure | LCMS [M + H]+ |
|---|---|---|---|
| 340 | (E)-3-(4-((E)-1-(1H-Indazol-5-yl)-2-(4-(3-methoxypropoxy)phenyl)but-1-en-1-yl)phenyl)acrylic acid | 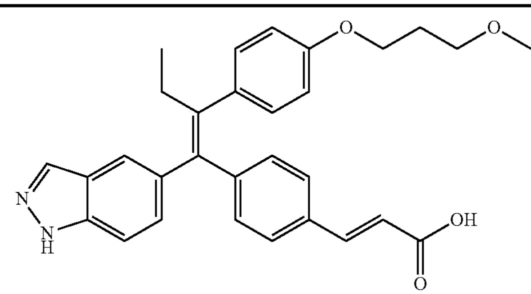 | 483 |
| 341 | (E)-3-(4-((E)-1-(1H-Indazol-5-yl)-2-(3-(2-methoxyethoxy)phenyl)but-1-en-1-yl)phenyl)acrylic acid | 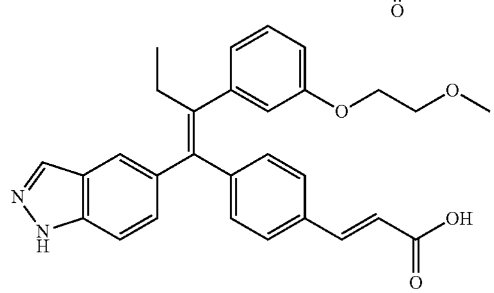 | 469 |
| 342 | (E)-3-(4-((E)-1-(1H-Indazol-5-yl)-2-(3-(3-methoxypropoxy)phenyl)but-1-en-1-yl)phenyl)acrylic acid | 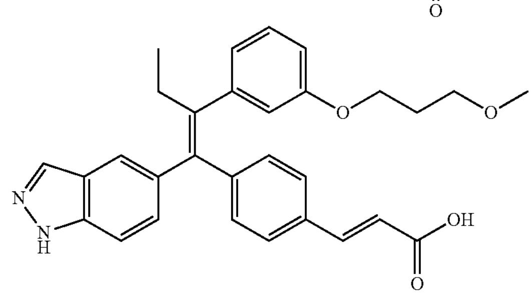 | 483 |
| 343 | (E)-3-(4-((E)-1-(4-Fluoro-1H-indazol-5-yl)-2-(3-((1-methylpiperidin-4-yl)oxy)phenyl)but-1-en-1-yl)phenyl)acrylic acid | 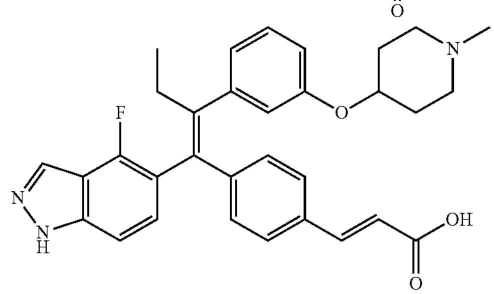 | 526 |
| 344 | (E)-3-(4-((E)-1-(4-Fluoro-1H-indazol-5-yl)-2-(3-((tetrahydro-2H-pyran-4-yl)oxy)phenyl)but-1-en-1-yl)phenyl)acrylic acid | 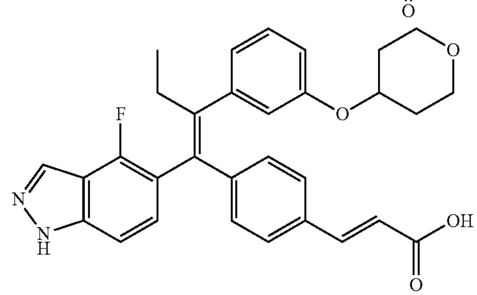 | 513 |
| 345 | (E)-3-(4-((E)-2-(3-(Cyclohexyloxy)phenyl)-1-(4-fluoro-1H-indazol-5-yl)but-1-en-1-yl)phenyl)acrylic acid | 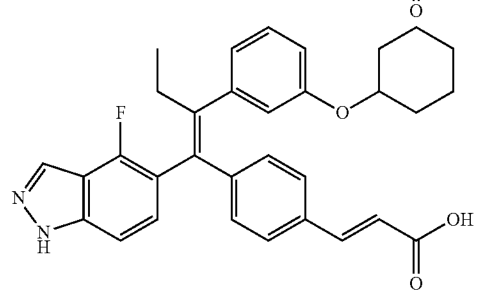 | 511 |

TABLE 1-continued

| Compound | Name | Structure | LCMS [M + H]+ |
|---|---|---|---|
| 346 | (E)-3-(4-((E)-2-(3-Butoxyphenyl)-1-(1H-indazol-5-yl)but-1-en-1-yl)phenyl)acrylic acid | 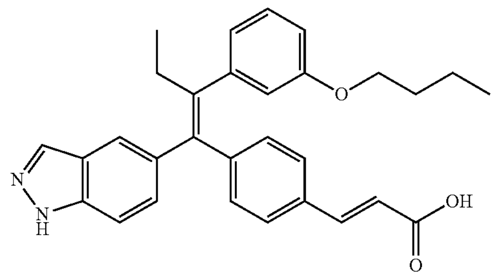 [SMILES: CCCCOc1cccc(/C(CC)=C(\c2ccc(/C=C/C(=O)O)cc2)c2ccc3[nH]ncc3c2)c1] | 467 |
| 347 | (E)-3-(4-((E)-2-(3-(Carboxymethoxy)phenyl)-1-(1H-indazol-5-yl)but-1-en-1-yl)phenyl)acrylic acid | 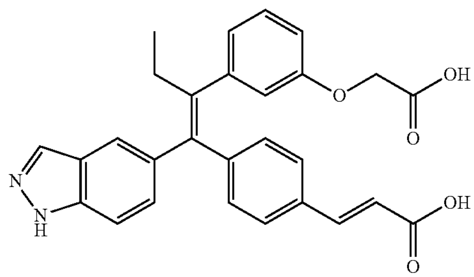 [SMILES: CC/C(=C(/c1ccc(/C=C/C(=O)O)cc1)c1ccc2[nH]ncc2c1)c1cccc(OCC(=O)O)c1] | 469 |
| 348 | (E)-3-(4-((E)-2-(4-(Carboxymethoxy)phenyl)-1-(1H-indazol-5-yl)but-1-en-1-yl)phenyl)acrylic acid | 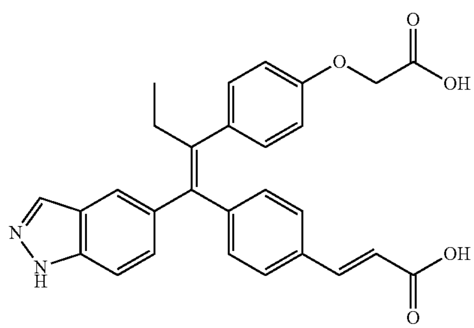 [SMILES: CC/C(=C(/c1ccc(/C=C/C(=O)O)cc1)c1ccc2[nH]ncc2c1)c1ccc(OCC(=O)O)cc1] | 469 |
| 349 | (E)-3-(4-((E)-1-(1H-Indazol-5-yl)-2-(3-(pentyloxy)phenyl)but-1-en-1-yl)phenyl)acrylic acid | 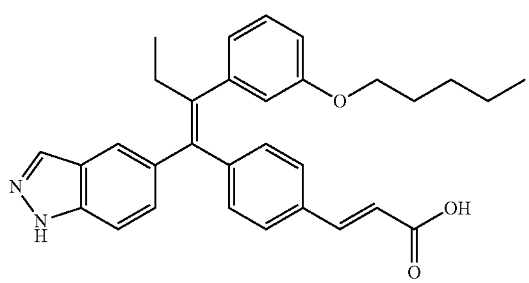 [SMILES: CCCCCOc1cccc(/C(CC)=C(\c2ccc(/C=C/C(=O)O)cc2)c2ccc3[nH]ncc3c2)c1] | 481 |
| 350 | (E)-3-(4-((E)-2-(3-(Hexyloxy)phenyl)-1-(1H-indazol-5-yl)but-1-en-1-yl)phenyl)acrylic acid | 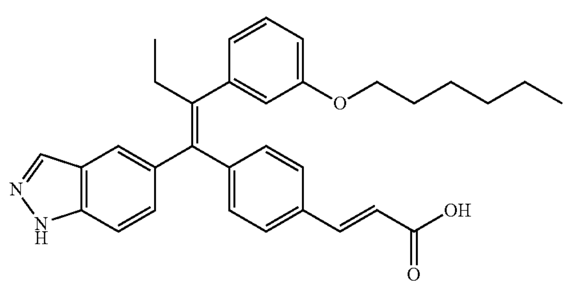 [SMILES: CCCCCCOc1cccc(/C(CC)=C(\c2ccc(/C=C/C(=O)O)cc2)c2ccc3[nH]ncc3c2)c1] | 495 |

TABLE 1-continued

| Compound | Name | Structure | LCMS [M + H]+ |
|---|---|---|---|
| 351 | 4-(3-((E)-1-(4-((E)-2-Carboxyvinyl)phenyl)-1-(1H-indazol-5-yl)but-1-en-2-yl)phenoxy)butanoic acid | 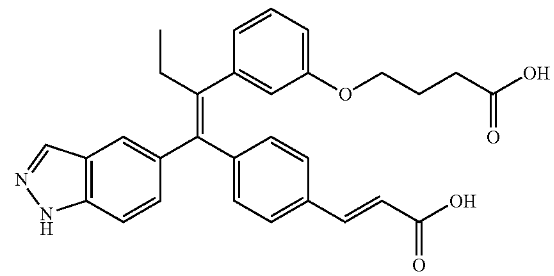 [SMILES: CC/C(=C(/c1ccc(/C=C/C(=O)O)cc1)c1ccc2[nH]ncc2c1)c1cccc(OCCCC(=O)O)c1] | 497 |
| 352 | 5-(3-((E)-1-(4-((E)-2-Carboxyvinyl)phenyl)-1-(1H-indazol-5-yl)but-1-en-2-yl)phenoxy)pentanoic acid | 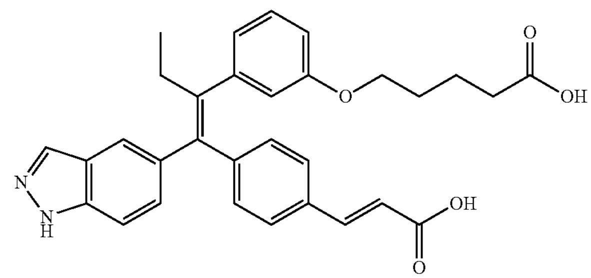 [SMILES: CC/C(=C(/c1ccc(/C=C/C(=O)O)cc1)c1ccc2[nH]ncc2c1)c1cccc(OCCCCC(=O)O)c1] | 511 |
| 353 | 4-(4-((E)-1-(4-((E)-2-Carboxyvinyl)phenyl)-1-(1H-indazol-5-yl)but-1-en-2-yl)phenoxy)butanoic acid | 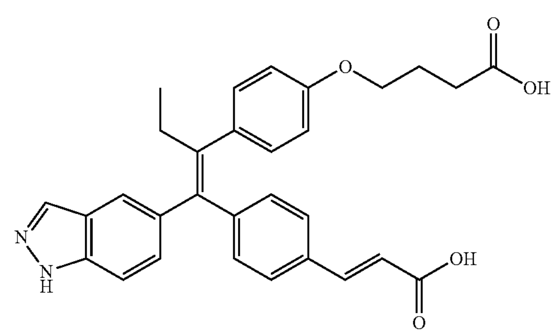 [SMILES: CC/C(=C(/c1ccc(/C=C/C(=O)O)cc1)c1ccc2[nH]ncc2c1)c1ccc(OCCCC(=O)O)cc1] | 497 |
| 354 | 5-(4-((E)-1-(4-((E)-2-Carboxyvinyl)phenyl)-1-(1H-indazol-5-yl)but-1-en-2-yl)phenoxy)pentanoic acid | 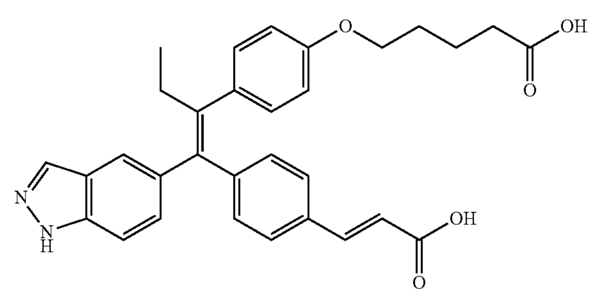 [SMILES: CC/C(=C(/c1ccc(/C=C/C(=O)O)cc1)c1ccc2[nH]ncc2c1)c1ccc(OCCCCC(=O)O)cc1] | 511 |
| 355 | (E)-3-(4-((E)-2-(4-Butoxyphenyl)-1-(1H-indazol-5-yl)but-1-en-1-yl)phenyl)acrylic acid | 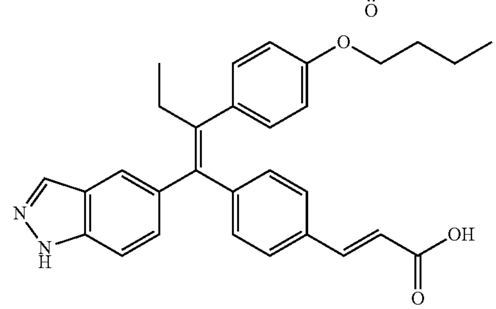 | 467 |

TABLE 1-continued

| Compound | Name | Structure | LCMS [M + H]+ |
|---|---|---|---|
| 356 | (E)-3-(4-((E)-1-(1H-Indazol-5-yl)-2-(4-(pentyloxy)phenyl)but-1-en-1-yl)phenyl)acrylic acid | 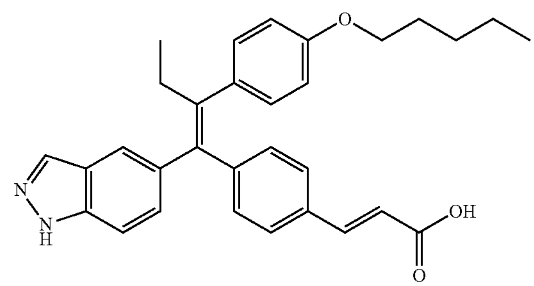 [SMILES: CCCCCOc1ccc(/C(CC)=C(\c2ccc(/C=C/C(=O)O)cc2)c2ccc3[nH]ncc3c2)cc1] | 481 |
| 357 | (E)-3-(4-((E)-2-(4-(Hexyloxy)phenyl)-1-(1H-indazol-5-yl)but-1-en-1-yl)phenyl)acrylic acid | 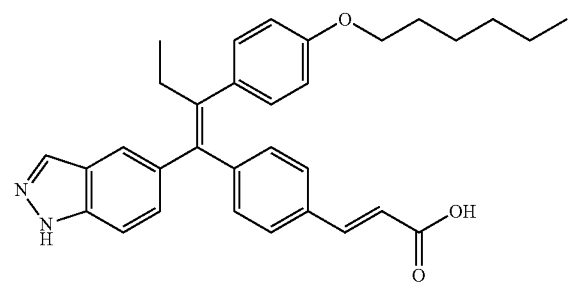 [SMILES: CCCCCCOc1ccc(/C(CC)=C(\c2ccc(/C=C/C(=O)O)cc2)c2ccc3[nH]ncc3c2)cc1] | 495 |
| 358 | (E)-3-(4-((E)-2-(3-(Benzyloxy)phenyl)-1-(1H-indazol-5-yl)but-1-en-1-yl)phenyl)acrylic acid | 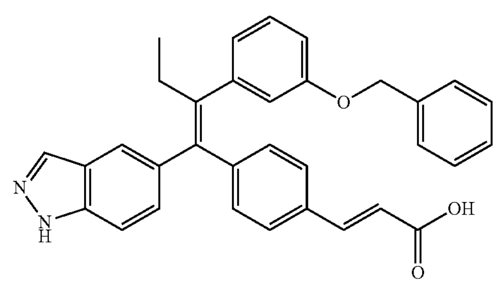 [SMILES: CC/C(=C(/c1ccc(/C=C/C(=O)O)cc1)c1ccc2[nH]ncc2c1)c1cccc(OCc2ccccc2)c1] | 501 |
| 359 | (E)-3-(4-((E)-1-(1H-Indazol-5-yl)-2-(3-(pyridin-3-ylmethoxy)phenyl)but-1-en-1-yl)phenyl)acrylic acid | 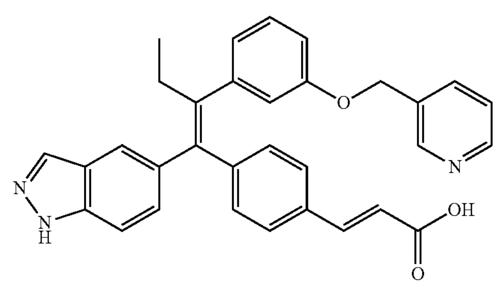 [SMILES: CC/C(=C(/c1ccc(/C=C/C(=O)O)cc1)c1ccc2[nH]ncc2c1)c1cccc(OCc2cccnc2)c1] | 502 |
| 360 | (E)-3-(4-((E)-2-(4-(2-Hydroxyethoxy)phenyl)-1-(1H-indazol-5-yl)but-1-en-1-yl)phenyl)acrylic acid | 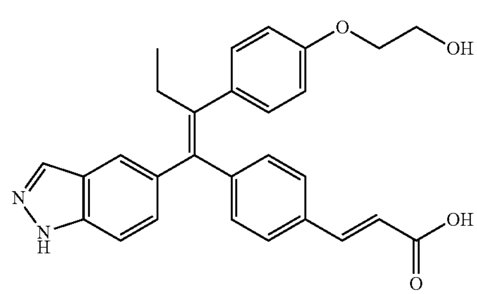 [SMILES: CC/C(=C(/c1ccc(/C=C/C(=O)O)cc1)c1ccc2[nH]ncc2c1)c1ccc(OCCO)cc1] | 455 |

TABLE 1-continued

| Compound | Name | Structure | LCMS [M + H]+ |
|---|---|---|---|
| 361 | (E)-3-(4-((E)-1-(1H-Indazol-5-yl)-2-(2-(methylsulfonyl)phenyl)but-1-en-1-yl)phenyl)acrylic acid | 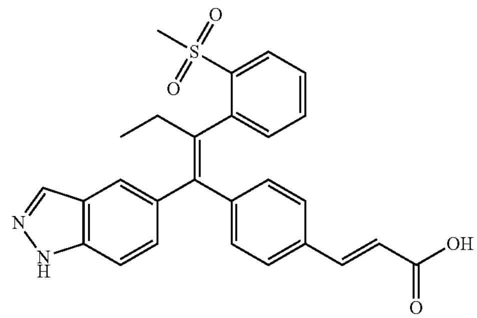 [SMILES: CC/C(=C(/c1ccc(/C=C/C(=O)O)cc1)c1ccc2[nH]ncc2c1)c1ccccc1S(C)(=O)=O] | 473 |
| 362 | (E)-3-(4-((E)-1-(1H-Indazol-5-yl)-2-(3-(pyridin-2-yloxy)phenyl)but-1-en-1-yl)phenyl)acrylic acid | 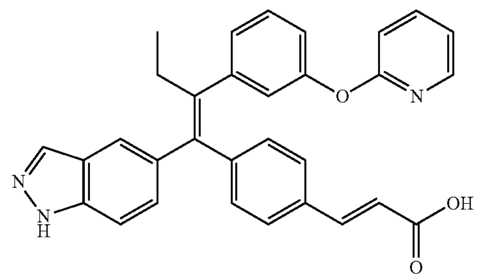 [SMILES: CC/C(=C(/c1ccc(/C=C/C(=O)O)cc1)c1ccc2[nH]ncc2c1)c1cccc(Oc2ccccn2)c1] | 488 |
| 363 | (E)-3-(4-((E)-1-(1H-Indazol-5-yl)-2-(3-(pyrimidin-2-yloxy)phenyl)but-1-en-1-yl)phenyl)acrylic acid | 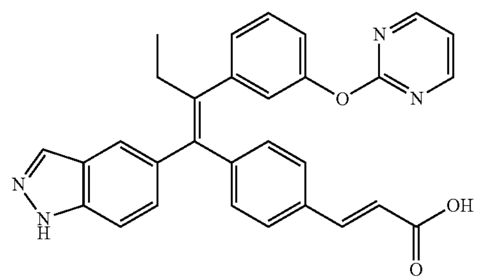 [SMILES: CC/C(=C(/c1ccc(/C=C/C(=O)O)cc1)c1ccc2[nH]ncc2c1)c1cccc(Oc2ncccn2)c1] | 489 |
| 364 | (E)-3-(4-((E)-1-(1H-Indazol-5-yl)-2-(3-(pyrimidin-4-yloxy)phenyl)but-1-en-1-yl)phenyl)acrylic acid | 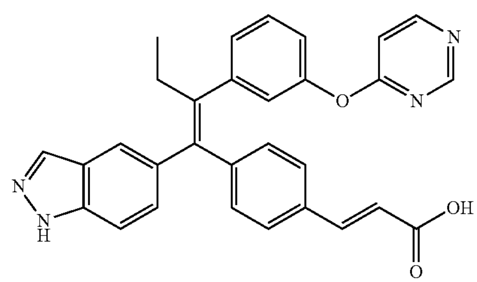 [SMILES: CC/C(=C(/c1ccc(/C=C/C(=O)O)cc1)c1ccc2[nH]ncc2c1)c1cccc(Oc2ccncn2)c1] | 489 |
| 365 | (E)-3-(4-((E)-1-(1H-Indazol-5-yl)-2-(3-(pyridin-3-yloxy)phenyl)but-1-en-1-yl)phenyl)acrylic acid | 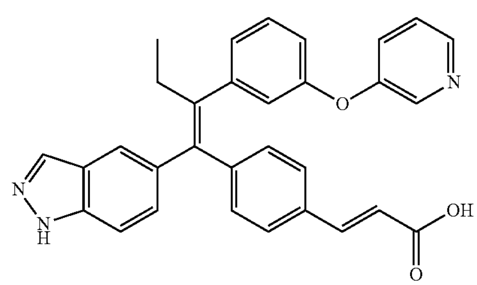 [SMILES: CC/C(=C(/c1ccc(/C=C/C(=O)O)cc1)c1ccc2[nH]ncc2c1)c1cccc(Oc2cccnc2)c1] | 488 |

TABLE 1-continued

| Compound | Name | Structure | LCMS [M + H]+ |
|---|---|---|---|
| 366 | (E)-3-(4-((E)-1-(1H-Indazol-5-yl)-2-(3-(pyridin-4-yloxy)phenyl)but-1-en-1-yl)phenyl)acrylic acid | 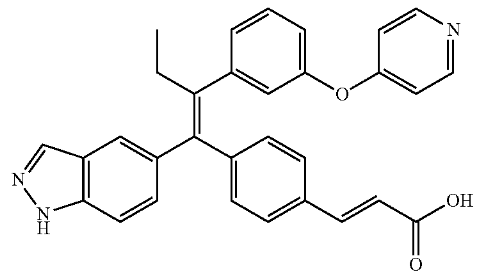 [SMILES: CC/C(=C(/c1ccc(/C=C/C(=O)O)cc1)c1ccc2[nH]ncc2c1)c1cccc(Oc2ccncc2)c1] | 488 |
| 367 | (E)-3-(4-((E)-2-(3-(2-Fluorophenoxy)phenyl)-1-(1H-indazol-5-yl)but-1-en-1-yl)phenyl)acrylic acid | 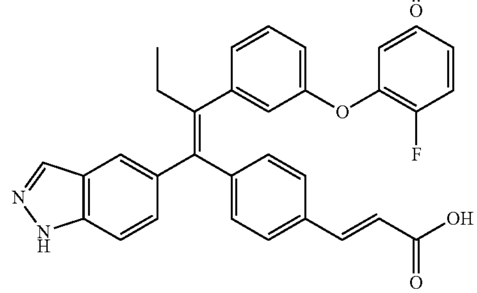 | 505 |
| 368 | (E)-3-(4-((E)-1-(1H-Indazol-5-yl)-2-(3-(o-tolyloxy)phenyl)but-1-en-1-yl)phenyl)acrylic acid | 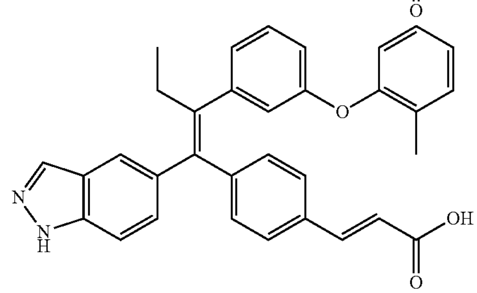 | 501 |
| 369 | (E)-3-(4-((E)-1-(1H-Indazol-5-yl)-2-(3-(pyrimidin-5-yloxy)phenyl)but-1-en-1-yl)phenyl)acrylic acid | 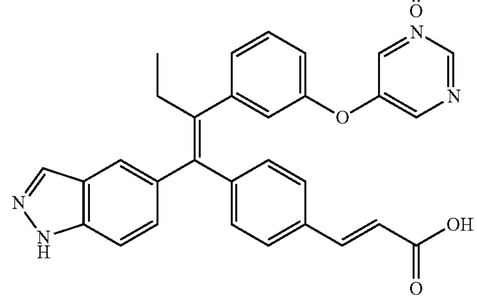 | 489 |
| 370 | (E)-3-(4-((E)-1-(1H-Indazol-5-yl)-2-(3-(thiazol-2-yloxy)phenyl)but-1-en-1-yl)phenyl)acrylic acid | 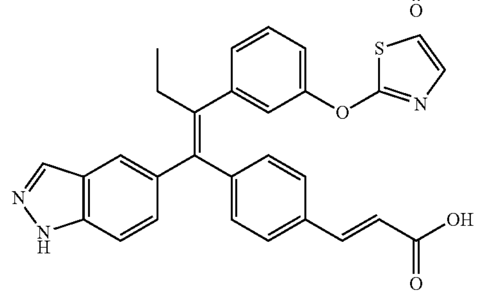 | 494 |
| 371 | (E)-3-(4-((E)-1-(1H-Indazol-5-yl)-2-(3-(pyrazin-2-yloxy)phenyl)but-1-en-1-yl)phenyl)acrylic acid | 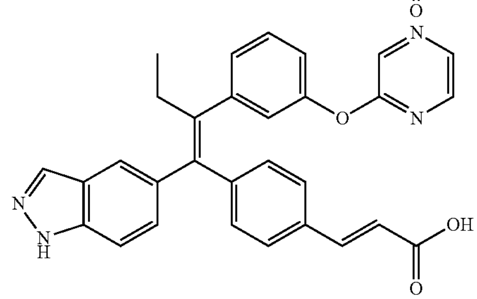 | 489 |

TABLE 1-continued

| Compound | Name | Structure | LCMS [M + H]+ |
|---|---|---|---|
| 372 | (E)-3-(4-((E)-1-(1H-Indazol-5-yl)-2-(3-((3-(trifluoromethyl)pyridin-4-yl)oxy)phenyl)but-1-en-1-yl)phenyl)acrylic acid | 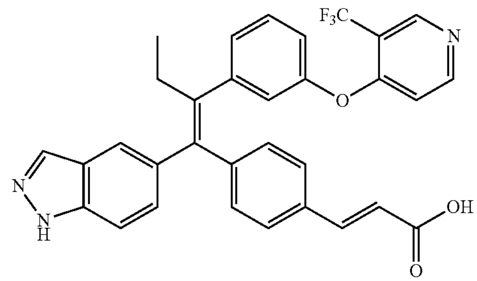 [SMILES: CC/C(=C(/c1ccc(/C=C/C(=O)O)cc1)c1ccc2[nH]ncc2c1)c1cccc(Oc2ccncc2C(F)(F)F)c1] | 556 |
| 373 | (E)-3-(4-((E)-1-(1H-Indazol-5-yl)-2-(3-(4-(methylsulfonyl)phenoxy)phenyl)but-1-en-1-yl)phenyl)acrylic acid | 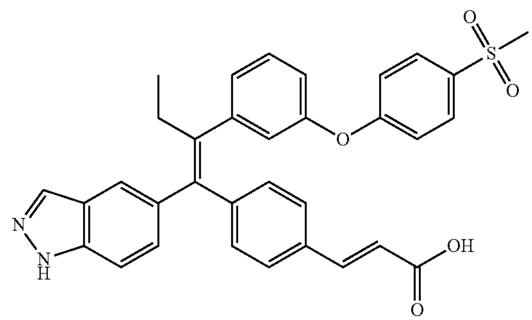 [SMILES: CC/C(=C(/c1ccc(/C=C/C(=O)O)cc1)c1ccc2[nH]ncc2c1)c1cccc(Oc2ccc(S(C)(=O)=O)cc2)c1] | 565 |
| 374 | (E)-3-(4-((E)-1-(1H-Indazol-5-yl)-2-(3-(2-(methylsulfonyl)phenoxy)phenyl)but-1-en-1-yl)phenyl)acrylic acid | 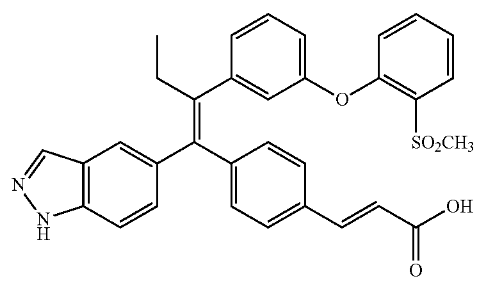 [SMILES: CC/C(=C(/c1ccc(/C=C/C(=O)O)cc1)c1ccc2[nH]ncc2c1)c1cccc(Oc2ccccc2S(C)(=O)=O)c1] | 565 |
| 375 | (E)-3-(4-((E)-1-(4-Fluoro-1H-indazol-5-yl)-2-(3-(pyridin-2-yloxy)phenyl)but-1-en-1-yl)phenyl)acrylic acid | 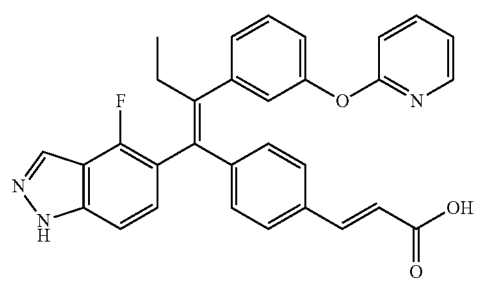 [SMILES: CC/C(=C(/c1ccc(/C=C/C(=O)O)cc1)c1ccc2[nH]ncc2c1F)c1cccc(Oc2ccccn2)c1] | 506 |
| 376 | (E)-3-(4-((E)-1-(4-Fluoro-1H-indazol-5-yl)-2-(3-(pyrimidin-2-yloxy)phenyl)but-1-en-1-yl)phenyl)acrylic acid | 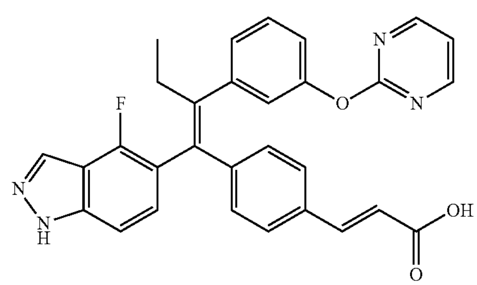 [SMILES: CC/C(=C(/c1ccc(/C=C/C(=O)O)cc1)c1ccc2[nH]ncc2c1F)c1cccc(Oc2ncccn2)c1] | 507 |

TABLE 1-continued

| Compound | Name | Structure | LCMS [M + H]+ |
|---|---|---|---|
| 377 | (E)-3-(4-((E)-1-(4-Fluoro-1H-indazol-5-yl)-2-(3-(pyrazin-2-yloxy)phenyl)but-1-en-1-yl)phenyl)acrylic acid | 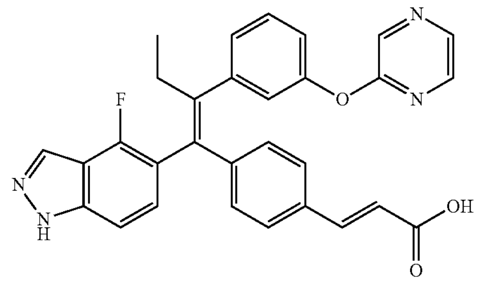 [SMILES: CC/C(=C(/c1ccc(/C=C/C(=O)O)cc1)c1ccc2[nH]ncc2c1F)c1cccc(Oc2cnccn2)c1] | 507 |
| 378 | (E)-3-(4-((E)-1-(4-Fluoro-1H-indazol-5-yl)-2-(3-((6-(methylsulfonyl)pyridin-3-yl)oxy)phenyl)but-1-en-1-yl)phenyl)acrylic acid | 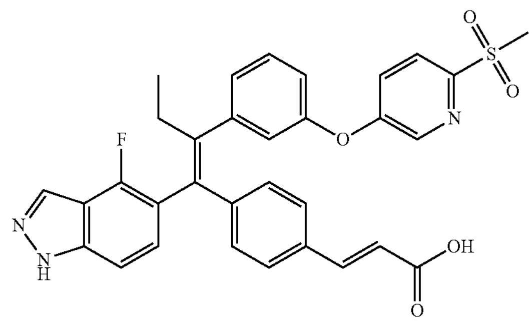 [SMILES: CC/C(=C(/c1ccc(/C=C/C(=O)O)cc1)c1ccc2[nH]ncc2c1F)c1cccc(Oc2ccc(S(C)(=O)=O)nc2)c1] | 584 |
| 379 | (E)-3-(4-((E)-1-(1H-Indazol-5-yl)-2-(3-((5-(methylsulfonyl)pyridin-2-yl)oxy)phenyl)but-1-en-1-yl)phenyl)acrylic acid | 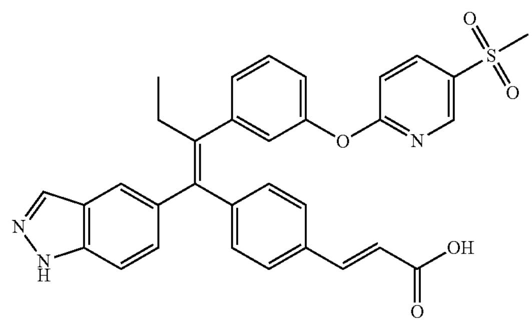 [SMILES: CC/C(=C(/c1ccc(/C=C/C(=O)O)cc1)c1ccc2[nH]ncc2c1)c1cccc(Oc2ccc(S(C)(=O)=O)cn2)c1] | 566 |
| 380 | (E)-3-(4-((E)-1-(1H-Indazol-5-yl)-2-(3-((6-(methylsulfonyl)pyridin-3-yl)oxy)phenyl)but-1-en-1-yl)phenyl)acrylic acid | 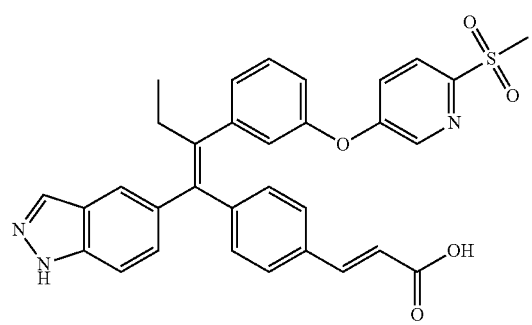 [SMILES: CC/C(=C(/c1ccc(/C=C/C(=O)O)cc1)c1ccc2[nH]ncc2c1)c1cccc(Oc2ccc(S(C)(=O)=O)nc2)c1] | 566 |
| 381 | (E)-3-(4-((E)-1-(1H-Indazol-5-yl)-2-(3-((5-(trifluoromethyl)pyridin-2-yl)oxy)phenyl)but-1-en-1-yl)phenyl)acrylic acid | 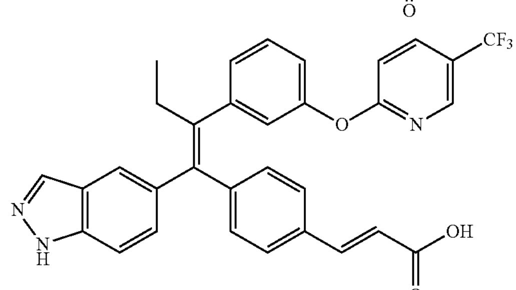 | 556 |

TABLE 1-continued

| Compound | Name | Structure | LCMS [M + H]+ |
|---|---|---|---|
| 382 | (E)-3-(4-((E)-1-(1H-Indazol-5-yl)-2-(3-((6-methylpyridin-3-yl)oxy)phenyl)but-1-en-1-yl)phenyl)acrylic acid | 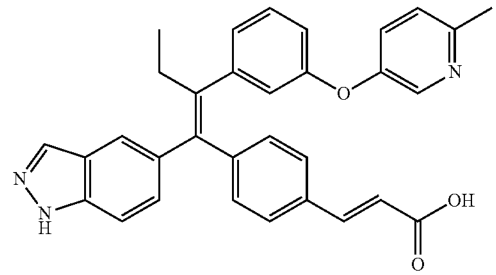 [SMILES: CC/C(=C(/c1ccc(/C=C/C(=O)O)cc1)c1ccc2[nH]ncc2c1)c1cccc(Oc2ccc(C)nc2)c1] | 502 |
| 383 | (E)-3-(4-((E)-1-(1H-Indazol-5-yl)-2-(4-(pyrimidin-5-yl)phenyl)but-1-en-1-yl)phenyl)acrylic acid | 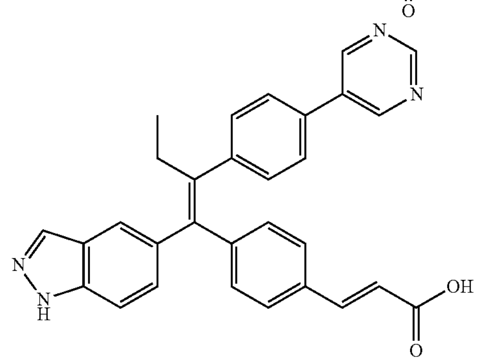 | 473 |
| 384 | (E)-3-(4-((E)-1-(1H-Indazol-5-yl)-2-(4-(1-methyl-1H-pyrazol-4-yl)phenyl)but-1-en-1-yl)phenyl)acrylic acid | 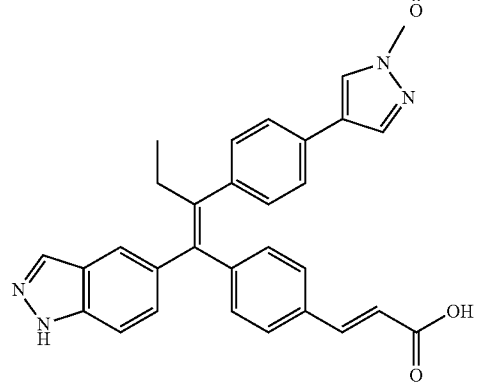 | 475 |
| 385 | (E)-3-(4-((E)-1-(1H-Indazol-5-yl)-2-(4-(pyridin-2-yl)phenyl)but-1-en-1-yl)phenyl)acrylic acid | 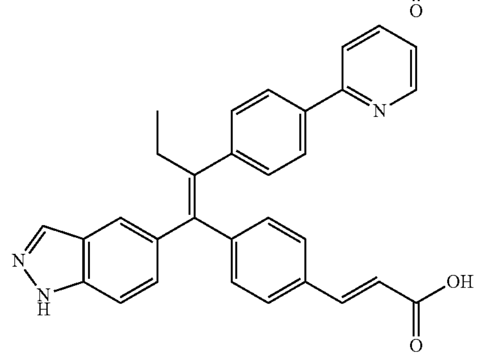 | 472 |
| 386 | (E)-3-(4-((E)-1-(1H-Indazol-5-yl)-2-(4-(thiophen-3-yl)phenyl)but-1-en-1-yl)phenyl)acrylic acid | 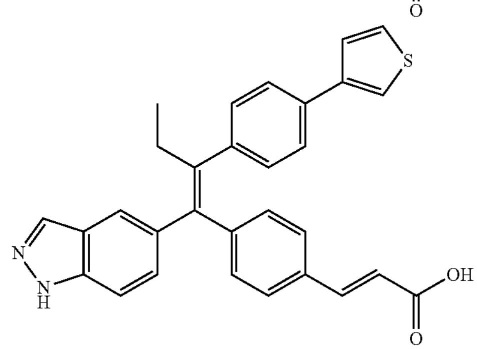 | 477 |

TABLE 1-continued

| Compound | Name | Structure | LCMS [M + H]+ |
|---|---|---|---|
| 387 | (E)-3-(4-((E)-1-(1H-Indazol-5-yl)-2-(4-(thiazol-2-yl)phenyl)but-1-en-1-yl)phenyl)acrylic acid | 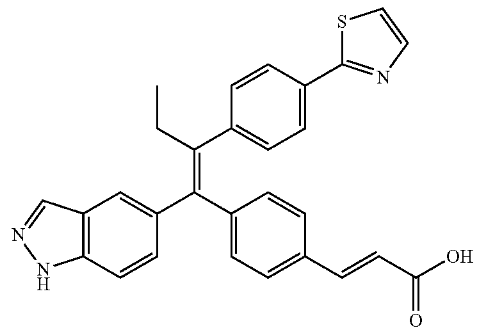 [SMILES: CC/C(=C(/c1ccc(/C=C/C(=O)O)cc1)c1ccc2[nH]ncc2c1)c1ccc(-c2nccs2)cc1] | 478 |
| 388 | (E)-3-(4-((E)-1-(1H-Indazol-5-yl)-2-(4-(thiazol-4-yl)phenyl)but-1-en-1-yl)phenyl)acrylic acid | 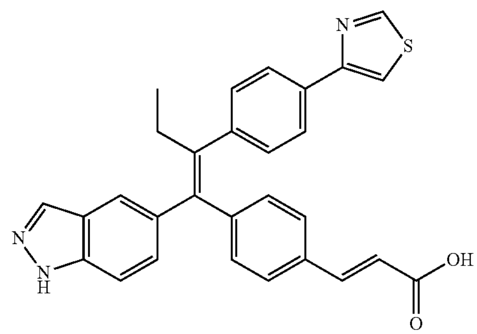 [SMILES: CC/C(=C(/c1ccc(/C=C/C(=O)O)cc1)c1ccc2[nH]ncc2c1)c1ccc(-c2cscn2)cc1] | 478 |
| 389 | (E)-3-(4-((E)-1-(1H-Indazol-5-yl)-2-(4-(pyrazin-2-yl)phenyl)but-1-en-1-yl)phenyl)acrylic acid | 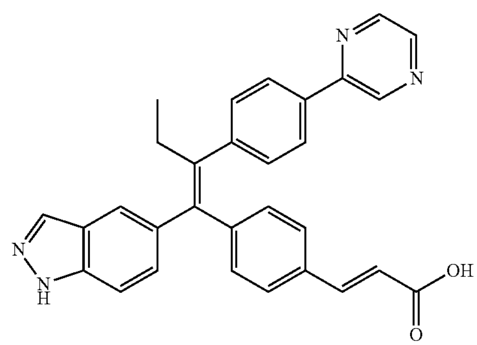 [SMILES: CC/C(=C(/c1ccc(/C=C/C(=O)O)cc1)c1ccc2[nH]ncc2c1)c1ccc(-c2cnccn2)cc1] | 473 |
| 390 | (E)-3-(4-((E)-1-(1H-Indazol-5-yl)-2-(3-(pyridin-2-yl)phenyl)but-1-en-1-yl)phenyl)acrylic acid | 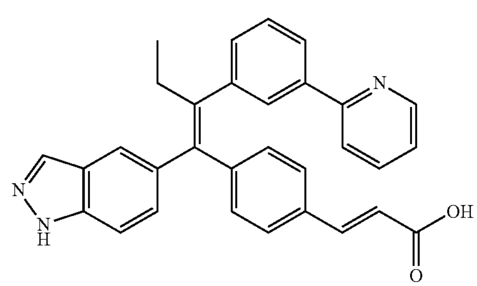 [SMILES: CC/C(=C(/c1ccc(/C=C/C(=O)O)cc1)c1ccc2[nH]ncc2c1)c1cccc(-c2ccccn2)c1] | 472 |
| 391 | (E)-3-(4-((E)-1-(1H-Indazol-5-yl)-2-(3-(thiazol-2-yl)phenyl)but-1-en-1-yl)phenyl)acrylic acid | 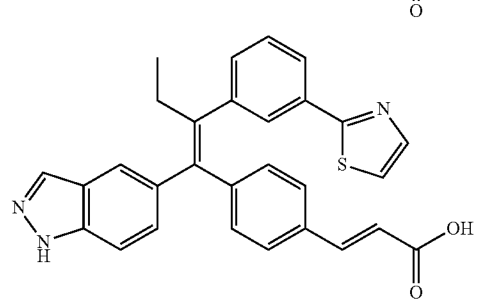 | 478 |

TABLE 1-continued

| Compound | Name | Structure | LCMS [M + H]+ |
|---|---|---|---|
| 392 | (E)-3-(4-((E)-1-(1H-Indazol-5-yl)-2-(3-(thiazol-4-yl)phenyl)but-1-en-1-yl)phenyl)acrylic acid | 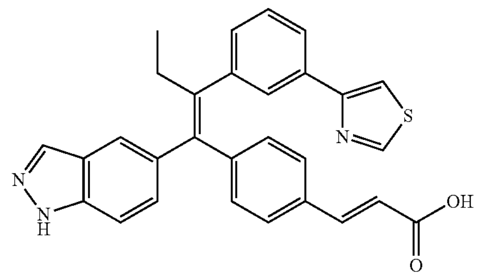 [SMILES: CC/C(=C(/c1ccc(/C=C/C(=O)O)cc1)c1ccc2[nH]ncc2c1)c1cccc(-c2cscn2)c1] | 478 |
| 393 | (E)-3-(4-((E)-1-(1H-Indazol-5-yl)-2-(3-(pyridin-3-yl)phenyl)but-1-en-1-yl)phenyl)acrylic acid | 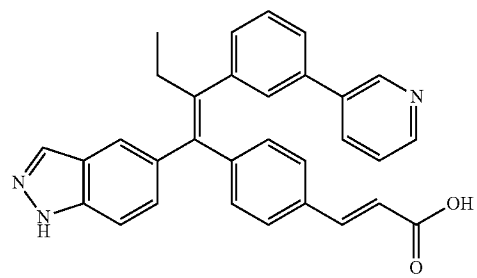 [SMILES: CC/C(=C(/c1ccc(/C=C/C(=O)O)cc1)c1ccc2[nH]ncc2c1)c1cccc(-c2cccnc2)c1] | 472 |
| 394 | (E)-3-(4-((E)-1-(1H-Indazol-5-yl)-2-(3-(pyridin-4-yl)phenyl)but-1-en-1-yl)phenyl)acrylic acid | 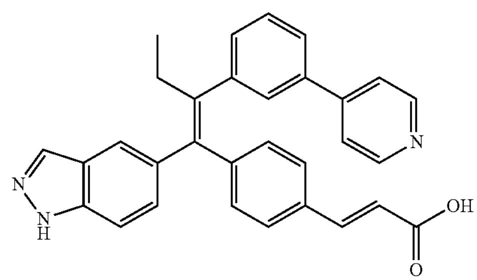 [SMILES: CC/C(=C(/c1ccc(/C=C/C(=O)O)cc1)c1ccc2[nH]ncc2c1)c1cccc(-c2ccncc2)c1] | 472 |
| 395 | (E)-3-(4-((E)-1-(1H-Indazol-5-yl)-2-(4-(isothiazol-4-yl)phenyl)but-1-en-1-yl)phenyl)acrylic acid | 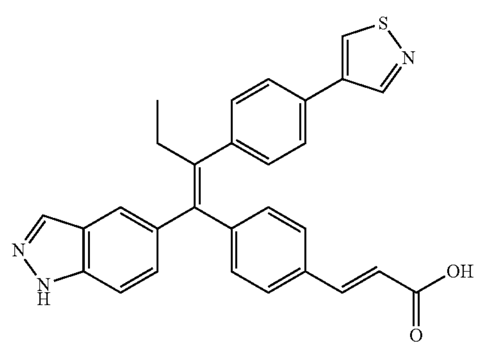 [SMILES: CC/C(=C(/c1ccc(/C=C/C(=O)O)cc1)c1ccc2[nH]ncc2c1)c1ccc(-c2cnsc2)cc1] | 478 |
| 396 | (E)-3-(4-((E)-1-(1H-Indazol-5-yl)-2-(4-(methyl(phenyl)amino)phenyl)but-1-en-1-yl)phenyl)acrylic acid | 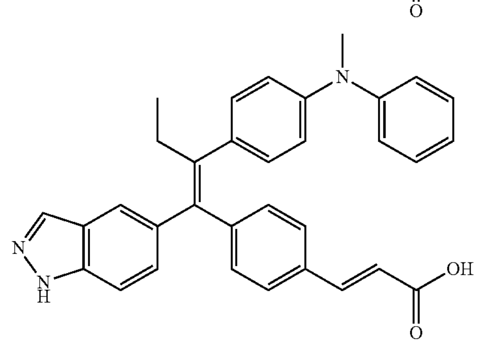 | 500 |

TABLE 1-continued

| Compound | Name | Structure | LCMS [M + H]+ |
|---|---|---|---|
| 397 | (E)-3-(4-((E)-1-(1H-Indazol-5-yl)-2-(4-(phenylamino)phenyl)but-1-en-1-yl)phenyl)acrylic acid | 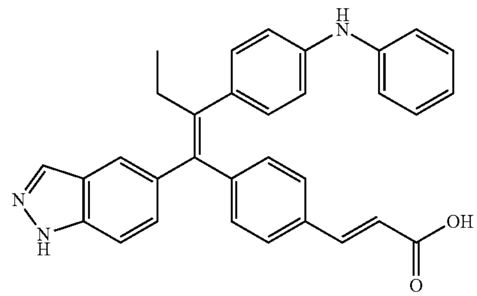 [SMILES: CC/C(=C(/c1ccc(/C=C/C(=O)O)cc1)c1ccc2[nH]ncc2c1)c1ccc(Nc2ccccc2)cc1] | 486 |
| 398 | (E)-3-(4-((E)-2-(2-Chlorophenyl)-1-(1-methyl-1H-indazol-5-yl)but-1-en-1-yl)phenyl)acrylic acid | 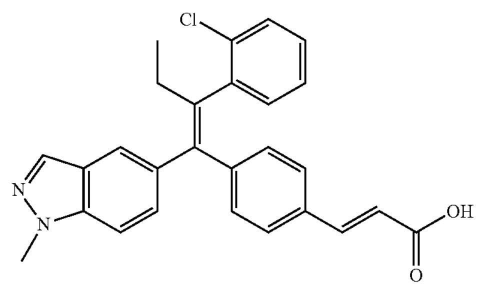 [SMILES: CC/C(=C(/c1ccc(/C=C/C(=O)O)cc1)c1ccc2c(cnn2C)c1)c1ccccc1Cl] | 443 |
| 399 | (E)-3-(4-((E)-2-Cyclobutyl-1-(1-methyl-1H-indazol-5-yl)-2-phenylvinyl)phenyl)acrylic acid | 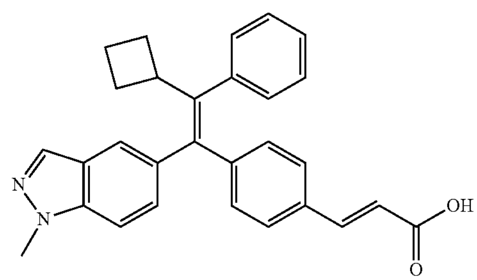 [SMILES: Cn1ncc2cc(/C(=C(/c3ccccc3)C3CCC3)c3ccc(/C=C/C(=O)O)cc3)ccc21] | 435 |
| 400 | (E)-3-(4-((E)-2-(2-Chloro-4-fluorophenyl)-1-(1-methyl-1H-indazol-5-yl)but-1-en-1-yl)phenyl)acrylic acid | 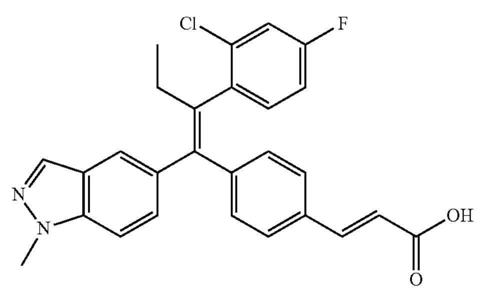 [SMILES: CC/C(=C(/c1ccc(/C=C/C(=O)O)cc1)c1ccc2c(cnn2C)c1)c1ccc(F)cc1Cl] | 461 |
| 401 | (E)-3-(4-((E)-2-(2-Chloro-4-fluorophenyl)-1-(1-(difluoromethyl)-1H-indazol-5-yl)but-1-en-1-yl)phenyl)acrylic acid | 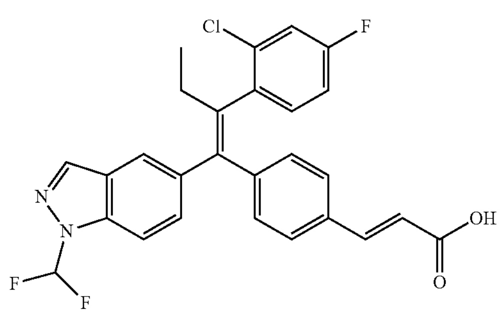 [SMILES: CC/C(=C(/c1ccc(/C=C/C(=O)O)cc1)c1ccc2c(cnn2C(F)F)c1)c1ccc(F)cc1Cl] | 497 |

TABLE 1-continued

| Compound | Name | Structure | LCMS [M + H]+ |
|---|---|---|---|
| 402 | (E)-3-(4-((E)-2-(2-Chloro-4-fluorophenyl)-1-(2-(difluoromethyl)-2H-indazol-5-yl)but-1-en-1-yl)phenyl)acrylic acid | 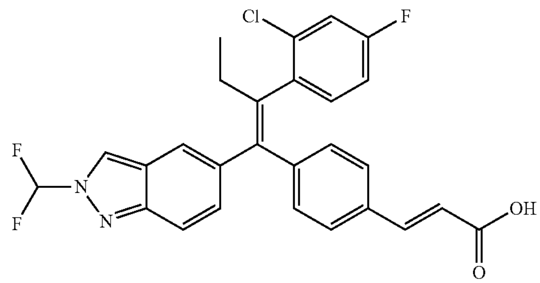 [SMILES: CC/C(=C(/c1ccc(/C=C/C(=O)O)cc1)c1ccc2nn(C(F)F)cc2c1)c1ccc(F)cc1Cl] | 497 |
| 403 | (E)-3-(4-((E)-1-(1-Acetyl-1H-indazol-5-yl)-2-(2-chloro-4-fluorophenyl)but-1-en-1-yl)phenyl)acrylic acid | 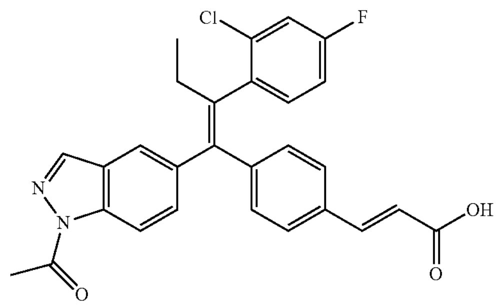 [SMILES: CC/C(=C(/c1ccc(/C=C/C(=O)O)cc1)c1ccc2c(cnn2C(C)=O)c1)c1ccc(F)cc1Cl] | 489 |
| 404 | (E)-3-(4-((E)-2-(2-Chloro-4-fluorophenyl)-1-(1-isobutyryl-1H-indazol-5-yl)but-1-en-1-yl)phenyl)acrylic acid | 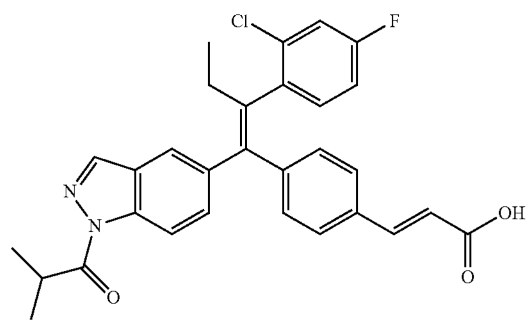 [SMILES: CC/C(=C(/c1ccc(/C=C/C(=O)O)cc1)c1ccc2c(cnn2C(=O)C(C)C)c1)c1ccc(F)cc1Cl] | 517 |
| 405 | (E)-3-(4-((E)-2-(2-Chloro-4-fluorophenyl)-1-(1-pivaloyl-1H-indazol-5-yl)but-1-en-1-yl)phenyl)acrylic acid | 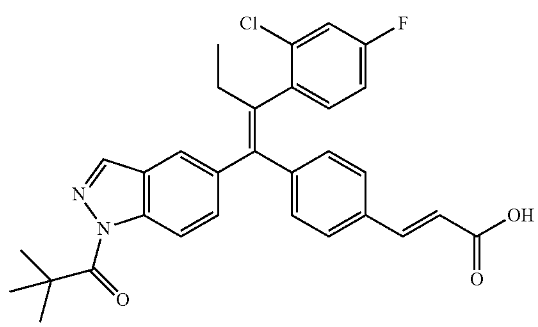 [SMILES: CC/C(=C(/c1ccc(/C=C/C(=O)O)cc1)c1ccc2c(cnn2C(=O)C(C)(C)C)c1)c1ccc(F)cc1Cl] | 531 |
| 406 | (E)-3-(4-((E)-2-(2-Chloro-4-fluorophenyl)-1-(1-(ethoxycarbonyl)-1H-indazol-5-yl)but-1-en-1-yl)phenyl)acrylic acid | 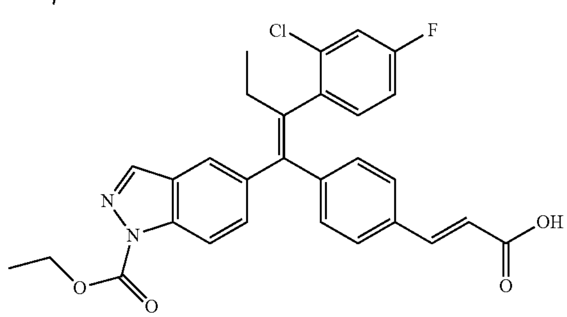 | 519 |

TABLE 1-continued

| Compound | Name | Structure | LCMS [M + H]+ |
|---|---|---|---|
| 407 | (E)-3-(4-((E)-2-(2-Chloro-4-fluorophenyl)-1-(1-(tetrahydro-2H-pyran-2-yl)-1H-indazol-5-yl)but-1-en-1-yl)phenyl)acrylic acid | 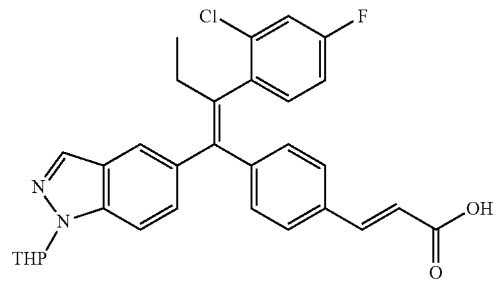 | 447 [(M − THP + H) + H]+ |
| 408 | (E)-3-(4-((E)-2-(2-Chloro-4-fluorophenyl)-1-(1H-indazol-5-yl)but-1-en-1-yl)phenyl)-N-(methylsulfonyl)acrylamide | 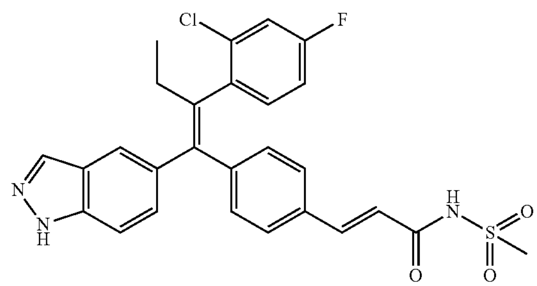 [SMILES: CC/C(=C(/c1ccc(/C=C/C(=O)NS(C)(=O)=O)cc1)c1ccc2[nH]ncc2c1)c1ccc(F)cc1Cl] | 524 |
| 409 | (E)-3-(4-((E)-2-(2-Chloro-4-fluorophenyl)-1-(1H-indazol-5-yl)but-1-en-1-yl)phenyl)-N-(propylsulfonyl)acrylamide | 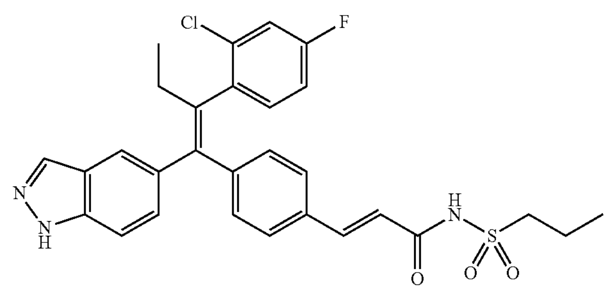 [SMILES: CCCS(=O)(=O)NC(=O)/C=C/c1ccc(/C(=C(/CC)c2ccc(F)cc2Cl)c2ccc3[nH]ncc3c2)cc1] | 552 |
| 410 | (E)-3-(4-((E)-2-(2-Chloro-4-fluorophenyl)-1-(1H-indazol-5-yl)but-1-en-1-yl)phenyl)-N-(pentylsulfonyl)acrylamide | 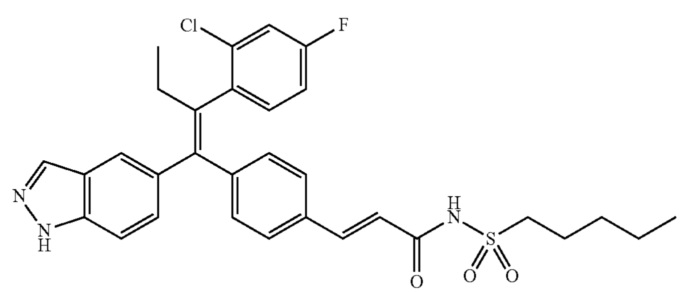 [SMILES: CCCCCS(=O)(=O)NC(=O)/C=C/c1ccc(/C(=C(/CC)c2ccc(F)cc2Cl)c2ccc3[nH]ncc3c2)cc1] | 580 |
| 411 | (E)-3-(4-((E)-2-Cyclobutyl-1-(1-methyl-1H-indazol-5-yl)-2-phenylvinyl)phenyl)-N-methylacrylamide | 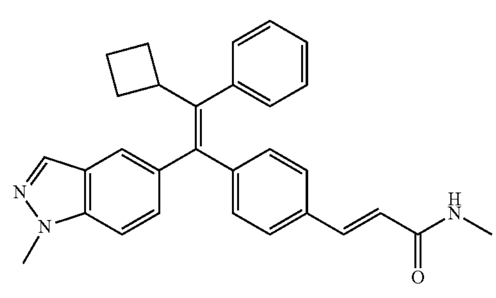 [SMILES: CNC(=O)/C=C/c1ccc(/C(=C(\c2ccccc2)C2CCC2)c2ccc3c(cnn3C)c2)cc1] | 448 |

TABLE 1-continued

| Compound | Name | Structure | LCMS [M + H]+ |
|---|---|---|---|
| 412 | (E)-3-(4-((E)-2-Cyclobutyl-1-(1H-indazol-5-yl)-2-phenylvinyl)phenyl)-N-methylacrylamide | 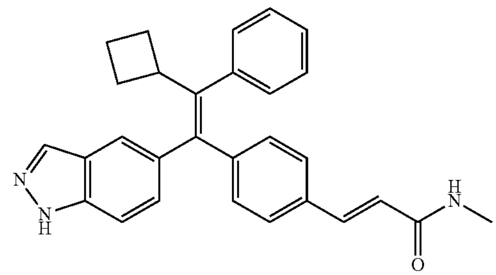 [SMILES: CNC(=O)/C=C/c1ccc(/C(=C(\c2ccccc2)C2CCC2)c2ccc3[nH]ncc3c2)cc1] | 434 |
| 413 | (E)-3-(4-((E)-2-Cyclobutyl-1-(3-fluoro-1H-indazol-5-yl)-2-phenylvinyl)phenyl)-N-cyclopropylacrylamide | 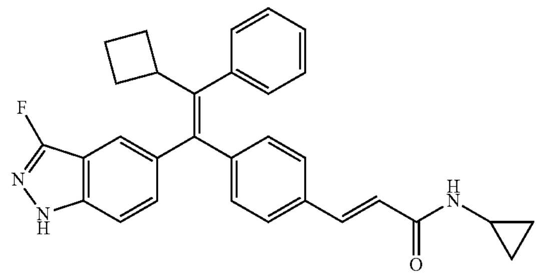 [SMILES: O=C(/C=C/c1ccc(/C(=C(\c2ccccc2)C2CCC2)c2ccc3[nH]nc(F)c3c2)cc1)NC1CC1] | 478 |
| 414 | (E)-3-(4-((E)-2-Cyclobutyl-1-(3-fluoro-1H-indazol-5-yl)-2-phenylvinyl)phenyl)-N-(2-hydroxyethyl)acrylamide | 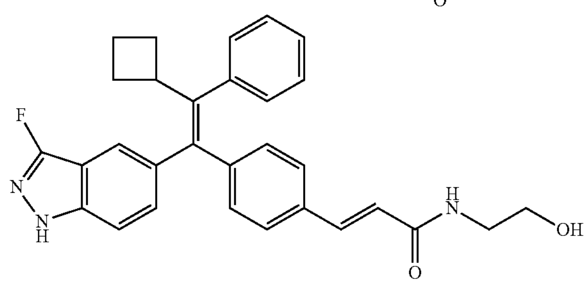 | 482 |
| 415 | (E)-3-(4-((E)-2-Cyclobutyl-1-(3-fluoro-1H-indazol-5-yl)-2-phenylvinyl)phenyl)-N-(2,2,2-trifluoroethyl)acrylamide | 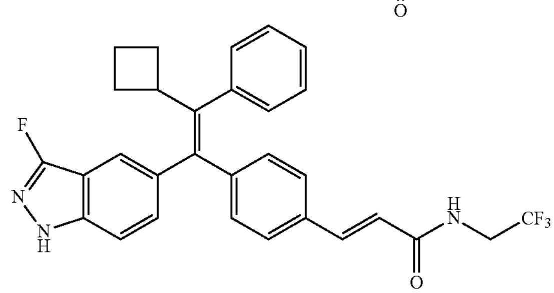 | 520 |
| 416 | (E)-3-(4-((E)-1-(Benzo[d]thiazol-5-yl)-2-(2-chloro-4-fluorophenyl)but-1-en-1-yl)phenyl)-N-(methylsulfonyl)acrylamide | 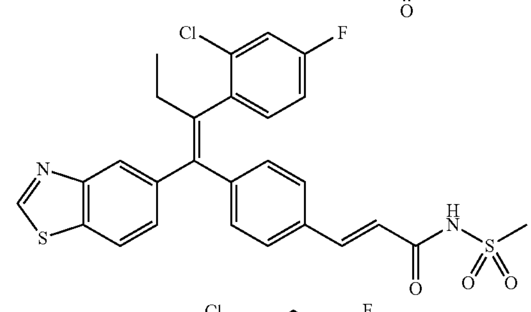 | 541 |
| 417 | (E)-3-(4-((E)-2-(2-Chloro-4-fluorophenyl)-1-(1H-indazol-5-yl)but-1-en-1-yl)phenyl)acrylamide | 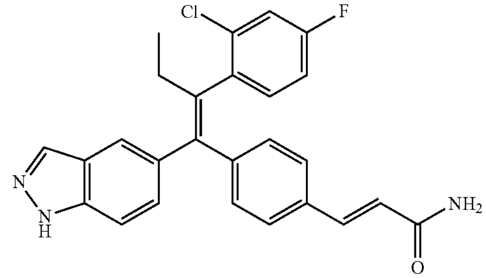 [SMILES: CC/C(=C(/c1ccc(/C=C/C(N)=O)cc1)c1ccc2[nH]ncc2c1)c1ccc(F)cc1Cl] | 446 |

TABLE 1-continued

| Compound | Name | Structure | LCMS [M + H]+ |
|---|---|---|---|
| 418 | (E)-3-(4-((E)-1-(1H-Indazol-5-yl)-2-phenylbut-1-en-1-yl)phenyl)-N-hydroxyacrylamide | 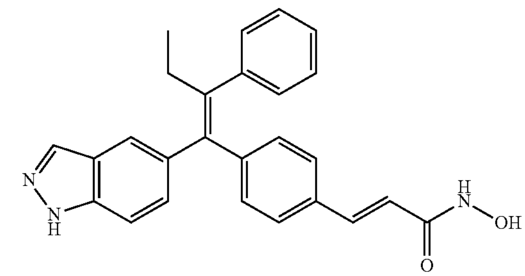 [SMILES: CC/C(=C(/c1ccc(/C=C/C(=O)NO)cc1)c1ccc2[nH]ncc2c1)c1ccccc1] | 410 |
| 419 | (E)-3-(4-((E)-1-(1H-Indazol-5-yl)-2-phenylbut-1-en-1-yl)phenyl)-N-isopropylacrylamide | 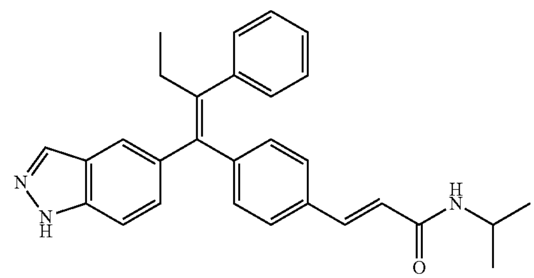 [SMILES: CC/C(=C(/c1ccc(/C=C/C(=O)NC(C)C)cc1)c1ccc2[nH]ncc2c1)c1ccccc1] | 436 |
| 420 | (E)-3-(4-((E)-2-(2-Chloro-4-fluorophenyl)-1-(1H-indazol-5-yl)but-1-en-1-yl)phenyl)-N-methylacrylamide | 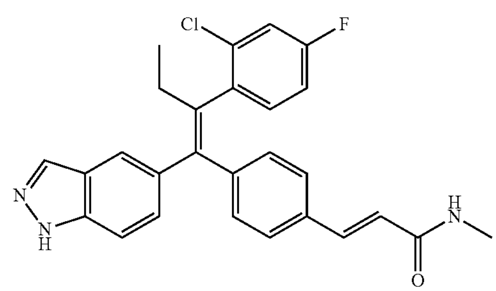 [SMILES: CC/C(=C(/c1ccc(/C=C/C(=O)NC)cc1)c1ccc2[nH]ncc2c1)c1ccc(F)cc1Cl] | 460 |
| 421 | (E)-3-(4-((E)-2-(2-Chloro-4-fluorophenyl)-1-(1H-indazol-5-yl)but-1-en-1-yl)phenyl)-N-methoxyacrylamide | 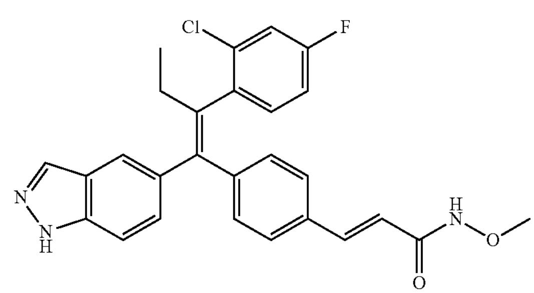 [SMILES: CC/C(=C(/c1ccc(/C=C/C(=O)NOC)cc1)c1ccc2[nH]ncc2c1)c1ccc(F)cc1Cl] | 476 |
| 422 | (E)-3-(4-((E)-2-(2-Chloro-4-fluorophenyl)-1-(1H-indazol-5-yl)but-1-en-1-yl)phenyl)-N-methoxy-N-methylacrylamide | 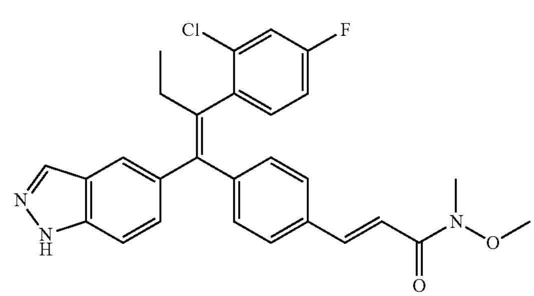 [SMILES: CC/C(=C(/c1ccc(/C=C/C(=O)N(C)OC)cc1)c1ccc2[nH]ncc2c1)c1ccc(F)cc1Cl] | 490 |

TABLE 1-continued

| Compound | Name | Structure | LCMS [M + H]+ |
|---|---|---|---|
| 423 | (E)-3-(4-((E)-1-(1H-Indazol-5-yl)-2-phenylbut-1-en-1-yl)phenyl)-N-(methylsulfonyl)acrylamide | 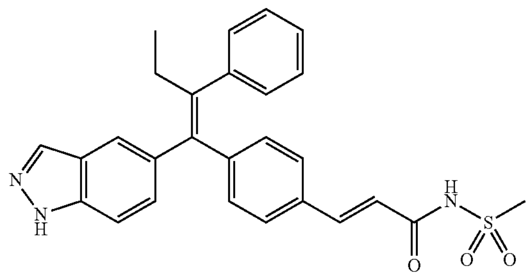 [SMILES: CC/C(=C(/c1ccc(/C=C/C(=O)NS(C)(=O)=O)cc1)c1ccc2[nH]ncc2c1)c1ccccc1] | 472 |
| 424 | (E)-3-(4-((E)-2-(2-Chloro-4-fluorophenyl)-1-(1-methyl-1H-indazol-5-yl)but-1-en-1-yl)phenyl)-N-(methylsulfonyl)acrylamide | 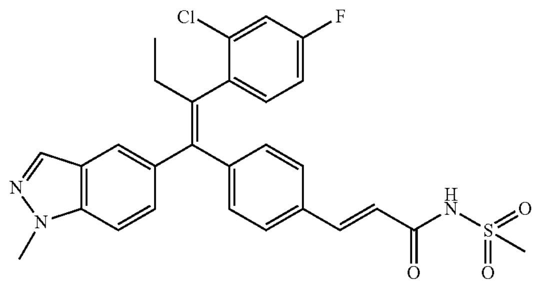 [SMILES: CC/C(=C(/c1ccc(/C=C/C(=O)NS(C)(=O)=O)cc1)c1ccc2c(cnn2C)c1)c1ccc(F)cc1Cl] | 538 |
| 425 | (E)-3-(4-((E)-2-(2-Chloro-4-fluorophenyl)-1-(1H-indazol-5-yl)but-1-en-1-yl)phenyl)-N-(2H-tetrazol-5-yl)acrylamide | 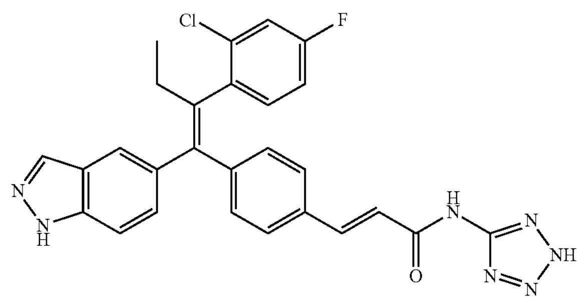 [SMILES: CC/C(=C(/c1ccc(/C=C/C(=O)Nc2nn[nH]n2)cc1)c1ccc2[nH]ncc2c1)c1ccc(F)cc1Cl] | 514 |
| 426 | (E)-3-(4-((E)-1-(Benzo[d]thiazol-5-yl)-2-phenylbut-1-en-1-yl)phenyl)acrylamide | 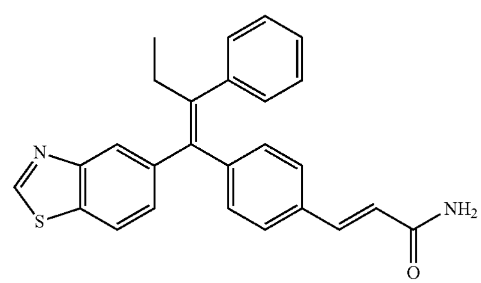 [SMILES: CC/C(=C(/c1ccc(/C=C/C(N)=O)cc1)c1ccc2scnc2c1)c1ccccc1] | 411 |
| 427 | (E)-3-(4-((E)-1-(Benzo[d]thiazol-5-yl)-2-phenylbut-1-en-1-yl)phenyl)-N-methylacrylamide | 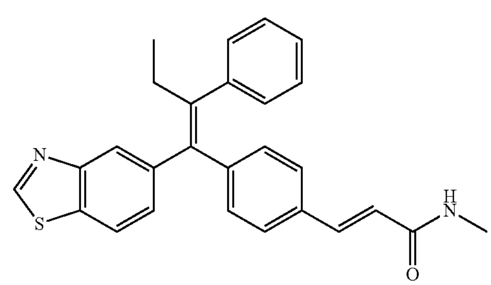 [SMILES: CC/C(=C(/c1ccc(/C=C/C(=O)NC)cc1)c1ccc2scnc2c1)c1ccccc1] | 425 |

TABLE 1-continued

| Compound | Name | Structure | LCMS [M + H]+ |
|---|---|---|---|
| 428 | (E)-3-(4-((E)-2-(2-Chloro-4-fluorophenyl)-1-(1H-indazol-5-yl)but-1-en-1-yl)phenyl)-N-(phenylsulfonyl)acrylamide | 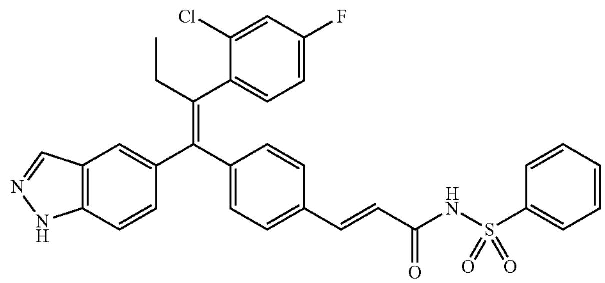 [SMILES: CC/C(=C(/c1ccc(/C=C/C(=O)NS(=O)(=O)c2ccccc2)cc1)c1ccc2[nH]ncc2c1)c1ccc(F)cc1Cl] | 586 |
| 429 | (E)-N-(Benzylsulfonyl)-3-(4-((E)-2-(2-chloro-4-fluorophenyl)-1-(1H-indazol-5-yl)but-1-en-1-yl)phenyl)acrylamide | 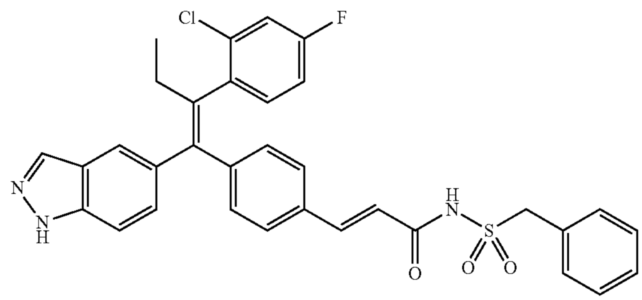 [SMILES: CC/C(=C(/c1ccc(/C=C/C(=O)NS(=O)(=O)Cc2ccccc2)cc1)c1ccc2[nH]ncc2c1)c1ccc(F)cc1Cl] | 600 |
| 430 | (E)-3-(4-((E)-1-(1H-Indazol-5-yl)-2-phenylbut-1-en-1-yl)phenyl)-N-(thiazol-2-yl)acrylamide | 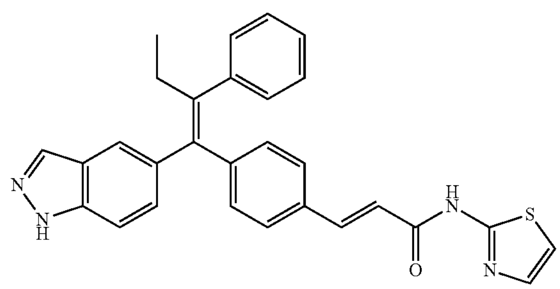 [SMILES: CC/C(=C(/c1ccc(/C=C/C(=O)Nc2nccs2)cc1)c1ccc2[nH]ncc2c1)c1ccccc1] | 477 |
| 431 | (E)-3-(4-((E)-1-(1H-Indazol-5-yl)-2-phenylbut-1-en-1-yl)phenyl)-N-cyclopentylacrylamide | 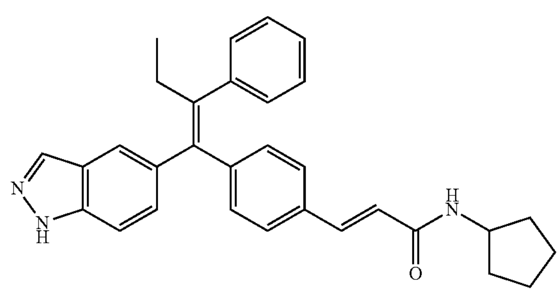 [SMILES: CC/C(=C(/c1ccc(/C=C/C(=O)NC2CCCC2)cc1)c1ccc2[nH]ncc2c1)c1ccccc1] | 462 |
| 432 | (E)-3-(4-((E)-2-(2-Chloro-4-fluorophenyl)-1-(1H-indazol-5-yl)but-1-en-1-yl)phenyl)-N-(pyridin-2-ylsulfonyl)acrylamide | 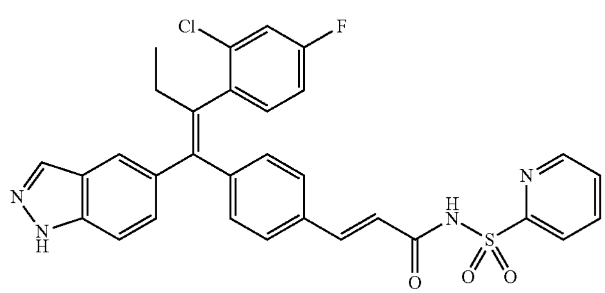 [SMILES: CC/C(=C(/c1ccc(/C=C/C(=O)NS(=O)(=O)c2ccccn2)cc1)c1ccc2[nH]ncc2c1)c1ccc(F)cc1Cl] | 587 |

TABLE 1-continued

| Compound | Name | Structure | LCMS [M + H]+ |
|---|---|---|---|
| 433 | (E)-3-(4-((E)-2-(2-Chloro-4-fluorophenyl)-1-(1H-indazol-5-yl)but-1-en-1-yl)phenyl)-N-(pyridin-3-ylsulfonyl)acrylamide | 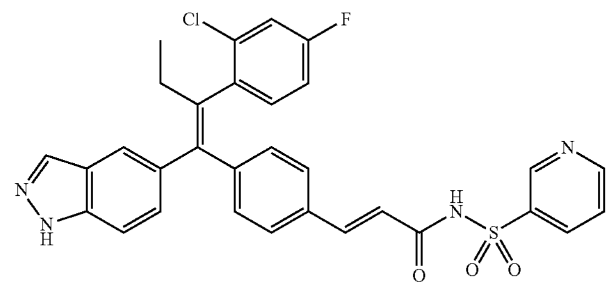 [SMILES: CC/C(=C(/c1ccc(/C=C/C(=O)NS(=O)(=O)c2cccnc2)cc1)c1ccc2[nH]ncc2c1)c1ccc(F)cc1Cl] | 587 |
| 434 | (E)-3-(4-((E)-2-(2-Chloro-4-fluorophenyl)-1-(1H-indazol-5-yl)but-1-en-1-yl)phenyl)-N-(pyridin-4-ylsulfonyl)acrylamide | 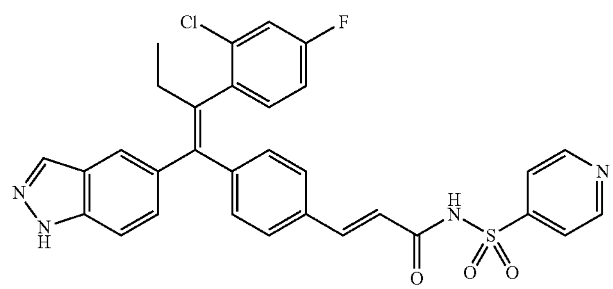 [SMILES: CC/C(=C(/c1ccc(/C=C/C(=O)NS(=O)(=O)c2ccncc2)cc1)c1ccc2[nH]ncc2c1)c1ccc(F)cc1Cl] | 587 |
| 435 | 3-((E)-4-((E)-1-(1H-Indazol-5-yl)-2-phenylbut-1-en-1-yl)styryl)-1,2,4-oxadiazol-5(4H)-one | 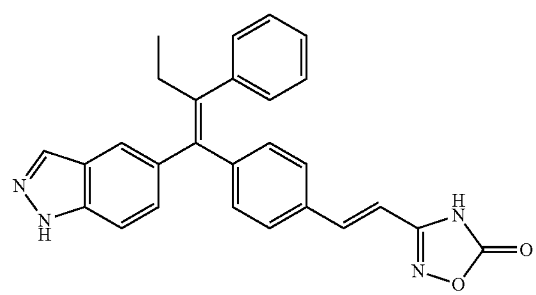 [SMILES: CC/C(=C(/c1ccc(/C=C/c2noc(=O)[nH]2)cc1)c1ccc2[nH]ncc2c1)c1ccccc1] | 435 |
| 436 | 3-((E)-4-((E)-1-(Benzo[d]thiazol-5-yl)-2-(2-chloro-4-fluorophenyl)but-1-en-1-yl)styryl)-1,2,4-oxadiazol-5(4H)-one | 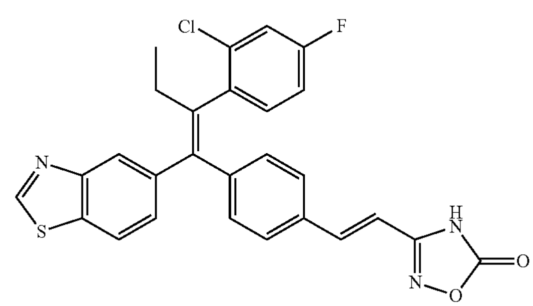 [SMILES: CC/C(=C(/c1ccc(/C=C/c2noc(=O)[nH]2)cc1)c1ccc2scnc2c1)c1ccc(F)cc1Cl] | 504 |
| 437 | 3-((E)-4-((E)-2-(2-Chloro-4-fluorophenyl)-1-(1H-indazol-5-yl)but-1-en-1-yl)styryl)-1,2,4-oxadiazol-5(4H)-one | 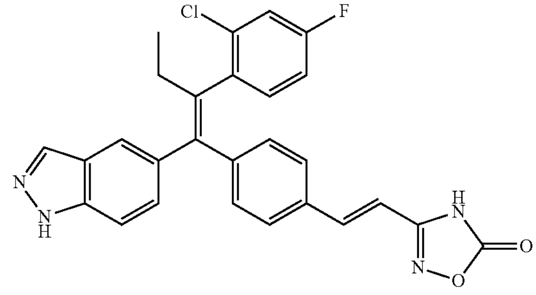 | 487 |

TABLE 1-continued

| Compound | Name | Structure | LCMS [M + H]+ |
|---|---|---|---|
| 438 | 3-((E)-4-((E)-1-(1H-Indazol-5-yl)-2-phenylbut-1-en-1-yl)styryl)-1,2,4-thiadiazol-5(4H)-one | 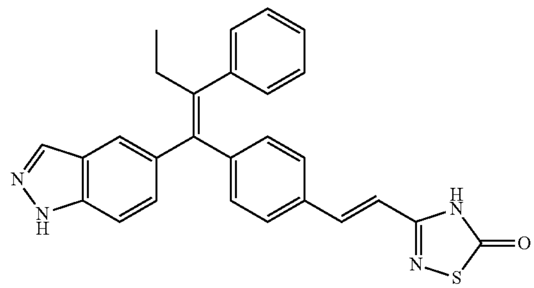 [SMILES: CC/C(=C(/c1ccc(/C=C/c2nsc(=O)[nH]2)cc1)c1ccc2[nH]ncc2c1)c1ccccc1] | 451 |
| 439 | 3-((E)-4-((E)-2-(2-Chloro-4-fluorophenyl)-1-(1H-indazol-5-yl)but-1-en-1-yl)styryl)-1,2,4-thiadiazol-5(4H)-one | 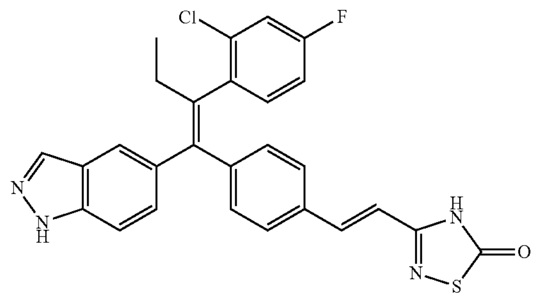 [SMILES: CC/C(=C(/c1ccc(/C=C/c2nsc(=O)[nH]2)cc1)c1ccc2[nH]ncc2c1)c1ccc(F)cc1Cl] | 503 |
| 440 | 3-((E)-4-((E)-1-(1H-Indazol-5-yl)-2-phenylbut-1-en-1-yl)styryl)-1,2,4-oxadiazole-5(4H)-thione | 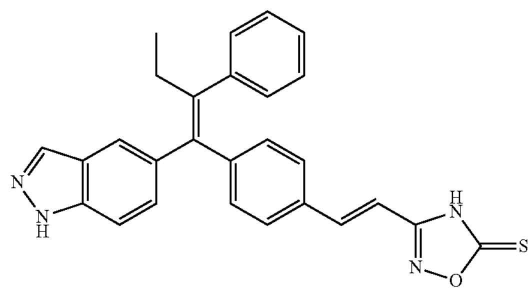 [SMILES: CC/C(=C(/c1ccc(/C=C/c2noc(=S)[nH]2)cc1)c1ccc2[nH]ncc2c1)c1ccccc1] | 451 |
| 441 | 3-((E)-4-((E)-2-(2-Chloro-4-fluorophenyl)-1-(1H-indazol-5-yl)but-1-en-1-yl)styryl)-1,2,4-oxadiazole-5(4H)-thione | 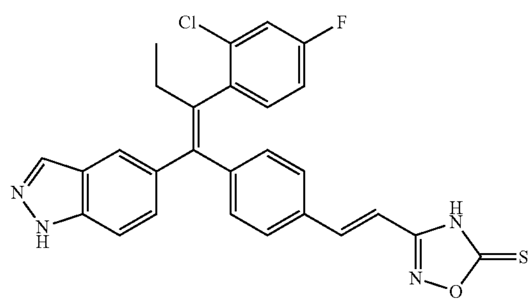 [SMILES: CC/C(=C(/c1ccc(/C=C/c2noc(=S)[nH]2)cc1)c1ccc2[nH]ncc2c1)c1ccc(F)cc1Cl] | 503 |
| 442 | 5-((E)-1-(4-((E)-2-(2H-Tetrazol-5-yl)vinyl)phenyl)-2-phenylbut-1-en-1-yl)-1H-indazole | 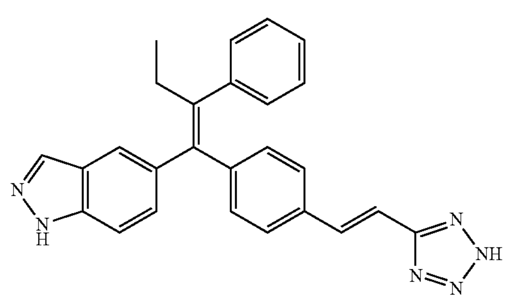 [SMILES: CC/C(=C(/c1ccc(/C=C/c2nn[nH]n2)cc1)c1ccc2[nH]ncc2c1)c1ccccc1] | 419 |

TABLE 1-continued

| Compound | Name | Structure | LCMS [M + H]+ |
|---|---|---|---|
| 443 | 5-((E)-1-(4-((E)-2-(2H-Tetrazol-5-yl)vinyl)phenyl)-2-(2-chlorophenyl)but-1-en-1-yl)-1H-indazole | 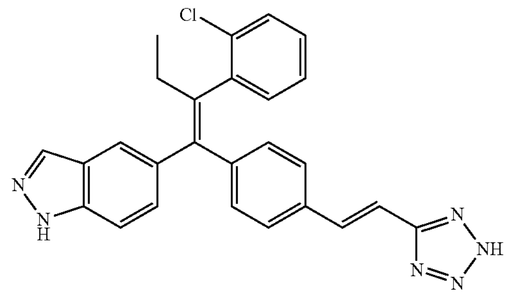 [SMILES: CC/C(=C(/c1ccc(/C=C/c2nn[nH]n2)cc1)c1ccc2[nH]ncc2c1)c1ccccc1Cl] | 453 |
| 444 | 5-((E)-1-(4-((E)-2-(2H-Tetrazol-5-yl)vinyl)phenyl)-2-phenylbut-1-en-1-yl)benzo[d]thiazole | 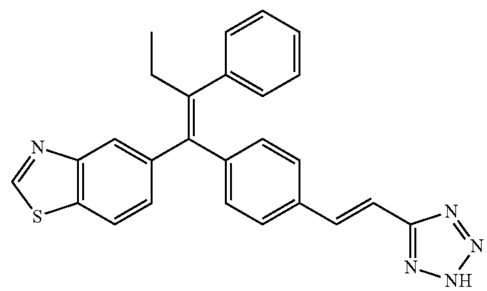 [SMILES: CC/C(=C(/c1ccc(/C=C/c2nn[nH]n2)cc1)c1ccc2scnc2c1)c1ccccc1] | 436 |
| 445 | 5-((E)-1-(4-((E)-2-(2H-Tetrazol-5-yl)vinyl)phenyl)-2-(2-chloro-4-fluorophenyl)but-1-en-1-yl)benzo[d]thiazole | 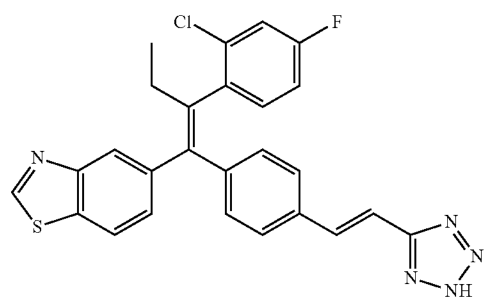 [SMILES: CC/C(=C(/c1ccc(/C=C/c2nn[nH]n2)cc1)c1ccc2scnc2c1)c1ccc(F)cc1Cl] | 488 |
| 446 | 5-((E)-1-(4-((E)-2-(2H-Tetrazol-5-yl)vinyl)phenyl)-2-(3-chloropyridin-4-yl)but-1-en-1-yl)benzo[d]thiazole | 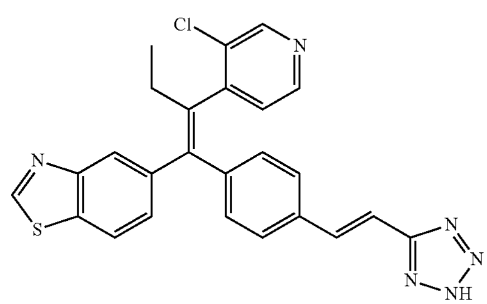 [SMILES: CC/C(=C(/c1ccc(/C=C/c2nn[nH]n2)cc1)c1ccc2scnc2c1)c1ccncc1Cl] | 471 |
| 447 | 5-((E)-1-(4-((E)-2-(2H-Tetrazol-5-yl)vinyl)phenyl)-2-(4-methylthiophen-3-yl)but-1-en-1-yl)benzo[d]thiazole | 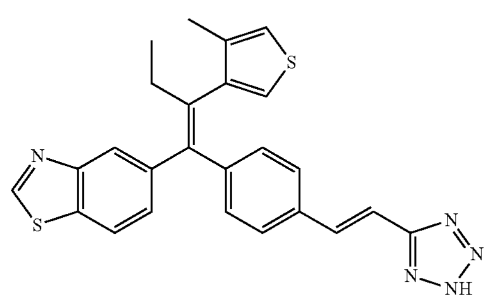 [SMILES: CC/C(=C(/c1ccc(/C=C/c2nn[nH]n2)cc1)c1ccc2scnc2c1)c1cscc1C] | 456 |

TABLE 1-continued

| Compound | Name | Structure | LCMS [M + H]+ |
|---|---|---|---|
| 448 | 5-((E)-1-(4-((E)-2-(2H-Tetrazol-5-yl)vinyl)phenyl)-2-cyclobutyl-2-(4-methylthiophen-3-yl)vinyl)benzo[d]thiazole | 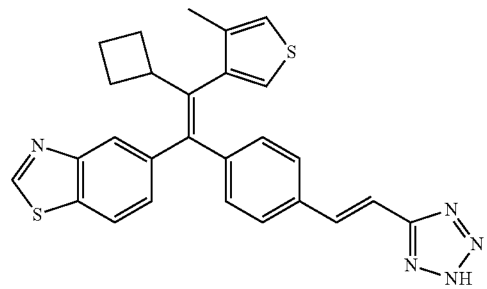 [SMILES: Cc1cscc1/C(=C(\c1ccc(/C=C/c2nn[nH]n2)cc1)c1ccc2scnc2c1)C1CCC1] | 482 |
| 449 | (E)-6-(1-(1H-Indazol-5-yl)-2-phenylbut-1-en-1-yl)-2-naphthoic acid | 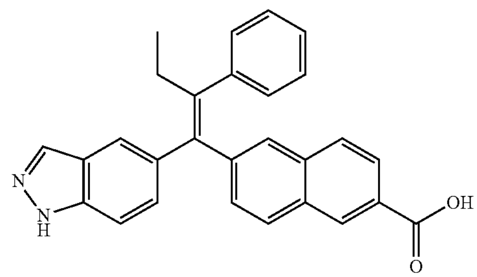 [SMILES: CC/C(=C(/c1ccc2cc(C(=O)O)ccc2c1)c1ccc2[nH]ncc2c1)c1ccccc1] | 419 |
| 450 | (E)-3-(4-((E)-2-(2-Chloro-4-fluorophenyl)-1-(7-hydroxybenzofuran-3-yl)but-1-en-1-yl)phenyl)acrylic acid | 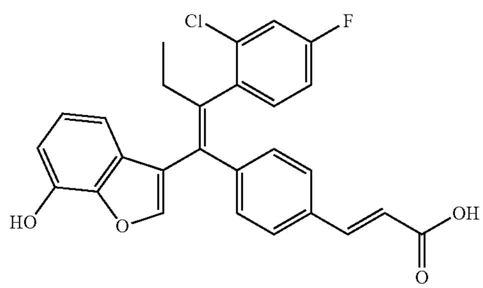 [SMILES: CC/C(=C(/c1ccc(/C=C/C(=O)O)cc1)c1coc2c(O)cccc12)c1ccc(F)cc1Cl] | 463 |
| 451 | (E)-3-(4-((E)-1-(7-Hydroxybenzofuran-3-yl)-2-phenylbut-1-en-1-yl)phenyl)acrylic acid | 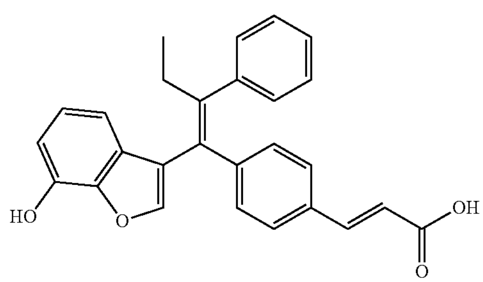 [SMILES: CC/C(=C(/c1ccc(/C=C/C(=O)O)cc1)c1coc2c(O)cccc12)c1ccccc1] | 411 |
| 452 | (E)-2-(4-((E)-1-(1H-Indazol-5-yl)-2-phenylbut-1-en-1-yl)phenyl)ethenesulfonamide | 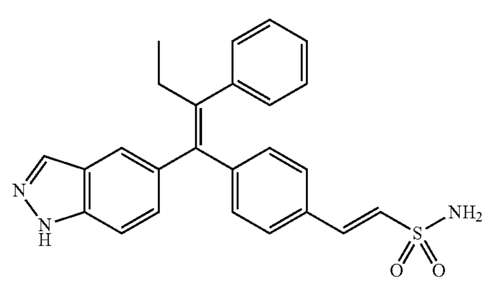 [SMILES: CC/C(=C(/c1ccc(/C=C/S(N)(=O)=O)cc1)c1ccc2[nH]ncc2c1)c1ccccc1] | 430 |

TABLE 1-continued

| Compound | Name | Structure | LCMS [M + H]+ |
|---|---|---|---|
| 453 | 4-((E)-1-(4-((E)-2-Carboxyvinyl)phenyl)-1-(7-fluoro-1H-indazol-5-yl)but-1-en-2-yl)-3-chloropyridine-1-oxide | 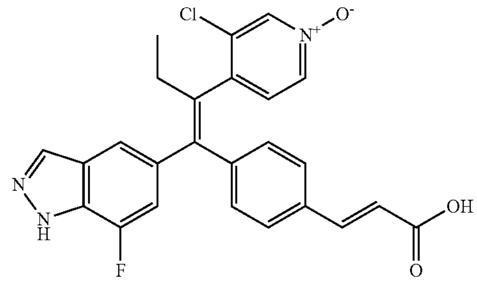 [SMILES: CC/C(=C(/c1ccc(/C=C/C(=O)O)cc1)c1cc(F)c2[nH]ncc2c1)c1cc[n+]([O-])cc1Cl] | 464 |

In some embodiments, there are provided methods of treating an estrogen receptor dependent or estrogen receptor mediated disease or condition in mammal comprising administering to the mammal a therapeutically effective amount of a compound of Formula (I), or a pharmaceutically acceptable salt thereof. In certain embodiments, the estrogen receptor dependent or estrogen receptor mediated disease or condition is selected from cancer, central nervous system (CNS) defects, cardiovascular system defects, hematological system defects, immune and inflammation diseases, susceptibility to infection, metabolic defects, neurological defects, psychiatric defects and reproductive defects. In some embodiments, the estrogen receptor dependent or estrogen receptor mediated disease or condition is selected from bone cancer, breast cancer, colorectal cancer, endometrial cancer, prostate cancer, ovarian cancer, uterine cancer, alcoholism, migraine, aortic aneurysm, susceptibility to myocardial infarction, aortic valve sclerosis, cardiovascular disease, coronary artery disease, hypertension, deep vein thrombosis, Graves' Disease, arthritis, multiple sclerosis, cirrhosis, hepatitis B, chronic liver disease, bone density, cholestasis, hypospadias, obesity, osteoarthritis, osteopenia, osteoporosis, Alzheimer's disease, Parkinson's disease, migraine, vertigo, anorexia nervosa, attention deficit hyperactivity disorder (ADHD), dementia, major depressive disorder, psychosis, age of menarche, endometriosis, and infertility. In some embodiments, the methods further comprise administering to the mammal radiation therapy. In certain embodiments, the compound of the methods is administered prior to or following surgery. In certain embodiments, the methods comprise administering to the mammal at least one additional anti-cancer agent.

In some embodiments, there are provided methods of treating cancer in a mammal comprising administering to the mammal a therapeutically effective amount of a compound of Formula (I), or a pharmaceutically acceptable salt thereof. In certain embodiments, the cancer is breast cancer, ovarian cancer, endometrial cancer, prostate cancer, or uterine cancer. In certain embodiments, the cancer is breast cancer. In certain embodiments, the cancer is a hormone dependent cancer. In certain embodiments, the cancer is an estrogen receptor dependent cancer. In certain embodiments, the cancer is an estrogen-sensitive cancer. In certain embodiments, the cancer is resistant to anti-hormonal treatment. In certain embodiments, the cancer is an estrogen-sensitive cancer or an estrogen receptor dependent cancer that is resistant to anti-hormonal treatment. In some embodiments, the anti-hormonal treatment includes treatment with at least one agent selected from tamoxifen, fulvestrant, steroidal aromatase inhibitors, and non-steroidal aromatase inhibitors. In some embodiments, the methods further comprise administering to the mammal radiation therapy. In certain embodiments, the compound of the methods is administered prior to or following surgery. In certain embodiments, the methods comprise administering to the mammal at least one additional anti-cancer agent.

In some embodiments, there are provided methods of treating hormone receptor positive metastatic breast cancer in a postmenopausal woman with disease progression following anti-estrogen therapy comprising administering to the woman an estrogen receptor degrading compound of Formula (I), or a pharmaceutically acceptable salt thereof. In some embodiments, the methods further comprise administering to the mammal radiation therapy. In certain embodiments, the compound of the methods is administered prior to or following surgery. In certain embodiments, the methods comprise administering to the mammal at least one additional anti-cancer agent.

In some embodiments, there are provided methods of treating a hormonal dependent benign or malignant disease of the breast or reproductive tract in a mammal comprising administering to the mammal an effective amount of a compound of Formula (I), or a pharmaceutically acceptable salt thereof. In certain embodiments, the benign or malignant disease is breast cancer. In some embodiments, the methods further comprise administering to the mammal radiation therapy. In certain embodiments, the compound of the methods is administered prior to or following surgery. In certain embodiments, the methods comprise administering to the mammal at least one additional anti-cancer agent.

In some embodiments, these methods further comprise administering to the mammal at least one additional therapeutic agent selected from abiraterone; abarelix; adriamycin; aactinomycin; acivicin; aclarubicin; acodazole hydrochloride; acronine; adozelesin; aldesleukin; alemtuzumab; allopurinol; alitretinoin; altretamine; ambomycin; ametantrone acetate; aminoglutethimide; aminolevulinic acid; amifostine; amsacrine; anastrozole; anthramycin; aprepitant; arsenic trioxide; asparaginase; asperlin; azacitidine; azetepa; azotomycin; batimastat; bendamustine hydrochloride; benzodepa; bevacizumab; bexarotene; bicalutamide; bisantrene hydrochloride; bisnafide dimesylate; bizelesin; bleomycin; bleomycin sulfate; bortezomib; brequinar sodium; bropirimine; busulfan; cactinomycin; calusterone; caracemide; carbetimer; carboplatin; carmustine; carubicin hydrochloride; carzelesin; capecitabine; cedefingol; cetuximab; chlorambucil; cirolemycin; cisplatin; cladribine; clofarabine; crisnatol mesylate; cyclophosphamide; cytarabine; dacarbazine; dasatinib; daunorubicin hydrochloride; dactinomycin; darbepoetin alfa; decitabine; degarelix; denileukin diftitox; dexormaplatin; dexrazoxane hydrochloride; dezaguanine; dezaguanine mesylate; diaziquone; docetaxel; doxorubicin; doxorubicin hydrochloride; droloxifene; droloxifene citrate;

dromostanolone propionate; duazomycin; edatrexate; eflornithine hydrochloride; elsamitrucin; eltrombopag olamine; enloplatin; enpromate; epipropidine; epirubicin hydrochloride; epoetin alfa; erbulozole; erlotinib hydrochloride; esorubicin hydrochloride; estramustine; estramustine phosphate sodium; etanidazole; etoposide; etoposide phosphate; etoprine; everolimus; exemestane; fadrozole hydrochloride; fazarabine; fenretinide; filgrastim; floxuridine; fludarabine phosphate; fluorouracil; flurocitabine; fosquidone; fostriecin sodium; fulvestrant; gefitinib; gemcitabine; gemcitabine hydrochloride; gemcitabine-cisplatin; gemtuzumab ozogamicin; goserelin acetate; histrelin acetate; hydroxyurea; idarubicin hydrochloride; ifosfamide; iimofosine; ibritumomab tiuxetan; idarubicin; ifosfamide; imatinib mesylate; imiquimod; interleukin II (including recombinant interleukin II, or rIL2), interferon alfa-2a; interferon alfa-2b; interferon alfa-n1; interferon alfa-n3; interferon beta-1 a; interferon gamma-1 b; iproplatin; irinotecan hydrochloride; ixabepilone; lanreotide acetate; lapatinib; lenalidomide; letrozole; leuprolide acetate; leucovorin calcium; leuprolide acetate; levamisole; liposomal cytarabine; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; methoxsalen; metoprine; meturedepa; mitindomide; mitocarcin; mitocromin; mitogillin; mitomalcin; mitomycin C; mitosper; mitotane; mitoxantrone hydrochloride; mycophenolic acid; nandrolone phenpropionate; nelarabine; nilotinib; nocodazoie; nofetumomab; nogalamycin; ofatumumab; oprelvekin; ormaplatin; oxaliplatin; oxisuran; paclitaxel; palifermin; palonosetron hydrochloride; pamidronate; pegfilgrastim; pemetrexed disodium; pentostatin; panitumumab; pazopanib hydrochloride; pemetrexed disodium; plerixafor; pralatrexate; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; quinacrine; raloxifene hydrochloride; rasburicase; recombinant HPV bivalent vaccine; recombinant HPV quadrivalent vaccine; riboprine; rogletimide; rituximab; romidepsin; romiplostim; safingol; safingol hydrochloride; sargramostim; semustine; simtrazene; sipuleucel-T; sorafenib; sparfosate sodium; sparsomycin; spirogermanium hydrochloride; spiromustine; spiroplatin; streptonigrin; streptozocin; sulofenur; sunitinib malate; talisomycin; tamoxifen citrate; tecogalan sodium; tegafur; teloxantrone hydrochloride; temozolomide; temoporfin; temsirolimus; teniposide; teroxirone; testolactone; thalidomide; thiamiprine; thioguanine; thiotepa; tiazofurin; tirapazamine; topotecan hydrochloride; toremifene; tositumomab; tositumomab and I 131 Iodine tositumomab; trastuzumab; trestolone acetate; tretinoin; triciribine phosphate; trimetrexate; trimetrexate glucuronate; triptorelin; tubulozole hydrochloride; uracil mustard; uredepa; valrubicin; vapreotide; verteporfin; vinblastine; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorinostat; vorozole; zeniplatin; zinostatin; zoledronic acid; and zorubicin hydrochloride.

Any combination of the groups described above for the various variables is contemplated herein. Throughout the specification, groups and substituents thereof are chosen by one skilled in the field to provide stable moieties and compounds.

Synthesis of Compounds

Compounds of Formula (I) described herein are synthesized using standard synthetic techniques or using methods known in the art in combination with methods described herein. In additions, solvents, temperatures and other reaction conditions presented herein may vary.

The starting material used for the synthesis of the compounds of Formula (I) are either synthesized or obtained from commercial sources, such as, but not limited to, Sigma-Aldrich, Fluka, Acros Organics, Alfa Aesar, and the like. The compounds described herein, and other related compounds having different substituents are synthesized using techniques and materials described herein or otherwise known, including those found in March, ADVANCED ORGANIC CHEMISTRY 4th Ed., (Wiley 1992); Carey and Sundberg, ADVANCED ORGANIC CHEMISTRY 4th Ed., Vols. A and B (Plenum 2000, 2001), and Green and Wuts, PROTECTIVE GROUPS IN ORGANIC SYNTHESIS 3rd Ed., (Wiley 1999). General methods for the preparation of compounds is optionally modified by the use of appropriate reagents and conditions for the introduction of the various moieties found in the formulae as provided herein.

In some embodiments, exemplary compounds of Formula (I) are prepared as outlined in the following Schemes.

Scheme 1:

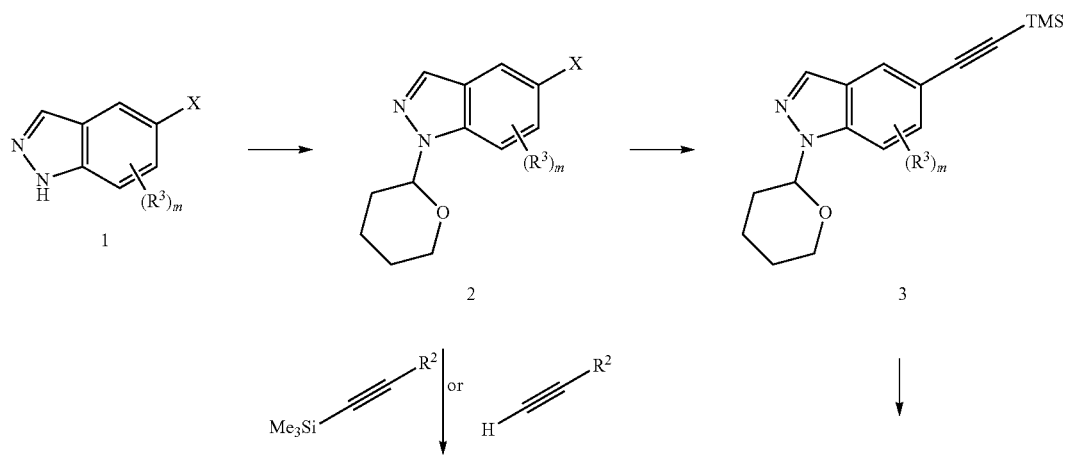

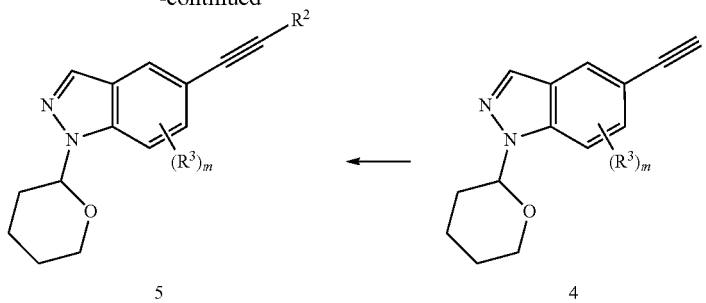

Protection of the acidic proton bearing nitrogen of compounds of Structure 1 with a protecting group provides compounds of Structure 2. In some embodiments, the protecting group is tetrahydropyran (THP). In some embodiments, the conditions for nitrogen protection require dihydropyran (DHP), an organic acid and a suitable solvent. In some embodiments, the organic acid is pyridinium p-toluenesulfonate (PPTS), and the suitable solvent is dicloromethane. In some embodiments, the reaction is performed at room temperature. Other conditions to protect the nitrogen of the starting material include the use of sodium hydride, p-methoxybenzyl chloride (PMBCl) in dimethylsulfoxide (DMSO). Yet other conditions to protect the nitrogen of the starting material include the use of p-methoxybenzyl alcohol (PMBOH), sulfuric acid, and toluene with the reaction performed at about 110° C. Other conditions to protect the nitrogen of the starting material are known and include protecting groups such as, but not limited to, methoxymethyl ether (MOM), tert-butyloxycarbonyl (BOC), acetyl (Ac), or triphenylmethyl (trityl). A detailed description of techniques applicable to the creation of protecting groups and their removal are described in Greene and Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure.

Compounds of Structure 2, where X is a halogen or other suitable leaving group, are reacted with a protected acetylene (e.g., trimethylsilylacetylene) under Sonagashira reaction conditions to provide compounds of Structure 3. In some embodiments, the Sonagashira coupling reaction conditions include the use of a palladium catalyst and a copper halide salt. In some embodiments, the Sonagashira reaction conditions in the use of $Pd(Ph_3P)_2Cl_2$, CuI, and triethylamine. In one embodiment, the reaction is performed at about 80° C. Other suitable reaction conditions are described in Rafael Chinchilla and Carmen Nájera (2007). Chem. Rev. 107 (3): 874-922.

The silyl protecting group of compounds of Structure 3 is removed under suitable reaction conditions to provide compounds of Structure 4. In some embodiments, the silyl protecting group is removed with potassium carbonate ($K_2CO_3$) in methanol. In other embodiments, the silyl protecting group is removed with tetrabutylammoniumfluoride (TBAF) in tetrahydrofuran.

In some embodiments, acetylenes of Structure 4 are reacted with $R^2$—X under basic condition to prepare compounds of Structure 5. In these instances, $R^2$ is $C_1$-$C_6$alkyl or $C_1$-$C_6$fluoroalkyl or $C_1$-$C_4$alkoxy or $C_1$-$C_4$fluoroalkoxy or $C_3$-$C_6$cycloalkyl, or the like, and X is a suitable leaving group. In some embodiments, $R^2$ moieties (such as halogen, CN, $NO_2$, —$SR^9$, —$S(=O)R^{10}$, —$S(=O)_2R^{10}$, —NHS$(=O)_2R^{10}$) are installed by other suitable conditions.

In some embodiments, compounds of Structure 2 are coupled with an alkynyl-trimethylsilane or a terminal-alkyne under Sonogashira reaction conditions to provide compounds of Structure 5. In some embodiments, the coupling of an alkynyl-trimethylsilane with compounds of Structure 2 includes the use of a base (e.g. cesium carbonate), a palladium catalyst (e.g. $Pd(OAc)_2$, dppf) and a copper halide salt (e.g. CuI) in a suitable solvent (e.g. dimethylacetamide) at elevated temperatures (e.g. about 80-90° C.). In some embodiments, the coupling of a terminal-alkyne with compounds of Structure 2 includes the use of $Pd(PPh_3)_2Cl_2$), CuI, and triethylamine with the reaction performed with at elevated temperatures (e.g. about 80-120° C.).

Scheme 2.

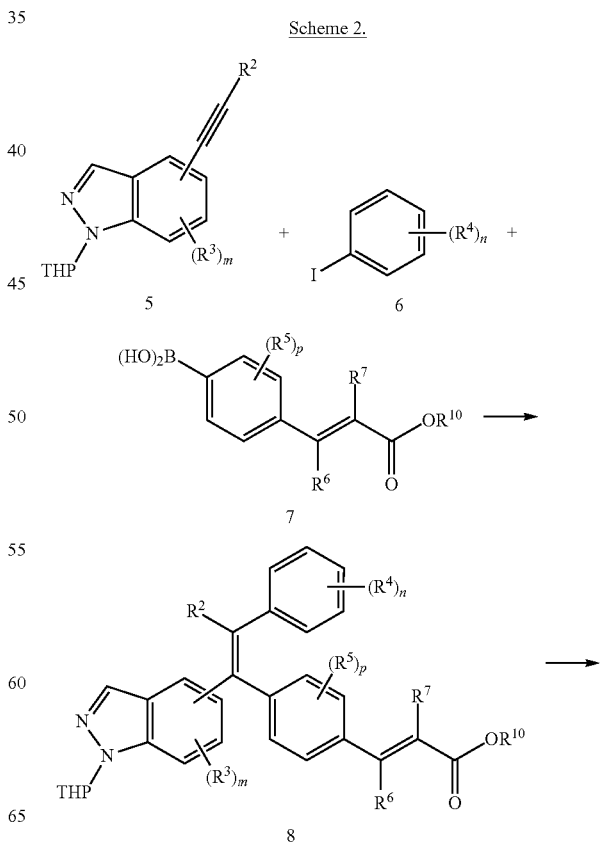

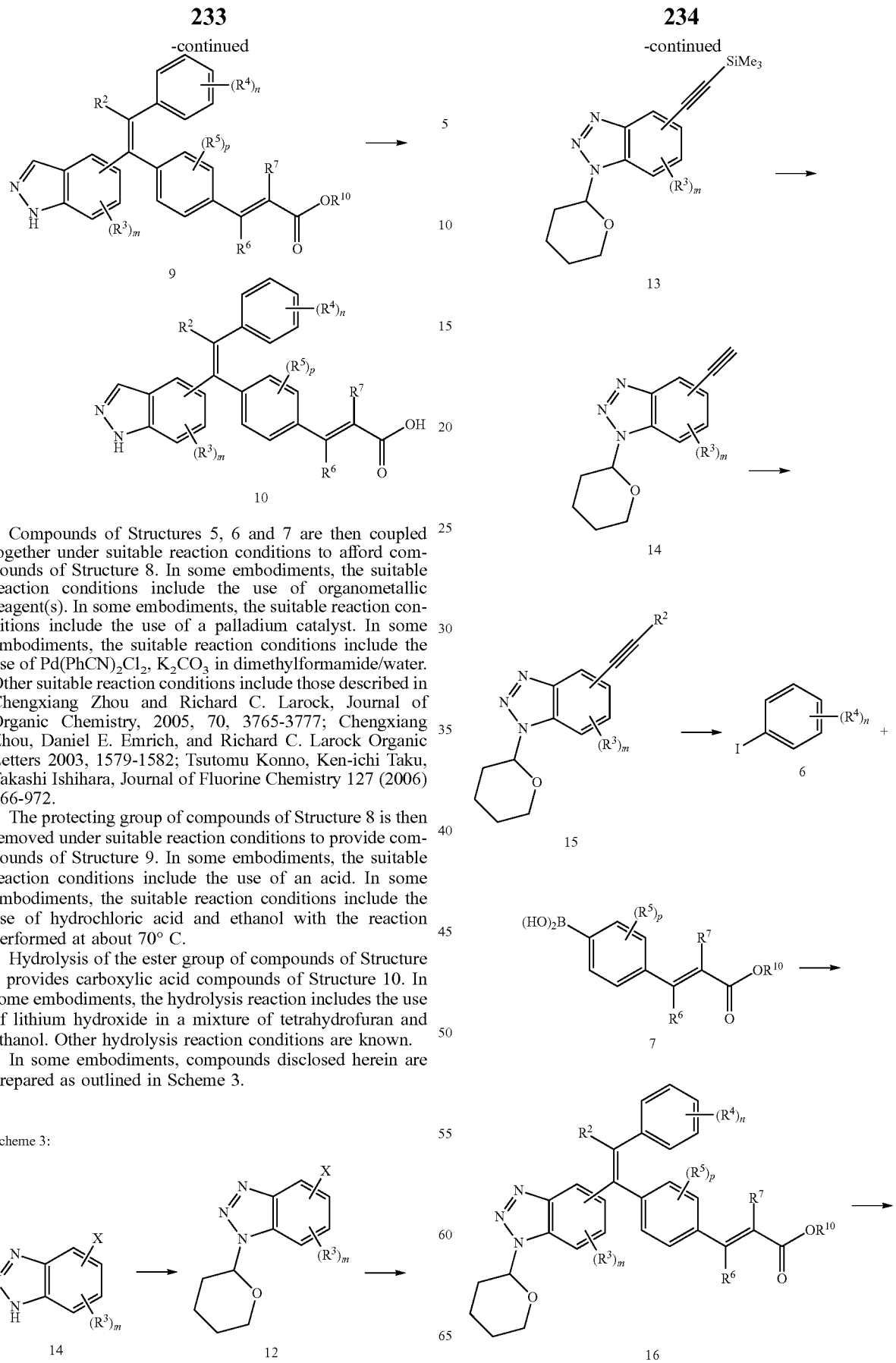

Compounds of Structures 5, 6 and 7 are then coupled together under suitable reaction conditions to afford compounds of Structure 8. In some embodiments, the suitable reaction conditions include the use of organometallic reagent(s). In some embodiments, the suitable reaction conditions include the use of a palladium catalyst. In some embodiments, the suitable reaction conditions include the use of $Pd(PhCN)_2Cl_2$, $K_2CO_3$ in dimethylformamide/water. Other suitable reaction conditions include those described in Chengxiang Zhou and Richard C. Larock, Journal of Organic Chemistry, 2005, 70, 3765-3777; Chengxiang Zhou, Daniel E. Emrich, and Richard C. Larock Organic Letters 2003, 1579-1582; Tsutomu Konno, Ken-ichi Taku, Takashi Ishihara, Journal of Fluorine Chemistry 127 (2006) 966-972.

The protecting group of compounds of Structure 8 is then removed under suitable reaction conditions to provide compounds of Structure 9. In some embodiments, the suitable reaction conditions include the use of an acid. In some embodiments, the suitable reaction conditions include the use of hydrochloric acid and ethanol with the reaction performed at about 70° C.

Hydrolysis of the ester group of compounds of Structure 9 provides carboxylic acid compounds of Structure 10. In some embodiments, the hydrolysis reaction includes the use of lithium hydroxide in a mixture of tetrahydrofuran and ethanol. Other hydrolysis reaction conditions are known.

In some embodiments, compounds disclosed herein are prepared as outlined in Scheme 3.

Scheme 3:

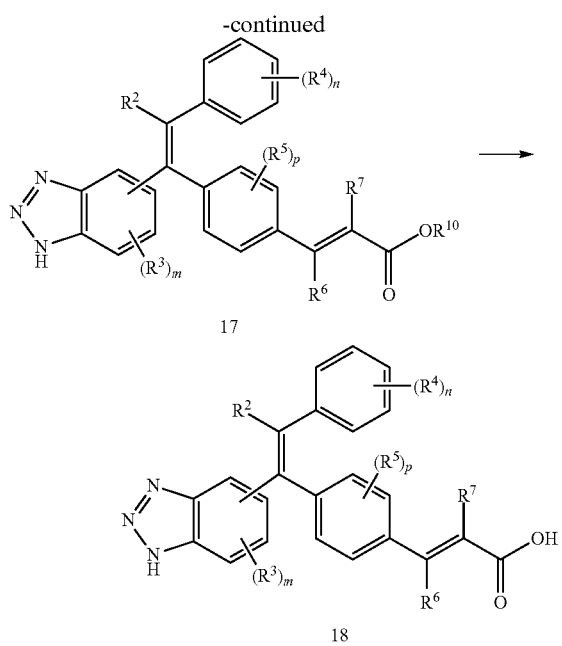

In some embodiments, the reaction conditions for the steps described in Scheme 3 are as described for Scheme 1 and Scheme 2.

In some embodiments, compounds disclosed herein are prepared as outlined in Scheme 4.

In some embodiments, compounds of Structure 5 are reacted with phenyl halides of Structure 6 and boronic acids of Structure 21 under suitable reaction conditions to provide compounds of Structure 22. In some embodiments, the suitable reaction conditions include the use of organometallic reagent(s). In some embodiments, the suitable organometallic reagent is a palladium catalyst. The aldehyde of compounds of Structure 22 is then transformed to an alkene under suitable reaction conditions to provide compounds of Structure 8. Suitable reaction conditions include a Horner-Wadsworth-Emmons olefination reaction or a Wittig olefination reaction conditions.

Alternatively, compounds of Structure 5 are reacted with a borylating agent in the presence of a suitable catalyst to provide compounds of Structure 24. In some embodiments, the suitable catalyst is an organometallic reagent such as a platinum catalyst. In some embodiments, the amount of catalyst impacts the rate of the reaction, but generally, not the yield or purity. In some embodiments, the solvent has a small impact on the rate of the reaction, but generally, not the yield or purity. In some embodiments, the temperature has a significant impact on the rate of the reaction, but generally, not the yield or purity. A Suzuki cross-coupling is then performed with compounds of Structure 24 and phenyl halides of Structure 25 to provide compounds of Structure 26. In some embodiments, 2 or 3 equivalents of base (e.g. $Cs_2CO_3$) are used in the Suzuki cross-coupling. In some embodiments, 1.3 equivalents of base (e.g. $Cs_2CO_3$) are used in the Suzuki cross-coupling. In some embodiments, Scheme 4.

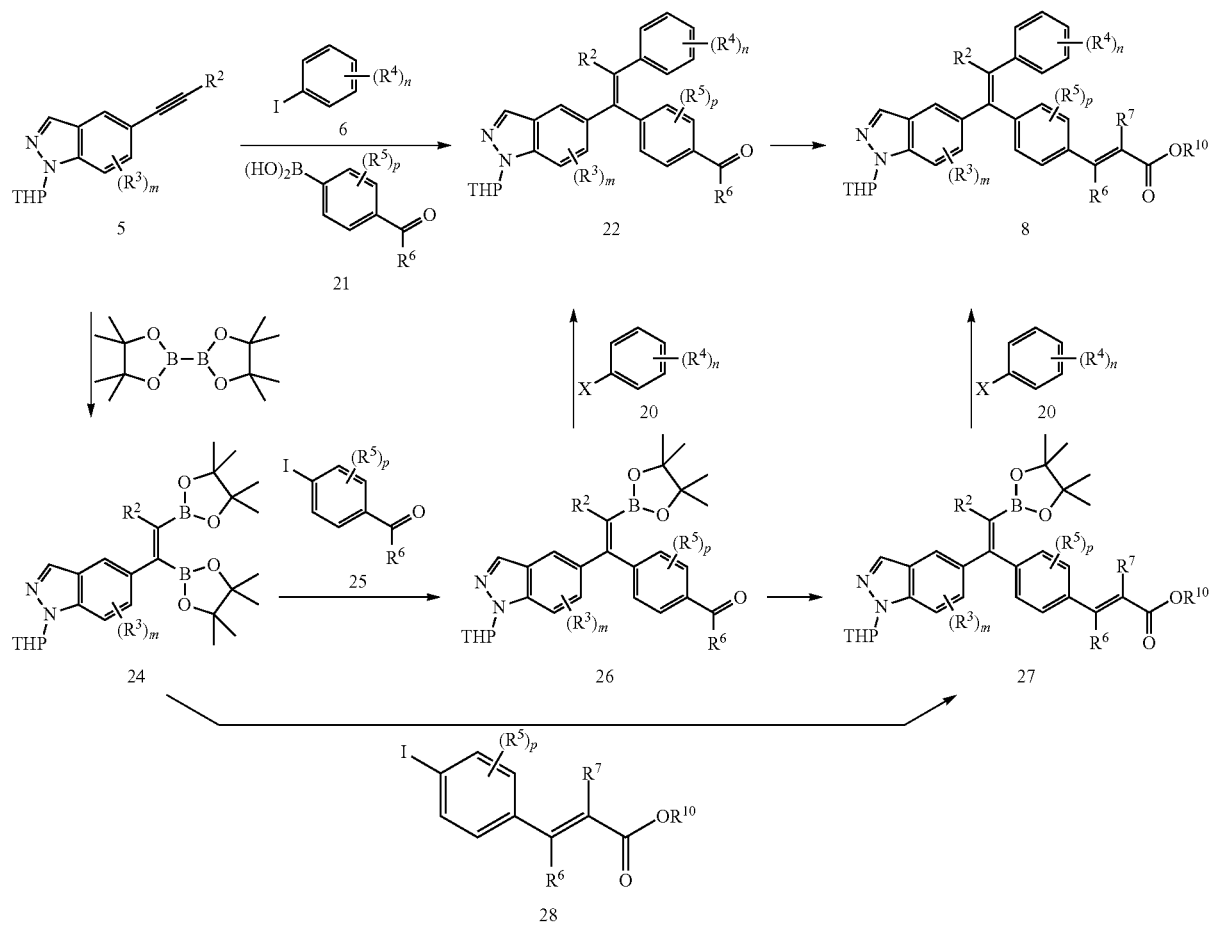

the solvent has a significant impact on the rate and regioselectivity of this reaction. In some embodiments, dioxane, DME, or 2-MeTHF is used. In some embodiments, water content has a significant impact on the rate and regioselectivity of this the Suzuki cross-coupling. A subsequent Suzuki cross-coupling is then performed between compounds of Structure 26 and phenyl halides of Structure 20 to provide compounds of Structure 22. Alternatively, compounds of Structure 26 are transformed to an alkene under suitable reaction conditions to provide compounds of Structure 27. In yet an another alternative procedure, a Suzuki cross-coupling is performed with compounds of Structure 24 and phenyl halides of Structure 28 to provide compounds of Structure 27. A subsequent Suzuki cross-coupling is then performed between compounds of Structure 27 and phenyl halides of Structure 20 to provide compounds of Structure 8.

Although Schemes 1, 2, 3 and 4 describe the synthesis of indazole and benzotriazole compounds, other heteroaryls and rings can be used in place of the indazoles and benzotriazoles. In some embodiments, any one of the phenyl groups may be replaced with a suitable heteroaryl.

In some instances, the ester groups of compounds of Structure 8 or Structure 16 are converted to other groups in order to prepare compounds of Structure 9 or Structure 17 where $OR^{10}$ is NHOH, $NR^8R^{8'}$, $NR^8S(=O)R^{10}$, $NR^8S(=O)_2R^{10}$, or $NHC(O)R^8$. In some embodiments, acrylic acid group of compounds of Formula (I) are elaborated into acrylamide groups as shown in Scheme 5.

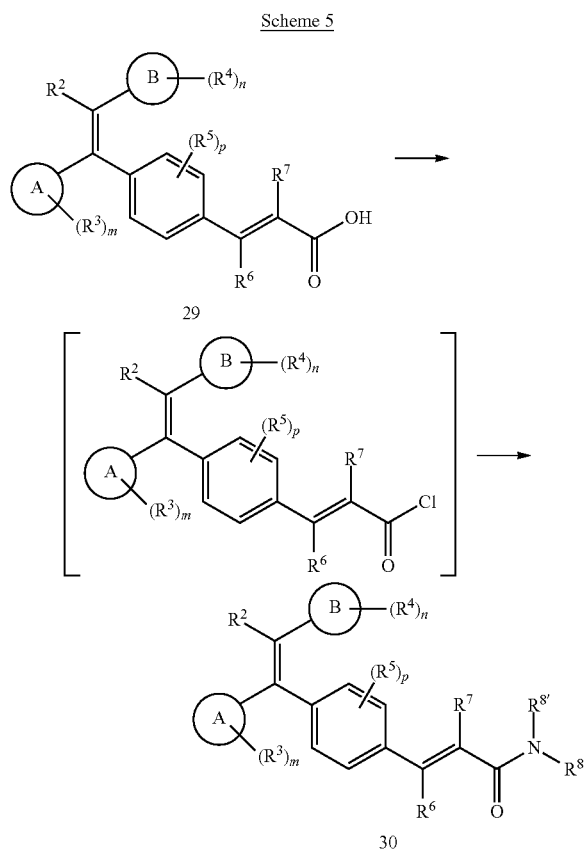

In some embodiments, acrylic acid compounds of Structure 29 are converted to acid chlorides under suitable reaction conditions, and the acid chloride that is formed is then reacted with a suitable amino containing compound (i.e. $R^8R^{8'}NH$) under suitable amide-forming reaction conditions to form acrylamide compounds of Structure 30. In some embodiments, the suitable reaction conditions for forming acid chlorides include the use oxalyl chloride, dimethylformamide and dichloromethane at room temperature. In some embodiments, the suitable amide-forming reaction conditions to form acrylamide compounds of Structure 30 from acrylic acid chlorides derived from compounds of Structure 29 includes the use of triethylamine, dioxane or dichloromethane, and cooling to approximately 0° C. In some embodiments, the suitable amide-forming reaction conditions includes the use of potassium carbonate, tetrahydrofuran and water. In some embodiments, the suitable amide-forming reaction conditions includes the use of sodium hydride and dimethylformamide.

In alternative embodiments, a coupling reagent is used to form amides of Structure 30 from acrylic acid compounds of Structure 29 and suitable amino containing compounds (i.e. $R^8R^{8'}NH$) as outlined in Scheme 6.

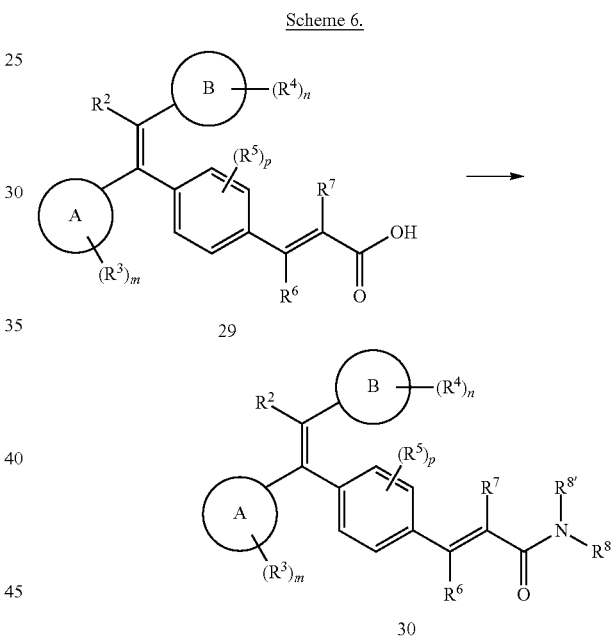

In some embodiments, acrylic acid compounds of Structure 29 are reacted with a suitable amino containing compound under suitable coupling conditions to form acrylamide compounds of Structure 30. In some embodiments, the suitable coupling conditions include the use of 1-ethyl-3-(3-dimethylaminopropyl) carbodiimide (EDC), dimethylaminopyridine, and tetrahydrofuran at room temperature. In some embodiments, the suitable coupling conditions include the use of O-(7-azabenzotriazol-1-yl)-N,N,N',N'-tetramethyluronium hexafluorophosphate (HATU), triethylamine and dichloromethane or dimethylformamide at room temperature. In some embodiments, the suitable coupling conditions include the use of 1,1'-carbonyldiimidazole (CDI), tetrahydrofuran and 1,8-diazabicyclo[5.4.0]undec-7-ene (DBU) at room temperature.

In some embodiments, the compounds of Formula (I) include a carboxylic acid bioisosetere. In some embodiments, the carboxylic acid bioisosteres are prepared as outlined in Scheme 7.

Scheme 7.

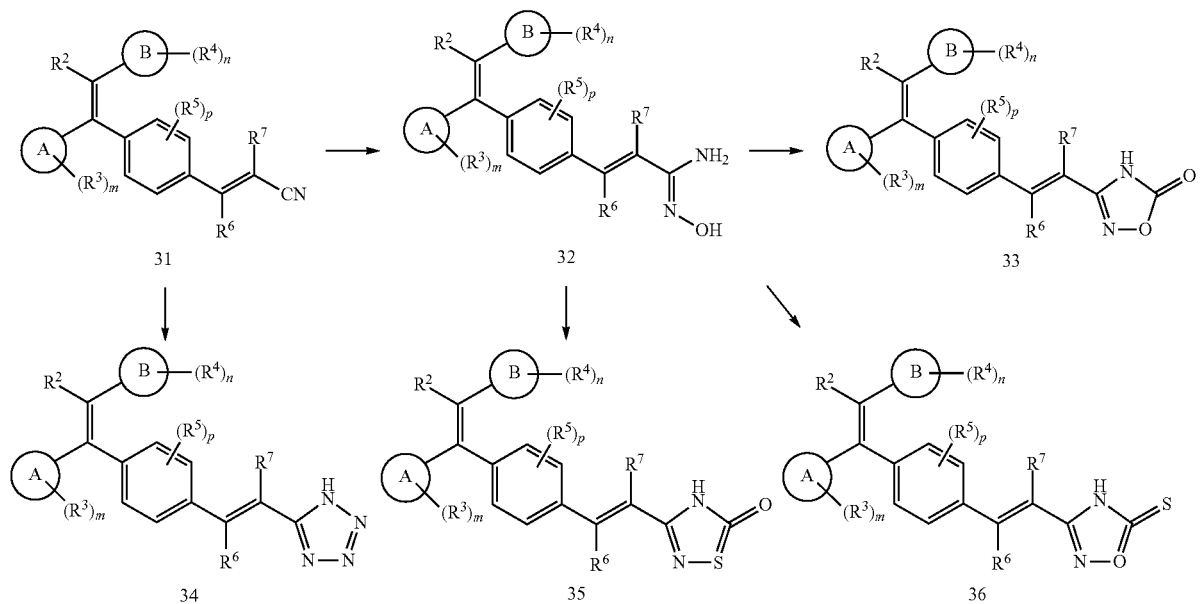

In some embodiments, acrylonitrile compounds of Structure 31 are treated with hydroxylamine hydrochloride, triethylamine, and dimethylsulfoxide at 75° C. for approximately 24 hours to provide compounds of Structure 32. In some embodiments, acrylonitrile compounds of Structure 31 are prepared as outlined in Schemes 1 to 4 for the acrylic acid compounds. Alternatively, acrylonitrile compounds of Structure 31 are treated with aqueous hydroxylamine and ethanol, and the reaction is refluxed for approximately 16 hours to provide compounds of Structure 32. In some embodiments, compounds of Structure 32 are treated 2-ethylhexylchloroformate at 0° C. for approximately 1 hour and then xylenes at 130° C. for approximately 2 hours to provide compounds of Structure 33. In alternative embodiments, compounds of Structure 32 are treated with CDI, DBU, and tetrahydrofuran at room temperature for approximately 16 hours to provide compounds of Structure 33. In some embodiments, compounds of Structure 32 are treated with 1,1'-thiocarbonyldiimidazole (TCDI) and tetrahydrofuran at room temperature for approximately 1 hour and then $BF_3$ etherate at room temperature for approximately 1 hour to provide compounds of Structure 35. In some embodiments, compounds of Structure 32 are treated with TCDI, DBU, and acetonitrile at room temperature for approximately 4 hours to provide compounds of Structure 36. In some embodiments, acrylonitrile compounds of Structure 31 are treated with $TMSN_3$, $Bu_2Sn(O)$, and toluene at reflux to provide tetrazoles of Structure 34.

In some embodiments, compounds of Formula (I) include a $R^4$ substituent, where $R^4$ is —$OR^9$ and $R^9$ is a substituted or unsubstituted aromatic ring. In such instances, the —$OR^9$ substituent is introduced as outlined in Scheme 8 (where ring D represents an aromatic ring and $R^{101}$ is an optional substitutent).

Scheme 8

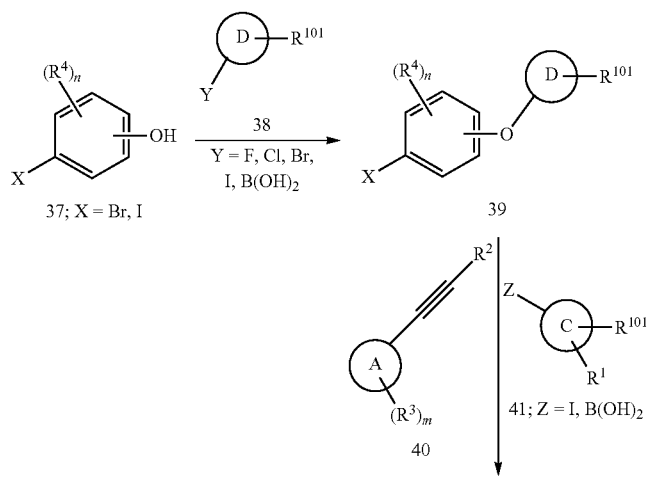

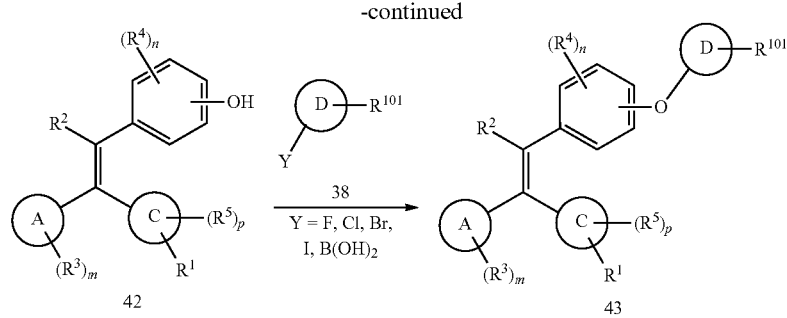

In some embodiments, when Y is a halide such as F, Cl, or Br, then a $S_NAr$ reaction is used to form the ether compounds of Structures 39 and 43. In some embodiments, the $S_NAr$ reaction includes the use of potassium carbonate or cesium carbonate in tetrahydrofuran, dimethylformamide or dimethylsulfoxide with heating at approximately 70-140° C. In some embodiments, when Y is a halide such as Br or I, then the coupling reaction to form the ether compounds of Structures 39 and 43 includes the use of CuBr, 1-(pyridin-2-yl)propan-2-one, cesium carbonate and dimethylsulfoxide at approximately 100° C. Alternately, when Y is a halide such as Br or I, then the coupling reaction to form the ether compounds of Structures 39 and 43 includes the use CuI, picolinic acid and potassium phosphate. In some embodiments, when Y is —B(OH)$_2$ then the coupling reaction to form the ether compounds of Structures 39 and 43 includes the use of Cu(OAc)$_2$, molecular sieves (4 Å), triethylamine, and dichloromethane at room temperature.

In some embodiments, compounds of Formula (I) include a $R^4$ substituent, where $R^4$ is a substituted or unsubstituted aromatic ring. In such instances, the substituted or unsubstituted aromatic ring is introduced as outlined in Scheme 9 (where ring D represents an aromatic ring and $R^{101}$ is an optional substitutent).

potassium hydroxide, 1,4-dioxane, and PdCl$_2$dppfDCM at approximately 70° C. for approximately 12-24 hours. In some embodiments, a Suzuki cross-coupling reaction between compounds of Structure 44 and compounds of Structure 47 is performed to provide compounds of Structure 48. In some embodiments, the Suzuki cross-coupling reaction includes the use of PdCl$_2$(PPh$_3$)$_2$ or Pd(PPh$_3$)$_4$, potassium carbonate, and toluene/ethanol (4:1) at approximately 90° C.

In one aspect, compounds of Formula (I) are synthesized as outlined in the Examples.

Throughout the specification, groups and substituents thereof are chosen by one skilled in the field to provide stable moieties and compounds.

A detailed description of techniques applicable to the creation of protecting groups and their removal are described in Greene and Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure.

Further Forms of Compounds

In one aspect, compounds of Formula (I) possess one or more stereocenters and each stereocenter exists indepen- Scheme 9.

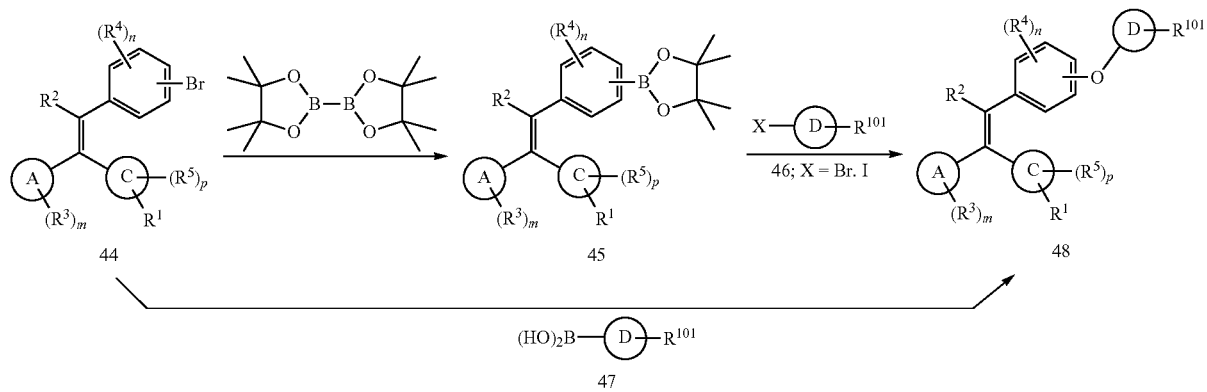

In some embodiments, compounds of Structure 44 are treated with bis(pinacolato)diboron, PdCl$_2$dppfDCM, potassium acetate, and 1,4-dioxane at 90° C. for approximately 12-24 hours to provide compounds of Structure 45. In some embodiments, a Suzuki cross-coupling reaction between compounds of Structure 45 and compounds of Structure 46 provides compounds of Structure 48. In some embodiments, the Suzuki cross-coupling reaction includes the use of dently in either the R or S configuration. The compounds presented herein include all diastereomeric, enantiomeric, atropisomers, and epimeric forms as well as the appropriate mixtures thereof. The compounds and methods provided herein include all cis, trans, syn, anti, entgegen (E), and zusammen (Z) isomers as well as the appropriate mixtures thereof.

Stereoisomers are obtained, if desired, by methods such as, stereoselective synthesis and/or the separation of stereoisomers by chiral chromatographic columns. In certain embodiments, compounds of Formula (I) are prepared as their individual stereoisomers by reacting a racemic mixture of the compound with an optically active resolving agent to form a pair of diastereoisomeric compounds/salts, separating the diastereomers and recovering the optically pure enantiomers. In some embodiments, resolution of enantiomers is carried out using covalent diastereomeric derivatives of the compounds described herein. In another embodiment, diastereomers are separated by separation/resolution techniques based upon differences in solubility. In other embodiments, separation of stereoisomers is performed by chromatography or by the forming diastereomeric salts and separation by recrystallization, or chromatography, or any combination thereof. Jean Jacques, Andre Collet, Samuel H. Wilen, "Enantiomers, Racemates and Resolutions", John Wiley And Sons, Inc., 1981. In some embodiments, stereoisomers are obtained by stereoselective synthesis.

In certain embodiments, the compounds presented herein are present as atropisomers. Atropisomers refer to stereoisomers resulting from hindered rotation about single bonds where the steric strain barrier to rotation allows for the isolation of conformers. Atropisomers display axial chirality. Separation of atropisomers is possible. In some embodiments, separation of atropisomers is possible by chiral resolution methods such as selective crystallization. Atropisomers are optionally characterized by NMR or other suitable characterization means.

For example, atropisomers of the compound with the structure

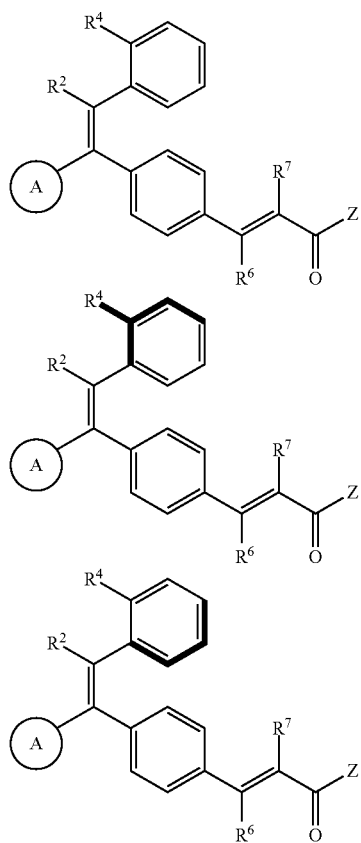

include: $R^4$ is above the plane of the alkene and $R^4$ is below the plane of the alkene.

The methods and compositions described herein include the use of amorphous forms as well as crystalline forms (also known as polymorphs). In one aspect, compounds described herein are in the form of pharmaceutically acceptable salts. As well, active metabolites of these compounds having the same type of activity are included in the scope of the present disclosure. In addition, the compounds described herein can exist in unsolvated as well as solvated forms with pharmaceutically acceptable solvents such as water, ethanol, and the like. The solvated forms of the compounds presented herein are also considered to be disclosed herein.

In some embodiments, compounds described herein are prepared as prodrugs. A "prodrug" refers to an agent that is converted into the parent drug in vivo. Prodrugs are often useful because, in some situations, they are easier to administer than the parent drug. They are, for instance, bioavailable by oral administration whereas the parent is not. Further or alternatively, the prodrug also has improved solubility in pharmaceutical compositions over the parent drug. In some embodiments, the design of a prodrug increases the effective water solubility. An example, without limitation, of a prodrug is a compound described herein, which is administered as an ester (the "prodrug") but then is metabolically hydrolyzed to provide the active entity. A further example of a prodrug is a short peptide (polyaminoacid) bonded to an acid group where the peptide is metabolized to reveal the active moiety. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound.

Prodrugs of the compounds described herein include, but are not limited to, esters, ethers, carbonates, thiocarbonates, N-acyl derivatives, N-acyloxyalkyl derivatives, quaternary derivatives of tertiary amines, N-Mannich bases, Schiff bases, amino acid conjugates, phosphate esters, and sulfonate esters. See for example Design of Prodrugs, Bundgaard, A. Ed., Elseview, 1985 and Method in Enzymology, Widder, K. et al., Ed.; Academic, 1985, vol. 42, p. 309-396; Bundgaard, H. "Design and Application of Prodrugs" in A Textbook of Drug Design and Development, Krosgaard-Larsen and H. Bundgaard, Ed., 1991, Chapter 5, p. 113-191; and Bundgaard, H., Advanced Drug Delivery Review, 1992, 8, 1-38, each of which is incorporated herein by reference. In some embodiments, a hydroxyl group in the compounds disclosed herein is used to form a prodrug, wherein the hydroxyl group is incorporated into an acyloxyalkyl ester, alkoxycarbonyloxyalkyl ester, alkyl ester, aryl ester, phosphate ester, sugar ester, ether, and the like. In some embodiments, a carboxyl group is used to provide an ester or amide (i.e. the prodrug), which is then metabolized in vivo to provide a carboxylic acid group. In some embodiments, compounds described herein are prepared as alkyl ester prodrugs.

Prodrug forms of the herein described compounds, wherein the prodrug is metabolized in vivo to produce a compound of Formula (I) as set forth herein are included within the scope of the claims. In some cases, some of the herein-described compounds is a prodrug for another derivative or active compound.

In some embodiments, sites on the aromatic ring portion of compounds of Formula (I) are susceptible to various metabolic reactions. Incorporation of appropriate substituents on the aromatic ring structures will reduce, minimize or eliminate this metabolic pathway. In specific embodiments, the appropriate substituent to decrease or eliminate the susceptibility of the aromatic ring to metabolic reactions is, by way of example only, a halogen, deuterium or an alkyl group.

In another embodiment, the compounds described herein are labeled isotopically (e.g. with a radioisotope) or by another other means, including, but not limited to, the use of chromophores or fluorescent moieties, bioluminescent labels, or chemiluminescent labels.

Compounds described herein include isotopically-labeled compounds, which are identical to those recited in the various formulae and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, fluorine and chlorine, such as, for example, $^{2}H$, $^{3}H$, $^{13}C$, $^{14}C$, $^{15}N$, $^{18}O$, $^{17}O$, $^{35}S$, $^{18}F$, $^{36}Cl$. In one aspect, isotopically-labeled compounds described herein, for example those into which radioactive isotopes such as $^{3}H$ and $^{14}C$ are incorporated, are useful in drug and/or substrate tissue distribution assays. In one aspect, substitution with isotopes such as deuterium affords certain therapeutic advantages resulting from greater metabolic stability, such as, for example, increased in vivo half-life or reduced dosage requirements.

In additional or further embodiments, the compounds described herein are metabolized upon administration to an organism in need to produce a metabolite that is then used to produce a desired effect, including a desired therapeutic effect.

"Pharmaceutically acceptable," as used herein, refers a material, such as a carrier or diluent, which does not abrogate the biological activity or properties of the compound, and is relatively nontoxic, i.e., the material is administered to an individual without causing undesirable biological effects or interacting in a deleterious manner with any of the components of the composition in which it is contained.

The term "pharmaceutically acceptable salt" refers to a formulation of a compound that does not cause significant irritation to an organism to which it is administered and does not abrogate the biological activity and properties of the compound. In some embodiments, pharmaceutically acceptable salts are obtained by reacting a compound of Formula (I) with acids. Pharmaceutically acceptable salts are also obtained by reacting a compound of Formula (I) with a base to form a salt.

Compounds described herein are optionally formed as, and/or used as, pharmaceutically acceptable salts. The type of pharmaceutical acceptable salts, include, but are not limited to: (1) acid addition salts, formed by reacting the free base form of the compound with a pharmaceutically acceptable: inorganic acid, such as, for example, hydrochloric acid, hydrobromic acid, sulfuric acid, phosphoric acid, metaphosphoric acid, and the like; or with an organic acid, such as, for example, acetic acid, propionic acid, hexanoic acid, cyclopentanepropionic acid, glycolic acid, pyruvic acid, lactic acid, malonic acid, succinic acid, malic acid, maleic acid, fumaric acid, trifluoroacetic acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, butyric acid, phenylacetic acid, phenylbutyric acid, valproic acid, and the like; (2) salts formed when an acidic proton present in the parent compound is replaced by a metal ion, e.g., an alkali metal ion (e.g. lithium, sodium, potassium), an alkaline earth ion (e.g. magnesium, or calcium), or an aluminum ion. In some cases, compounds described herein coordinate with an organic base, such as, but not limited to, ethanolamine, diethanolamine, triethanolamine, tromethamine, N-methylglucamine, dicyclohexylamine, tris(hydroxymethyl)methylamine. In other cases, compounds described herein form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, sodium hydroxide, and the like. In some embodiments, the compounds provided herein are prepared as lysine salts, sodium salts or other suitable amino acid salts. In some embodiments, the compounds provided herein are prepared as a sodium salt. In some embodiments, the compounds provided herein are prepared as an N-methylglucamine salt. In some embodiments, the compounds provided herein are prepared as a hydrochloride salt.

It should be understood that a reference to a pharmaceutically acceptable salt includes the solvent addition forms. In some embodiments, solvates contain either stoichiometric or non-stoichiometric amounts of a solvent, and are formed during the process of crystallization with pharmaceutically acceptable solvents such as water, ethanol, and the like. Hydrates are formed when the solvent is water, or alcoholates are formed when the solvent is alcohol. Solvates of compounds described herein are conveniently prepared or formed during the processes described herein. In addition, the compounds provided herein optionally exist in unsolvated as well as solvated forms.

The methods and formulations described herein include the use of N-oxides (if appropriate), crystalline forms (also known as polymorphs), or pharmaceutically acceptable salts of compounds having the structure of Formula (I), as well as active metabolites of these compounds having the same type of activity.

Certain Terminology

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. Unless otherwise indicated, conventional methods of mass spectroscopy, NMR, HPLC, protein chemistry, biochemistry, recombinant DNA techniques and pharmacology are employed. In this application, the use of "or" or "and" means "and/or" unless stated otherwise. Furthermore, use of the term "including" as well as other forms, such as "include", "includes," and "included," is not limiting. The section headings used herein are for organizational purposes only and are not to be construed as limiting the subject matter described.

An "alkyl" group refers to an aliphatic hydrocarbon group. The alkyl group is branched or straight chain. In some embodiments, the "alkyl" group has 1 to 6 carbon atoms (whenever it appears herein, a numerical range such as "1 to 6" refers to each integer in the given range; e.g., "1 to 6 carbon atoms" means that the alkyl group includes moieties that consist of 1 carbon atom, 2 carbon atoms, 3 carbon atoms, etc., up to and including 6 carbon atoms, although the present definition also covers the occurrence of the term "alkyl" where no numerical range is designated). In one aspect the alkyl is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, sec-butyl, tertiary butyl, pentyl, neopentyl, hexyl, allyl, but-2-enyl, but-3-enyl, and the like.

"Deuteroalkyl" refers to an alkyl group where 1 or more hydrogen atoms of an alkyl are replaced with deuterium.

The term "alkylene" refers to a divalent alkyl radical. Any of the above mentioned monovalent alkyl groups are optionally an alkylene by abstraction of a second hydrogen atom from the alkyl. Typical alkylene groups include, but are not limited to, —$CH_2$—, —$CH(CH_3)$—, —$C(CH_3)_2$—, —$CH_2CH_2$—, and the like.

The term "alkenyl" refers to a type of alkyl group in which at least one carbon-carbon double bond is present. In one embodiment, an alkenyl group has the formula —C(R)=$CR_2$, wherein R refers to the remaining portions of the alkenyl group, which may be the same or different. Non-limiting examples of an alkenyl group include —CH=$CH_2$, —$C(CH_3)$=$CH_2$, —CH=$CHCH_3$ and —$C(CH_3)$=$CHCH_3$. Depending on the structure, an alkenyl group can be a monoradical or a diradical (i.e., an alkenylene group).

The term "alkynyl" refers to a type of alkyl group in which at least one carbon-carbon triple bond is present. In one embodiment, an alkenyl group has the formula —C≡C—R, wherein R refers to the remaining portions of the alkynyl group. Non-limiting examples of an alkynyl group include —C≡CH, —C≡$CCH_3$ and —C≡$CCH_2CH_3$. Depending on the structure, an alkynyl group can be a monoradical or a diradical (i.e., an alkynylene group).

An "alkoxy" group refers to a (alkyl)O— group, where alkyl is as defined herein.

The term "alkylamine" refers to the —$N(alkyl)_xH_y$ group, where x and y are selected from the group x=1, y=1 and x=2, y=0.

The term "aromatic" refers to a planar ring having a delocalized π-electron system containing 4n+2π electrons, where n is an integer. Aromatics are optionally substituted. The term "aromatic" includes both carbocyclic aryl ("aryl", e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups.

The term "carbocyclic" or "carbocycle" refers to a ring or ring system where the atoms forming the backbone of the ring are all carbon atoms. The term thus distinguishes carbocyclic from heterocyclic rings in which the ring backbone contains at least one atom which is different from carbon. In some embodiments, at least one of the two rings of a bicyclic carbocycle is aromatic. In some embodiments, both rings of a bicyclic carbocycle are aromatic.

As used herein, the term "aryl" refers to an aromatic ring wherein each of the atoms forming the ring is a carbon atom. Aryl groups are optionally substituted. In one aspect, an aryl is a phenyl or a naphthalenyl. In one aspect, an aryl is a phenyl. In one aspect, an aryl is a $C_6$-$C_{10}$aryl. Depending on the structure, an aryl group is optionally a monoradical or a diradical (i.e., an arylene group).

The term "cycloalkyl" refers to a monocyclic or polycyclic aliphatic, non-aromatic radical, wherein each of the atoms forming the ring (i.e. skeletal atoms) is a carbon atom. Cycloalkyls include moieties that are saturated, or partially unsaturated. Cycloalkyls are optionally fused with an aromatic ring, and the point of attachment is at a carbon that is not an aromatic ring carbon atom. Cycloalkyl groups include groups having from 3 to 10 ring atoms. In some embodiments, cycloalkyl groups are selected from among cyclopropyl, cyclobutyl, cyclopentyl, cyclopentenyl, cyclohexyl, cyclohexenyl, cycloheptyl, and cyclooctyl. Cycloalkyl groups are optionally substituted or unsubstituted. Depending on the structure, a cycloalkyl group is optionally a monoradical or a diradical (i.e., an cycloalkylene group, such as, but not limited to, cyclopropan-1,1-diyl, cyclobutan-1,1-diyl, cyclopentan-1,1-diyl, cyclohexan-1,1-diyl, cyclohexan-1,4-diyl, cycloheptan-1,1-diyl, and the like). In one aspect, a cycloalkyl is a $C_3$-$C_6$cycloalkyl.

The term "halo" or, alternatively, "halogen" or "halide" means fluoro, chloro, bromo or iodo.

The term "fluoroalkyl" refers to an alkyl in which one or more hydrogen atoms are replaced by a fluorine atom. In one aspect, a fluoralkyl is a $C_1$-$C_6$fluoroalkyl.

The term "heteroalkyl" refers to an alkyl group in which one or more skeletal atoms of the alkyl are selected from an atom other than carbon, e.g., oxygen, nitrogen (e.g. —NH—, —N(alkyl)-, sulfur, or combinations thereof. In one aspect, a heteroalkyl is a $C_1$-$C_6$heteroalkyl.

The term "heterocycle" or "heterocyclic" refers to heteroaromatic rings (also known as heteroaryls) and heterocycloalkyl rings (also known as heteroalicyclic groups) containing one to four heteroatoms in the ring(s), where each heteroatom in the ring(s) is selected from O, S and N, wherein each heterocyclic group has from 4 to 10 atoms in its ring system, and with the proviso that the any ring does not contain two adjacent O or S atoms. Non-aromatic heterocyclic groups (also known as heterocycloalkyls) include groups having only 3 atoms in their ring system, but aromatic heterocyclic groups must have at least 5 atoms in their ring system. The heterocyclic groups include benzo-fused ring systems. An example of a 3-membered heterocyclic group is aziridinyl. An example of a 4-membered heterocyclic group is azetidinyl. An example of a 5-membered heterocyclic group is thiazolyl. An example of a 6-membered heterocyclic group is pyridyl, and an example of a 10-membered heterocyclic group is quinolinyl. Examples of non-aromatic heterocyclic groups are pyrrolidinyl, tetrahydrofuranyl, dihydrofuranyl, tetrahydrothienyl, oxazolidinonyl, tetrahydropyranyl, dihydropyranyl, tetrahydrothiopyranyl, piperidinyl, morpholinyl, thiomorpholinyl, thioxanyl, piperazinyl, aziridinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, pyrrolin-2-yl, pyrrolin-3-yl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl, indolin-2-onyl, isoindolin-1-onyl, isoindoline-1,3-dionyl, 3,4-dihydroisoquinolin-1(2H)-onyl, 3,4-dihydroquinolin-2(1H)-onyl, isoindoline-1,3-dithionyl, benzo[d]oxazol-2(3H)-onyl, 1H-benzo[d]imidazol-2(3H)-onyl, benzo[d]thiazol-2(3H)-onyl, and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups are either C-attached (or C-linked) or N-attached where such is possible. For instance, a group derived from pyrrole includes both pyrrol-1-yl (N-attached) or pyrrol-3-yl (C-attached). Further, a group derived from imidazole includes imidazol-1-yl or imidazol-3-yl (both N-attached) or imidazol-2-yl, imidazol-4-yl or imidazol-5-yl (all C-attached). The heterocyclic groups include benzo-fused ring systems. Heterocycles are optionally substituted with one or two oxo (=O) moieties, such as pyrrolidin-2-one. In some embodiments, at least one of the two rings of a bicyclic heterocycle is aromatic. In some embodiments, both rings of a bicyclic heterocycle are aromatic.

The terms "heteroaryl" or, alternatively, "heteroaromatic" refers to an aryl group that includes one or more ring heteroatoms selected from nitrogen, oxygen and sulfur. Illustrative examples of heteroaryl groups include:

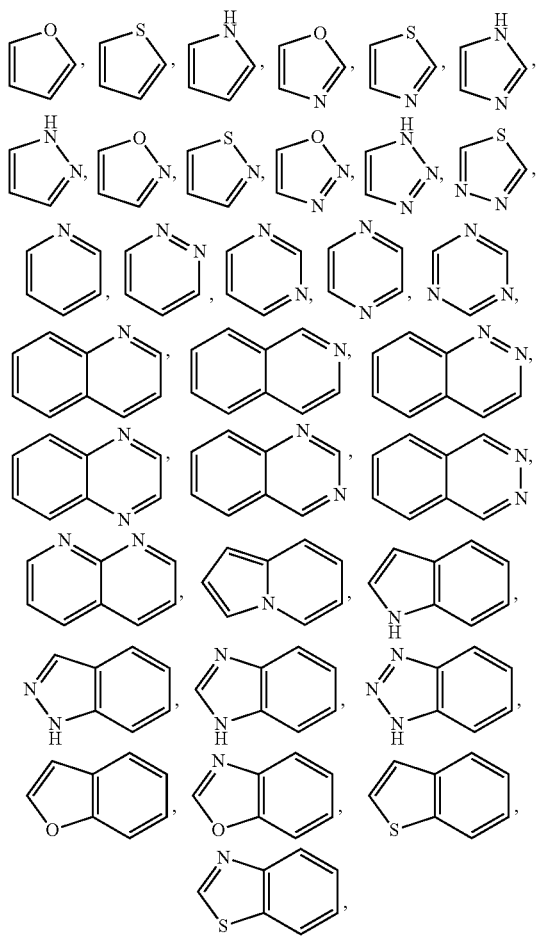

and the like. Monocyclic include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl. In some embodiments, a heteroaryl contains 0-4 N atoms in the ring. In some embodiments, a heteroaryl contains 1-4 N atoms in the ring. In some embodiments, a heteroaryl contains 0-4 N atoms, 0-1 O atoms, and 0-1 S atoms in the ring. In some embodiments, a heteroaryl is a monocyclic or bicyclic heteroaryl. In some embodiments, heteroaryl is a $C_1$-$C_9$heteroaryl. In some embodiments, monocyclic heteroaryl is a $C_1$-$C_5$heteroaryl. In some embodiments, monocyclic heteroaryl is a 5-membered or 6-membered heteroaryl. In some embodiments, bicyclic heteroaryl is a $C_6$-$C_9$heteroaryl. Depending on the structure, a heteroaryl group is optionally a monoradical or a diradical (i.e., a heteroarylene group).

A "heterocycloalkyl" or "heteroalicyclic" group refers to a cycloalkyl group that includes at least one heteroatom selected from nitrogen, oxygen and sulfur. In some embodiments, a heterocycloalkyl is fused with an aryl or heteroaryl. In some embodiments, a heterocycloalkyl is fused with a phenyl or monocyclic heteroaryl. In some embodiments, a heterocycloalkyl is fused with a phenyl or monocyclic heteroaryl and the point of attachment to the rest of the molecule is through a carbon atom of the fused phenyl or fused monocyclic heteroaryl. In some embodiments, the heterocycloalkyl is oxazolidinonyl, pyrrolidinyl, tetrahydrofuranyl, tetrahydrothienyl, tetrahydropyranyl, tetrahydrothiopyranyl, piperidinyl, morpholinyl, thiomorpholinyl, piperazinyl, piperidin-2-onyl, pyrrolidine-2,5-dithionyl, pyrrolidine-2,5-dionyl, pyrrolidinonyl, imidazolidinyl, imidazolidin-2-onyl, or thiazolidin-2-onyl. The term heteroalicyclic also includes all ring forms of the carbohydrates, including but not limited to the monosaccharides, the disaccharides and the oligosaccharides. In one aspect, a heterocycloalkyl is a $C_2$-$C_{10}$heterocycloalkyl. In another aspect, a heterocycloalkyl is a $C_4$-$C_{10}$heterocycloalkyl. In some embodiments, a heterocycloalkyl contains 0-2 N atoms in the ring. In some embodiments, a heterocycloalkyl contains 0-2 N atoms, 0-2 O atoms and 0-1 S atoms in the ring.

"Aza" when added to the name of a heterocyclic ring, denotes that the ring includes 1 or 2 additional N atoms in the heterocyclic ring.

The term "bond" or "single bond" refers to a chemical bond between two atoms, or two moieties when the atoms joined by the bond are considered to be part of larger substructure. In one aspect, when a group described herein is a bond, the referenced group is absent thereby allowing a bond to be formed between the remaining identified groups.

The term "moiety" refers to a specific segment or functional group of a molecule. Chemical moieties are often recognized chemical entities embedded in or appended to a molecule.

The term "carboxylic acid bioisostere" refers to a functional group or moiety that exhibits similar physical, biological and/or chemical properties as a carboxylic acid moiety. Examples of carboxylic acid bioisosteres include, but are not limited to,

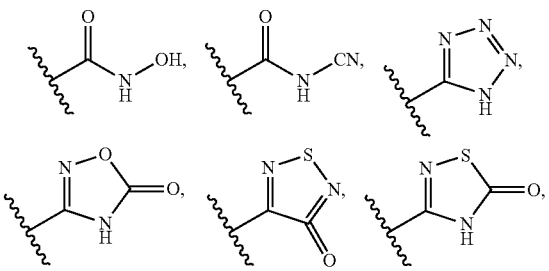

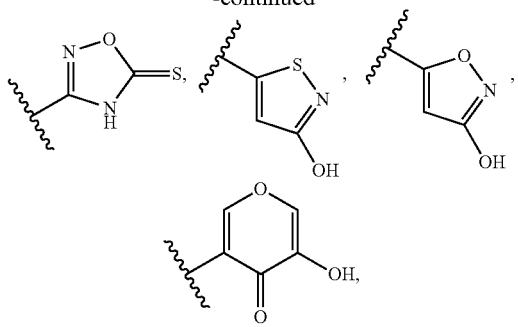

and the like.

The term "optionally substituted" or "substituted" means that the referenced group is optionally substituted with one or more additional group(s) individually and independently selected from alkyl, cycloalkyl, aryl, heteroaryl, heteroalicyclic, hydroxy, alkoxy, aryloxy, alkylthio, arylthio, alkylsulfoxide, arylsulfoxide, alkylsulfone, arylsulfone, cyano, halo, nitro, haloalkyl, fluoroalkyl, fluoroalkoxy, and amino, including mono- and di-substituted amino groups, and the protected derivatives thereof. In some embodiments, optional substituents are independently selected from halogen, —CN, —NH$_2$, —NH(CH$_3$), —N(CH$_3$)$_2$, —OH, —CO$_2$H, —CO$_2$alkyl, —C(=O)NH$_2$, —C(=O)NH(alkyl), —C(=O)N(alkyl)$_2$, —S(=O)$_2$NH$_2$, —S(=O)$_2$NH(alkyl), —S(=O)$_2$N(alkyl)$_2$, alkyl, cycloalkyl, fluoroalkyl, heteroalkyl, alkoxy, fluoroalkoxy, heterocycloalkyl, aryl, heteroaryl, aryloxy, alkylthio, arylthio, alkylsulfoxide, arylsulfoxide, alkylsulfone, and arylsulfone. In some other embodiments, optional substituents are independently selected from halogen, —CN, —NH$_2$, —NH(CH$_3$), —N(CH$_3$)$_2$, —OH, —CO$_2$H, —CO$_2$(C$_1$-C$_4$alkyl), —C(=O)NH$_2$, —C(=O)NH(C$_1$-C$_4$alkyl), —C(=O)N(C$_1$-C$_4$alkyl)$_2$, —S(=O)$_2$NH$_2$, —S(=O)$_2$NH(C$_1$-C$_4$alkyl), —S(=O)$_2$N(C$_1$-C$_4$alkyl)$_2$, C$_1$-C$_4$alkyl, C$_3$-C$_6$cycloalkyl, C$_1$-C$_4$fluoroalkyl, C$_1$-C$_4$heteroalkyl, C$_1$-C$_4$alkoxy, C$_1$-C$_4$fluoroalkoxy, —SC$_1$-C$_4$alkyl, —S(=O)C$_1$-C$_4$alkyl, and —S(=O)$_2$C$_1$-C$_4$alkyl. In some embodiments, optional substituents are independently selected from halogen, —CN, —NH$_2$, —OH, —NH(CH$_3$), —N(CH$_3$)$_2$, —CH$_3$, —CH$_2$CH$_3$, —CF$_3$, —OCH$_3$, and —OCF$_3$. In some embodiments, substituted groups are substituted with one or two of the preceding groups. In some embodiments, an optional substituent on an aliphatic carbon atom (acyclic or cyclic, saturated or unsaturated carbon atoms, excluding aromatic carbon atoms) includes oxo (=O).

The term "acceptable" with respect to a formulation, composition or ingredient, as used herein, means having no persistent detrimental effect on the general health of the subject being treated.

The term "modulate" as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator" as used herein, refers to a molecule that interacts with a target either directly or indirectly. The interactions include, but are not limited to, the interactions of an agonist, partial agonist, an inverse agonist, antagonist, degrader, or combinations thereof. In some embodiments, a modulator is an antagonist. In some embodiments, a modulator is a degrader.

"Selective estrogen receptor modulator" or "SERM" as used herein, refers to a molecule that differentially modulates the activity of estrogen receptors in different tissues. For example, in some embodiments, a SERM displays ER antagonist activity in some tissues and ER agonist activity in other tissues. In some embodiments, a SERM displays ER antagonist activity in some tissues and minimal or no ER agonist activity in other tissues. In some embodiments, a SERM displays ER antagonist activity in breast tissues, ovarian tissues, endometrial tissues, and/or cervical tissues but minimal or no ER agonist activity in uterine tissues.

The term "antagonist" as used herein, refers to a small-molecule agent that binds to a nuclear hormone receptor and subsequently decreases the agonist induced transcriptional activity of the nuclear hormone receptor.

The term "agonist" as used herein, refers to a small-molecule agent that binds to a nuclear hormone receptor and subsequently increases nuclear hormone receptor transcriptional activity in the absence of a known agonist.

The term "inverse agonist" as used herein, refers to a small-molecule agent that binds to a nuclear hormone receptor and subsequently decreases the basal level of nuclear hormone receptor transcriptional activity that is present in the absence of a known agonist.

The term "degrader" as used herein, refers to a small molecule agent that binds to a nuclear hormone receptor and subsequently lowers the steady state protein levels of said receptor. In some embodiments, a degrader as described herein lowers steady state estrogen receptor levels by at least 10%, at least 20%, at least 30%, at least 40%, at least 50%, at least 60%, at least 65%, at least 70%, at least 75%, at least 80%, at least 85%, at least 90% or at least 95%.

The term "selective estrogen receptor degrader" or "SERD" as used herein, refers to a small molecule agent that preferentially binds to estrogen receptors versus other receptors and subsequently lowers the steady state estrogen receptor levels.

The term "ER-dependent", as used herein, refers to diseases or conditions that would not occur, or would not occur to the same extent, in the absence of estrogen receptors.

The term "ER-mediated", as used herein, refers to diseases or conditions that occur in the absence of estrogen receptors but can occur in the presence of estrogen receptors.

The term "ER-sensitive", as used herein, refers to diseases or conditions that would not occur, or would not occur to the same extent, in the absence of estrogens.

The term "cancer" as used herein refers to an abnormal growth of cells which tend to proliferate in an uncontrolled way and, in some cases, to metastasize (spread). The types of cancer include, but is not limited to, solid tumors (such as those of the bladder, bowel, brain, breast, endometrium, heart, kidney, lung, uterus, lymphatic tissue (lymphoma), ovary, pancreas or other endocrine organ (thyroid), prostate, skin (melanoma or basal cell cancer) or hematological tumors (such as the leukemias and lymphomas) at any stage of the disease with or without metastases.

Additional non-limiting examples of cancers include, acute lymphoblastic leukemia, acute myeloid leukemia, adrenocortical carcinoma, anal cancer, appendix cancer, astrocytomas, atypical teratoid/rhabdoid tumor, basal cell carcinoma, bile duct cancer, bladder cancer, bone cancer (osteosarcoma and malignant fibrous histiocytoma), brain stem glioma, brain tumors, brain and spinal cord tumors, breast cancer, bronchial tumors, Burkitt lymphoma, cervical cancer, chronic lymphocytic leukemia, chronic myelogenous leukemia, colon cancer, colorectal cancer, craniopharyngioma, cutaneous T-Cell lymphoma, embryonal tumors, endometrial cancer, ependymoblastoma, ependymoma, esophageal cancer, ewing sarcoma family of tumors, eye cancer, retinoblastoma, gallbladder cancer, gastric (stomach) cancer, gastrointestinal carcinoid tumor, gastrointestinal stromal tumor (GIST), gastrointestinal stromal cell tumor, germ cell tumor, glioma, hairy cell leukemia, head and neck cancer, hepatocellular (liver) cancer, hodgkin lymphoma, hypopharyngeal cancer, intraocular melanoma, islet cell tumors (endocrine pancreas), Kaposi sarcoma, kidney cancer, Langerhans cell histiocytosis, laryngeal cancer, leukemia, Acute lymphoblastic leukemia, acute myeloid leukemia, chronic lymphocytic leukemia, chronic myelogenous leukemia, hairy cell leukemia, liver cancer, non-small cell lung cancer, small cell lung cancer, Burkitt lymphoma, cutaneous T-cell lymphoma, Hodgkin lymphoma, non-Hodgkin lymphoma, lymphoma, Waldenström macroglobulinemia, medulloblastoma, medulloepithelioma, melanoma, mesothelioma, mouth cancer, chronic myelogenous leukemia, myeloid leukemia, multiple myeloma, nasopharyngeal cancer, neuroblastoma, non-Hodgkin lymphoma, non-small cell lung cancer, oral cancer, oropharyngeal cancer, osteosarcoma, malignant fibrous histiocytoma of bone, ovarian cancer, ovarian epithelial cancer, ovarian germ cell tumor, ovarian low malignant potential tumor, pancreatic cancer, papillomatosis, parathyroid cancer, penile cancer, pharyngeal cancer, pineal parenchymal tumors of intermediate differentiation, pineoblastoma and supratentorial primitive neuroectodermal tumors, pituitary tumor, plasma cell neoplasm/multiple myeloma, pleuropulmonary blastoma, primary central nervous system lymphoma, prostate cancer, rectal cancer, renal cell (kidney) cancer, retinoblastoma, rhabdomyosarcoma, salivary gland cancer, sarcoma, Ewing sarcoma family of tumors, sarcoma, kaposi, Sézary syndrome, skin cancer, small cell Lung cancer, small intestine cancer, soft tissue sarcoma, squamous cell carcinoma, stomach (gastric) cancer, supratentorial primitive neuroectodermal tumors, T-cell lymphoma, testicular cancer, throat cancer, thymoma and thymic carcinoma, thyroid cancer, urethral cancer, uterine cancer, uterine sarcoma, vaginal cancer, vulvar cancer, Waldenström macroglobulinemia, Wilms tumor.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is optionally determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound of Formula (I), or a pharmaceutically acceptable salt thereof, and a co-agent, are both administered to a patient simultaneously in the form of a single entity or dosage. The term "non-fixed combination" means that the active ingredients, e.g. a compound of Formula (I), or a pharmaceutically acceptable salt thereof, and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The terms "kit" and "article of manufacture" are used as synonyms.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Metabolites of the compounds disclosed herein are optionally identified either by administration of compounds to a host and analysis of tissue samples from the host, or by incubation of compounds with hepatic cells in vitro and analysis of the resulting compounds.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Routes of Administration

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, a compound as described herein is administered in a local rather than systemic manner, for example, via injection of the compound directly into an organ, often in a depot preparation or sustained release formulation. In specific embodiments, long acting formulations are administered by implantation (for example subcutaneously or intramuscularly) or by intramuscular injection. Furthermore, in other embodiments, the drug is delivered in a targeted drug delivery system, for example, in a liposome coated with organ-specific antibody. In such embodiments, the liposomes are targeted to and taken up selectively by the organ. In yet other embodiments, the compound as described herein is provided in the form of a rapid release formulation, in the form of an extended release formulation, or in the form of an intermediate release formulation. In yet other embodiments, the compound described herein is administered topically.

Pharmaceutical Compositions/Formulations

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that are used pharmaceutically. Proper formulation is dependent upon the route of administration chosen. A summary of pharmaceutical compositions described herein is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

In some embodiments, there are provided a pharmaceutical composition comprising a therapeutically effective amount of a compound of Formula (I), or a pharmaceutically acceptable salt thereof.

Provided herein are pharmaceutical compositions that include a compound of Formula (I), or a pharmaceutically acceptable salt thereof, and at least one pharmaceutically acceptable inactive ingredient. In some embodiments, the compounds described herein are administered as pharmaceutical compositions in which a compound of Formula (I), or a pharmaceutically acceptable salt thereof, is mixed with other active ingredients, as in combination therapy. In other embodiments, the pharmaceutical compositions include other medicinal or pharmaceutical agents, carriers, adjuvants, preserving, stabilizing, wetting or emulsifying agents, solution promoters, salts for regulating the osmotic pressure, and/or buffers. In yet other embodiments, the pharmaceutical compositions include other therapeutically valuable substances.

A pharmaceutical composition, as used herein, refers to a mixture of a compound of Formula (I), or a pharmaceutically acceptable salt thereof, with other chemical components (i.e. pharmaceutically acceptable inactive ingredients), such as carriers, excipients, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, antifoaming agents, antioxidants, preservatives, or one or more combination thereof. The pharmaceutical composition facilitates administration of the compound to a mammal.

A therapeutically effective amount depends, inter alia, on the severity of the disease, the age and relative health of the subject, the potency of the compound used and other factors. The compounds are optionally used singly or in combination with one or more therapeutic agents as components of mixtures.

The pharmaceutical formulations described herein are administered to a subject by appropriate administration routes, including but not limited to, oral, parenteral (e.g., intravenous, subcutaneous, intramuscular), intranasal, buccal, topical, rectal, or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

Pharmaceutical compositions including a compound of Formula (I), or a pharmaceutically acceptable salt thereof, are manufactured in a conventional manner, such as, by way of example only, by means of conventional mixing, dissolving, granulating, dragee-making, levigating, emulsifying, encapsulating, entrapping or compression processes.

The pharmaceutical compositions will include at least one compound of Formula (I), or a pharmaceutically acceptable salt thereof, as an active ingredient in free-acid or free-base form, or in a pharmaceutically acceptable salt form. In addition, the methods and pharmaceutical compositions described herein include the use of N-oxides (if appropriate), crystalline forms, amorphous phases, as well as active metabolites of these compounds having the same type of activity. In some embodiments, compounds described herein exist in unsolvated form or in solvated forms with pharmaceutically acceptable solvents such as water, ethanol, and the like. The solvated forms of the compounds presented herein are also considered to be disclosed herein.

The pharmaceutical compositions described herein, which include a compound of Formula (I), or a pharmaceutically acceptable salt thereof, are formulated into any suitable dosage form, including but not limited to, aqueous oral dispersions, liquids, gels, syrups, elixirs, slurries, suspensions, solid oral dosage forms, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations.

In some embodiments, the pharmaceutical composition is formulated for intravenous injection, subcutaneous injection, oral administration, or topical administration. In some embodiments, the pharmaceutical composition is a tablet, a pill, a capsule, a liquid, a suspension, a gel, a dispersion, a solution, an emulsion, an ointment, or a lotion.

Pharmaceutical preparations that are administered orally include push-fit capsules made of gelatin, as well as soft, sealed capsules made of gelatin and a plasticizer, such as glycerol or sorbitol. The push-fit capsules contain the active ingredients in admixture with filler such as lactose, binders such as starches, and/or lubricants such as talc or magnesium stearate and, optionally, stabilizers. In some embodiments, the push-fit capsules do not include any other ingredient besides the capsule shell and the active ingredient. In soft capsules, the active compounds are dissolved or suspended in suitable liquids, such as fatty oils, liquid paraffin, or liquid polyethylene glycols. In some embodiments, stabilizers are added.

All formulations for oral administration are in dosages suitable for such administration.

In one aspect, solid oral soage forms are prepared by mixing a compound of Formula (I), or a pharmaceutically acceptable salt thereof, with one or more of the following: antioxidants, flavoring agents, and carrier materials such as binders, suspending agents, disintegration agents, filling agents, surfactants, solubilizers, stabilizers, lubricants, wetting agents, and diluents.

In some embodiments, the solid dosage forms disclosed herein are in the form of a tablet, (including a suspension tablet, a fast-melt tablet, a bite-disintegration tablet, a rapid-disintegration tablet, an effervescent tablet, or a caplet), a pill, a powder, a capsule, solid dispersion, solid solution, bioerodible dosage form, controlled release formulations, pulsatile release dosage forms, multiparticulate dosage forms, beads, pellets, granules. In other embodiments, the pharmaceutical formulation is in the form of a powder. In still other embodiments, the pharmaceutical formulation is in the form of a tablet. In other embodiments, pharmaceutical formulation is in the form of a capsule.

In some embodiments, solid dosage forms, e.g., tablets, effervescent tablets, and capsules, are prepared by mixing particles of a compound of Formula (I), or a pharmaceutically acceptable salt thereof, with one or more pharmaceutical excipients to form a bulk blend composition. The bulk blend is readily subdivided into equally effective unit dosage forms, such as tablets, pills, and capsules. In some embodiments, the individual unit dosages include film coatings. These formulations are manufactured by conventional formulation techniques.

Conventional formulation techniques include, e.g., one or a combination of methods: (1) dry mixing, (2) direct compression, (3) milling, (4) dry or non-aqueous granulation, (5) wet granulation, or (6) fusion. Other methods include, e.g., spray drying, pan coating, melt granulation, granulation, fluidized bed spray drying or coating (e.g., wurster coating), tangential coating, top spraying, tableting, extruding and the like.

In some embodiments, tablets will include a film surrounding the final compressed tablet. In some embodiments, the film coating provides a delayed release of the compound of Formula (I), or a pharmaceutically acceptable salt thereof, from the formulation. In other embodiments, the film coating aids in patient compliance (e.g., Opadry® coatings or sugar coating). Film coatings including Opadry® typically range from about 1% to about 3% of the tablet weight.

A capsule is prepared, for example, by placing the bulk blend of the formulation of the compound described above, inside of a capsule. In some embodiments, the formulations (non-aqueous suspensions and solutions) are placed in a soft gelatin capsule. In other embodiments, the formulations are placed in standard gelatin capsules or non-gelatin capsules such as capsules comprising HPMC. In other embodiments, the formulation is placed in a sprinkle capsule, wherein the capsule is swallowed whole or the capsule is opened and the contents sprinkled on food prior to eating.

In various embodiments, the particles of the compound of Formula (I), or a pharmaceutically acceptable salt thereof, and one or more excipients are dry blended and compressed into a mass, such as a tablet, having a hardness sufficient to provide a pharmaceutical composition that substantially disintegrates within less than about 30 minutes, less than about 35 minutes, less than about 40 minutes, less than about 45 minutes, less than about 50 minutes, less than about 55 minutes, or less than about 60 minutes, after oral administration, thereby releasing the formulation into the gastrointestinal fluid.

In still other embodiments, effervescent powders are also prepared. Effervescent salts have been used to disperse medicines in water for oral administration.

In some embodiments, the pharmaceutical solid oral dosage forms are formulated to provide a controlled release of the active compound. Controlled release refers to the release of the active compound from a dosage form in which it is incorporated according to a desired profile over an extended period of time. Controlled release profiles include, for example, sustained release, prolonged release, pulsatile release, and delayed release profiles. In contrast to immediate release compositions, controlled release compositions allow delivery of an agent to a subject over an extended period of time according to a predetermined profile. Such release rates provide therapeutically effective levels of agent for an extended period of time and thereby provide a longer period of pharmacologic response while minimizing side effects as compared to conventional rapid release dosage forms. Such longer periods of response provide for many inherent benefits that are not achieved with the corresponding short acting, immediate release preparations.

In some embodiments, the solid dosage forms described herein are formulated as enteric coated delayed release oral dosage forms, i.e., as an oral dosage form of a pharmaceutical composition as described herein which utilizes an enteric coating to affect release in the small intestine or large intestine. In one aspect, the enteric coated dosage form is a compressed or molded or extruded tablet/mold (coated or uncoated) containing granules, powder, pellets, beads or particles of the active ingredient and/or other composition components, which are themselves coated or uncoated. In one aspect, the enteric coated oral dosage form is in the form of a capsule containing pellets, beads or granules.

Conventional coating techniques such as spray or pan coating are employed to apply coatings. The coating thickness must be sufficient to ensure that the oral dosage form remains intact until the desired site of topical delivery in the intestinal tract is reached.

In other embodiments, the formulations described herein are delivered using a pulsatile dosage form. A pulsatile dosage form is capable of providing one or more immediate release pulses at predetermined time points after a controlled lag time or at specific sites. Exemplary pulsatile dosage forms and methods of their manufacture are disclosed in U.S. Pat. Nos. 5,011,692, 5,017,381, 5,229,135, 5,840,329 and 5,837,284. In one embodiment, the pulsatile dosage form includes at least two groups of particles, (i.e. multiparticulate) each containing the formulation described herein. The first group of particles provides a substantially immediate dose of the active compound upon ingestion by a mammal. The first group of particles is either uncoated or include a coating and/or sealant. In one aspect, the second group of particles comprises coated particles. The coating on the second group of particles provides a delay of from about 2 hours to about 7 hours following ingestion before release of the second dose. Suitable coatings for pharmaceutical compositions are described herein or in the art.

In some embodiments, pharmaceutical formulations are provided that include particles of a compound of Formula (I), or a pharmaceutically acceptable salt thereof, and at least one dispersing agent or suspending agent for oral administration to a subject. In some embodiments, the formulations are a powder and/or granules for suspension, and upon admixture with water, a substantially uniform suspension is obtained.

In one aspect, liquid formulation dosage forms for oral administration are in the form of aqueous suspensions selected from the group including, but not limited to, pharmaceutically acceptable aqueous oral dispersions, emulsions, solutions, elixirs, gels, and syrups. See, e.g., Singh et al., Encyclopedia of Pharmaceutical Technology, 2nd Ed., pp. 754-757 (2002). In addition to the particles of the compound of Formula (I), or a pharmaceutically acceptable salt thereof, the liquid dosage forms include additives, such as: (a) disintegrating agents; (b) dispersing agents; (c) wetting agents; (d) at least one preservative, (e) viscosity enhancing agents, (f) at least one sweetening agent, and (g) at least one flavoring agent. In some embodiments, the aqueous dispersions further include a crystalline inhibitor.

Buccal formulations that include a compound of Formula (I), or a pharmaceutically acceptable salt thereof, are administered using a variety of formulations known in the art. For example, such formulations include, but are not limited to, U.S. Pat. Nos. 4,229,447, 4,596,795, 4,755,386, and 5,739,136. In addition, the buccal dosage forms described herein optionally further include a bioerodible (hydrolysable) polymeric carrier that also serves to adhere the dosage form to the buccal mucosa. For buccal or sublingual administration, the compositions optionally take the form of tablets, lozenges, or gels formulated in a conventional manner.

In some embodiments, a compound of Formula (I), or a pharmaceutically acceptable salt thereof, is prepared part of a transdermal dosage form. In one embodiment, the transdermal formulations described herein include at least three components: (1) a formulation of a compound of Formula (I), or a pharmaceutically acceptable salt thereof, (2) a penetration enhancer; and (3) an aqueous adjuvant. In some embodiments the transdermal formulations include additional components such as, but not limited to, gelling agents, creams and ointment bases, and the like. In some embodiments, the transdermal formulation further includes a woven or non-woven backing material to enhance absorption and prevent the removal of the transdermal formulation from the skin. In other embodiments, the transdermal formulations described herein maintain a saturated or supersaturated state to promote diffusion into the skin.

In one aspect, formulations suitable for transdermal administration of compounds described herein employ transdermal delivery devices and transdermal delivery patches and include lipophilic emulsions or buffered, aqueous solutions, dissolved and/or dispersed in a polymer or an adhesive. In one aspect, such patches are constructed for continuous, pulsatile, or on demand delivery of pharmaceutical agents. Still further, transdermal delivery of the compounds described herein is accomplished by means of iontophoretic patches and the like. In one aspect, transdermal patches provide controlled delivery of the active compound. In one aspect, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

In one aspect, a compound of Formula (I), or a pharmaceutically acceptable salt thereof, is formulated into a pharmaceutical composition suitable for intramuscular, subcutaneous, or intravenous injection. In one aspect, formulations suitable for intramuscular, subcutaneous, or intravenous injection include physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles include water, ethanol, polyols (propyleneglycol, polyethylene-glycol, glycerol, cremophor and the like), vegetable oils and organic esters, such as ethyl oleate. In some embodiments, formulations suitable for subcutaneous injection contain additives such as preserving, wetting, emulsifying, and dispensing agents. Prolonged absorption of the injectable pharmaceutical form is optionally brought about by the use of agents delaying absorption, such as aluminum monostearate and gelatin.

For intravenous injections, compounds described herein are formulated in aqueous solutions, preferably in physiologically compatible buffers such as Hank's solution, Ringer's solution, or physiological saline buffer.

For transmucosal administration, penetrants appropriate to the barrier to be permeated are used in the formulation. Such penetrants are generally known in the art. For other parenteral injections, appropriate formulations include aqueous or nonaqueous solutions, preferably with physiologically compatible buffers or excipients. Such excipients are known.

Parenteral injections involve either bolus injection and/or continuous infusion. Formulations for injection are optionally presented in unit dosage form, e.g., in ampoules or in multi-dose containers, with an added preservative. In some embodiments, the pharmaceutical composition described herein are in a form suitable for parenteral injection as a sterile suspensions, solutions or emulsions in oily or aqueous vehicles, and contain formulatory agents such as suspending, stabilizing and/or dispersing agents. In one aspect, the active ingredient is in powder form for constitution with a suitable vehicle, e.g., sterile pyrogen-free water, before use.

In certain embodiments, delivery systems for pharmaceutical compounds are employed, such as, for example, liposomes and emulsions. In certain embodiments, compositions provided herein also optionally include an mucoadhesive polymer, selected from among, for example, carboxymethylcellulose, carbomer (acrylic acid polymer), poly(methylmethacrylate), polyacrylamide, polycarbophil, acrylic acid/butyl acrylate copolymer, sodium alginate and dextran.

In some embodiments, the compounds described herein are administered topically and are formulated into a variety of topically administrable compositions, such as solutions, suspensions, lotions, gels, pastes, medicated sticks, balms, creams or ointments. Such pharmaceutical compounds optionally contain solubilizers, stabilizers, tonicity enhancing agents, buffers and preservatives.

Methods of Dosing and Treatment Regimens

In one embodiment, the compounds of Formula (I), or a pharmaceutically acceptable salt thereof, are used in the preparation of medicaments for the treatment of diseases or conditions in a mammal that would benefit from a reduction of estrogen receptor activity. Methods for treating any of the diseases or conditions described herein in a mammal in need of such treatment, involves administration of pharmaceutical compositions that include at least one compound of Formula (I) or a pharmaceutically acceptable salt, active metabolite, prodrug, or pharmaceutically acceptable solvate thereof, in therapeutically effective amounts to said mammal.

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation clinical trial.

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in a patient, effective amounts for this use will depend on the severity and course of the disease, disorder or condition, previous therapy, the patient's health status and response to the drugs, and the judgment of the treating physician. In one aspect, prophylactic treatments include administering to a mammal, who previously experienced at least one symptom of the disease being treated and is currently in remission, a pharmaceutical composition comprising a compound of Formula (I), or a pharmaceutically acceptable salt thereof, in order to prevent a return of the symptoms of the disease or condition.

In certain embodiments wherein the patient's condition does not improve, upon the doctor's discretion the administration of the compounds are administered chronically, that is, for an extended period of time, including throughout the duration of the patient's life in order to ameliorate or otherwise control or limit the symptoms of the patient's disease or condition.

In certain embodiments wherein a patient's status does improve, the dose of drug being administered is temporarily reduced or temporarily suspended for a certain length of time (i.e., a "drug holiday"). In specific embodiments, the length of the drug holiday is between 2 days and 1 year, including by way of example only, 2 days, 3 days, 4 days, 5 days, 6 days, 7 days, 10 days, 12 days, 15 days, 20 days, 28 days, or more than 28 days. The dose reduction during a drug holiday is, by way of example only, by 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

Once improvement of the patient's conditions has occurred, a maintenance dose is administered if necessary. Subsequently, in specific embodiments, the dosage or the frequency of administration, or both, is reduced, as a function of the symptoms, to a level at which the improved disease, disorder or condition is retained. In certain embodiments, however, the patient requires intermittent treatment on a long-term basis upon any recurrence of symptoms.

The amount of a given agent that corresponds to such an amount varies depending upon factors such as the particular compound, disease condition and its severity, the identity (e.g., weight, sex) of the subject or host in need of treatment, but nevertheless is determined according to the particular circumstances surrounding the case, including, e.g., the specific agent being administered, the route of administration, the condition being treated, and the subject or host being treated.

In general, however, doses employed for adult human treatment are typically in the range of 0.01 mg-5000 mg per day. In one aspect, doses employed for adult human treatment are from about 1 mg to about 1000 mg per day. In one embodiment, the desired dose is conveniently presented in a single dose or in divided doses administered simultaneously or at appropriate intervals, for example as two, three, four or more sub-doses per day.

In one embodiment, the daily dosages appropriate for the compound of Formula (I), or a pharmaceutically acceptable salt thereof, described herein are from about 0.01 to about 50 mg/kg per body weight. In some embodiments, the daily dosage or the amount of active in the dosage form are lower or higher than the ranges indicated herein, based on a number of variables in regard to an individual treatment regime. In various embodiments, the daily and unit dosages are altered depending on a number of variables including, but not limited to, the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens are determined by standard pharmaceutical procedures in cell cultures or experimental animals, including, but not limited to, the determination of the $LD_{50}$ and the $ED_{50}$. The dose ratio between the toxic and therapeutic effects is the therapeutic index and it is expressed as the ratio between $LD_{50}$ and $ED_{50}$. In certain embodiments, the data obtained from cell culture assays and animal studies are used in formulating the therapeutically effective daily dosage range and/or the therapeutically effective unit dosage amount for use in mammals, including humans. In some embodiments, the daily dosage amount of the compounds described herein lies within a range of circulating concentrations that include the $ED_{50}$ with minimal toxicity. In certain embodiments, the daily dosage range and/or the unit dosage amount varies within this range depending upon the dosage form employed and the route of administration utilized.

Combination Treatments

In certain instances, it is appropriate to administer at least one compound of Formula (I), or a pharmaceutically acceptable salt thereof, in combination with one or more other therapeutic agents. In certain embodiments, the pharmaceutical composition further comprises one or more anti-cancer agents.

In one embodiment, the therapeutic effectiveness of one of the compounds described herein is enhanced by administration of an adjuvant (i.e., by itself the adjuvant has minimal therapeutic benefit, but in combination with another therapeutic agent, the overall therapeutic benefit to the patient is enhanced). Or, in some embodiments, the benefit experienced by a patient is increased by administering one of the compounds described herein with another therapeutic agent (which also includes a therapeutic regimen) that also has therapeutic benefit.

In one specific embodiment, a compound of Formula (I), or a pharmaceutically acceptable salt thereof, is co-administered with a second therapeutic agent, wherein the compound of Formula (I), or a pharmaceutically acceptable salt thereof, and the second therapeutic agent modulate different aspects of the disease, disorder or condition being treated, thereby providing a greater overall benefit than administration of either therapeutic agent alone.

In any case, regardless of the disease, disorder or condition being treated, the overall benefit experienced by the patient is simply be additive of the two therapeutic agents or the patient experiences a synergistic benefit.

In certain embodiments, different therapeutically-effective dosages of the compounds disclosed herein will be utilized in formulating pharmaceutical composition and/or in treatment regimens when the compounds disclosed herein are administered in combination with one or more additional agent, such as an additional therapeutically effective drug, an adjuvant or the like. Therapeutically-effective dosages of drugs and other agents for use in combination treatment regimens is optionally determined by means similar to those set forth hereinabove for the actives themselves. Furthermore, the methods of prevention/treatment described herein encompasses the use of metronomic dosing, i.e., providing more frequent, lower doses in order to minimize toxic side effects. In some embodiments, a combination treatment regimen encompasses treatment regimens in which administration of a compound of Formula (I), or a pharmaceutically acceptable salt thereof, is initiated prior to, during, or after treatment with a second agent described herein, and continues until any time during treatment with the second agent or after termination of treatment with the second agent. It also includes treatments in which a compound of Formula (I), or a pharmaceutically acceptable salt thereof, and the second agent being used in combination are administered simultaneously or at different times and/or at decreasing or increasing intervals during the treatment period. Combination treatment further includes periodic treatments that start and stop at various times to assist with the clinical management of the patient.

It is understood that the dosage regimen to treat, prevent, or ameliorate the condition(s) for which relief is sought, is modified in accordance with a variety of factors (e.g. the disease, disorder or condition from which the subject suffers; the age, weight, sex, diet, and medical condition of the subject). Thus, in some instances, the dosage regimen actually employed varies and, in some embodiments, deviates from the dosage regimens set forth herein.

For combination therapies described herein, dosages of the co-administered compounds vary depending on the type of co-drug employed, on the specific drug employed, on the disease or condition being treated and so forth. In additional embodiments, when co-administered with one or more other therapeutic agents, the compound provided herein is administered either simultaneously with the one or more other therapeutic agents, or sequentially.

In combination therapies, the multiple therapeutic agents (one of which is one of the compounds described herein) are administered in any order or even simultaneously. If administration is simultaneous, the multiple therapeutic agents are, by way of example only, provided in a single, unified form, or in multiple forms (e.g., as a single pill or as two separate pills).

The compounds of Formula (I), or a pharmaceutically acceptable salt thereof, as well as combination therapies, are administered before, during or after the occurrence of a disease or condition, and the timing of administering the composition containing a compound varies. Thus, in one embodiment, the compounds described herein are used as a prophylactic and are administered continuously to subjects with a propensity to develop conditions or diseases in order to prevent the occurrence of the disease or condition. In another embodiment, the compounds and compositions are administered to a subject during or as soon as possible after the onset of the symptoms. In specific embodiments, a compound described herein is administered as soon as is practicable after the onset of a disease or condition is detected or suspected, and for a length of time necessary for the treatment of the disease. In some embodiments, the length required for treatment varies, and the treatment length is adjusted to suit the specific needs of each subject. For example, in specific embodiments, a compound described herein or a formulation containing the compound is administered for at least 2 weeks, about 1 month to about 5 years.

Exemplary Agent for Use in Combination Therapy

In some embodiments, methods for treatment of estrogen receptor-dependent or estrogen receptor-mediated conditions or diseases, such as proliferative disorders, including cancer, comprises administration to a mammal a compound of Formula (I), or a pharmaceutically acceptable salt thereof, in combination with at least one additional therapeutic agent.

In some embodiments, a compound of Formula (I), or a pharmaceutically acceptable salt thereof, in combination with hormone blocking therapy, chemotherapy, radiation therapy, monoclonal antibodies, or combinations thereof.

Hormone blocking therapy includes the use of agents that block the production of estrogens or block the estrogen receptors. In some embodiments, hormone blocking therapy includes the use of estrogen receptor modulators and/or aromatase inhibitors. Estrogen receptor modulators include triphenylethylene derivatives (e.g. tamoxifen, toremifene, droloxifene, 3-hydroxytamoxifen, idoxifene, TAT-59 (a phosphorylated derivative of 4-hydroxytamoxifen) and GW5638 (a carboxylic acid derivative of tamoxifen)); non-steroidal estrogen receptor modulators (e.g. raloxifene, LY353381 (SERM3) and LY357489); steroidal estrogen receptor modulators (e.g. ICI-182,780). Aromatase inhibitors include steroidal aromatase inhibitors and non-steroidal aromatase inhibitors. Steroidal aromatase inhibitors include, but are not limited to, such exemestane. Non-steroidal aromatase inhibitors include, but are not limited to, as anastrozole, and letrozole.

Chemotherapy includes the use of anti-cancer agents.

Monoclonal antibodies include, but are not limited to, trastuzumab (Herceptin).

In some embodiments, the at least one additional therapeutic agent for use in combination with a compound of Formula (I), or a pharmaceutically acceptable salt thereof, include one or more of the following: abiraterone; abarelix; adriamycin; actinomycin; acivicin; aclarubicin; acodazole hydrochloride; acronine; adozelesin; aldesleukin; alemtuzumab; allopurinol; alitretinoin; altretamine; ambomycin; ametantrone acetate; aminoglutethimide; aminolevulinic acid; amifostine; amsacrine; anastrozole; anthramycin; aprepitant; arsenic trioxide; asparaginase; asperlin; azacitidine; azetepa; azotomycin; batimastat; bendamustine hydrochloride; benzodepa; bevacizumab; bexarotene; bicalutamide; bisantrene hydrochloride; bisnafide dimesylate; bizelesin; bleomycin; bleomycin sulfate; bortezomib; brequinar sodium; bropirimine; busulfan; cactinomycin; calusterone; caracemide; carbetimer; carboplatin; carmustine; carubicin hydrochloride; carzelesin; capecitabine; cedefingol; cetuximab; chlorambucil; cirolemycin; cisplatin; cladribine; clofarabine; crisnatol mesylate; cyclophosphamide; cytarabine; dacarbazine; dasatinib; daunorubicin hydrochloride; dactinomycin; darbepoetin alfa; decitabine; degarelix; denileukin diftitox; dexormaplatin; dexrazoxane hydrochloride; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; eltrombopag olamine; enloplatin; enpromate; epipropidine; epirubicin hydrochloride; epoetin alfa; erbulozole; erlotinib hydrochloride; esorubicin hydrochloride; estramustine; estramustine phosphate sodium; etanidazole; etoposide; etoposide phosphate; etoprine; everolimus; exemestane; fadrozole hydrochloride; fazarabine; fenretinide; filgrastim; floxuridine; fludarabine phosphate; fluorouracil; flurocitabine; fosquidone; fostriecin sodium; fulvestrant; gefitinib; gemcitabine; gemcitabine hydrochloride; gemcitabine-cisplatin; gemtuzumab ozogamicin; goserelin acetate; histrelin acetate; hydroxyurea; idarubicin hydrochloride; ifosfamide; iimofosine; ibritumomab tiuxetan; idarubicin; ifosfamide; imatinib mesylate; imiquimod; interleukin II (including recombinant interleukin II, or rIL2), interferon alfa-2a; interferon alfa-2b; interferon alfa-n1; interferon alfa-n3; interferon beta-1 a; interferon gamma-1 b; iproplatin; irinotecan hydrochloride; ixabepilone; lanreotide acetate; lapatinib; lenalidomide; letrozole; leuprolide acetate; leucovorin calcium; leuprolide acetate; levamisole; liposomal cytarabine; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; methoxsalen; metoprine; meturedepa; mitindomide; mitocarcin; mitocromin; mitogillin; mitomalcin; mitomycin C; mitosper; mitotane; mitoxantrone hydrochloride; mycophenolic acid; nandrolone phenpropionate; nelarabine; nilotinib; nocodazoie; nofetumomab; nogalamycin; ofatumumab; oprelvekin; ormaplatin; oxaliplatin; oxisuran; paclitaxel; palifermin; palonosetron hydrochloride; pamidronate; peg-filgrastim; pemetrexed disodium; pentostatin; panitumumab; pazopanib hydrochloride; pemetrexed disodium; plerixafor; pralatrexate; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; quinacrine; raloxifene hydrochloride; rasburicase; recombinant HPV bivalent vaccine; recombinant HPV quadrivalent vaccine; riboprine; rogletimide; rituximab; romidepsin; romiplostim; safingol; safingol hydrochloride; sargramostim; semustine; simtrazene; sipuleucel-T; sorafenib; sparfosate sodium; sparsomycin; spirogermanium hydrochloride; spiromustine; spiroplatin; streptonigrin; streptozocin; sulofenur; sunitinib malate; talisomycin; tamoxifen citrate; tecogalan sodium; tegafur; teloxantrone hydrochloride; temozolomide; temoporfin; temsirolimus; teniposide; teroxirone; testolactone; thalidomide; thiamiprine; thioguanine; thiotepa; tiazofurin; tirapazamine; topotecan hydrochloride; toremifene; tositumomab and I 131 Iodine tositumomab; trastuzumab; trestolone acetate; tretinoin; triciribine phosphate; trimetrexate; trimetrexate glucuronate; triptorelin; tubulozole hydrochloride; uracil mustard; uredepa; valrubicin; vapreotide; verteporfin; vinblastine; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorinostat; vorozole; zeniplatin; zinostatin; zoledronic acid; and zorubicin hydrochloride.

In some embodiments, the at least one additional chemotherapeutic agent is selected from, by way of example only, alemtuzumab, arsenic trioxide, asparaginase (pegylated or non-), bevacizumab, cetuximab, platinum-based compounds such as cisplatin, cladribine, daunorubicin/doxorubicin/idarubicin, irinotecan, fludarabine, 5-fluorouracil, gemtuzumab, methotrexate, taxol, temozolomide, thioguanine, or classes of drugs including hormones (an antiestrogen, an antiandrogen, or gonadotropin releasing hormone analogues, interferons such as alpha interferon, nitrogen mustards such as busulfan or melphalan or mechlorethamine, retinoids such as tretinoin, topoisomerase inhibitors such as irinotecan or topotecan, tyrosine kinase inhibitors such as gefinitinib or imatinib, or agents to treat signs or symptoms induced by such therapy including allopurinol, filgrastim, granisetron/ondansetron/palonosetron, dronabinol.

In one aspect, the compound of Formula (I), or a pharmaceutically acceptable salt thereof, is administered or formulated in combination with one or more anti-cancer agents. In some embodiments, one or more of the anti-cancer agents are proapoptotic agents. Examples of anti-cancer agents include, but are not limited to, any of the following: gossypol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib, geldanamycin, 17-N-Allylamino-17-Demethoxygeldanamycin (17-AAG), flavopiridol, LY294002, bortezomib, trastuzumab, BAY 11-7082, PKC412, or PD184352, paclitaxel, and analogs of paclitaxel. Compounds that have the basic taxane skeleton as a common structure feature, have also been shown to have the ability to arrest cells in the G2-M phases due to stabilized microtubules and are optionally useful for treating cancer in combination with the compounds described herein.

Further examples of anti-cancer agents for use in combination with a compound of Formula (I), or a pharmaceutically acceptable salt thereof, include inhibitors of mitogen-activated protein kinase signaling, e.g., U0126, PD98059, PD184352, PD0325901, ARRY-142886, SB239063, SP600125, BAY 43-9006, wortmannin, or LY294002; Syk inhibitors; mTOR inhibitors; and antibodies (e.g., rituxan).

Further examples of anti-cancer agents for use in combination with a compound of Formula (I), or a pharmaceutically acceptable salt thereof, include aromatase inhibitors. Aromatase inhibitors include steroidal aromatase inhibitors and non-steroidal aromatase inhibitors. Steroidal aromatase inhibitors include, but are not limited to, exemestane. Non-steroidal aromatase inhibitors include, but are not limited to, anastrozole, and letrozole.

Yet other anticancer agents for use in combination with a compound of Formula (I), or a pharmaceutically acceptable salt thereof, include alkylating agents, antimetabolites, natural products, or hormones, e.g., nitrogen mustards (e.g., mechloroethamine, cyclophosphamide, chlorambucil, etc.), alkyl sulfonates (e.g., busulfan), nitrosoureas (e.g., carmustine, lomusitne, etc.), or triazenes (decarbazine, etc.). Examples of antimetabolites include but are not limited to folic acid analog (e.g., methotrexate), or pyrimidine analogs (e.g., Cytarabine), purine analogs (e.g., mercaptopurine, thioguanine, pentostatin).

Examples of natural products for use in combination with a compound of Formula (I), or a pharmaceutically acceptable salt thereof, include but are not limited to vinca alkaloids (e.g., vinblastin, vincristine), epipodophyllotoxins (e.g., etoposide), antibiotics (e.g., daunorubicin, doxorubicin, bleomycin), enzymes (e.g., L-asparaginase), or biological response modifiers (e.g., interferon alpha).

Examples of alkylating agents for use in combination with a compound of Formula (I), or a pharmaceutically acceptable salt thereof, include, but are not limited to, nitrogen mustards (e.g., mechloroethamine, cyclophosphamide, chlorambucil, meiphalan, etc.), ethylenimine and methylmelamines (e.g., hexamethylmelamine, thiotepa), alkyl sulfonates (e.g., busulfan), nitrosoureas (e.g., carmustine, lomusitne, semustine, streptozocin, etc.), or triazenes (decarbazine, etc.).

In some embodiments, a compound of Formula (I), or a pharmaceutically acceptable salt thereof, is used to treat cancer in combination with: a second antiestrogen (e.g., tamoxifen), an antiandrogen (e.g., bicalutamide, flutamide), a gonadotropin releasing hormone analog (e.g., leuprolide).

Other agents that are optionally used in the methods and compositions described herein for the treatment or prevention of cancer include platinum coordination complexes (e.g., cisplatin, carboblatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide).

Examples of anti-cancer agents which act by arresting cells in the G2-M phases due to stabilized microtubules include without limitation the following marketed drugs and drugs in development: Erbulozole, Dolastatin 10, Mivobulin isethionate, Vincristine, NSC-639829, Discodermolide, ABT-751, Altorhyrtins (such as Altorhyrtin A and Altorhyrtin C), Spongistatins (such as Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride, Epothilones (such as Epothilone A, Epothilone B, Epothilone C, Epothilone D, Epothilone E, Epothilone F, Epothilone B N-oxide, Epothilone A N-oxide, 16-aza-epothilone B, 21-aminoepothilone B, 21-hydroxyepothilone D, 26-fluoroepothilone, Auristatin PE, Soblidotin, Vincristine sulfate, Cryptophycin 52, Vitilevuamide, Tubulysin A, Canadensol, Centaureidin, Oncocidin A1 Fijianolide B, Laulimalide, Narcosine, Nascapine, Hemiasterlin, Vanadocene acetylacetonate, Indanocine Eleutherobins (such as Desmethyleleutherobin, Desaetyleleutherobin, Isoeleutherobin A, and Z-Eleutherobin), Caribaeoside, Caribaeolin, Halichondrin B, Diazonamide A, Taccalonolide A, Diozostatin, (−)-Phenylahistin, Myoseverin B, Resverastatin phosphate sodium.

In one aspect, a compound of Formula (I), or a pharmaceutically acceptable salt thereof, is co-administered with thrombolytic agents (e.g., alteplase anistreplase, streptokinase, urokinase, or tissue plasminogen activator), heparin, tinzaparin, warfarin, dabigatran (e.g., dabigatran etexilate), factor Xa inhibitors (e.g., fondaparinux, draparinux, rivaroxaban, DX-9065a, otamixaban, LY517717, or YM150), ticlopidine, clopidogrel, CS-747 (prasugrel, LY640315), ximelagatran, or BIBR 1048.

In some embodiments, a compound of Formula (I), or a pharmaceutically acceptable salt thereof, is used in combination with anti-emetic agents to treat nausea or emesis, which result from the use of a compound of Formula (I), or a pharmaceutically acceptable salt thereof, anti-cancer agent(s) and/or radiation therapy.

Anti-emetic agents include, but are not limited to: neurokinin-1 receptor antagonists, 5HT3 receptor antagonists (such as ondansetron, granisetron, tropisetron, palonosetron, and zatisetron), $GABA_B$ receptor agonists (such as baclofen), corticosteroids (such as dexamethasone, prednisone, prednisolone, or others), dopamine antagonists (such as, but not limited to, domperidone, droperidol, haloperidol, chlorpromazine, promethazine, prochlorperazine, metoclopramide), antihistamines (H1 histamine receptor antagonists, such as but not limited to, cyclizine, diphenhydramine, dimenhydrinate, meclizine, promethazine, hydroxyzine), cannabinoids (such as but not limited to, cannabis, marinol, dronabinol), and others (such as, but not limited to, trimethobenzamide; ginger, emetrol, propofol).

In some embodiments, a compound of Formula (I), or a pharmaceutically acceptable salt thereof, is used in combination with an agent useful in the treatment of anemia. Such an anemia treatment agent is, for example, a continuous eythropoiesis receptor activator (such as epoetin-α).

In some embodiments, a compound of Formula (I), or a pharmaceutically acceptable salt thereof, is used in combination with an agent useful in the treatment of neutropenia. Examples of agents useful in the treatment of neutropenia include, but are not limited to, a hematopoietic growth factor which regulates the production and function of neutrophils such as a human granulocyte colony stimulating factor, (G-CSF). Examples of a G-CSF include filgrastim.

In some embodiments, a compound of Formula (I), or a pharmaceutically acceptable salt thereof, is administered with corticosteroids. Corticosteroids, include, but are not limited to: betamethasone, prednisone, alclometasone, aldosterone, amcinonide, beclometasone, betamethasone, budesonide, ciclesonide, clobetasol, clobetasone, clocortolone, cloprednol, cortisone, cortivazol, deflazacort, deoxycorticosterone, desonide, desoximetasone, desoxycortone, dexamethasone, diflorasone, diflucortolone, difluprednate, fluclorolone, fludrocortisone, fludroxycortide, flumetasone, flunisolide, fluocinolone acetonide, fluocinonide, fluocortin, fluocortolone, fluorometholone, fluperolone, fluprednidene, fluticasone, formocortal, halcinonide, halometasone, hydrocortisone/cortisol, hydrocortisone aceponate, hydrocortisone buteprate, hydrocortisone butyrate, loteprednol, medrysone, meprednisone, methylprednisolone, methylprednisolone aceponate, mometasone furoate, parametasone, prednicarbate, prednisone/prednisolone, rimexolone, tixocortol, triamcinolone, and ulobetasol.

In one embodiment, a compound of Formula (I), or a pharmaceutically acceptable salt thereof, is administered to a mammal in combination with a non-steroidal anti-inflammatory drug (NSAID). NSAIDs include, but are not limited to: aspirin, salicylic acid, gentisic acid, choline magnesium salicylate, choline salicylate, choline magnesium salicylate, choline salicylate, magnesium salicylate, sodium salicylate, diflunisal, carprofen, fenoprofen, fenoprofen calcium, flurobiprofen, ibuprofen, ketoprofen, nabutone, ketolorac, ketorolac tromethamine, naproxen, oxaprozin, diclofenac, etodolac, indomethacin, sulindac, tolmetin, meclofenamate, meclofenamate sodium, mefenamic acid, piroxicam, meloxicam, COX-2 specific inhibitors (such as, but not limited to, celecoxib, rofecoxib, valdecoxib, parecoxib, etoricoxib, lumiracoxib, CS-502, JTE-522, L-745,337 and NS398).

In some embodiments, a compound of Formula (I), or a pharmaceutically acceptable salt thereof, is coadministered with an analgesic.

In some embodiments, a compound of Formula (I), or a pharmaceutically acceptable salt thereof, is used in combination with radiation therapy (or radiotherapy). Radiation therapy is the treatment of cancer and other diseases with ionizing radiation. Radiation therapy is optionally used to treat localized solid tumors, such as cancers of the skin, tongue, larynx, brain, breast, prostate, colon, uterus and/or cervix. It is also optionally used to treat leukemia and lymphoma (cancers of the blood-forming cells and lymphatic system, respectively).

A technique for delivering radiation to cancer cells is to place radioactive implants directly in a tumor or body cavity. This is called internal radiotherapy (brachytherapy, interstitial irradiation, and intracavitary irradiation are types of internal radiotherapy.) Using internal radiotherapy, the radiation dose is concentrated in a small area, and the patient stays in the hospital for a few days. Internal radiotherapy is frequently used for cancers of the tongue, uterus, prostate, colon, and cervix.

The term "radiotherapy" or "ionizing radiation" include all forms of radiation, including but not limited to α, β, and γ radiation and ultraviolet light.

Kits/Articles of Manufacture

For use in the therapeutic applications described herein, kits and articles of manufacture are also described herein. Such kits optionally comprise a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. The containers are formed from any acceptable material including, e.g., glass or plastic.

For example, the container(s) comprise(s) one or more compounds described herein, optionally in a composition or in combination with another agent as disclosed herein. The container(s) optionally have a sterile access port (for example the container is an intravenous solution bag or a vial having a stopper pierceable by a hypodermic injection needle). Such kits optionally comprising a compound with an identifying description or label or instructions relating to its use in the methods described herein.

A kit will typically comprise one or more additional containers, each with one or more of various materials (such as reagents, optionally in concentrated form, and/or devices) desirable from a commercial and user standpoint for use of a compound described herein. Non-limiting examples of such materials include, but not limited to, buffers, diluents, filters, needles, syringes; carrier, package, container, vial and/or tube labels listing contents and/or instructions for use, and package inserts with instructions for use. A set of instructions will also typically be included.

A label is optionally on or associated with the container. A label is optionally on a container when letters, numbers or other characters forming the label are attached, molded or etched into the container itself, a label is optionally associated with a container when it is present within a receptacle or carrier that also holds the container, e.g., as a package insert. A label is optionally used to indicate that the contents are to be used for a specific therapeutic application. The label optionally indicates directions for use of the contents, such as in the methods described herein.

EXAMPLES

These examples are provided for illustrative purposes only and not to limit the scope of the claims provided herein.

Example 1

Preparation of 5-Bromo-1-(tetrahydro-2H-pyran-2-yl)-1H-indazole (Intermediate 1)

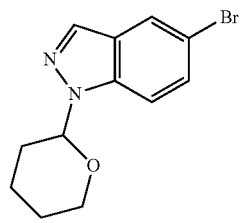 [SMILES: Brc1ccc2c(cnn2C2CCCCO2)c1]

A 250-mL round-bottom flask equipped with a magnetic stir bar, a rubber septum, and a $N_2$ inlet was charged with 5-bromo-1H-indazole (10 g, 50.7 mmol) and anhydrous dichloromethane (101 mL). To this solution, 3,4-dihydro-2H-pyran (23 mL, 253.8 mmol) was added in one portion at room temperature followed by addition of PPTS (1.28 g, 5 mmol). The resulting mixture was stirred at room temperature for 48 h. Upon completion by TLC, the reaction mixture was quenched with water and extracted with dichloromethane (3×100 mL). The combined organic extracts were washed with water (100 mL), washed with brine (50 mL), dried over sodium sulfate, filtered, concentrated, and purified by silica gel chromatography (0-10% ethyl acetate in hexanes) to give the title compound (13 g) as a pale yellow oil. $^1$H NMR (300 MHz, DMSO-$d_6$): δ 8.10 (s, 1H), 8.02 (d, 1H), 7.73 (d, 1H), 7.53 (dd, 1H), 5.86 (dd, 1H), 3.89-3.85 (m, 1H), 3.73-3.69 (m, 1H), 2.43-2.31 (m, 1H), 2.06-1.92 (m, 2H), 1.80-1.64 (m, 1H), 1.60-150 (m, 2H).

Example 2

Preparation of 5-Ethynyl-1-(tetrahydro-2H-pyran-2-yl)-1H-indazole (Intermediate 2)

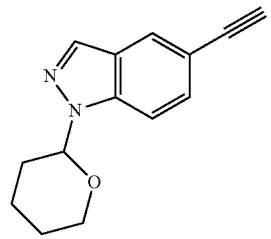 [SMILES: C#Cc1ccc2c(cnn2C2CCCCO2)c1]

Step 1: 1-(Tetrahydro-2H-pyran-2-yl)-5-((trimethylsilyl)ethynyl)-1H-indazole

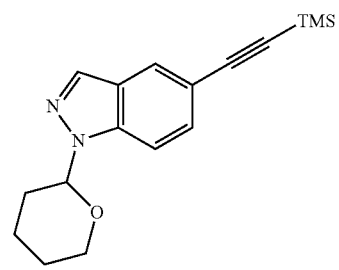 [SMILES: C[Si](C)(C)C#Cc1ccc2c(cnn2C2CCCCO2)c1]

To a 250-mL pressure tube, 5-bromo-1-(tetrahydro-2H-pyran-2-yl)-1H-indazole (11.9 g, 42.3 mmol; Intermediate 1), Pd(Ph$_3$P)$_2$Cl$_2$ (1.48 g, 0.05 mmol), CuI (0.8 g, 4.2 mmol) and THF/triethylamine (5:1, 85 mL) were added. This mixture was degassed with three vacuum/$N_2$ cycles, and then trimethylsilylacetylene (9 mL, 63.5 mmol) was added. The pressure tube was sealed and heated at 80° C. for 2 days. Upon completion by LCMS, the reaction mixture was cooled down to room temperature and filtered through Celite with ethyl acetate (200 mL). The filtrate was concentrated to give the crude product that was used directly in the next step. LCMS: 299 (M+H)$^+$.

Note: For this compound and other compounds prepared using this reaction, alternate procedures have been employed using an amine, such as triethylamine or pyrrolidine, as the sole solvent.

Step 2: 5-Ethynyl-1-(tetrahydro-2H-pyran-2-yl)-1H-indazole

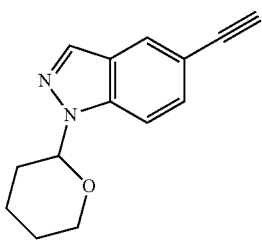 [SMILES: C#Cc1ccc2c(cnn2C2CCCCO2)c1]

A 250-mL round-bottom flask equipped with a magnetic stir bar, a rubber septum, and a N₂ inlet was charged with a solution of 1-(tetrahydro-2H-pyran-2-yl)-5-((trimethylsilyl)ethynyl)-1H-indazole (12.6 g, 42.2 mmol) in MeOH. To this solution, solid K₂CO₃ (0.58 g, 4.2 mmol) was added in one portion. The resulting mixture was stirred at room temperature for 4 h. Upon completion by TLC, the reaction mixture was filtered, concentrated, and purified by silica gel chromatography (0-10% ethyl acetate in hexanes) to give the title compound (4.7 g) as a pale yellow solid. ¹H NMR (300 MHz, DMSO-d₆): δ 8.13 (s, 1H), 7.96 (s, 1H), 7.75 (d, 1H), 7.47 (dd, 1H), 5.86 (dd, 1H), 4.10 (s, 1H), 3.90-3.86 (m, 1H), 3.78-3.68 (m, 1H), 2.43-2.32 (m, 1H), 2.06-1.93 (m, 2H), 1.81-1.66 (m, 1H), 1.60-1.50 (m, 2H).

Example 3

Preparation of 5-(But-1-yn-1-yl)-1-(tetrahydro-2H-pyran-2-yl)-1H-indazole (Intermediate 3)

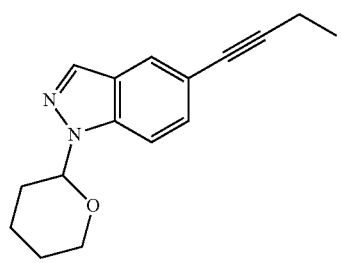 [SMILES: CCC#Cc1ccc2c(cnn2C2CCCCO2)c1]

A 250-mL round-bottom flask equipped with a magnetic stir bar, a rubber septum, and a N₂ inlet was charged with 5-ethynyl-1-(tetrahydro-2H-pyran-2-yl)-1H-indazole (4.2 g, 18.6 mmol; Intermediate 2) and anhydrous THF/TMEDA (9:1, 93 mL). This solution was cooled to −78° C. in an IPA/dry ice bath, and n-BuLi (17.4 mL solution in hexanes, 27.84 mmol) was added dropwise over 15 minutes. The resulting mixture was stirred for 30 minutes at −78° C., and then iodoethane (2.23 mL, 27.84 mmol) was added dropwise over 5 minutes. The mixture was gradually warmed to room temperature, stirred for 1 h, and then heated at 40° C. overnight. Upon completion by LCMS, the reaction mixture was cooled to room temperature, quenched with water (100 mL), and extracted with ethyl acetate (2×100 mL). The combined organics were washed with water (100 mL), washed with brine (50 mL), dried over sodium sulfate, filtered, concentrated, and purified by silica gel chromatography (0-10% ethyl acetate in hexanes) to give the title compound (1.42 g) as a pale yellow solid. ¹H NMR (300 MHz, DMSO-d₆): δ 8.08 (s, 1H), 7.82 (s, 1H), 7.69 (d, 1H), 7.39 (d, 1H), 5.84 (dd, 1H), 3.89-3.86 (m, 1H), 3.76-3.72 (m, 1H), 2.45-2.36 (m, 3H), 2.04-1.94 (m, 2H), 1.74 (m, 1H), 1.57-1.20 (m, 2H), 1.16 (t, 3H); LCMS: 255 (M+H)⁺.

Note: For this compound and other compounds prepared using this reaction, lithium bis(trimethylsilyl)amide has been employed as the base in THF at 0° C. followed by alkylation with alkyl-halide at reflux.

Example 4

Preparation of 5-(But-1-yn-1-yl)-1-(tetrahydro-2H-pyran-2-yl)-1H-benzo[d][1,2,3]triazole (Intermediate 4)

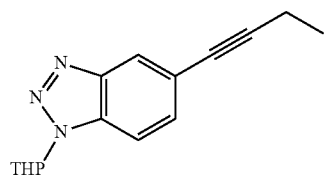

Step 1: 5-Bromo-1-(tetrahydro-2H-pyran-2-yl)-1H-benzo[d][1,2,3]triazole

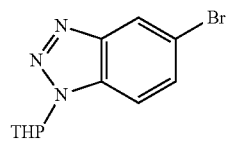

A 250-mL round-bottom flask equipped with a magnetic stir bar, a rubber septum and N₂ inlet was charged with 5-bromo-1H-benzo[d][1,2,3]triazole (4.5 g, 22.7 mmol) and anhydrous dichloromethane (114 mL). To this solution, 3,4-dihydro-2H-pyran (10.3 mL, 113.6 mmol) was added in one portion at room temperature followed by addition of PPTS (0.57 g, 2.27 mmol). The resulting mixture was stirred at room temperature for 48 h. The reaction was monitored by TLC. Upon completion, the reaction mixture was quenched with water and extracted with dichloromethane (3×100 mL). The combined organic layers were washed with saturated NaHCO₃ (50 mL), water (100 mL), and then brine (50 mL), dried over sodium sulfate, filtered and concentrated to give the crude product that was purified on a silica gel column eluted with 0-10% ethyl acetate in hexanes affording the title compound as a clear oil (3.6 g). LCMS: 198 [(M-THP+H)+H]⁺.

Step 2: 1-(Tetrahydro-2H-pyran-2-yl)-5-((trimethylsilyl)ethynyl)-1H-benzo[d][1,2,3]triazole

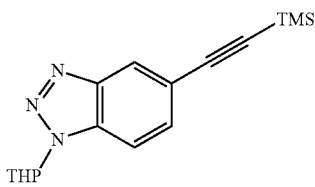

A 100-mL round-bottom flask equipped with a magnetic stir bar, a rubber septum and N$_2$ inlet was charged with 5-bromo-1-(tetrahydro-2H-pyran-2-yl)-1H-benzo[d][1,2,3]triazole (3.5 g, 12.4 mmol), Pd(Ph$_3$P)$_2$Cl$_2$ (0.87 g, 1.24 mmol), CuI (0.47 g, 0.48 mmol), and triethylamine (62 mL). This mixture was degassed with three vacuum/N$_2$ cycles. Trimethylsilylacetylene (3.5 mL, 24.8 mmol) was added, and the mixture was heated at 80° C. for 4 h. The reaction was monitored by LCMS. Upon completion, the reaction mixture was cooled down to room temperature, filtered through Celite, washed with ethyl acetate (100 mL), and concentrated. The crude product was purified on a silica gel column eluting with 5% ethyl acetate in hexanes to afford the title compound as a pale yellow oil (3.6 g). LCMS: 216 [(M-THP+H)+H]$^+$.

Step 3: 5-Ethynyl-1-(tetrahydro-2H-pyran-2-yl)-1H-benzo[d][1,2,3]triazole

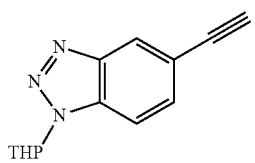

A 100-mL round-bottom flask equipped with a magnetic stir bar, a rubber septum and N$_2$ inlet was charged with a solution of 1-(tetrahydro-2H-pyran-2-yl)-5-((trimethylsilyl)ethynyl)-1H-benzo[d][1,2,3]triazole (3.5 g, 11.7 mmol) in MeOH (59 mL). To this solution, solid K$_2$CO$_3$ (0.16 g, 1.17 mmol) was added in one portion. The resulting mixture was stirred at room temperature for 5 h. Reaction was monitored by TLC. Upon completion, the reaction mixture was filtered and concentrated to give the crude material. This crude product was purified on a silica gel column eluted with 5% ethyl acetate in hexanes affording the title compound as a pale yellow solid (2.6 g). LCMS: 144 [(M-THP+H)+H]$^+$.

Step 4: 5-(But-1-yn-1-yl)-1-(tetrahydro-2H-pyran-2-yl)-1H-benzo[d][1,2,3]triazole

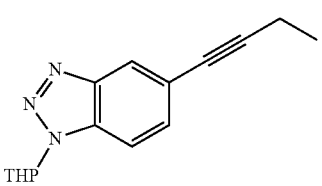

A 200-mL round-bottom flask equipped with a magnetic stir bar, a rubber septum and N$_2$ inlet was charged with 5-ethynyl-1-(tetrahydro-2H-pyran-2-yl)-1H-benzo[d][1,2,3]triazole (2.5 g, 11 mmol) and anhydrous THF (110 mL). This solution was then cooled down to 0° C. in an ice bath. Then, a solution of LiHMDS (27 mL, 1M THF, 27 mmol) was added dropwise over 15 minutes. The resulting mixture was stirred for 1 h at 0° C. To this mixture at 0° C., iodoethane (4.4 mL, 55 mmol) was added dropwise over 5 minutes. The mixture was gradually warmed to room temperature, stirred for 1 h, and then heated at reflux overnight. The reaction was monitored by LCMS. Upon completion, the reaction mixture was cooled down to room temperature, quenched with water (100 mL), and extracted with ethyl acetate (2×100 mL). The combined organics were washed with water (100 mL), washed with brine (50 mL), dried over sodium sulfate, filtered, and concentrated to give the crude product. This crude material was purified on a silica gel column eluted with 5% ethyl acetate in hexanes affording the title compound as a pale yellow oil (1.6 g). $^1$H NMR (300 MHz, DMSO-d$_6$): δ 7.92 (s, 1H), 7.85 (dd, 1H), 7.33 (dd, 1H), 6.01 (dd, 1H), 3.86-3.80 (m, 1H), 3.75-3.64 (m, 1H), 2.45-2.36 (m, 3H), 2.08-1.91 (m, 2H), 1.74-1.62 (m, 1H), 1.58-1.50 (m, 2H), 1.11 (t, 3H); LCMS: 172 [(M-THP+H)+H]$^+$.

The Intermediates in Table 2 were prepared from known or commercial starting materials following the procedures outlined for Intermediates 1-4.

TABLE 2

| | | Structure |
|---|---|---|
| Intermediate 5 | 6-(But-1-yn-1-yl)-1-(tetrahydro-2H-pyran-2-yl)-1H-indazole | 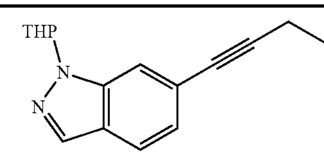 |
| Intermediate 6 | 4-(But-1-yn-1-yl)-1-(tetrahydro-2H-pyran-2-yl)-1H-indazole | 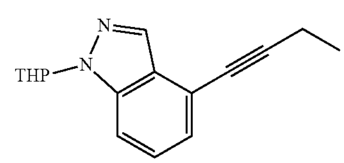 |
| Intermediate 7 | 1-(Tetrahydro-2H-pyran-2-yl)-5-(4,4,4-trideuterobut-1-yn-1-yl)-1H-indazole | 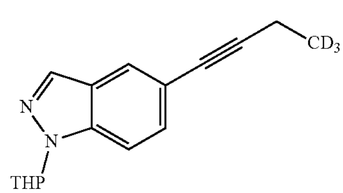 |
| Intermediate 8 | 5-(But-1-yn-1-yl)-7-chloro-1-(tetrahydro-2H-pyran-2-yl)-1H-indazole | 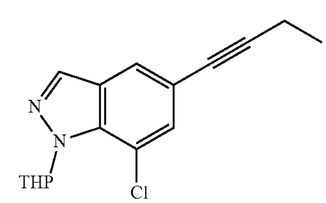 |
| Intermediate 9 | 5-(But-1-yn-1-yl)-7-methyl-1-(tetrahydro-2H-pyran-2-yl)-1H-indazole | 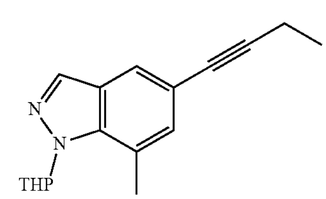 |

TABLE 2-continued

| | | |
|---|---|---|
| Intermediate 10 | 5-(But-1-yn-1-yl)-3-methyl-1-(tetrahydro-2H-pyran-2-yl)-1H-indazole | 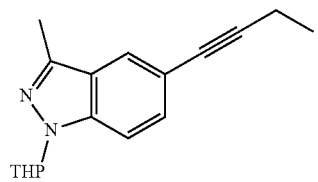 |
| Intermediate 11 | 5-(But-1-yn-1-yl)-3-chloro-1-(tetrahydro-2H-pyran-2-yl)-1H-indazole | 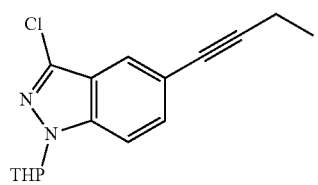 |
| Intermediate 12 | 5-(Prop-1-yn-1-yl)-1-(tetrahydro-2H-pyran-2-yl)-1H-indazole | 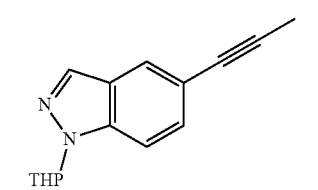 |
| Intermediate 13 | 5-(Pent-1-yn-1-yl)-1-(tetrahydro-2H-pyran-2-yl)-1H-indazole | 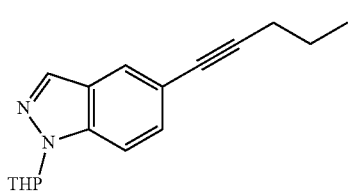 |
| Intermediate 14 | 5-(Perdeuterobut-1-yn-1-yl)-1-(tetrahydro-2H-pyran-2-yl)-1H-indazole | 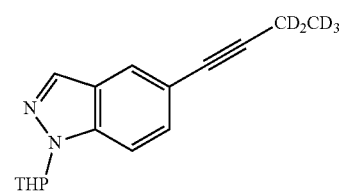 |

Example 5

Preparation of 5-(But-1-yn-1-yl)-4-methyl-1-(tetrahydro-2H-pyran-2-yl)-1H-indazole (Intermediate 15)

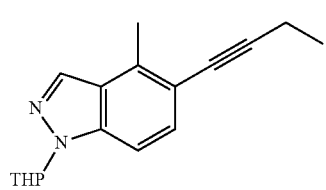

Step 1: 4-Methyl-1-(tetrahydro-2H-pyran-2-yl)-5-((trimethylsilyl)ethynyl)-1H-indazole

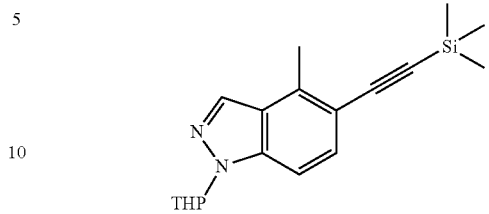

A mixture of 5-bromo-4-methyl-1-(tetrahydro-2H-pyran-2-yl)-1H-indazole (915 mg, 3.10 mmol; prepared from 5-bromo-4-methyl-H-indazole following the procedure outlined for Intermediate 1), copper iodide (72 mg, 0.38 mmol), sodium tetrachloropalladate (55 mg, 0.19 mmol), 2-(di-tert-butylphosphino)-1-phenyl-1H-indole (128 mg, 0.379 mmol), and TMEDA:$H_2O$ (9:1, 10 mL) was degassed with three vacuum/nitrogen cycles. Ethynyltrimethylsilane was added to the reaction, and the mixture was heated at 80° C. for 90 min and then cooled to room temperature. The reaction mixture was filtered through Celite and the Celite was washed with ethyl acetate (100 mL). The filtrate was washed (2×50 mL sat'd $NaHCO_3$), dried ($Na_2SO_4$), and concentrated under reduced pressure. The crude material was purified on a silica gel column to yield the desired compound. $^1$H NMR (300 MHz, DMSO-$d_6$): δ 8.24 (s, 1H), 7.54 (d, 1H), 7.39 (d, 1H), 5.82 (dd, 1H), 3.88 (m, 1H), 3.71 (m, 1H), 2.63 (s, 3H), 2.39 (m, 1H), 2.00 (m, 2H), 1.72 (m, 1H), 1.58 (m, 2H), 0.24 (s, 9H); LCMS: 313 (M+H)$^+$ Step 2: 5-(But-1-yn-1-yl)-4-methyl-1-(tetrahydro-2H-pyran-2-yl)-1H-indazole

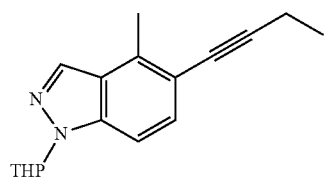

The title compound was prepared from 4-methyl-1-(tetrahydro-2H-pyran-2-yl)-5-((trimethylsilyl)ethynyl)-1H-indazole following the procedures outlined for Intermediate 2 (step 2) and Intermediate 3. $^1$H NMR (300 MHz, DMSO-$d_6$): δ 7.97 (s, 1H), 7.27 (d, 1H), 7.11 (d, 1H), 5.59 (dd, 1H), 3.58 (m, 1H), 3.50 (m, 1H), 2.38 (s, 3H), 2.17 (q, 2H), 2.13 (m, 1H), 1.77 (m, 2H), 1.50 (m, 1H), 1.36 (m, 2H), 0.98 (t, 3H).

The Intermediate in Table 3 was prepared from 5-bromo-6-methyl-1H-indazole following the procedures outlined for Intermediate 15.

TABLE 3

| | | |
|---|---|---|
| Intermediate 16 | 5-(But-1-yn-1-yl)-6-methyl-1-(tetrahydro-2H-pyran-2-yl)-1H-indazole | 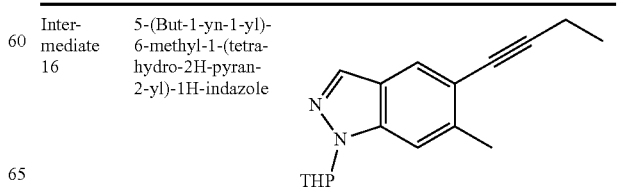 |

Example 6

Preparation of 5-(Cyclopropylethynyl)-1-(tetrahydro-2H-pyran-2-yl)-1H-indazole (Intermediate 17)

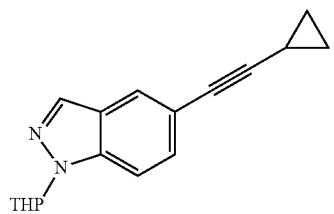

A 1 L three-necked round bottom flask was charged with 5-bromo-1-(tetrahydro-2H-pyran-2-yl)-1H-indazole (31.2 g, 111 mmol; Intermediate 1) and triethylamine (500 mL). The flask was degassed with three vacuum/$N_2$ cycles, followed by the addition of Pd(PPh$_3$)$_2$Cl$_2$ (7.7 g, 11 mmol) and CuI (2.1 g, 11 mmol) under $N_2$ atmosphere. The flask was again degassed with three vacuum/$N_2$ cycles. Ethynylcyclopropane (70% in toluene, 20.9 g, 222 mmol) was then added via syringe and the reaction mixture was stirred at 80° C. for 16 hours. Upon completion, the solvent was evaporated. The residue was diluted with dichloromethane (600 mL), washed with water (2×200 mL) and brine (200 mL), dried over anhydrous sodium sulfate, and concentrated in vacuo. The residue was further purified on silica gel column (1:100-1:20 EtOAc/petroleum ether) affording the title compound (27.0 g). $^1$H NMR (400 MHz, DMSO-d$_6$): δ 8.09 (s, 1H), 7.82 (s, 1H), 7.70 (d, 1H), 7.39 (m, 1H), 5.84 (dd, 1H), 3.91-3.87 (m, 1H), 3.78-3.73 (m, 1H), 2.52-2.37 (m, 1H), 2.05-1.94 (m, 2H), 1.76-1.72 (m, 1H), 1.60-1.52 (m, 3H), 0.92- 0.87 (m, 2H), 0.78-0.73 (m, 2H); LCMS: 267 (M+H)$^+$.

Example 7

Preparation of 5-(4-Methylpent-1-yn-1-yl)-1-(tetrahydro-2H-pyran-2-yl)-1H-indazole (Intermediate 18)

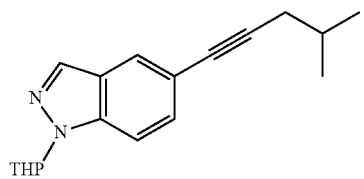

To a mixture of 5-bromo-1-(tetrahydro-2H-pyran-2-yl)-1H-indazole (3.0 g, 10.7 mmol; Intermediate 1), Pd(PPh$_3$)$_2$Cl$_2$ (1.03 g, 1.07 mmol) and CuI (203 mg, 1.07 mmol) in triethylamine (30 mL), was added 4-methylpent-1-yne (2.23 g, 27.8 mmol) under $N_2$ atmosphere. The resulting mixture was stirred at 80° C. for 16 hours under $N_2$ atmosphere. Upon completion, the reaction mixture was diluted with EtOAc and filtered. The filtrate was washed with water (3×10 mL), dried over Na$_2$SO$_4$ and concentrated in vacuo. The residue was purified by column chromatography on silica gel (0~10% EtOAc in petroleum ether) affording the title compound (2.2 g) as yellow solid. $^1$H NMR (400 MHz, DMSO-d$_6$): δ 8.09 (s, 1H), 7.84 (s, 1H), 7.69 (d, 1H), 7.39 (dd, 1H), 5.83 (dd, 1H), 3.90-3.86 (m, 1H), 3.77-3.73 (m, 1H), 2.42-2.32 (m, 1H), 2.33 (d, 2H), 2.05-1.94 (m, 2H), 1.86 (m, 1H), 1.76-1.71 (m, 1H), 1.60-1.54 (m, 2H), 1.02 (d, 6H); LCMS: 283 (M+H)$^+$.

Example 8

Preparation of 3-(1-(Tetrahydro-2H-pyran-2-yl)-1H-indazol-5-yl)prop-2-yn-1-ol (Intermediate 19)

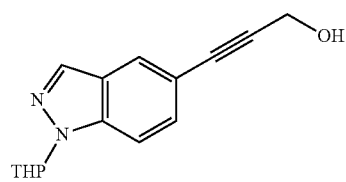

A 500 mL three-necked round bottom flask was charged with 5-bromo-1-(tetrahydro-2H-pyran-2-yl)-1H-indazole (14.0 g, 50 mmol; Intermediate 1) and triethylamine (300 mL). The flask was degassed with 3 cycles of vacuum/$N_2$, followed by the addition of Pd(PPh$_3$)$_2$Cl$_2$ (3.5 g, 5 mmol) and CuI (0.95 g, 5 mmol) under $N_2$ atmosphere. The flask was again degassed with 3 cycles of vacuum/$N_2$. Prop-2-yn-1-ol (8.4 g, 150 mmol) was added via syringe and the reaction mixture was stirred at 80° C. for 16 hours. Upon completion, the solvent was evaporated. The residue was diluted with dichloromethane (400 mL), washed with water (3×200 mL) and brine (200 mL), dried over anhydrous sodium sulfate, and concentrated in vacuo. The residue was further purified on silica gel column (1:100-1:20 EtOAc/petroleum ether) affording the title compound (11.1 g). $^1$H NMR (400 MHz, DMSO-d$_6$): δ 8.13 (s, 1H), 7.90 (s, 1H), 7.75 (d, 1H), 7.44 (d, 1H), 5.86 (dd, 1H), 5.33 (t, 1H), 4.33 (d, 2H), 3.89-3.86 (m, 1H), 3.79-3.73 (m, 1H), 2.45-2.35 (m, 1H), 2.05-1.95 (m, 2H), 1.80-1.70 (m, 1H), 1.60-1.56 (m, 2H); LCMS: 257 (M+H)$^+$.

Example 9

Preparation of 4-(1-(Tetrahydro-2H-pyran-2-yl)-1H-indazol-5-yl)but-3-yn-1-ol (Intermediate 20)

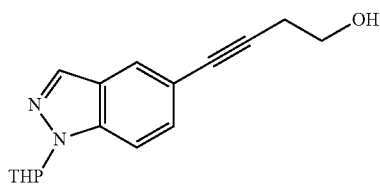

To a mixture of 5-bromo-1-(tetrahydro-2H-pyran-2-yl)-1H-indazole (17.0 g, 60.7 mmol; Intermediate 1), Pd(PPh$_3$)$_2$Cl$_2$ (5.80 g, 6.07 mmol), CuI (1.20 g, 6.07 mmol), and triethylamine (170 mL) was added but-3-yn-1-ol (6.80 g, 97.2 mmol) under $N_2$ atmosphere. The resulting mixture was stirred at 80° C. for 16 hours under $N_2$ atmosphere. Upon completion, the reaction mixture was diluted with EtOAc and washed with water (3×50 mL). The organic layer was dried over Na$_2$SO$_4$ and concentrated in vacuo. The residue was purified by column chromatography on silica gel (30~50% EtOAc in petroleum ether) affording the title compound (8.0 g). $^1$H NMR (400 MHz, DMSO-$d_6$): δ 8.09 (s, 1H), 7.83 (s, 1H), 7.70 (d, 1H), 7.40 (d, 1H), 5.84 (dd, 1H), 4.90 (br, 1H), 3.91-3.87 (m, 1H), 3.77-3.70 (m, 1H), 3.60 (t, 2H), 2.56 (t, 2H), 2.48-2.33 (m, 1H), 2.04-1.94 (m, 2H), 1.76-1.69 (m, 1H), 1.60-1.55 (m, 2H); LCMS: 271 (M+H)$^+$.

Example 10

Preparation of 5-Bromo-4-fluoro-1-(tetrahydro-2H-pyran-2-yl)-1H-indazole (Intermediate 21)

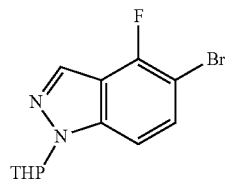

Step 1: 4-Bromo-3-fluoro-2-methylaniline

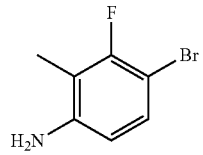

To a solution of 3-fluoro-2-methylaniline (20 g, 0.16 mol) in CH$_3$CN (500 mL) was added NBS (31.3 g, 0.176 mol) in portions at 10° C. The resulting mixture was stirred at room temperature for 30 minutes. Upon completion, saturated Na$_2$S$_2$O$_3$ (500 mL) was added slowly into the reaction mixture at 10° C. The organic layer was separated, and the aqueous layer was extracted with EtOAc. The combined organic layers were dried over Na$_2$SO$_4$ and concentrated in vacuo. The residue was washed with petroleum ether affording the title compound (20 g), which was used in the next step without further purification. $^1$H NMR (300 MHz, DMSO-$d_6$): δ 7.08 (t, 1H), 6.40 (dd, 1H), 5.35 (br, 2H), 1.98 (d, 3H).

Step 2: 5-Bromo-4-fluoro-1H-indazole

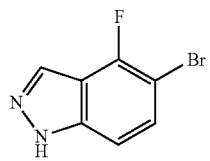

To a solution of 4-bromo-3-fluoro-2-methylaniline (20 g, 98.0 mmol) in CH$_3$CO$_2$H (600 mL) was added NaNO$_2$ (8.1 g, 118 mmol) at 10° C. The resulting mixture was stirred at room temperature for 4 hours. Upon completion, aqueous NaOH (50%) was added to the reaction mixture until pH was ~7-8. The mixture was extracted with EtOAc. The organic layer was dried over Na$_2$SO$_4$ and concentrated in vacuo. The residue was purified by column chromatography on silica gel (0~40% EtOAc in petroleum ether) affording the title compound (16 g). $^1$H NMR (300 MHz, DMSO-$d_6$): δ 13.58 (br, 1H), 8.22 (s, 1H), 7.53 (t, 1H), 7.38 (d, 1H).

Step 3: 5-Bromo-4-fluoro-1-(tetrahydro-2H-pyran-2-yl)-1H-indazole

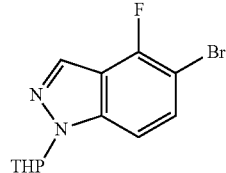

To a mixture of 5-bromo-4-fluoro-1H-indazole (50 g, 0.23 mol) and 3,4-dihydro-2H-pyran (23 g, 0.28 mol) in dry dichloromethane (1000 mL) was added p-TsOH (2.2 g, 11.5 mmol) at room temperature. The resulting mixture was stirred overnight at that temperature. Upon completion, saturated aqueous NaHCO$_3$ (100 mL) was added slowly into the reaction mixture. The organic layer was separated, dried over Na$_2$SO$_4$, and concentrated in vacuo. The residue was purified by column chromatography on silica gel (0~2% EtOAc in petroleum ether) and then re-crystallized from petroleum ether to afford the title compound (55 g). $^1$H NMR (300 MHz, DMSO-$d_6$): δ 8.28 (s, 1H), 7.58-7.66 (m, 2H), 5.89 (dd, 1H), 3.90-3.85 (m, 1H), 3.79-3.70 (m, 1H), 2.42-2.29 (m, 1H), 2.06-1.94 (m, 2H), 1.77-1.68 (m, 1H), 1.60-1.53 (m, 2H); LCMS: 299 (M+H)$^+$.

Example 11

Preparation of 5-(Cyclopropylethynyl)-4-fluoro-1-(tetrahydro-2H-pyran-2-yl)-1H-indazole (Intermediate 22)

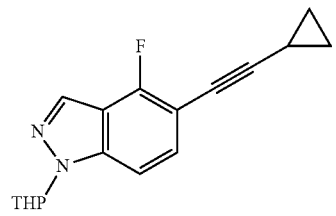

In a high pressure tube, a mixture of 5-bromo-4-fluoro-1-(tetrahydro-2H-pyran-2-yl)-1H-indazole (8.0 g, 26.8 mmol; Intermediate 21), PdCl$_2$(PPh$_3$)$_2$ (3.7 g, 5.35 mmol), CuI (1.0 g, 5.35 mmol), and triethylamine (30 mL) was deoxygenated with three cycles of vacuum/nitrogen. Ethynylcyclopropane (8.9 g, 134 mmol) was added under N$_2$ atmosphere. The tube was sealed and the reaction mixture was heated at 120° C. for 63 hours. Upon completion, the reaction mixture was diluted with ethyl acetate and filtered through Celite. The filtrate was concentrated in vacuo and the residue was purified by column chromatography on silica gel (0~10% ethyl acetate in petroleum ether) affording the title compound (4.3 g). $^1$H NMR (400 MHz, DMSO-$d_6$): δ 8.25 (s, 1H), 7.55 (d, 1H), 7.40 (dd, 1H), 5.88 (dd, 1H), 3.88-3.85 (m, 1H), 3.76-3.73 (m, 2H), 2.43-2.33 (m, 1H), 2.05-1.95 (m, 2H), 1.76-1.72 (m, 1H), 1.62-1.56 (m, 3H), 0.93-0.89 (m, 2H), 0.79-0.74 (m, 2H); LCMS: 285 (M+H)$^+$.

The Intermediates in Table 4 were prepared from Intermediate 1 (or the 4-bromo isomer) following the procedures outlined for Intermediates 17-20, 22.

TABLE 4

| Intermediate 23 | 4-(Cyclopropylethynyl)-1-(tetrahydro-2H-pyran-2-yl)-1H-indazole | 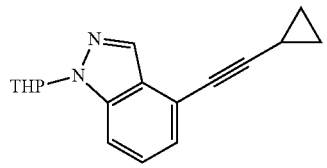 |
|---|---|---|
| Intermediate 24 | 5-(Cyclopentylethynyl)-1-(tetrahydro-2H-pyran-2-yl)-1H-indazole | 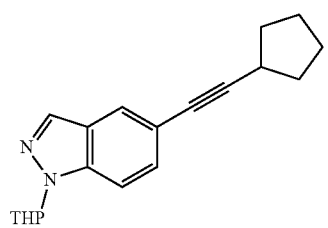 |
| Intermediate 25 | 5-(Cyclohexylethynyl)-1-(tetrahydro-2H-pyran-2-yl)-1H-indazole | 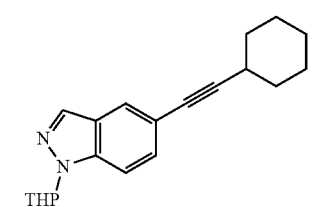 |
| Intermediate 26 | 5-(3-Methylbut-1-yn-1-yl)-1-(tetrahydro-2H-pyran-2-yl)-1H-indazole | 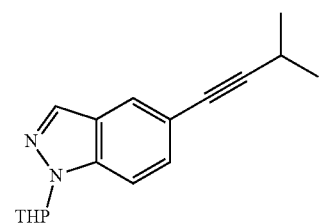 |
| Intermediate 27 | 5-(Hex-1-yn-1-yl)-1-(tetrahydro-2H-pyran-2-yl)-1H-indazole | 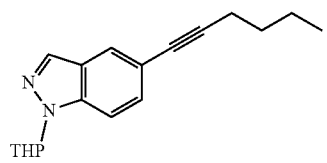 |
| Intermediate 28 | 5-(3-Cyclopentylprop-1-yn-1-yl)-1-(tetrahydro-2H-pyran-2-yl)-1H-indazole | 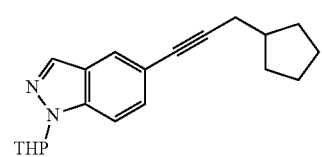 |

Example 12

Preparation of 5-(4-Chlorobut-1-yn-1-yl)-1-(tetrahydro-2H-pyran-2-yl)-1H-indazole (Intermediate 29)

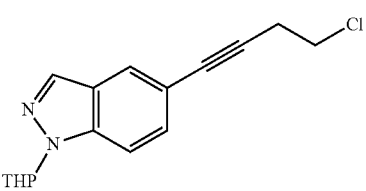

To a solution of 4-(1-(tetrahydro-2H-pyran-2-yl)-1H-indazol-5-yl)but-3-yn-1-ol (1.0 g, 3.7 mmol; Intermediate 20) in dry pyridine (10 mL) was added dropwise POCl$_3$ (2.4 g, 14.7 mmol) under N$_2$ atmosphere. The resulting solution was stirred at room temperature for 16 hours. Upon completion, the reaction mixture was concentrated in vacuo. The residue was poured into ice-water and extracted with EtOAc (2×10 mL). The combined organic layers were washed with brine, dried over Na$_2$SO$_4$ and concentrated in vacuo. The residue was further purified on silica gel column (0~20% EtOAc in petroleum ether) affording the title compound (400 mg). $^1$H NMR (400 MHz, DMSO-d$_6$): δ 8.11 (s, 1H), 7.86 (s, 1H), 7.72 (d, 1H), 7.42 (dd, 1H), 5.86 (dd, 1H), 3.90-3.86 (m, 1H), 3.81 (t, 2H), 3.77-3.70 (m, 1H), 2.93 (t, 2H), 2.41-2.34 (m, 1H), 2.05-1.94 (m, 2H), 1.75-1.71 (m, 1H), 1.60-1.55 (m, 2H); LCMS: 289 (M+H)$^+$.

Example 13

Preparation of 5-(3,3-Difluoroprop-1-yn-1-yl)-1-(tetrahydro-2H-pyran-2-yl)-1H-indazole (Intermediate 30)

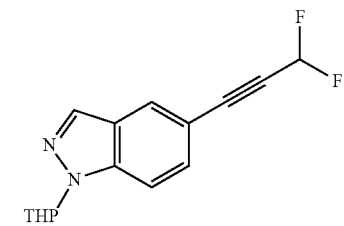

Step 1: 3-(1-(Tetrahydro-2H-pyran-2-yl)-1H-indazol-5-yl)propiolaldehyde

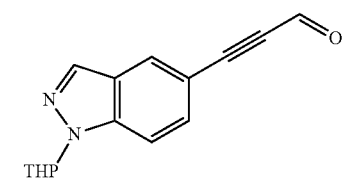

A 500 mL three-necked round bottom flask was charged with 3-(1-(tetrahydro-2H-pyran-2-yl)-1H-indazol-5-yl)prop-2-yn-1-ol (11.4 g, 44.2 mmol; Intermediate 19), dichloromethane (300 mL) and MnO$_2$ (38.4 g, 442 mmol). The resulting mixture was stirred at room temperature for 16 hours. Upon completion, the reaction mixture was filtered. The filtrate was dried over anhydrous sodium sulfate and concentrated in vacuo. The residue was purified by column chromatography on silica gel (1:100-1:20 EtOAc/petroleum ether) affording the title compound (6.4 g). ¹H NMR (400 MHz, DMSO-d₆): δ 9.45 (s, 1H), 8.27-8.25 (m, 2H), 7.87 (d, 1H), 7.66 (dd, 1H), 5.86 (dd, 1H), 3.91-3.87 (m, 1H), 3.79-3.72 (m, 1H), 2.40-2.36 (m, 1H), 2.05-1.96 (m, 2H), 1.78-1.72 (m, 1H), 1.61-1.56 (m, 2H); LCMS: 255 (M+H)⁺.

Step 2: 5-(3,3-Difluoroprop-1-yn-1-yl)-1-(tetrahydro-2H-pyran-2-yl)-1H-indazole

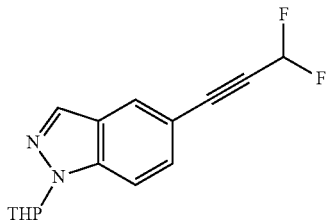

A 500 mL round bottom flask was charged with dry dichloromethane (200 mL), triethylamine.3HF (8.06 g, 50.1 mmol) and XtalFluor-E (8.61 g, 37.6 mmol) under N₂ atmosphere. The resulting solution was stirred at room temperature for 10 minutes. 3-(1-(Tetrahydro-2H-pyran-2-yl)-1H-indazol-5-yl)propiolaldehyde (3.21 g, 12.5 mmol) was added, and the mixture was stirred at room temperature for 1 hour. Upon completion, saturated NaHCO₃ (100 mL) was added into the mixture. The organic layer was separated, and the aqueous layer was extracted with dichloromethane (2×100 mL). The combined organic layers were dried over Na₂SO₄ and concentrated in vacuo. The residue was purified by column chromatography on silica gel (1:100-1:20 EtOAc/petroleum ether) affording the title compound (1.71 g). ¹H NMR (400 MHz, DMSO-d₆): δ 8.20 (s, 1H), 8.14 (s, 1H), 7.83 (d, 1H), 7.58 (dd, 1H), 6.99 (t, 1H), 5.90 (dd, 1H), 3.90-3.87 (m, 1H), 3.79-3.73 (m, 1H), 2.45-2.37 (m, 1H), 2.05-1.96 (m, 2H), 1.79-1.65 (m, 1H), 1.60-1.56 (m, 2H); LCMS: 277 (M+H)⁺.

Example 14

Preparation of 5-(4-Fluorobut-1-yn-1-yl)-1-(tetrahydro-2H-pyran-2-yl)-1H-indazole (Intermediate 31)

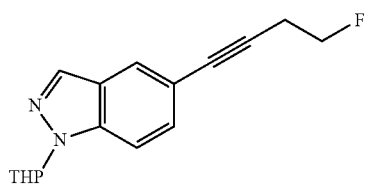

To a solution of 4-(1-(tetrahydro-2H-pyran-2-yl)-1H-indazol-5-yl)but-3-yn-1-ol (1.0 g, 3.7 mmol; Intermediate 20) in dry dichloromethane (25 mL), was added triethylamine.3HF (1.2 g, 7.4 mmol). XtalFluor-E (1.2 g, 5.5 mmol) was then added. The resulting solution was stirred at room temperature for 30 minutes. Upon completion, the reaction solution was neutralized by slow addition of saturated NaHCO₃ (10 mL). The organic layer was dried over Na₂SO₄ and concentrated in vacuo. The residue was purified by column chromatography on silica gel (0~20% EtOAc in petroleum ether) affording the title compound (100 mg). ¹H NMR (400 MHz, DMSO-d₆): δ 8.12 (s, 1H), 7.88 (s, 1H), 7.73 (d, 1H), 7.42 (dd, 1H), 5.86 (dd, 1H), 4.60 (dt, 2H), 3.88 (m, 1H), 3.78-3.71 (m, 1H), 2.89 (dt, 2H), 2.48-2.34 (m, 1H), 2.06-1.95 (m, 2H), 1.78-1.72 (m, 1H), 1.58 (m, 2H); LCMS: 273 (M+H)⁺.

Example 15

Preparation of 1-(Tetrahydro-2H-pyran-2-yl)-5-(3,3,3-trifluoroprop-1-yn-1-yl)-1H-indazole (Intermediate 32)

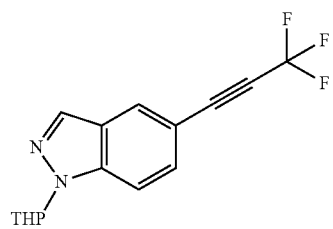

Step 1: 5-Iodo-1H-indazole

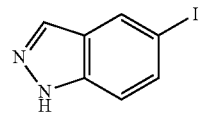

To a solution of 4-iodo-2-methylaniline (1.09 g, 4.68 mmol) in CH₃CO₂H (40 mL), were added NaNO₂ (0.39 g, 5.65 mmol) and water (1 mL) at 10° C. The resulting mixture was stirred at room temperature for 6 hours. Upon completion, the reaction mixture was extracted with EtOAc. The combined organic layers were dried over Na₂SO₄ and concentrated in vacuo. The residue was purified by column chromatography on silica gel (0~40% EtOAc in petroleum ether) affording the title compound (0.90 g). ¹H NMR (DMSO-d₆, 400 MHz): δ 13.23 (br, 1H), 8.18 (s, 1H), 8.02 (s, 1H), 7.57 (d, 1H), 7.41 (d, 1H).

Step 2: 5-iodo-1-(tetrahydro-2H-pyran-2-yl)-1H-indazole

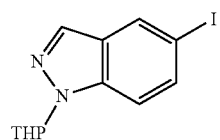

To a mixture of 5-iodo-1H-indazole (0.90 g, 3.69 mmol) and 3,4-dihydro-2H-pyran (1.57 g, 18.7 mmol) in dry dichloromethane (20 mL), was added p-TsOH (0.08 g, 0.41 mmol) at room temperature. The resulting mixture was stirred overnight. Upon completion, saturated aqueous NaHCO₃ (30 mL) was added slowly into the reaction mixture. The organic layer was separated, dried over Na₂SO₄, and concentrated in vacuo. The residue was purified by column chromatography on silica gel (0~5% EtOAc in petroleum ether) affording the title compound (1.0 g). ¹H NMR (400 MHz, DMSO-d₆): δ 8.21 (s, 1H), 8.08 (s, 1H), 7.67 (dd, 1H), 7.61 (d, 1H), 5.85 (dd, 1H), 3.88-3.85 (m, 1H), 3.78-3.72 (m, 1H), 2.41-2.29 (m, 1H), 2.05-1.95 (m, 2H), 1.77-1.72 (m, 1H), 1.61-1.56 (m, 2H).

Step 3: 1-(Tetrahydro-2H-pyran-2-yl)-5-(3,3,3-trif-luoroprop-1-yn-1-yl)-1H-indazole

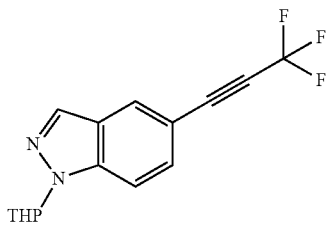

To a solution of LDA (2 M in THF, 3.2 mL, 6.4 mmol) in anhydrous THF (10 mL) was added dropwise 2-bromo-3,3,3-trifluoroprop-1-ene (0.55 g, 3.1 mmol) at −78° C. The resulting mixture was stirred at that temperature for 15 minutes, followed by the addition of $ZnCl_2$ (1 M in ethyl ether, 6.5 mL, 6.5 mmol) and TMEDA (1 mL, 6.5 mmol). The mixture was stirred at −78° C. for further 30 minutes and then 30 minutes at room temperature. 5-Iodo-1-(tetrahydro-2H-pyran-2-yl)-1H-indazole (0.99 g, 3.0 mmol) and $Pd(PPh_3)_4$ (0.21 g, 0.18 mmol) were added. The reaction mixture was heated at 80° C. for 6 hours under $N_2$ atmosphere. Upon completion, the reaction mixture was quenched with water (100 mL) and then diluted with ethyl acetate (300 mL). The organic layer was separated, dried over $Na_2SO_4$ and concentrated in vacuo. The residue was purified by column chromatography on silica gel (0~20% EtOAc in petroleum ether) affording the title compound (299 mg). $^1$H NMR (300 MHz, DMSO-$d_6$): δ 8.28 (s, 1H), 8.24 (s, 1H), 7.87 (d, 1H), 7.68 (dd, 1H), 5.91 (dd, 1H), 3.90-3.86 (m, 1H), 3.79-3.72 (m, 1H), 2.41-2.36 (m, 1H), 2.05-1.96 (m, 2H), 1.76-1.72 (m, 1H), 1.60-1.56 (m, 2H); LCMS: 295 (M+H)$^+$.

Example 16

Preparation of 5-(4-Chlorobut-1-yn-1-yl)-4-fluoro-1-(tetrahydro-2H-pyran-2-yl)-1H-indazole (Intermediate 33)

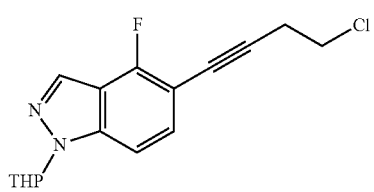

Step 1: 4-(4-Fluoro-1-(tetrahydro-2H-pyran-2-yl)-1H-indazol-5-yl but-3-yn-1-ol

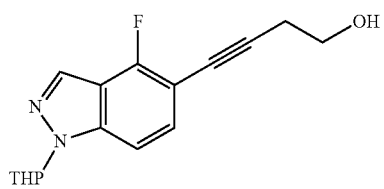

To a mixture of 5-bromo-4-fluoro-1-(tetrahydro-2H-pyran-2-yl)-1H-indazole (2.80 g, 9.36 mmol, Intermediate 21), $Pd(PPh_3)_2Cl_2$ (660 mg, 0.94 mmol), CuI (180 mg, 0.94 mmol), and triethylamine (50 mL) was added but-3-yn-1-ol (2.0 g, 28.1 mmol) under $N_2$ atmosphere. The resulting mixture was stirred at 60° C. for 16 hours. Upon completion, the reaction mixture was diluted with EtOAc, and washed with water (3×10 mL). The organic layer was dried over $Na_2SO_4$ and concentrated in vacuo. The residue was purified on silica gel column (0~20% EtOAc in petroleum ether) affording the title compound (2.0 g). $^1$H NMR (300 MHz, DMSO-$d_6$): δ 8.33 (s, 1H), 7.64 (d, 1H), 7.49 (dd, 1H), 5.94 (dd, 1H), 4.99 (t, 1H), 3.98-3.92 (m, 1H), 3.85-3.77 (m, 1H), 3.68 (t, 2H), 2.67 (t, 2H), 2.48-2.35 (m, 1H), 2.12-2.02 (m, 2H), 1.84-1.78 (m, 1H), 1.68-1.62 (m, 2H).

Step 2: 5-(4-Chlorobut-1-yn-1-yl)-4-fluoro-1-(tetrahydro-2H-pyran-2-yl)-1H-indazole

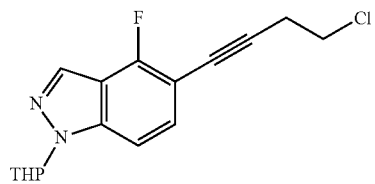

To a mixture of 4-(4-fluoro-1-(tetrahydro-2H-pyran-2-yl)-1H-indazol-5-yl)but-3-yn-1-ol (4.6 g, 16.0 mmol) in pyridine (50 mL), was added $POCl_3$ (10.3 g, 67.3 mmol). The resulting solution was stirred at room temperature for 2 hours. Upon completion, the reaction solution was poured into water (250 mL) and extracted with EtOAc. The organic layer was dried over $Na_2SO_4$ and concentrated in vacuo. The residue was purified on silica gel column (0~10% EtOAc in petroleum ether) affording the title compound (2.62 g). $^1$H NMR (300 MHz, DMSO-$d_6$): δ 8.13 (s, 1H), 7.58 (d, 1H), 7.43 (dd, 1H), 5.87 (dd, 1H), 3.90-3.69 (m, 2H), 3.83 (t, 2H), 2.98 (t, 1H), 2.41-2.29 (m, 1H), 2.06-1.94 (m, 2H), 1.78-1.70 (m, 1H), 1.60-1.54 (m, 2H); LCMS: 307 (M+H)$^+$.

Example 17

Preparation of 4-Fluoro-5-(4-fluorobut-1-yn-1-yl)-1-(tetrahydro-2H-pyran-2-yl)-1H-indazole (Intermediate 34)

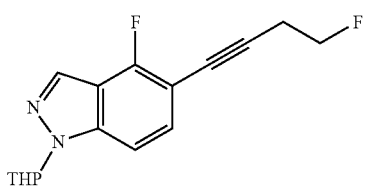

To a solution of 4-(4-fluoro-1-(tetrahydro-2H-pyran-2-yl)-1H-indazol-5-yl)but-3-yn-1-ol (3.4 g, 11.8 mmol; Intermediate 33, Step 1) in dry dichloromethane (100 mL), was added triethylamine.3HF (7.6 g, 47.2 mmol). XtalFluor-E (8.0 g, 34.9 mmol) was then added. The resulting solution was stirred at room temperature for 30 minutes. Upon completion, the reaction solution was neutralized by slow addition of saturated $NaHCO_3$ (30 mL). The organic layer was dried over Na$_2$SO$_4$ and concentrated in vacuo. The residue was purified by column chromatography on silica gel (0~20% EtOAc in petroleum ether), and then re-crystallized from petroleum ether to afford the title compound (1.3 g). $^1$H NMR (300 MHz, DMSO-d$_6$): δ 8.27 (s, 1H), 7.58 (d, 1H), 7.44 (dd, 1H), 5.89 (dd, 1H), 4.60 (dt, 2H), 3.91-3.85 (m, 1H), 3.80-3.69 (m, 1H), 2.93 (dt, 2H), 2.46-2.28 (m, 1H), 2.06-1.95 (m, 2H), 1.78-1.67 (m, 1H), 1.60-1.52 (m, 2H); LCMS: 291 (M+H)$^+$.

1H), 7.47-7.45 (m, 1H), 5.85-5.83 (m, 1H), 4.38 (s, 2H), 3.76-3.71 (m, 2H), 3.35 (s, 3H), 2.40-2.37 (m, 1H), 2.03-1.94 (m, 2H), 1.73-1.72 (m, 1H), 1.57-1.55 (m, 2H). LCMS: 271 (M+H)$^+$.

The Intermediates in Table 5 were prepared from Intermediate 1 following the procedures outlined for Intermediates 19, 20 & 35.

TABLE 5

| Intermediate 36 | 5-(4-Methoxybut-1-yn-1-yl)-1-(tetrahydro-2H-pyran-2-yl)-1H-indazole | 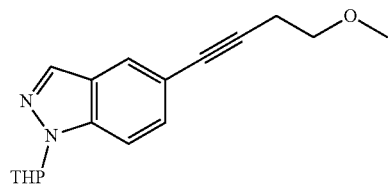 |
|---|---|---|
| Intermediate 37 | 5-(5-Methoxypent-1-yn-1-yl)-1-(tetrahydro-2H-pyran-2-yl)-1H-indazole | 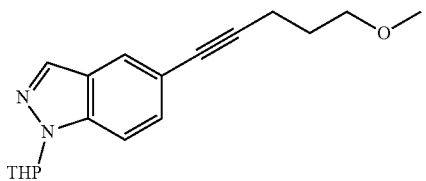 |
| Intermediate 38 | 5-(6-Methoxyhex-1-yn-1-yl)-1-(tetrahydro-2H-pyran-2-yl)-1H-indazole | 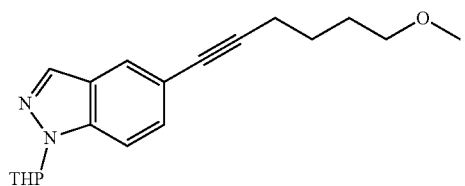 |

Example 18

Preparation of 5-(3-Methoxyprop-1-yn-1-yl)-1-(tetrahydro-2H-pyran-2-yl)-1H-indazole (Intermediate 35)

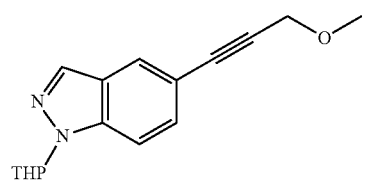

Sodium hydride (60% in mineral oil, 0.42 g, 10.5 mmol) was added to a solution of 3-(1-(tetrahydro-2H-pyran-2-yl)-1H-indazol-5-yl)prop-2-yn-1-ol (1.01 g, 3.94 mmol; Intermediate 19) in THF (20 mL) at 0° C. The mixture was stirred at 0° C. for 30 minutes, and then iodomethane (1.67 g, 11.8 mmol) was added. The resulting mixture was stirred at room temperature for 16 h. The reaction mixture was poured into ice water (100 mL) and extracted with EtOAc (3×100 mL). The combined organic layers were washed with brine (100 mL), dried over anhydrous sodium sulfate, and concentrated in vacuo. The residue was purified by column chromatography on silica gel (EtOAc/petroleum ether=1:30) to afford the title compound (0.714 g, yield 67.3%). $^1$H NMR (DMSO-d$_6$, 300 MHz): δ 8.21 (s, 1H), 7.93 (s, 1H), 7.73 (d,

Example 19

Preparation of But-1-yn-1-yltrimethylsilane (Intermediate 39)

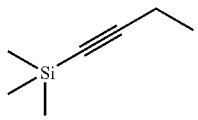

A 3 L three-necked round bottom flask was charged with (trimethylsilyl)acetylene (116 g, 1.19 mol) and dry THF (400 mL). The solution was cooled to −78° C. To this solution, butyllithium in hexane (2.5 M, 500 mL, 1.25 mol) was added dropwise over 2 hours. The resulting mixture was warmed to 0° C. for 10 minutes and then re-cooled to −78° C. HMPA (234 g, 1.31 mol) was added, and the mixture was stirred at −78° C. for 30 minutes. To this solution, iodoethane (200 g, 1.28 mol) was added. The reaction mixture was allowed to warm to room temperature and stirred overnight. Upon completion, the reaction mixture was washed with water (4×600 mL) and then brine (2×500 mL). The organic layer was dried over anhydrous sodium sulfate and filtered. Hexane and THF were distilled off at 75~110° C. But-1-yn-1-yltrimethylsilane was distilled between 125 to 135° C. affording 91 g of a colorless liquid (61%). $^1$H NMR (400 MHz, DMSO-d$_6$) δ 2.20 (q, 2H), 1.05 (t, 3H), 0.11 (s, 9H); $^{13}$C NMR (100 MHz, CDCl$_3$): δ 108.8, 83.3, 13.7, 13.4, 0.0.

Example 20

Alternate Preparation of Intermediate 3

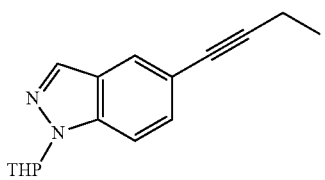

A mixture of 5-bromo-1-(tetrahydro-2H-pyran-2-yl)-1H-indazole (39.6 g, 0.142 mol; Intermediate 1), Cs$_2$CO$_3$ (60.0 g, 184 mmol), CuI (1.35 g, 7.08 mmol), Pd(OAc)$_2$ (1.59 g, 7.08 mmol), dppf (3.93 g, 7.08 mmol), and N,N-dimethylacetamide (DMA, 160 mL) was degassed with three vacuum/nitrogen cycles. But-1-yn-1-yltrimethylsilane (23.2 g, 184 mmol; Intermediate 39) was added, and the resulting mixture was heated at 80° C. for 5 h under N$_2$. Upon completion by LCMS, the reaction mixture was diluted with EtOAc (300 mL) and H$_2$O (300 mL) and then filtered. The organic layer of the filtrate was separated, and the aqueous layer was extracted with EtOAc (3×150 mL). The combined organic layers were washed with brine (2×100 mL), dried over anhydrous Na$_2$SO$_4$, filtered and concentrated. The residue was purified on silica gel column (300-400 mesh, 20 cm in diameter and 15 cm in height) using EtOAc/petroleum ether (1 L of petroleum ether; then 1 L of EtOAc/petroleum ether=1/50; and then EtOAc/Petroleum ether=1/30 until the by-product was washed out; then EtOAc/petroleum ether=1/10 to collect the product) affording a yellow oil (33 g) which solidified over time in the 4° C. refrigerator. The resulting solid was further washed with petroleum ether (200 mL, then 3×50 mL) affording the title compound as an off-white solid (26 g, 73%).

Example 21

Preparation of 5-(But-1-yn-1-yl)-4-fluoro-1-(tetrahydro-2H-pyran-2-yl)-1H-indazole (Intermediate 40)

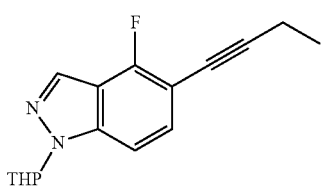

Nitrogen was bubbled into a solution of 5-bromo-4-fluoro-1-(tetrahydro-2H-pyran-2-yl)-1H-indazole (19.7 g, 65.9 mmol; Intermediate 21) and DMA (60 mL). After 5 min, CuI (1.25 g, 6.6 mmol), Pd(OAc)$_2$ (1.48 g, 6.6 mmol), dppf (3.66 g, 6.6 mmol), Cs$_2$CO$_3$ (34.3 g, 105.4 mmol), and but-1-yn-1-yltrimethylsilane (11.6 g, 92.3 mmol; Intermediate 39) were added sequentially with continued N$_2$ bubbling. The resulting mixture was heated at 80° C. for 18 h under N$_2$. The reaction mixture was diluted with EtOAc (900 mL) and H$_2$O (500 mL) and then filtered. The organic layer of the filtrate was separated, and the aqueous layer was extracted with EtOAc (2×100 mL). The combined organic layers were washed with brine (3×100 mL), dried over anhydrous Na$_2$SO$_4$, concentrated, and purified by silica gel chromatography (1:30 EtOAc/petroleum ether) to give the title compound (15.2 g) as a white solid. $^1$H NMR (DMSO-d$_6$, 400 MHz): δ 8.26 (s, 1H), 7.57 (d, 1H), 7.42 (dd, 1H), 5.87 (dd, 1H), 3.90-3.86 (m, 1H), 3.78-3.71 (m, 1H), 2.48 (q, 2H), 2.40-2.30 (m, 1H), 2.05-1.95 (m, 2H), 1.77-1.71 (m, 1H), 1.59- 1.57 (m, 2H), 1.19 (t, 3H); LCMS: 273 (M+H)$^+$.

Example 22

Preparation of 1-(5-(But-1-yn-1-yl)-1H-indol-1-yl)ethanone (Intermediate 41)

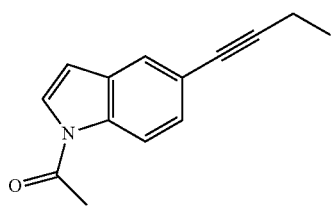 [SMILES: CCC#Cc1ccc2c(ccn2C(C)=O)c1]

Step 1: 1-(5-Iodo-1H-indol-1-yl)ethanone

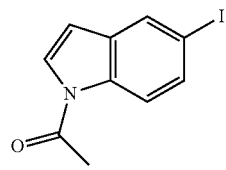

A solution of 5-iodo-1H-indole (530 mg, 2.18 mmol), DMAP (53 mg, 0.43 mmol), triethylamine (0.46 mL, 3.30 mmol), acetic anhydride (0.81 mL, 8.57 mmol), and 1,2-dichloroethane (5.5 mL) was heated at 60° C. overnight. The reaction mixture was diluted with ethyl acetate (100 mL), washed (50 mL saturated NH$_4$Cl then 50 mL brine), dried over Na$_2$SO$_4$, and concentrated under reduced pressure. The residue was purified by silica gel chromatography to yield the title compound as a white solid (600 mg, 96%). $^1$H NMR (300 MHz, DMSO-d$_6$): δ 8.17 (d, 1H), 8.01 (d, 1H), 7.87 (d, 1H), 7.58 (dd, 1H), 6.70 (d, 1H), 2.64 (s, 3H).

Step 2: 1-(5-(But-1-yn-1-yl)-1H-indol-1-yl)ethanone

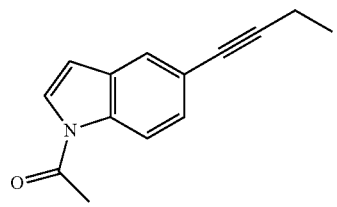 [SMILES: CCC#Cc1ccc2c(ccn2C(C)=O)c1]

To a degassed (3× vacuum/nitrogen cycles) solution of TBAF (3.56 mL, 0.5 M THF, 1.78 mmol), but-1-yn-1-yltrimethylsilane (250 mg, 1.98 mmol; Intermediate 39) was added. The solution was stirred at rt for a few minutes before transferring into a reaction vessel containing 1-(5-iodo-1H- indol-1-yl)ethanone (254 mg, 089 mmol), Pd(PPh₃)₄ (203 mg, 0.18 mmol), and CuI (69 mg, 0.36 mmol). The reaction mixture was stirred at room temperature overnight, diluted with ethyl acetate (50 mL), washed (50 mL saturated NaHCO₃ then 50 mL brine), dried over Na₂SO₄, and concentrated under reduced pressure. The residue was purified by silica gel chromatography to yield the title compound as orange oil (180 mg, 96%). $^1$H NMR (300 MHz, DMSO-d₆): δ 8.26 (d, 1H), 7.89 (d, 1H), 7.64 (d, 1H), 7.32 (dd, 1H), 6.71 (d, 1H), 2.64 (s, 3H), 2.40 (q, 2H), 1.18 (t, 3H).

Example 23

Preparation of 5-(But-1-yn-1-yl)-4-chloro-1-(tetrahydro-2H-pyran-2-yl)-1H-indazole (Intermediate 42)

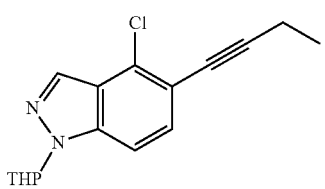

Step 1: 4-Bromo-3-chloro-2-methylaniline

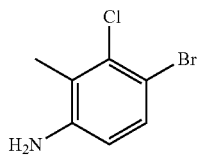

To a solution of 3-chloro-2-methylaniline (30 g, 0.212 mol) in CH₃CN (300 mL) was added NBS (45.2 g, 0.254 mol) in portions at 10° C. The resulting mixture was stirred at room temperature for 30 minutes. Upon completion, saturated Na₂S₂O₃ (500 mL) was added slowly into the reaction mixture at 10° C. The organic layer was separated, and the aqueous layer was extracted with EtOAc. The combined organic layers were dried over Na₂SO₄ and concentrated in vacuo. The residue was washed with petroleum ether to afford the title compound (30 g), which was used in the next step without further purification. $^1$H NMR (300 MHz, CDCl₃): δ 7.24 (d, 1H), 6.48 (d, 1H), 3.70 (br, 2H), 2.28 (s, 3H).

Step 2: 5-Bromo-4-chloro-1H-indazole

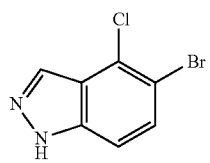

To a solution of 4-bromo-3-chloro-2-methylaniline (11 g, 49.9 mmol) in acetic acid (450 mL) was added NaNO₂ (5.4 g, 78.3 mmol) in H₂O (15 mL) at 10° C. The resulting mixture was stirred at room temperature for 30 minutes. Upon completion, the reaction mixture was diluted with H₂O (500 mL) and extracted with EtOAc. The organic layer was dried over Na₂SO₄ and concentrated in vacuo. The residue was triturated with petroleum ether affording the title compound (4.5 g) as yellow solid. $^1$H NMR (400 MHz, DMSO-d₆): δ 13.60 (s, 1H), 8.15 (s, 1H), 7.62 (d, 1H), 7.52 (d, 1H).

Step 3: 5-Bromo-4-chloro-1-(tetrahydro-2H-pyran-2-yl)-1H-indazole

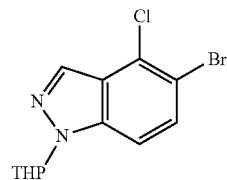

To a mixture of 5-bromo-4-chloro-1H-indazole (8.0 g, 34.6 mmol) and 3,4-dihydro-2H-pyran (8.72 g, 0.104 mol) in dry dichloromethane (200 mL) was added p-TsOH (0.657 g, 3.46 mmol) at room temperature. The resulting mixture was stirred at room temperature overnight. Upon completion, saturated aqueous NaHCO₃ (100 mL) was added slowly to the reaction mixture. The organic layer was separated, dried over Na₂SO₄, and concentrated in vacuo. The residue was purified by column chromatography on silica gel (0~3% EtOAc in petroleum ether) affording the title compound (8.9 g). $^1$H NMR (300 MHz, DMSO-d₆): δ 8.19 (s, 1H), 7.71 (m, 2H), 5.88 (dd, 1H), 3.89-3.84 (m, 1H), 3.79-3.73 (m, 1H), 2.42-2.32 (m, 1H), 2.05-1.95 (m, 2H), 1.75-1.70 (m, 1H), 1.60-1.54 (m, 2H).

Step 4: 5-(But-1-yn-1-yl)-4-chloro-1-(tetrahydro-2H-pyran-2-yl)-1H-indazole

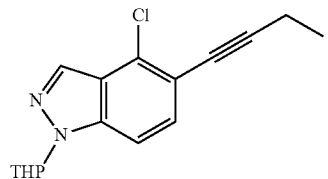

In a 20 mL microwave tube, nitrogen was bubbled through triethylamine (6 mL) for 10 minutes. 5-bromo-4-chloro-1-(tetrahydro-2H-pyran-2-yl)-1H-indazole (2.00 g, 6.34 mmol), tetrabutylammonium fluoride (3.70 g, 14.3 mmol), CuI (0.24 g, 1.3 mmol) and Pd(PPh₃)₄ (1.46 g, 1.26 mmol) were added under nitrogen atmosphere, and bubbling of nitrogen was continued for another 5 minutes. But-1-yn-1-yltrimethylsilane (1.80 g, 14.3 mmol; Intermediate 39) was then added and the tube was sealed immediately. The reaction mixture was heated in a microwave reactor at 120° C. for 3 hours. Four of these reactions (4×2 g scale per run) were combined, mixed with water (100 mL), and extracted with ethyl acetate (2×100 mL). The combined organic layers were dried over Na₂SO₄ and concentrated in vacuo. The residue was purified by column chromatography on silica gel (0~3% ethyl acetate in petroleum ether) affording the title compound (4.5 g, 90%), which was then triturated with petroleum ether (8 mL). The solid was collected and dried to afford a pale yellow powder (3.5 g). This powder was re-crystallized from ethyl acetate (2 mL) to afford the pure title compound as pale yellow crystals (3.0 g). ¹H NMR (400 MHz, DMSO-d₆): δ 8.19 (s, 1H), 7.72 (d, 1H), 7.49 (d, 1H), 5.88 (dd, 1H), 3.89-3.85 (m, 1H), 3.79-3.73 (m, 1H), 2.50 (q, 2H), 2.43-2.33 (m, 1H), 2.05-1.95 (m, 2H), 1.75-1.70 (m, 1H), 1.60- 1.55 (m, 2H), 1.21 (t, 3H); LCMS: 289 (M+H)⁺.

Example 24

Preparation of 5-(But-1-yn-1-yl)-7-fluoro-1-(tetrahydro-2H-pyran-2-yl)-1H-indazole (Intermediate 43)

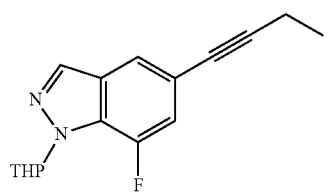

Step 1: 5-Bromo-2,3-difluorobenzaldehyde

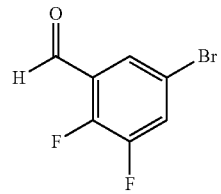

To a solution of 2,3-difluorobenzaldehyde (42 g, 0.296 mol) in H₂SO₄ (150 mL), was added NBS (63 g, 0.354 mol) in three portions over a period of 30 minutes at 60° C. The resulting mixture was heated for 6 hours at this temperature under N₂. Work-up: the reaction mixture was poured into ice water. Petroleum ether (300 mL) was added, and the mixture was stirred for 10 minutes. The organic layer was separated, and the aqueous layer was extracted with more petroleum ether (300 mL). The combined organic layers were dried over Na₂SO₄ and concentrated in vacuo. The residue was purified by column chromatography on silica gel (0~0.5% EtOAc in petroleum ether) to give 5-bromo-2,3-difluorobenzaldehyde (17.4 g). ¹H NMR (300 MHz, CDCl₃): δ 10.32 (s, 1H), 7.81-7.79 (m, 1H), 7.65-7.60 (m, 1H).

Step 2: (E)-5-Bromo-2,3-difluorobenzaldehyde O-methyl oxime

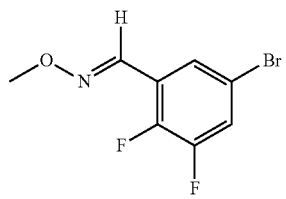

A mixture of 5-bromo-2,3-difluorobenzaldehyde (17.38 g, 78.6 mmol), O-methylhydroxylamine hydrochloride (7.23 g, 86.46 mmol), and K₂CO₃ (13 g, 94.32 mmol) in DME (80 mL) was heated at 40° C. for 14 h. Work-up: the reaction mixture was filtered. The filtrate was concentrated in vacuo, and the residue was purified by column chromatography on silica gel (0~2% EtOAc in petroleum ether), to give (E)-5-bromo-2,3-difluorobenzaldehyde O-methyl oxime (19.65 g). ¹H NMR (CDCl₃, 300 MHz): δ 8.20 (s, 1H), 7.76-7.73 (m, 1H), 7.35-7.29 (m, 1H), 4.01 (s, 3H).

Step 3: 5-Bromo-7-fluoro-1H-indazole

A mixture of (E)-5-bromo-2,3-difluorobenzaldehyde O-methyl oxime (19.65 g, 78.6 mmol), hydrazine hydrate (80 mL), and dry THF (80 mL), was heated at 90° C. for 84 h. Work-up: the organic solvent was evaporated. The resulting mixture was diluted with EtOAc (400 mL), washed with water (150 mL), dried over Na₂SO₄, and concentrated in vacuo. The residue was purified by column chromatography on silica gel (0~20% EtOAc in petroleum ether) to give 5-bromo-7-fluoro-1H-indazole as a white solid (9.3 g). ¹H NMR (300 MHz, CDCl₃): δ 13.83 (br, 1H), 8.16 (s, 1H), 7.87 (s, 1H), 7.45 (d, 1H).

Step 4: 5-Bromo-7-fluoro-1-(tetrahydro-2H-pyran-2-yl)-1H-indazole

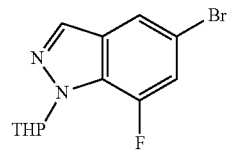

To a mixture of 5-bromo-7-fluoro-1H-indazole (9.3 g, 43.26 mmol) and 3,4-dihydro-2H-pyran (4.36 g, 51.9 mmol) in dry dichloromethane (100 mL), was added p-TsOH (424 mg, 2.16 mmol) at room temperature. The resulting mixture was stirred overnight. Work-up: saturated aqueous NaHCO₃ (30 mL) was slowly added to the reaction mixture. The organic layer was separated, dried over Na₂SO₄, and concentrated in vacuo. The residue was purified by column chromatography on silica gel (0~10% EtOAc in petroleum ether) to give 5-bromo-7-fluoro-1-(tetrahydro-2H-pyran-2-yl)-1H-indazole as a light yellow solid. (7.8 g). ¹H NMR (300 MHz, CDCl₃): δ 7.98 (s, 1H), 7.64 (s, 1H), 7.22 (dd, 1H), 5.84 (dd, 1H), 4.07-4.02 (m, 1H), 3.78-3.71 (m, 1H), 2.62-2.53 (m, 1H), 2.16-2.07 (m, 2H), 1.79-1.71 (m, 2H), 1.63- 1.33 (m, 1H).

Step 5: 5-(But-1-yn-1-yl)-7-fluoro-1-(tetrahydro-2H-pyran-2-yl)-1H-indazole

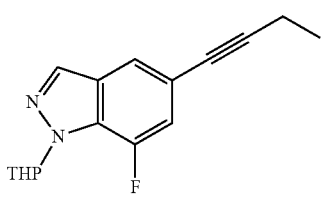

Nitrogen was bubbled into a solution of 5-bromo-7-fluoro-1-(tetrahydro-2H-pyran-2-yl)-1H-indazole (7.5 g, 25.33 mmol) and DMA (100 mL). After 5 min, CuI (241 mg, 1.27 mmol), Pd(OAc)$_2$ (284 mg, 1.27 mmol), dppf (704 mg, 1.27 mmol), K$_2$CO$_3$ (4.89 g, 35.46 mmol), and but-1-yn-1-yltrimethylsilane (4.46 g, 35.46 mmol; Intermediate 39) were added sequentially with continued N$_2$ bubbling. The resulting mixture was heated at 80° C. for 10 h under N$_2$. The reaction mixture was diluted with EtOAc (250 mL) and H$_2$O (200 mL) and filtered. The organic layer of the filtrate was separated, and the aqueous layer was extracted with EtOAc (2×100 mL). The combined organic layers were washed with brine (3×50 mL), dried over anhydrous Na$_2$SO$_4$, concentrated, and purified by silica gel chromatography (1:30 EtOAc/petroleum ether) to give the pure product as a yellow solid (3.6 g) and an impure product (2 g; further purified to give additional 1.47 g). $^1$H NMR (300 MHz, DMSO-d$_6$): δ 8.19 (d, 1H), 7.68 (d, 1H), 7.26 (dd, 1H), 5.79 (dd, 1H), 3.92-3.87 (m, 1H), 3.69-3.60 (m, 1H), 2.47-2.34 (m, 1H), 2.43 (q, 2H), 2.07-2.02 (m, 2H), 1.76-1.69 (m, 1H), 1.57-1.50 (m, 2H), 1.17 (t, 3H); LCMS: 273 (M+H)$^+$.

Example 25

Preparation of tert-Butyl 5-(but-1-yn-1-yl)-7-fluoro-1H-indole-1-carboxylate (Intermediate 44)

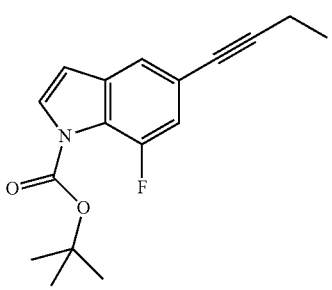 [SMILES: CCC#Cc1cc(F)c2c(ccn2C(=O)OC(C)(C)C)c1]

Step 1: tert-Butyl 7-fluoro-5-iodo-1H-indole-1-carboxylate

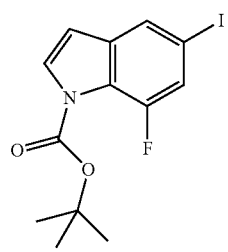 [SMILES: CC(C)(C)OC(=O)n1ccc2cc(I)cc(F)c21]

A solution of 7-fluoro-5-iodo-1H-indole (651 mg, 2.49 mmol), DMAP (31 mg, 0.25 mmol), and di-tert-butyl dicarbonate (655 mg, 3.00 mmol) in dichloromethane (5.0 mL) was stirred at room temperature overnight. The reaction mixture was diluted with dichloromethane (50 mL), washed (2×25 mL saturated NaHCO$_3$ and 25 mL brine), dried over Na$_2$SO$_4$, and concentrated under reduced pressure. The residue was purified by silica gel chromatography to yield the title compound as white solid (780 mg, 86%). $^1$H NMR (300 MHz, DMSO-d$_6$): δ 7.85 (d, 1H), 7.73 (d, 1H), 7.47 (dd, 1H), 6.73 (dd, 1H), 1.59 (s, 9H).

Step 2: tert-Butyl 5-(but-1-yn-1-yl)-7-fluoro-1H-indole-1-carboxylate

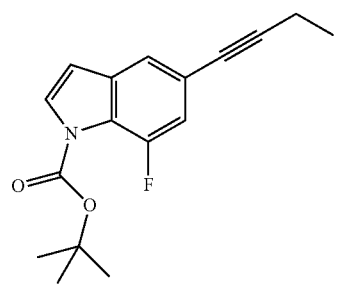 [SMILES: CCC#Cc1cc(F)c2c(ccn2C(=O)OC(C)(C)C)c1]

To a degassed (3× vacuum/nitrogen cycles) solution of TBAF (4.0 mL, 0.5 M THF, 2.00 mmol), but-1-yn-1-yltrimethylsilane (267 mg, 2.11 mmol; Intermediate 39) was added. The solution was stirred at room temperature for a few minutes before transferring into a reaction vessel containing tert-butyl 7-fluoro-5-iodo-1H-indole-1-carboxylate (360 mg, 1.00 mmol), Pd(PPh$_3$)$_4$ (232 mg, 0.20 mmol), and CuI (76 mg, 0.40 mmol). The reaction mixture was stirred at room temperature overnight, diluted with ethyl acetate (100 mL), washed (50 mL water then 50 mL brine), dried over Na$_2$SO$_4$, and concentrated under reduced pressure. The residue was purified by silica gel chromatography to yield the title compound as brown oil (260 mg, 91%). $^1$H NMR (300 MHz, DMSO-d$_6$): δ 7.85 (d, 1H), 7.58 (d, 1H), 7.21 (dd, 1H), 6.83 (dd, 1H), 2.51 (q, 2H), 1.68 (s, 9H), 1.26 (t, 3H).

Example 26

Preparation of 5-Bromo-3-fluoro-1-(tetrahydro-2H-pyran-2-yl)-1H-indazole (Intermediate 45)

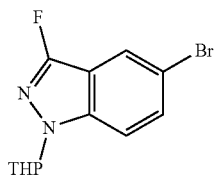

Step 1: 5-Bromo-3-fluoro-1H-indazole

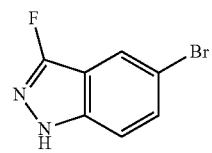

A mixture of 5-bromo-1-(tetrahydro-2H-pyran-2-yl)-1H-indazole (10.0 g, 35.7 mmol; Intermediate 1), acetic acid (4 mL), Selectfluor (25.3 g, 71.4 mmol), and acetonitrile (100 mL) was refluxed under $N_2$ for 2 h. The reaction was allowed to cool to rt, diluted with ethyl acetate (420 mL), and then washed with water (270 mL). The organic layer was dried over $Na_2SO_4$ and concentrated in vacuo. The residue was purified on a silica gel column using EtOAc in petroleum ether (1:20) to afford the title compound as yellow solids (6.0 g, yield 78.1%). $^1$H NMR (DMSO-$d_6$, 400 MHz): δ 12.77 (s, 1H), 7.96 (s, 1H), 7.54 (d, 1H), 7.48 (d, 1H).

Step 2: 5-Bromo-3-fluoro-1-(tetrahydro-2H-pyran-2-yl)-1H-indazole

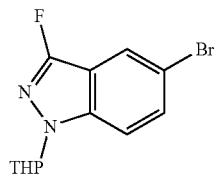

A mixture of 5-bromo-3-fluoro-1H-indazole (6.0 g, 27.9 mmol), p-TsOH (530.7 mg, 2.79 mmol) and 3,4-dihydro-2H-pyran (3.05 g, 36.3 mmol) in dichloromethane (80 mL) was stirred at room temperature for 18 h. The reaction mixture was diluted with dichloromethane (370 mL) and washed with water (230 mL). The organic layer was dried over $Na_2SO_4$ and concentrated in vacuo. The residue was purified on a silica gel column using EtOAc in petroleum ether (1:100 to 1:15) to afford the title compound as a yellow solid (6.2 g, yield 74.3%). $^1$H NMR (DMSO-$d_6$, 400 MHz): δ 7.96 (s, 1H), 7.70 (d, 1H), 7.60 (d, 1H), 5.76 (dd, 1H), 3.84-3.80 (m, 1H), 3.71-3.64 (m, 1H), 2.20-2.15 (m, 1H), 1.97-1.87 (m, 2H), 1.69-1.64 (m, 1H), 1.53-1.47 (m, 2H).

Example 27

Preparation of 5-(But-1-yn-1-yl)-3-fluoro-1-(tetrahydro-2H-pyran-2-yl)-1H-indazole (Intermediate 46)

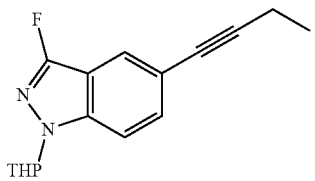

A 100 mL round bottom flask was charged with 5-bromo-3-fluoro-1-(tetrahydro-2H-pyran-2-yl)-1H-indazole (6.2 g, 20.7 mmol; Intermediate 45), DMA (20 mL), CuI (393.3 mg, 2.07 mmol), Pd(OAc)$_2$ (465.0 mg, 2.07 mmol), dppf (1.1 g, 2.07 mmol), Cs$_2$CO$_3$ (10.8 g, 33.1 mmol), and but-1-yn-1-yltrimethylsilane (3.4 g, 26.9 mmol; Intermediate 39) sequentially while $N_2$ was bubbled through the solution. The resulting mixture was heated at 80° C. for 10 h under $N_2$. The reaction mixture was diluted with EtOAc (350 mL) and H$_2$O (300 mL) and filtered. The organic layer of the filtrate was separated, and the aqueous layer was extracted with EtOAc (2×50 mL). The combined organic layers were washed with brine (3×100 mL), dried over anhydrous Na$_2$SO$_4$, and concentrated in vacuo. The residue was purified on a silica gel column using EtOAc in petroleum ether (1:30) to afford the title compound as a yellow solid (3.9 g, yield 69.1%). $^1$H NMR (DMSO-$d_6$, 400 MHz): δ 7.76-7.71 (m, 2H), 7.49 (d, 1H), 5.79 (dd, 1H), 3.88-3.85 (m, 1H), 3.74-3.71 (m, 1H), 2.44 (q, 2H), 2.24-2.21 (m, 1H), 2.01-1.91 (m, 2H), 1.70-1.65 (m, 1H), 1.57-1.54 (m, 2H), 1.18 (t, 3H); LCMS: 273 (M+H)$^+$.

Example 28

Preparation of 5-(3-Cyclopropylprop-1-yn-1-yl)-1-(tetrahydro-2H-pyran-2-yl)-1H-indazole (Intermediate 47)

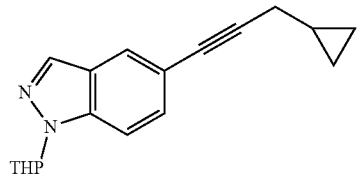

Step 1: (3-Cyclopropylprop-1-yn-1-yl)trimethylsilane

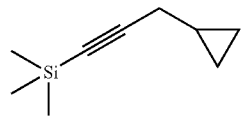

A 500 mL three-necked round bottom flask was charged with (trimethylsilyl)acetylene (15 g, 153 mmol) and dry THF (75 mL). The solution was cooled to −78° C., and a solution of n-butyllithium in hexane (2.5 M, 75 mL, 188 mmol) was added dropwise over 30 minutes. The resulting mixture was stirred at 0° C. for 10 minutes and then re-cooled to −78° C. HMPA (40 g, 223 mmol) was added, and the mixture was stirred at −78° C. for 30 minutes. (Bromomethyl)cyclopropane (20.6 g, 153 mmol) was then added. The reaction mixture was allowed to warm to room temperature and stirred overnight. Upon completion, the reaction mixture was washed with water (4×100 mL) and brine (2×100 mL) sequentially. The organic layer was dried over anhydrous sodium sulfate. Hexane and THF was distilled off at 75~110° C. then distillation at 138~142° C. afforded the title compound (12 g). $^1$H NMR (400 MHz, DMSO-$d_6$): δ 2.27 (d, 2H), 0.91-0.84 (m, 1H), 0.43-0.34 (m, 2H), 0.19-0.14 (m, 2H), 0.11 (s, 9H).

Step 2: 5-(3-Cyclopropylprop-1-yn-1-yl)-1-(tetrahydro-2H-pyran-2-yl)-1H-indazole

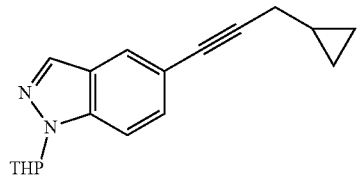

To a mixture of 5-bromo-1-(tetrahydro-2H-pyran-2-yl)-1H-indazole (4.0 g, 14.3 mmol; Intermediate 1), Pd(PPh$_3$)$_2$Cl$_2$ (1.0 g, 1.43 mmol), CuI (271 mg, 1.43 mmol), TBAF (11.2 g, 42.8 mmol), triethylamine (20 mL), and THF (20 mL), was added (3-cyclopropylprop-1-yn-1-yl)trimethylsilane (7.9 g, 42.8 mmol) under $N_2$ atmosphere. The resulting mixture was stirred at 80° C. for 16 hours under $N_2$ atmosphere. Upon completion, the reaction mixture was diluted with EtOAc and filtered. The filtrate was washed with water (3×10 mL), dried over $Na_2SO_4$ and concentrated in vacuo. The residue was purified by column chromatography on silica gel (0~10% EtOAc in petroleum ether) affording the title compound as yellow solid (3.4 g). $^1$H NMR (400 MHz, DMSO-d$_6$): δ 8.09 (s, 1H), 7.84 (s, 1H), 7.69 (d, 1H), 7.39 (dd, 1H), 5.83 (dd, 1H), 3.89-3.86 (m, 1H), 3.77-3.70 (m, 1H), 2.49 (d, 2H), 2.43-2.34 (m, 1H), 2.05-1.94 (m, 2H), 1.79-1.71 (m, 1H), 1.60-1.55 (m, 2H), 1.06-0.96 (m, 1H), 0.52-0.46 (m, 2H), 0.30-0.25 (m, 2H); LCMS: 281 (M+H)$^+$.

Example 29

Preparation of (Cyclobutylethynyl)trimethylsilane (Intermediate 48)

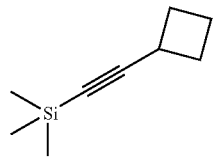

Step 1: (6-chlorohex-1-yn-1-yl)trimethylsilane

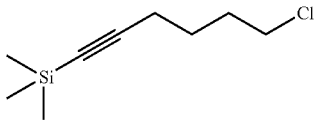

To a solution of 6-chlorohex-1-yne (100 mL, 94.6 g, 0.82 mol) in anhydrous $Et_2O$ (500 mL) at −78° C., n-butyllithium (2.5 M in hexane, 360 mL, 0.90 mol) was added over 40 minutes. The resulting mixture was stirred for 30 minutes at −78° C. Chlorotrimethylsilane (125 mL, 1.0 mol) was then added. The mixture was allowed to warm to room temperature and stirred for 16 h. The reaction mixture was carefully quenched with saturated aqueous NH$_4$Cl (300 mL) at room temperature and extracted with $Et_2O$ (2×200 mL). The combined organic layers were washed with brine (200 mL), dried over anhydrous $Na_2SO_4$, and concentrated in vacuo to afford the title compound (144 g, yield 93%). $^1$H NMR (DMSO-d$_6$, 400 MHz): δ 3.65 (t, 2H), 2.25 (t, 2H), 1.82-1.75 (m, 2H), 1.58-1.51 (m, 2H), 0.12 (s, 9H).

Step 2: (Cyclobutylethynyl)trimethylsilane

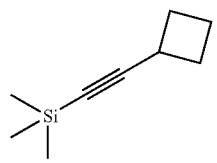

To a solution of diisopropylamine (153 g, 1.52 mol) in anhydrous THF (1.0 L) at 0° C., n-butyllithium (2.5 M in hexane, 608 mL, 1.52 mol) was added dropwise. The mixture was stirred for 20 minutes at 0° C. and then cooled to −78° C. To this mixture, a solution of (6-chlorohex-1-yn-1-yl)trimethylsilane (144 g, 0.76 mol) in anhydrous THF (200 mL) was added dropwise. The resulting mixture was allowed to warm to room temperature and stirred for 16 h. The reaction mixture was carefully quenched at room temperature with saturated aqueous NH$_4$Cl (500 mL), and then extracted with pentane (2×200 mL). The combined organic layers were washed with brine (500 mL) and dried over anhydrous $Na_2SO_4$. The solvent was evaporated on a rotary evaporator. The residue was distilled at 160-162° C./760 Torr to afford the title compound as a colorless liquid (81 g, yield 70%). $^1$H NMR (CDCl$_3$, 400 MHz): δ 3.05-3.01 (m, 1H), 2.26-2.20 (m, 2H), 2.17-2.10 (m, 2H), 1.93-1.84 (m, 2H), 0.11 (s, 9H).

Example 30

Preparation of 5-(Cyclobutylethynyl)-1-(tetrahydro-2H-pyran-2-yl)-1H-indazole (Intermediate 49)

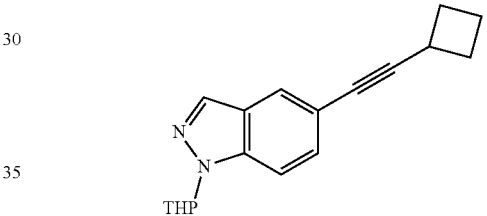

A 100 mL round bottom flask was charged with 5-bromo-1-(tetrahydro-2H-pyran-2-yl)-1H-indazole (6.8 g, 24.2 mmol; Intermediate 1), DMA (30 mL), CuI (0.46 g, 2.4 mmol), Pd(OAc)$_2$ (0.55 g, 2.4 mmol), dppf (1.35 g, 2.4 mmol), Cs$_2$CO$_3$ (11.2 g, 34.4 mmol), and (cyclobutylethynyl)trimethylsilane (5.2 g, 34.1 mmol; Intermediate 48) sequentially while $N_2$ was bubbled through the mixture. The resulting mixture was heated at 80° C. under $N_2$ atmosphere for 2 hours. The reaction mixture was cooled to room temperature, diluted with EtOAc (100 mL) and H$_2$O (100 mL) and filtered. The organic layer of the filtrate was separated, and the aqueous layer was extracted with additional EtOAc (2×50 mL). The combined organic layers were washed with brine (3×100 mL), dried over anhydrous Na$_2$SO$_4$, and concentrated in vacuo. The residue was purified on a silica gel column using 0-10% EtOAc in petroleum ether to afford the title compound as yellow oil (4.8 g, 71%). $^1$H NMR (DMSO-d$_6$): δ 8.08 (s, 1H), 7.82 (s, 1H), 7.68 (d, 1H), 7.39 (dd, 1H), 5.82 (dd, 1H), 3.89-3.85 (m, 1H), 3.76-3.69 (m, 1H), 3.30-3.24 (m, 1H), 2.39-2.26 (m, 3H), 2.19-2.09 (m, 2H), 2.03-1.84 (m, 4H), 1.75-1.70 (m, 1H), 1.58-1.55 (m, 2H); LCMS: 281 (M+H)$^+$.

The Intermediate in Table 6 was prepared from Intermediate 45 & 48 following the procedures outlined for Intermediate 49.

TABLE 6

| Intermediate 50 | 5-(Cyclobutyl-ethynyl)-3-fluoro-1-(tetrahydro-2H-pyran-2-yl)-1H-indazole | 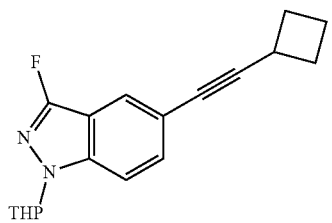 |
|---|---|---|

Example 31

Preparation of 3-(But-1-yn-1-yl)-7-methoxybenzofuran (Intermediate 51)

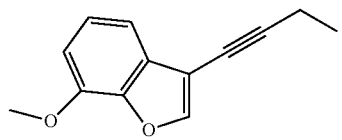

Step 1: 7-Methoxybenzofuran-3-yl trifluoromethanesulfonate

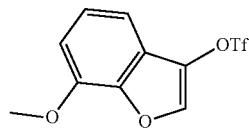 [SMILES: COc1cccc2c(OS(=O)(=O)C(F)(F)F)coc12]

Trifluoromethanesulfonic anhydride (4.6 g, 16.3 mmol) was added dropwise to a solution of 7-methoxybenzofuran-3(2H)-one (1.8 g, 10.9 mmol), triethylamine (2.2 g, 21.8 mmol), and dichloromethane (40 mL) at −20 OC. The resulting mixture was stirred at −20 OC for 2 h. The reaction mixture was neutralized with saturated aqueous NaHCO$_3$ (22 mL). The organic layer was separated, washed with water (40 mL) and brine (40 mL), dried over Na$_2$SO$_4$, and concentrated in vacuo. The residue was purified on a silica gel column using petroleum ether to afford the title compound as yellow oil (2.3 g, yield 71%). $^1$H NMR (DMSO-d$_6$, 400 MHz): δ 8.67 (s, 1H), 7.36 (t, 1H), 7.21 (d, 1H), 7.20 (d, 1H), 3.96 (s, 3H).

Step 2: 3-(But-1-yn-1-yl)-7-methoxybenzofuran

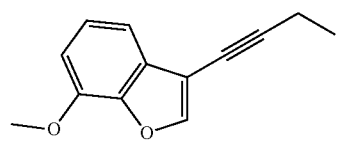

The title compound was prepared from 7-methoxybenzofuran-3-yl trifluoromethanesulfonate and Intermediate 39 following General Procedure B. $^1$H NMR (DMSO-d$_6$, 400 MHz): δ 8.24 (s, 1H), 7.26 (t, 1H), 7.17 (d, 1H), 6.99 (d, 1H), 3.94 (s, 3H), 2.52-2.47 (m, 2H), 1.21 (t, 3H). LCMS: 201 (M+H)$^+$.

Example 32

Preparation of (R)-1-((S)-1-(4-iodophenoxy)propan-2-yl)-3-methylpyrrolidine (Intermediate 52)

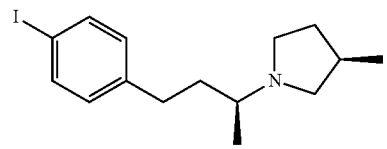 [SMILES: C[C@@H]1CCN([C@@H](C)CCc2ccc(I)cc2)C1]

Step 1: (R)-2-Methylbutane-1,4-diyl dimethanesulfonate

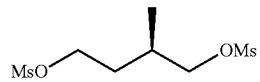

To a solution of (R)-2-methylbutane-1,4-diol (30 g, 0.29 mol) in dichloromethane (600 mL) was added triethylamine (100 mL, 0.72 mol). The solution was cooled to −20° C., and methanesulfonyl chloride (49 mL, 0.63 mol) was added dropwise over 30 min with vigorous stirring. The resulting mixture was stirred for additional 1 h while the temperature was maintained between −20 and −15° C. The mixture was allowed to warm to 0° C. and then poured into cold 1N HCl solution (100 mL). The organic layer was separated, and aqueous phase was extracted with dichloromethane (100 mL). The combined organic extracts were washed with sat'd NaHCO$_3$ solution, brine, dried over MgSO$_4$, filtered and concentrated in vacuo. The resulting product (75.9 g, quant) was used directly for the next step. $^1$H NMR (400 MHz, CDCl$_3$): δ 4.41-4.24 (m, 2H), 4.12 (dq, 2H), 3.02 (d, 6H), 2.13 (td, 1H), 1.95 (td, 1H), 1.80-1.65 (m, 1H), 1.07 (d, 3H).

Step 2: ((S)-2-((R)-3-methylpyrrolidin-1-yl)propan-1-ol

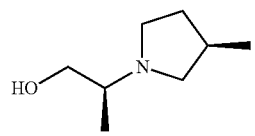

(R)-2-Methylbutane-1,4-diyl dimethanesulfonate (37.5 g, 0.144 mol) was added to neat (S)-2-aminopropan-1-ol (54.8 g, 0.730 mol). The mixture was stirred in a room temperature water bath to minimize the exotherm. After 24 h, the reaction was diluted with dichloromethane (150 mL), sat'd K$_2$CO$_3$ solution (150 mL), and just enough water (60 mL) to dissolve the resulting ppt. The organic layer was separated, and the aqueous layer was extracted with dichloromethane (150 mL). The organic layers were combined, dried (Na$_2$SO$_4$), filtered, concentrated, and purified by silica gel chromatography (10:7; ethyl acetate:hexanes→10:7:2:1;

ethyl acetate: hexanes: methanol: triethylamine) to give (S)-2-((R)-3-methylpyrrolidin-1-yl)propan-1-ol (17.9 g) as a pale yellow oil. $^1$H NMR (400 MHz, DMSO-d$_6$): δ 4.33 (t, 1H), 3.48 (m, 1H), 3.18 (m, 1H), 2.79 (dd, 1H), 2.58 (m, 1H), 2.48 (m, 1H), 2.26 (m, 1H), 2.08 (m, 1H), 2.01 (dd, 1H), 1.88 (m, 1H), 1.20 (m, 1H), 0.98 (d, 3H), 0.96 (d, 3H); LCMS: 144.3 (M+H)$^+$.

Step 3: (R)-1-((S)-1-(4-iodophenoxy)propan-2-yl)-3-methylpyrrolidine

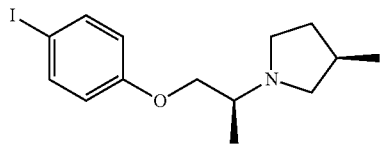 [SMILES: C[C@@H]1CCN([C@@H](C)COc2ccc(I)cc2)C1]

A mixture of 1,4-diiodobenzene (2.07 g, 6.27 mmol), ((S)-2-((R)-3-methylpyrrolidin-1-yl)propan-1-ol (0.6 g, 4.18 mmol), CuI (80 mg, 0.4 mmol), cesium carbonate (1.36 g, 4.18 mmol) in butyronitrile (4 mL) was degassed and then heated at 125° C. overnight. The mixture was cooled to room temperature, filtered through celite and washed with EtOAc. The filtrate was concentrated and purified on a silica gel column using 0-10% methanol in dichloromethane to afford (R)-1-((S)-1-(4-iodophenoxy)propan-2-yl)-3-methylpyrrolidine (1.1 g, 78%). $^1$H NMR (400 MHz, DMSO-d$_6$) δ: 7.57 (d, 2H), 6.79 (d, 2H), 4.04-3.99 (m, 1H), 3.89-3.78 (m, 1H), 2.94-2.85 (m, 1H), 2.66-2.56 (m, 2H), 2.56 (m, 1H), 2.15-2.05 (m, 2H), 1.90-1.86 (m, 1H), 1.24-1.22 (m, 1H), 1.10 (d, 3H), 0.96 (d, 3H). LCMS: 346 (M+H)$^+$.

Example 33

Preparation of (2-(Ethoxycarbonyl)-2,3-dihydro-1H-inden-5-yl)boronic acid (Intermediate 53)

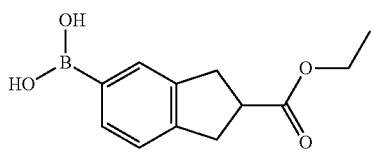 [SMILES: CCOC(=O)C1Cc2ccc(B(O)O)cc2C1]

Step 1: (4-Bromo-1,2-phenylene)dimethanol

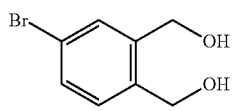

Lithium aluminumhydride (320 mg, 8.81 mmol) was added to a solution of 5-bromoisobenzofuran-1,3-dione (1 g, 4.4 mmol) in THF at room temperature. The mixture was heated at reflux for 3 h, cooled to −30° C., and then quenched with water. The mixture was extracted with EtOAc. The organic layer was dried over MgSO$_4$ and concentrated to afford the title compound (1.2 g). $^1$H NMR (400 MHz, DMSO-d$_6$): δ 7.54 (d, 1H), 7.42 (dd, 1H), 7.33-7.31 (m, 1H), 5.23 (t, 1H), 5.15 (t, 1H), 4.51 (d, 2H), 4.45 (d, 2H).

Step 2: 4-Bromo-1,2-bis(bromomethyl)benzene

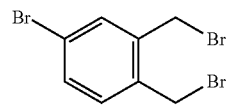

Phosphorous tribromide (4.0 g, 15.21 mmol) was added to a solution of (4-bromo-1,2-phenylene)dimethanol (1.1 g, 5.07 mmol) in 1,2-dichloroethane (10 mL) at 0° C. The resulting mixture was stirred at room temperature overnight, quenched with water (20 mL), and then extracted with EtOAc (3×20 mL). The organic layers were washed with saturated aqueous NaHCO$_3$ (2×20 mL), dried over MgSO$_4$ and concentrated in vacuo to afford the title compound as white solid (1.5 g, 88%). $^1$HNMR (400 MHz, DMSO-d$_6$): δ 7.73 (d, 1H), 7.56 (dd, 1H), 7.47-7.43 (m, 1H), 4.80 (s, 4H).

Step 3: Diethyl 5-bromo-1H-indene-2,2(3H)-dicarboxylate

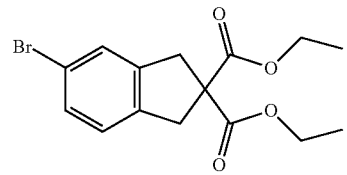 [SMILES: CCOC(=O)C1(C(=O)OCC)Cc2ccc(Br)cc2C1]

Sodium hydride (60% in mineral oil, 123 mg, 3.1 mmol) was added in small portions to EtOH (2 mL) in Et$_2$O (6 mL) at room temperature under N$_2$. After the addition was complete, the nearly clear and colorless solution was stirred for 5 min. To this solution, diethyl malonate (234 mg, 1.46 mmol) was added followed by the addition of 4-bromo-1,2-bis(bromomethyl)benzene (500 mg, 1.46 mmol). Immediately, a precipitate was formed, and the resulting mixture was stirred at room temperature for 30 minutes. The reaction mixture was filtered, and the filtrate was concentrated. The residue was purified on silica gel column using 0-10% EtOAc in petroleum ether to afford the title compound (360 mg, 72%). $^1$HNMR (400 MHz, DMSO-d$_6$): δ 7.44 (d, 1H), 7.35 (d, 1H), 7.20-7.18 (m, 1H), 4.15 (q, 4H), 3.48 (s, 2H), 3.43 (s, 2H), 1.16 (t, 6H).

Step 4: Ethyl 5-bromo-2,3-dihydro-1H-indene-2-carboxylate

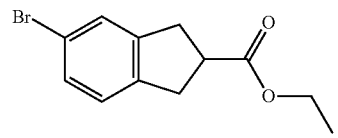

Lithium chloride (66 mg, 1.55 mmol) was added to a solution of diethyl 5-bromo-1H-indene-2,2(3H)-dicarboxylate (200 mg, 0.58 mmol), DMSO (2 mL), and H$_2$O (0.2 mL). The mixture was stirred overnight at 160° C. After cooled to room temperature, the reaction mixture was diluted with water (20 mL) and extracted with EtOAc (3×15 mL). The combined organic layers were washed with saturated aqueous NaHCO$_3$ (2×20 mL), dried over MgSO$_4$ and concentrated in vacuo to afford the title compound (120 mg, 76%). $^1$H NMR (400 MHz, DMSO-d$_6$): δ 7.42 (s, 1H), 7.31 (d, 1H), 7.18 (d, 1H), 4.10 (q, 2H), 3.39-3.34 (m, 1H), 3.17-3.01 (m, 4H).

Step 5: Ethyl 5-(4,4,5,5-tetramethyl-1,3,2-dioxaborolan-2-yl)-2,3-dihydro-1H-indene-2-carboxylate

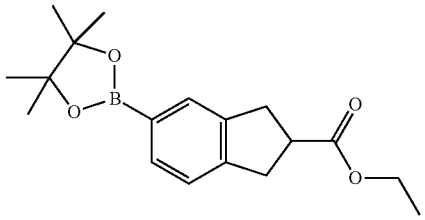 [SMILES: CCOC(=O)C1Cc2ccc(B3OC(C)(C)C(C)(C)O3)cc2C1]

A mixture of ethyl 5-bromo-2,3-dihydro-1H-indene-2-carboxylate (60 mg, 0.223 mmol), bis(pinacolato)diboron (62 mg, 0.245 mmol), CH$_3$CO$_2$K (66 mg, 0.669 mmol), PdCl$_2$(dppf) (10 mg, 0.014 mmol), and DMSO (2 mL) was heated at 90° C. for 4 h under N$_2$. After cooling to room temperature, the reaction mixture was quenched with water and extracted with EtOAc (20 mL). The organic layer was dried over MgSO$_4$ and concentrated in vacuo. The residue was purified on a silica gel column using 0-10% EtOAc in petroleum ether to afford the title compound (40 mg, 57%). $^1$HNMR (400 MHz, DMSO-d$_6$): δ 7.52 (s, 1H), 7.46 (d, 1H), 7.23 (d, 1H), 4.10 (q, 2H), 3.36-3.32 (m, 1H), 3.20-3.01 (m, 4H), 1.29 (s, 12H), 1.20 (t, 3H).

Step 6: (2-(Ethoxycarbonyl)-2,3-dihydro-1H-inden-5-yl)boronic acid

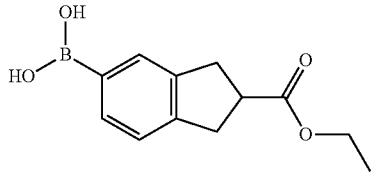 [SMILES: CCOC(=O)C1Cc2ccc(B(O)O)cc2C1]

A mixture of ethyl 5-(4,4,5,5-tetramethyl-1,3,2-dioxaborolan-2-yl)-2,3-dihydro-1H-indene-2-carboxylate (16 g, 50% purity, 25.3 mmol), NaIO$_4$ (24 g, 0.112 mol), CH$_3$COONH$_4$ (5.2 g, 0.068 mol), acetone (100 mL), and water (10 mL) was stirred at room temperature overnight. The acetone was evaporated, and the aqueous residue was extracted with EtOAc (3×100 mL). The organic layer was dried over MgSO$_4$ and concentrated in vacuo to afford the title compound as white solid (3.5 g). $^1$HNMR (400 MHz, DMSO-d$_6$): δ 7.91 (s, 2H), 7.62 (s, 1H), 7.57 (d, 1H), 7.17 (d, 1H), 4.10 (q, 2H), 3.36-3.32 (m, 1H), 3.09-3.07 (m, 4H), 1.20 (t, 3H).

Example 34

Preparation of 5-(4-Iodophenyl)-3-(methoxymethoxy)isoxazole (Intermediate 54)

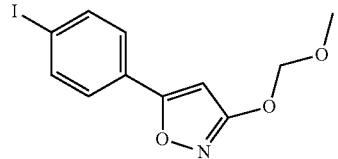 [SMILES: COCOc1cc(-c2ccc(I)cc2)on1]

Step 1: Ethyl 3-(4-iodophenyl)propiolate

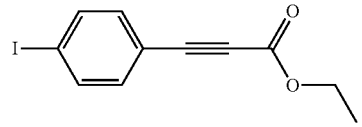

To a mixture of 1,4-diiodobenzene (1.0 g, 3.03 mmol), Pd(PPh$_3$)$_2$Cl$_2$ (580 mg, 0.606 mmol) and CuI (115 mg, 0.606 mmol) in triethylamine (20 mL), ethyl propiolate (590 mg, 6.06 mmol) was added under N$_2$. The resulting mixture was stirred at 80° C. for 16 h under N$_2$. The reaction mixture was diluted with EtOAc (50 mL) and filtered. The filtrate was washed with water (3×10 mL), dried over Na$_2$SO$_4$ and concentrated in vacuo. The residue was purified on a silica gel column using 0-10% EtOAc in petroleum ether to afford the title compound (360 mg, 30%). $^1$H NMR (DMSO-d$_6$, 400 MHz): δ 7.86 (d, 2H), 7.45 (d, 2H), 4.24 (q, 2H), 1.25 (t, 3H).

Step 2: 5-(4-Iodophenyl)isoxazol-3-ol

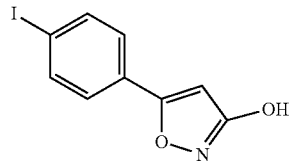 [SMILES: Oc1cc(-c2ccc(I)cc2)on1]

To a solution of ethyl 3-(4-iodophenyl)propiolate (420 mg, 1.39 mmol) in MeOH (10 mL), were added hydroxylamine hydrochloride (391 mg, 5.20 mmol) and KOH (5 M in methanol, 1.7 mL, 8.5 mmol). The mixture was stirred at room temperature overnight and then concentrated in vacuo. The residue was redissolved in water (15 mL) and acidified with 2 M aqueous HCl to pH 2-3. The precipitate was collected by filtration to afford the title compound (228 mg, 57%). $^1$H NMR (DMSO-d$_6$, 400 MHz): δ 11.51 (brs, 1H), 7.94 (d, 2H), 7.65 (d, 2H), 6.67 (s, 1H).

Step 3:
5-(4-Iodophenyl)-3-(methoxymethoxy)isoxazole

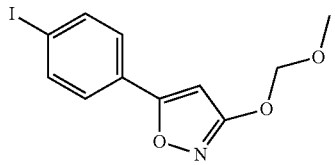 [SMILES: COCOc1cc(-c2ccc(I)cc2)on1]

To a solution of 5-(4-iodophenyl)isoxazol-3-ol (128 mg, 0.43 mmol) in Et$_3$N/DMSO (10:1 v/v, 5.5 mL) at 0° C., chloro(methoxy)methane (45 mg, 0.64 mmol) was added dropwise. After stirring at 0° C. for 0.5 h, the reaction mixture was poured into ice-water (50 mL) and extracted with EtOAc (3×20 mL). The combined organic layers were dried over MgSO$_4$ and concentrated in vacuo. The residue was purified on a silica gel column using EtOAc in petroleum ether (1:20) to afford the title compound as white solid (55 mg, 40%). $^1$H NMR (DMSO-d$_6$, 400 MHz): δ 7.79 (d, 2H), 7.46 (d, 2H), 6.23 (s, 1H), 5.36 (s, 2H), 3.57 (s, 3H). LCMS: 332 (M+H)$^+$.

Example 35

Preparation of 3-(4-Iodophenyl)-5-(methoxymethoxy)isoxazole (Intermediate 55)

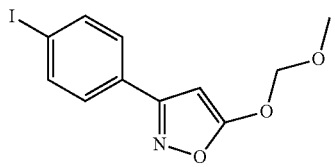

Step 1: Ethyl 3-(4-iodophenyl)-3-oxopropanoate

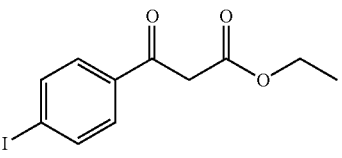

A solution of EtOAc (6 mL) in Et$_2$O (15 mL) was added to a solution of LDA (2 M in THF, 60 mL, 120 mmol) in Et$_2$O (80 mL) at −78° C. The resulting solution was stirred at −78° C. for 45 minutes. To this solution, a solution of 4-iodobenzoyl chloride (16 g, 60.5 mmol) in Et$_2$O (30 mL) was added at −78° C. The reaction mixture was allowed to warm to room temperature and stirred for 15 h. The reaction mixture was poured into iced-sulfuric acid (300 g, 10%), stirred for 15 minutes, and extracted with Et$_2$O (3×80 mL). The combined organic layers were dried over MgSO$_4$ and concentrated in vacuo to afford the title compound as light orange oil (9 g, 47%). Compound exists as a mixture of ketone and enol forms (3:1). $^1$H NMR (CDCl$_3$, 400 MHz): (ketone form) δ 7.87 (d, 2H), 7.67 (d, 2H), 4.26 (q, 2H), 3.95 (s, 2H), 1.24 (t, 3H); (enol form) δ 12.55 (s, 1H), 7.78 (d, 2H), 7.50 (q, 2H), 5.65 (s, 1H), 4.59 (q, 2H), 1.34 (t, 3H).

Step 2: 3-(4-Iodophenyl)isoxazol-5(4H)-one

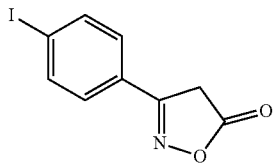 [SMILES: O=C1CC(c2ccc(I)cc2)=NO1]

Ethyl 3-(4-iodophenyl)-3-oxopropanoate (3.0 g, 9.4 mmol) was added slowly to a solution of hydroxylamine hydrochloride (660 mg, 9.44 mmol), NaOH (795 mg, 19.8 mmol), and water (12 mL) at 0° C. The reaction mixture was kept at 0° C. for 1 h. The precipitate was collected by filtration, rinsed with water, and dried under vacuum to afford the title compound as white solid (2.0 g, 64%). $^1$H NMR (CDCl$_3$, 400 MHz): δ 7.84 (d, 2H), 7.40 (d, 2H), 3.78 (s, 2H). $^{13}$C NMR (acetone-d$_6$, 100 MHz): δ 176.1, 164.6, 139.1, 129.2, 129.0, 98.6, 34.4.

Step 3:
3-(4-Iodophenyl)-5-(methoxymethoxy)isoxazole

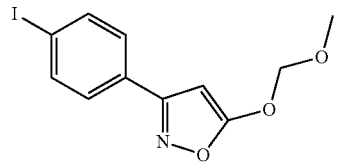 [SMILES: COCOc1cc(-c2ccc(I)cc2)no1]

Sodium hydride (360 mg, 9.0 mmol, 60% in mineral oil) was added into a solution of 3-(4-iodophenyl)isoxazol-5(4H)-one (2.0 g, 6.97 mmol) in anhydrous THF (20 mL) at 0° C. The mixture was stirred at 0° C. for 2 h. Chloro(methoxy)methane (1.12 g, 14 mmol) was added dropwise at 0° C. The reaction mixture was stirred at room temperature for 2 h, poured into ice-water, and extracted with EtOAc (3×60 mL). The combined organic layers were dried over MgSO$_4$ and concentrated in vacuo. The residue was purified on a silica gel column using EtOAc in petroleum ether (1:20) to afford the title compound as pale solid (960 mg, 42%). $^1$H NMR (DMSO-d$_6$, 400 MHz): δ 7.96 (d, 2H), 7.45 (d, 2H), 5.99 (s, 1H), 4.95 (s, 2H), 3.27 (s, 3H). LCMS: 332 (M+H)$^+$.

Example 36

Preparation of 4-Iodobenzofuran (Intermediate 56)

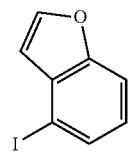

Step 1: 1-(2,2-Dimethoxyethoxy)-3-iodobenzene

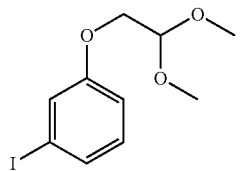

3-Iodophenol (5.35 g, 24.3 mmol) was added to a suspension of NaH (1.46 g, 36.5 mmol, 60% in mineral oil) in anhydrous DMF (30 mL) at 0° C. After hydrogen evolution had ceased, 15-crown-5 (0.535 g, 2.43 mmol) and 2-bromo-1,1-dimethoxyethane (7.1 g, 42 mmol) were added. The resulting mixture was heated at 130° C. for 3 h, cooled to room temperature, poured into water (200 mL), and extracted with Et$_2$O (3×150 mL). The combined organic layers were washed with water (100 mL) and brine (100 mL), dried over Na$_2$SO$_4$, and concentrated in vacuo. The residue was purified on a silica gel column using EtOAc in petroleum ether (1:50) to afford the title compound (6.36 g, 85%). $^1$H NMR (DMSO-d$_6$, 400 MHz): δ 7.32 (s, 1H), 7.30-7.26 (m, 1H), 7.07 (t, 1H), 7.00-6.94 (m, 1H), 4.66 (t, 2H), 3.98 (d, 1H), 3.33 (s, 6H).

Step 2: 4-Iodobenzofuran

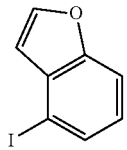

Polyphosphoric acid (3.3 g, 9.7 mmol) was added to a solution of 1-(2,2-dimethoxyethoxy)-3-iodobenzene (3.0 g, 9.7 mmol) in toluene (30 mL). The mixture was refluxed for 2 h. The reaction mixture was poured onto ice-water, extracted with EtOAc, and concentrated to give the crude material that was purified on a silica gel column using petroleum ether to afford a 1:1 mixture of 4-iodobenzofuran and 6-iodobenzofuran (1.7 g). $^1$H NMR (DMSO-d$_6$, 400 MHz): δ 8.12 (d, 1H), 8.05 (s, 1H), 7.97 (d, 1H), 7.67-7.64 (m, 2H), 7.59-7.56 (m, 1H), 7.50-7.49 (d, 1H), 7.15-7.11 (t, 1H), 6.97 (d, 1H), 6.78 (d, 1H).

Example 37

Preparation of 1-Bromo-4-((trifluoromethyl)sulfonyl)benzene (Intermediate 57)

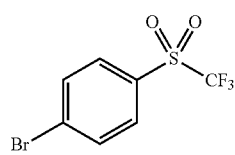 [SMILES: O=S(=O)(c1ccc(Br)cc1)C(F)(F)F]

Chromium trioxide (1.2 g, 11.7 mmol) was added to a solution of (4-bromophenyl)(trifluoromethyl)sulfane (1.5 g, 5.83 mmol), concentrated H$_2$SO$_4$ (6 mL), and H$_2$O (10 mL). After stirring at rt for 2 h, the reaction mixture was poured into ice-water and extracted with EtOAc (3×60 mL). The combined organic layers were dried (MgSO$_4$), concentrated, and purified by column chromatography on silica gel (EtOAc/petroleum ether=1:100) to give 960 mg of 1-bromo-4-((trifluoromethyl)sulfonyl)benzene as a white solid. $^1$H NMR (CDCl$_3$, 400 MHz): δ 7.89 (d, 2H), 7.85-7.81 (m, 2H). $^{13}$C NMR (CDCl$_3$, 100 MHz): δ 133.4, 132.8, 132.1, 130.4, 119.7 (q, J=320 Hz).

Example 38

Preparation of 1-Bromo-4-((trifluoromethyl)sulfinyl)benzene (Intermediate 58)

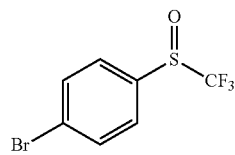 [SMILES: O=S(c1ccc(Br)cc1)C(F)(F)F]

meta-Chloroperbenzoic acid (1.2 g, 11.7 mmol) was added to a solution of (4-bromophenyl)(trifluoromethyl)sulfane (1.7 g, 6.61 mmol) in dichloromethane (30 mL). After stirring at rt for 12 h, the reaction mixture was poured into ice-water and extracted with EtOAc (3×60 mL). The combined organic layers were dried (MgSO$_4$), concentrated, and purified by column chromatography on silica gel (EtOAc/petroleum ether=0:100 to 1:50) to give 859 mg of 1-bromo-4-((trifluromethyl)sulfinyl)benzene as a white solid. $^1$H NMR (CDCl$_3$, 400 MHz): δ 7.79-7.75 (m, 2H), 7.66 (d, 2H). $^{13}$C NMR (CDCl$_3$, 100 MHz): δ 134.8, 133.0, 128.7, 127.4, 124.4 (q, J=330 Hz).

Example 39

Preparation of 2-(4-Iodophenoxy)pyrazine (Intermediate 59)

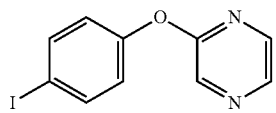 [SMILES: Ic1ccc(Oc2cnccn2)cc1]

A mixture of chloropyrazine (124 mg, 1.08 mmol), K$_2$CO$_3$ (749 mg, 5.42 mmol), and 4-iodophenol (263 mg, 1.20 mmol) in DMF (24 mL) was heated at 100° C. for 9.5 h and then stirred at rt overnight. The reaction was diluted with EtOAc and washed with H$_2$O (40 mL). The aqueous wash was back extracted with EtOAc (20 mL). The organic extracts were combined, washed with H$_2$O (2×40 mL), washed with brine (40 mL), dried (MgSO$_4$), filtered, concentrated and purified by silica gel chromatography (0%-20% EtOAc in hexanes) to give 289 mg of 2-(4-iodophenoxy)pyrazine (containing 15% of 4-iodophenol) as a white semi-solid. $^1$H NMR (400 MHz, DMSO-d$_6$): δ 8.57 (d, 1H), 8.41 (d, 1H), 8.21 (dd, 1H), 7.78 (d, 2H), 7.07 (d, 2H).

The Intermediates in Table 7 were prepared following the procedure outlined for Intermediate 59.

TABLE 7

| Intermediate 60 | 2-(4-Iodophenoxy)pyrimidine | 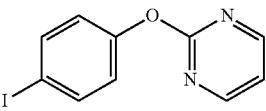 [SMILES: Ic1ccc(Oc2ncccn2)cc1] |
| --- | --- | --- |
| Intermediate 61 | 2-(4-Iodophenoxy)-5-(methylsulfonyl)pyridine | 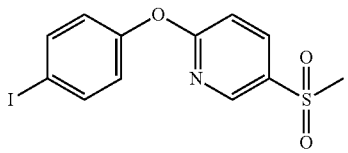 [SMILES: CS(=O)(=O)c1ccc(Oc2ccc(I)cc2)nc1] |

Example 40

Preparation of 3-(4-Bromophenoxy)pyridine (Intermediate 62)

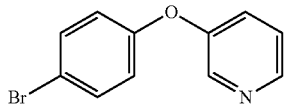 [SMILES: Brc1ccc(Oc2cccnc2)cc1]

A mixture of 3-iodopyridine (602 mg, 2.94 mmol), 4-bromophenol (560 mg, 3.24 mmol), CuBr (23 mg, 0.16 mmol), 1-(pyridin-2-yl)propan-2-one (53 mg, 0.39 mmol), $Cs_2CO_3$ (1.92 g, 5.89 mmol), and DMSO (6 mL) was degassed with three vacuum/$N_2$ cycles, heated at 100° C. for 9 h, and then stirred at rt overnight. The reaction was filtered through Celite with EtOAc. The filtrate was washed with $H_2O$ (100 mL) and brine (100 mL). The aqueous wash was back extracted with EtOAc (3×40 mL). The organic extracts were combined, dried ($MgSO_4$), filtered, concentrated, and purified by silica gel chromatography (0%-20% EtOAc in hexanes) to give 250 mg of 3-(4-bromophenoxy)pyridine as a clear liquid. $^1$H NMR (400 MHz, DMSO-$d_6$): δ 8.39-8.42 (m, 2H), 7.58-7.61 (m, 2H), 7.43-7.51 (m, 2H), 7.02-7.07 (m, 2H).

The Intermediates in Table 8 were prepared following the procedure outlined for Intermediate 62.

TABLE 8

| Intermediate 63 | 2-(4-Bromophenoxy)pyridine | 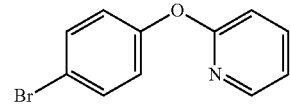 [SMILES: Brc1ccc(Oc2ccccn2)cc1] |
| --- | --- | --- |
| Intermediate 64 | 4-(4-Bromophenoxy)pyridine | 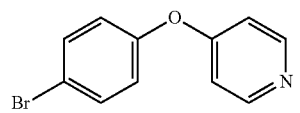 [SMILES: Brc1ccc(Oc2ccncc2)cc1] |

Example 41

Preparation of 1-Bromo-2-chloro-4-phenoxybenzene (Intermediate 65)

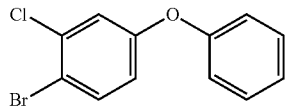

Triethylamine (0.52 mL, 3.75 mmol) was added to a mixture of 4-bromo-3-chlorophenol (156 mg, 0.75 mmol), phenyl boronic acid (187 mg, 1.53 mmol), Cu(OAc)$_2$ (208 mg, 1.15 mmol), molecular sieves (4 Å), and dichloromethane (7.5 mL). The mixture was stirred at room temperature overnight, and then additional phenyl boronic acid (186, 1.53 mmol) was added. The reaction was stirred at rt for an additional 7 h and filtered through Celite with dichloromethane. The filtrate was concentrated and purified by silica gel chromatography (100% hexanes) to give 1-bromo-2-chloro-4-phenoxybenzene (90 mg) as a clear liquid. $^1$H NMR (400 MHz, DMSO-$d_6$): δ 7.75 (d, 1H), 7.42-7.47 (m, 2H), 7.27 (d, 1H), 7.23 (t, 1H), 7.11 (d, 2H), 6.92 (dd, 1H).

The Intermediates in Table 9 were prepared following the procedure outlined for Intermediate 65.

TABLE 9

| Intermediate 66 | 4-Bromo-1-fluoro-2-phenoxybenzene | 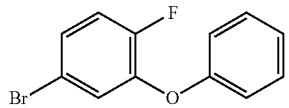 [SMILES: Fc1ccc(Br)cc1Oc1ccccc1] |
| --- | --- | --- |
| Intermediate 67 | 4-Bromo-2-fluoro-1-phenoxybenzene | 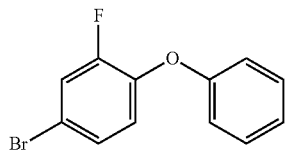 [SMILES: Fc1cc(Br)ccc1Oc1ccccc1] |
| Intermediate 68 | 2-Bromo-1-methyl-4-phenoxybenzene | 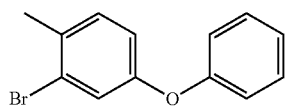 |
| Intermediate 69 | 1-Bromo-2-fluoro-3-phenoxybenzene | 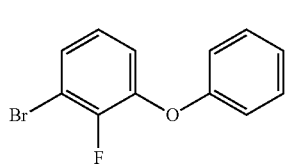 [SMILES: Fc1c(Br)cccc1Oc1ccccc1] |
| Intermediate 70 | 4-Bromo-1-methyl-2-phenoxybenzene | 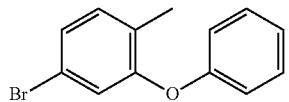 |
| Intermediate 71 | 1-Bromo-2-methyl-4-phenoxybenzene | 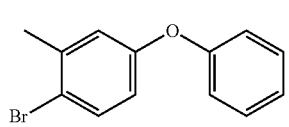 |

TABLE 9-continued

| Intermediate 72 | 4-Bromo-2-methyl-1-phenoxybenzene | 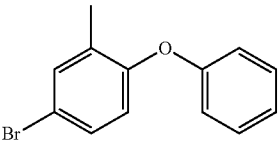 |
| --- | --- | --- |
| Intermediate 73 | (1-Iodo-3-(3-(methylsulfonyl)phenoxy)benzene | 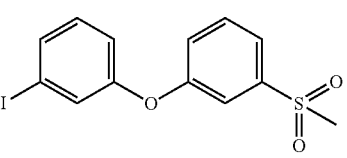 [SMILES: CS(=O)(=O)c1cccc(Oc2cccc(I)c2)c1] |

Example 42

Preparation of 2-Bromo-5-methyl-4,5,6,7-tetrahydrothieno[3,2-c]pyridine (Intermediate 74)

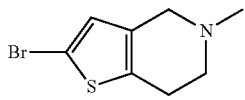

Step 1:
5-Methyl-4,5,6,7-tetrahydrothieno[3,2-c]pyridine

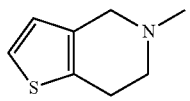

Sodium cyanoborohydride (10 g, 160 mmol) was slowly added to a mixture of 4,5,6,7-tetrahydrothieno[3,2-c]pyridine hydrochloride (7.0 g, 40.0 mmol) and formaldehyde (35% in water, 10 mL) in dichloromethane (100 mL) at room temperature. The resulting mixture was stirred at room temperature for 16 h. Work-up: the reaction mixture was partitioned between ethyl acetate (300 mL) and water (200 mL). The organic layer was separated, washed with brine (100 mL), dried over Na$_2$SO$_4$, and concentrated in vacuo. The residue was purified by column chromatography on silica gel (EtOAc/petroleum ether=1:5-1:1) to afford the title compound as a white solids (2.0 g, 33%). $^1$H NMR (DMSO-d$_6$, 400 MHz): δ 7.26 (d, 1H), 6.77 (d, 1H), 3.37 (s, 2H), 2.80-2.77 (m, 2H), 2.64-2.60 (m, 2H), 2.34 (s, 3H).

Step 2: 2-Bromo-5-methyl-4,5,6,7-tetrahydrothieno[3,2-c]pyridine

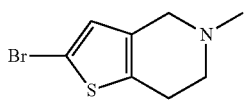

Bromine (0.3 mL) in HOAc (10 mL) was slowly added over 5 min to a mixture of 5-methyl-4,5,6,7-tetrahydrothieno[3,2-c]pyridine (1.0 g, 6.5 mmol) in acetic acid (10 mL) and water (10 mL) at 0° C. The resulting mixture was stirred at 0° C. for 1 h. Work-up: the reaction mixture was partitioned between ethyl acetate (300 mL) and water (200 mL). The organic layer was separated, washed with saturated aqueous NaHCO$_3$ (300 mL) and brine (100 mL), dried over Na$_2$SO$_4$, and concentrated in vacuo. The residue was recrystallized from 1:4 EtOAc/petroleum ether (150 mL) to afford the title compound as white solid (660 mg, 43%). $^1$H NMR (DMSO-d$_6$, 400 MHz): δ 6.91 (s, 1H), 3.33 (s, 2H), 2.73-2.71 (m, 2H), 2.52-2.51 (m, 2H), 2.33 (s, 3H). LCMS: 233 (M+H)$^+$.

Example 43

Preparation of 3-Fluoro-4-iodo-N,N-dimethylbenzamide (Intermediate 75)

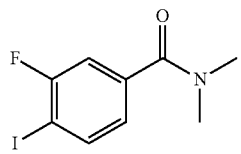

To a solution of 3-fluoro-4-iodobenzoic acid (1.3 g, 4.9 mmol) in anhydrous CH$_2$Cl$_2$ (20 mL) at 0° C. was added oxalyl chloride (1.2 mL, 15.0 mmol) followed by catalytic DMF (7 drops). The reaction mixture was allowed to warm to room temperature, stirred for 2 h, and then concentrated in vacuo to provide 1.2 g of 3-fluoro-4-iodobenzoyl chloride as a yellow solid. The acid chloride (600 mg, 2.1 mmol) was dissolved in anhydrous CH$_2$Cl$_2$, and dimethylamine (2.1 mL, 4.2 mmol, 2M in THF) was added followed by triethylamine (0.6 mL, 4.2 mmol). The reaction mixture was stirred at room temperature for 2 h and then diluted with CH$_2$Cl$_2$. The organic layer was washed with water, washed with brine, dried (MgSO$_4$), filtered, and concentrated. The resulting solid was stirred with diethyl ether and filtered to afford 353 mg of the title compound as a white solid. $^1$H NMR (300 MHz, DMSO-d$_6$): δ 7.91 (dd, 1H), 7.32 (dd, 1H), 7.04 (dd, 1H), 2.97 (s, 3H), 2.89 (s, 3H).

The Intermediate in Table 10 was prepared following the procedure outlined for Intermediate 75.

TABLE 10

| Intermediate 76 | 3-Fluoro-4-iodo-N-methylbenzamide | 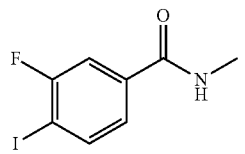 |
| --- | --- | --- |

General Procedure A:
Installation of a protecting group for the OH or NH of halo-heterocycles.

The most common protecting group was THP, especially for indazoles: 3,4-Dihydro-2H-pyran (1.1-10 equiv) was added to a solution of the appropriate halo-heterocycle (1.0 equiv), PPTS (or pTsOH, 0.05-0.3 equiv), and dichloromethane (~2 mL/mmol) at room temperature. The reaction was stirred under N$_2$ for 6-48 h (until complete by TLC or LCMS), quenched with water, and then extracted with dichloromethane. The extracts were dried, filtered, concentrated, and purified by silica gel chromatography to give the protected halo-heterocycle. In cases where THP is not a suitable protecting group, MOM was commonly installed: Sodium hydride (1.1 equiv) was added to a solution of the appropriate halo-heterocycle (1.0 equiv) and an appropriate solvent (THF, DMF, etc.) at 0° C. Chloromethyl methyl ether (1-2 equiv) was added, and the reaction was stirred at the appropriate temperature (0-60° C.) until complete by TLC or LCMS. The reaction was quenched with water and extracted with an appropriate solvent. The extracts were dried, filtered, concentrated, and purified by silica gel chromatography to give the protected halo-heterocycle. Other protecting groups less commonly used include acetyl, BOC, SEM, trityl.

General Procedure B:

Coupling of the halo-heterocycles with alkynyl-trimethylsilanes.

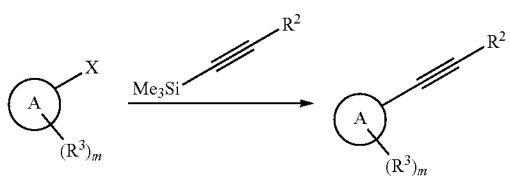

A mixture of the appropriate halo-heterocycle (1.0 equiv), $Cs_2CO_3$ (1.3-3.0 equiv), CuI (0.05-0.2 equiv), $Pd(OAc)_2$ (0.05-0.2 equiv), dppf (0.05-0.2 equiv), and N,N-dimethylacetamide (DMA, 1-2 mL/mmol) was degassed with three vacuum/nitrogen cycles. The appropriate alkynyl-trimethylsilane (1.3-2.0 equiv) was added, and the reaction was heated at 80° C. under $N_2$ for 2-24 hours (until complete by TLC or LCMS). The reaction was allowed to cool to room temperature, diluted with ethyl acetate and water, and then filtered through Celite. The aqueous layer was separated and extracted with ethyl acetate. The organics were combined, dried, filtered, concentrated, and then purified by silica gel column chromatography to give the alkynyl-heterocycle.

Note: Alternate bases include $K_2CO_3$ and CsF; Alternate ligands include 1,3-Bis(2,4,6-trimethylphenyl)imidazolium chloride and $Ph_3P$; Alternate catalysts include $Pd(PPh_3)_4$ and $PdCl_2(PPh_3)_2$; Alternate solvents include THF and pyrrolidine. Alternate temperatures include 70-100° C. Water content seems to impact the rate of this reaction: when anhydrous $Cs_2CO_3$ and anhydrous solvent were used, 1% water (v/v with respect to solvent) was added to the reaction, and when the $Cs_2CO_3$ and/or solvent were not anhydrous, no water was added.

An alternate procedure has also been employed, especially with iodo-heterocycles: The appropriate alkynyl-trimethylsilane (2.1 equiv) was added to a degassed solution of TBAF (2.0 equiv, 0.5M in THF). After 5-30 min, the appropriate halo-heterocycle (1.0 equiv), CuI (0.05-0.3 equiv), and $Pd(PPh_3)_4$ (0.05-0.2 equiv) were added. The reaction was stirred at room temperature under $N_2$ for 2-24 hours (until complete by TLC or LCMS), then diluted with water, and extracted with an appropriate solvent. The extracts were combined, dried, filtered, concentrated, and then purified by silica gel column chromatography to give the alkynyl-heterocycle.

Note: Alternate catalysts include $PdCl_2(PPh_3)_2$; Cosolvents include triethylamine and pyrrolidine; When employing bromo-heterocycles, the reaction temperature was increased (80-120° C.).

General Procedure C:

Multi-component cross-coupling of the alkynyl-heterocycles.

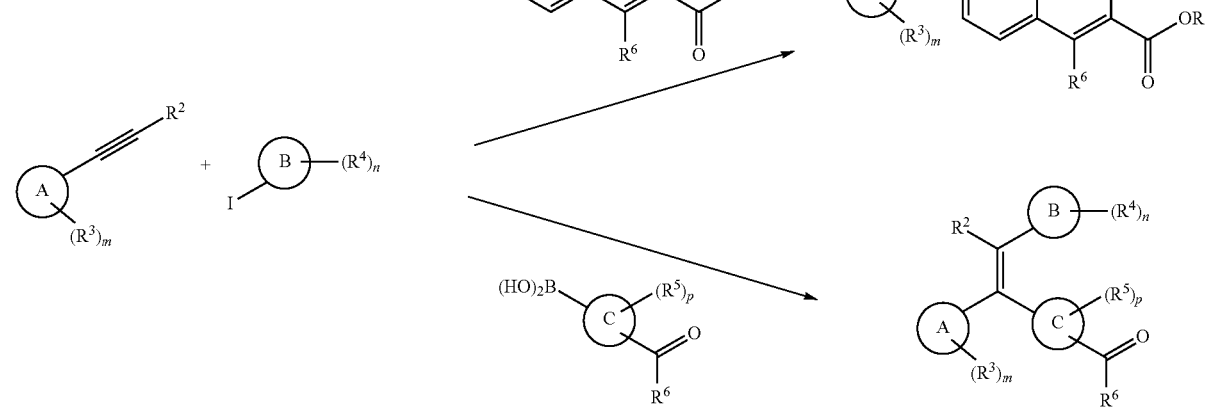

A mixture of the appropriate alkynyl-heterocycle (1.0 equiv), aryl-iodide (3.0 equiv), aryl-boronic acid (3.0 equiv; Note 1), $K_2CO_3$ (3.0 equiv), and N,N-dimethylformamide (DMF)/water (2:1, 50 mL/mmol) was degassed with three vacuum/$N_2$ cycles and then heated at 45° C. After 10 min (or when homogenous), a solution of $Pd(PhCN)_2Cl_2$ (0.01 equiv) in DMF was added (Note 2). The reaction was stirred at 45° C. for 4-24 h (until complete by TLC or LCMS; Note 3), allowed to cool to room temperature, quenched with water, and then extracted with ethyl acetate. The extracts were washed with water, washed with brine, dried, filtered, concentrated, and purified by silica gel chromatography to give the desired tetra-substituted alkene.

Note 1: Boronic acids not defined by the scheme of this general procedure have also been utilized. (E)-(4-(2-Cyanovinyl)phenyl)boronic acid is one example; 4-Bromophenylboronic acid is another.

Note 2: In some instances, all chemicals were simply mixed at room temperature, degassed, and then heated. In other instances, the boronic acid was added last as a DMF/water solution.

Note 3: When incomplete conversion of alkynyl-heterocycle was observed (especially with ortho-substituted aryl-iodides), additional aryl-iodide, aryl-boronic acid, and $K_2CO_3$ (1-3 equiv each) were added, and heating was continued for 8-24 h. In some instances, this was repeated multiple times to improve the conversion and yield.

General Procedure D:

Alternate multi-component cross-coupling of the alkynyl-heterocycles.

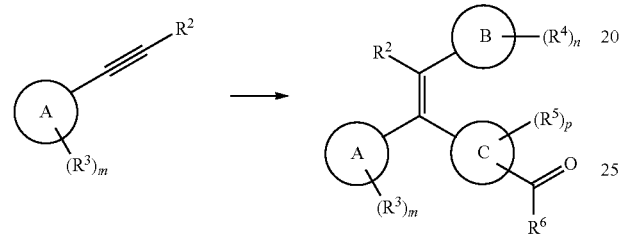

Step 1: Formation of bis(pinacolato)diboryl-alkene

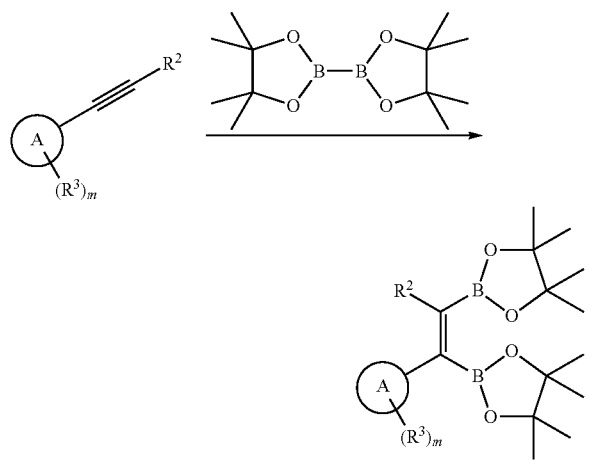

A solution of the appropriate alkynyl-heterocycle (1.0 equiv), bis(pinacolato)diboron (1.01-1.02 equiv), Pt(PPh$_3$)$_4$ (0.0025-0.03 equiv; Note 1), and solvent (2 mL/mmol of dioxane, DME, 2-MeTHF, PhMe, or DMA; Note 2) was degassed with three vacuum/N$_2$ cycles and then heated at 80-120° C. (Note 3) under N$_2$ for 1-8 h (until complete by TLC or LCMS). The reaction was allowed to cool to room temperature and then either 1) taken directly into Step 2; 2) concentrated to give a crude residue [usually a foam]; or 3) concentrated and purified by silica gel chromatography to give the pure bis(pinacolato)diboryl-alkene.

Note 1: Most commonly, 0.01 equivalents were utilized.
Note 2: Most commonly, 2-MeTHF or dioxane was utilized.
Note 3: Most commonly, reactions were refluxed.

Step 2: Cross-coupling of the bis(pinacolato)diboryl-alkene

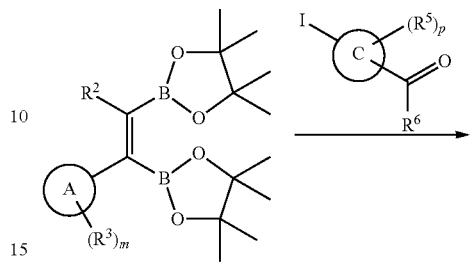

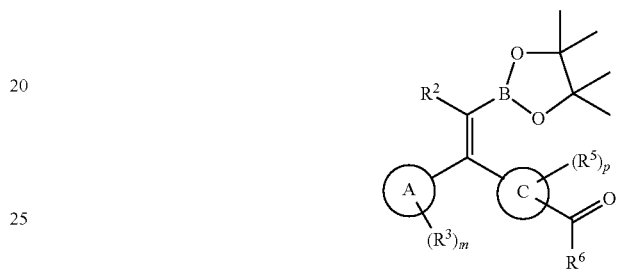

A mixture of bis(pinacolato)diboryl-alkene (1.0 equiv), an appropriate 4-iodoaryl-aldehyde (1.0 equiv), PdCl$_2$(PPh$_3$)$_2$ (0.02-0.1 equiv; Note 1), Cs$_2$CO$_3$ (1.3-3 equiv; Note 2), solvent (4 mL/mmol: dioxane, DME, 2-MeTHF, PhMe, DMA; Note 3 & 4), and water (0-3% v/v; Note 5) was stirred vigorously at 20-40° C. (Note 6) under N$_2$ (Note 7) for 1-24 h (until complete by TLC or LCMS). The reaction was then either 1) taken directly into Step 3; or 2) processed to isolate the 1-aryl-2-(pinacolato)boryl-alkene: [The reaction was diluted with ethyl ether (or ethyl acetate) and washed with water (1-3 times). The aqueous phases were back extracted with ethyl ether (or ethyl acetate). The extracts were combined, dried, filtered, concentrated and then purified by silica gel chromatography].

Note 1: Most commonly, 0.1 equivalents were used. Alternate catalysts include PdCl$_2$(dppf).

Note 2: Most commonly, 2 or 3 equivalents were used. Water content of the Cs$_2$CO$_3$ affects this reaction, see Note 5.

Note 3: Most commonly, 2-MeTHF or dioxane was used.

Note 4: When the bis(pinacolato)diboryl-alkene is brought into this step as a solution from Step 1, solvent (2 mL/mmol) is added to make the final volume of solvent approximately 4 mL/mmol.

Note 5: Most commonly, anhydrous Cs$_2$CO$_3$ and anhydrous solvent were used, so 1-2% water (v/v with respect to solvent) was added to the reaction. When the Cs$_2$CO$_3$ and/or solvent were not anhydrous, no water was added.

Note 6: Most commonly, reactions were run at room temperature.

Note 7: In some instances, this reaction was degassed with three vacuum/N$_2$ cycles.

Step 3: Cross-coupling of the 1-aryl-2-(pinacolato)boryl-alkene

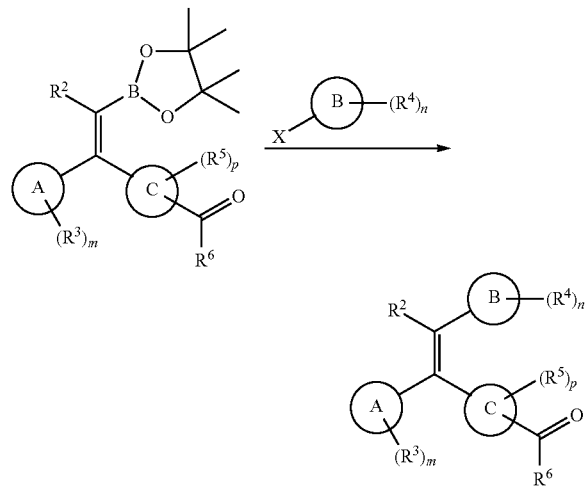

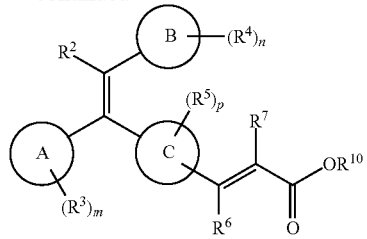

A mixture of 1-aryl-2-(pinacolato)boryl-alkene (1.0 equiv), an appropriate aryl-halide or heteroaryl-halide (1.3-2 equiv; Note 1), PdCl$_2$(PPh$_3$)$_2$ (0.02-0.1 equiv; Note 2), solvent (4 mL/mmol: dioxane, DME, 2-MeTHF, DMSO; Notes 3 & 4), and KOH (3-6M, 5-6 equiv; Note 5) was degassed with three vacuum/N$_2$ cycles and then heated at 80-100° C. (Note 6) under N$_2$ for 1-24 h (until complete by TLC or LCMS). The reaction was allowed to cool to room temperature, diluted with ethyl ether (or ethyl acetate), and washed with water (1-3 times). The aqueous phases were back extracted with ethyl ether (or ethyl acetate). The extracts were combined, dried, filtered, concentrated and then purified by silica gel chromatography to give the desired tetra-substituted alkene.

Note 1: Most commonly, 1.5 equivalents of iodides or bromides were used.

Note 2: Most commonly, 0.1 equivalents were used. Alternate catalysts include PdCl$_2$(dppf) and Pd(PPh$_3$)$_4$.

Note 3: Most commonly, 2-MeTHF or dioxane was used.

Note 4: When the 1-aryl-2-(pinacolato)boryl-alkene is brought into this step directly from Step 2, no additional solvent or PdCl$_2$(PPh$_3$)$_2$ was added. Only the aryl-halide (or heteroaryl-halide) and KOH were added.

Note 5: Most commonly, 6 equiv of KOH are used, and the aqueous solution of KOH is 4M or 6M. For some compounds, especially those with sensitive functionality, K$_2$CO$_3$ (6 equiv, 4M aqueous) is used in place of KOH, and DMSO is used as either the sole solvent or a co-solvent.

Note 6: Most commonly, reactions were refluxed.

General Procedure E:

Olefination of the tetrasubstituted-alkene aryl-aldehydes.

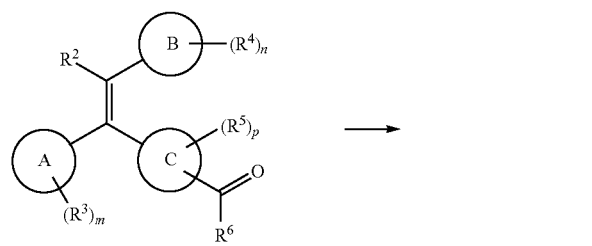

1,8-Diazabicyclo[5.4.0]undec-7-ene (DBU, 1.1 equiv) was added dropwise to a mixture of the appropriate aryl-aldehyde (1.0 equiv), triethylphosphonoacetate (1.1-1.3 equiv), lithium chloride (2.0 equiv), and anhydrous acetonitrile (2 mL/mmol) at room temperature. The resulting mixture was stirred for 1-4 h (until complete by TLC or LCMS) and then concentrated. Dichloromethane (or ethyl acetate or ether) was added, and the mixture was washed with water, washed with brine, dried, filtered, concentrated, and purified by silica gel column chromatography to give the desired acrylic ester.

Note 1: In some instances, alternate phosphonate reagents were utilized to give the desired alkene.

Note 2: Alternate reaction conditions: 1-2 equivalents of phosphonate in THF at −78° C. or 0° C. were treated with n-BuLi or NaH (1-2 equiv). Then aryl-aldehyde (1 equiv) was added, and the reaction was continued at −78° C., 0° C., or room temperature until complete by TLC and/or LCMS.

General Procedure F:

Removal of the protecting group.

Removing THP: A solution of HCl (Note 1) was added to a solution of the protected-heterocycle (1.0 equiv) in ethanol (2-5 mL/mmol; Note 2) at room temperature. The mixture was heated at 70° C. (Note 3) for 2-8 h (until complete by TLC or LCMS), allowed to cool to room temperature, and concentrated to give a crude product that was either carried on directly to the next step or purified by silica gel chromatography.

Note 1: Most commonly, 2M HCl in diethyl ether or 1.25M HCl in ethanol were used. Most commonly, the volume of HCl solution used was 10% of the solvent volume.

Note 2: Most commonly, the concentration was 5 mL/mmol. In some instances, methanol or isopropanol were used.

Note 3: In some instances, the reaction was heated at 80° C. or reflux.

A variety of conditions have been utilized to remove the MOM protecting group including 1) the same as above for removing THP, 2) ethereal HCl in refluxing THF, 3) aqueous HCl in refluxing ethanol, 4) HCl in 80-100° C. dioxane/water, and 5) refluxing trifluoroacetic acid. Other protecting groups (acetyl, BOC, SEM, trityl) were removed under standard conditions.

General Procedure G:

Hydrolysis of the acrylic ester to the acrylic acid.

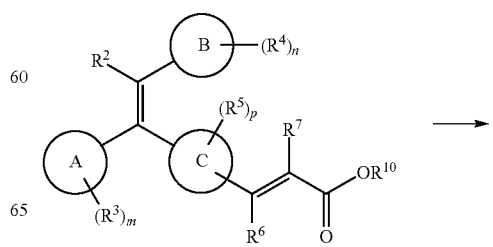

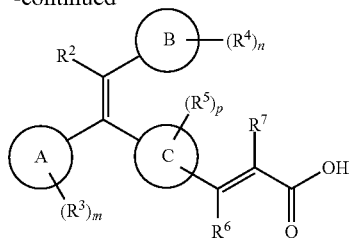

An aqueous solution of LiOH (2-20 equiv; Note 1) was added to a solution of the appropriate ester (1.0 equiv) in ethanol/tetrahydrofuran (1:1, 10 mL/mmol; Note 2) at room temperature, and the mixture was stirred for 4-24 h (until complete by TLC or LCMS). A solution of HCl (1M aqueous) was added until the pH was 3 (Note 3). The mixture was diluted with water and extracted with ethyl acetate (or dichloromethane or ether). The organic layer was washed with water, washed with brine, dried, filtered, concentrated, and purified by silica gel chromatography or preparative-HPLC to give the desired acrylic acid.

Note 1: Most commonly, a 2M solution of aqueous LiOH was used, or the LiOH was dissolved in a minimum amount of water. In some instances, NaOH or KOH was used.

Note 2: In some instances, a single solvent (ethanol, dioxane, or tetrahydrofuran) was used.

Note 3: Alternate work-up procedures have been employed including: i) the use of sat'd $NH_4Cl$ in place of aqueous HCl and ii) removal of the organic solvent by rotary evaporation prior to acid quench.

Example 44

Preparation of (E)-Ethyl 3-(4-((E)-1-(1H-indazol-5-yl)-2-phenylbut-1-en-1-yl)phenyl)acrylate (Compound 1)

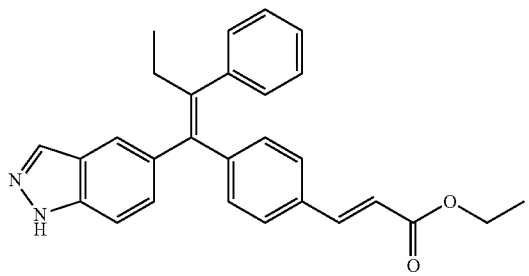

Step 1: (E)-Ethyl 3-(4-((E)-2-phenyl-1-(1-(tetrahydro-2H-pyran-2-yl)-1H-indazol-5-yl)but-1-en-1-yl)phenyl)acrylate

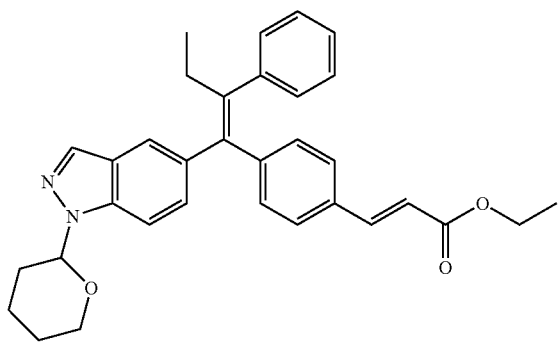 [SMILES: CCOC(=O)/C=C/c1ccc(/C(=C(/CC)c2ccccc2)c2ccc3c(cnn3C3CCCCO3)c2)cc1]

A solution of 5-(but-1-yn-1-yl)-1-(tetrahydro-2H-pyran-2-yl)-1H-indazole (2.5 g, 9.83 mmol, Intermediate 3), iodobenzene (6 g, 29.5 mmol), (E)-(4-(3-ethoxy-3-oxoprop-1-en-1-yl)phenyl)boronic acid (6.49 g, 29.5 mmol), $K_2CO_3$ (4.08 g, 29.5 mmol), and N,N-dimethylformamide/water (2:1, 492 mL) was degassed with 3 vacuum/$N_2$ cycles and then heated at 45° C. until it was a homogenous solution. A solution of $Pd(PhCN)_2Cl_2$ (38 mg, 0.098 mmol) in N,N-dimethylformamide (0.5 mL) was added. The resulting mixture was stirred at 45° C. overnight. Upon completion, the reaction mixture was cooled down to room temperature, quenched with water (500 mL), and extracted with ethyl acetate (3×500 mL). The combined organics were washed with water, washed with brine, dried over sodium sulfate, filtered, and concentrated to give the crude product. This crude material was purified on a silica gel column eluted with 0-50% ethyl acetate in hexanes affording the title compound as off-white foam (3.71 g). LCMS: 423 [(M-THP+H)+H]$^+$.

Step 2: (E)-Ethyl 3-(4-((E)-1-(1H-indazol-5-yl)-2-phenylbut-1-en-1-yl)phenyl)acrylate

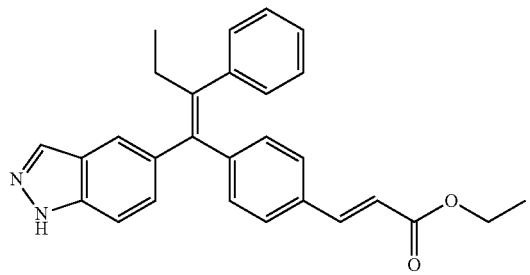 [SMILES: CCOC(=O)/C=C/c1ccc(/C(=C(/CC)c2ccccc2)c2ccc3[nH]ncc3c2)cc1]

To a solution of (E)-ethyl 3-(4-((E)-2-phenyl-1-(1-(tetrahydro-2H-pyran-2-yl)-1H-indazol-5-yl)but-1-en-1-yl)phenyl)acrylate (3.5 g, 6.9 mmol) in ethyl alcohol (69 mL), HCl (6 mL, 2M in diethyl ether) was added at room temperature. The resulting mixture was then heated at 70° C. for 2 h. Upon completion, the mixture was cooled down to room temperature and concentrated to give the crude product. This crude material was purified on a silica gel column eluted with 0-100% ethyl acetate in hexanes affording an off-white solid (2.5 g). $^1$H NMR (300 MHz, DMSO-d$_6$): δ 13.10 (s, 1H), 8.08 (s, 1H), 7.69 (s, 1H), 7.53 (d, 1H), 7.48 (d, 1H), 7.39 (d, 2H), 7.27-7.11 (m, 6H), 6.89 (d, 2H), 6.45 (d, 1H), 4.20 (q, 2H), 2.43 (q, 2H), 1.22 (t, 3H), 0.87 (t, 3H); LCMS: 423 (M+H)$^+$.

Example 45

Preparation of (E)-3-(4-((E)-1-(1H-Indazol-5-yl)-2-phenylbut-1-en-1-yl)phenyl)acrylic acid (Compound 2)

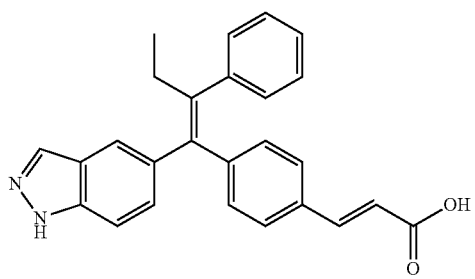

323

To a solution of (E)-ethyl 3-(4-((E)-1-(1H-indazol-5-yl)-2-phenylbut-1-en-1-yl)phenyl)acrylate (2.5 g, 5.9 mmol; Compound 1) in THF-EtOH (1:1, 59 mL), an aqueous solution of LiOH (2.8 g, 118 mmol; dissolved in a minimum amount of water) was added at room temperature. The resulting mixture was stirred overnight. The reaction was monitored by LCMS. Upon completion, 1N aqueous HCl was added until pH was 3. Then, the mixture was diluted with water and extracted with ethyl acetate (3×200 mL). The combined organic layers were washed with water, washed with brine, dried over sodium sulfate, filtered, and concentrated to give the crude product. This crude material was purified on a silica gel column eluted with 0-20% methanol in dichloromethane affording the title compound as a pale yellow solid (1.9 g). $^1$H NMR (300 MHz, DMSO-$d_6$): δ 13.11 (s, 1H), 12.30 (br, 1H), 8.08 (s, 1H), 7.65 (s, 1H), 7.53 (d, 1H), 7.43 (d, 1H), 7.37 (d, 2H), 7.29-7.11 (m, 6H), 6.88 (d, 2H), 6.37 (d, 1H), 2.44 (q, 2H), 0.87 (t, 3H); LCMS: 395 (M+H)$^+$.

Example 46

Preparation of (E)-3-(4-((E)-1-(1H-Benzo[d][1,2,3]triazol-5-yl)-2-phenylbut-1-en-1-yl)phenyl)acrylic acid (Compound 3)

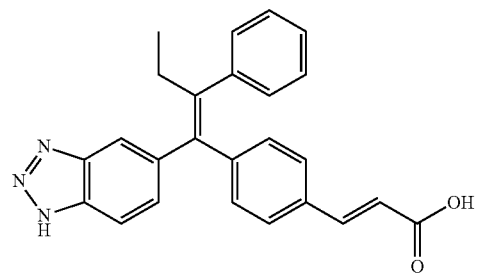

Step 1: (E)-Ethyl 3-(4-((E)-2-phenyl-1-(1-(tetrahydro-2H-pyran-2-yl)-1H-benzo[d][1,2,3]triazol-5-yl)but-1-en-1-yl)phenyl)acrylate

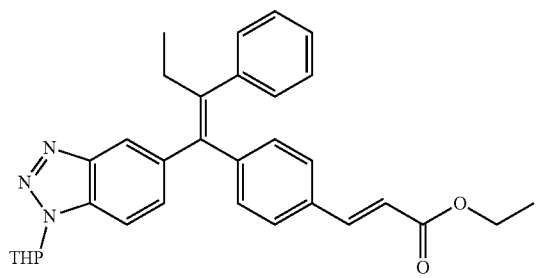

A 100-mL round-bottom flask equipped with a magnetic stir bar, a rubber septum and N$_2$ inlet was charged with 5-(but-1-yn-1-yl)-1-(tetrahydro-2H-pyran-2-yl)-1H-benzo[d][1,2,3]triazole (0.2 g, 0.78 mmol), iodobenzene (0.48 g, 2.35 mmol), (E)-(4-(3-ethoxy-3-oxoprop-1-en-1-yl)phenyl)boronic acid (0.51 g, 2.35 mmol), K$_2$CO$_3$ (0.32 g, 2.35 mmol), and N,N-dimethylformamide/water (2:1, 39 mL). This mixture was degassed with three vacuum/N$_2$ cycles and then heated at 45° C. for 10 minutes. With continued heating, a solution of Pd(PhCN)$_2$Cl$_2$ (0.003 g, 0.008 mmol) in N,N-dimethylformamide (0.2 mL) was added dropwise. The resulting mixture was stirred at 45° C. overnight. The reaction was monitored by TLC. Upon completion, the reaction mixture was cooled down to room temperature, quenched with water (100 mL), and extracted with ethyl acetate (2×200 mL). The combined organics were washed with water (100 mL), washed with brine (50 mL), dried over sodium sulfate, filtered, and concentrated to give the crude product. This crude material was purified on a silica gel column eluted with 0-25% ethyl acetate in hexanes affording the title compound as an off-white solid (0.28 g). LCMS: 424 [(M-THP+H)+H]$^+$.

Step 2: (E)-Ethyl 3-(4-((E)-1-(1H-benzo[d][1,2,3]triazol-5-yl)-2-phenylbut-1-en-1-yl)phenyl)acrylate

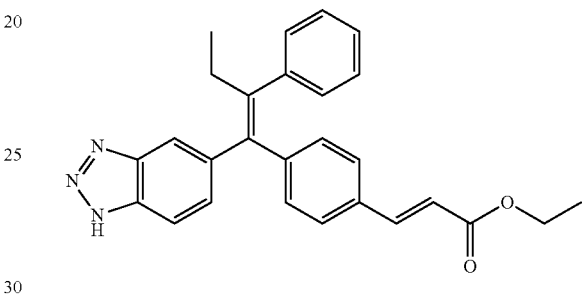

Hydrochloric acid (2.7 mL, 2M in diethyl ether) was added to a solution of (E)-ethyl 3-(4-((E)-2-phenyl-1-(1-(tetrahydro-2H-pyran-2-yl)-1H-benzo[d][1,2,3]triazol-5-yl)but-1-en-1-yl)phenyl)acrylate (0.28 g, 0.55 mmol) in ethyl alcohol (27 mL) at room temperature, and the resulting mixture was heated at 70° C. for 2 h. The reaction was monitored by TLC. Upon completion, the mixture was cooled down to room temperature and concentrated to give a pale yellow solid. This solid was dissolved in ethyl acetate (100 mL), washed with saturated NaHCO$_3$ (50 mL), water (100 mL) and brine (50 mL). The organic layer was dried over sodium sulfate, filtered, and concentrated to give the crude product. This crude material was purified on a silica gel column eluted with 0-50% ethyl acetate in hexanes affording the title compound. LCMS: 424 (M+H)$^+$.

Step 3: (E)-3-(4-((E)-1-(1H-Benzo[d][1,2,3]triazol-5-yl)-2-phenylbut-1-en-1-yl)phenyl) acrylic acid

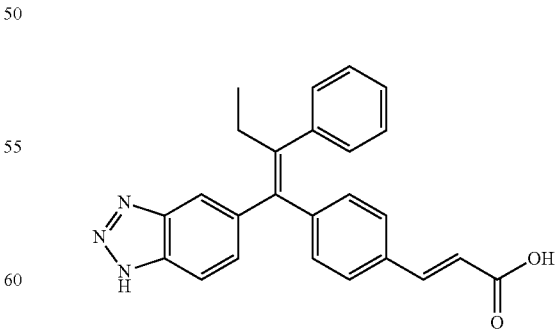

An aqueous solution of LiOH (0.22 g, 9.4 mmol) was added to a solution of (E)-ethyl 3-(4-((E)-1-(1H-benzo[d][1,2,3]triazol-5-yl)-2-phenylbut-1-en-1-yl)phenyl)acrylate (0.2 g, 0.47 mmol) in THF-EtOH (1:1, 24 mL) at room temperature, and the resulting mixture was stirred overnight. The reaction was monitored by LCMS. Upon completion, 1N aqueous HCl was added until the pH was 3. Then, the mixture was diluted with water and extracted with ethyl acetate (3×100 mL). The combined organic layers were washed with water (100 mL), washed with brine (50 mL), dried over sodium sulfate, filtered, and concentrated to give the crude product. This crude material was purified on a silica gel column eluted with 0-20% methanol in dichloromethane affording the title compound as an off-white solid (0.12 g). $^1$H NMR (300 MHz, DMSO-$d_6$): δ 15.65 (br, 1H), 12.29 (br, 1H), 7.92 (d, 1H), 7.78 (s, 1H), 7.48-7.35 (m, 3H), 7.24-7.13 (m, 7H), 6.91 (d, 2H), 6.37 (d, 1H), 2.39 (q, 2H), 0.89 (t, 3H); LCMS: 396 (M+H)$^+$.

Compounds 4 to 175 were prepared from alkynyl-intermediates following General Procedures C, F (optionally), & G. The alkynyl-intermediates have either i) been described herein or ii) were prepared from known or commercially available halo-heterocycles (or aryl-halides) following General Procedures A (optionally) & B.

Example 47

Preparation of (E)-3-(4-((E)-1-(1H-Indazol-5-yl)-2-phenylbut-1-en-1-yl)phenyl)-2-methylacrylic acid (Compound 176)

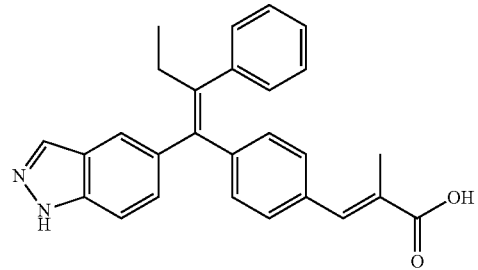 [SMILES: CC/C(=C(/c1ccc(/C=C(\C)C(=O)O)cc1)c1ccc2[nH]ncc2c1)c1ccccc1]

Step 1: (E)-4-(2-Phenyl-1-(1-(tetrahydro-2H-pyran-2-yl)-1H-indazol-5-yl)but-1-en-1-yl)benzaldehyde

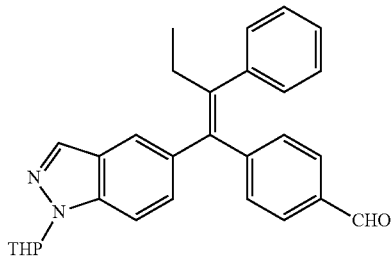

The title compound was prepared from Intermediate 3, iodobenzene, and (4-formylphenyl)boronic acid following General Procedure C. LCMS: 353 [(M-THP+H)+H]$^+$.

Step 2: (E)-Ethyl 2-methyl-3-(4-((E)-2-phenyl-1-(1-(tetrahydro-2H-pyran-2-yl)-1H-indazol-5-yl)but-1-en-1-yl)phenyl)acrylate

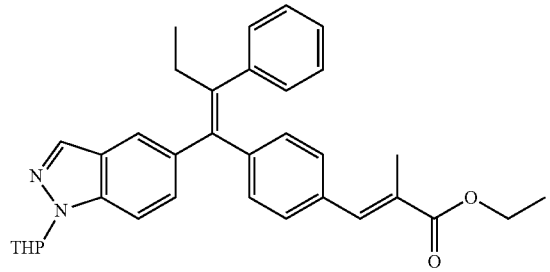

To a suspension of NaH (80 mg, 2 mmol, 60% dispersion in mineral oil) in THF (10 mL) at 0° C., ethyl 2-(diethoxyphosphoryl)propanoate (0.36 g, 1.5 mmol) was added. The reaction was stirred at 0° C. for 1 h, and then a THF solution of (E)-4-(2-phenyl-1-(1-(tetrahydro-2H-pyran-2-yl)-1H-indazol-5-yl)but-1-en-1-yl)benzaldehyde (0.44 g, 1 mmol) was added. The resulting mixture was gradually warmed to room temperature and stirred overnight. The reaction mixture was quenched with saturated ammonium chloride solution and extracted with EtOAc (2×100 mL). The combined organic layers were washed with water, brine, dried over sodium sulfate, filtered and concentrated to give the crude material as pale yellow oil. LCMS: 437 [(M-THP+H)+H]$^+$.

Step 3: (E)-3-(4-((E)-1-(1H-Indazol-5-yl)-2-phenyl-but-1-en-1-yl)phenyl)-2-methylacrylic acid

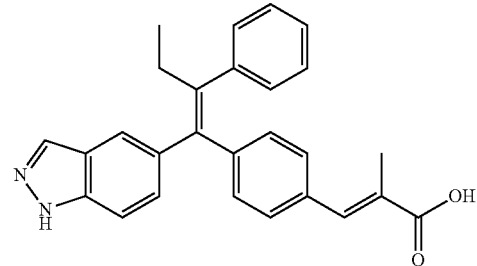 [SMILES: CC/C(=C(/c1ccc(/C=C(\C)C(=O)O)cc1)c1ccc2[nH]ncc2c1)c1ccccc1]

The title compound was prepared from (E)-ethyl 2-methyl-3-(4-((E)-2-phenyl-1-(1-(tetrahydro-2H-pyran-2-yl)-1H-indazol-5-yl)but-1-en-1-yl)phenyl)acrylate following General Procedures F & G. $^1$H NMR (300 MHz, DMSO-$d_6$): δ 13.11 (s, 1H), 12.55 (br, 1H), 8.08 (d, 1H), 7.65 (s, 1H), 7.53 (d, 1H), 7.42 (d, 1H), 7.21-7.11 (m, 8H), 6.90 (d, 2H), 2.40 (q, 2H), 1.92 (d, 3H), 0.87 (t, 3H); LCMS: 409 (M+H)$^+$.

Compounds 177 to 189 were prepared from the appropriate boronic acid or phosphonate following the procedures outlined for Compound 176 or General Procedures C, E, F & G.

Compounds 190 to 192 were prepared from the appropriate boronic acid following General Procedures C, F & optionally G.

Example 48

Preparation of (E)-Ethyl 3-(4-((E)-2-(2-chloro-4-fluorophenyl)-1-(1-(tetrahydro-2H-pyran-2-yl)-1H-indazol-5-yl)but-1-en-1-yl)phenyl)acrylate (Compound 193)

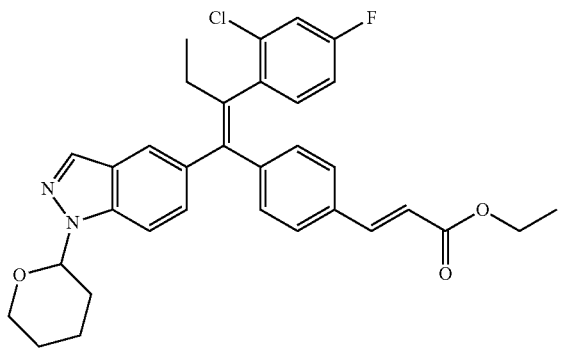 [SMILES: CCOC(=O)/C=C/c1ccc(/C(=C(/CC)c2ccc(F)cc2Cl)c2ccc3c(cnn3C3CCCCO3)c2)cc1]

Step 1: (E)-4-(2-(2-Chloro-4-fluorophenyl)-1-(1-(tetrahydro-2H-pyran-2-yl)-1H-indazol-5-yl)but-1-en-1-yl)benzaldehyde

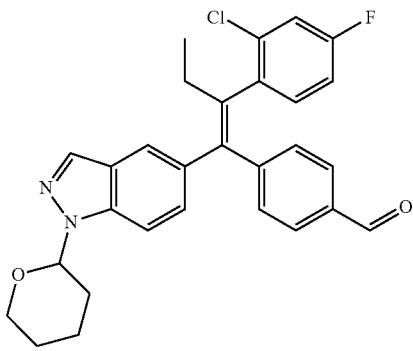 [SMILES: CC/C(=C(/c1ccc(C=O)cc1)c1ccc2c(cnn2C2CCCCO2)c1)c1ccc(F)cc1Cl]

A round-bottom flask equipped with a magnetic stir bar, a reflux condenser, an internal thermometer, and a $N_2$ inlet was charged with 5-(but-1-yn-1-yl)-1-(tetrahydro-2H-pyran-2-yl)-1H-indazole (50.0 g, 197 mmol; Intermediate 3), bis(pinacolato)diboron (50.4 g, 199 mmol), and anhydrous 2-methyltetrahydrofuran (393 mL) followed by Pt(PPh$_3$)$_4$ (1.83 g, 1.5 mmol). This mixture was degassed with three vacuum/$N_2$ cycles, heated at 83° C. (internal temperature; oil bath at 95° C.) for 5 h under $N_2$, and then allowed to cool to room temperature. 2-Methyltetrahydrofuran (393 mL), cesium carbonate (128.1 g, 393 mmol), and water (11.8 mL, 1.5% v/v) were added, and the reaction was cooled to 4° C. 4-Iodobenzaldehyde (45.6 g, 197 mmol) and PdCl$_2$(PPh$_3$)$_2$ (6.90 g, 9.8 mmol) were added, and the reaction was degassed with three vacuum/$N_2$ cycles. The mixture was allowed to warm to room temperature and stirred overnight. Aqueous KOH solution (4M, 275 mL, 1100 mmol) and 2-chloro-4-fluoroiodobenzene (70.6 g, 275 mmol) were added. The reaction was degassed with three vacuum/$N_2$ cycles, heated at 75° C. (internal temperature; oil bath at 90° C.) for 7 h under $N_2$, and then allowed to cool to room temperature. The layers were separated, and the organic layer was washed with brine (800 mL), dried over sodium sulfate, filtered, and concentrated. The crude product was purified by silica gel chromatography (0-20% ethyl acetate in hexanes) to give the title compound (82.6 g, 7:1 mixture of regioisomers) as a pale yellow foam. Data for major isomer; (E)-4-(2-(2-chloro-4-fluorophenyl)-1-(1-(tetrahydro-2H-pyran-2-yl)-1H-indazol-5-yl)but-1-en-1-yl)benzaldehyde: $^1$H NMR (300 MHz, DMSO-d$_6$): δ 9.82 (s, 1H), 8.15 (s, 1H), 7.78-7.71 (m, 2H), 7.61 (d, 2H), 7.43-7.27 (m, 3H), 7.15 (m, 3H), 5.86 (dd, 1H), 3.93-3.85 (m, 1H), 3.79-3.68 (m, 1H), 2.44-2.36 (m, 3H), 2.10-1.96 (m, 2H), 1.81-1.67 (m, 1H), 1.63-1.53 (m, 2H), 0.92 (t, 3H); LCMS: 405 [(M-THP+H)+H]$^+$.

Step 2: (E)-Ethyl 3-(4-((E)-2-(2-chloro-4-fluorophenyl)-1-(1-(tetrahydro-2H-pyran-2-yl)-1H-indazol-5-yl)but-1-en-1-yl)phenyl)acrylate

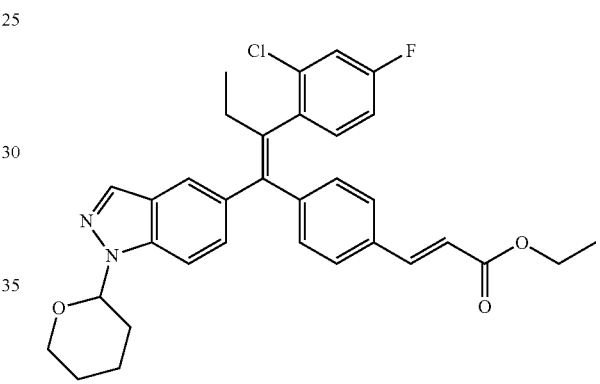

A round-bottom flask equipped with a magnetic stir bar, an addition funnel, and a $N_2$ inlet was charged with (E)-4-(2-(2-chloro-4-fluorophenyl)-1-(1-(tetrahydro-2H-pyran-2-yl)-1H-indazol-5-yl)but-1-en-1-yl)benzaldehyde (82.6 g, 169 mmol), triethylphosphonoacetate (40.6 mL, 203 mmol), lithium chloride (14.5 g, 338 mmol), and anhydrous acetonitrile (338 mL). The reaction was cooled to 0° C. and then degassed with three vacuum/$N_2$ cycles. A solution of DBU (27.8 mL, 186 mmol) in acetonitrile (60 mL) was added dropwise over 35 min, and then the ice water bath was removed. The reaction was stirred at room temperature for 1 h, concentrated, and then partitioned between dichloromethane (250 mL) and H$_2$O (250 mL). The layers were separated, and the organic layer was washed with brine (400 mL), dried over sodium sulfate, filtered, and concentrated. The crude product was passed through a silica gel column (300 g, 20% ethyl acetate in hexanes) and concentrated to give the title compound (89.6 g) as a pale yellow foam. $^1$H NMR (300 MHz, DMSO-d$_6$): δ 8.14 (s, 1H), 7.75 (d, 1H), 7.50-7.33 (m, 6H), 7.27 (dt, 1H), 7.14 (dt, 1H), 6.95 (d, 2H), 6.48 (d, 1H), 5.86 (dd, 1H), 4.14 (q, 2H), 3.94-3.86 (m, 1H), 3.78-3.70 (m, 1H), 2.45-2.34 (m, 3H), 2.06-1.95 (m, 2H), 1.78-1.67 (m, 1H), 1.62-1.53 (m, 2H), 1.19 (t, 3H), 0.90 (t, 3H); LCMS: 475 [(M-THP+H)+H]$^+$.

Example 49

Preparation of (E)-Ethyl 3-(4-((E)-2-(2-chloro-4-fluorophenyl)-1-(1H-indazol-5-yl)but-1-en-1-yl)phenyl)acrylate hydrochloride (Compound 194)

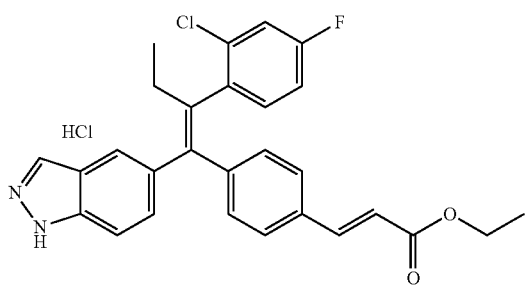 [SMILES: CCOC(=O)/C=C/c1ccc(/C(=C(/CC)c2ccc(F)cc2Cl)c2ccc3[nH]ncc3c2)cc1 ; Cl]

A round-bottom flask equipped with a magnetic stir bar was charged with (E)-ethyl 3-(4-((E)-2-(2-chloro-4-fluorophenyl)-1-(1-(tetrahydro-2H-pyran-2-yl)-1H-indazol-5-yl)but-1-en-1-yl)phenyl)acrylate (255.9 g, 457.8 mmol; Compound 193) and a solution of HCl (732 mL, 1.25 M in ethyl alcohol). The reaction was heated at 80° C. for 2.5 h, allowed to cool to room temperature, and then concentrated to an orange gel. tert-Butyl methyl ether (2.3 L) was added. After stirring for 5 min, solids began to precipitate. The mixture was stirred at room temperature for 2 h and then filtered. The solids were washed with MTBE (700 mL) and dried to give the title compound (193 g) as an off-white solid. $^1$H NMR (DMSO-d$_6$): δ 8.11 (s, 1H), 7.69 (s, 1H), 7.57-7.50 (m, 2H), 7.45-7.33 (m, 4H), 7.21-7.10 (m, 2H), 6.96 (d, 2H), 6.48 (d, 1H), 4.14 (q, 2H), 2.38 (q, 2H), 1.19 (t, 3H), 0.90 (t, 3H); LCMS: 475 (M+H)$^+$.

Example 50

Preparation of (E)-3-(4-((E)-2-(2-Chloro-4-fluorophenyl)-1-(1H-indazol-5-yl)but-1-en-1-yl)phenyl)acrylic acid (Compound 195)

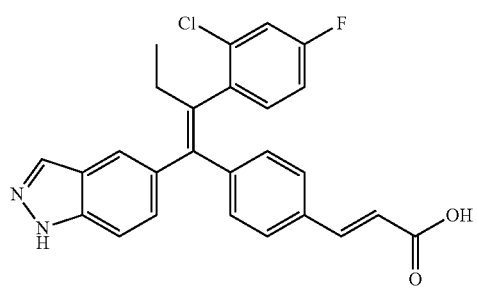

A round-bottom flask equipped with a magnetic stir bar was charged with (E)-ethyl 3-(4-((E)-2-(2-chloro-4-fluorophenyl)-1-(1H-indazol-5-yl)but-1-en-1-yl)phenyl)acrylate hydrochloride (198.5 g, 388 mmol; Compound 194) and ethyl alcohol (517 mL). A solution of LiOH (27.9 g, 1164 mmol) in water (388 mL) was added, and the mixture was stirred at room temperature overnight. The ethyl alcohol was removed by rotary evaporation, and the remaining solution was cooled to 0° C. and acidified with 2M aqueous HCl to pH 3. Dichloromethane (500 mL) was added, the mixture was stirred, and then the layers were separated. The organic layer was washed with water, washed with brine, dried over sodium sulfate, filtered, and concentrated. The crude product was passed through a silica column (800 g, 5% MeOH in DCM) and concentrated. The product was then dissolved in DCM (400 mL), and acetonitrile (500 mL) was added. Approximately 200 mL of DCM was removed by rotary evaporation (solids began to precipitate). Acetonitrile (550 mL) was added followed by water (25 mL). The mixture was stirred at room temperature for 2 h. The solvent was decanted, and then acetonitrile:DCM (10:1; 550 mL) was added. The mixture stirred at room temperature for 1.5 h, the solvent was again decanted, and then acetonitrile:DCM (10:1; 550 mL) was added. The mixture was again stirred at room temperature for 1.5 h and then filtered. The solids were resuspended in acetonitrile:DCM (10:1; 550 mL), stirred at room temperature for 1.5 h, filtered, and washed to give the title compound (123.9 g) as an off-white powder. $^1$H NMR (DMSO-d$_6$): δ 13.12 (s, 1H), 12.34 (br, 1H), 8.11 (d, 1H), 7.69 (s, 1H), 7.56 (d, 1H), 7.44-7.33 (m, 5H), 7.21-7.10 (m, 2H), 6.96 (d, 2H), 6.38 (d, 1H), 2.34 (q, 2H), 0.90 (t, 3H); LCMS: 447 (M+H)$^+$.

Example 51

Preparation of (E)-Ethyl 3-(4-((E)-2-(2,4-dichlorophenyl)-1-(1H-indazol-5-yl)but-1-en-1-yl)phenyl)acrylate (Compound 196)

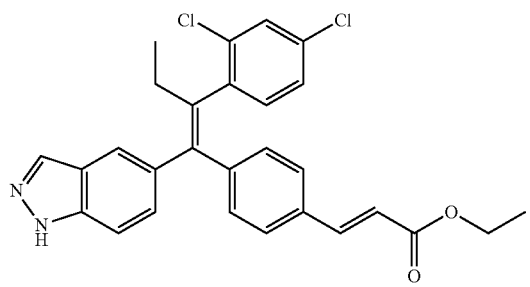 [SMILES: CCOC(=O)/C=C/c1ccc(/C(=C(/CC)c2ccc(Cl)cc2Cl)c2ccc3[nH]ncc3c2)cc1]

Step 1: (E)-4-(2-(2,4-Dichlorophenyl)-1-(1-(tetrahydro-2H-pyran-2-yl)-1H-indazol-5-yl)but-1-en-1-yl)benzaldehyde

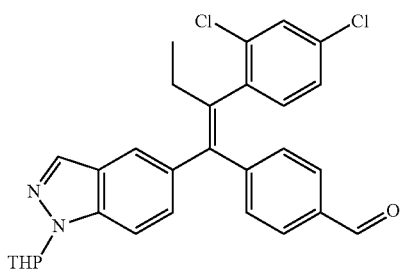

A round-bottom flask equipped with a magnetic stir bar, a reflux condenser, and a N$_2$ inlet was charged with 5-(but-1-yn-1-yl)-1-(tetrahydro-2H-pyran-2-yl)-1H-indazole (20.0 g, 78.6 mmol; Intermediate 3), bis(pinacolato)diboron (20.17 g, 79.4 mmol), tetrakis(triphenylphosphine)platinum (0) (0.98 g, 0.8 mmol), and anhydrous 1,4-dioxane (160 mL). This mixture was degassed with three vacuum/N₂ cycles and refluxed for 4 h. The solution was then allowed to cool to room temperature, and 4-iodobenzaldehyde (18.25 g, 78.6 mmol), trans-dichloro(triphenylphosphine)palladium (II) (5.52 g, 7.9 mmol), cesium carbonate (51.24 g, 157.3 mmol), and 1,4-dioxane (160 mL) were added. This mixture was degassed with three vacuum/N₂ cycles, and then water (4.7 mL) was added. This mixture was stirred at room temperature for 6 h. 2,4-Dichloroiodobenzene (12.8 mL, 94.4 mmol) and 6M aqueous KOH (62.9 mL) were added, and the mixture was degassed with three vacuum/N₂ cycles and refluxed for 4 h. Upon completion, the reaction mixture was filtered through a Celite/silica pad and washed with EtOAc. The filtrate was washed with water (600 mL), washed with brine (300 mL), dried over sodium sulfate, filtered, and concentrated. The crude product was purified by silica gel chromatography (0-20% ethyl acetate in hexanes) to give the title compound (27.2 g, 7:1 mixture of regioisomers) as a yellow foam. Data for major regioisomer: $^1$H NMR (400 MHz, DMSO-d₆): δ 9.83 (s, 1H), 8.16 (s, 1H), 7.77 (d, 1H), 7.73 (s, 1H), 7.65 (d, 2H), 7.53 (d, 1H), 7.41-7.36 (m, 2H), 7.31-7.28 (m, 1H), 7.17 (d, 2H), 5.86 (dd, 1H), 3.92-3.86 (m, 1H), 3.78-3.71 (m, 1H), 2.47-2.38 (m, 3H), 2.10-1.96 (m, 2H), 1.81-1.71 (m, 1H), 1.64-1.58 (m, 2H), 0.94 (t, 3H); LCMS: 421 [(M-THP+H)+H]⁺.

Step 2: (E)-Ethyl 3-(4-((E)-2-(2,4-dichlorophenyl)-1-(1-(tetrahydro-2H-pyran-2-yl)-1H-indazol-5-yl)but-1-en-1-yl)phenyl)acrylate

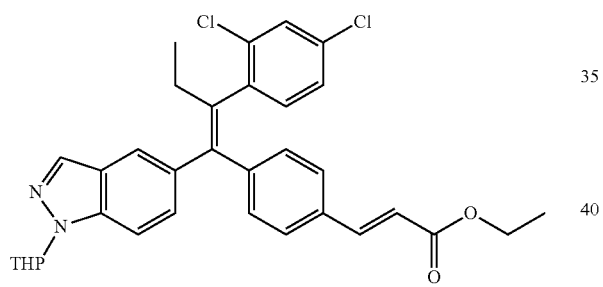

A round-bottom flask equipped with a magnetic stir bar, a rubber septum, and a N₂ inlet was charged with (E)-4-(2-(2,4-dichlorophenyl)-1-(1-(tetrahydro-2H-pyran-2-yl)-1H-indazol-5-yl)but-1-en-1-yl)benzaldehyde (26.7 g, 52.8 mmol), triethylphosphonoacetate (12.7 mL, 63.4 mmol), lithium chloride (4.53 g, 105.7 mmol), and anhydrous acetonitrile (106 mL). A solution of DBU (8.7 mL, 58.1 mmol) in acetonitrile (27 mL) was slowly added dropwise via addition funnel. The resulting mixture was stirred at room temperature for 4 h. Upon completion, the reaction was concentrated and redissolved in DCM. This solution was washed with water (300 mL), washed with brine (250 mL), dried over sodium sulfate, filtered and concentrated. The crude product was purified by silica gel chromatography (0-20% ethyl acetate in hexanes) to give the title compound (29.0 g) as a pale yellow foam. $^1$H NMR (400 MHz, DMSO-d₆): δ 8.14 (s, 1H), 7.75 (d, 1H), 7.72 (s, 1H), 7.54 (d, 1H), 7.48 (d, 1H), 7.43 (d, 2H), 7.37-7.35 (m, 2H), 7.29-7.26 (m, 1H), 6.97 (d, 2H), 6.48 (d, 1H), 5.86 (dd, 1H), 4.14 (q, 2H), 3.91-3.86 (m, 1H), 3.77-3.71 (m, 1H), 2.48-2.35 (m, 3H), 2.06-1.96 (m, 2H), 1.78-1.71 (m, 1H), 1.62-1.55 (m, 2H), 1.22 (t, 3H), 0.90 (t, 3H); LCMS: 491 [(M-THP+H)+H]⁺.

Step 3: (E)-Ethyl 3-(4-((E)-2-(2,4-dichlorophenyl)-1-(1H-indazol-5-yl)but-1-en-1-yl)phenyl)acrylate

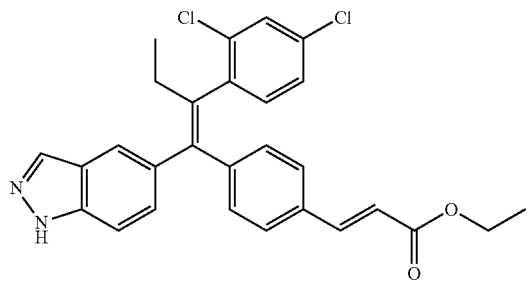 [SMILES: CCOC(=O)/C=C/c1ccc(/C(=C(/CC)c2ccc(Cl)cc2Cl)c2ccc3[nH]ncc3c2)cc1]

A solution of HCl (5.0 mL, 2.0 M in diethyl ether) was added to a solution of (E)-ethyl 3-(4-((E)-2-(2,4-dichlorophenyl)-1-(tetrahydro-2H-pyran-2-yl)-1H-indazol-5-yl)but-1-en-1-yl)phenyl)acrylate (3.0 g, 5.2 mmol) in ethyl alcohol (25 mL) at room temperature. The resulting mixture was heated at 70° C. for 2 h. Upon completion, the mixture was cooled down to room temperature and concentrated to give a pale yellow solid. This crude material was dissolved in DCM and washed with water (50 mL), washed with brine (50 mL), dried over sodium sulfate, filtered, and concentrated. The crude product was purified by silica gel chromatography (0-100% ethyl acetate in hexanes) to give the title compound (2.37 g) as a pale yellow solid. $^1$H NMR (400 MHz, DMSO-d₆): δ 13.17 (s, 1H), 8.11 (s, 1H), 7.69 (s, 1H), 7.58-7.52 (m, 2H), 7.48 (d, 1H), 7.43 (d, 2H), 7.36-7.32 (m, 2H), 7.19 (dd, 1H), 6.97 (d, 2H), 6.49 (d, 1H), 4.15 (q, 2H), 2.39 (q, 2H), 1.22 (t, 3H), 0.90 (t, 3H); LCMS: 491 (M+H)⁺.

Example 52

Preparation of (E)-3-(4-((E)-2-(2,4-Dichlorophenyl)-1-(1H-indazol-5-yl)but-1-en-1-yl)phenyl)acrylic acid (Compound 197)

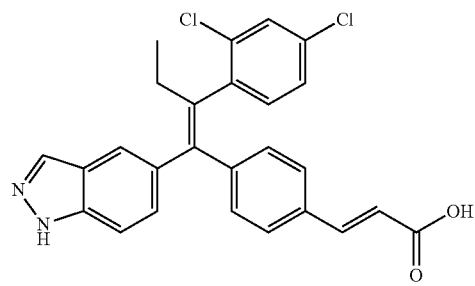

A solution of LiOH (0.23 g, 9.6 mmol) in water (3.2 mL) was added to a solution of (E)-ethyl 3-(4-((E)-2-(2,4-dichlorophenyl)-1-(1H-indazol-5-yl)but-1-en-1-yl)phenyl)acrylate (2.37 g, 4.8 mmol; Compound 196) in EtOH (20 mL) at room temperature. The resulting mixture was stirred overnight. Upon completion, 1N aqueous HCl was added until the pH was 3. The mixture was diluted with water and extracted with ethyl acetate (2×25 mL). The combined organic layers were washed with water (50 mL), washed with brine (50 mL), dried over sodium sulfate, filtered, and concentrated. The crude product was purified on a preparative reversed-phased HPLC column using 80-95% acetonitrile in water in the presence of 0.1% TFA to give the title compound (1.3 g) as an off-white solid. $^1$H NMR (400 MHz, DMSO-d$_6$): δ 13.11 (s, 1H), 12.36 (br, 1H), 8.11 (d, 1H), 7.69 (s, 1H), 7.57-7.53 (m, 2H), 7.44-7.35 (m, 5H), 7.19 (dd, 1H), 6.97 (d, 2H), 6.39 (d, 1H), 2.39 (q, 2H), 0.90 (t, 3H); LCMS: 463 (M+H)$^+$.

Compounds 198 to 313 were prepared from alkynyl-intermediates following General Procedures D, E, F (optionally), & G. The alkynyl-intermediates have either i) been described herein or ii) were prepared from known or commercially available halo-heterocycles (or aryl-halides) following General Procedures A (optionally) & B.

Example 53

Preparation of (E)-Ethyl 3-(4-((Z)-1-(1-(tetrahydro-2H-pyran-2-yl)-1H-indazol-5-yl)-2-(4,4,5,5-tetramethyl-1,3,2-dioxaborolan-2-yl)but-1-en-1-yl)phenyl) acrylate (Intermediate 77)

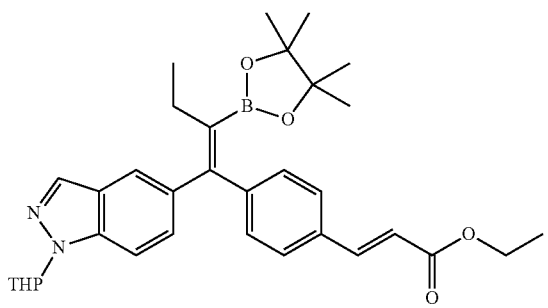

Step 1: (E)-Ethyl 3-(4-iodophenyl)acrylate

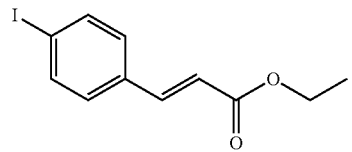

N-Iodosuccinimide (2.5 g, 11 mmol) was added to a suspension of 4-(E-3-ethoxy-3-oxo-1-propen-1-yl)phenylboronic acid (2.2 g, 10 mmol) in CH$_3$CN (50 mL) at room temperature. The reaction was covered with foil, stirred for 26 h, and then diluted with EtOAc. The resulting mixture was washed with water (2×100 mL), washed with sodium thiosulfate (100 mL), dried (MgSO$_4$), filtered, and concentrated. The crude material was purified by silica gel chromatography (0-50% EtOAc in hexanes) to give 2.6 g of (E)-ethyl 3-(4-iodophenyl)acrylate as a yellow oil. $^1$H NMR (400 MHz, DMSO-d$_6$): δ 7.79 (d, 2H), 7.60 (d, 1H), 7.53 (d, 2H), 6.68 (d, 1H), 4.19 (q, 2H), 1.26 (t, 3H); LCMS: 303 (M+H)$^+$.

Step 2: (E)-Ethyl 3-(4-((Z)-1-(1-(tetrahydro-2H-pyran-2-yl)-1H-indazol-5-yl)-2-(4,4,5,5-tetramethyl-1,3,2-dioxaborolan-2-yl)but-1-en-1-yl)phenyl)acrylate

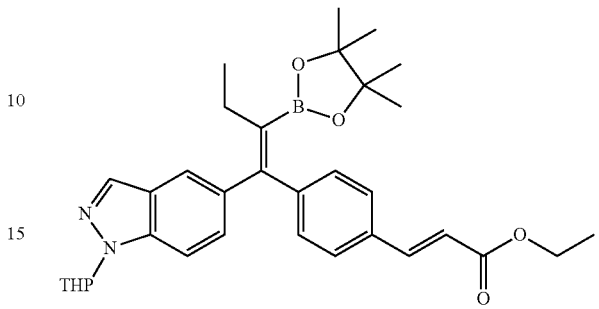

The title compound was be prepared from Intermediate 3 and (E)-ethyl 3-(4-iodophenyl)acrylate following General Procedure D, Steps 1-2. $^1$H NMR (400 MHz, DMSO-d$_6$): δ 8.09 (s, 1H), 7.70 (d, 1H), 7.58-7.63 (m, 3H), 7.49 (s, 1H), 7.11 (d, 3H), 6.58 (d, 1H), 5.84 (dd, 1H), 4.18 (q, 2H), 3.86-3.91 (m, 1H), 3.70-3.77 (m, 1H), 2.36-2.48 (m, 1H), 2.08-2.15 (m, 2H), 1.95-2.08 (m, 2H), 1.70-1.81 (m, 1H), 1.56-1.62 (m, 2H), 1.25 (t, 3H), 1.12 (s, 12H), 1.01 (t, 3H); LCMS: 473 [(M-THP+H)+H]$^+$.

Compounds 314 to 326 were prepared from Intermediate 77 following General Procedures D (Step 3; K$_2$CO$_3$ modification), F, & G.

Example 54

Preparation of (E)-3-(4-((E)-2-(3-(Carboxymethyl)phenyl)-1-(1H-indazol-5-yl)but-1-en-1-yl)phenyl) acrylic acid (Compound 327)

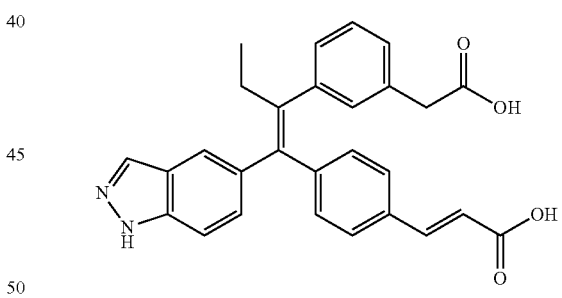

(E)-Ethyl 3-(4-((Z)-1-(1-(tetrahydro-2H-pyran-2-yl)-1H-indazol-5-yl)-2-(4,4,5,5-tetramethyl-1,3,2-dioxaborolan-2-yl)but-1-en-1-yl)phenyl)acrylate (Intermediate 77) and ethyl 2-(3-bromophenyl)acetate were coupled according to general procedure D, step 3. The KOH used in this coupling resulted in hydrolysis of both esters, so the reaction was then treated with 12M HCl and heated at 80° C. for 80 min to remove the THP. Upon cooling, the reaction was diluted with diethyl ether and H$_2$O. The aqueous layer was extracted with diethyl ether, and the organic extracts were combined, dried (MgSO$_4$), filtered, and concentrated. The crude material was purified by reverse-phase HPLC (CH$_3$CN, H$_2$O, TFA) to give (E)-3-(4-((E)-2-(4-(carboxymethyl)phenyl)-1-(1H-indazol-5-yl)but-1-en-1-yl)phenyl)acrylic acid. $^1$H NMR (400 MHz, DMSO-d$_6$): δ 13.09 (bs, 1H), 8.08 (s, 1H), 7.65 (s, 1H), 7.54 (d, 1H), 7.41 (d, 1H), 7.34 (d, 2H), 7.10-7.18 (m, 3H), 7.05 (d, 1H), 6.97 (d, 1H), 6.89 (d, 2H), 6.36 (d, 1H), 3.49 (s, 2H), 2.42 (q, 2H), 0.90 (t, 3H); LCMS: 453 (M+H)⁺.

Compound 328 was prepared from ethyl 2-(4-bromophenyl)acetate following the procedure outlined for Compound 327.

Compounds 329 to 334 were prepared from Intermediate 3 and the appropriate aryl-halide intermediates following General Procedures D, F, and optionally G. The aryl-halide intermediates have been described herein or are known in the literature.

Example 55

Preparation of (E)-3-(4-((E)-2-(3-Hydroxyphenyl)-1-(1H-indazol-5-yl)but-1-en-1-yl)phenyl)acrylic acid (Compound 335)

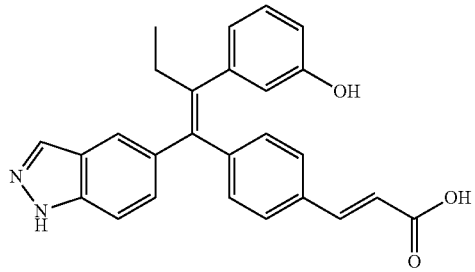

A 10-mL recovery flask equipped with a magnetic stir bar, a rubber septum and N₂ inlet was charged with (E)-3-(4-((E)-1-(1H-indazol-5-yl)-2-(3-methoxyphenyl)but-1-en-1-yl)phenyl)acrylic acid (30 mg, 0.07 mmol, Compound 7) and DCM (1.4 mL). This solution was cooled down to 0° C. in an ice-bath. Then, BBr₃ (88 mg, 0.35 mmol) was added dropwise. The reaction mixture was stirred at 0° C. for 1 h. Upon completion, the reaction was quenched with methanol (5 mL) at 0° C. The resulting mixture was concentrated under reduced pressure to give the crude product that was directly purified on a reversed phased C-18 column eluted with 40-100% acetonitrile in water in the presence of 0.1% TFA affording the title compound as an off-white solid (11 mg). ¹H NMR (300 MHz, DMSO-d₆): δ 13.11 (s, 1H), 12.32 (br, 1H), 9.23 (s, 1H), 8.08 (s, 1H), 7.62 (s, 1H), 7.52 (d, 1H), 7.45-7.35 (m, 3H), 7.12 (d, 1H), 7.00 (t, 1H), 6.90 (d, 2H), 6.59-6.53 (m, 3H), 6.36 (d, 1H), 2.37 (q, 2H), 0.89 (t, 3H); LCMS: 411 (M+H)⁺.

Example 56

Preparation of (E)-3-(4-((E)-2-(2-Hydroxyphenyl)-1-(1H-indazol-5-yl)but-1-en-1-yl)phenyl)acrylic acid (Compound 336)

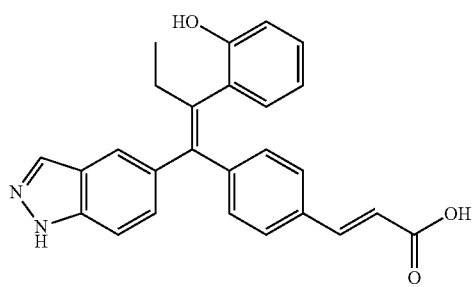

A 10-mL recovery flask equipped with a magnetic stir bar, a rubber septum and N₂ inlet was charged with (E)-ethyl 3-(4-((E)-1-(1H-indazol-5-yl)-2-(2-methoxyphenyl)but-1-en-1-yl)phenyl)acrylate (145 mg, 0.32 mmol, an intermediate in the synthesis of Compound 14) in DCM (6 mL). This solution was cooled down to −78° C. in an IPA/dry ice-bath. Then, BBr₃ (241 mg, 0.96 mmol) was added dropwise via a syringe. The reaction mixture was gradually warmed to 0° C. for 1 h. Upon completion, the reaction was quenched with methanol (5 mL) at 0° C. The resulting mixture was concentrated under reduced pressure to give the crude product. Then, this crude product was dissolved in THF-EtOH (1:1, 6 mL), and an aqueous solution of LiOH (0.15 g, 6.4 mmol) was added at room temperature. The resulting mixture was stirred overnight. The reaction was monitored by LCMS. Upon completion, 1N aqueous HCl was added until pH was 3. Then, the mixture was diluted with water and extracted with ethyl acetate (3×100 mL). The combined organic layers were washed with water (100 mL), washed with brine (50 mL), dried over sodium sulfate, filtered, and concentrated to give the crude product. This crude material was purified on a reversed phase C-18 column eluted with 40-100% acetonitrile in water in the presence of 0.1% TFA affording the title compound. ¹H NMR (300 MHz, DMSO-d₆): δ 13.07 (s, 1H), 12.34 (br, 1H), 9.33 (br, 1H), 8.08 (d, 1H), 7.65 (s, 1H), 7.53 (d, 1H), 7.40 (d, 1H), 7.32 (d, 2H), 7.15 (dd, 1H), 7.00-6.94 (m, 3H), 6.81-6.76 (m, 2H), 6.57 (dt, 1H), 6.34 (d, 1H), 2.43-2.30 (m, 2H), 0.88 (t, 3H); LCMS: 411 (M+H)⁺.

Compound 337 was prepared following the procedure outlined for Compound 336.

Example 57

Preparation of (E)-3-(4-(1-(1H-Indazol-5-yl)-2-phenylbut-1-en-1-yl)phenyl)propanoic acid (Compound 338)

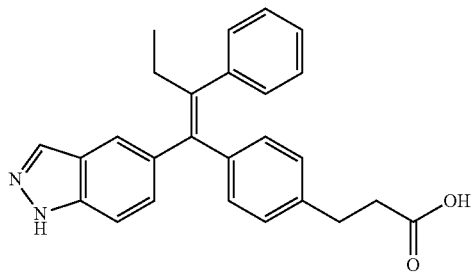

A 10-mL recovery flask equipped with a magnetic stir bar and a rubber septum was charged with Compound 1 (50 mg, 0.126 mmol) and EtOH-EtOAc (1:1, 2.5 mL). To this solution, palladium on carbon (13 mg, 10% Pd/C) was added in one portion. The flask was equipped with a hydrogen balloon, and the resulting mixture was stirred at room temperature 36 h. This mixture was filtered through Celite, concentrated, and purified on a RP-C18 column using 30-100% acetonitrile in water in the presence of 0.1% TFA to afford the title compound (24 mg). ¹H NMR (300 MHz, Acetone-d₆): δ; 7.94 (s, 1H), 7.58 (br, 1H), 7.44 (d, 1H), 7.17-6.97 (m, 6H), 6.8-6.73 (m, 4H), 2.64 (t, 2H), 2.39-2.32 (m, 4H), 0.80 (t, 3H), (NH and CO₂H protons not observed). LCMS: 397 (M+H)⁺.

Example 58

Preparation of (E)-3-(4-((E)-1-(1H-Indazol-5-yl)-2-(4-(2-methoxyethoxy)phenyl)but-1-en-1-yl)phenyl)acrylic acid (Compound 339)

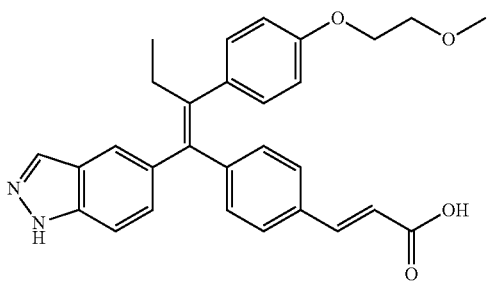 [SMILES: CC/C(=C(/c1ccc(/C=C/C(=O)O)cc1)c1ccc2[nH]ncc2c1)c1ccc(OCCOC)cc1]

Step 1: (E)-Ethyl 3-(4-((E)-2-(4-hydroxyphenyl)-1-(1-(tetrahydro-2H-pyran-2-yl)-1H-indazol-5-yl)but-1-en-1-yl)phenyl)acrylate

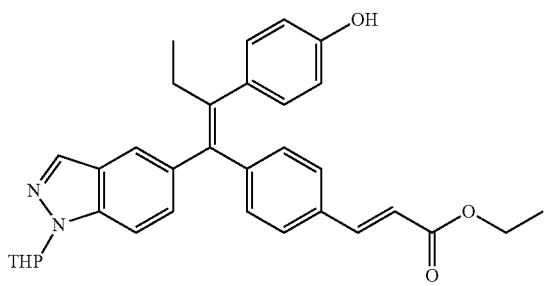

The title compound was prepared from Intermediate 3, 4-iodophenol, and (E)-(4-(3-ethoxy-3-oxoprop-1-en-1-yl)phenyl)boronic acid following General Procedure C. LCMS: 439 [(M-THP+H)+H]$^+$.

Step 2: (E)-Ethyl 3-(4-((E)-2-(4-(2-methoxyethoxy)phenyl)-1-(1-(tetrahydro-2H-pyran-2-yl)-1H-indazol-5-yl)but-1-en-1-yl)phenyl)acrylate

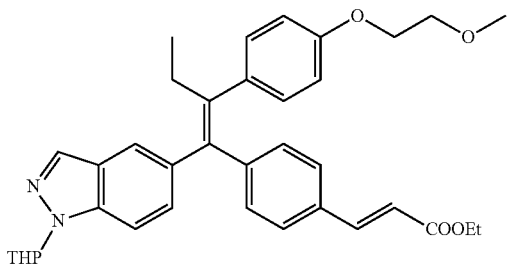

A mixture of (E)-ethyl 3-(4-((E)-2-(4-hydroxyphenyl)-1-(1-(tetrahydro-2H-pyran-2-yl)-1H-indazol-5-yl)but-1-en-1-yl)phenyl)acrylate (222 mg, 0.42 mmol), 2-methoxyethanol (0.1 mL, 1.26 mmol), diisopropyl azidocarboxylate (0.24 mL, 1.26 mmol), and triphenylphosphine (330 mg, 1.26 mmol) in THF (5 mL) was stirred at room temperature overnight. The reaction mixture was absorbed on silica gel and purified by flash chromatography on silica gel eluting with 0 to 50% ethyl acetate/hexanes to afford 139 mg of the title compound as a yellow solid. $^1$H NMR (400 MHz, DMSO-d$_6$): δ 8.11 (s, 1H), 7.72 (d, 1H), 7.62 (s, 1H), 7.48 (d, 1H), 7.40 (d, 2H), 7.21 (d, 1H), 7.08 (d, 2H), 6.88 (d, 2H), 6.79 (d, 2H), 6.47 (d, 1H), 5.85 (dd, 1H), 4.13 (qt, 2H), 4.02 (m, 2H), 3.90 (m, 1H), 3.74 (m, 1H), 3.62 (m, 2H), 3.29 (s, 3H), 2.47-2.37 (m, 3H), 2.01 (m, 2H), 1.76 (m, 1H), 1.59 (m, 2H), 1.22 (t, 3H), 0.89 (t, 3H).

Step 3: (E)-3-(4-((E)-1-(1H-Indazol-5-yl)-2-(4-(2-methoxyethoxy)phenyl)but-1-en-1-yl)phenyl)acrylic acid

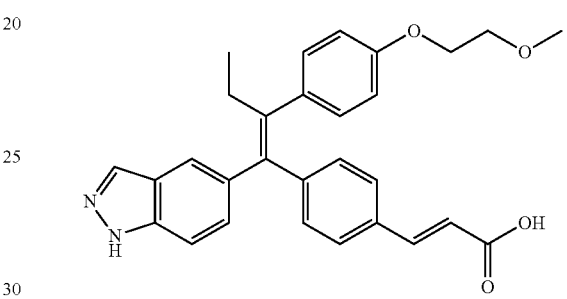

The title compound was prepared from (E)-ethyl 3-(4-((E)-2-(4-(2-methoxyethoxy)phenyl)-1-(1-(tetrahydro-2H-pyran-2-yl)-1H-indazol-5-yl)but-1-en-1-yl)phenyl)acrylate following General Procedures F and G. $^1$H NMR (400 MHz, DMSO-d$_6$): δ NH and COOH not observed, 8.08 (s, 1H), 7.62 (s, 1H), 7.53 (d, 1H), 7.42 (d, 1H), 7.37 (d, 2H), 7.13 (dd, 1H), 7.07 (d, 2H), 6.88 (d, 2H), 6.78 (d, 2H), 6.37 (d, 1H), 4.02 (m, 2H), 3.62 (m, 2H), 3.29 (s, 3H), 2.41 (qt, 2H), 0.89 (t, 3H). LCMS: 469 (M+H)$^+$.

Compounds 340 to 345 were prepared following the procedures outlined for Compound 339.

Example 59

Preparation of (E)-3-(4-((E)-2-(3-Butoxyphenyl)-1-(1H-indazol-5-yl)but-1-en-1-yl)phenyl)acrylic acid (Compound 346)

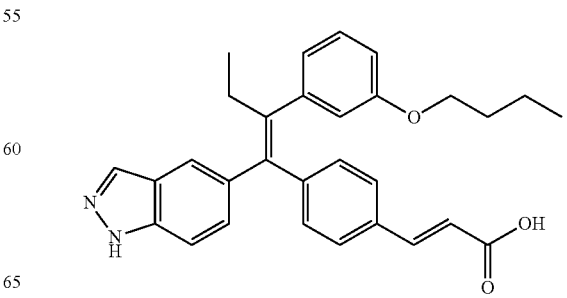

339

Step 1: (E)-Ethyl 3-(4-((E)-2-(3-hydroxyphenyl)-1-(1-(tetrahydro-2H-pyran-2-yl)-1H-indazol-5-yl)but-1-en-1-yl)phenyl)acrylate

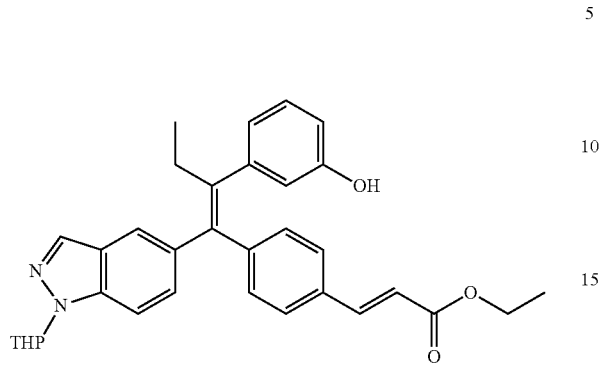

The title compound was prepared from Intermediate 3, 3-iodophenol, and (E)-(4-(3-ethoxy-3-oxoprop-1-en-1-yl)phenyl)boronic acid following General Procedure C.

Step 2: (E)-Ethyl 3-(4-((E)-2-(3-butoxyphenyl)-1-(1-(tetrahydro-2H-pyran-2-yl)-1H-indazol-5-yl)but-1-en-1-yl)phenyl)acrylate

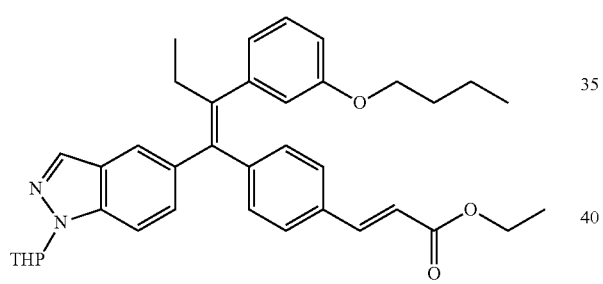

Potassium carbonate (53 mg, 0.38 mmol) was added to (E)-ethyl 3-(4-((E)-2-(3-hydroxyphenyl)-1-(1-(tetrahydro-2H-pyran-2-yl)-1H-indazol-5-yl)but-1-en-1-yl)phenyl)acrylate (101 mg, 0.19 mmol) in CH$_3$CN (1 mL). After stirring for 15 min, iodobutane (2 µL, 0.21 mmol) was added. The reaction was stirred at rt for 15 h. Additional iodobutane (24 µL, 0.21 mmol) was added, and the reaction was stirred at 60° C. for 10 h and then at rt for 48 h. The reaction was diluted with dichloromethane and filtered through celite. The filtrate was concentrated and purified by silica gel chromatography (0-20% EtOAc in hexanes) to give 97 mg of (E)-ethyl 3-(4-((E)-2-(3-butoxyphenyl)-1-(1-(tetrahydro-2H-pyran-2-yl)-1H-indazol-5-yl)but-1-en-1-yl)phenyl)acrylate as a white foam. $^1$H NMR (400 MHz, DMSO-d$_6$): δ 8.12 (s, 1H), 7.73 (d, 1H), 7.64 (s, 1H), 7.49 (d, 1H), 7.41 (d, 2H), 7.24 (dd, 1H), 7.12 (t, 1H), 6.91 (d, 2H), 6.76 (d, 1H), 6.67-6.72 (m, 2H), 6.48 (d, 1H), 5.86 (d, 1H), 4.15 (q, 2H), 3.86-3.94 (m, 1H), 3.72-3.80 (m, 3H), 2.38-2.46 (m, 3H), 1.96-2.10 (m, 2H), 1.70-1.82 (m, 1H), 1.52-1.63 (m, 4H), 1.31-1.37 (m, 2H), 1.22 (t, 3H), 0.85-0.92 (m, 6H); LCMS: 495 [(M-THP+H)+H]$^+$.

Step 3: (E)-3-(4-((E)-2-(3-Butoxyphenyl)-1-(1H-indazol-5-yl)but-1-en-1-yl)phenyl)acrylic acid

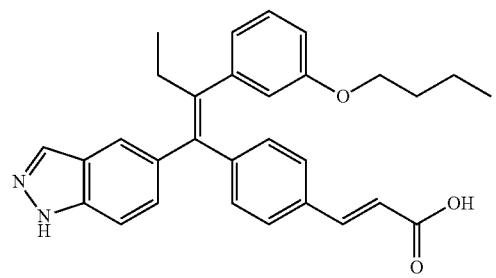 [SMILES: CCCCOc1cccc(/C(CC)=C(\c2ccc(/C=C/C(=O)O)cc2)c2ccc3[nH]ncc3c2)c1]

The title compound was prepared from (E)-ethyl 3-(4-((E)-2-(3-butoxyphenyl)-1-(1-(tetrahydro-2H-pyran-2-yl)-1H-indazol-5-yl)but-1-en-1-yl)phenyl)acrylate following General Procedures F and G. $^1$H NMR (400 MHz, DMSO-d$_6$): δ 13.11 (bs, 1H), 12.33 (bs, 1H), 8.08 (s, 1H), 7.64 (s, 1H), 7.54 (d, 1H), 7.43 (d, 1H), 7.37 (d, 2H), 7.10-7.17 (m, 2H), 6.91 (d, 2H), 6.75 (d, 1H), 6.66-6.72 (m, 2H), 6.37 (d, 1H), 3.78 (t, 2H), 2.43 (q, 2H), 1.52-1.60 (m, 2H), 1.29-1.38 (m, 2H), 0.85-0.92 (m, 6H); LCMS: 467 (M+H)$^+$.

Compounds 347 to 359 were prepared following the procedures outlined for Compound 346.

Example 60

Preparation of (E)-3-(4-((E)-2-(4-(2-Hydroxyethoxy)phenyl)-1-(1H-indazol-5-yl)but-1-en-1-yl)phenyl)acrylic acid (Compound 360)

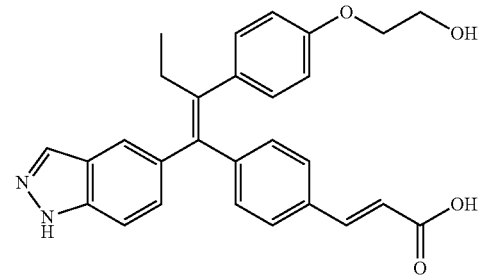 [SMILES: CC/C(=C(/c1ccc(/C=C/C(=O)O)cc1)c1ccc2[nH]ncc2c1)c1ccc(OCCO)cc1]

Step 1: (E)-Ethyl 3-(4-((E)-2-(4-(2-hydroxyethoxy)phenyl)-1-(1-(tetrahydro-2H-pyran-2-yl)-1H-indazol-5-yl)but-1-en-1-yl)phenyl)acrylate

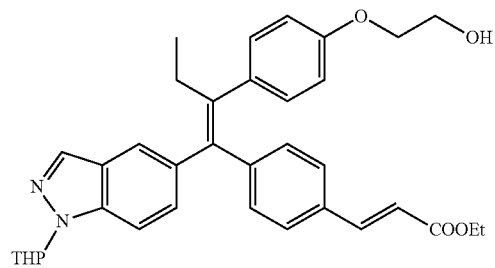

A mixture of (E)-ethyl 3-(4-((E)-2-(4-hydroxyphenyl)-1-(1-(tetrahydro-2H-pyran-2-yl)-1H-indazol-5-yl)but-1-en-1-yl)phenyl)acrylate (352 mg, 0.67 mmol; Compound 339, Step 1), 1,3-dioxolan-2-one (296 mg, 3.37 mmol), and potassium carbonate (185 mg, 1.34 mmol) in DMF (7 mL) was heated to 90° C. overnight. The mixture was cooled to room temperature and poured into ethyl acetate. The organic phase was washed with brine (3×), dried over sodium sulfate, and purified by flash chromatography on silica gel eluting with 0 to 100% ethyl acetate/hexanes to afford 182 mg of the title compound as a yellow foam. $^1$H NMR (400 MHz, DMSO-$d_6$): δ 8.11 (s, 1H), 7.72 (d, 1H), 7.62 (s, 1H), 7.47 (d, 1H), 7.40 (d, 2H), 7.21 (dd, 1H), 7.08 (d, 2H), 6.88 (d, 2H), 6.78 (d, 2H), 6.48 (d, 1H), 5.85 (dd, 1H), 4.83 (t, 1H), 4.14 (qt, 2H), 4.17-3.88 (m, 3H), 3.76 (m, 1H), 3.69 (m, 2H), 2.44-2.37 (m, 3H), 2.00 (m, 2H), 1.75 (m, 1H), 1.60 (m, 2H), 1.21 (t, 3H), 0.89 (t, 3H). LCMS: 483 [(M-THP+H)+H]$^+$.

Step 2: (E)-3-(4-((E)-2-(4-(2-Hydroxyethoxy)phenyl)-1-(1H-indazol-5-yl)but-1-en-1-yl)phenyl)acrylic acid

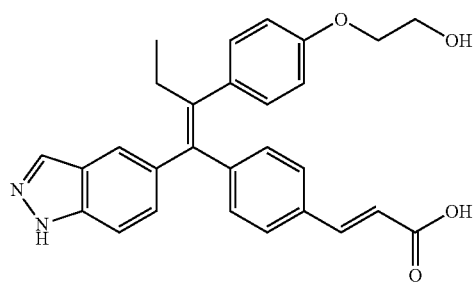 [SMILES: CC/C(=C(/c1ccc(/C=C/C(=O)O)cc1)c1ccc2[nH]ncc2c1)c1ccc(OCCO)cc1]

The title compound was prepared from (E)-ethyl 3-(4-((E)-2-(4-(2-hydroxyethoxy)phenyl)-1-(1-(tetrahydro-2H-pyran-2-yl)-1H-indazol-5-yl)but-1-en-1-yl)phenyl)acrylate following General Procedures F and G. $^1$H NMR (400 MHz, DMSO-$d_6$): δ NH, COOH, and OH not observed, 8.08 (s, 1H), 7.62 (s, 1H), 7.53 (d, 1H), 7.42 (d, 1H), 7.37 (d, 2H), 7.12 (dd, 1H), 7.07 (d, 2H), 6.88 (d, 2H), 6.79 (d, 2H), 6.37 (d, 1H), 3.92 (m, 2H), 3.68 (m, 2H), 2.41 (qt, 2H), 0.89 (t, 3H). LCMS: 455 (M+H)$^+$.

Example 61

Preparation of (E)-3-(4-((E)-1-(1H-Indazol-5-yl)-2-(2-(methylsulfonyl)phenyl)but-1-en-1-yl)phenyl)acrylic acid (Compound 361)

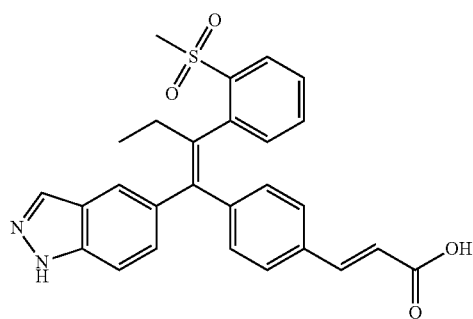 [SMILES: CC/C(=C(/c1ccc(/C=C/C(=O)O)cc1)c1ccc2[nH]ncc2c1)c1ccccc1S(C)(=O)=O]

Step 1: (E)-Ethyl 3-(4-((E)-2-(2-(methylthio)phenyl)-1-(1-(tetrahydro-2H-pyran-2-yl)-1H-indazol-5-yl)but-1-en-1-yl)phenyl)acrylate

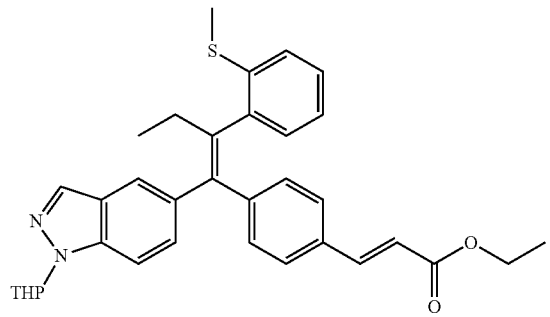

The title compound was prepared from Intermediate 3, 2-iodothioanisole, and (E)-(4-(3-ethoxy-3-oxoprop-1-en-1-yl)phenyl)boronic acid following General Procedure C. $^1$H NMR (DMSO-$d_6$, 300 MHz): δ 8.14 (s, 1H), 7.75 (d, 1H), 7.72-7.65 (m, 1H), 7.44 (d, 1H), 7.35 (d, 2H), 7.29-7.24 (m, 1H), 7.22-7.11 (m, 3H), 7.09-7.03 (m, 1H), 7.01 (d, 2H), 6.44 (d, 1H), 5.85 (dd, 1H), 4.13 (q, 2H), 3.94-3.83 (m, 1H), 3.80-3.68 (m, 1H), 2.47-2.27 (m, 6H), 2.09-1.93 (m, 2H), 1.83-1.69 (m, 1H), 1.67-1.52 (m, 2H), 1.20 (t, 3H), 0.88 (t, 3H).

Step 2: (E)-Ethyl 3-(4-((E)-2-(2-(methylsulfonyl)phenyl)-1-(1-(tetrahydro-2H-pyran-2-yl)-1H-indazol-5-yl)but-1-en-1-yl)phenyl)acrylate

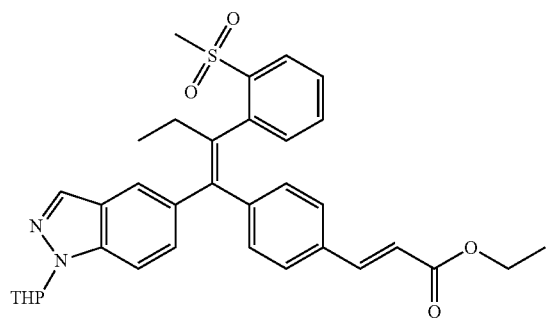

Potassium peroxymonosulfate (521 mg, 0.85 mmol) was added to a slurry of (E)-ethyl 3-(4-((E)-2-(2-(methylthio)phenyl)-1-(1-(tetrahydro-2H-pyran-2-yl)-1H-indazol-5-yl)but-1-en-1-yl)phenyl)acrylate (156 mg, 0.28 mmol) in MeOH:H$_2$O (1:1, 6 mL) at room temperature, and the reaction was stirred overnight. DCM and water were added, and the layers were separated. The aqueous layer was washed with DCM (×2). The organic layers were combined, washed with water, washed with brine, dried over Na$_2$SO$_4$, filtered, and concentrated. The crude material was purified on a silica gel column eluted with 0-50% ethyl acetate in hexane affording the title compound. $^1$H NMR (DMSO-$d_6$, 300 MHz): δ 8.15 (s, 1H), 7.91 (d, 1H), 7.77-7.71 (m, 2H), 7.49-7.46 (m, 3H), 7.41-7.31 (m, 4H), 7.01 (d, 2H), 6.45 (d, 1H), 5.87 (dd, 1H), 4.12 (q, 2H), 3.92-3.85 (m, 1H), 3.82-3.69 (m, 1H), 2.93 (s, 3H), 2.46-2.27 (m, 2H), 2.09-1.97 (m, 3H), 1.85-1.67 (m, 1H), 1.63-1.51 (m, 2H), 1.18 (t, 3H), 0.83 (t, 3H). LCMS: 501 [(M-THP+H)+H]$^+$.

Step 3: (E)-3-(4-((E)-1-(1H-Indazol-5-yl)-2-(2-(methylsulfonyl)phenyl)but-1-en-1-yl)phenyl)acrylic acid

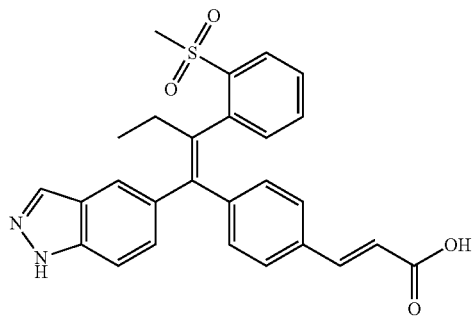 [SMILES: CC/C(=C(/c1ccc(/C=C/C(=O)O)cc1)c1ccc2[nH]ncc2c1)c1ccccc1S(C)(=O)=O]

The title compound was prepared from (E)-ethyl 3-(4-((E)-2-(2-(methylsulfonyl)phenyl)-1-(1-(tetrahydro-2H-pyran-2-yl)-1H-indazol-5-yl)but-1-en-1-yl)phenyl)acrylate following General Procedures F & G. ¹H NMR (DMSO-d₆, 300 MHz): δ 13.14 (br s, 1H), 12.29 (br s, 1H), 8.11 (d, 1H), 7.92 (dd, 1H), 7.71 (s, 1H), 7.66-7.54 (m, 2H), 7.53-7.44 (m, 2H), 7.42-7.33 (m, 3H), 7.26 (dd, 1H), 7.01 (d, 2H), 6.34 (d, 1H), 2.94 (s, 3H), 2.42-2.30 (m, 2H), 0.83 (t, 3H); LCMS: 473 (M+H)⁺.

Example 62

Preparation of (E)-3-(4-((E)-1-(1H-Indazol-5-yl)-2-(3-(pyridin-2-yloxy)phenyl)but-1-en-1-yl)phenyl)acrylic acid (Compound 362)

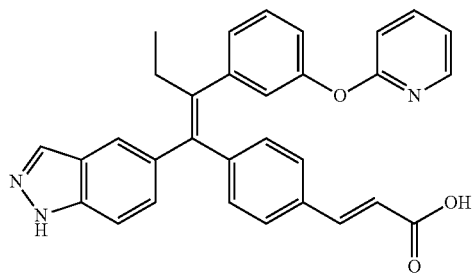 [SMILES: CC/C(=C(/c1ccc(/C=C/C(=O)O)cc1)c1ccc2[nH]ncc2c1)c1cccc(Oc2ccccn2)c1]

Step 1: (E)-Ethyl 3-(4-((E)-2-(3-(pyridin-2-yloxy)phenyl)-1-(1-(tetrahydro-2H-pyran-2-yl)-1H-indazol-5-yl)but-1-en-1-yl)phenyl)acrylate

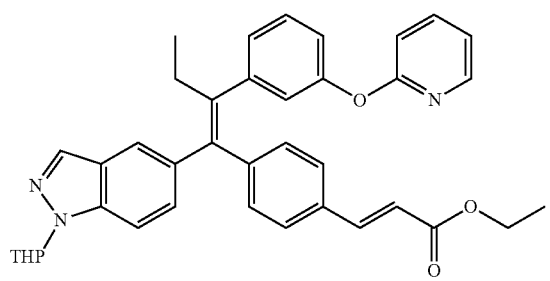

A mixture of (E)-ethyl 3-(4-((E)-2-(3-hydroxyphenyl)-1-(1-(tetrahydro-2H-pyran-2-yl)-1H-indazol-5-yl)but-1-en-1-yl)phenyl)acrylate (300 mg, 0.57 mmol; Compound 346, Step 1), CuBr (3.6 mg, 0.025 mmol), Cs₂CO₃ (320 mg, 0.98 mmol), 2-iodopyridine (103 mg, 0.50 mmol), 1-(pyridin-2-yl)propan-2-one (15 mg, 0.11 mmol), and DMSO (1 mL) was degassed with three vacuum/N₂ cycles, heated at 80° C. for 5 h, heated at 90° C. for 2 h, and then stirred at rt for 14 h. The reaction was diluted with EtOAc and filtered through Celite. The organic filtrate was washed with H₂O (50 mL), washed with brine (40 mL), dried (MgSO₄), filtered, concentrated, and purified by silica gel chromatography (10%-30% EtOAc in hexanes) to give 193 mg of (E)-ethyl 3-(4-((E)-2-(3-(pyridin-2-yloxy)phenyl)-1-(1-(tetrahydro-2H-pyran-2-yl)-1H-indazol-5-yl)but-1-en-1-yl)phenyl)acrylate as a white foam. ¹H NMR (400 MHz, DMSO-d₆): δ 8.13 (dd, 1H), 8.11 (s, 1H), 7.69-7.75 (m, 2H), 7.64 (s, 1H), 7.52 (d, 1H), 7.44 (d, 2H), 7.30 (t, 1H), 7.23 (dd, 1H), 7.06-7.10 (m, 2H), 6.90-6.95 (m, 3H), 6.85-6.88 (m, 1H), 6.65 (d, 1H), 6.52 (d, 1H), 5.85 (d, 1H), 4.16 (q, 2H), 3.87-3.92 (m, 1H), 3.70-3.78 (m, 1H), 2.38-2.48 (m, 3H), 1.95-2.08 (m, 2H), 1.70-1.81 (m, 1H), 1.56-1.62 (m, 2H), 1.25 (t, 3H), 0.94 (t, 3H); LCMS: 600 (M+H)⁺.

Note: For other derivatives, CuI, picolinic acid, and K₃PO₄ were used in place of CuBr, 1-(pyridin-2-yl)propan-2-one, and Cs₂CO₃. And in some cases, copper catalyst and ligand were not needed, and various bases (Cs₂CO₃ or K₂CO₃) and solvents (THF, DMF, or DMSO) were used.

Step 2: (E)-3-(4-((E)-1-(1H-Indazol-5-yl)-2-(3-(pyridin-2-yloxy)phenyl)but-1-en-1-yl)phenyl) acrylic acid

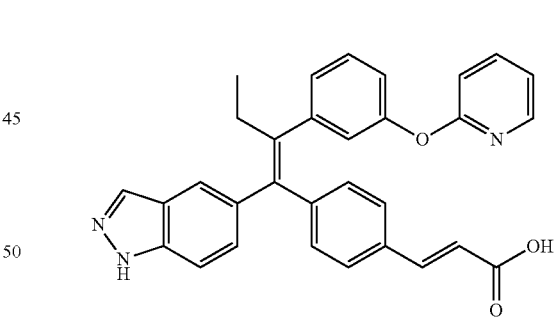

The title compound was prepared from (E)-ethyl 3-(4-((E)-2-(3-(pyridin-2-yloxy)phenyl)-1-(1-(tetrahydro-2H-pyran-2-yl)-1H-indazol-5-yl)but-1-en-1-yl)phenyl)acrylate following General Procedures F and G. ¹H NMR (400 MHz, DMSO-d₆): δ 8.14 (dd, 1H), 8.08 (s, 1H), 7.69-7.74 (m, 1H), 7.64 (s, 1H), 7.53 (d, 1H), 7.47 (d, 1H), 7.41 (d, 2H), 7.30 (t, 1H), 7.14 (dd, 1H), 7.06-7.10 (m, 2H), 6.90-6.94 (m, 3H), 6.85-6.87 (m, 1H), 6.64 (d, 1H), 6.41 (d, 1H), 2.43 (q, 2H), 0.93 (t, 3H); LCMS: 488 (M+H)⁺.

Compounds 363 to 381 were prepared following the procedures outlined for Compound 362.

Example 63

Preparation of (E)-3-(4-((E)-1-(1H-Indazol-5-yl)-2-(3-((6-methylpyridin-3-yl)oxy)phenyl)but-1-en-1-yl)phenyl)acrylic acid (Compound 382)

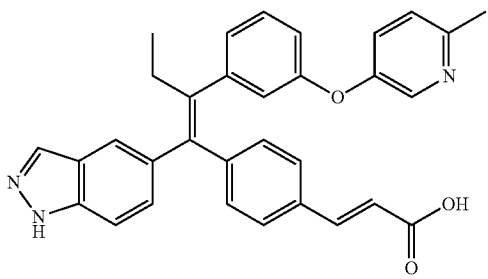 [SMILES: CC/C(=C(/c1ccc(/C=C/C(=O)O)cc1)c1ccc2[nH]ncc2c1)c1cccc(Oc2ccc(C)nc2)c1]

The title compound was prepared from (E)-ethyl 3-(4-((E)-2-(3-hydroxyphenyl)-1-(1-(tetrahydro-2H-pyran-2-yl)-1H-indazol-5-yl)but-1-en-1-yl)phenyl)acrylate (Compound 346, Step 1) and (6-methylpyridin-3-yl)boronic acid following the procedure outlined for Intermediate 65 and then General Procedures F and G. LCMS: 502 (M+H)⁺.

Example 64

Preparation of (E)-3-(4-((E)-1-(1H-Indazol-5-yl)-2-(4-(pyrimidin-5-yl)phenyl)but-1-en-1-yl)phenyl)acrylic acid (Compound 383)

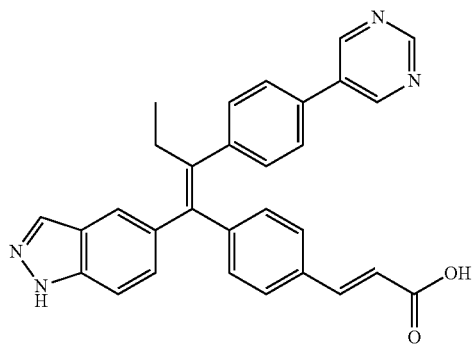 [SMILES: CC/C(=C(/c1ccc(/C=C/C(=O)O)cc1)c1ccc2[nH]ncc2c1)c1ccc(-c2cncnc2)cc1]

Step 1: (E)-Ethyl 3-(4-((E)-2-(4-bromophenyl)-1-(1-(tetrahydro-2H-pyran-2-yl)-1H-indazol-5-yl)but-1-en-1-yl)phenyl)acrylate

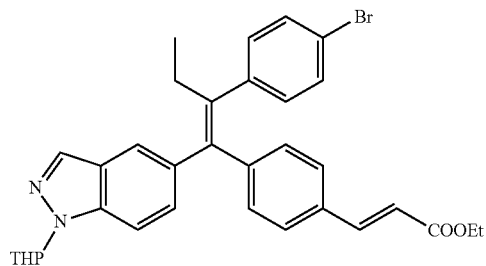

The title compound was prepared from Intermediate 3, 1-bromo-4-iodobenzene, and (E)-(4-(3-ethoxy-3-oxoprop-1-en-1-yl)phenyl)boronic acid following General Procedure C. ¹H NMR (400 MHz, DMSO-d₆): δ 8.12 (s, 1H), 7.73 (d, 1H), 7.64 (s, 1H), 7.49 (d, 1H), 7.51-7.40 (m, 4H), 7.23 (dd, 1H), 7.13 (d, 2H), 6.90 (d, 2H), 6.49 (d, 1H), 5.85 (dd, 1H), 4.13 (qt, 2H), 3.90 (m, 1H), 3.75 (m, 1H), 2.44- 2.39 (m, 3H), 2.00 (m, 2H), 1.75 (m, 1H), 1.58 (m, 2H), 1.22 (t, 3H), 0.88 (t, 3H). LCMS: 501 [(M-THP+H)+H]⁺.

Step 2: (E)-Ethyl 3-(4-((E)-2-(4-(pyrimidin-5-yl)phenyl)-1-(1-(tetrahydro-2H-pyran-2-yl)-1H-indazol-5-yl)but-1-en-1-yl)phenyl)acrylate

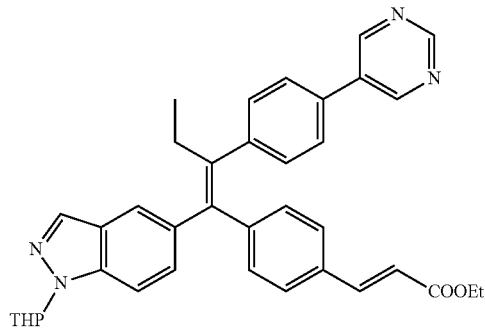

A mixture of (E)-ethyl 3-(4-((E)-2-(4-bromophenyl)-1-(1-(tetrahydro-2H-pyran-2-yl)-1H-indazol-5-yl)but-1-en-1-yl)phenyl)acrylate (212 mg, 0.36 mmol), pyrimidin-5-ylboronic acid (67 mg, 0.54 mmol) and potassium carbonate (100 mg, 0.72 mmol) in toluene/ethanol (4:1, 5 mL) was degassed with nitrogen. Pd(PPh₃)₄ (41 mg, 0.036 mmol) was added and the mixture was heated to 90° C. overnight. The reaction was not done so additional pyrimidin-5-ylboronic acid (67 mg, 0.54 mmol), potassium carbonate (100 mg, 0.72 mmol) and Pd(PPh₃)₄ (41 mg, 0.036 mmol) were added, and the mixture was heated to 90° C. for an additional 4 h. The mixture was cooled to room temperature and poured into ethyl acetate. The organic phase was washed with brine (3×), dried over sodium sulfate, and purified by flash chromatography on silica gel eluting with 0 to 100% ethyl acetate/hexanes to afford 100 mg of the title compound as a yellow foam. ¹H NMR (400 MHz, DMSO-d₆): δ 9.16 (s, 1H), 9.15 (s, 2H), 8.13 (s, 1H), 7.76-7.67 (m, 4H), 7.48 (d, 1H), 7.42 (d, 2H), 7.35 (d, 2H), 7.26 (dd, 1H), 6.95 (d, 2H), 6.48 (d, 1H), 5.86 (dd, 1H), 4.14 (qt, 2H), 3.90 (m, 1H), 3.75 (m, 1H), 2.49-2.42 (m, 3H), 2.01 (m, 2H), 1.78 (m, 1H), 1.59 (m, 2H), 1.21 (t, 3H), 0.92 (t, 3H).

Step 3: (E)-3-(4-((E)-1-(1H-Indazol-5-yl)-2-(4-(pyrimidin-5-yl)phenyl)but-1-en-1-yl)phenyl)acrylic acid

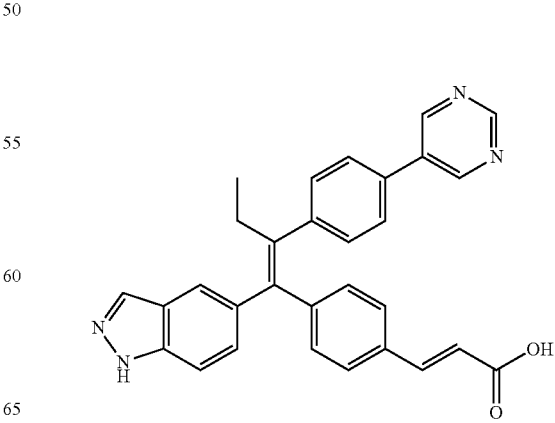

The title compound was prepared from (E)-ethyl 3-(4-((E)-2-(4-(pyrimidin-5-yl)phenyl)-1-(1-(tetrahydro-2H-pyran-2-yl)-1H-indazol-5-yl)but-1-en-1-yl)phenyl)acrylate following General Procedures F and G. ¹H NMR (400 MHz, DMSO-d₆): δ NH and COOH not observed, 9.16 (s, 1H), 9.14 (s, 2H), 8.10 (s, 1H), 7.73 (d, 2H), 7.67 (s, 1H), 7.55 (d, 1H), 7.44-7.34 (m, 5H), 7.17 (dd, 1H), 6.95 (d, 2H), 6.37 (d, 1H), 2.48 (qt, 2H), 0.92 (t, 3H). LCMS: 473 (M+H)⁺.

Compound 384 was prepared following the procedures outlined for Compound 383.

Example 65

Preparation of (E)-3-(4-((E)-1-(1H-Indazol-5-yl)-2-(4-(pyridin-2-yl)phenyl)but-1-en-1-yl)phenyl)acrylic acid (Compound 385)

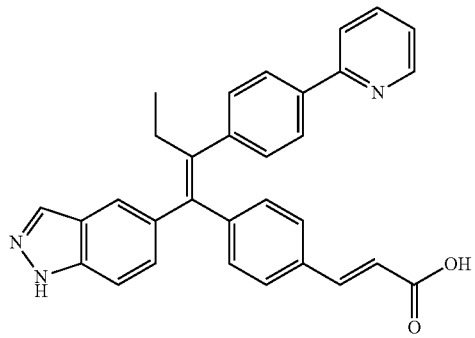 [SMILES: CC/C(=C(/c1ccc(/C=C/C(=O)O)cc1)c1ccc2[nH]ncc2c1)c1ccc(-c2ccccn2)cc1]

Step 1: (E)-4-(2-(4-Bromophenyl)-1-(1-(tetrahydr-2H-pyran-2-yl)-1H-indazol-5-yl)but-1-en-1-yl)benzaldehyde

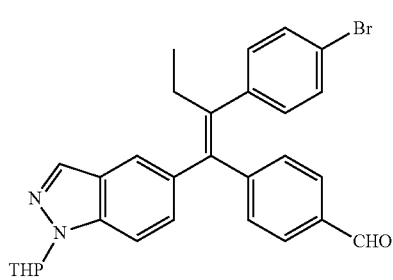

The title compound was prepared from Intermediate 3, 4-iodobenzaldehyde, and 1-bromo-4-iodobenzene following General Procedure D. ¹H NMR (400 MHz, DMSO-d₆): δ 9.84 (s, 1H), 8.13 (s, 1H), 7.75 (d, 1H), 7.66 (s, 1H), 7.62 (d, 2H), 7.41 (d, 2H), 7.25 (dd, 1H), 7.13 (d, 2H), 7.10 (d, 2H), 5.85 (dd, 1H), 3.90 (m, 1H), 3.75 (m, 1H), 2.47-2.41 (m, 3H), 2.00 (m, 2H), 1.73 (m, 1H), 1.59 (m, 2H), 0.90 (t, 3H).

Step 2: (E)-4-(1-(1-(Tetrahydro-2H-pyran-2-yl)-1H-indazol-5-yl)-2-(4-(4,4,5,5-tetramethyl-1,3,2-dioxaborolan-2-yl)phenyl)but-1-en-1-yl)benzaldehyde

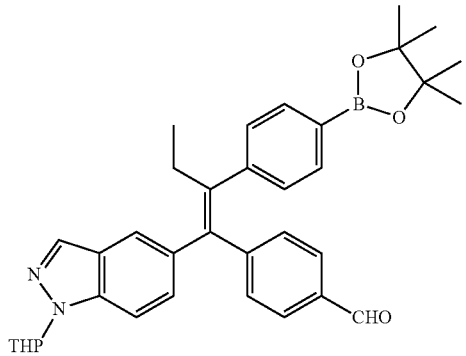

A mixture of (E)-4-(2-(4-bromophenyl)-1-(1-(tetrahydro-2H-pyran-2-yl)-1H-indazol-5-yl)but-1-en-1-yl)benzaldehyde (1.1 g, 2.13 mmol), bis(pinacolato)diboron (650 mg, 2.56 mmol), and potassium acetate (471 mg, 4.26 mmol) in 1,4-dioxane (21 mL) was degassed with nitrogen. PdCl₂dppf.DCM (174 mg, 0.21 mmol) was added and the resulting mixture was heated to 90° C. overnight. The mixture was cooled to room temperature and poured into ethyl acetate. The organic phase was washed with brine (3×), dried over sodium sulfate, and purified by flash chromatography on silica gel eluting with 0 to 20% ethyl acetate/hexanes to afford 900 mg of the title compound as a greenish foam. ¹H NMR (400 MHz, DMSO-d₆): δ 9.82 (s, 1H), 8.12 (s, 1H), 7.75 (d, 1H), 7.66 (s, 1H), 7.59 (d, 2H), 7.51 (d, 2H), 7.25 (dd, 1H), 7.19 (d, 2H), 7.09 (d, 2H), 5.86 (dd, 1H), 3.91 (m, 1H), 3.75 (m, 1H), 2.48-2.41 (m, 3H), 2.00 (m, 2H), 1.76 (m, 1H), 1.59 (m, 2H), 1.27 (s, 12H), 0.88 (t, 3H).

Step 3: (E)-4-(2-(4-(Pyridin-2-yl)phenyl)-1-(1-(tetrahydro-2H-pyran-2-yl)-1H-indazol-5-yl)but-1-en-1-yl)benzaldehyde

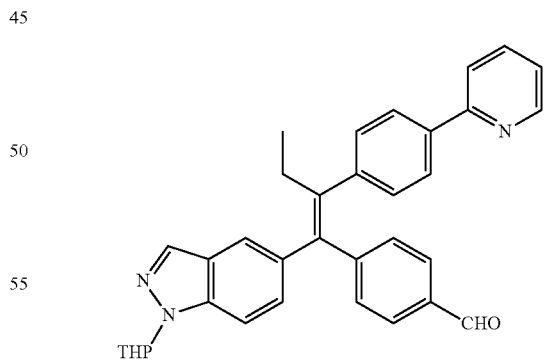

A mixture of (E)-4-(1-(1-(tetrahydro-2H-pyran-2-yl)-1H-indazol-5-yl)-2-(4-(4,4,5,5-tetramethyl-1,3,2-dioxaborolan-2-yl)phenyl)but-1-en-1-yl)benzaldehyde (220 mg, 0.39 mmol), 2-iodopyridine (0.062 mL, 0.58 mmol), and KOH (6M aq., 0.40 mL, 2.34 mmol) in 1,4-dioxane was degassed with nitrogen. PdCl₂dppf.DCM (31 mg, 0.04 mmol) was added and the resulting mixture was heated to 70° C. overnight. The mixture was cooled to room temperature and poured into ethyl acetate. The organic phase was washed with brine (3×), dried over sodium sulfate, and purified by flash chromatography on silica gel eluting with 0 to 50% ethyl acetate/hexanes to afford 82 mg of the title compound as a yellow foam. LCMS: 514 (M+H)⁺.

Step 4: (E)-3-(4-((E)-1-(1H-Indazol-5-yl)-2-(4-(pyridin-2-yl)phenyl)but-1-en-1-yl)phenyl)acrylic acid

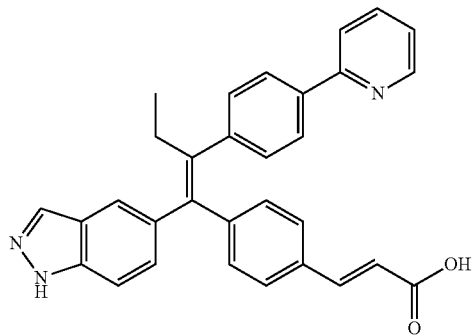 [SMILES: CC/C(=C(/c1ccc(/C=C/C(=O)O)cc1)c1ccc2[nH]ncc2c1)c1ccc(-c2ccccn2)cc1]

The title compound was prepared from (E)-4-(2-(4-(pyridin-2-yl)phenyl)-1-(1-(tetrahydro-2H-pyran-2-yl)-1H-indazol-5-yl)but-1-en-1-yl)benzaldehyde following General Procedures E, F, and G. TFA salt obtained after HPLC purification. ¹H NMR (400 MHz, DMSO-d₆): δ NH and COOH not observed, 8.67 (d, 1H), 8.10 (s, 1H), 8.02-7.94 (m, 4H), 7.67 (s, 1H), 7.55 (d, 1H), 7.43-7.37 (m, 4H), 7.32 (d, 2H), 7.17 (dd, 1H), 6.94 (d, 2H), 6.37 (d, 1H), 2.47 (qt, 2H), 0.93 (t, 3H). LCMS: 472 (M+H)⁺.

Compounds 386 to 395 were prepared following the procedures outlined for Compound 385.

Example 66

Preparation of (E)-3-(4-((E)-1-(1H-Indazol-5-yl)-2-(4-(methyl(phenyl)amino)phenyl)but-1-en-1-yl)phenyl)acrylic acid & (E)-3-(4-((Z)-1-(1H-indazol-5-yl)-2-(4-(methyl(phenyl)amino)phenyl)but-1-en-1-yl)phenyl)acrylic acid (1:1 mixture) (Compound 396)

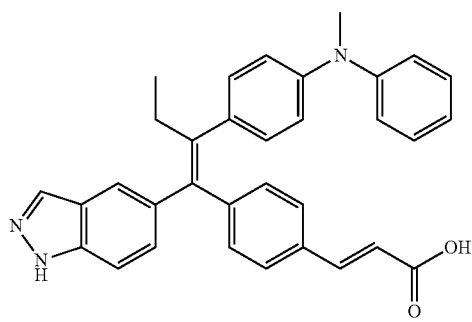

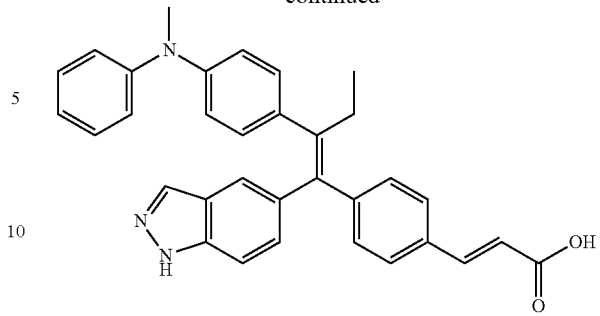

A mixture of (E)-ethyl 3-(4-((E)-2-(4-bromophenyl)-1-(1-(tetrahydro-2H-pyran-2-yl)-1H-indazol-5-yl)but-1-en-1-yl)phenyl)acrylate (225 mg, 0.384 mmol; Compound 383, Step 1), N-methylaniline (125 uL, 1.15 mmol), palladium acetate (9 mg, 0.04 mmol), BINAP (50 mg, 0.08 mmol), and cesium carbonate (250 mg, 0.769 mmol) in dioxane (2 mL) was heated at 100° C. overnight. The reaction was diluted with ethyl acetate (20 mL), washed (2×20 mL H₂O), dried (Na₂SO₄), and concentrated under reduced pressure. The crude material was purified on a silica gel column to give a mixture of (E)-ethyl 3-(4-((E)-2-(4-(methyl(phenyl)amino)phenyl)-1-(1-(tetrahydro-2H-pyran-2-yl)-1H-indazol-5-yl)but-1-en-1-yl)phenyl)acrylate and (E)-ethyl 3-(4-((E)-2-phenyl-1-(1-(tetrahydro-2H-pyran-2-yl)-1H-indazol-5-yl)but-1-en-1-yl)phenyl)acrylate. LCMS: 612 (M+H)⁺. Following General Procedures F and G, this mixture gave the title compounds as a 1:1 mixture. ¹H NMR (300 MHz, DMSO-d₆): δ 8.07 (d, 1H), 7.87 (d, 1H), 7.66 (d, 2H), 7.60 (d, 2H), 7.55 (d, 1H), 7.45 (d, 1H), 7.39 (d, 2H), 7.30-7.20 (m, 8H), 7.13 (dd, 1H), 7.40 (m, 4H), 7.00 (m, 2H), 6.98-6.88 (m, 7H), 6.82 (d, 2H), 6.77 (d, 2H), 6.52 (d, 1H), 6.39 (d, 1H), 3.22 (s, 3H), 3.18 (s, 3H), 2.50-2.39 (m, 4H), 0.99-0.90 (m, 6H); LCMS: 500 (M+H)⁺

Compound 397 was prepared following the procedure outlined for Compound 396.

Example 67

Preparation of (E)-3-(4-((E)-2-(2-Chlorophenyl)-1-(1-methyl-1H-indazol-5-yl)but-1-en-1-yl)phenyl)acrylic acid (Compound 398)

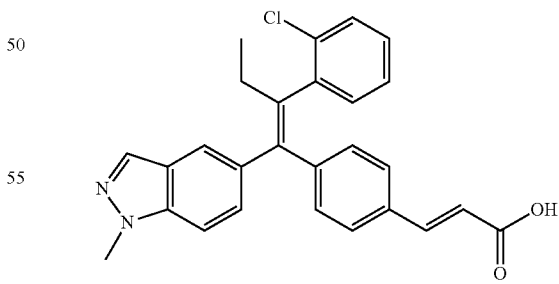

To a mixture of (E)-3-(4-((E)-2-(2-chlorophenyl)-1-(1H-indazol-5-yl)but-1-en-1-yl)phenyl)acrylic acid (80 mg, 0.19 mmol; Compound 16) and Cs₂CO₃ (0.15 g, 0.46 mmol) in DMF (3.8 mL) at room temperature, iodomethane (65 mg, 0.46 mmol) was added. The mixture was stirred at room temperature overnight, diluted with water, extracted with EtOAc, and concentrated to give the (E)-methyl 3-(4-((E)-

2-(2-chlorophenyl)-1-(1-methyl-1H-indazol-5-yl)but-1-en-1-yl)phenyl)acrylate. This residue was redissolved in THF-MeOH (3.8 mL) and an aqueous solution of LiOH (89 mg, 3.7 mmol; dissolved in a minimum amount of water) was added at room temperature. The reaction mixture was stirred overnight, quenched with 1N HCl, extracted with EtOAc, dried over sodium sulfate, filtered, and concentrated to give the crude material. This crude product was purified on a RP-C18 column using 50-100% acetonitrile in water in the presence of 0.1% TFA to afford the title compound. $^1$H NMR (300 MHz, DMSO-d$_6$): δ 12.28 (s, 1H), 8.07 (s, 1H), 7.67-7.64 (m, 2H), 7.48-7.11 (m, 8H), 6.95 (d, 2H), 6.35 (d, 1H), 4.05 (s, 3H), 2.36 (q, 2H), 0.90 (t, 3H). LCMS: 443 (M+H)$^+$.

Example 68

Preparation of (E)-3-(4-((E)-2-Cyclobutyl-1-(1-methyl-1H-indazol-5-yl)-2-phenylvinyl)phenyl) acrylic acid (Compound 399)

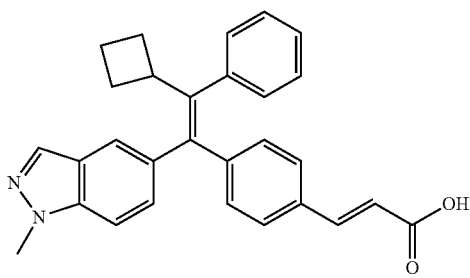 [SMILES: Cn1ncc2cc(/C(=C(/c3ccccc3)C3CCC3)c3ccc(/C=C/C(=O)O)cc3)ccc21]

Step 1: (E)-Ethyl 3-(4-((E)-2-cyclobutyl-1-(1-methyl-1H-indazol-5-yl)-2-phenylvinyl)phenyl) acrylate

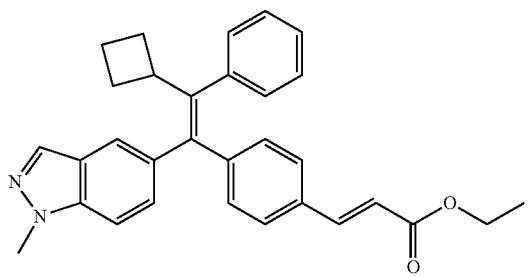 [SMILES: CCOC(=O)/C=C/c1ccc(/C(=C(\c2ccccc2)C2CCC2)c2ccc3c(cnn3C)c2)cc1]

Iodomethane (80 mg, 0.84 mmol) was added to a mixture of (E)-ethyl 3-(4-((E)-2-cyclobutyl-1-(1H-indazol-5-yl)-2-phenylvinyl)phenyl)acrylate (0.25 g, 0.56 mmol; intermediate in the preparation of Compound 155), K$_2$CO$_3$ (0.12 g, 0.84 mmol), and DMF (5.6 mL) at room temperature. The resulting mixture was stirred overnight, diluted with water, and extracted with EtOAc. The extract was washed with water, washed with brine, dried over sodium sulfate, filtered, concentrated, and then purified on a silica gel column using 0-50% EtOAc in hexanes to afford the title compound. LCMS: 463 (M+H)$^+$.

Step 2: (E)-3-(4-((E)-2-Cyclobutyl-1-(1-methyl-1H-indazol-5-yl)-2-phenylvinyl)phenyl)acrylic acid

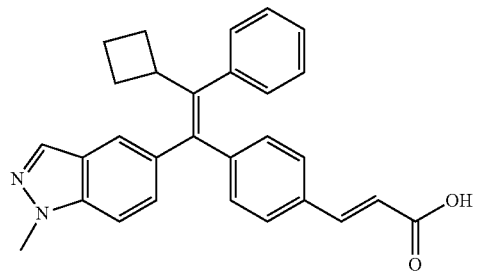 [SMILES: Cn1ncc2cc(/C(=C(/c3ccccc3)C3CCC3)c3ccc(/C=C/C(=O)O)cc3)ccc21]

The title compound was prepared from (E)-ethyl 3-(4-((E)-2-cyclobutyl-1-(1-methyl-1H-indazol-5-yl)-2-phenyl-vinyl)phenyl) acrylate following General Procedure G. $^1$H NMR (400 MHz, DMSO-d$_6$): δ 12.26 (s, 1H), 8.06 (s, 1H), 7.68-7.61 (m, 2H), 7.37 (d, 1H), 7.31-7.12 (m, 8H), 6.92 (d, 2H), 6.36 (d, 1H), 4.09 (s, 3H), 3.46-3.39 (m, 1H), 1.84-1.76 (m, 4H), 1.63-1.52 (m, 1H), 1.37-1.32 (m, 1H); LCMS: 435 (M+H)$^+$.

Compound 400 was prepared following the procedures outlined for Compound 399.

Example 69

Preparation of (E)-3-(4-((E)-2-(2-Chloro-4-fluoro-phenyl)-1-(1-(difluoromethyl)-1H-indazol-5-yl)but-1-en-1-yl)phenyl)acrylic acid (Compound 401)

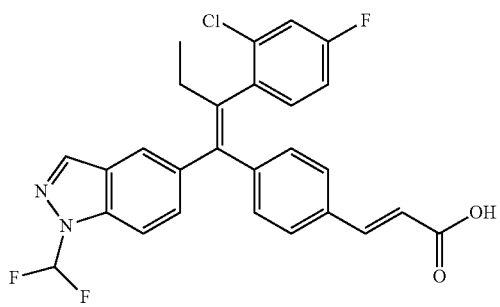 [SMILES: CC/C(=C(/c1ccc(/C=C/C(=O)O)cc1)c1ccc2c(cnn2C(F)F)c1)c1ccc(F)cc1Cl]

A solution of (E)-ethyl 3-(4-((E)-2-(2-chloro-4-fluoro-phenyl)-1-(1H-indazol-5-yl)but-1-en-1-yl)phenyl)acrylate (105, mg, 0.22 mmol; freebase of Compound 194) in DMF (1 mL) was added to a suspension of sodium hydride (11 mg, 0.27 mmol) in DMF (1 mL). The mixture was stirred at room temperature for 1 h, and then difluoroiodomethane was bubbled in for 10 min. The reaction mixture was heated at 80° C. for 3 h and then cooled to room temperature. Difluoroiodomethane was bubbled in for additional 10 min, and the mixture was heated for an additional 1.5 h. The reaction mixture was cooled to room temperature, diluted with ethyl acetate (50 mL), washed (2×25 mL H$_2$O), dried (Na$_2$SO$_4$), and concentrated under reduced pressure. The crude material was purified on a silica gel column to yield a mixture containing the desired intermediate. LCMS: 525 (M+H)$^+$. Following General Procedure G, this intermediate gave the title compound. $^1$H NMR (300 MHz, DMSO-d$_6$): δ 8.91 (s, 1H), 8.17 (t, 1H), 7.77 (s, 1H), 7.74 (d, 1H), 7.45-7.35 (m, 5H), 7.20 (dd, 1H), 7.15 (dt, 1H), 7.00 (d, 2H), 6.38 (d, 2H), 2.41 (q, 2H), 0.92 (t, 3H); LCMS: 497 (M+H)⁺.

Compound 402 was prepared from its ethyl ester following General Procedure G. This ethyl ester was isolated during purification of the ethyl ester precursor to Compound 401.

Example 70

Preparation of (E)-3-(4-((E)-1-(1-Acetyl-1H-indazol-5-yl)-2-(2-chloro-4-fluorophenyl)but-1-en-1-yl)phenyl)acrylic acid (Compound 403)

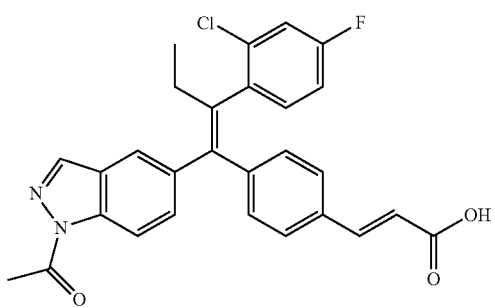 [SMILES: CC/C(=C(/c1ccc(/C=C/C(=O)O)cc1)c1ccc2c(cnn2C(C)=O)c1)c1ccc(F)cc1Cl]

To a solution of (E)-3-(4-((E)-2-(2-chloro-4-fluorophenyl)-1-(1H-indazol-5-yl)but-1-en-1-yl)phenyl)acrylic acid (0.25 g, 0.56 mmol; Compound 195) in DCM (5.6 mL) at room temperature, acetic anhydride (57 mg, 0.56 mmol) was added followed by N,N-dimethylpyridin-4-amine (6 mg, 0.056 mmol). The reaction was stirred at room temperature over the weekend, quenched with water, and then extracted with DCM (2×50 mL). The combined organic layers were washed with water, brine, dried over sodium sulfate, filtered, and concentrated to give the crude product. This crude material was purified on a silica gel column using 0-20% ethyl acetate in hexanes to afford the title compound. $^1$H NMR (400 MHz, DMSO-d$_6$): δ 12.34 (br, 1H), 8.52 (s, 1H), 8.30 (d, 1H), 7.80 (s, 1H), 7.50 (d, 1H), 7.45-7.40 (m, 5H), 7.20-7.10 (m, 1H), 6.94 (d, 2H), 6.39 (d, 1H), 2.77 (s, 3H), 2.34 (q, 2H), 0.87 (t, 3H); LCMS: 489 (M+H)⁺.

Compounds 404 to 406 were prepared following the procedure outlined for Compound 403.

Example 71

Preparation of (E)-3-(4-((E)-2-(2-Chloro-4-fluorophenyl)-1-(1-(tetrahydro-2H-pyran-2-yl)-1H-indazol-5-yl)but-1-en-1-yl)phenyl)acrylic acid (Compound 407)

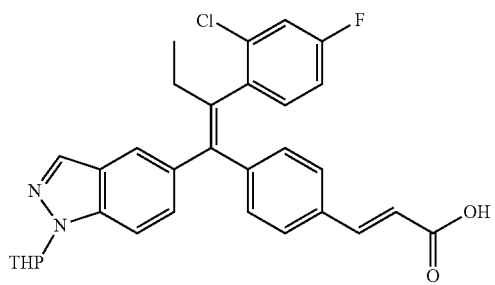

The title compound was prepared from Compound 193 following General Procedure G. $^1$H NMR (400 MHz, DMSO-d$_6$): δ 12.28 (s, 1H), 8.11 (s, 1H), 7.72 (d, 1H), 7.69 (s, 1H), 7.47-7.36 (m, 5H), 7.35-7.32 (m, 1H), 7.28-7.23 (m, 1H), 6.95 (d, 2H), 6.40 (d, 1H), 5.86 (dd, 1H), 3.91-3.88 (m, 1H), 3.74-3.71 (m, 1H), 2.44-2.33 (m, 3H), 2.06-1.97 (m, 2H), 1.74 (m, 1H), 1.60-1.59 (m, 2H), 0.90 (t, 3H). LCMS: 447 [(M-THP+H)+H]⁺.

Example 72

Preparation of (E)-3-(4-((E)-2-(2-Chloro-4-fluorophenyl)-1-(1H-indazol-5-yl)but-1-en-1-yl)phenyl)-N-(methylsulfonyl)acrylamide (Compound 408)

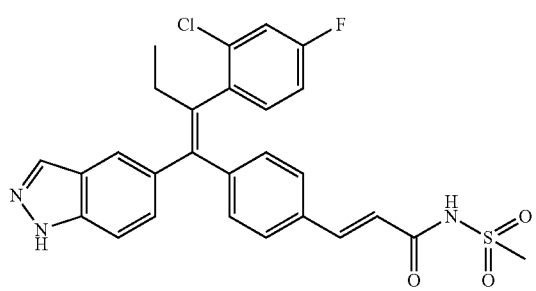

A mixture of (E)-3-(4-((E)-2-(2-chloro-4-fluorophenyl)-1-(1-(tetrahydro-2H-pyran-2-yl)-1H-indazol-5-yl)but-1-en-1-yl)phenyl)acrylic acid (0.26 g, 0.5 mmol; Compound 407), DMAP (92 mg, 0.75 mmol), methane sulfonamide (0.19 g, 2 mmol) and EDC (0.14 g, 0.75 mmol) in THF (2.5 mL) was stirred at room temperature overnight. The reaction mixture was quenched with 1N HCl, diluted with water, and extracted with ethyl acetate (2×50 mL). The combined organic layers were concentrated to give the crude product that was purified on a silica gel column using 5% methanol in DCM to afford a pale yellow solid. This solid was redissolved in EtOH (5 mL), and then HCl (1 mL, 1.25 N HCl in ethanol) was added. The reaction was heated at 70° C. for 3 h, cooled to room temperature, diluted with water, and then extracted with ethyl acetate (2×50 mL). The combined organic layers were washed with water, brine, dried over sodium sulfate, filtered, and concentrated to give the crude product. This crude material was purified on a RP-C18 column using 40-100% acetonitrile in water in the presence of 0.1% TFA to afford the title compound. $^1$H NMR (300 MHz, DMSO-d$_6$): δ 13.13 (s, 1H), 11.80 (s, 1H), 8.11 (s, 1H), 7.70 (s, 1H), 7.63-7.53 (m, 2H), 7.39-7.30 (m, 4H), 7.21-7.12 (m, 2H), 7.00 (d, 2H), 6.49 (d, 1H), 3.28 (s, 3H), 2.36 (q, 2H), 0.89 (t, 3H). LCMS: 524 (M+H)⁺.

Note: For other derivatives, the amine was coupled to the carboxylic acid using HATU with triethylamine in DMF at room temperature.

Compounds 409 to 416 were prepared following the procedure outlined for Compound 408.

Example 73

Preparation of (E)-3-(4-((E)-2-(2-Chloro-4-fluorophenyl)-1-(1H-indazol-5-yl)but-1-en-1-yl)phenyl)acrylamide (Compound 417)

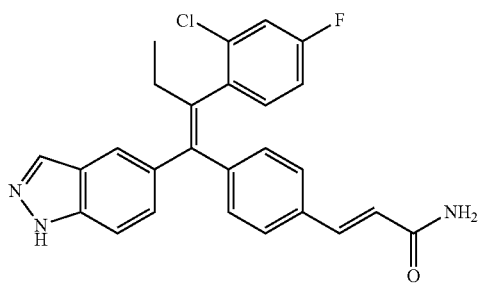 [SMILES: CC/C(=C(/c1ccc(/C=C/C(N)=O)cc1)c1ccc2[nH]ncc2c1)c1ccc(F)cc1Cl]

Step 1: (E)-3-(4-((E)-2-(2-Chloro-4-fluorophenyl)-1-(1-(tetrahydro-2H-pyran-2-yl)-1H-indazol-5-yl)but-1-en-1-yl)phenyl)acryloyl chloride

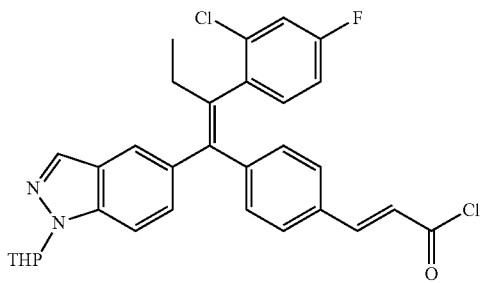

To a solution of (E)-3-(4-((E)-2-(2-chloro-4-fluorophenyl)-1-(1-(tetrahydro-2H-pyran-2-yl)-1H-indazol-5-yl)but-1-en-1-yl)phenyl)acrylic acid (1 g, 1.88 mmol; Compound 407) in DCM (9.4 mL) at room temperature, oxalyl dichloride (0.33 mL, 3.76 mmol) was added. After the addition of DMF (2 drops), the mixture was stirred at room temperature for 1 h. The resulting mixture was concentrated to afford a pale yellow solid. This material was used without further purification.

Step 2: (E)-3-(4-((E)-2-(2-Chloro-4-fluorophenyl)-1-(1H-indazol-5-yl)but-1-en-1-yl)phenyl)acrylamide

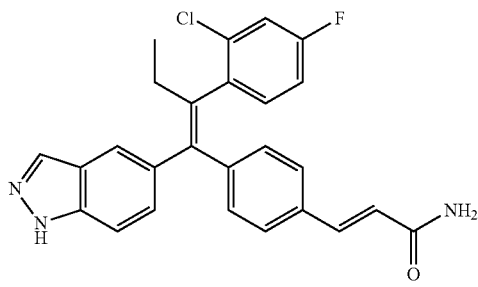 [SMILES: CC/C(=C(/c1ccc(/C=C/C(N)=O)cc1)c1ccc2[nH]ncc2c1)c1ccc(F)cc1Cl]

To a solution of (E)-3-(4-((E)-2-(2-chloro-4-fluorophenyl)-1-(1-(tetrahydro-2H-pyran-2-yl)-1H-indazol-5-yl)but-1-en-1-yl)phenyl)acryloyl chloride (0.15 g, 0.27 mmol) in dioxane (2.7 mL) at 0° C., ammonia (2.6 mL, 0.5M solution in dioxane) and triethylamine (0.136 g, 1.35 mmol) were added sequentially. The resulting mixture was warmed to room temperature and stirred for 6 h. The mixture was concentrated down to give a residue that was redissolved in EtOH (5.4 mL). HCl (0.5 mL, 2N HCl in diethyl ether) was added, and the reaction was heated at 70° C. for 4 h. Then, the mixture was diluted with water and extracted with ethyl acetate (2×50 mL). The combined organic layers were washed with water, brine, dried over sodium sulfate, filtered, and concentrated to give the crude product. This crude material was purified on a RP-C18 column using 40-100% acetonitrile in water in the presence of 0.1% TFA to afford the title compound. $^1$H NMR (400 MHz, DMSO-$d_6$): δ 13.12 (s, 1H), 8.11 (s, 1H), 7.69 (s, 1H), 7.56 (d, 1H), 7.43 (s, 1H), 7.38-7.30 (m, 2H), 7.26-7.11 (m, 5H), 7.03 (s, 1H), 6.98 (d, 2H), 6.44 (d, 1H), 2.36 (q, 2H), 0.89 (t, 3H). LCMS: 446 (M+H)$^+$.

Note: For other derivatives, the amine was coupled to the acid-chloride using sodium hydride in DMF or potassium carbonate in THF/water (4:1).

Compounds 418 to 427 were prepared following the procedures outlined for Compound 417.

Example 74

Preparation of (E)-3-(4-((E)-2-(2-Chloro-4-fluorophenyl)-1-(1H-indazol-5-yl)but-1-en-1-yl)phenyl)-N-(phenylsulfonyl)acrylamide (Compound 428)

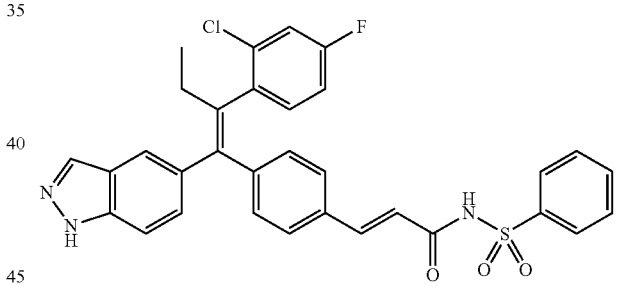

A solution of (E)-3-(4-((E)-2-(2-chloro-4-fluorophenyl)-1-(1-(tetrahydro-2H-pyran-2-yl)-1H-indazol-5-yl)but-1-en-1-yl)phenyl)acrylic acid (163 mg, 0.307 mmol; Compound 407) and CDI (57 mg, 0.35 mmol) in THF (10 mL) was heated at 65° C. for 75 min and then cooled to room temperature. Benzenesulfonamide (77 mg, 0.49 mmol) and DBU (57 uL, 0.38 mmol) were added, and the mixture was stirred overnight, diluted with ethyl acetate (50 mL), washed (50 mL H$_2$O, 50 mL brine), dried (Na$_2$SO$_4$), and concentrated under reduced pressure. The crude material was purified on a silica gel column to give the intermediate acyl-sulfonamide. The title compound was prepared from this acyl-sulfonamide following General Procedure F. $^1$H NMR (300 MHz, DMSO-$d_6$): δ 13.12 (br s, 1H), 12.21 (s, 1H), 8.10 (d, 1H), 7.93 (m, 2H), 7.70 (m, 2H), 7.64 (m, 2H), 7.58 (d, 1H), 7.47 (d, 1H), 7.34 (m, 2H), 7.27 (d, 2H), 7.18 (dd, 1H), 7.15 (dt, 1H), 6.97 (d, 2H), 6.44 (d, 1H), 2.40 (q, 2H), 0.90 (t, 3H); LCMS: 586 (M+H)$^+$.

Compounds 429 to 434 were prepared following the procedure outlined for Compound 428.

Example 75

Preparation of 3-((E)-4-((E)-1-(1H-Indazol-5-yl)-2-phenylbut-1-en-1-yl)styryl)-1,2,4-oxadiazol-5(4H)-one (Compound 435)

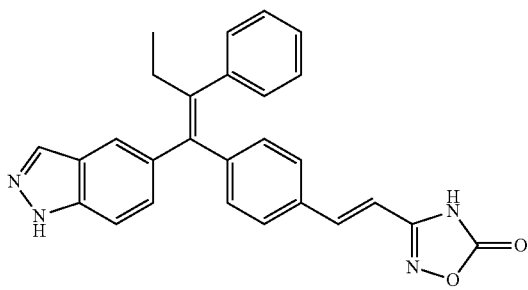 [SMILES: CC/C(=C(/c1ccc(/C=C/c2noc(=O)[nH]2)cc1)c1ccc2[nH]ncc2c1)c1ccccc1]

Step 1: (E)-3-(4-((E)-2-Phenyl-1-(1-(tetrahydro-2H-pyran-2-yl)-1H-indazol-5-yl)but-1-en-1-yl)phenyl)acrylonitrile

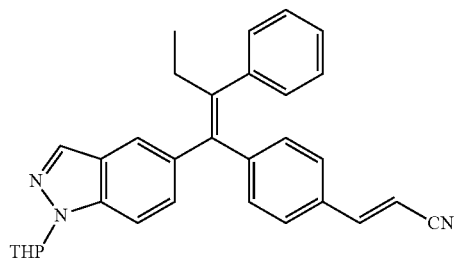

The title compound was prepared from Intermediate 3, iodobenzene, and (E)-(4-(2-cyanovinyl)phenyl)boronic acid following General Procedure C. LCMS: 376 [(M-THP+H)+H]+.

Step 2: (1Z,2E)-N'-Hydroxy-3-(4-((E)-2-phenyl-1-(1-(tetrahydro-2H-pyran-2-yl)-1H-indazol-5-yl)but-1-en-1-yl)phenyl)acrylimidamide

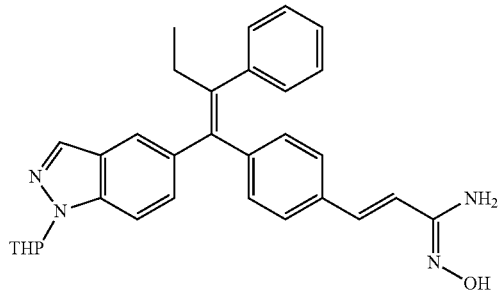

To a solution of (E)-3-(4-((E)-2-phenyl-1-(1-(tetrahydro-2H-pyran-2-yl)-1H-indazol-5-yl)but-1-en-1-yl)phenyl)acrylonitrile (380 mg, 0.83 mmol) and hydroxylamine hydrochloride (265 mg, 3.8 mmol) in DMSO (8 mL) was added triethylamine (0.5 mL, 3.8 mmol), and the mixture was heated at 75° C. for 24 h. After cooling, water was added, and the solution was extracted with EtOAc (3×). The combined organics were washed with brine (2×), dried (MgSO$_4$) and concentrated. Purification by silica gel chromatography (0 to 65% EtOAc/hexanes) provided 116 mg of the title compound as a yellow foam. LCMS: 409 [(M-THP+H)+H]+.

Step 3: 3-((E)-4-((E)-2-Phenyl-1-(1-(tetrahydro-2H-pyran-2-yl)-1H-indazol-5-yl)but-1-en-1-yl)styryl)-1,2,4-oxadiazol-5(4H)-one

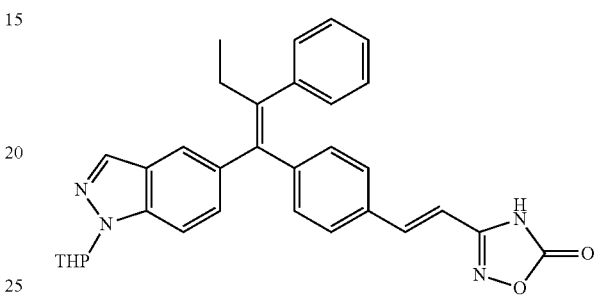

To a solution of (1Z,2E)-N'-hydroxy-3-(4-((E)-2-phenyl-1-(1-(tetrahydro-2H-pyran-2-yl)-1H-indazol-5-yl)but-1-en-1-yl)phenyl)acrylimidamide (51 mg, 0.1 mmol) in anhydrous DMF (0.4 mL) was added 2-ethylhexylchloroformate (20 μL, 0.1 mmol) followed by pyridine (9 μL, 0.11 mmol). The reaction mixture was stirred at 0° C. for 1 h and then partitioned between water and EtOAc. The aqueous layer was extracted with EtOAc (2×), and the combined organics were dried over MgSO$_4$ and concentrated. The residue was dissolved in xylenes (1 mL), heated at 130° C. for 2 h, and then concentrated to afford 25 mg of the title compound. LCMS: 519 (M+H)+.

Step 4: 3-((E)-4-((E)-1-(1H-Indazol-5-yl)-2-phenyl-but-1-en-1-yl)styryl)-1,2,4-oxadiazol-5(4H)-one

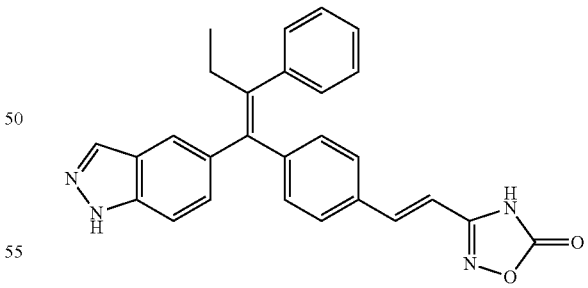

The title compound was prepared from 3-((E)-4-((E)-2-phenyl-1-(1-(tetrahydro-2H-pyran-2-yl)-1H-indazol-5-yl)but-1-en-1-yl)styryl)-1,2,4-oxadiazol-5(4H)-one following General Procedure F. $^1$H NMR (400 MHz, DMSO-d$_6$): δ 13.1 (s, 1H), 12.6 (s, 1H), 8.09 (s, 1H), 7.66 (s, 1H), 7.54 (d, 1H), 7.32 (d, 2H), 7.25-7.13 (m, 7H), 6.91 (d, 2H), 6.81 (d, 1H), 2.45 (q, 2H), 0.90 (t, 3H). LCMS: 435 (M+H)+.

Compound 436 was prepared following the procedures outlined for Compound 435.

Example 76

Preparation of 3-((E)-4-((E)-2-(2-Chloro-4-fluorophenyl)-1-(1H-indazol-5-yl)but-1-en-1-yl)styryl)-1,2,4-oxadiazol-5(4H)-one (Compound 437)

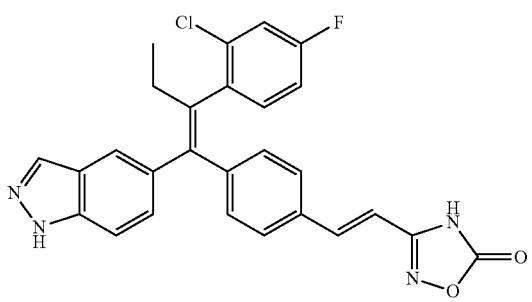

Step 1: (E)-3-(4-((E)-2-(2-Chloro-4-fluorophenyl)-1-(1-(tetrahydro-2H-pyran-2-yl)-1H-indazol-5-yl)but-1-en-1-yl)phenyl)acrylonitrile

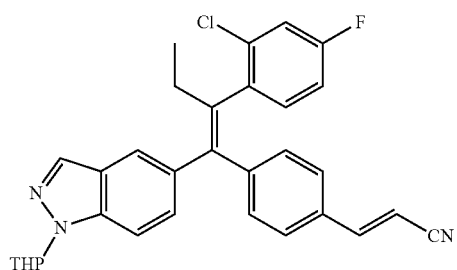

The title compound was prepared from (E)-4-(2-(2-chloro-4-fluorophenyl)-1-(1-(tetrahydro-2H-pyran-2-yl)-1H-indazol-5-yl)but-1-en-1-yl)benzaldehyde (Compound 193, Step 1) and diethyl (cyanomethyl)phosphonate following General Procedure E. LCMS: 428 [(M-THP+H)+H]$^+$.

Step 2: (1Z,2E)-3-(4-((E)-2-(2-Chloro-4-fluorophenyl)-1-(1-(tetrahydro-2H-pyran-2-yl)-1H-indazol-5-yl)but-1-en-1-yl)phenyl)-N'-hydroxyacrylimidamide

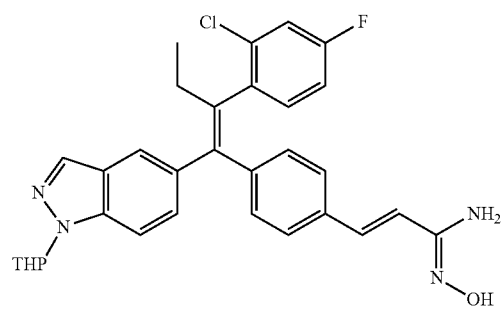

A mixture of (E)-3-(4-((E)-2-(2-chloro-4-fluorophenyl)-1-(1-(tetrahydro-2H-pyran-2-yl)-1H-indazol-5-yl)but-1-en-1-yl)phenyl)acrylonitrile (920 mg, 1.8 mmol) and hydroxylamine (0.18 mL, 2.7 mmol, 50% wt. in water) in ethanol (2 mL) was heated at reflux for 16 h. The ethanol was removed in vacuo, and dichloromethane and water were added. The aqueous layer was extracted with dichloromethane (2×), and the combined organics were washed with brine, dried (MgSO$_4$) and concentrated. Purification by silica gel chromatography (0 to 70% EtOAc/hexanes) provided 433 mg of the title compound as a pale yellow foam. LCMS: 461 [(M-THP+H)+H]$^+$.

Step 3: 3-((E)-4-((E)-2-(2-Chloro-4-fluorophenyl)-1-(1-(tetrahydro-2H-pyran-2-yl)-1H-indazol-5-yl)but-1-en-1-yl)styryl)-1,2,4-oxadiazol-5(4H)-one

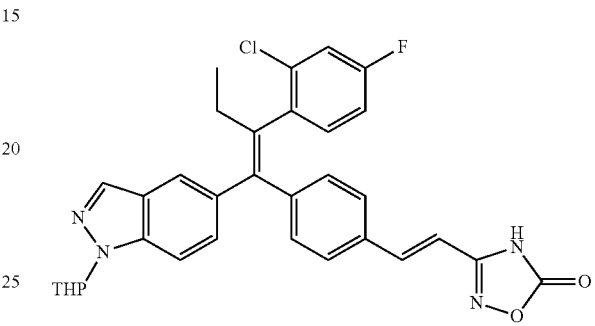

To a mixture of 3-((E)-4-((E)-2-(2-chloro-4-fluorophenyl)-1-(1-(tetrahydro-2H-pyran-2-yl)-1H-indazol-5-yl)but-1-en-1-yl)styryl)-1,2,4-oxadiazol-5(4H)-one (100 mg, 0.18 mmol) and carbonyldiimidazole (45 mg, 0.28 mmol) in anhydrous THF (1.2 mL) was added DBU (0.11 mL, 0.73 mmol), and the resulting solution was stirred at room temperature for 16 h. The reaction mixture was then directly absorbed onto silica gel and purified by column chromatography (0 to 85% EtOAc/hexanes, then 10% MeOH/dichloromethane) to afford 100 mg of the title compound as an off-white solid. LCMS: 487 [(M-THP+H)+H]$^+$.

Step 4: 3-((E)-4-((E)-2-(2-Chloro-4-fluorophenyl)-1-(1H-indazol-5-yl)but-1-en-1-yl)styryl)-1,2,4-oxadiazol-5(4H)-one

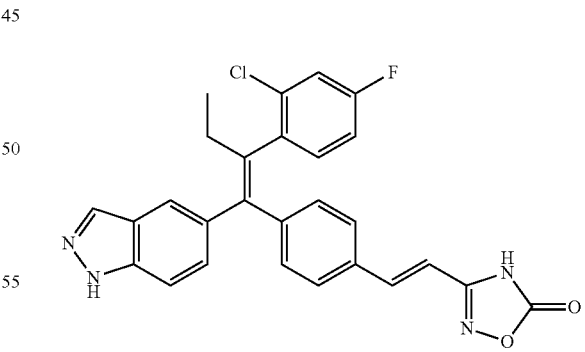

The title compound was prepared from 3-((E)-4-((E)-2-(2-chloro-4-fluorophenyl)-1-(1-(tetrahydro-2H-pyran-2-yl)-1H-indazol-5-yl)but-1-en-1-yl)styryl)-1,2,4-oxadiazol-5(4H)-one following General Procedure F. $^1$H NMR (400 MHz, DMSO-d$_6$): δ 13.1 (s, 1H), 12.6 (br s, 1H), 8.11 (s, 1H), 7.70 (s, 1H), 7.56 (d, 1H), 7.39-7.34 (m, 4H), 7.22 (d, 1H), 7.20 (dd, 1H), 7.15 (ddd, 1H), 6.99 (d, 2H), 6.82 (d, 1H), 2.39 (q, 2H), 0.91 (t, 3H). LCMS: 487 (M+H)$^+$.

Example 77

Preparation of 3-((E)-4-((E)-1-(1H-Indazol-5-yl)-2-phenylbut-1-en-1-yl)styryl)-1,2,4-thiadiazol-5(4H)-one (Compound 438)

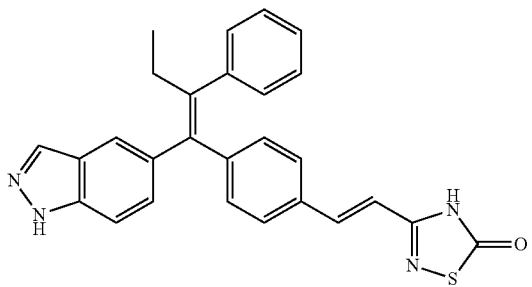 [SMILES: CC/C(=C(/c1ccc(/C=C/c2nsc(=O)[nH]2)cc1)c1ccc2[nH]ncc2c1)c1ccccc1]

Step 1: 3-((E)-4-((E)-2-Phenyl-1-(1-(tetrahydro-2H-pyran-2-yl)-1H-indazol-5-yl)but-1-en-1-yl)styryl)-1,2,4-thiadiazol-5(4H)-one

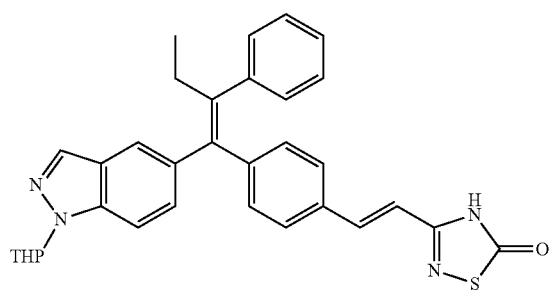

A solution of (1Z,2E)-N'-hydroxy-3-(4-((E)-2-phenyl-1-(1-(tetrahydro-2H-pyran-2-yl)-1H-indazol-5-yl)but-1-en-1-yl)phenyl)acrylimidamide (200 mg, 0.4 mmol; Compound 435, Step 2) and thiocarbonyldiimidazole (80 mg, 0.45 mmol) in anhydrous THF (2 mL) was stirred at room temperature for 1 h. Water (10 mL) was added, and the aqueous layer was extracted with EtOAc (3×20 mL). The combined organics were washed with brine, dried over MgSO$_4$ and concentrated to provide 132 mg of a yellow foam. The foam was dissolved in anhydrous THF (1.5 mL) and treated with BF$_3$.OEt$_2$ (0.13 mL, 1.0 mmol), and the resulting solution was allowed to stir at room temperature for 1 h. The reaction mixture was then partitioned between water and EtOAc, and the aqueous layer was extracted with EtOAc. The combined organics were washed with water (2×) and brine, then dried (MgSO$_4$) and concentrated to provide the crude product as a mixture of the desired product and THP-deprotected product. Purification by silica gel chromatography (0 to 50% EtOAc/hexanes, then 10% methanol/dichloromethane) provided 50 mg of the title compound as an orange oil. LCMS: 451 [(M-THP+H)+H]$^+$.

Step 2: 3-((E)-4-((E)-1-(1H-Indazol-5-yl)-2-phenylbut-1-en-1-yl)styryl)-1,2,4-thiadiazol-5(4H)-one

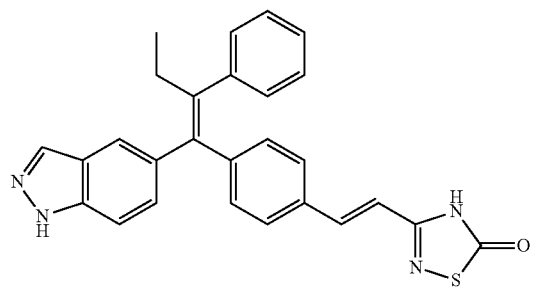 [SMILES: CC/C(=C(/c1ccc(/C=C/c2nsc(=O)[nH]2)cc1)c1ccc2[nH]ncc2c1)c1ccccc1]

The title compound was prepared from 3-((E)-4-((E)-2-phenyl-1-(1-(tetrahydro-2H-pyran-2-yl)-1H-indazol-5-yl)but-1-en-1-yl)styryl)-1,2,4-thiadiazol-5(4H)-one following General Procedure F. $^1$H NMR (400 MHz, DMSO-d$_6$): δ 13.2 (br s, 1H), 13.1 (s, 1H), 8.09 (s, 1H), 7.65 (s, 1H), 7.54 (d, 1H), 7.33 (d, 1H), 7.29-7.13 (m, 8H), 6.90 (d, 2H), 6.72 (d, 1H), 2.45 (q, 2H), 0.89 (t, 3H). LCMS: 451 (M+H)$^+$.

Compound 439 was prepared following the procedures outlined for Compound 438.

Example 78

Preparation of 3-((E)-4-((E)-1-(1H-Indazol-5-yl)-2-phenylbut-1-en-1-yl)styryl)-1,2,4-oxadiazole-5(4H)-thione (Compound 440)

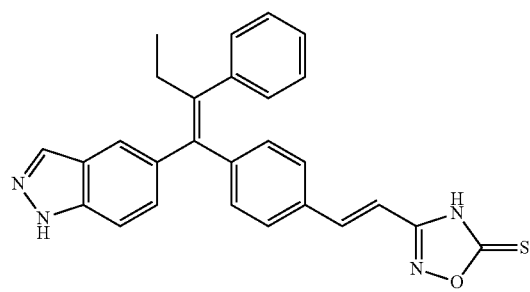 [SMILES: CC/C(=C(/c1ccc(/C=C/c2noc(=S)[nH]2)cc1)c1ccc2[nH]ncc2c1)c1ccccc1]

Step 1: 3-((E)-4-((E)-2-Phenyl-1-(1-(tetrahydro-2H-pyran-2-yl)-1H-indazol-5-yl)but-1-en-1-yl)styryl)-1,2,4-oxadiazole-5(4H)-thione

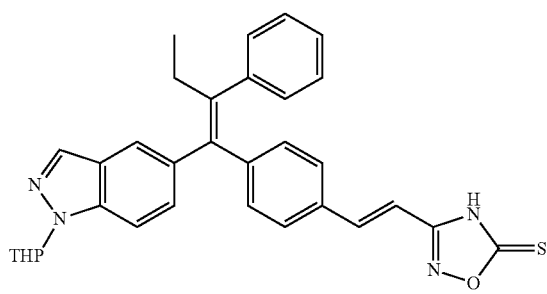

To a solution of (1Z,2E)-N'-hydroxy-3-(4-((E)-2-phenyl-1-(1-(tetrahydro-2H-pyran-2-yl)-1H-indazol-5-yl)but-1-en-1-yl)phenyl)acrylimidamide (90 mg, 0.18 mmol; Compound 435, Step 2) and thiocarbonyldiimidazole (50 mg, 0.28 mmol) in anhydrous acetonitrile (1.5 mL) was added DBU (0.11 mL, 0.72 mmol). The solution was stirred at room temperature for 4 h then directly concentrated onto silica gel. Purification by column chromatography (0 to 80% EtOAc/hexanes) afforded 69 mg of the title compound as an orange oil. LCMS: 451 [(M-THP+H)+H]$^+$.

Step 2: 3-((E)-4-((E)-1-(1H-Indazol-5-yl)-2-phenyl-but-1-en-1-yl)styryl)-1,2,4-oxadiazole-5(4H)-thione

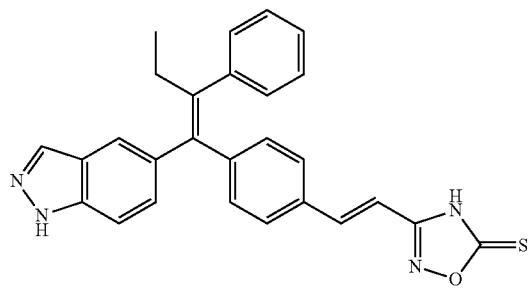

The title compound was prepared from 3-((E)-4-((E)-2-phenyl-1-(1-(tetrahydro-2H-pyran-2-yl)-1H-indazol-5-yl)but-1-en-1-yl)styryl)-1,2,4-oxadiazole-5(4H)-thione following General Procedure F. $^1$H NMR (400 MHz, DMSO-d$_6$): one NH proton not observed; δ 13.1 (br s, 1H), 8.09 (s, 1H), 7.66 (s, 1H), 7.54 (d, 1H), 7.41 (d, 1H), 7.34 (d, 2H), 7.25-7.14 (m, 6H), 6.95-6.91 (m, 3H), 2.45 (q, 2H), 0.90 (t, 3H). LCMS: 451 (M+H)$^+$.

Compound 441 was prepared following the procedures outlined for Compound 440.

Example 79

Preparation of 5-((E)-1-(4-((E)-2-(2H-Tetrazol-5-yl)vinyl)phenyl)-2-phenylbut-1-en-1-yl)-1H-indazole (Compound 442)

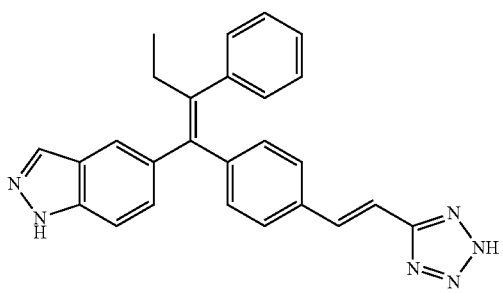 [SMILES: CC/C(=C(/c1ccc(/C=C/c2nn[nH]n2)cc1)c1ccc2[nH]ncc2c1)c1ccccc1]

Step 1: (E)-3-(4-((E)-2-Phenyl-1-(1-(tetrahydro-2H-pyran-2-yl)-1H-indazol-5-yl)but-1-en-1-yl)phenyl)acrylonitrile

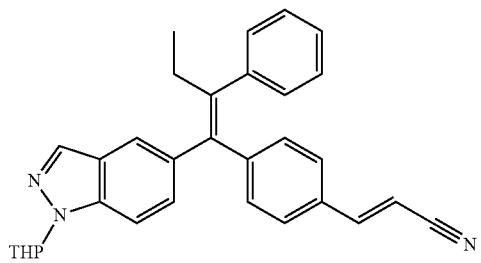

The title compound was prepared from Intermediate 3, iodobenzene, and (E)-(4-(2-cyanovinyl)phenyl)boronic acid following General Procedure C. $^1$H NMR (DMSO-d$_6$, 300 MHz): δ 8.11 (s, 1H), 7.81 (d, 1H), 7.64 (m, 1H), 7.47 (d, 1H), 7.32 (d, 2H), 7.27-7.12 (m, 6H), 6.90 (d, 2H), 6.29 (d, 1H), 5.86 (dd, 1H), 3.97-3.85 (m, 1H), 3.78-3.70 (m, 1H), 2.47-2.36 (m, 3H), 2.06-1.96 (m, 2H), 1.78-1.67 (m, 1H), 1.63-1.51 (m, 2H), 0.89 (t, 3H).

Step 2: 5-((E)-1-(4-((E)-2-(2H-Tetrazol-5-yl)vinyl)phenyl)-2-phenylbut-1-en-1-yl)-1-(tetrahydro-2H-pyran-2-yl)-1H-indazole

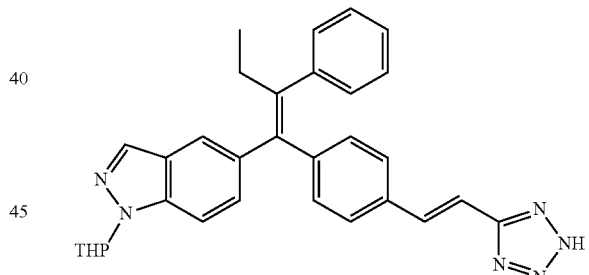

A 40 mL vial equipped with a magnetic stir bar was charged with (E)-3-(4-((E)-2-phenyl-1-(1-(tetrahydro-2H-pyran-2-yl)-1H-indazol-5-yl)but-1-en-1-yl)phenyl)acrylonitrile (100 mg, 0.22 mmol), trimethylsilylazide (289 μL, 2.2 mmol), and di-n-butyltin oxide (11 mg, 0.04 mmol) in anhydrous toluene (2 mL). This mixture was degassed with 3 vacuum/N$_2$ cycles, and then refluxed overnight. The reaction was poured onto silica and eluted with hexane (50 mL) and then 20% methanol in DCM (100 mL). The filtrate was concentrated to give the crude product that was purified on a silica gel column eluted with 0-15% methanol in DCM affording the title compound (49 mg, 45%). $^1$H NMR (DMSO-d$_6$, 300 MHz): δ 8.13 (s, 1H), 7.74 (d, 1H), 7.66 (m, 1H), 7.49-7.36 (m, 3H), 7.29-7.13 (m, 7H), 6.91 (d, 2H), 5.87 (dd, 1H), 3.92-3.89 (m, 1H), 3.84-3.71 (m, 1H), 2.49-2.42 (m, 3H), 2.09-1.97 (m, 2H), 1.85-1.67 (m, 1H), 1.63-1.51 (m, 2H), 0.90 (t, 3H). LCMS: 503 (M+H)$^+$.

Step 3: 5-((E)-1-(4-((E)-2-(2H-Tetrazol-5-yl)vinyl) phenyl)-2-phenylbut-1-en-1-yl)-1H-indazole

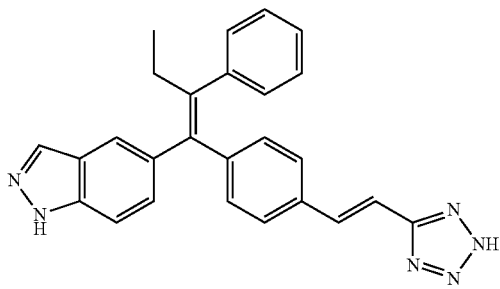 [SMILES: CC/C(=C(/c1ccc(/C=C/c2nn[nH]n2)cc1)c1ccc2[nH]ncc2c1)c1ccccc1]

The title compound was prepared from 5-((E)-1-(4-((E)-2-(2H-tetrazol-5-yl)vinyl)phenyl)-2-phenylbut-1-en-1-yl)-1-(tetrahydro-2H-pyran-2-yl)-1H-indazole following General Procedure F. $^1$H NMR (DMSO-$d_6$, 300 MHz): δ 13.11 (br s, 1H), 8.09 (s, 1H), 7.66 (s, 1H), 7.57-7.36 (m, 4H), 7.25-7.13 (m, 7H), 6.92 (d, 2H), 2.45 (q, 2H), 0.90 (t, 3H); LCMS: 419 (M+H)$^+$.

Compounds 443 to 448 were prepared following the procedures outlined for Compound 442, or in some instances, the acrylonitrile intermediate was prepared following General Procedures D and E.

Example 80

Preparation of (E)-6-(1-(1H-Indazol-5-yl)-2-phenylbut-1-en-1-yl)-2-naphthoic acid (Compound 449)

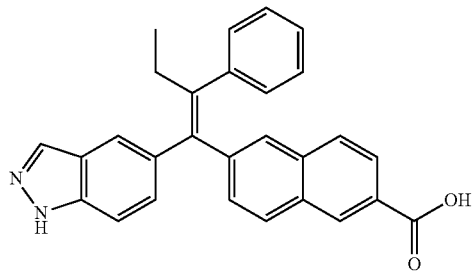 [SMILES: CC/C(=C(/c1ccc2cc(C(=O)O)ccc2c1)c1ccc2[nH]ncc2c1)c1ccccc1]

Step 1: (E)-6-(2-Phenyl-1-(1-(tetrahydro-2H-pyran-2-yl)-1H-indazol-5-yl)but-1-en-1-yl)-2-naphthaldehyde

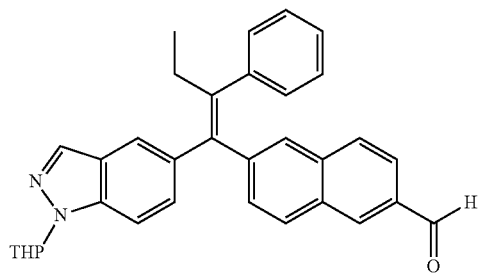

The title compound was prepared from Intermediate 3, iodobenzene, and (6-formylnaphthalene-2-yl)boronic acid following General Procedure C. $^1$H NMR (DMSO-$d_6$, 300 MHz): δ 10.05 (s, 1H), 8.47 (s, 1H), 8.13 (s, 1H), 7.97-7.69 (m, 5H), 7.48 (s, 1H), 7.29 (dd, 1H), 7.22-7.07 (m, 6H), 5.87 (dd, 1H), 3.94-3.83 (m, 1H), 3.80-3.68 (m, 1H), 2.59-2.35 (m, 3H), 2.09-1.95 (m, 2H), 1.85-1.68 (m, 1H), 1.65-1.52 (m, 2H), 0.91 (t, 3H). LCMS: 403 [(M-THP+H)+H]$^+$.

Step 2: (E)-6-(2-Phenyl-1-(1-(tetrahydro-2H-pyran-2-yl)-1H-indazol-5-yl)but-1-en-1-yl)-2-naphthoic acid

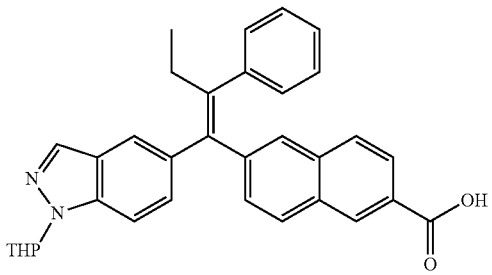

Potassium permanganate (5 mL of 1.0 M aqueous solution) was added to a solution of (E)-6-(2-phenyl-1-(1-(tetrahydro-2H-pyran-2-yl)-1H-indazol-5-yl)but-1-en-1-yl)-2-naphthaldehyde (240 mg, 0.49 mmol) and acetone:H$_2$O (2:1, 15 mL) at room temperature. The reaction was stirred for 3 h, quenched with sat. Na$_2$SO$_3$, acidified to pH 5 with 1.0 M aqueous HCl soln, and then extracted with 2×EtOAc. The organic layers were combined, washed with water then brine, dried over Na$_2$SO$_4$, and concentrated. The crude material was used without further purification. LCMS: 419 [(M-THP+H)+H]$^+$.

Step 3: (E)-6-(1-(1H-Indazol-5-yl)-2-phenylbut-1-en-1-yl)-2-naphthoic acid

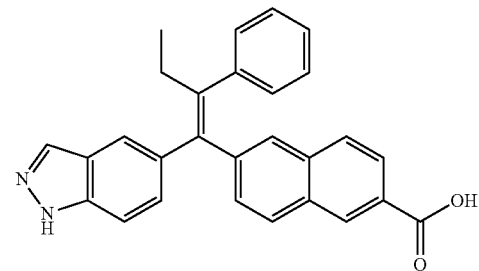 [SMILES: CC/C(=C(/c1ccc2cc(C(=O)O)ccc2c1)c1ccc2[nH]ncc2c1)c1ccccc1]

Hydrochloric acid (1 mL, 2M in ethyl ether) was added to a solution of (E)-6-(2-phenyl-1-(1-(tetrahydro-2H-pyran-2-yl)-1H-indazol-5-yl)but-1-en-1-yl)-2-naphthoic acid (190 mg, 0.38 mmol) and EtOH (5 mL). The reaction was heated at 70° C. for 30 min, concentrated, and then redissolved in THF:EtOH (1:1, 5 mL). Lithium hydroxide (90 mg, 3.8 mmol) in H$_2$O was added. The reaction was stirred at room temperature for 2 h, acidified to pH 3 with 1.0 M aqueous HCl soln, and then extracted with EtOAc (×2). The organic layers were combined, washed with water then brine, dried over Na$_2$SO$_4$, and concentrated. The crude material was purified on a reversed phase C-18 column eluted with 70-90% acetonitrile in water in the presence of 0.1% TFA affording the title compound as a beige solid (42 mg, 26%). $^1$H NMR (DMSO-$d_6$, 300 MHz): δ 13.08 (br, 2H), 8.39 (s, 1H), 8.09 (d, 1H), 7.82-7.65 (m, 4H), 7.53 (d, 1H), 7.44 (s, 1H), 7.21-7.06 (m, 7H), 2.49 (q, 2H), 0.93 (t, 3H); LCMS: 419 (M+H)$^+$.

Example 81

Preparation of (E)-3-(4-((E)-2-(2-Chloro-4-fluorophenyl)-1-(7-hydroxybenzofuran-3-yl)but-1-en-1-yl)phenyl)acrylic acid (Compound 450)

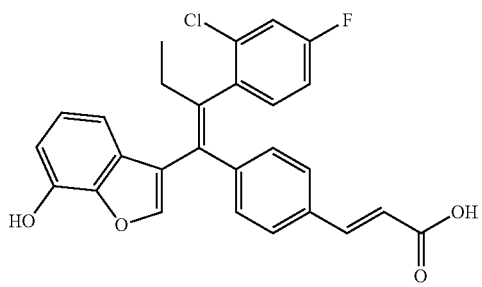 [SMILES: CC/C(=C(/c1ccc(/C=C/C(=O)O)cc1)c1coc2c(O)cccc12)c1ccc(F)cc1Cl]

To a solution of (E)-ethyl 3-(4-((E)-2-(2-chloro-4-fluorophenyl)-1-(7-methoxybenzofuran-3-yl)but-1-en-1-yl)phenyl)acrylate (0.1 g, 0.2 mmol; intermediate in the preparation of Compound 164) in DCM (4 mL) at 0° C., BBr$_3$ (1 mL, 1M in DCM, 1 mmol) was added dropwise. The reaction mixture was stirred at 0° C. for 1 h. Upon completion, the reaction was quenched with methanol (5 mL) at 0° C. The resulting mixture was concentrated under reduced pressure. The crude residue was converted into the title compound following General Procedure G. $^1$H NMR (400 MHz, DMSO-$d_6$): δ 12.31 (s, 1H), 10.08 (s, 1H), 8.10 (s, 1H), 7.47-7.31 (m, 5H), 7.20-7.13 (dt, 1H), 7.03 (d, 2H), 6.96 (t, 1H), 6.74 (d, 1H), 6.63 (d, 1H), 6.38 (d, 1H), 2.45 (q, 2H), 0.89 (t, 3H). LCMS: 463 (M+H)$^+$.

Compound 451 was prepared following the procedure outlined for Compound 450.

Example 82

Preparation of (E)-2-(4-((E)-1-(1H-Indazol-5-yl)-2-phenylbut-1-en-1-yl)phenyl)ethenesulfonamide (Compound 452)

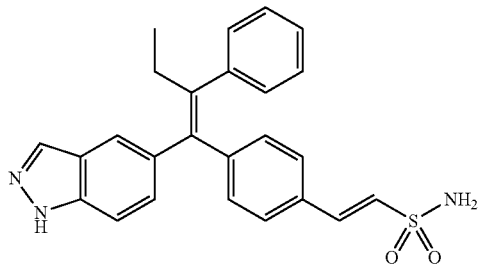 [SMILES: CC/C(=C(/c1ccc(/C=C/S(N)(=O)=O)cc1)c1ccc2[nH]ncc2c1)c1ccccc1]

Step 1: (E)-5-(1-(4-Bromophenyl)-2-phenylbut-1-en-1-yl)-1-(tetrahydro-2H-pyran-2-yl)-1H-indazole

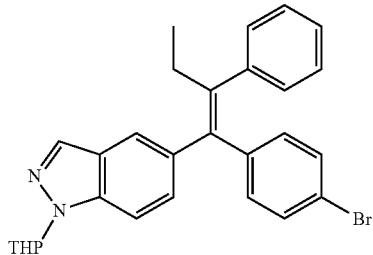

The title compound was prepared from Intermediate 3, iodobenzene, and (4-bromophenyl)boronic acid following General Procedure C. LCMS: 403 [(M-THP+H)+H]$^+$.

Step 2: (E)-2-(4-((E)-1-(1H-Indazol-5-yl)-2-phenylbut-1-en-1-yl)phenyl)ethenesulfonamide

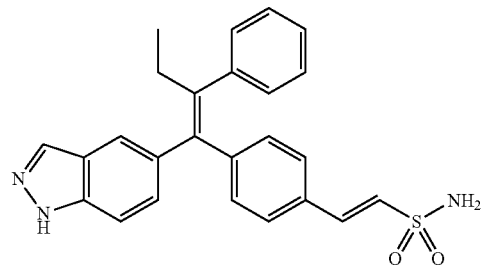 [SMILES: CC/C(=C(/c1ccc(/C=C/S(N)(=O)=O)cc1)c1ccc2[nH]ncc2c1)c1ccccc1]

A mixture of (E)-5-(1-(4-bromophenyl)-2-phenylbut-1-en-1-yl)-1-(tetrahydro-2H-pyran-2-yl)-1H-indazole (0.1 g, 0.25 mmol), ethenesulfonamide (80 mg, 0.74 mmol), Pd(Ph$_3$P)$_2$Cl$_2$ (18 mg, 0.025 mmol), triethylamine (0.25 g, 2.5 mmol) in DMF (1.25 mL) was degassed with 3 vacuum/nitrogen cycles, heated at 100° C. overnight, and then cooled to room temperature. The reaction mixture was diluted with water, extracted with EtOAc, washed with water, brine, dried over sodium sulfate, and filtered. The filtrate was concentrated down to give a residue that was redissolved in EtOH (2.5 ml). HCl (0.5 mL, 1.25 N HCl in ethanol) was added, and the mixture was heated at 80° C. for 1 h, diluted with water, and then extracted with ethyl acetate (2×50 mL). The combined organic layers were washed with water, brine, dried over sodium sulfate, filtered, and concentrated to give the crude product. This crude material was purified on a RP-C18 column using 30-100% acetonitrile in water in the presence of 0.1% TFA to afford the title compound. LCMS: 430 (M+H)$^+$.

Example 83

Preparation of 4-((E)-1-(4-((E)-2-Carboxyvinyl)phenyl)-1-(7-fluoro-1H-indazol-5-yl)but-1-en-2-yl)-3-chloropyridine-1-oxide (Compound 453)

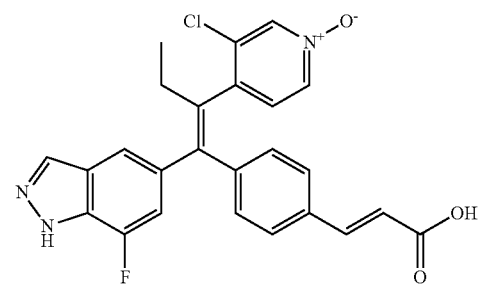 [SMILES: CC/C(=C(/c1ccc(/C=C/C(=O)O)cc1)c1cc(F)c2[nH]ncc2c1)c1cc[n+]([O-])cc1Cl]

A mixture of (E)-3-(4-((E)-2-(3-chloropyridin-4-yl)-1-(7-fluoro-1H-indazol-5-yl)but-1-en-1-yl)phenyl)acrylic acid (14.1 mg, 0.031 mmol, Compound 245), mCPBA (11 mg, 0.048 mmol), and dichloromethane (0.5 mL) was stirred vigorously for 15 h. Additional starting material (20 mg, 0.045 mmol) and mCPBA (15 mg, 0.065 mmol) were added and stirring was continued for 3 d. The reaction was concentrated and then purified by reverse-phase HPLC (CH$_3$CN, H$_2$O, TFA) to give 4-((E)-1-(4-((E)-2-carboxyvinyl)phenyl)-1-(7-fluoro-1H-indazol-5-yl)but-1-en-2-yl)-3-chloropyridine-1-oxide. $^1$H NMR (400 MHz, DMSO-d$_6$): δ 8.44 (d, 1H), 8.25 (d, 1H), 8.16 (dd, 2H), 7.56 (s, 1H), 7.50-7.42 (m, 4H), 7.05-6.96 (m, 3H), 6.43 (d, 1H), 2.41 (q, 2H), 0.94 (t, 3H); LCMS: 464.0 (M+H)$^+$.

Example 84

3×ERE MCF-7 Reporter Assay

MCF7 cells were maintained in RPMI 1640 supplemented with 10% FCS. Transcriptional assays were performed by seeding 100 µL of cells at a density of 250,000 cells/mL into 96-well cell culture plates in RPMI 1640 supplemented with 10% charcoal stripped serum and allowed to attach overnight. Cells were transiently transfected using Lipofectin (Life Technologies) according to the manufacturer's protocol. Triplicate transfections were performed using 300 ng 3λ ERE-TK-Luc (reporter vector), 50 ng CMVpRL (normalization vector), and 130 ng pCMX (filler DNA). Transfected cells were incubated overnight then treated with ligand. For ER agonist assays, the compounds were serially diluted and 50 µL of compound plus RPMI 1640 supplemented with charcoal stripped serum was added to the cells. For ER antagonist assays, the compounds were serially diluted and 50 µL of compound with RPMI plus 17β-estradiol supplemented with charcoal stripped serum were added to the cells. The final 17β-estradiol concentration used in the antagonist assays was 0.1 nM. Following 24 hour incubation the medium was removed and the cells were lysed in 40 µL of lysis buffer (25 mM Tris Phosphate, 2 mM CDTA, 10% Glycerol, 0.5% Triton X-100, 2 mM DTT). Firefly luciferase activity was measured immediately following the addition of 40 µL luciferase buffer (20 mM tricine, 0.1 mM EDTA, 1.07 mM (MgCo$_3$)$_4$ Mg(OH)$_2$.5H$_2$O, 2.67 mM MgSO$_4$, 33.3 mM DTT, 270 M Coenzyme A, 470 µM luciferin, 530 µM ATP). Renilla luciferase was measured following the addition of 40 µL colelenterazine buffer (1.1 M NaCl, 2.2 mM Na$_2$EDTA, 0.22 M KxPO$_4$ (pH 5.1), 0.44 mg/mL BSA, 1.3 mM NaN$_3$, 1.43 µM coelenterazine, final pH adjusted to 5.0).

Example 85

Breast Cancer Cell Viability Assays

MCF-7 cells were adjusted to a concentration of 20,000 cells per mL in RPMI containing 10% FBS and 20 mM HEPES. 16 microliters of the cell suspension (320 cells) was added to each well of a 384 well plate, and the cells were incubated overnight to allow the cells to adhere. The following day an eleven point, serial semilog dilution of each compound was added to the cells in 16 µL at a final concentration ranging from 0.3-0.000003 µM. After 5 days' compound exposure, 16 µL of CellTiter-GLo (Promega, Madison Wis.) was added to the cells and the relative luminescence units (RLUs) of each well was determined. CellTiter-Glo added to 32 µL of medium without cells was used to obtain a background value. The Percent viability of each sample was determined as follows: (RLU sample-RLU background/RLU untreated cells-RLU background)×100=% viability.

Viability effects in additional ER+ breast cancer cell lines, including BT474, CAMA1, MDA-MB-361, ZR-75-1, T47D, can be profiled in assays similar to Example 85.

Example 86

Breast Cancer Cell ER-α in Cell Western Assay (SP1)

MCF-7 cells were adjusted to a concentration of 200,000 cells per mL in RPMI containing 10% charcoal-stripped FBS and 20 mM HEPES. 16 microliters of the cell suspension (3200 cells) was added to each well of a poly-D-lysine 384 well plate, and the cells were incubated overnight to allow the cells to adhere. The following day an eleven point, serial semilog dilution of each compound was added to the cells in 16 µL at a final concentration ranging from 0.3-0.000003 µM. At 4 or 24 hr post compound addition, the cells were fixed (10% formalin in PBS) for 20 minutes. Cells were permeabalized in PBS 0.1% Triton and blocked with LICOR blocking buffer (50 µl/well, 90'). The wells were then incubated overnight at 4° C. with SP1 rabbit monoclonal Ab (Thermo Scientific) diluted 1:1000 in LICOR blocking buffer/0.1% Tween-20. Wells which were treated with blocking buffer with Tween but no antibody were used as a background control. Wells were washed with 0.1% Tween-20/PBS and then incubated in goat anti-rabbit IRDye™ 800CW (LICOR Inc.; 1:1000) and DRAQ5 DNA dye (1:2000 for 2 mM stock) diluted in LICOR blocking buffer containing 0.1% Tween-20 and 0.01% SDS for 60 minutes. Cells were washed (50 µl/well, 5' each) in 0.1% Tween-20/PBS. Plates were scanned on a LICOR Odyssey infrared imaging system. Integrated intensities in the 800 nm channel and 700 nm channel were measured to determine levels of ER and DNA respectively. Percent ER levels were determined as follows: (Integrated intensity 800 nm sample/integrated intensity 700 nm sample)/(Integrated intensity 800 nm untreated cells/integrated intensity 700 nm untreated cells)×100=% ER levels.

Effects on steady state levels of ER-α in additional ER+ breast cancer cell lines, including BT474, CAMA1, MDA-MB-361, ZR-75-1, T47D, can be profiled in assays similar to Example 86.

Illustrative biological data for representative compounds disclosed herein is presented in the following table:

TABLE 11

| | MCF7 Viability Assay | | ER-α In Cell Western Assay (SP1) | |
|---|---|---|---|---|
| Compound | IC$_{50}$ | Max Response | IC$_{50}$ | Max Response |
| 1 | A | + | A | ++ |
| 2 | A | ++ | A | ++ |
| 3 | A | ++ | A | ++ |
| 4 | A | ++ | A | ++ |
| 5 | B | ++ | B | ++ |
| 6 | A | ++ | A | ++ |
| 7 | A | ++ | A | ++ |
| 8 | B | ++ | A | ++ |
| 9 | A | ++ | A | ++ |
| 10 | B | ++ | A | ++ |
| 11 | A | ++ | A | ++ |
| 12 | A | ++ | A | ++ |

TABLE 11-continued

| Compound | MCF7 Viability Assay IC$_{50}$ | Max Response | ER-α In Cell Western Assay (SP1) IC$_{50}$ | Max Response |
|---|---|---|---|---|
| 13 | A | ++ | A | ++ |
| 14 | A | ++ | A | ++ |
| 15 | A | ++ | A | ++ |
| 16 | A | ++ | A | ++ |
| 17 | A | ++ | A | ++ |
| 18 | A | ++ | A | ++ |
| 19 | A | ++ | A | ++ |
| 20 | A | ++ | A | ++ |
| 21 | A | ++ | A | ++ |
| 22 | A | ++ | A | ++ |
| 23 | A | ++ | A | ++ |
| 24 | A | ++ | A | ++ |
| 25 | B | ++ | B | ++ |
| 26 | A | ++ | A | ++ |
| 27 | A | ++ | A | ++ |
| 28 | B | ++ | B | ++ |
| 29 | A | ++ | A | ++ |
| 30 | A | ++ | A | ++ |
| 31 | A | ++ | A | ++ |
| 32 | A | ++ | A | ++ |
| 33 | A | ++ | A | ++ |
| 34 | A | ++ | A | ++ |
| 35 | A | ++ | A | ++ |
| 36 | A | ++ | A | ++ |
| 37 | A | ++ | A | ++ |
| 38 | A | ++ | A | ++ |
| 39 | A | ++ | A | ++ |
| 40 | A | ++ | A | ++ |
| 41 | A | ++ | A | ++ |
| 42 | A | ++ | A | ++ |
| 43 | A | ++ | A | ++ |
| 44 | A | ++ | A | ++ |
| 45 | A | ++ | A | ++ |
| 46 | A | ++ | A | ++ |
| 47 | A | ++ | A | ++ |
| 48 | A | ++ | A | ++ |
| 49 | B | ++ | B | ++ |
| 50 | A | ++ | A | ++ |
| 51 | B | ++ | B | ++ |
| 52 | B | ++ | B | ++ |
| 53 | A | ++ | A | ++ |
| 54 | A | ++ | A | ++ |
| 55 | A | ++ | A | ++ |
| 56 | B | ++ | A | ++ |
| 57 | A | ++ | A | ++ |
| 58 | A | ++ | A | ++ |
| 59 | B | + | B | ++ |
| 60 | A | ++ | A | ++ |
| 61 | A | ++ | A | ++ |
| 62 | B | ++ | B | ++ |
| 63 | A | ++ | A | ++ |
| 64 | A | ++ | A | ++ |
| 65 | A | ++ | A | ++ |
| 66 | A | ++ | A | ++ |
| 67 | B | ++ | B | ++ |
| 68 | B | ++ | B | ++ |
| 69 | A | ++ | A | ++ |
| 70 | A | ++ | A | ++ |
| 71 | A | ++ | A | ++ |
| 72 | A | ++ | A | ++ |
| 73 | A | ++ | A | ++ |
| 74 | A | ++ | A | ++ |
| 75 | B | ++ | B | ++ |
| 76 | A | ++ | A | ++ |
| 77 | A | ++ | A | ++ |
| 78 | A | ++ | A | ++ |
| 79 | A | ++ | A | ++ |
| 80 | A | ++ | A | ++ |
| 81 | B | ++ | B | ++ |
| 82 | A | ++ | A | ++ |
| 83 | B | ++ | B | ++ |
| 84 | A | ++ | A | ++ |
| 85 | A | ++ | A | ++ |
| 86 | A | ++ | A | ++ |
| 87 | A | ++ | A | ++ |
| 88 | B | ++ | B | ++ |
| 89 | A | ++ | A | ++ |
| 90 | B | ++ | B | ++ |
| 91 | A | ++ | A | ++ |
| 92 | A | ++ | A | ++ |
| 93 | A | ++ | A | ++ |
| 94 | A | ++ | A | ++ |
| 95 | A | ++ | A | ++ |
| 96 | A | ++ | A | ++ |
| 97 | A | ++ | B | ++ |
| 98 | A | ++ | A | ++ |
| 99 | A | ++ | A | ++ |
| 100 | B | ++ | B | ++ |
| 101 | B | ++ | B | ++ |
| 102 | B | + | B | ++ |
| 103 | B | ++ | B | ++ |
| 104 | B | ++ | B | ++ |
| 105 | B | ++ | B | ++ |
| 106 | A | ++ | A | ++ |
| 107 | B | ++ | B | ++ |
| 108 | A | ++ | A | ++ |
| 109 | A | ++ | A | ++ |
| 110 | A | ++ | A | ++ |
| 111 | A | ++ | A | ++ |
| 112 | A | ++ | A | ++ |
| 113 | A | ++ | A | ++ |
| 114 | A | ++ | A | ++ |
| 115 | A | ++ | A | ++ |
| 116 | A | ++ | A | ++ |
| 117 | A | ++ | A | ++ |
| 118 | B | ++ | B | ++ |
| 119 | A | ++ | A | ++ |
| 120 | A | ++ | A | ++ |
| 121 | A | ++ | A | ++ |
| 122 | B | ++ | B | ++ |
| 123 | B | ++ | A | ++ |
| 124 | B | + | B | ++ |
| 125 | B | ++ | B | ++ |
| 126 | B | ++ | A | ++ |
| 127 | B | + | B | + |
| 128 | B | ++ | B | ++ |
| 129 | B | ++ | A | ++ |
| 130 | B | ++ | B | ++ |
| 131 | B | ++ | B | ++ |
| 131 | B | + | B | + |
| 133 | B | ++ | B | ++ |
| 134 | B | + | B | + |
| 135 | A | + | B | ++ |
| 136 | B | + | B | ++ |
| 137 | B | + | B | ++ |
| 138 | B | + | B | ++ |
| 139 | B | ++ | A | ++ |
| 140 | B | ++ | A | ++ |
| 141 | A | ++ | A | ++ |
| 142 | A | ++ | A | ++ |
| 143 | B | ++ | B | ++ |
| 144 | B | ++ | B | ++ |
| 145 | B | ++ | B | ++ |
| 146 | B | ++ | B | ++ |
| 147 | A | ++ | A | ++ |
| 148 | B | ++ | B | ++ |
| 149 | B | + | B | ++ |
| 150 | B | + | B | ++ |
| 151 | A | ++ | A | ++ |
| 152 | B | + | B | ++ |
| 153 | A | ++ | A | ++ |
| 154 | A | ++ | A | ++ |
| 155 | A | ++ | A | ++ |
| 156 | B | ++ | B | ++ |
| 157 | A | ++ | A | ++ |
| 158 | A | ++ | A | ++ |
| 159 | B | ++ | B | ++ |
| 160 | A | ++ | A | ++ |
| 161 | A | ++ | A | ++ |
| 162 | A | ++ | A | ++ |

TABLE 11-continued

| Compound | MCF7 Viability Assay IC$_{50}$ | Max Response | ER-α In Cell Western Assay (SP1) IC$_{50}$ | Max Response |
|---|---|---|---|---|
| 163 | A | ++ | A | ++ |
| 164 | A | ++ | A | ++ |
| 165 | A | ++ | A | ++ |
| 166 | A | ++ | A | ++ |
| 167 | A | ++ | A | ++ |
| 168 | B | ++ | B | ++ |
| 169 | A | ++ | A | ++ |
| 170 | A | ++ | A | ++ |
| 171 | A | + | A | ++ |
| 172 | A | + | B | ++ |
| 173 | A | + | | |
| 174 | A | + | | |
| 175 | A | + | A | ++ |
| 176 | A | ++ | A | ++ |
| 177 | A | ++ | A | ++ |
| 178 | A | ++ | A | ++ |
| 179 | A | ++ | A | ++ |
| 180 | A | ++ | A | ++ |
| 181 | B | ++ | A | ++ |
| 182 | B | ++ | A | ++ |
| 183 | A | ++ | A | ++ |
| 184 | A | ++ | A | ++ |
| 185 | B | ++ | A | ++ |
| 186 | B | + | B | ++ |
| 187 | A | ++ | A | ++ |
| 188 | A | ++ | A | ++ |
| 189 | B | ++ | B | ++ |
| 190 | B | ++ | B | ++ |
| 191 | A | ++ | A | ++ |
| 192 | B | ++ | B | ++ |
| 193 | A | + | B | ++ |
| 194 | A | + | A | ++ |
| 195 | A | ++ | A | ++ |
| 196 | A | + | A | ++ |
| 197 | A | ++ | A | ++ |
| 198 | A | ++ | A | ++ |
| 199 | A | ++ | A | ++ |
| 200 | A | ++ | A | ++ |
| 201 | A | ++ | A | ++ |
| 202 | A | ++ | A | ++ |
| 203 | A | ++ | A | ++ |
| 204 | A | ++ | A | ++ |
| 205 | A | ++ | A | ++ |
| 206 | A | ++ | A | ++ |
| 207 | A | ++ | A | ++ |
| 208 | B | + | B | ++ |
| 209 | A | ++ | A | ++ |
| 210 | A | ++ | A | ++ |
| 211 | A | ++ | A | ++ |
| 212 | B | ++ | B | ++ |
| 213 | B | + | B | ++ |
| 214 | A | ++ | A | ++ |
| 215 | A | ++ | A | ++ |
| 216 | A | ++ | A | ++ |
| 217 | B | ++ | B | ++ |
| 218 | B | ++ | B | ++ |
| 219 | B | ++ | B | ++ |
| 220 | B | + | B | + |
| 221 | B | + | B | + |
| 222 | A | ++ | A | ++ |
| 223 | A | ++ | A | ++ |
| 224 | A | ++ | A | ++ |
| 225 | B | ++ | B | ++ |
| 226 | A | ++ | A | ++ |
| 227 | A | ++ | A | ++ |
| 228 | B | + | B | + |
| 229 | B | ++ | B | ++ |
| 230 | A | ++ | A | ++ |
| 231 | A | ++ | A | ++ |
| 232 | A | ++ | A | ++ |
| 233 | A | ++ | A | ++ |
| 234 | A | ++ | A | ++ |
| 235 | A | ++ | A | ++ |
| 236 | A | ++ | A | ++ |
| 237 | A | ++ | A | ++ |
| 238 | B | ++ | B | ++ |
| 239 | A | ++ | A | ++ |
| 240 | A | ++ | A | ++ |
| 241 | A | ++ | A | ++ |
| 242 | A | ++ | A | ++ |
| 243 | B | + | B | ++ |
| 244 | A | ++ | A | ++ |
| 245 | A | ++ | A | ++ |
| 246 | B | + | B | ++ |
| 247 | A | ++ | A | ++ |
| 248 | A | ++ | A | ++ |
| 249 | B | ++ | A | ++ |
| 250 | A | ++ | A | ++ |
| 251 | B | ++ | B | ++ |
| 252 | B | ++ | A | ++ |
| 253 | A | ++ | A | ++ |
| 254 | A | ++ | A | ++ |
| 255 | A | ++ | A | ++ |
| 256 | A | ++ | A | ++ |
| 257 | A | ++ | A | ++ |
| 258 | B | ++ | A | ++ |
| 259 | A | ++ | A | ++ |
| 260 | B | + | B | + |
| 261 | A | ++ | A | ++ |
| 262 | B | ++ | B | ++ |
| 263 | A | ++ | A | ++ |
| 264 | B | ++ | B | ++ |
| 265 | B | ++ | B | ++ |
| 266 | A | ++ | A | ++ |
| 267 | A | ++ | A | ++ |
| 268 | B | ++ | A | ++ |
| 269 | A | ++ | A | ++ |
| 270 | B | ++ | B | ++ |
| 271 | A | ++ | A | ++ |
| 272 | A | ++ | A | ++ |
| 273 | A | ++ | A | ++ |
| 274 | A | ++ | A | ++ |
| 275 | A | ++ | A | ++ |
| 276 | A | ++ | A | ++ |
| 277 | A | ++ | A | ++ |
| 278 | A | ++ | A | ++ |
| 279 | A | ++ | A | ++ |
| 280 | A | ++ | A | ++ |
| 281 | B | ++ | A | ++ |
| 282 | A | ++ | A | ++ |
| 283 | A | ++ | A | ++ |
| 284 | A | ++ | A | ++ |
| 285 | A | ++ | A | ++ |
| 286 | A | ++ | A | ++ |
| 287 | A | ++ | A | ++ |
| 288 | B | ++ | A | ++ |
| 289 | B | ++ | A | ++ |
| 290 | A | ++ | A | ++ |
| 291 | A | ++ | A | ++ |
| 292 | A | ++ | A | ++ |
| 293 | A | ++ | A | ++ |
| 294 | A | ++ | A | ++ |
| 295 | A | ++ | A | ++ |
| 296 | A | ++ | A | ++ |
| 297 | A | ++ | A | ++ |
| 298 | A | ++ | A | ++ |
| 299 | B | ++ | A | ++ |
| 300 | B | ++ | A | ++ |
| 301 | B | ++ | A | ++ |
| 302 | A | ++ | A | ++ |
| 303 | B | ++ | B | ++ |
| 304 | A | ++ | A | ++ |
| 305 | A | ++ | A | ++ |
| 306 | A | ++ | A | ++ |
| 307 | A | ++ | A | ++ |
| 308 | A | ++ | A | ++ |
| 309 | A | ++ | A | ++ |
| 310 | A | ++ | A | ++ |
| 311 | A | ++ | A | ++ |
| 312 | A | ++ | A | ++ |

TABLE 11-continued

| Compound | MCF7 Viability Assay IC$_{50}$ | Max Response | ER-α In Cell Western Assay (SP1) IC$_{50}$ | Max Response |
|---|---|---|---|---|
| 313 | A | ++ | A | ++ |
| 314 | A | ++ | A | ++ |
| 315 | A | ++ | A | ++ |
| 316 | A | ++ | A | ++ |
| 317 | A | ++ | A | ++ |
| 318 | B | ++ | A | ++ |
| 319 | A | ++ | A | ++ |
| 320 | A | ++ | A | ++ |
| 321 | A | ++ | A | ++ |
| 322 | A | ++ | A | ++ |
| 323 | B | ++ | A | ++ |
| 324 | A | ++ | A | ++ |
| 325 | B | ++ | A | ++ |
| 326 | A | ++ | A | ++ |
| 327 | B | + | B | + |
| 328 | B | + | B | + |
| 329 | A | ++ | A | ++ |
| 330 | A | ++ | A | ++ |
| 331 | A | ++ | A | ++ |
| 332 | B | ++ | B | ++ |
| 333 | A | ++ | A | ++ |
| 334 | B | + | A | ++ |
| 335 | A | ++ | A | ++ |
| 336 | B | ++ | A | ++ |
| 337 | A | ++ | A | ++ |
| 338 | B | ++ | A | ++ |
| 339 | A | ++ | A | ++ |
| 340 | A | ++ | A | ++ |
| 341 | A | ++ | A | ++ |
| 342 | A | ++ | A | ++ |
| 343 | B | ++ | B | ++ |
| 344 | B | ++ | A | ++ |
| 345 | A | ++ | A | ++ |
| 346 | A | ++ | A | ++ |
| 347 | B | + | B | + |
| 348 | B | + | B | + |
| 349 | A | ++ | A | ++ |
| 350 | B | ++ | A | ++ |
| 351 | B | + | B | ++ |
| 352 | B | + | B | ++ |
| 353 | B | + | B | ++ |
| 354 | B | + | B | ++ |
| 355 | A | ++ | A | ++ |
| 356 | B | ++ | A | ++ |
| 357 | B | ++ | B | ++ |
| 358 | A | ++ | A | ++ |
| 359 | A | ++ | A | ++ |
| 360 | B | ++ | B | ++ |
| 361 | A | ++ | A | ++ |
| 362 | A | ++ | A | ++ |
| 363 | A | ++ | A | ++ |
| 364 | A | ++ | A | ++ |
| 365 | A | ++ | A | ++ |
| 366 | A | ++ | A | ++ |
| 367 | A | ++ | A | ++ |
| 368 | A | ++ | A | ++ |
| 369 | B | ++ | A | ++ |
| 370 | A | ++ | A | ++ |
| 371 | A | ++ | A | ++ |
| 372 | B | ++ | A | ++ |
| 373 | A | ++ | A | ++ |
| 374 | B | ++ | B | ++ |
| 375 | A | ++ | A | ++ |
| 376 | A | ++ | A | ++ |
| 377 | A | ++ | A | ++ |
| 378 | A | ++ | A | ++ |
| 379 | A | ++ | A | ++ |
| 380 | B | ++ | A | ++ |
| 381 | A | ++ | A | ++ |
| 382 | A | ++ | A | ++ |
| 383 | B | ++ | B | ++ |
| 384 | B | ++ | B | ++ |
| 385 | B | ++ | A | ++ |
| 386 | B | ++ | A | ++ |
| 387 | B | ++ | A | ++ |
| 388 | B | ++ | A | ++ |
| 389 | B | ++ | A | ++ |
| 390 | A | ++ | A | ++ |
| 391 | A | ++ | A | ++ |
| 392 | A | ++ | A | ++ |
| 393 | A | ++ | A | ++ |
| 394 | B | ++ | A | ++ |
| 395 | B | ++ | A | ++ |
| 396 | B | ++ | B | ++ |
| 397 | A | ++ | A | ++ |
| 398 | A | ++ | A | ++ |
| 399 | A | ++ | A | ++ |
| 400 | A | ++ | A | ++ |
| 401 | B | ++ | A | ++ |
| 402 | A | ++ | A | ++ |
| 403 | A | ++ | A | ++ |
| 404 | A | ++ | A | ++ |
| 405 | A | ++ | A | ++ |
| 406 | A | ++ | A | ++ |
| 407 | | | | |
| 408 | A | ++ | A | ++ |
| 409 | A | ++ | A | ++ |
| 410 | A | ++ | A | ++ |
| 411 | A | ++ | A | ++ |
| 412 | A | ++ | A | ++ |
| 413 | A | ++ | A | ++ |
| 414 | A | ++ | A | ++ |
| 415 | A | ++ | A | ++ |
| 416 | A | ++ | A | ++ |
| 417 | A | ++ | A | ++ |
| 418 | A | ++ | A | ++ |
| 419 | A | ++ | A | ++ |
| 420 | A | ++ | A | ++ |
| 421 | A | ++ | A | ++ |
| 422 | A | ++ | A | ++ |
| 423 | A | ++ | A | ++ |
| 424 | B | ++ | A | ++ |
| 425 | A | ++ | A | ++ |
| 426 | A | ++ | A | ++ |
| 427 | A | ++ | A | ++ |
| 428 | A | ++ | A | ++ |
| 429 | A | ++ | A | ++ |
| 430 | A | ++ | A | ++ |
| 431 | A | ++ | A | ++ |
| 432 | A | ++ | A | ++ |
| 433 | A | ++ | A | ++ |
| 434 | A | ++ | A | ++ |
| 435 | A | ++ | A | ++ |
| 436 | A | ++ | A | ++ |
| 437 | A | ++ | A | ++ |
| 438 | A | ++ | A | ++ |
| 439 | A | ++ | A | ++ |
| 440 | A | + | A | ++ |
| 441 | A | + | A | ++ |
| 442 | A | ++ | A | ++ |
| 443 | A | ++ | A | ++ |
| 444 | B | ++ | A | ++ |
| 445 | A | ++ | A | ++ |
| 446 | A | ++ | A | ++ |
| 447 | A | ++ | A | ++ |
| 448 | A | ++ | A | ++ |
| 449 | A | ++ | A | ++ |
| 450 | A | ++ | A | ++ |
| 451 | A | ++ | A | ++ |
| 452 | A | ++ | A | ++ |
| 453 | B | ++ | B | ++ |

A = single IC$_{50}$ ≤ 100 nM
B = single IC$_{50}$ > 100 nM;
+ = a single % value < 40%
++ = a single % value ≥ 40%

Example 87

Ishikawa Uterine Cell Alkaline Phosphatase Assay

Subconfluent Ishikawa cells in a T225 are incubated 24 hours in an estrogen free basal medium (EFBM) consisting of DMEM:Ham's F-12 50:50 phenol red free basal medium containing 5% Charcoal Dextran treated FBS and 20 mM HEPES. Cells are plated the following day in EFBM in clear 384 well plates at a concentration of $2.5 \times 10^5$ cells per mL, 16 µL per well (4000 cells per well). A 12 point semilog dilution of each compound is carried out in DMSO and subsequently diluted in EFBM. An equal volume of compound in EFBM is added immediately after plating cells, and the cells are incubated for 3 days. The cells are fixed with 5% formalin, and rinsed with PBS. Alkaline Phosphatase substrate 4-Nitrophenyl phosphate disodium salt hexahydrate is added to a solution containing 2 mM $MgCl_2$, 1 M diethanolamine, and adjusted to pH 9.0. The substrate solution is added to the cell cultures (16 µL per well), and OD405 is measured in a multiwall plate spectrophotometer when the optical density at 405 nm wavelength of cells treated with 17β-estradiol in the concentration range of 1-30 nM reaches 1.0-1.2 absorbance units. Cells treated with DMSO alone serve as a background control. Percent activity in background subtracted samples is measured as follows: % activity=OD405 sample/OD405 max of 17β-estradiol treated cells×100.

Example 88

Ovarian Cancer Cell Viability Assays

BG-1, cells were adjusted to a concentration of 20,000 cells per mL in RPMI containing 10% FBS and 20 mM HEPES. 16 microliters of the cell suspension (320 cells) was added to each well of a 384 well plate, and the cells were incubated overnight to allow the cells to adhere. The following day an eleven point, serial semilog dilution of each compound was added to the cells in 16 µL at a final concentration ranging from 0.3-0.000003 µM. After 5 days' compound exposure, 16 µL of CellTiter-GLo (Promega, Madison Wis.) was added to the cells the relative luminescence units (RLUs) of each well was determined. CellTiter-Glo added to 32 µL of medium without cells was used to obtain a background value. The Percent viability of each sample was determined as follows: (RLU sample-RLU background/RLU untreated cells-RLU background)×100=% viability.

Viability effects in additional ER+ ovarian cancer cell lines, including A1847, SKOV3, SW626, A2780, can be profiled in assays similar to Example 88.

Example 89

Ovarian Cancer Cell ER-α in Cell Western Assay

BG-1 cells were adjusted to a concentration of 200,000 cells per mL in RPMI containing 10% charcoal-stripped FBS and 20 mM HEPES. 16 microliters of the cell suspension (3200 cells) was added to each well of a poly-D-lysine 384 well plate, and the cells were incubated overnight to allow the cells to adhere. The following day an eleven point, serial semilog dilution of each compound was added to the cells in 16 µL at a final concentration ranging from 0.3-0.000003 µM. At 4 or 24 hr post compound addition, the cells were fixed (10% formalin in PBS) for 20 minutes. Cells were permeabalized in PBS 0.1% Triton and blocked with LICOR blocking buffer (50 µl/well, 90'). The wells were then incubated overnight at 4° C. with ER1D5 (Santa Cruz Biotechnology) diluted 1:100 in LICOR blocking buffer/ 0.1% Tween-20. Wells which were treated with blocking buffer with Tween but no antibody were used as a background control. Wells were washed with 0.1% Tween-20/ PBS and then incubated in goat anti-mouse IRDye™ 800CW (LICOR Inc.; 1:1000) and DRAQ5 DNA dye (1:2000 for 2 mM stock) diluted in LICOR blocking buffer containing 0.1% Tween-20 and 0.01% SDS for 60 minutes. Cells were washed (50 µl/well, 5' each) in 0.1% Tween-20/ PBS. Plates were scanned on a LICOR Odyssey infrared imaging system. Integrated intensities in the 800 nm channel and 700 nm channel were measured to determine levels of ER and DNA respectively. Percent ER levels were determined as follows:

(Integrated intensity 800 nm sample/integrated intensity 700 nm sample)/(Integrated intensity 800 nm untreated cells/integrated intensity 700 nm untreated cells)×100=% ER levels.

Effects on steady state levels of ER-α in additional ER+ ovarian cancer cell lines, including A1847, SKOV3, SW626, A2780, can be profiled in assays similar to Example 89.

Other cancer cell lines contemplated for testing compounds described herein include: ER-positive endometrial cell lines (Ishikawa, ECC1, HEC-1, EnCa-101) and ER-positive cervical cell lines (Caski, HeLa, SiHa).

Example 90

Breast Cancer Model; Xenograft Assay (MCF-7)

Time release pellets containing 0.72 mg 17-β Estradiol were subcutaneously implanted into nu/nu mice. MCF-7 cells were grown in RPMI containing 10% FBS at 5% $CO_2$, 37° C. Cells were spun down and re-suspended in 50% RPMI (serum free) and 50% Matrigel at $1 \times 10^7$ cells/mL. MCF-7 cells were subcutaneously injected (100 µL/animal) on the right flank 2-3 days post pellet implantation. Tumor volume (length×width$^2$/2) was monitored bi-weekly. When tumors reached an average volume of ~200 mm$^3$ animals were randomized and treatment was started. Animals were treated with Vehicle or Compound daily for 4 weeks. Tumor volume and body weight were monitored bi-weekly throughout the study. At the conclusion of the treatment period, plasma and tumor samples were taken for pharmacokinetic and pharmacodynamic analyses, respectively.

Example 91

Breast Cancer Model; Xenograft Assay (MCF-7 Derivative)

Female nu/nu mice (with supplemental 17-β Estradiol pellets; 0.72 mg; 60 day slow release) bearing MCF-7 tumors (mean tumor volume 200 mm$^3$) were treated with Tamoxifen (citrate) by oral gavage. Tumor volume (length× width$^2$/2) and body weight were monitored twice weekly. Following a significant anti-tumor response in which tumor volume remained static, evident tumor growth was first observed at approximately 100 days of treatment. At 120 days of treatment, tamoxifen dose was increased. Rapidly growing tumors were deemed tamoxifen resistant and selected for in vivo passage into new host animals. Tumor Fragments (~100 mm$^3$/animal) from the tamoxifen resistant tumors were subcutaneously implanted into the right flank of female nu/nu mice (with 17-β Estradiol pellets (0.72 mg; 60 day slow release)). Passaged tumors were maintained under constant Tamoxifen selection, and Tumor volume (length×width$^2$/2) was monitored weekly. When tumor volume reached ~150-250 mm$^3$, animals were randomized into treatment groups (mean tumor volume 200 mm$^3$) and tamoxifen treatment was terminated (except for a tamoxifen control arm). Animals were treated with Vehicle or Compound daily for 4 weeks. Tumor volume and body weight were monitored twice weekly for the duration of the study. At the conclusion of the treatment period; plasma and tumor samples were taken for pharmacokinetic and pharmacodynamic analyses, respectively.

Example 92

Ovarian Cancer Model; Xenograft Assay (BG-1)

Time release pellets (0.72 mg 17-β Estradiol/60 days) were subcutaneously implanted into female nu/nu mice. BG-1 cells were grown in DMEM Ham's F-12 50/50 containing 10% FBS, 10 mM Sodium Pyruvate, 10 mM Non-Essential Amino Acids at 5% $CO_2$, 37° C. Cells were spun down and re-suspended in 50% DMEM Ham's F-12 (serum free) and 50% Matrigel at 5×10$^7$ cells/mL. BG-1 cells were subcutaneously injected (100 μL/animal) on the right flank 2-3 days post pellet implantation. Tumor volume (length×width$^2$/2) was monitored bi-weekly. When tumors reached an average volume of ~250 mm$^3$ animals were randomized and treatment was started. Animals were treated with Vehicle or Compound daily for 4 weeks. Tumor volume and body weight were monitored bi-weekly throughout the study. At the conclusion of the treatment period; plasma and tumor samples were taken for pharmacokinetic and pharmacodynamic analyses, respectively.

Example 93

Immature Uterine Wet Weight-Antagonist Mode

Female immature CD-IGS rats (21 days old upon arrival) were treated for three days. Animals were dosed daily for three days. Vehicle or test compound was administered orally by gavage followed 15 minutes later by an oral dose of 0.1 mg/kg Ethynyl Estradiol. On the fourth day 24 hours after dose, plasma was collected for pharmacokinetic analysis. Immediately following plasma collection, the animals were euthanized and the uterus was removed and weighed.

Example 94

Immature Uterine Wet Weight-Agonist Mode

Female immature CD-IGS rats (21 days old upon arrival) were treated for three days. Animals were dosed daily for three days. Vehicle or test compound was administered orally by gavage followed 15 minutes later by a second oral dose of vehicle. On the fourth day 24 hours after dose, plasma was collected for pharmacokinetic analysis. Immediately following plasma collection, the animals were euthanized and the uterus was removed and weighed.

Example 95

Breast Cancer Clinical Trial

Purpose: The purposes of this study are to assess the efficacy of a compound of Formula (I), or a pharmaceutically acceptable salt thereof, as first- or second-line treatment of estrogen receptor (ER) positive metastatic breast cancer, collect information on any side effects the compound may cause, and evaluate the pharmacokinetic properties of the compound.

Intervention: Patients are administered 1-50 mg/kg of a compound of Formula (I), or a pharmaceutically acceptable salt thereof, per day or twice a day.

Outcome Measures: Primary Outcome Measures: tumor response and/or disease control.

Secondary Outcome Measures: (a) side-effects; (b) pharmacokinetic properties; (c) proportion of patients that have complete or partial response or stable disease at defined time points; (d) time to progression and overall survival; and (e) biomarkers predictive of clinical response.

Detailed Description: Patients will be given a compound of Formula (I), or a pharmaceutically acceptable salt thereof, orally once or twice a day. Prior to each dosing cycle, a physical exam, blood work and assessment of any side effects will be performed. Every 12 weeks the patient's cancer will be re-evaluated with either a CT scan or MRI to determine whether the treatment is working. Participation in this study will last until disease progression or unacceptable toxicity.

Eligibility: Female subjects that are 18 years and older.

Inclusion Criteria: Histologically or cytologically confirmed diagnosis of invasive breast cancer, stage IV disease; at least one measurable target lesion as defined by RECIST that has not been previously treated with local therapy; post-menopausal status; ER positive breast cancer; HER2-negative breast cancer; up to one prior hormonal therapy for advanced or metastatic disease; ECOG performance status 0-1; life expectancy>12 weeks; adequate liver and bone marrow function: AST<2.5×ULN; Bilirubin<1.5×ULN; ANC>1,500/ul; platelet count>100,000/ul; normal PT and PTT; at least 2 weeks since prior radiation and recovered from treatment-related toxicity.

Exclusion Criteria: HER2-positive breast cancer; prior chemotherapy regimen for metastatic disease; history of, or presence of brain metastases; concurrent investigational drug treatment; prior bone marrow or stem cell transplant; history of other malignancy within the last 5 years, not including curatively-treated carcinoma in situ of the cervix or non-melanoma skin cancer; uncontrolled infection; active bleeding, or history of bleeding requiring transfusion; active cardiac disease; serious medical or psychiatric illness.

Example 96

Endometrial Carcinoma Clinical Trial

Purpose: The purposes of this study are to assess the efficacy of a compound of Formula (I), or a pharmaceutically acceptable salt thereof, in the treatment of advanced or metastatic endometrial carcinoma, collect information on any side effects the compound may cause, and evaluate the pharmacokinetic properties of the compound.

Intervention: Patients are administered 1-50 mg/kg of a compound of Formula (I), or a pharmaceutically acceptable salt thereof, per day or twice a day.

Outcome Measures: Primary Outcome Measures: tumor response and/or disease control Secondary Outcome Measures: (a) side-effects; (b) pharmacokinetic properties; (c) proportion of patients that have complete or partial response or stable disease at defined time points; (d) time to progression and overall survival; and (e) biomarkers predictive of clinical response.

Detailed Description: Patients will be given a compound of Formula (I) orally once or twice a day. Prior to each dosing cycle, a physical exam, blood work and assessment of any side effects will be performed. Every 12 weeks the patient's cancer will be re-evaluated with either a CT scan or MRI to determine whether the treatment is working. Participation in this study will last until disease progression or unacceptable toxicity.

Eligibility: Female subjects that are 18 years and older.

Inclusion Criteria: Histologically or cytologically confirmed diagnosis of advanced or metastatic endometrial carcinoma; at least one measurable target lesion as defined by RECIST that has not been previously treated with local therapy; hormone receptor positive endometrial carcinoma; ECOG performance status 0-1; life expectancy>12 weeks; adequate liver and bone marrow function: AST<2.5×ULN; Bilirubin<1.5×ULN; ANC>1,500/ul; platelet count>100,000/ul; normal PT and PTT; at least 2 weeks since prior radiation and recovered from prior surgery or treatment-related toxicity.

Exclusion Criteria: History of, or presence of brain metastases; concurrent investigational drug treatment; prior bone marrow or stem cell transplant; history of other malignancy within the last 5 years, not including curatively-treated carcinoma in situ of the cervix or non-melanoma skin cancer; uncontrolled infection; active bleeding, or history of bleeding requiring transfusion; active cardiac disease; serious medical or psychiatric illness.

Example 97

Ovarian Cancer Clinical Trial

Purpose: The purposes of this study are to assess the efficacy of a compound of Formula (I), or a pharmaceutically acceptable salt thereof, in the treatment of advanced ovarian cancer, collect information on any side effects the compound may cause, and evaluate the pharmacokinetic properties of the compound.

Intervention: Patients are administered 1-50 mg/kg of a compound of Formula (I), or a pharmaceutically acceptable salt thereof, per day or twice a day.

Outcome Measures: Primary Outcome Measures: tumor response and/or disease control Secondary Outcome Measures: (a) side-effects; (b) pharmacokinetic properties; (c) proportion of patients that have complete or partial response or stable disease at defined time points; (d) time to progression and overall survival; and (e) biomarkers predictive of clinical response.

Detailed Description: Patients will be given a compound of Formula (I) orally once or twice a day. Prior to each dosing cycle, a physical exam, blood work (including tumor markers, e.g., CA-125) and assessment of any side effects will be performed. Every 12 weeks the patient's cancer will be re-evaluated with either a CT scan or MRI to determine whether the treatment is working. Participation in this study will last until disease progression or unacceptable toxicity.

Eligibility: Female subjects that are 18 years and older.

Inclusion Criteria: Histologically or cytologically confirmed diagnosis of advanced ovarian cancer; at least one measurable target lesion as defined by RECIST that has not been previously treated with local therapy; ER positive ovarian cancer; ECOG performance status 0-1; life expectancy>12 weeks; adequate liver and bone marrow function: AST<2.5×ULN; Bilirubin<1.5×ULN; ANC>1,500/ul; platelet count>100,000/ul; normal PT and PTT; at least 2 weeks since prior radiation and recovered from prior surgery or treatment-related toxicity.

Exclusion Criteria: History of, or presence of brain metastases; concurrent investigational drug treatment; prior bone marrow or stem cell transplant; history of other malignancy within the last 5 years, not including curatively-treated carcinoma in situ of the cervix or non-melanoma skin cancer; uncontrolled infection; active bleeding, or history of bleeding requiring transfusion; active cardiac disease; serious medical or psychiatric illness.

Example 98

ER-Positive NSCLC Clinical Trial

Purpose: The purposes of this study are to assess the efficacy of a compound of Formula (I), or a pharmaceutically acceptable salt thereof, as single agent or in combination in the treatment of advanced or metastatic estrogen receptor (ER) positive non-small cell lung cancer (NSCLC), collect information on any side effects the compound may cause as single agent or in combination, and evaluate the pharmacokinetic properties of the compound as single agent or in combination.

Intervention: Patients are administered 1-50 mg/kg of a compound of Formula (I), or a pharmaceutically acceptable salt thereof, per day or twice a day as single agent or in combination.

Outcome Measures: Primary Outcome Measures: tumor response and/or disease control. Secondary Outcome Measures: (a) side-effects; (b) pharmacokinetic properties; (c) proportion of patients that have complete or partial response or stable disease at defined time points; (d) time to progression and overall survival; and (e) biomarkers predictive of clinical response.

Detailed Description: Patients will be given a compound of Formula (I), or a pharmaceutically acceptable salt thereof, orally once or twice a day as single agent or in combination. Prior to each dosing cycle, a physical exam, blood work and assessment of any side effects will be performed. Every 12 weeks the patient's cancer will be re-evaluated with either a CT scan or MRI to determine whether the treatment is working. Participation in this study will last until disease progression or unacceptable toxicity.

Eligibility: Male and female subjects that are 18 years and older.

Inclusion Criteria: Histologically or cytologically confirmed diagnosis of advanced or metastatic ER-positive NSCLC; at least one measurable target lesion as defined by RECIST that has not been previously treated with local therapy; ECOG performance status 0-1; life expectancy>12 weeks; adequate liver and bone marrow function: AST<2.5× ULN; Bilirubin<1.5×ULN; ANC>1,500/ul; platelet count>100,000/ul; normal PT and PTT; at least 2 weeks since prior radiation and recovered from prior surgery or treatment-related toxicity.

Exclusion Criteria: History of, or presence of brain metastases; concurrent investigational drug treatment; prior bone marrow or stem cell transplant; history of other malignancy within the last 5 years, not including curatively-treated carcinoma in situ of the cervix or non-melanoma skin cancer; uncontrolled infection; active bleeding, or history of bleeding requiring transfusion; active cardiac disease; serious medical or psychiatric illness.

Example 99

Endometriosis Clinical Trial

Purpose: The purposes of this study are to assess the efficacy of a compound of Formula (I), or a pharmaceutically acceptable salt thereof, as single agent or in combination in the treatment of patients with symptomatic/severe endometriosis, collect information on any side effects the compound may cause as single agent or in combination, and evaluate the pharmacokinetic properties of the compound as single agent or in combination.

Intervention: Patients are administered 1-50 mg/kg of a compound of Formula (I), or a pharmaceutically acceptable salt thereof, per day or twice a day as single agent or in combination.

Outcome Measures: The outcome measures of this study are symptoms improvement and/or pain relief and shrinkage of endometrial tissue.

Detailed Description: Patients will be given a compound of Formula (I), or a pharmaceutically acceptable salt thereof, orally once or twice a day as single agent or in combination. Prior to each dosing cycle, a physical exam, blood work and assessment of any side effects will be performed.

Eligibility: Female subjects that are 18 years and older.
Inclusion Criteria: Diagnosis of symptomatic endometriosis; pre- or peri-menopausal status; ECOG performance status 0-1; adequate liver and bone marrow function: AST<2.5×ULN; Bilirubin<1.5×ULN; ANC>1,500/ul; platelet count>100,000/ul; normal PT and PTT; at least 2 weeks since prior surgery or treatment-related toxicity.

Exclusion Criteria: Pregnancy or lactating; history of other malignancy within the last 5 years, not including curatively-treated carcinoma in situ of the cervix or non-melanoma skin cancer; concurrent investigational drug treatment; uncontrolled infection; active cardiac disease; a serious medical or psychiatric illness.

Example 100

Uterine Leiomyoma Clinical Trial

Purpose: The purposes of this study are to assess the efficacy of a compound of Formula (I), or a pharmaceutically acceptable salt thereof, as single agent or in combination in the treatment of patients with symptomatic uterine leiomyoma, collect information on any side effects the compound may cause as single agent or in combination, and evaluate the pharmacokinetic properties of the compound as single agent or in combination.

Intervention: Patients are administered 1-50 mg/kg of a compound of Formula (I), or a pharmaceutically acceptable salt thereof, per day or twice a day as single agent or in combination.

Outcome Measures: The outcome measures of this study are symptoms improvement and/or pain relief and shrinkage of leiomyomas.

Detailed Description: Patients will be given a compound of Formula (I), or a pharmaceutically acceptable salt thereof, orally once or twice a day as single agent or in combination. Prior to each dosing cycle, a physical exam, blood work and assessment of any side effects will be performed.

Eligibility: Female subjects that are 18 years and older.
Inclusion Criteria: Diagnosis of symptomatic uterine leiomyoma; pre- or peri-menopausal status; ECOG performance status 0-1; adequate liver and bone marrow function: AST<2.5×ULN; Bilirubin<1.5×ULN; ANC>1,500/ul; platelet count>100,000/ul; normal PT and PTT; at least 2 weeks since prior surgery or treatment-related toxicity.

Exclusion Criteria: Pregnancy or lactating; history of other malignancy within the last 5 years, not including curatively-treated carcinoma in situ of the cervix or non-melanoma skin cancer; concurrent investigational drug treatment; uncontrolled infection; active cardiac disease; serious medical or psychiatric illness.

Example 101

Parenteral Pharmaceutical Composition

To prepare a parenteral pharmaceutical composition suitable for administration by injection (subcutaneous, intravenous), 100 mg of a water-soluble salt of a compound of Formulas (I) is dissolved in sterile water and then mixed with 10 mL of 0.9% sterile saline. The mixture is incorporated into a dosage unit form suitable for administration by injection In another embodiment, the following ingredients are mixed to form an injectable formulation: 1.2 g of a compound of Formula (I), or a pharmaceutically acceptable salt thereof, 2.0 mL of sodium acetate buffer solution (0.4 M), HCl (1 N) or NaOH (1 M) (q.s. to suitable pH), water (distilled, sterile) (q.s. to 20 mL). All of the above ingredients, except water, are combined and stirred and if necessary, with slight heating if necessary. A sufficient quantity of water is then added.

Example 102

Oral Solution

To prepare a pharmaceutical composition for oral delivery, an aqueous 20% propylene glycol solution is prepared. To this is added a sufficient amount of a compound of Formula (I), or a pharmaceutically acceptable salt thereof, to provide a 20 mg/mL solution.

Example 103

Oral Capsule

To prepare a pharmaceutical composition for oral delivery, 100-500 mg of a compound of Formula (I), or a pharmaceutically acceptable salt thereof, is mixed with starch. The mixture is incorporated into an oral dosage unit such as a hard gelatin capsule, which is suitable for oral administration.

In another embodiment, 100-500 mg of a compound of Formula (I), or a pharmaceutically acceptable salt thereof, is placed into Size 4 capsule, or size 1 capsule (hypromellose or hard gelatin) and the capsule is closed.

Example 104

Oral Tablet

A tablet is prepared by mixing 48% by weigh of a compound of Formula (I), or a pharmaceutically acceptable salt thereof, 45% by weight of microcrystalline cellulose, 5% by weight of low-substituted hydroxypropyl cellulose, and 2% by weight of magnesium stearate. Tablets are prepared by direct compression. The total weight of the compressed tablets is maintained at 250-500 mg.

Example 105

Topical Gel Composition

To prepare a pharmaceutical topical gel composition, a compound of Formula (I), or a pharmaceutically acceptable salt thereof, is mixed with hydroxypropyl celluose, propylene glycol, isopropyl myristate and purified alcohol USP. The resulting gel mixture is then incorporated into containers, such as tubes, which are suitable for topical administration.

The examples and embodiments described herein are for illustrative purposes only and various modifications or changes suggested to persons skilled in the art are to be included within the spirit and purview of this application and scope of the appended claims.

What is claimed is:

1. A method of treating breast cancer comprising administering a therapeutically effective amount of (E)-3-(4-((E)-2-(2-Chloro-4-fluorophenyl)-1-(1H-indazol-5-yl)but-1-en-1-yl)phenyl)acrylic acid, or a pharmaceutically acceptable salt thereof, to a patient.

2. The N-methylglucamine salt of (E)-3-(4-((E)-2-(2-Chloro-4-fluorophenyl)-1-(1H-indazol-5-yl)but-1-en-1-yl)phenyl)acrylic acid.

3. A pharmaceutical composition comprising (E)-3-(4-((E)-2-(2-Chloro-4-fluorophenyl)-1-(1H-indazol-5-yl)but-1-en-1-yl)phenyl)acrylic acid, or a pharmaceutically acceptable salt thereof, and an excipient or carrier.

4. The pharmaceutical composition of claim 3 wherein the pharmaceutically acceptable salt of (E)-3 -(4-((E)-2-(2-Chloro-4-fluorophenyl)-1-(1H-indazol-5-yl)but-1-en-1-yl)phenyl)acrylic acid is the N-methylglucamine salt.

5. The method of claim 1, wherein the therapeutically effective amount of (E)-3-(4-((E)-2-(2-Chloro-4-fluorophenyl)-1-(1H-indazol-5-yl)but-1-en-1-yl)phenyl)acrylic acid or a pharmaceutically acceptable salt thereof is administered before the patient has received surgery.

6. The method of claim 1, wherein the therapeutically effective amount of (E)-3-(4-((E)-2-(2-Chloro-4-fluorophenyl)-1-(1H-indazol-5-yl)but-1-en-1-yl)phenyl)acrylic acid or a pharmaceutically acceptable salt thereof is administered after the patient has received surgery.

7. The method of claim 1, wherein the patient has hormone receptor positive metastatic breast cancer.

8. The method of claim 7, wherein the patient has disease progression following anti-estrogen therapy before said administration.

9. A method of treating breast cancer, the method comprising administering a therapeutically effective amount of the N-methylglucamine salt of (E)-3-(4-((E)-2-(2-Chloro-4-fluorophenyl)-1-(1H-indazol5 -yl)but-1-en-1-yl)phenyl)acrylic acid to a patient.

10. The method of claim 9, wherein the therapeutically effective amount of the N-methylglucamine salt of (E)-3-(4 ((E)-2-(2-Chloro-4-fluorophenyl)-1-(1H-indazol-5-yl)but-1-en-1-yl)phenyl)acrylic acid is administered before the patient has received surgery.

11. The method of claim 9, wherein the therapeutically effective amount of the N-methylglucamine salt of (E)-3-(4 ((E)-2-(2-Chloro-4-fluorophenyl)-1-(1H-indazol-5-yl)but-1-en-1-yl)phenyl)acrylic acid is administered after the patient has received surgery.

12. The method of claim 9, wherein the patient has hormone receptor positive metastatic breast cancer.

13. The method of claim 12, wherein the patient has disease progression following anti-estrogen therapy before said administration.

14. A method of treating breast cancer comprising administering a therapeutically effective amount of the pharmaceutical composition of claim 3 to a patient having breast cancer.

15. The method of claim 14, wherein the pharmaceutical composition is administered before the patient has received surgery.

16. The method of claim 14, wherein the pharmaceutical composition is administered after the patient has received surgery.

17. The method of claim 14, wherein the patient has hormone receptor positive metastatic breast cancer.

18. The method of claim 17, wherein the patient has disease progression following anti-estrogen therapy before said administration.

* * * * *